(12) United States Patent
Chee et al.

(10) Patent No.: US 12,292,446 B2
(45) Date of Patent: *May 6, 2025

(54) KITS FOR ANALYSIS USING NUCLEIC ACID ENCODING AND/OR LABEL

(71) Applicant: Encodia, Inc., San Diego, CA (US)

(72) Inventors: Mark S. Chee, Encinitas, CA (US); John M. Beierle, San Diego, CA (US); Norihito Muranaka, San Diego, CA (US); Kevin L. Gunderson, Encinitas, CA (US); Michael Phillip Weiner, San Diego, CA (US); Lei Shi, San Diego, CA (US); Robert C. James, San Diego, CA (US); Luca Monfregola, San Diego, CA (US)

(73) Assignee: ENCODIA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/787,946

(22) Filed: Jul. 29, 2024

(65) Prior Publication Data
US 2024/0377409 A1 Nov. 14, 2024

Related U.S. Application Data

(63) Continuation of application No. 17/819,263, filed on Aug. 11, 2022, now Pat. No. 12,130,291, which is a
(Continued)

(51) Int. Cl.
C40B 40/10 (2006.01)
C40B 70/00 (2006.01)
G01N 33/68 (2006.01)

(52) U.S. Cl.
CPC ......... *G01N 33/6842* (2013.01); *C40B 40/10* (2013.01); *C40B 70/00* (2013.01); *G01N 33/6845* (2013.01)

(58) Field of Classification Search
CPC .... C12N 9/6416; C12N 15/10; C12Q 1/6804; C12Q 1/6869; C12Q 2565/619;
(Continued)

(56) References Cited

U.S. PATENT DOCUMENTS 4,863,870 A 9/1989 Stoloqitz et al.
5,049,507 A 9/1991 Hawke et al.
(Continued)

FOREIGN PATENT DOCUMENTS

EP 0743320 11/1996
EP 0841945 5/1998
(Continued)

OTHER PUBLICATIONS

Kivioja et al. (Nature Methods, 2012, 9(1):72-76) (Year: 2012).*
(Continued)

*Primary Examiner* — Jeremy C Flinders
(74) *Attorney, Agent, or Firm* — DLA PIPER LLP (US)

(57) ABSTRACT

Kits and methods of using the kits for analyzing macromolecules, including peptides, polypeptides, and proteins, employing nucleic acid encoding are disclosed. The sample analysis kits employ nucleic acid encoding and/or nucleic acid recording of a molecular interaction and/or reaction, such as recognition events (e.g., between an antigen and an antibody, between a modified terminal amino acid residue, or between a small molecule or peptide therapeutic and a target, etc.). Additional barcoding reagents, such as those for cycle-specific barcoding (e.g., "clocking"), compartment barcoding, combinatorial barcoding, spatial barcoding, or any combination thereof, may be included in the kits. The sample may comprise macromolecules, including peptides, polypeptides, and proteins, and the recording may generate molecular interaction and/or reaction information, and/or polypeptide sequence information. The kits may be used in
(Continued)

high-throughput, multiplexed, and/or automated analysis, and are suitable for analysis of a proteome or subset thereof.

20 Claims, 85 Drawing Sheets

Specification includes a Sequence Listing.

Related U.S. Application Data continuation of application No. 16/760,028, filed as application No. PCT/US2018/058565 on Oct. 31, 2018, now Pat. No. 11,513,126.

(60) Provisional application No. 62/583,448, filed on Nov. 8, 2017, provisional application No. 62/582,312, filed on Nov. 6, 2017, provisional application No. 62/579,844, filed on Oct. 31, 2017.

(58) Field of Classification Search
CPC ........ C12Q 2535/122; C12Q 2537/125; C12Q 2563/131; C12Q 2563/149; C12Q 2563/179; C12Q 2565/537; C40B 30/04; C40B 40/10; C40B 70/00; G01N 33/543; G01N 33/6842; G01N 33/6845; G01N 2570/00
See application file for complete search history.

(56) References Cited

U.S. PATENT DOCUMENTS

| | | |
|---|---|---|
| 5,484,735 A | 1/1996 | Davis et al. |
| 5,770,358 A | 6/1998 | Dover |
| 5,831,012 A | 11/1998 | Nilsoon et al. |
| 5,834,252 A | 11/1998 | Stemmer et al. |
| 5,900,481 A | 5/1999 | Lough et al. |
| 6,060,596 A | 5/2000 | Lemer et al. |
| 6,207,446 B1 | 3/2001 | Szostak et al. |
| 6,429,300 B1 | 8/2002 | Kurz et al. |
| 6,511,809 B2 | 1/2003 | Baez et al. |
| 6,875,851 B1 | 4/2005 | Travis et al. |
| 7,169,894 B2 | 1/2007 | Martin |
| 7,198,900 B2 | 4/2007 | Woudenberg et al. |
| 7,229,769 B2 | 6/2007 | Kozlov et al. |
| 7,306,904 B2 | 12/2007 | Landegren et al. |
| 7,501,237 B2 | 3/2009 | Solus et al. |
| 7,611,834 B2 | 11/2009 | Chhabra et al. |
| 7,704,925 B2 | 4/2010 | Gouliaev et al. |
| 7,807,438 B2 | 10/2010 | Abrignani et al. |
| 8,148,068 B2 | 4/2012 | Brenner |
| 8,568,994 B2 | 10/2013 | Altevogt et al. |
| 8,609,344 B2 | 12/2013 | Labaer et al. |
| 8,758,991 B2 | 6/2014 | Klein et al. |
| 9,005,888 B2 | 4/2015 | Antes et al. |
| 9,039,888 B2 | 5/2015 | Rothberg et al. |
| 9,085,798 B2 | 7/2015 | Chee |
| 9,175,340 B2 | 11/2015 | Liu et al. |
| 9,371,598 B2 | 6/2016 | Chee |
| 9,435,810 B2 | 9/2016 | Havranek et al. |
| 9,469,876 B2 | 10/2016 | Kuslich et al. |
| 9,476,095 B2 | 10/2016 | Vogelstein et al. |
| 9,528,984 B2 | 12/2016 | Mitra |
| 9,566,335 B1 | 2/2017 | Emili et al. |
| 9,574,189 B2 | 2/2017 | Franch et al. |
| 9,625,469 B2 | 4/2017 | Marcotte et al. |
| 9,777,315 B2 | 10/2017 | Fredriksson et al. |
| 9,835,626 B2 | 12/2017 | Schroit et al. |
| 9,958,448 B2 | 5/2018 | Halbert et al. |
| 10,011,868 B2 | 7/2018 | Liu et al. |
| 10,053,723 B2 | 8/2018 | Hindson et al. |
| 10,053,725 B2 | 8/2018 | Liu et al. |
| 10,174,361 B2 | 1/2019 | Skog et al. |
| 10,287,576 B2 | 5/2019 | Franch et al. |
| 10,288,608 B2 | 5/2019 | Kozlov et al. |
| 10,345,310 B2 | 7/2019 | Schroit et al. |
| 10,428,326 B2 | 10/2019 | Belhocine et al. |
| 10,465,183 B2 | 11/2019 | Skog et al. |
| 10,545,153 B2 | 1/2020 | Marcotte et al. |
| 10,590,407 B2 | 3/2020 | Nguyen et al. |
| 10,731,206 B2 | 8/2020 | Fredriksson et al. |
| 10,852,305 B2 | 12/2020 | Havranek et al. |
| 11,340,232 B2 | 5/2022 | Kozlov et al. |
| 11,513,126 B2 | 11/2022 | Chee et al. |
| 11,782,062 B2 | 10/2023 | Chee et al. |
| 11,959,922 B2 | 4/2024 | Chee et al. |
| 12,019,077 B2 | 6/2024 | Chee et al. |
| 12,019,078 B2 | 6/2024 | Chee et al. |
| 12,123,878 B2 | 10/2024 | Chee et al. |
| 12,130,291 B2 | 10/2024 | Chee et al. |
| 2002/0058273 A1 | 5/2002 | Shipwash |
| 2003/0087232 A1 | 5/2003 | Christians et al. |
| 2003/0138831 A1 | 7/2003 | Kwagh et al. |
| 2003/0143680 A1 | 7/2003 | Marliere |
| 2005/0003361 A1 | 1/2005 | Fredriksson |
| 2005/0084927 A1 | 4/2005 | Norioka et al. |
| 2005/0260653 A1 | 11/2005 | Labaer et al. |
| 2006/0172300 A1 | 8/2006 | Wolf et al. |
| 2006/0199279 A1 | 9/2006 | Lopez-Avila et al. |
| 2006/0259995 A1 | 11/2006 | Cayouette et al. |
| 2007/0020640 A1 | 1/2007 | Mccloskey et al. |
| 2007/0020669 A1 | 1/2007 | Ericsson |
| 2007/0218503 A1 | 9/2007 | Mitra |
| 2008/0107660 A1 | 5/2008 | Self |
| 2008/0305957 A1 | 12/2008 | Thisted et al. |
| 2009/0246879 A1 | 10/2009 | Drmanac et al. |
| 2009/0264300 A1 | 10/2009 | Franch et al. |
| 2010/0311114 A1 | 12/2010 | Eyckerman et al. |
| 2011/0245101 A1 | 10/2011 | Chee |
| 2011/0245111 A1 | 10/2011 | Chee |
| 2012/0245040 A1 | 9/2012 | Morgan et al. |
| 2012/0220494 A1 | 10/2012 | Samuels et al. |
| 2013/0052665 A1 | 2/2013 | Ling et al. |
| 2013/0059741 A1 | 3/2013 | Weiner |
| 2013/0288929 A1 | 10/2013 | Hansen et al. |
| 2014/0102915 A1 | 4/2014 | Hu et al. |
| 2014/0273004 A1 | 9/2014 | Havranek et al. |
| 2014/0349860 A1 | 11/2014 | Marcotte et al. |
| 2014/0378322 A1 | 12/2014 | Hindson et al. |
| 2015/0148239 A1 | 5/2015 | Peter et al. |
| 2015/0160204 A1 | 6/2015 | Mitra |
| 2015/0185199 A1 | 7/2015 | Joo et al. |
| 2015/0241440 A1 | 8/2015 | Fasan et al. |
| 2015/0315567 A1 | 11/2015 | Pedersen et al. |
| 2015/0376609 A1 | 12/2015 | Hindson et al. |
| 2015/0376700 A1 | 12/2015 | Schnall-levin et al. |
| 2016/0001248 A1 | 1/2016 | Fan et al. |
| 2016/0032379 A1 | 2/2016 | Gloeckner et al. |
| 2016/0054331 A1 | 2/2016 | Stoll et al. |
| 2016/0060687 A1 | 3/2016 | Zhu et al. |
| 2016/0083786 A1 | 3/2016 | Liu et al. |
| 2016/0122417 A1 | 5/2016 | Shusta et al. |
| 2016/0122753 A1 | 5/2016 | Mikkelsen et al. |
| 2016/0253584 A1 | 9/2016 | Fodor et al. |
| 2016/0279257 A1 | 9/2016 | Koussa et al. |
| 2016/0291007 A1* | 10/2016 | Kozlov ............ G01N 33/54306 |
| 2016/0319361 A1 | 11/2016 | Spetzler et al. |
| 2017/0052194 A1 | 2/2017 | Havranek et al. |
| 2017/0074855 A1 | 3/2017 | Morin et al. |
| 2017/0107566 A1 | 4/2017 | Church et al. |
| 2017/0166959 A1 | 6/2017 | Hashimoto et al. |
| 2017/0196818 A1 | 7/2017 | Shin et al. |
| 2017/0247688 A1 | 8/2017 | Franch et al. |
| 2018/0251825 A1 | 9/2018 | Stoeckius et al. |
| 2019/0145982 A1 | 5/2019 | Chee et al. |
| 2019/0219578 A1 | 7/2019 | Mitsuhashi |
| 2019/0301985 A1 | 10/2019 | Tao et al. |
| 2020/0348307 A1 | 11/2020 | Beierle et al. |
| 2020/0348308 A1 | 11/2020 | Chee et al. |
| 2021/0302431 A1 | 9/2021 | Chee et al. |
| 2021/0304839 A1 | 9/2021 | Patel et al. |
| 2021/0355483 A1 | 11/2021 | Chee et al. |
| 2021/0405058 A1 | 12/2021 | Chee et al. |
| 2023/0054691 A1 | 2/2023 | Chee et al. |

(56) References Cited

U.S. PATENT DOCUMENTS

| | | |
|---|---|---|
| 2023/0168254 A1 | 6/2023 | Chee et al. |
| 2024/0295563 A1 | 9/2024 | Chee et al. |
| 2024/0302381 A1 | 9/2024 | Chee et al. |
| 2024/0302382 A1 | 9/2024 | Chee et al. |
| 2024/0393344 A1 | 11/2024 | Chee et al. |

FOREIGN PATENT DOCUMENTS

| | | |
|---|---|---|
| EP | 2638057 | 9/2013 |
| EP | 2707381 | 3/2014 |
| EP | 2748335 | 7/2014 |
| EP | 2903597 | 8/2015 |
| EP | 3111212 | 1/2017 |
| JP | 2007/524105 | 8/2007 |
| JP | 2014/504880 | 2/2014 |
| JP | 2015/528283 | 9/2015 |
| WO | WO-1997/05900 | 2/1997 |
| WO | WO-2000/057183 | 9/2000 |
| WO | WO-2005/015239 | 2/2005 |
| WO | WO-2005/083431 A2 | 9/2005 |
| WO | WO-2005/083431 A3 | 10/2005 |
| WO | WO-2007/062664 | 6/2007 |
| WO | WO-2009/050261 A1 | 4/2009 |
| WO | WO-2009/050261 A9 | 6/2009 |
| WO | WO-2010/065322 | 6/2010 |
| WO | WO-2010/065531 | 6/2010 |
| WO | WO-2012/064993 | 5/2012 |
| WO | WO-2012/142213 | 10/2012 |
| WO | WO-2012/155014 | 11/2012 |
| WO | WO-2012/178023 | 12/2012 |
| WO | WO-2013/028788 | 2/2013 |
| WO | WO-2013/112745 | 8/2013 |
| WO | WO-2013/123442 | 8/2013 |
| WO | WO-2013/138510 | 9/2013 |
| WO | WO-2013/142389 | 9/2013 |
| WO | WO-2014/055775 | 4/2014 |
| WO | WO 2014/145123 | 9/2014 |
| WO | WO 2014/189768 | 11/2014 |
| WO | WO-2014/210225 | 12/2014 |
| WO | WO-2015/042506 | 3/2015 |
| WO | WO-2015/131153 | 9/2015 |
| WO | WO-2015/148606 | 10/2015 |
| WO | WO-2015/164212 A1 | 10/2015 |
| WO | WO-2015/166768 | 11/2015 |
| WO | WO-2016/019360 | 2/2016 |
| WO | WO-2016/061517 | 4/2016 |
| WO | WO-2016/130704 | 8/2016 |
| WO | WO-2016/138496 | 9/2016 |
| WO | WO-2016/145416 | 9/2016 |
| WO | WO-2015/164212 A9 | 10/2016 |
| WO | WO-2016/164530 | 10/2016 |
| WO | WO-2017/117358 | 7/2017 |
| WO | WO-2017/143006 | 8/2017 |
| WO | WO-2017/192633 | 11/2017 |
| WO | WO-2017/205719 | 11/2017 |
| WO | WO-2018/005720 | 1/2018 |
| WO | WO-2018/017914 | 1/2018 |
| WO | WO-2019/089836 | 5/2019 |

OTHER PUBLICATIONS

U.S. Appl. No. 18/660,053, filed May 9, 2024, by Chee et al. (Copy not submitted herewith pursuant to the waiver of 37 C.F.R. § 1.98(a)(2)(iii) issued by the Office on Sep. 21, 2004).

U.S. Appl. No. 18/659,813, filed May 9, 2024, by Chee et al. (Copy not submitted herewith pursuant to the waiver of 37 C.F.R. § 1.98(a)(2)(iii) issued by the Office on Sep. 21, 2004).

U.S. Appl. No. 18/659,334, filed May 9, 2024, by Chee et al. (Copy not submitted herewith pursuant to the waiver of 37 C.F.R. § 1.98(a)(2)(iii) issued by the Office on Sep. 21, 2004).

U.S. Appl. No. 18/800,910, filed Aug. 12, 2024, by Chee et al. (Copy not submitted herewith pursuant to the waiver of 37 C.F.R. § 1.98(a)(2)(iii) issued by the Office on Sep. 21, 2004).

Akbani, R. et al. (Jul. 2014, e-pub. Apr. 28, 2014). "Realizing The Promise Of Reverse Phase Protein Arrays For Clinical, Translational, And Basic Research: A Workshop Report: The RPPA (Reverse Phase Protein Array) Society," Molecular & Cellular Proteomics MCP 13(7):1625-1643.

Alfaro, J. A. et al. (Jun. 2021, e-pub. Jun. 7, 2022). "The Emerging Landscape Of Single-Molecule Protein Sequencing Technologies," Nature Methods 18(6):604-617.

Ames, T.D. et al. (Jan./Feb. 2011). "Bacterial Aptamers That Selectively Bind Glutamine," RNA Biology 8:82-89.

Amini, S. et al. (Dec. 2014). "Haplotype-Resolved Whole-Genome Sequencing By Contiguity Preserving Transposition And Combinatorial Indexing," Nature Genetics 46(12):1343-1349, 21 pages.

Assadi, M. et al. (Sep. 2013, e-pub. May 7, 2013). "Multiple Protein Analysis Of Formalin-Fixed And Paraffin-Embedded Tissue Samples With Reverse Phase Protein Arrays," Molecular & Cellular Proteomics: MCP 12(9):2615-2622.

Bailey, J. M. et al. (Mar. 27, 1990). "Carboxy-Terminal Sequencing: Formation And Hydrolysis Of C-Terminal Peptidylthiohydantoins," Biochemistry 29(12):3145-3156.

Ballester, L.Y. et al. (2016, e-pub. Jan. 18, 2016). "Advances In Clinical Next-Generation Sequencing: Target Enrichment And Sequencing Technologies," Expert Review Of Molecular Diagnostics 16(3):357-372.

Bandara, H.M.D. et al. (2009, e-pub Jul. 27, 2009). "Photoinduced Release Of Zn2+ With Zincleav-1: A Nitrobenzyl-Based Caged Complex," Inorganic Chemistry 48(17):8445-8555.

Bandara, H.M.D. et al. (Mar. 28, 2011, e-pub Mar. 1, 2011). "A Second-Generation Photocage For Zn2+ Inspired By TPEN: Characterization And Insight Into The Uncaging Quantum Yields Of Zincleav Chelators," Chemistry 17(14):3932-3941.

Banta, S. et al. (2013, e-pub. Apr. 29, 2013). "Replacing Antibodies: Engineering New Binding Proteins," Annu. Rev. Biomed. Eng. 15:93-113.

Barrett, G.C. et al. (1985). "Edman Stepwise Degradation of Polypeptides: A New Strategy Employing Mild Basic Cleavage Conditions," Tetrahedron Lett. 26(36):4375-4378.

Basle, E. et al. (Mar. 26, 2010). "Protein Chemical Modification On Endogenous Amino Acids," Chem Biol 17(3):213-227.

Bell, J.C. et al. (Sep. 18, 2015). "Imaging And Energetics Of Single SSB-ssDNA Molecules Reveal Intramolecular Condensation And Insight Into RecOR Function," Elife. 4:e08646, 21 pages.

Bell, J.C. et al. (Nov. 8, 2012, e-pub. Oct. 24, 2012). "Direct Imaging Of RecA Nucleation And Growth On Single Molecules Of SSB-Coated ssDNA," Nature 491(7423):274-278.

Ben-Meir, D. et al. (Feb. 15, 1993). "Specificity Of Streptomyces Griseus Aminopeptidase And Modulation Of Activity By Divalent Metal Ion Binding And Substitution," European Journal Of Biochemistry 212(1):107-112.

Bilgicer, B. et al. (Jul. 8, 2009). "A Non-Chromatographic Method For The Purification Of A Bivalently Active Monoclonal IgG Antibody From Biological Fluids," J Am Chem Soc 131(26):9361-9367.

Bochman, M. L. et al. (Nov. 2012, e-pub. Oct. 3, 2012). "DNA Secondary Structures: Stability And Function Of G-Quadruplex Structures," Nat Rev Genet 13(11):770-780, 25 pages.

Bodi, K. et al. (Jul. 2013). "Comparison Of Commercially Available Target Enrichment Methods For Next-Generation Sequencing," Journal Of Biomolecular Techniques: JBT 24(2):73-86.

Borgo, B. et al. (Mar. 2014, e-pub. Feb. 4, 2014). "Motif-Directed Redesign Of Enzyme Specificity," Protein Sci 23(3):312-320.

Boyd et al., "Measurement and Clinical Monitoring of Human Lymphocyte Clonality by Massively Parallel V-D-J Pyrosequencing," Science Translational Medicine (Dec. 2009) 1(12):12ra23, 8 pages.

Brouzes, E. et al. (Aug. 25, 2009, e-pub. Jul. 15, 2009). "Droplet Microfluidic Technology For Single-Cell High-Throughput Screening," Proc Natl Acad Sci USA 106(34):14195-14200.

Brudno, Y. et al. (Feb. 2010, e-pub. Dec. 27, 2009). "An In Vitro Translation, Selection And Amplification System For Peptide Nucleic Acids," Nat Chem Biol 6(2):148-155, 23 pages.

(56) References Cited

OTHER PUBLICATIONS

Buschmann, T. et al. (Sep. 11, 2013). "Levenshtein Error-Correcting Barcodes For Multiplexed DNA Sequencing," BMC Bioinformatics 14(272):1-10.

Calcagno, S. et al. (Aug. 2016, e-pub. Mar. 29, 2016). "N-Terminal Methionine Processing By The Zinc-Activated Plasmodium Falciparum Methionine Aminopeptidase 1b," Appl Microbiol Biotechnol 100(16):7091-7102.

Camarero, J.A. et al. (Nov. 17, 2004, e-pub. Oct. 23, 2004). "Chemoselective Attachment Of Biologically Active Proteins To Surfaces By Expressed Protein Ligation And Its Application For "Protein Chip" Fabrication," Journal Of The American Chemical Society 126(45):14730-14731.

Cao, Y. et al. (Dec. 18, 2015). "Butelase-Mediated Synthesis Of Protein Thioesters And Its Application For Tandem Chemoenzymatic Ligation," Chem Commun (Camb) 51(97):17289-17292.

Carty, R.P. et al. (Oct. 25, 1968). "Modification Of Bovine Pancreatic Ribonuclease A With 4-Sulfonyloxy-2-Nitrofluorobenzene. Isolation And Identification Of Modified Proteins," J Biol Chem 243(20):5244-5253.

Cazalis, C.S. et al. (Sep./Oct. 2004). "C-Terminal Site-Specific PEGylation Of A Truncated Thrombomodulin Mutant With Retention Of Full Bioactivity," Bioconjugate Chemistry 15(5):1005-1009.

Champoux, J. J. (2001). "DNA Topoisomerases: Structure, Function, And Mechanism," Annual Review Of Biochemistry 70:369-413.

Chan, A. et al. (Jun. 2015, e-pub. Feb. 24, 2015). "Novel Selection Methods For DNA-Encoded Chemical Libraries," Current Opinion In Chemical Biology 26:55-61.

Chan, L. et al. (Nov. 14, 2007). "Covalent Attachment Of Proteins To Solid Supports And Surfaces Via Sortase-Mediated Ligation," PLoS One 2(11):e1164, 5pgs.

Chang, L. et al. (Apr. 30, 2012, e-pub. Feb. 20, 2012). "Single Molecule Enzyme-Linked Immunosorbent Assays: Theoretical Considerations," J Immunol Methods 378(1-2):102-115.

Chang, Y.Y. et al. (Mar. 2, 2015). "Structural Basis For Substrate-Specific Acetylation Of Nalpha-Acetyltransferase Ard1 From Sulfolobus Solfataricus," Sci Rep. 5:8673, 1-9 pages.

Chen, D. et al. (Apr. 1, 2017, e-pub. Jan. 9, 2017). "Selective N-Terminal Functionalization Of Native Peptides And Proteins," Chemical Science 8(4):2717-2722.

Chen et al., "Post-translational Modifications of the Protein Termini," Front Cell Dev Biol. (Jul. 2021) 9:719590, 14 pages.

Christoforou, A. et al. (Jan. 12, 2016). "A Draft Map Of The Mouse Pluripotent Stem Cell Spatial Proteome," Nat Commun 7:8992, 1-12 pages.

Colas, P. (Feb. 2000). "Combinatorial Protein Reagents To Manipulate Protein Function," Current Opinion In Chemical Biology 4(1):54-59.

Creighton, C. J. et al. (Jul. 7, 2015). "Reverse Phase Protein Arrays In Signaling Pathways: A Data Integration Perspective," Drug Des Devel Ther. 5(9):3519-3527.

Crosetto, N. et al. (Jan. 2015, e-pub. Dec. 2, 2014). "Spatially Resolved Transcriptomics And Beyond," Nat Rev Genet. 16(1):57-66.

Cusanovich, D.A. et al. (May 22, 2015, e-pub. May 7, 2015). "Multiplex Single-Cell Profiling Of Chromatin Accessibility By Combinatorial Cellular Indexing," Science 348(6237):910-914.

Davidson, G.R. et al. (2011). "Positional Proteomics At The N-Terminus As A Means Of Proteome Simplification," Methods In Molecular Biology 753:229-242.

Decreau, R.A. et al. (Apr. 13, 2007, e-pub. Mar. 22, 2007). "Syntheses Of Hemoprotein Models That Can Be Covalently Attached Onto Electrode Surfaces By Click Chemistry," The Journal Of Organic Chemistry 72(8):2794-2802.

Derrington, I.M. et al. (Sep. 14, 2010, e-pub. Aug. 26, 2010). "Nanopore DNA Sequencing with MspA," Proc Natl Acad Sci USA 107(37):16060-16065.

Dragulescu-Andrasi, A. et al. (Aug. 9, 2006). "A Simple Gamma-Backbone Modification Preorganizes Peptide Nucleic Acid Into A Helical Structure," Journal of the American Chemical Society 128(31):10258-10267.

Drmanac, R. et al. (Jan. 1, 2010, e-pub. Nov. 5, 2009). "Human Genome Sequencing Using Unchained Base Reads On Self-Assembling DNA Nanoarrays," Science 327(5961):78-81.

Du, Z. et al. (Jul. 2003). "Amplification Of High-Quantity Serial Analysis Of Gene Expression Ditags And Improvement Of Concatemer Cloning Efficiency," BioTechniques 35(1):66-72.

El-Sagheer, A. H. et al. (Jul. 12, 2011, e-pub. Jun. 27, 2011). "Biocompatible Artificial DNA Linker That Is Read Through By DNA Polymerases And Is Functional In *Escherichia coli*," Proc Natl Acad Sci USA 108(28):11338-11343.

El-Sagheer, A. H. et al. (Jan. 7, 2011, e-pub. Nov. 11, 2010). "Rapid Chemical Ligation Of Oligonucleotides By The Diels-Alder Reaction," Org Biomol Chem 9(1):232-235.

Erde, J. et al. (Apr. 4, 2014, e-pub. Mar. 6, 2014). "Enhanced FASP (eFASP) To Increase Proteome Coverage And Sample Recovery For Quantitative Proteomic Experiments," J Proteome Res 13(4):1885-1895.

Eriquez, L.A. et al. (Nov. 1980). "Aminopeptidases Highly Specific For Glutamyl Residues From Neisseria Meningitidis And Moraxella Urethralis," Journal Of Clinical Microbiology 12(5):667-671.

Extended European Search Report For European Patent Application EP17793198.7, mailed Nov. 7, 2019, 11 Pages.

Extended European Search Report for European Patent Application 18874783.6, mailed Sep. 24, 2021, 8 pages.

Famulok, M. et al. (Mar. 1, 1994). "Molecular Recognition of Amino Acids by RNA-Aptamers: An L-Citrulline Binding RNA Motif and Its Evolution into an L-Arginine Binder," J. Am. Chem. Soc. 116(5):1698-1706.

Fan, C.H. et al. (Feb. 6, 2015). "Combinatorial Labeling Of Single Cells For Gene Expression Cytometry," Science 347(6222):1258367, 10 pages.

Farries, T.C. et al. (Mar. 28, 1991). "Removal Of N-Acetyl Groups From Blocked Peptides With Acylpeptide Hydrolase. Stabilization Of The Enzyme And Its Application To Protein Sequencing," Eur J Biochem 196(3):679-685.

Feist, P. et al. (Feb. 5, 2015). "Proteomic Challenges: Sample Preparation Techniques For Microgram-Quantity Protein Analysis From Biological Samples," Int J Mol Sci 16(2):3537-3563.

Fernandez-Gacio, A. et al. (Sep. 2003). "Phage Display As A Tool For The Directed Evolution Of Enzymes," Trends In Biotechnology 21(9):408-414.

Fowler, E. et al. (May 2001). "Removal Of N-Terminal Blocking Groups From Proteins," Current Protocols In Protein Science Chapter 11:11.1-11.17.

Friedmann, D.R. et al. (Nov. 2013, e-pub. Jun. 28, 2013). "Structure And Mechanism Of Non-Histone Protein Acetyltransferase Enzymes," Febs J 280(22):5570-5581.

Frokjaer, S et al. (Apr. 2005). "Protein Drug Stability: A Formulation Challenge," Nat. Rev. Drug. Discov. 4(4):298-306.

Fujii, Y. et al. (Mar. 2014, e-pub. Jan. 28, 2014). "PA Tag: A Versatile Protein Tagging System Using A Super High Affinity Antibody Against A Dodecapeptide Derived From Human Podoplanin," Protein Expr Purif 95:240-247.

Gabrys, R. et al. (Jun. 2, 2015). "Asymmetric Lee Distance Codes for DNA-based Storage," IEEE Symposium on Information Theory (ISIT) 63(8):4982-4995, 19 pages.

Gamper, H.B. et al. (Jun. 6, 2006). "Unrestricted Hybridization of Oligonucleotides to Structure-free DNA," Biochemistry 45(22):6978-6986.

Gebauer, M. et al. (2012). "Anticalins: Small Engineered Binding Proteins Based On The Lipocalin Scaffold," Methods Enzymol 503:157-188.

Genshaft, A.S. et al. (Sep. 19, 2016). "Multiplexed, Targeted Profiling Of Single-Cell Proteomes And Transcriptomes In A Single Reaction," Genome Biol. 17(1):188, 1-15 pages.

Gerry, N. P. et al. (Sep. 17, 1999). "Universal DNA Microarray Method For Multiplex Detection Of Low Abundance Point Mutations," J Mol Biol 292(2):251-262.

(56) References Cited

OTHER PUBLICATIONS

Girish, A. et al. (May 16, 2005). "Site-Specific Immobilization Of Proteins In A Microarray Using Intein-Mediated Protein Splicing," Bioorg. Med. Chem. Lett. 15(10):2447-2451.

Gogliettino, M. et al. (2012, e-pub. May 24, 2012). "Identification And Characterization Of A Novel Acylpeptide Hydrolase From Sulfolobus Solfataricus: Structural And Functional Insights," PLoS One 7(5): e37921, 13 pages.

Gogliettino, M. et al. (Jan. 2014, e-pub. Dec. 10, 2013). "A Novel Class Of Bifunctional Acylpeptide Hydrolases—Potential Role In The Antioxidant Defense Systems Of The Antarctic Fish Trematomus Bernacchii," Febs J 281(1):401-415.

Gold, L. et al. (1995). "Diversity Of Oligonucleotide Functions," Annu. Rev. Biochem. 64:763-797.

Granvogl, B. et al. (Oct. 2007, e-pub. Jul. 17, 2007). "Sample Preparation By In-Gel Digestion For Mass Spectrometry-Based Proteomics," Anal Bioanal Chem 389(4):991-1002.

Groll, J. et al. (Mar./Apr. 2005) "Comparison Of Coatings From Reactive Star Shaped PEG-Stat-PPG Prepolymers And Grafted Linear PEG For Biological And Medical Applications," Biomacromolecules 6(2):956-962.

Groll, J. et al. (2010). "Star Polymer Surface Passivation For Single-Molecule Detection," Methods Enzymol. 472:1-18.

Gu et al., "Multiplex single-molecule interaction profiling of DNA-barcoded proteins," Nature (2014) 515(7528):554-557.

Gunderson, K.L. et al. (Nov. 1998). "Mutation Detection By Ligation To Complete N-Mer DNA Arrays," Genome Res 8(11):1142-1153.

Gunderson, K.L. et al. (May 2004, e-pub. Apr. 12, 2004). "Decoding Randomly Ordered DNA Arrays," Genome Res. 14(5):870-877.

Guo, H. et al. (Sep. 24, 2012). "An Efficient Procedure For Protein Extraction From Formalin-Fixed, Paraffin-Embedded Tissues For Reverse Phase Protein Arrays," Proteome Sci 10(1):56, 1-12 pages.

Gupta, A. et al. (Mar. 21, 2016). "Nanoemulsions: Formation, Properties And Applications," Soft Matter. 12(11):2826-2841.

Halpin, D.R. et al. (Jul. 2004, e-pub. Jun. 22, 2004). "DNA Display III. Solid-Phase Organic Synthesis on Unprotected DNA," PLoS Biol 2(7):e175, 1031-1038.

Hamada, Y. (Apr. 1, 2016, e-pub. Feb. 21, 2016). "A Novel N-Terminal Degradation Reaction Of Peptides Via N-Amidination," Bioorg Med Chem Lett 26(7):1690-1695.

Harris, T.D. et al. (Apr. 4, 2008). "Single-Molecule DNA Sequencing of a Viral Genome," Science 320(5872):106-109.

Hennessy, B.T. et al. (Dec. 2010). "A Technical Assessment of the Utility of Reverse Phase Protein Arrays for the Study of the Functional Proteome in Non-microdissected Human Breast Cancers," Clinical Proteomics 6(4):129-151.

Hernandez-Moreno, A.V. et al. (2014). "Kinetics And Conformational Stability Studies Of Recombinant Leucine Aminopeptidase," Int J Biol Macromol 64: 306-312.

Ho, B. et al. (Feb. 28, 2018, e-pub. Jan. 17, 2018). "Unification of Protein Abundance Datasets Yields a Quantitative *Saccharomyces cerevisiae* Proteome," Cell Syst. 6(2):192-205, 18 pages.

Hori, M. et al. (2007). "Uniform Amplification Of Multiple DNAs By Emulsion PCR," Biochem Biophys Res Commun 352(2): 323-328.

Horisawa, K. (2014). "Specific And Quantitative Labeling Of Biomolecules Using Click Chemistry," Front Physiol 5(457):1-6.

Hoshika, D. et al. (2010). "Artificial Genetic Systems: Self-Avoiding DNA In PCR And Multiplexed PCR," Angewandte Chemie (International ed. in English) 49(32):5554-5557.

Hua, B. et al. (2014). "An Improved Surface Passivation Method For Single-Molecule Studies," Nat. Methods 11(12):1233-1236, 13 pages.

Huang, J. et al. (2014). "Enrichment And Separation Techniques For Large-Scale Proteomics Analysis Of The Protein Post-Translational Modifications," J. Chromato. 1372:1-17.

Hughes, A.J. et al. (2014). "Single-Cell Western Blotting." Nat Methods 11(7): 749-755.

Hughes, C.S. et al. (2014). "Ultrasensitive Proteome Analysis Using Paramagnetic Bead Technology," Mol Syst Biol 10(75):1-14.

International Preliminary Report On Patentability For International Patent Application PCT/US2017/30702, issue date of May 16, 2018, filed May 2, 2017, 95 Pages.

International Preliminary Report on Patentability for International Application PCT/US2018/058565, issue date of May 5, 2020, filed Oct. 31, 2018, 26 pages.

International Preliminary Report on Patentability for International Application PCT/US2018/058575, issue date of May 5, 2020, filed Oct. 31, 2018, 8 pages.

International Preliminary Report on Patentability for International Application PCT/US2018/058583, issue date of May 5, 2020, filed Oct. 31, 2018, 9 pages.

International Search Report and Written Opinion for International Application PCT/US2018/058565, mailed Jan. 29, 2019, filed Oct. 31, 2018, 30 pages.

International Search Report and Written Opinion For International Application PCT/US2018/058575, mailed Apr. 15, 2019, filed Oct. 31, 2018, 13 pages.

International Search Report and Written Opinion for International Application PCT/US2018/058583, mailed Jan. 22, 2019, filed Oct. 31, 2018, 12 pages.

International Search Report and Written Opinion for International Application PCT/US2017/030702, mailed Sep. 8, 2017, filed May 2, 2017, 17 pages.

Jayasena, S.D. (1999). "Aptamers: An Emerging Class Of Molecules That Rival Antibodies In Diagnostics," Clin Chem 45(9):1628-1650.

Kalia, J. et al. (2007). "General Method For Site-Specific Protein Immobilization By Staudinger Ligation," Bioconjug. Chem. 18:1064-1069.

Kang, C.C. et al. (2016). "Single Cell-Resolution Western Blotting," Nat Protoc 11(8):1508-1530.

Kang, T.S. et al. (2010). "Converting An Injectable Protein Therapeutic Into An Oral Form: Phenylalanine Ammonia Lyase For Phenylketonuria," Mol Genet Metab 99(1): 4-9, 14 pages.

Katritzky, A. R. et al. (2005). "Recent Developments In Guanylating Agents," Arkivoc (IV):49-87.

Kiah, H.M. et al. (2015). "Codes For DNA Sequence Profiles," IEEE International Symposium on Information Theory (ISIT) 62(6):3125-3146, 5 pages.

Kishor, N. et al. (2015). "Direct N-Terminal Sequencing Of Polypeptides Using A Thermostable Bacterial Aminopeptidase And MALDI-TOF Mass Spectrometry," Anal. Biochem. 488:6-8.

Klein, A.M. et al. (2015). "Droplet Barcoding For Single-Cell Transcriptomics Applied To Embryonic Stem Cells," Cell 161(5):1187-1201.

Klein et al., "Methionine aminopeptidase 2 and its autoproteolysis product have different binding sites on the ribosome," Nat Commun. (Jan. 2024) 15(1):716, 10 pages.

Knall, A-C. et al. (2014). "Kinetic Studies Of Inverse Electron Demand Diels-Alder Reactions (Iedda) Of Norbornenes And 3,6-Dipyridin-2-Yl-1,2,4,5-Tetrazine," Tetrahedron Lett 55(34):4763-4766.

Kodal, A.L.B. et al. (2016). "DNA-Templated Introduction of an Aldehyde Handle in Proteins," ChemBioChem 17:1338-1342.

Korlach, J. et al. (2008). "Selective Aluminum Passivation For Targeted Immobilization Of Single DNA Polymerase Molecules In Zero-Mode Waveguide Nanostructures," Proc. Natl. Acad. Sci. 105:1176-1181.

Krishna, R.G. et al. (1991). "N-Terminal Sequence Analysis Of N Alpha-Acetylated Proteins After Unblocking With N-Acylaminoacyl-Peptide Hydrolase," Anal. Biochem. 199:45-50.

Kusser, W. et al. (2000). "Chemically Modified Nucleic Acid Aptamers For In Vitro Selections: Evolving Evolution," J. Biotechnol 74: 27-38.

Lahoud, G. et al. (2008). "Enzymatic Synthesis Of Structure-Free DNA With Pseudo-Complementary Properties," Nucleic Acids Res. 36(10):3409-3419.

Laszlo, A.H. et al. (2014). "Decoding Long Nanopore Sequencing Reads Of Natural DNA," Nat. Biotechnol. 32(8):829-833.

(56) References Cited

OTHER PUBLICATIONS

Laure, C. et al. (2016). "Coding in 2D: Using Intentional Dispersity to Enhance the Information Capacity of Sequence-Coded Polymer Barcodes," Angew. Chem. Int. Ed. 55(36):10722-10725.
Le, Z.G. et al. (2005). "Organic Reactions in Ionic Liquids: Ionic Liquid-promoted Efficient Synthesis of Disubstituted and Trisubstituted Thioureas Derivatives," Chinese Chemical Letters 16(2): 201-204.
Lesch, V. et al. (2015). "Peptides In The Presence Of Aqueous Ionic Liquids: Tunable Co-Solutes As Denaturants Or Protectants?" Phys Chem Phys 17(39): 26049-26053.
Li, G. et al. (2013). "Photoaffinity Labeling Of Small-Molecule-Binding Proteins By DNA-Templated Chemistry," Angew Chem Int Ed Engl 52(36): 9544-9549.
Li, G. et al. (2014). "Multivalent Photoaffinity Probe For Labeling Small Molecule Binding Proteins," Bioconjug Chem. 25(6):1172-1180.
Li, L. et al. (Jan. 2014). "Structural Analysis and Optimization of the Covalent Association between SpyCatcher and a Peptide Tag," J Mol Biol. 426(2):309-317, 15 pages.
Liao, Y-D. et al. (2004). "Removal Of N-Terminal Methionine From Recombinant Proteins By Engineered *E. coli* Methionine Aminopeptidase," Prot. Sci. 13:1802-1810.
Liebscher, S. et al. (2014). "N-Terminal Protein Modification By Substrate-Activated Reverse Proteolysis," Angew Chem Int Ed Engl 53:3024-3028.
Litovchick, A. et al. (2014). "Universal Strategies For The DNA-Encoding Of Libraries Of Small Molecules Using The Chemical Ligation Of Oligonucleotide Tags," Artif DNA PNA XNA 5(1):e27896-1-e27896-11.
Liu, Y. et al. (2001). "Chemical Carboxyl-Terminal Sequence Analysis Of Peptides And Proteins Using Tribenzylsilyl Isothiocyanate," J Protein Chem 20(7): 535-541.
Los, G.V. et al. (2008). "HaloTag: A Novel Protein Labeling Technology for Cell Imaging and Protein Analysis," ACS Chem. Biol. 3(6):373-382.
Lu, K. et al. (2010). "Chemical Strategies For The Synthesis Of Peptide-Oligonucleotide Conjugates," Bioconjug. Chem. 21(2):187-202.
Lund, V. et al. (Nov. 25, 1988). "Assessment Of Methods For Covalent Binding Of Nucleic Acids To Magnetic Beads, Dynabeads, And The Characteristics Of The Bound Nucleic Acids In Hybridization Reaction," Nucleic Acids Research 16(22):10861-10880.
Lutz, J. F. (2015). "Coding Macromolecules: Inputting Information in Polymers Using Monomer-Based Alphabets," Macromolecules 48:4759-4767.
Macosko, E.Z. et al. (May 21, 2015). "Highly Parallel Genome-Wide Expression Profiling of Individual Cells Using Nanoliter Droplets," Cell 161:1202-1214.
Mamanova, L. et al. (2010). "Target-Enrichment Strategies For Next-Generation Sequencing," Nature Methods 7(2):111-118.
Mannironi, C. et al. (2000). "Molecular Recognition Of Amino Acids By RNA Aptamers: The Evolution Into An L-Tyrosine Binder Of A Dopamine-Binding RNA Motif," RNA 6:520-527.
Marx, V. (2015). "Mapping Proteins With Spatial Proteomics," Nat Methods 12(9):815-819.
Mashaghi, S. et al. (2015). "External Control Of Reactions In Microdroplets," Sci Rep 5(11837):1-8.
Maynard, J. et al. (2000). "Antibody Engineering," Annu Rev Biomed Eng 2:339-376.
McCormick, R.M. et al. (1989). "A Solid-Phase Extraction Procedure For DNA Purification," Anal Biochem 181(1): 66-74.
McGregor, L.M. et al. (2014). "Identification of Ligand-Target Pairs from Combined Libraries of Small Molecules and Unpurified Protein Targets in Cell Lysates," Journal of The American Chemical Society 136:3264-3270.
McKay, C.S. et al. (Sep. 18, 2014). "Click Chemistry in Complex Mixtures: Bioorthogonal Bioconjugation," Chemistry & Biology 21:1015-1101.
Melkko, S. et al. (Jun. 2007). "Lead Discovery By DNA-Encoded Chemical Libraries," Drug Discovery Today 12 (11/12):465-471, 7 pages.
Mendoza, V.L. et al. (2009). "Probing Protein Structure By Amino Acid-Specific Covalent Labeling And Mass Spectrometry," Mass Spectrom Rev 28(5): 785-815.
Mertes, F. et al. (2011). "Targeted Enrichment Of Genomic DNA Regions For Next-Generation Sequencing," Brief Funct. Genomics 10(6):374-386.
Mikami, T. et al. (2012). "N (alpha) Selective Acetylation of Peptides," Mass Spectrom 1(2): A0010, 1-3.
Moghaddam, M.J. et al. (2012). "Chelating DTPA Amphiphiles: Ion-Tunable Self-Assembly Structures And Gadolinium Complexes," Phys Chem Phys 14(37):12854-12862.
Molina et al., "The Ras/Raf/MAPK pathway," J Thorac Oncol (2006) 1(1):7-9.
Muecke, M. et al. (2008). "Preparation of Multimilligram Quantities of Large, Linear DNA Molecules for Structural Studies," Structure 16:837-841.
Mukherjee et al. (2015). "A New Versatile Immobilization Tag Based on the Ultra High Affinity and Reversibility of the Calmodulin-Calmodulin Binding Peptide Interaction," J Mol Biol 427(16): 2707-2725.
Naganathan, S. et al. (Jan. 27, 2015, e-pub. Jan. 8, 2015). "Multiplex Detection Of Functional G Protein-Coupled Receptors Harboring Site-Specifically Modified Unnatural Amino Acids," Biochemistry 54(3):776-786.
Namimatsu, S. et al. (2005). "Reversing The Effects Of Formalin Fixation With Citraconic Anhydride And Heat: A Universal Antigen Retrieval Method," J Histochem Cytochem 53(1): 3-11.
Nguyen, G.K.T. et al. (2014). "Butelase 1 Is An Asx-Specific Ligase Enabling Peptide Macrocyclization And Synthesis," Nat Chem Biol 10(9): 732-738.
Nguyen, G.K.T. et al. (2015). "Butelase 1: A Versatile Ligase for Peptide and Protein Macrocyclization," J Am Chem Soc. 137(49):15398-15401.
Nguyen, G.K.T. et al. (2015). "Site-Specific N-Terminal Labeling of Peptides and Proteins Using Butelase 1 and Thiodepsipeptide," Angew Chem Int Ed Engl 54(52):15694-15698.
Nguyen, G.K.T. et al. (2016). "Butelase-Mediated Cyclization And Ligation Of Peptides And Proteins," Nat Protoc. 11(10):1977-1988.
Nilsson, M. et al. (1994). "Padlock Probes: Circularizing Oligonucleotides For Localized DNA Detection," Science 265:2085-2088.
Nishikawa, T. et al. (2012). "Directed Evolution of Proteins Through In Vitro Protein Synthesis in Liposomes" J Nucleic Acids. 2012(923214):1-11.
Nishizuka, S.S. et al. (2016). "New Era Of Integrated Cancer Biomarker Discovery Using Reverse-Phase Protein Arrays," Druq Metab Pharmacokinet 31(1): 35-45.
Niu, J. et al. (2013). "Enzyme-Free Translation Of DNA Into Sequence-Defined Synthetic Polymers Structurally Unrelated To Nucleic Acids," Nat. Chem. 5(4):282-292.
Ohkubo, A. et al. (2008). "'Protected DNA Probes' Capable Of Strong Hybridization Without Removal Of Base Protecting Groups," Nucleic Acids Res 36(6):1952-1964.
Ohshiro, T. et al. (2012). "Single-Molecule Electrical Random Resequencing Of DNA And RNA," Sci Rep 2(501):1-7.
Ojha, B. et al. (2010). "2-Alkylmalonic Acid: Amphiphilic Chelator And A Potent Inhibitor Of Metalloenzyme," J Phys Chem B 114(33):10835-10842.
Pan, H. et al. (2015). "A Simple Procedure To Improve The Surface Passivation For Single Molecule Fluorescence Studies," Phys. Biol. 12(045006):8 pages.
Park, J. et al. (2016). "Investigation of Specific Binding Proteins to Photoaffinity Linkers for Efficient Deconvolution of Target Protein," ACS Chem Biol. 11(1):44-52.
Parthasarathy, R. et al. (2007). "Sortase A as a Novel Molecular "Stapler" for Sequence-Specific Protein Conjugation," Bioconjugate Chem. 18(2):469-476.
Patel, D.J. et al. (2000). "Structure, Recognition And Discrimination In RNA Aptamer Complexes With Cofactors, Amino Acids, Drugs And Aminoglycoside Antibiotics," J. Biotech. 74:39-60.

(56) References Cited

OTHER PUBLICATIONS

Peng, X. et al. (2010). "A Template-Mediated Click-Click Reaction: PNA-DNA, PNA-PNA (or Peptide) Ligation, and Single Nucleotide Discrimination," European J Org Chem (22): 4194-4197, 12 pages.
Perbandt, M. et al. (2007). "High Resolution Structure Of Streptavidin In Complex With A Novel High Affinity Peptide Tag Mimicking The Biotin Binding Motif," Proteins 67(4):1147-1153.
Ponsard, I. et al. (2001), "Selection of Metalloenzymes by Catalytic Activity Using Phage Display and Catalytic Elution," Chembiochem. 2(4):253-259.
Prabakaran, S. et al. (2012). "Post-Translational Modification: Nature's Escape From Genetic Imprisonment And The Basis For Dynamic Information Encoding," Wiley Interdiscip Rev Syst Biol Med 4(6):565-583.
Rauth, S. et al. (2016). "High-Affinity Anticalins With Aggregation-Blocking Activity Directed Against The Alzheimer Beta-Amyloid Peptide," Biochem J 473(11):1563-1578.
Ray, A. et al. (2000). "Peptide Nucleic Acid (PNA): Its Medical And Biotechnical Applications And Promise For The Future," FASEB J 14(9):1041-1060.
Response to Extended European Search Report for EP Application 18874783.6, dated Apr. 13, 2022, 10 pages.
Riley, N.M. et al. (2016). "Proteomics Moves Into The Fast Lane," Cell Svst 2(3): 142-143.
Roloff, A. et al. (2013). "The Role Of Reactivity In DNA Templated Native Chemical PNA Ligation During PCR," Bioorg Med Chem 21(12):3458-3464.
Roloff, A. et al. (2014). "DNA-Templated Native Chemical Ligation Of Functionalized Peptide Nucleic Acids: A Versatile Tool For Single Base-Specific Detection Of Nucleic Acids," Methods Mol Biol 1050:131-141.
Rosen, C.B. et al. (2014). "Template-Directed Covalent Conjugation Of DNA To Native Antibodies, Transferring And Other Metal-Binding Proteins," Nature Chemistry 6:804-809.
Rothberg et al., "The development and impact of 454 sequencing," Nat Biotechnol (Oct. 2008) 26(10):1117-24.
Roy, R.K. et al. (2015). "Design And Synthesis Of Digitally Encoded Polymers That Can Be Decoded And Erased," Nat. Commun. 6(7237):1-8.
Ryckelynck, M. et al. (2015). "Using Droplet-Based Microfluidics To Improve The Catalytic Properties Of RNA Under Multiple-Turnover Conditions," RNA 21(3):458-469.
Sakurai, K. et al. (2005). "DNA-Templated Functional Group Transformations Enable Sequence-Programmed Synthesis Using Small-Molecule Reagents," J Am Chem Soc 127(6): 1660-1661.
Schneider, K. et al. (1995). "Increased Stability Of Nucleic Acids Containing 7-Deaza-Guanosine And 7-Deaza-Adenosine May Enable Rapid DNA Sequencing By Matrix-Assisted Laser Desorption Mass Spectrometry," Nucleic Acids Res 23(9): 1570-1575.
Schutze, T. et al. (2011). "A Streamlined Protocol For Emulsion Polymerase Chain Reaction And Subsequent Purification," Anal Biochem. 410(1):155-157.
Selvaraj, R. et al. (2013). "Trans-Cyclooctene-A Stable, Voracious Dienophile For Bioorthogonal Labeling," Curr Opin Chem Biol 17(5): 753-760.
Seo, J. et al. (Jan. 2004). "Post-Translational Modifications and Their Biological Functions: Proteomic Analysis and Systematic Approaches," Biochemistry and Molecular Biology 37(1):35-44.
Service, R.F. (2006). "Gene Sequencing. The Race For The $1000 Genome," Science 311(5767):1544-1546.
Shagin, D.A. et al. (2002). "A Novel Method For SNP Detection Using A New Duplex-Specific Nuclease From Crab Hepatopancreas," Genome Res. 12:1935-1942.
Sharma, A.K. et al. (2012). "Enzyme-Linked Small-Molecule Detection Using Split Aptamer Ligation," Anal Chem 84(14): 6104-6109.
Shembekar, N. et al. (2016). "Droplet-Based Microfluidics In Drug Discovery, Transcriptomics And High-Throughput Molecular Genetics," Lab Chip 16(8): 1314-1331.

Shenoy, N.R. et al. (1993). "Studies In C-Terminal Sequencing: New Reagents For The Synthesis Of Peptidylthiohydantoins," J Protein Chem 12(2): 195-205.
Shim, J.W. et al. (2009). "Single-Molecule Detection Of Folding And Unfolding Of The G-Quadruplex Aptamer In A Nanopore Nanocavity," Nucleic Acids Res 37(3): 972-982.
Shim, J. U. et al. (2013). "Ultrarapid Generation Of Femtoliter Microfluidic Droplets For Single-Molecule-Counting Immunoassays," ACS Nano 7(7): 5955-5964.
Shuman, S. (1994). "Novel Approach To Molecular Cloning And Polynucleotide Synthesis Using Vaccinia DNA Topoisomerase," J. Biol. Chem. 269(51):32678-32684.
Sidoli, S. et al. (2015). "Drawbacks In The Use Of Unconventional Hydrophobic Anhydrides For Histone Derivatization In Bottom-Up Proteomics PTM Analysis," Proteomics 15(9): 1459-1469, 18 pages.
Skerra, A. (2008). "Alternative Binding Proteins: Anticalins—Harnessing the Structural Plasticity of the Lipocalin Ligand Pocket to Engineer Novel Binding Activities," Febs J. 275(11):2677-2683.
Sletten, E.M. et al. (2009). "Bioorthogonal Chemistry: Fishing For Selectivity In A Sea Of Functionality," Angew Chem Int Ed Engl 48(38): 6974-6998.
Smith, E. et al. (2015). "Photoaffinity Labeling In Target And Binding-Site Identification," Future Med Chem. 7(2):159-183.
Soellner, M.B. et al. (Oct. 1, 2003). "Site-Specific Protein Immobilization By Staudinger Ligation," J. Am. Chem. Soc. 125(39):11790-11791.
Spencer, S.J. et al. (Feb. 2016). "Massively Parallel Sequencing Of Single Cells By Epicpcr Links Functional Genes With Phylogenetic Markers," ISME J 10(2):427-436.
Spicer, C.D. et al. (Sep. 5, 2014). "Selective Chemical Protein Modification," Nat Commun 5:4740, 1-14 pages.
Spiropulos, N.G. et al. (Jul. 1, 2012). "Templating Effect In DNA Proximity Ligation Enables Use Of Non-Bioorthogonal Chemistry In Biological Fluids," Artif DNA PNA XNA 3(3):123-128.
Spungin, A. et al. (1989)."Streptomyces Griseus Aminopeptidase Is A Calcium-Activated Zinc Metalloprotein Purification And Properties Of The Enzyme," Eur. J. Biochem. 183(2):471-477.
Stahl, P.L. et al. (Jul. 1, 2016). "Visualization And Analysis Of Gene Expression In Tissue Sections By Spatial Transcriptomics," Science 353(6294):78-82.
Stavis, C. et al. (Jan. 18, 2011, e-pub. Sep. 30, 2010). "Surface Functionalization Of Thin-Film Diamond For Highly Stable And Selective Biological Interfaces," Proc. Natl. Acad. Sci. USA 108(3):983-988.
Steinberg, G. et al. (Apr. 5, 2004). "Strategies For Covalent Attachment Of DNA To Beads," Biopolymers 73(5):597-605.
Sun, X-L. et al. (Jan./Feb. 2006). "Carbohydrate And Protein Immobilization Onto Solid Surfaces By Sequential Diels-Alder And Azide-Alkyne Cycloadditions," Bioconjug. Chem. 17(1):52-57.
Swaminathan, J. et al. (Feb. 25, 2015, e-pub. Feb. 2015) "A Theoretical Justification For Single Molecule Peptide Sequencing," Plos Comput. Biol. 11(2):E1004080, 17 pages.
Switzar, L. et al. (Mar. 1, 2013, e-pub. Feb. 13, 2015). "Protein Digestion: An Overview Of The Available Techniques And Recent Developments," J Proteome Res 12(3):1067-1077.
Tamminen, M.V. et al. (Mar. 11, 2015). "Single Gene-Based Distinction Of Individual Microbial Genomes From A Mixed Population Of Microbial Cells," Front Microbiol 6:195, 1-10 pages.
Tessler, L. (Jan. 1, 2011). "Digital Protein Analysis: Technologies For Protein Diagnostics And Proteomics Through Single-Molecule Detection." Washington University In St. Louis 147 Pages.
Tran et al., "KRAS interaction with RAF1 RAS-binding domain and cysteine-rich domain provides insights into RAS-mediated RAF activation," Nat Commun (2021) 12(1):1176, 16 pages.
Tse, B.N. et al. (Nov. 19, 2008). "Translation Of DNA Into A Library Of 13,000 Synthetic Small-Molecule Macrocycles Suitable For In Vitro Selection," J Am Chem Soc. 130(46):15611-15626.
Tullman et al. (Jul. 2, 2020). "Leveraging Nature's Biomolecular Designs In Next-Generation Protein Sequencing Reagent Development," Applied Microbiology And Biotechnology 104:7261-7271.
Turner, D.J. et al. (2009). "High-Throughput Haplotype Determination Over Long Distances By Haplotype Fusion PCR And Ligation Haplotyping," Nat. Protoc. 4(12):1771-1783.

(56) References Cited

OTHER PUBLICATIONS

Tyson, J. et al. (Dec. 11, 2012). "Determination Of Haplotypes At Structurally Complex Regions Using Emulsion Haplotype Fusion PCR," BMC Genomics 13:693, 1-12 pages.

Vandernoot, V.A. et al. (Dec. 2012). "cDNA Normalization By Hydroxyapatite Chromatography To Enrich Transcriptome Diversity In RNA-seq Applications," Biotechniques 53(6):373-380.

Van Den Bremer et al., "Human IgG is produced in a pro-form that requires clipping of C-terminal lysines for maximal complement activation," MAbs (2015) 7(4):672-80.

Varland, S. et al. (Jul. 2015, e-pub. Jun. 16, 2015). "N-Terminal Modifications Of Cellular Proteins: The Enzymes Involved, Their Substrate Specificities And Biological Effects," Proteomics 15(14):2385-2401.

Vauquelin, G. et al. (Apr. 2013). "Exploring Avidity: Understanding The Potential Gains In Functional Affinity And Target Residence Time Of Bivalent And Heterobivalent Ligands," Br J Pharmacol 168(8):1771-1785.

Veggiani, G. et al. (Feb. 2, 2016, e-pub. Jan. 19, 2016). "Programmable polyproteams built using twin peptide superglues," Proc Natl Acad Sci USA 113(5):1202-1207.

Vitak, S.A. et al. (Mar. 2017, e-pub. Jan. 30, 2017). "Sequencing thousands of single-cell genomes with combinatorial indexing," Nat Methods 14(3):302-308.

Wagner, A.M. et al. (Sep. 28, 2011, e-pub. Sep. 6, 2011). "N-Terminal Protein Modification Using Simple Aminoacyl Transferase Substrates," J Am Chem Soc 133(38):15139-15147.

Wang, K.H. et al. (Nov. 7, 2008). "The Molecular Basis Of N-End Rule Recognition," Mol Cell 32(3):406-414.

Wang, D. et al. (Mar. 1, 2009). "N-Terminal Derivatization Of Peptides With Isothiocyanate Analogues Promoting Edman-Type Cleavage And Enhancing Sensitivity In Electrospray Ionization Tandem Mass Spectrometry Analysis," Anal Chem 81(5):1893-1900.

Warren, W.C. et al. (Oct. 3, 1996). "Increased Production Of Peptide Deformylase Eliminates Retention Of Formylmethionine In Bovine Somatotropin Overproduced In *Escherichia coli*," Gene 174(2):235-238.

Watzke, A. et al. (Feb. 20, 2006). "Site-Selective Protein Immobilization By Staudinger Ligation," Angew Chem. Int. Ed. Engl 45(9):1408-1412.

Whiteaker, J.R. et al. (Mar. 1, 2007, e-pub. Dec. 20, 2006). "Antibody-Based Enrichment Of Peptides On Magnetic Beads For Mass-Spectrometry-Based Quantification Of Serum Biomarkers," Anal. Biochem 362(1):44-54.

Wilce, M.C. et al. (Mar. 31, 1998). "Structure And Mechanism Of A Proline-Specific Aminopeptidase From *Escherichia coli*," Proc. Natl. Acad. Sci. USA 95(7):3472-3477.

Williams, R. et al. (Jul. 2006). "Amplification Of Complex Gene Libraries By Emulsion PCR," Nat Methods 3(7):545-550.

Williams, B.A.R. et al. (Sep. 2010). "Synthesis Of Peptide-Oligonucleotide Conjugates Using A Heterobifunctional Crosslinker," Curr Protoc Nucleic Acid Chem Chapter 4:Unit 4.41, 1-29 pages.

Wu, H. et al. (Feb. 2016, e-pub. Dec. 22, 2015). "Inverse Electron-Demand Diels-Alder Bioorthogonal Reactions," Top Curr Chem 374(1):3, 1-22 pages.

Xiao, W. et al. (Jul. 2013). "Immobilized OBOC Combinatorial Bead Array To Facilitate Multiplicative Screening," Combinatorial Chemistry & High Throughput Screening 16(6):441-448.

Xiong, A-S. et al. (May 2008, e-pub. Apr. 2, 2008). "Chemical Gene Synthesis: Strategies, Softwares, Error Corrections, And Applications," FEMS Microbiol Rev 32(3):522-540.

Xu, B. et al. (Dec. 27, 2013). "Protein Complex Identification By Integrating Protein-Protein Interaction Evidence From Multiple Sources," Plos One 8(12):E83841, 1-12 pages.

Yang, S-W. et al. (Oct. 1, 2002). "Mutant Thermotoga Neapolitana DNA Polymerase I: Altered Catalytic Properties For Non-Templated Nucleotide Addition And Incorporation Of Correct Nucleotides," Nucleic Acids Res 30(19):4314-4320.

Yao, Y. et al. (Aug. 12, 2015). "Single-Molecule Protein Sequencing Through Fingerprinting: Computational Assessment," Phys Biol 12(5):055003, 7 pages.

Yazdi, S.M.H.T. et al. (2015). "A Rewritable, Random-Access DNA-Based Storage System," Sci Rep 5:14138, 1-10 pages.

Yazdi, S.M.H.T. et al. (Sep. 2015). "DNA-Based Storage: Trends And Methods," IEEE Transactions On Molecular, Biological And Multi-Scale Communications 1(3):230-248.

Yoo, C. et al. (Oct. 8, 2010, e-pub. Sep. 7, 2010). "An Aminopeptidase From *Streptomyces* Sp. KK565 Degrades Beta Amyloid Monomers, Oligomers And Fibrils," FEBS Lett. 584(19):4157-4162.

Young, D.D. et al. (Jan. 28, 2008, e-pub. Nov. 14, 2007). "Light-Triggered Polymerase Chain Reaction," Chem Commun (Camb) (4):462-464.

Yuan, L. et al. (Sep. 2005). "Laboratory-Directed Protein Evolution," Microbiol. Mol. Biol. Rev. 69(3):373-392.

Zakeri, B. et al. (Mar. 20, 2012, e-pub. Feb. 24, 2012). "Peptide Tag Forming a Rapid Covalent Bond to a Protein, Through Engineering a Bacterial Adhesin," PNAS USA 109(12):E690-E697.

Zhang, L. et al. (Apr. 19, 2016, e-pub. Apr. 6, 2016). "Single-Molecule Analysis Of Human Telomere Sequence Interactions With G-Quadruplex Ligand," Anal Chem 88(8):4533-4540.

Zhang, L. et al. (2016, e-pub. Feb. 26, 2016). "The Use Of Lectin Microarray For Assessing Glycosylation Of Therapeutic Proteins," mAbs 8(3):524-535.

Zhou, H. et al. (Jan. 17, 2012, e-pub. Nov. 15, 2011). "Advancements In Top-Down Proteomics," Anal Chem 84(2):720-734.

Zilionis, R. et al. (Jan. 2017, e-pub. Dec. 8, 2016). "Single-Cell Barcoding And Sequencing Using Droplet Microfluidics," Nat Protoc 12(1):44-73.

U.S. Appl. No. 18/923,452, Chee et al. filed Oct. 22, 2024. (Copy not submitted herewith pursuant to the waiver of 37 C.F.R. § 1.98(a)(2)(iii) issued by the Office on Sep. 21, 2004).

U.S. Appl. No. 18/965,991, Chee et al. filed Dec. 2, 2024. (Copy not submitted herewith pursuant to the waiver of 37 C.F.R. § 1.98(a)(2)(iii) issued by the Office on Sep. 21, 2004).

\* cited by examiner

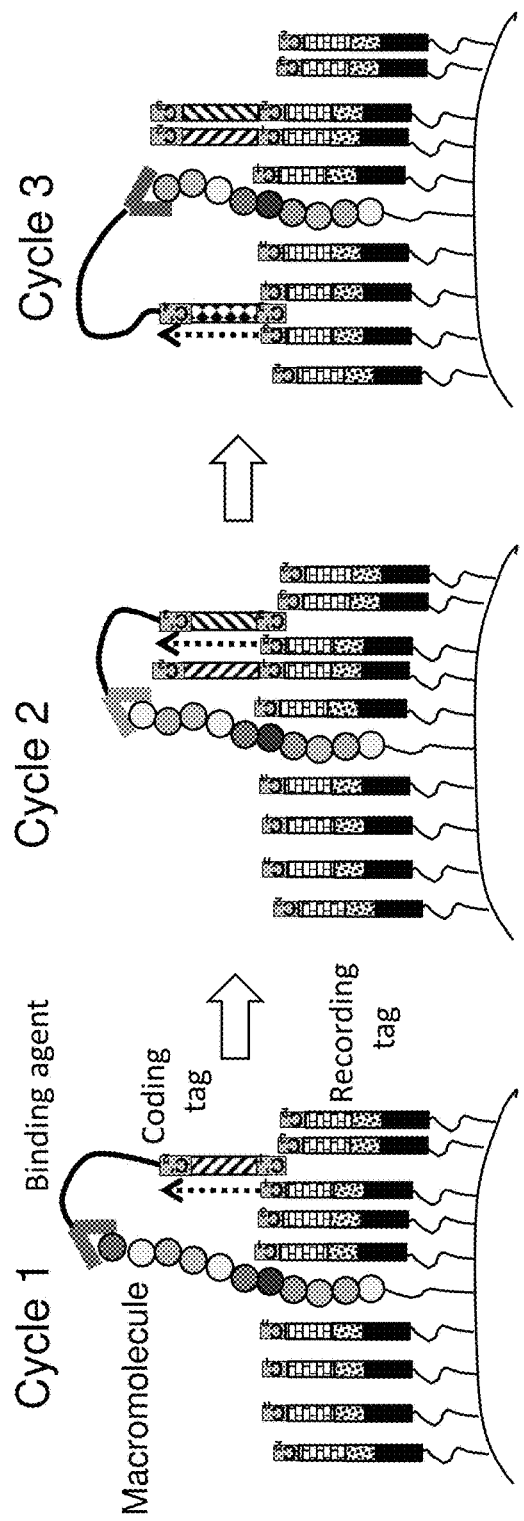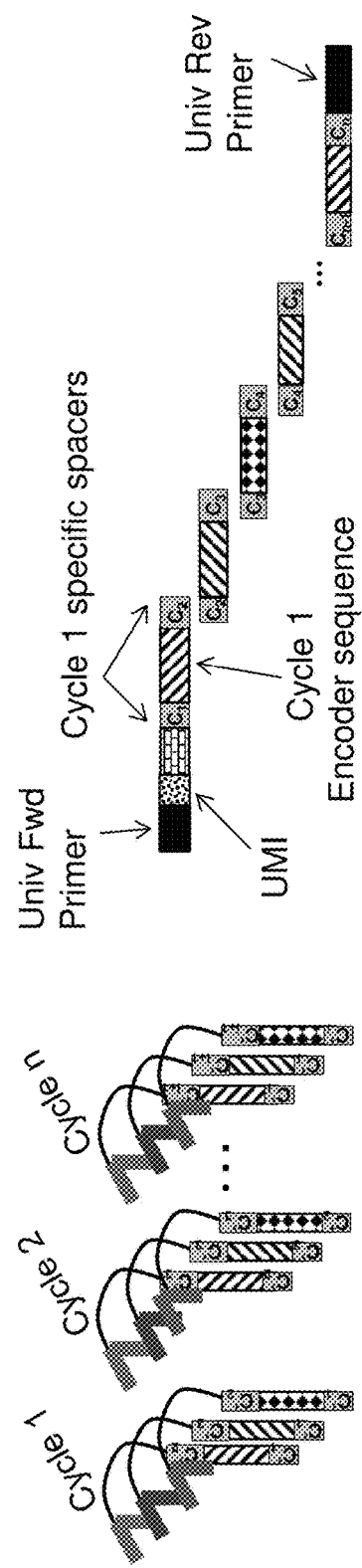
Fig. 10A
Fig. 10B
Fig. 10C

A. DNA tag labeling of Protein/Polypeptide

B. Compartmentalization with Barcode Bead

C. Annealing barcodes to DNA tags

D. Crack emulsion/Primer extend/GluC Digest

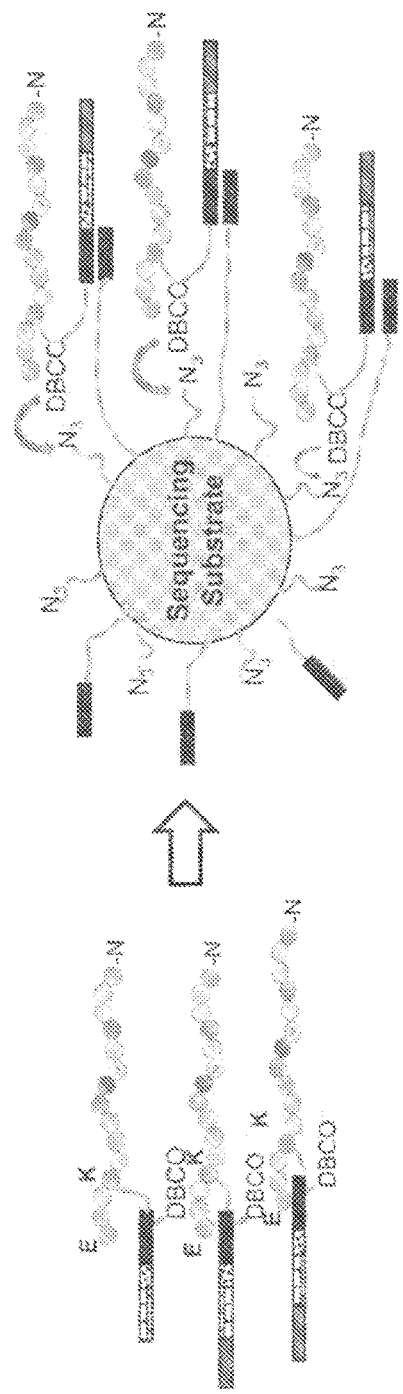

G. DNA tag labeling of "click" pre-labeled protein

H. Compartmentalization with Barcode Bead i. Annealing barcodes to DNA tags j. Crack emulsion/Primer extend/GluC Digest k. Recording tagged peptides l. Immobilization to sequencing substrate

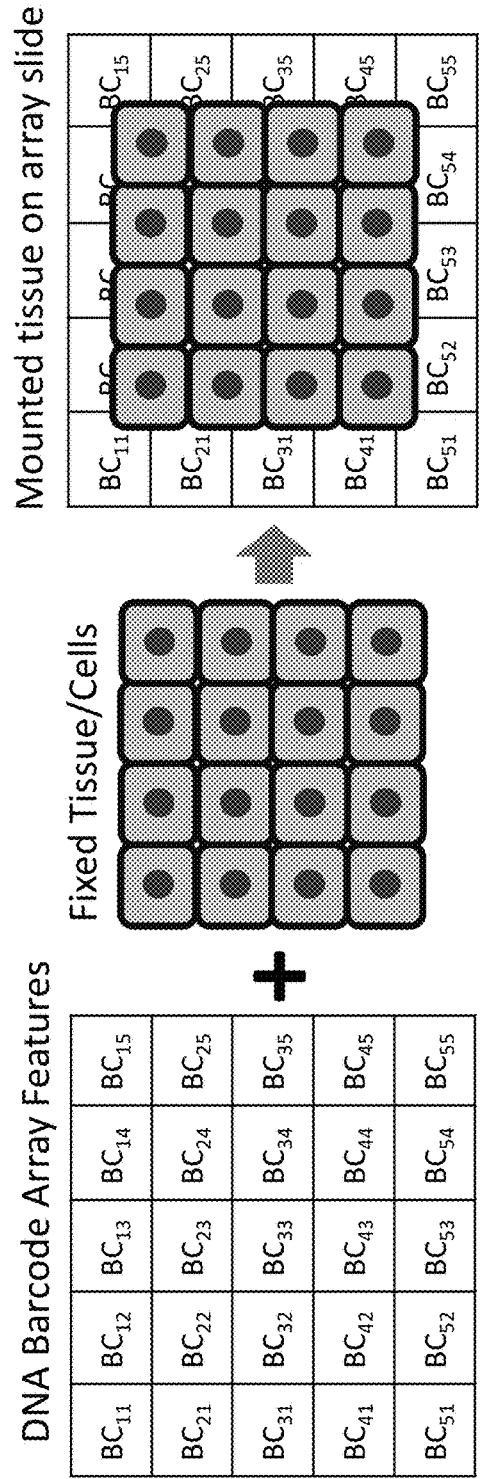
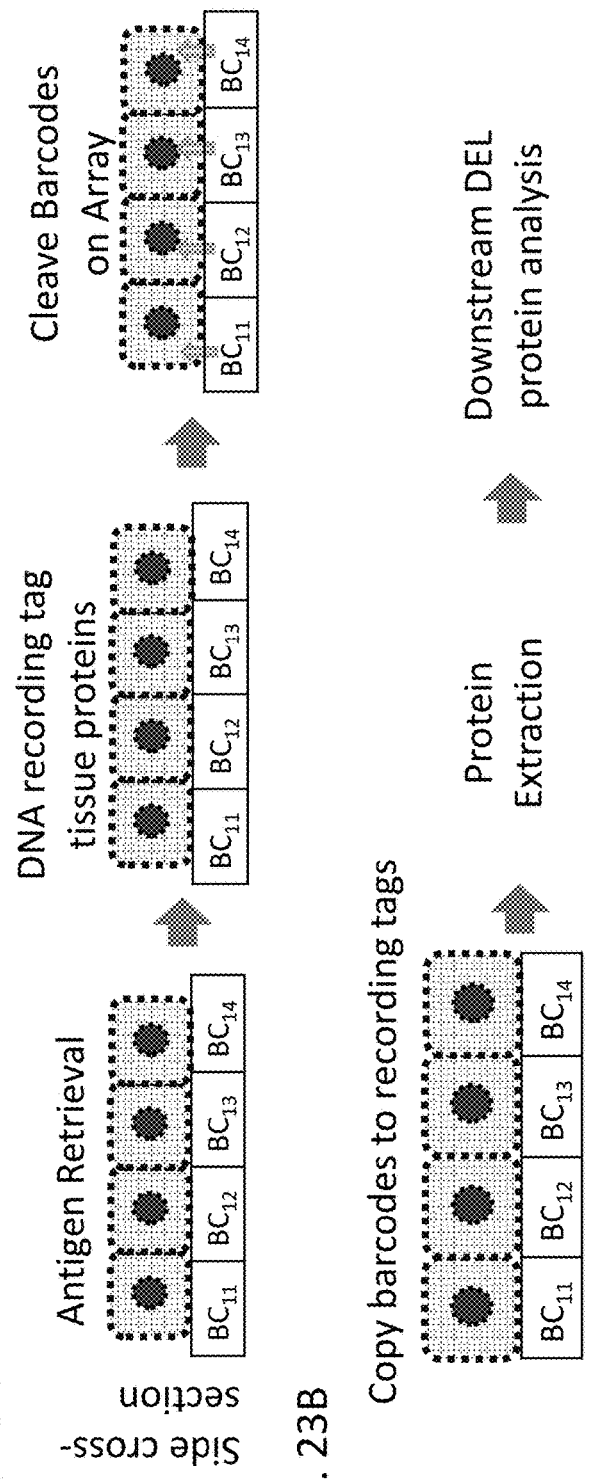
Fig. 23A
Fig. 23B
Fig. 23C

Fig. 27D

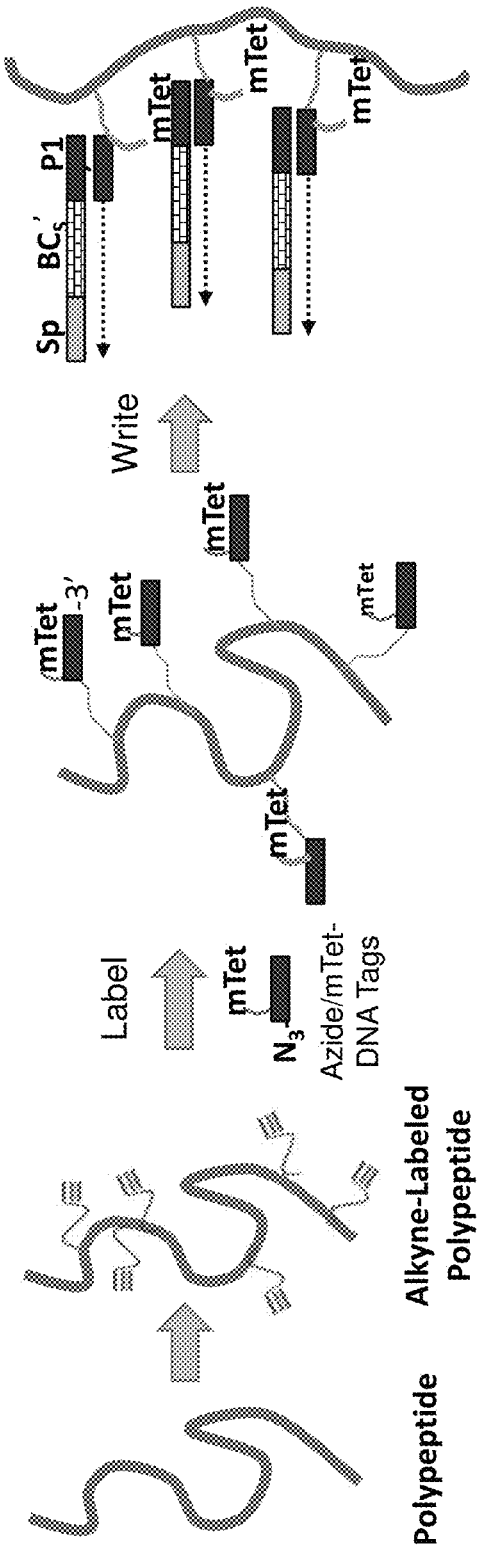
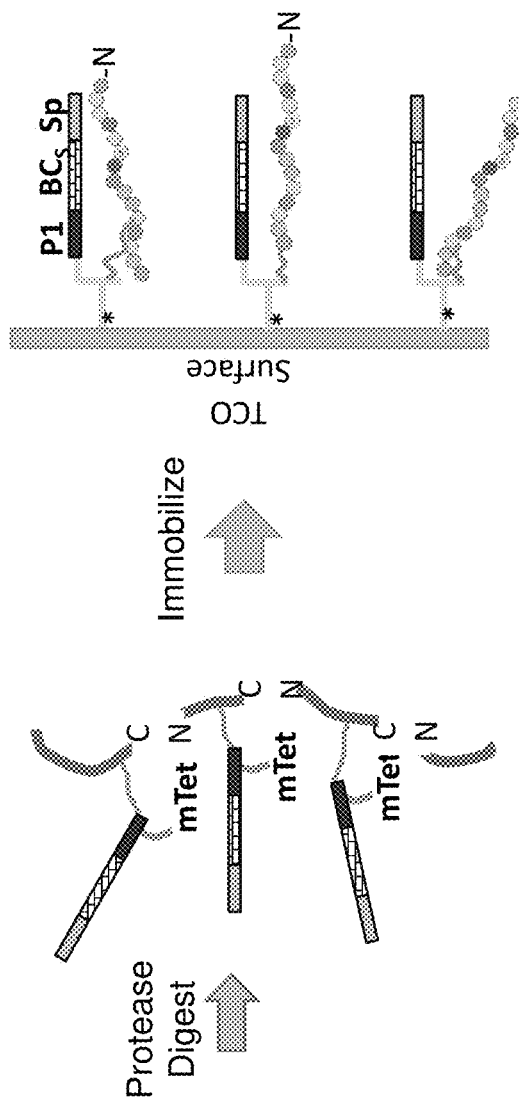
Fig. 30A  Fig. 30B  Fig. 30C  Fig. 30D  Fig. 30E

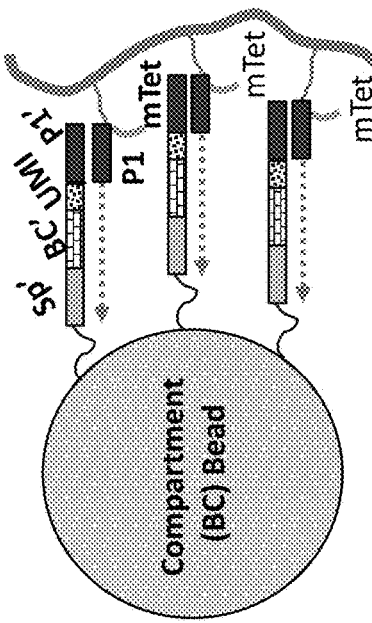
Fig. 31A
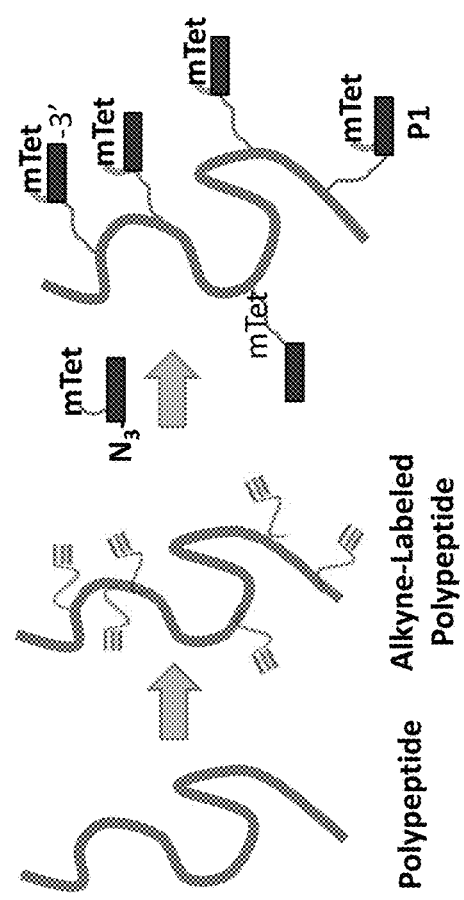
Fig. 31B
Fig. 31C
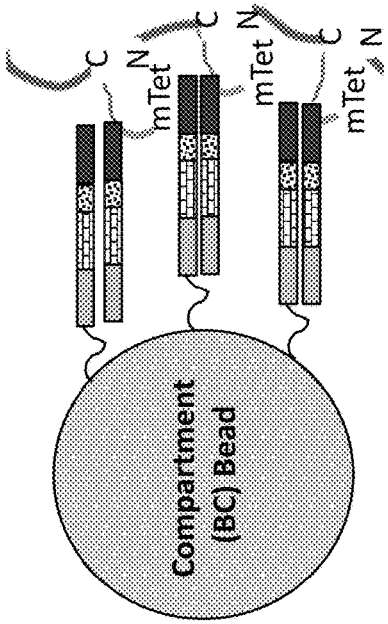
Fig. 31D
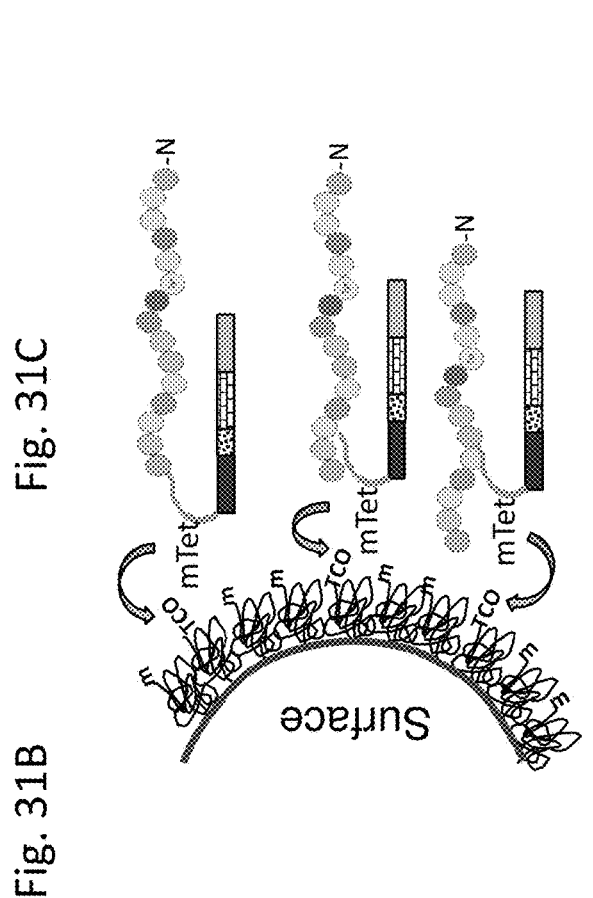
Fig. 31E

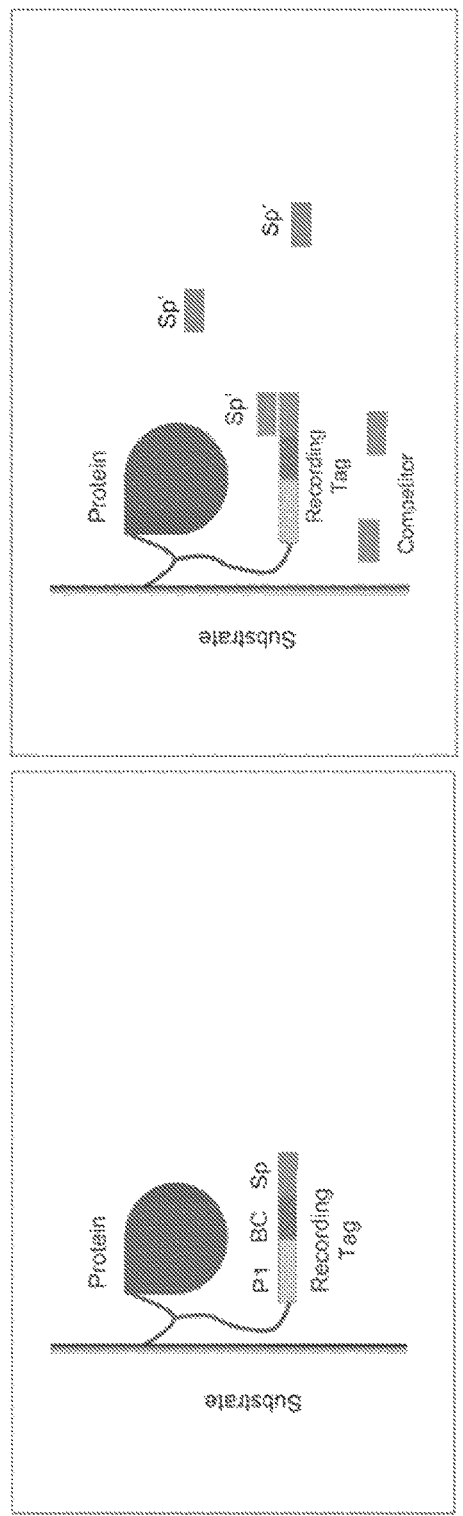
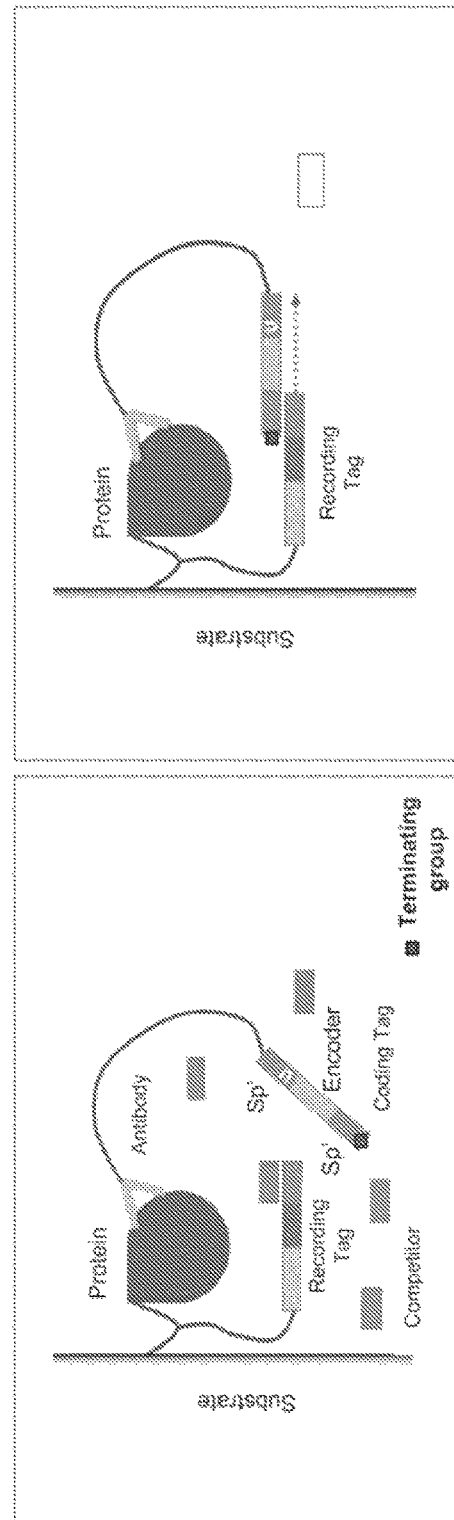

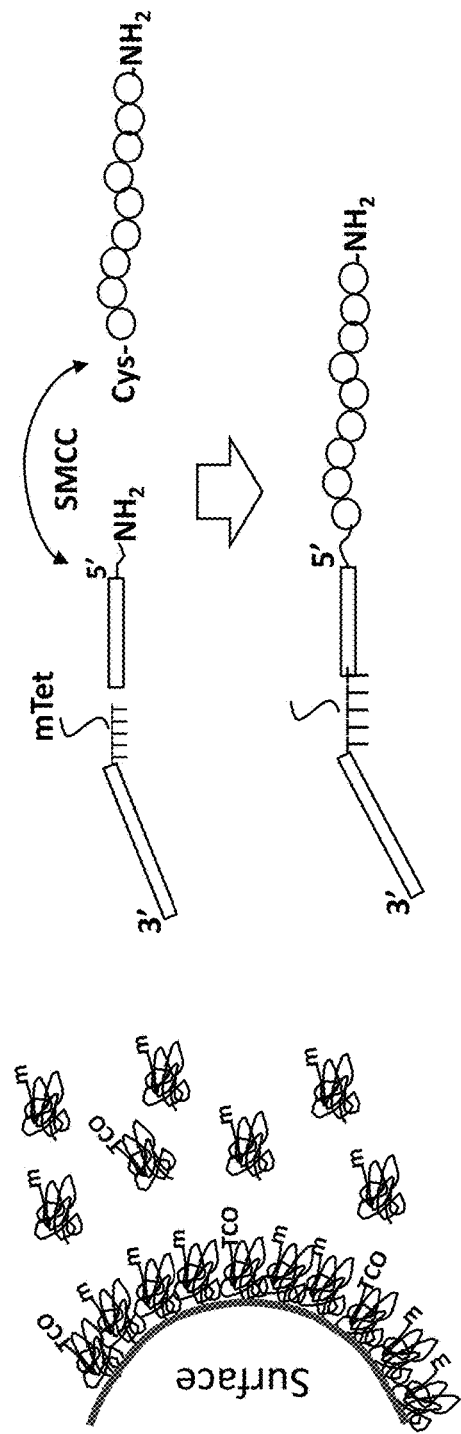
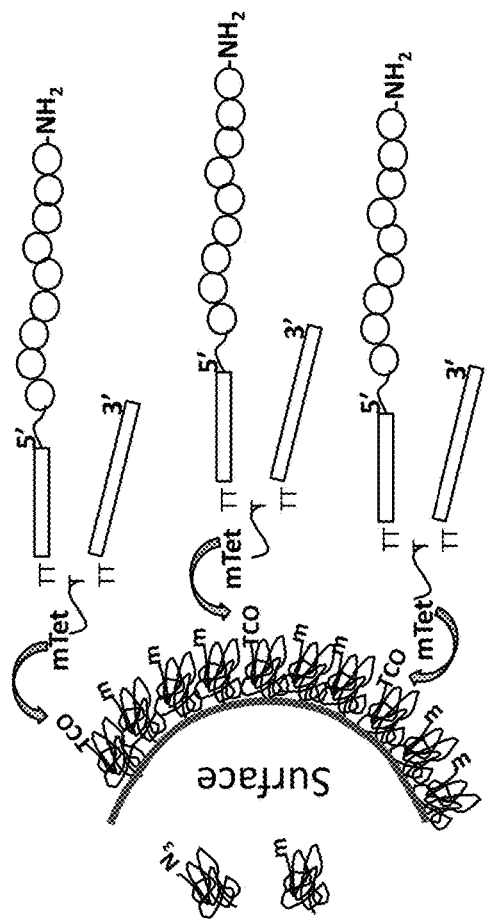
Fig. 34A
Fig. 34B
Fig. 34C

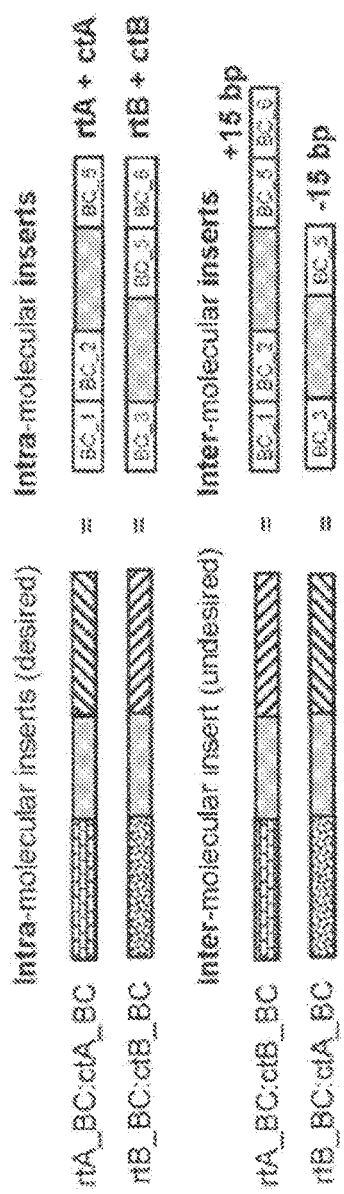
Fig. 36B
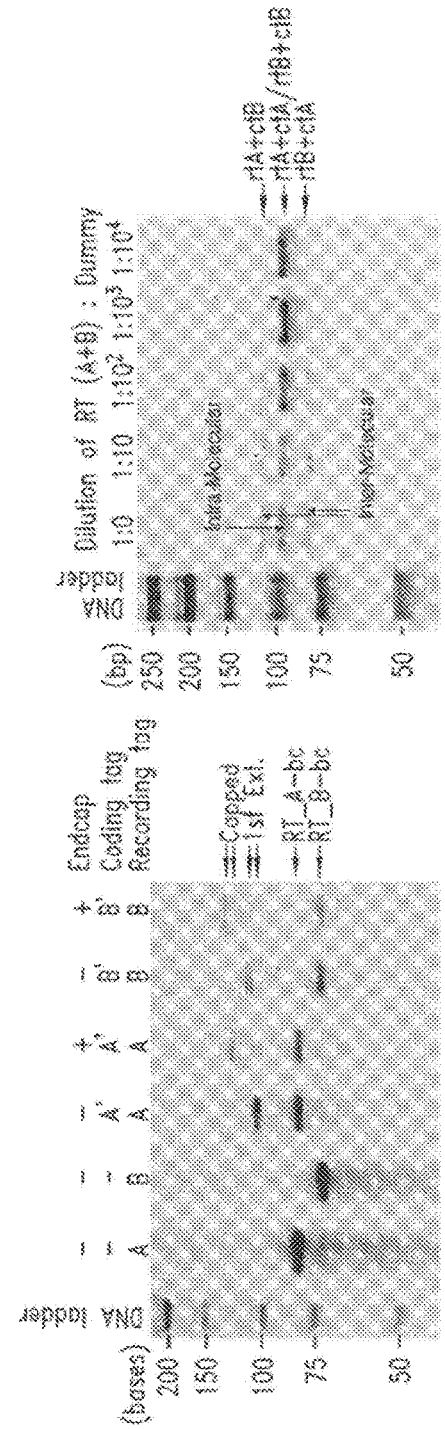
Fig. 36C
Fig. 36D

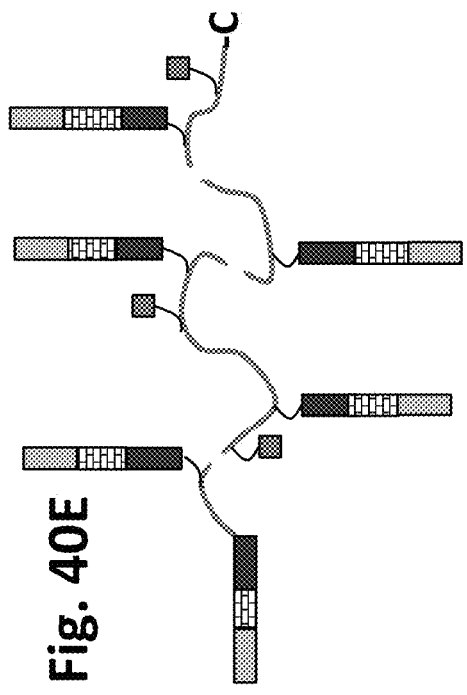
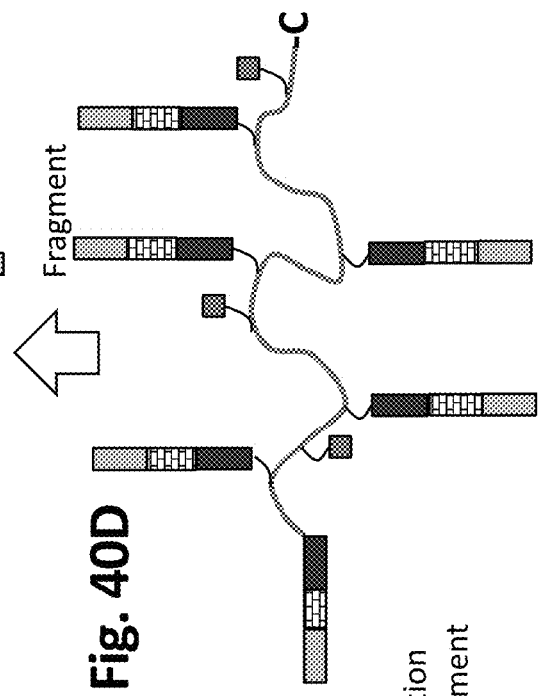
Fig. 40A
Fig. 40B Acid Anhydride Labeling
Fig. 40C DNA Tag Attachment (click chemistry)
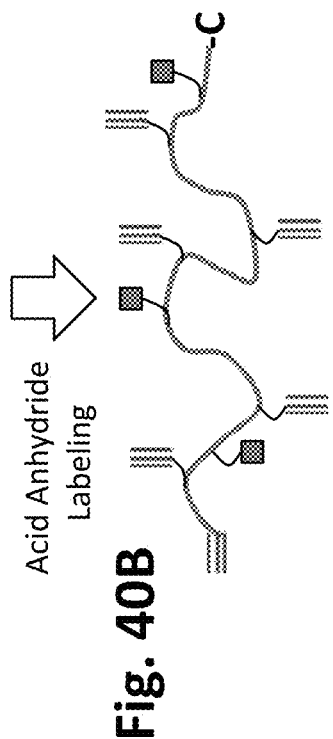
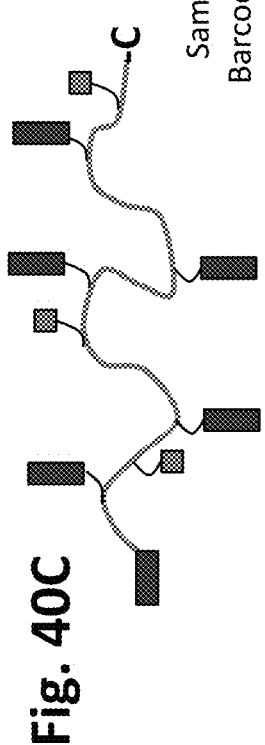
Fig. 40D Sample/Partition Barcode Attachment
Fig. 40E Fragment C-terminal ligation Surface Conjugation Moiety Writing Recording Tag to C-terminus DNA tag Cleaving internal Recording Tags

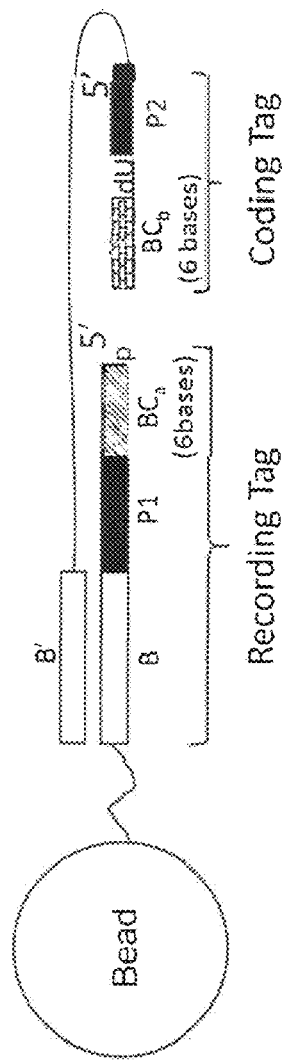
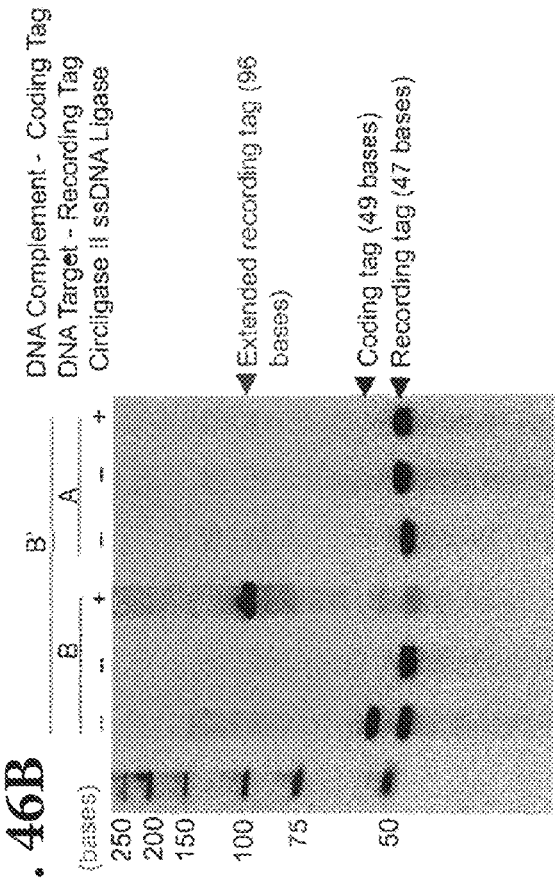
Fig. 46A
Fig. 46B

Fig. 48C
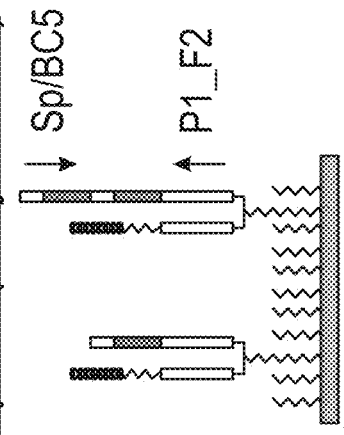
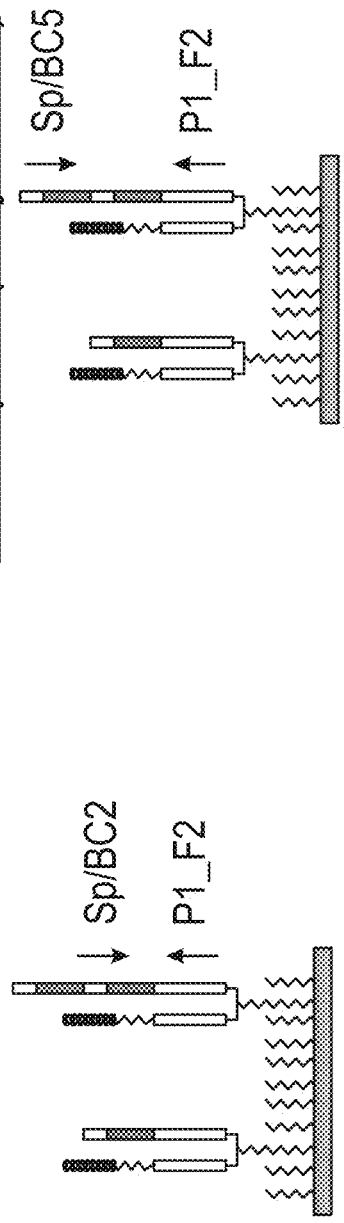
P1_F2 - Sp/BC2 (18 Cycles PCR)
Fig. 48D
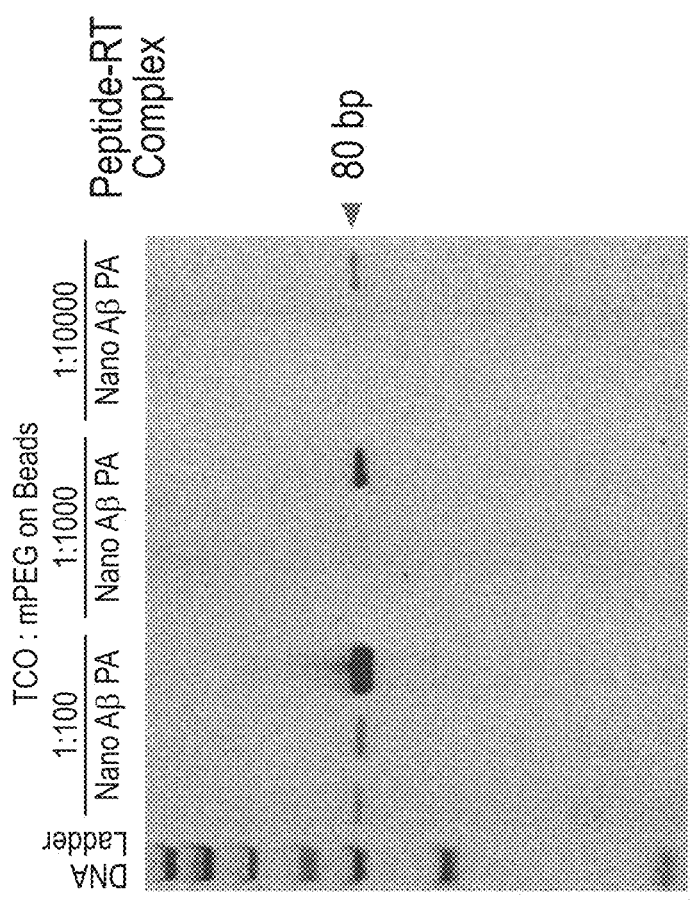
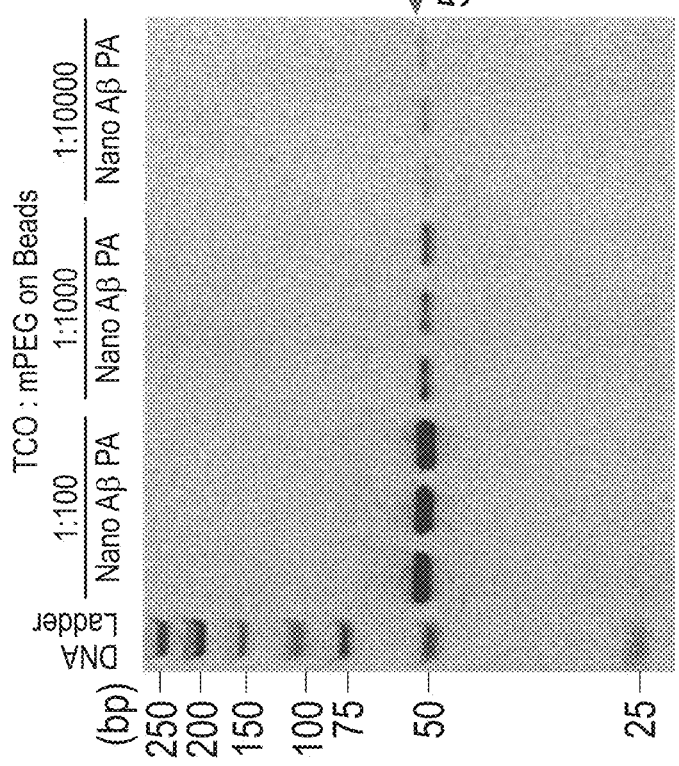
P1_F2 - Sp/BC5 (21 Cycles PCR)

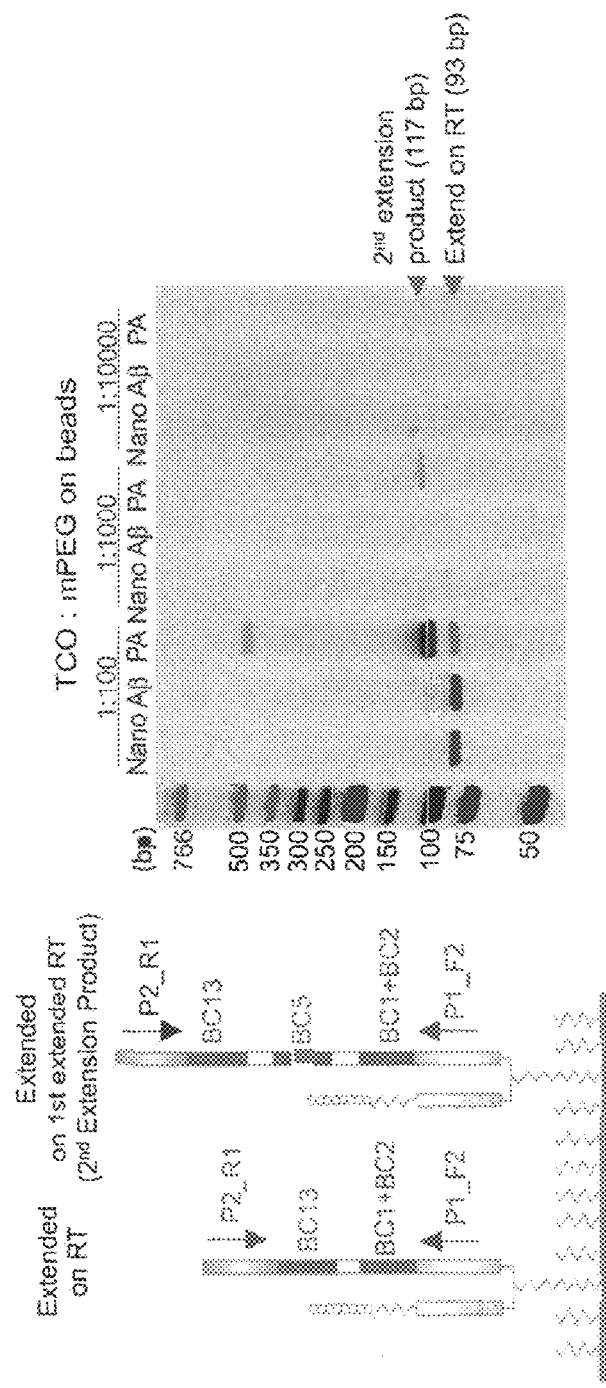

\>sp|P04637|P53_HUMAN
MEEPQSDPSVEPPLSQETFSDLWKLLPENNVLSPLPSQAMDDLMLSPDDIEQWFTEDPGPDE
APRMPEAAPPVAPAPAAPTPAAPAPAPSWPLSSSVPSQKTYQGSYGFRLGFLHSGTAK
SVTCTYSPALNKMFCQLAKTCPVQLWVDSTPPPGTRVRAMAIYKQSQHMTEVVRRCPHHE
RCSDSDGLAPPQHLIRVEGNLRVEYLDDRNTFRHSVVVPYEPPEVGSDCTTIHYNYMCNS
SCMGGMNRRPILTIITLEDSSGNLLGRNSFEVRVCACPGRDRRTEEENLRKKGEPHHELP
PGSTKRALPNNTSSSPQPKKKPLDGEYFTLQIRGRERFEMFRELNEALELKDAQAGKEPG
GSRAHSSHLKSKKGQSTSRHKKLMFKTBGPDSD

Sequencing Read CPXQXWXDXT maps
uniquely to p53 within the human
proteome

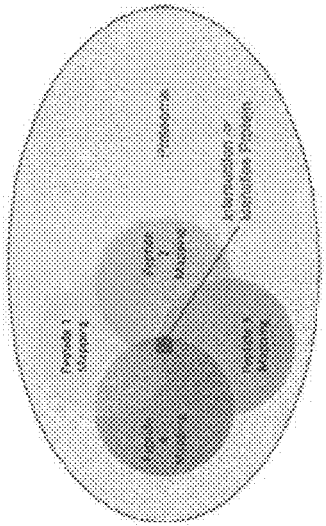

MEEPXSDPXZEXPLSQ                    ZMXDLMLSPXDIEQX
SZEPPXSQEXFSD    PEXNZLSPLXSQ
         QETFXDLMKLXPENNZL                DXEQWFXEDPZP
PQXDPS

Adapted from Kozlov, I et al. (2012) PLoS One 7(6): e37441 http://openinnovation.gsk.com/img/on-DNA.png

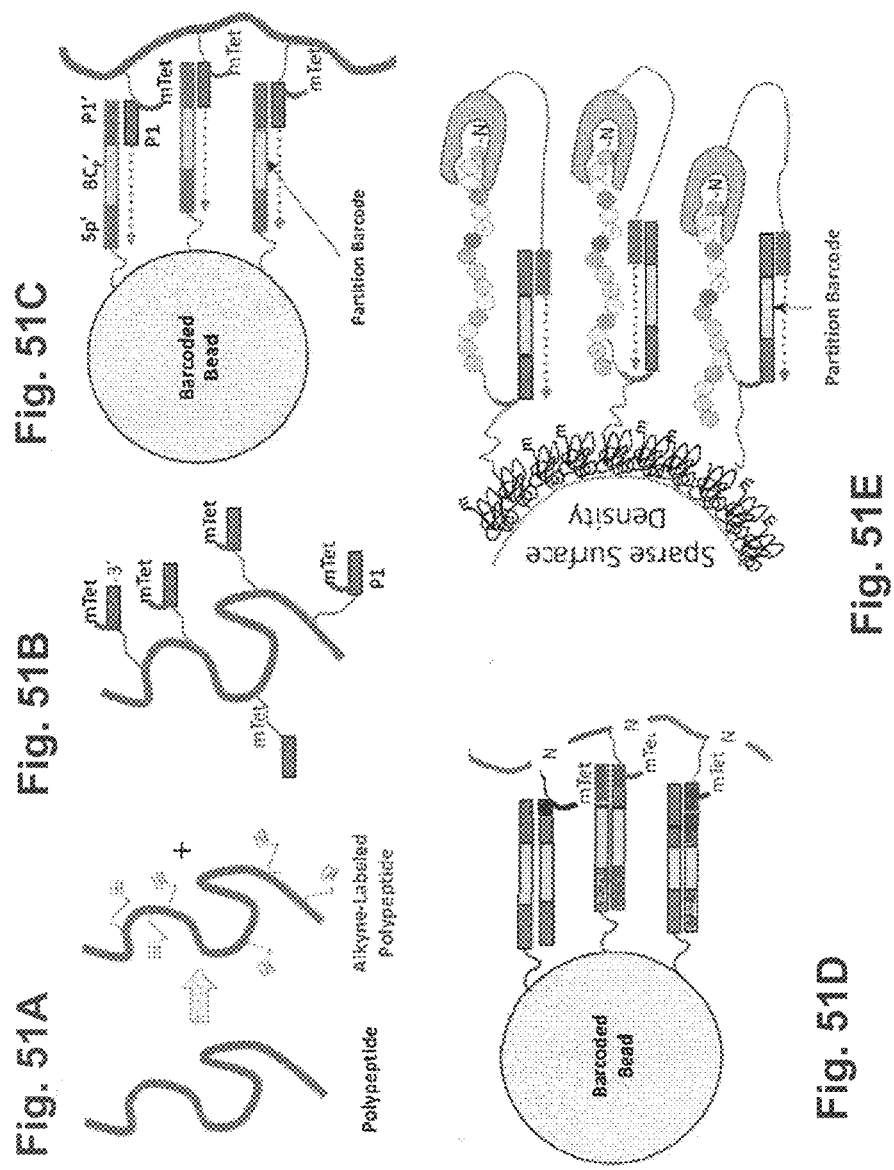

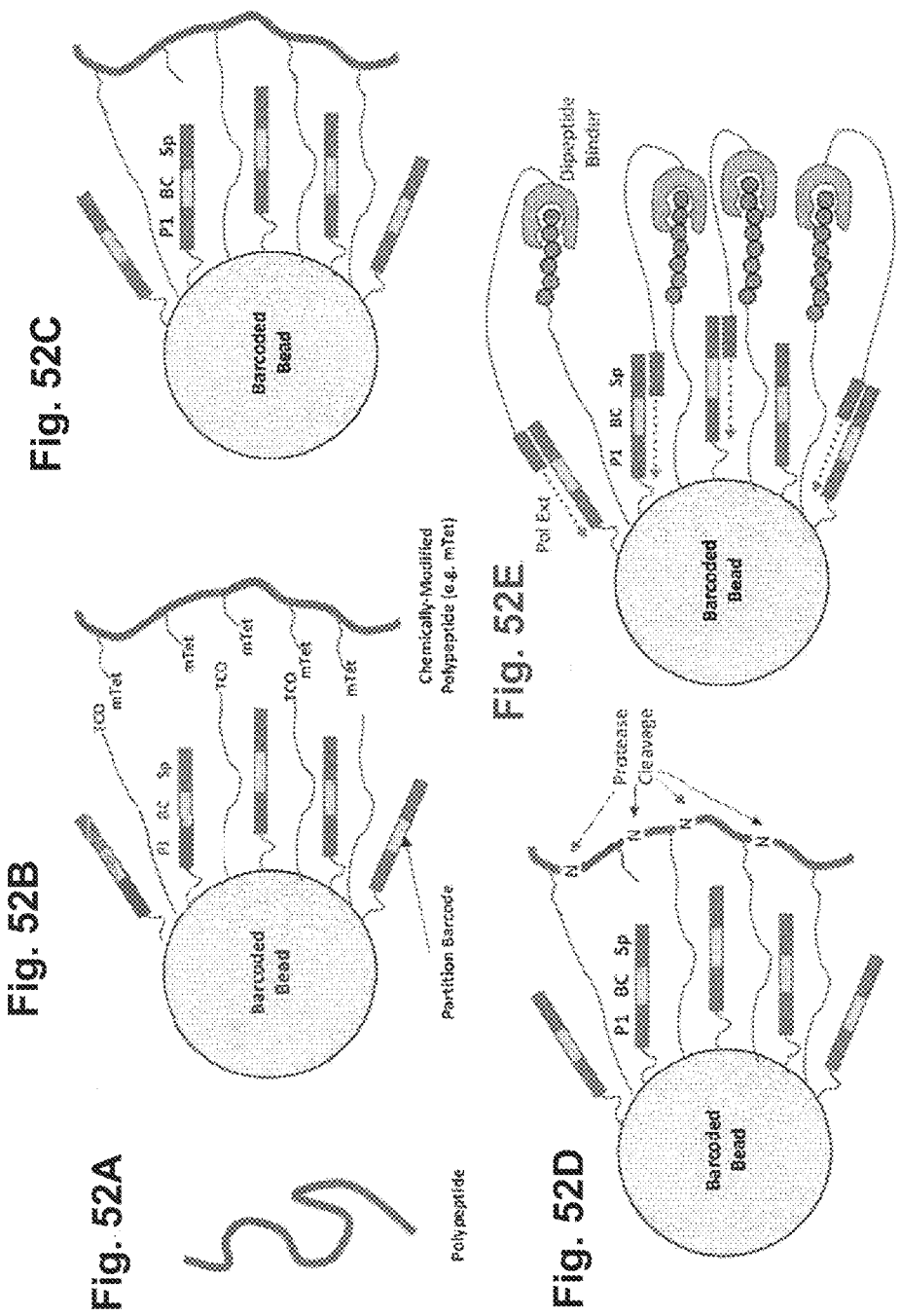

```
                            SEQUENCE LISTING

Sequence total quantity: 228
SEQ ID NO: 1            moltype = DNA  length = 15
FEATURE                 Location/Qualifiers
misc_feature            1..15
                        note = oligonucleotide barcode BC_1
source                  1..15
                        mol_type = other DNA
                        organism = synthetic construct
SEQUENCE: 1
atgtctagca tgccg                                                          15

SEQ ID NO: 2            moltype = DNA  length = 15
FEATURE                 Location/Qualifiers
misc_feature            1..15
                        note = oligonucleotide barcode BC_2
source                  1..15
                        mol_type = other DNA
                        organism = synthetic construct
SEQUENCE: 2
ccgtgtcatg tggaa                                                          15

SEQ ID NO: 3            moltype = DNA  length = 15
FEATURE                 Location/Qualifiers
misc_feature            1..15
                        note = oligonucleotide barcode BC_3
source                  1..15
                        mol_type = other DNA
                        organism = synthetic construct
SEQUENCE: 3
taagccggta tatca                                                          15

SEQ ID NO: 4            moltype = DNA  length = 15
FEATURE                 Location/Qualifiers
misc_feature            1..15
                        note = oligonucleotide barcode BC_4
source                  1..15
                        mol_type = other DNA
                        organism = synthetic construct
SEQUENCE: 4
ttcgatatga cggaa                                                          15

SEQ ID NO: 5            moltype = DNA  length = 15
FEATURE                 Location/Qualifiers
misc_feature            1..15
                        note = oligonucleotide barcode BC_5
source                  1..15
                        mol_type = other DNA
                        organism = synthetic construct
SEQUENCE: 5
cgtatacgcg ttagg                                                          15

SEQ ID NO: 6            moltype = DNA  length = 15
FEATURE                 Location/Qualifiers
misc_feature            1..15
                        note = oligonucleotide barcode BC_6
```

```
source                      1..15
                            mol_type = other DNA
                            organism = synthetic construct
SEQUENCE: 6
aactgccgag attcc                                                            15

SEQ ID NO: 7                moltype = DNA   length = 15
FEATURE                     Location/Qualifiers
misc_feature                1..15
                            note = oligonucleotide barcode BC_7
source                      1..15
                            mol_type = other DNA
                            organism = synthetic construct
SEQUENCE: 7
tgatcttagc tgtgc                                                            15

SEQ ID NO: 8                moltype = DNA   length = 15
FEATURE                     Location/Qualifiers
misc_feature                1..15
                            note = oligonucleotide barcode BC_8
source                      1..15
                            mol_type = other DNA
                            organism = synthetic construct
SEQUENCE: 8
gagtcggtac cttga                                                            15

SEQ ID NO: 9                moltype = DNA   length = 15
FEATURE                     Location/Qualifiers
misc_feature                1..15
                            note = oligonucleotide barcode BC_9
source                      1..15
                            mol_type = other DNA
                            organism = synthetic construct
SEQUENCE: 9
ccgcttgtga tctgg                                                            15

SEQ ID NO: 10               moltype = DNA   length = 15
FEATURE                     Location/Qualifiers
misc_feature                1..15
                            note = oligonucleotide barcode BC_10
source                      1..15
                            mol_type = other DNA
                            organism = synthetic construct
SEQUENCE: 10
agatagcgta ccgga                                                            15

SEQ ID NO: 11               moltype = DNA   length = 15
FEATURE                     Location/Qualifiers
misc_feature                1..15
                            note = oligonucleotide barcode BC_11
source                      1..15
                            mol_type = other DNA
                            organism = synthetic construct
SEQUENCE: 11
tccaggctca tcatc                                                            15

SEQ ID NO: 12               moltype = DNA   length = 15
FEATURE                     Location/Qualifiers
misc_feature                1..15
                            note = oligonucleotide barcode BC_12
source                      1..15
                            mol_type = other DNA
                            organism = synthetic construct
SEQUENCE: 12
gagtactaga gccaa                                                            15

SEQ ID NO: 13               moltype = DNA   length = 15
FEATURE                     Location/Qualifiers
misc_feature                1..15
                            note = oligonucleotide barcode BC_13
source                      1..15
                            mol_type = other DNA
                            organism = synthetic construct
SEQUENCE: 13
gagcgtcaat aacgg                                                            15

SEQ ID NO: 14               moltype = DNA   length = 15
FEATURE                     Location/Qualifiers
misc_feature                1..15
```

```
                          note = oligonucleotide barcode BC_14
source                    1..15
                          mol_type = other DNA
                          organism = synthetic construct
SEQUENCE: 14
gcggtatcta cactg                                                          15

SEQ ID NO: 15             moltype = DNA   length = 15
FEATURE                   Location/Qualifiers
misc_feature              1..15
                          note = oligonucleotide barcode BC_15
source                    1..15
                          mol_type = other DNA
                          organism = synthetic construct
SEQUENCE: 15
cttctccgaa gagaa                                                          15

SEQ ID NO: 16             moltype = DNA   length = 15
FEATURE                   Location/Qualifiers
misc_feature              1..15
                          note = oligonucleotide barcode BC_16
source                    1..15
                          mol_type = other DNA
                          organism = synthetic construct
SEQUENCE: 16
tgaagcctgt gttaa                                                          15

SEQ ID NO: 17             moltype = DNA   length = 15
FEATURE                   Location/Qualifiers
misc_feature              1..15
                          note = oligonucleotide barcode BC_17
source                    1..15
                          mol_type = other DNA
                          organism = synthetic construct
SEQUENCE: 17
ctggatggtt gtcga                                                          15

SEQ ID NO: 18             moltype = DNA   length = 15
FEATURE                   Location/Qualifiers
misc_feature              1..15
                          note = oligonucleotide barcode BC_18
source                    1..15
                          mol_type = other DNA
                          organism = synthetic construct
SEQUENCE: 18
actgcacggt tccaa                                                          15

SEQ ID NO: 19             moltype = DNA   length = 15
FEATURE                   Location/Qualifiers
misc_feature              1..15
                          note = oligonucleotide barcode BC_19
source                    1..15
                          mol_type = other DNA
                          organism = synthetic construct
SEQUENCE: 19
cgagagatgg tcctt                                                          15

SEQ ID NO: 20             moltype = DNA   length = 15
FEATURE                   Location/Qualifiers
misc_feature              1..15
                          note = oligonucleotide barcode BC_20
source                    1..15
                          mol_type = other DNA
                          organism = synthetic construct
SEQUENCE: 20
tcttgagaga caaga                                                          15

SEQ ID NO: 21             moltype = DNA   length = 15
FEATURE                   Location/Qualifiers
misc_feature              1..15
                          note = oligonucleotide barcode BC_21
source                    1..15
                          mol_type = other DNA
                          organism = synthetic construct
SEQUENCE: 21
aattcgcact gtgtt                                                          15

SEQ ID NO: 22             moltype = DNA   length = 15
FEATURE                   Location/Qualifiers
```

```
misc_feature               1..15
                           note = oligonucleotide barcode BC_22
source                     1..15
                           mol_type = other DNA
                           organism = synthetic construct
SEQUENCE: 22
gtagtgccgc taaga                                                              15

SEQ ID NO: 23              moltype = DNA  length = 15
FEATURE                    Location/Qualifiers
misc_feature               1..15
                           note = oligonucleotide barcode BC_23
source                     1..15
                           mol_type = other DNA
                           organism = synthetic construct
SEQUENCE: 23
cctatagcac aatcc                                                              15

SEQ ID NO: 24              moltype = DNA  length = 15
FEATURE                    Location/Qualifiers
misc_feature               1..15
                           note = oligonucleotide barcode BC_24
source                     1..15
                           mol_type = other DNA
                           organism = synthetic construct
SEQUENCE: 24
atcaccgagg ttgga                                                              15

SEQ ID NO: 25              moltype = DNA  length = 15
FEATURE                    Location/Qualifiers
misc_feature               1..15
                           note = oligonucleotide barcode BC_25
source                     1..15
                           mol_type = other DNA
                           organism = synthetic construct
SEQUENCE: 25
gattcaacgg agaag                                                              15

SEQ ID NO: 26              moltype = DNA  length = 15
FEATURE                    Location/Qualifiers
misc_feature               1..15
                           note = oligonucleotide barcode BC_26
source                     1..15
                           mol_type = other DNA
                           organism = synthetic construct
SEQUENCE: 26
acgaacctcg cacca                                                              15

SEQ ID NO: 27              moltype = DNA  length = 15
FEATURE                    Location/Qualifiers
misc_feature               1..15
                           note = oligonucleotide barcode BC_27
source                     1..15
                           mol_type = other DNA
                           organism = synthetic construct
SEQUENCE: 27
aggacttcaa gaaga                                                              15

SEQ ID NO: 28              moltype = DNA  length = 15
FEATURE                    Location/Qualifiers
misc_feature               1..15
                           note = oligonucleotide barcode BC_28
source                     1..15
                           mol_type = other DNA
                           organism = synthetic construct
SEQUENCE: 28
ggttgaatcc tcgca                                                              15

SEQ ID NO: 29              moltype = DNA  length = 15
FEATURE                    Location/Qualifiers
misc_feature               1..15
                           note = oligonucleotide barcode BC_29
source                     1..15
                           mol_type = other DNA
                           organism = synthetic construct
SEQUENCE: 29
aaccaacctc tagcg                                                              15

SEQ ID NO: 30              moltype = DNA  length = 15
```

-continued

```
FEATURE                 Location/Qualifiers
misc_feature            1..15
                        note = oligonucleotide barcode BC_30
source                  1..15
                        mol_type = other DNA
                        organism = synthetic construct SEQUENCE: 30
acgcgaatat ctaac                                                          15

SEQ ID NO: 31           moltype = DNA   length = 15
FEATURE                 Location/Qualifiers
misc_feature            1..15
                        note = oligonucleotide barcode BC_31
source                  1..15
                        mol_type = other DNA
                        organism = synthetic construct SEQUENCE: 31
gttgagaatt acacc                                                          15

SEQ ID NO: 32           moltype = DNA   length = 15
FEATURE                 Location/Qualifiers
misc_feature            1..15
                        note = oligonucleotide barcode BC_32
source                  1..15
                        mol_type = other DNA
                        organism = synthetic construct SEQUENCE: 32
ctctctctgt gaacc                                                          15

SEQ ID NO: 33           moltype = DNA   length = 15
FEATURE                 Location/Qualifiers
misc_feature            1..15
                        note = oligonucleotide barcode BC_33
source                  1..15
                        mol_type = other DNA
                        organism = synthetic construct SEQUENCE: 33
gccatcagta agaga                                                          15

SEQ ID NO: 34           moltype = DNA   length = 15
FEATURE                 Location/Qualifiers
misc_feature            1..15
                        note = oligonucleotide barcode BC_34
source                  1..15
                        mol_type = other DNA
                        organism = synthetic construct SEQUENCE: 34
gcaacgtgaa ttgag                                                          15

SEQ ID NO: 35           moltype = DNA   length = 15
FEATURE                 Location/Qualifiers
misc_feature            1..15
                        note = oligonucleotide barcode BC_35
source                  1..15
                        mol_type = other DNA
                        organism = synthetic construct SEQUENCE: 35
ctaagtagag ccaca                                                          15

SEQ ID NO: 36           moltype = DNA   length = 15
FEATURE                 Location/Qualifiers
misc_feature            1..15
                        note = oligonucleotide barcode BC_36
source                  1..15
                        mol_type = other DNA
                        organism = synthetic construct SEQUENCE: 36
tgtctgttgg aagcg                                                          15

SEQ ID NO: 37           moltype = DNA   length = 15
FEATURE                 Location/Qualifiers
misc_feature            1..15
                        note = oligonucleotide barcode BC_37
source                  1..15
                        mol_type = other DNA
                        organism = synthetic construct SEQUENCE: 37
ttaatagaca gcgcg                                                          15
```

| | | |
|---|---|---|
| SEQ ID NO: 38
FEATURE
misc_feature source

SEQUENCE: 38
cgacgctcta acaag | moltype = DNA   length = 15
Location/Qualifiers
1..15
note = oligonucleotide barcode BC_38
1..15
mol_type = other DNA
organism = synthetic construct | 15 |
| SEQ ID NO: 39
FEATURE
misc_feature source SEQUENCE: 39
catggcttat tgaga | moltype = DNA   length = 15
Location/Qualifiers
1..15
note = oligonucleotide barcode BC_39
1..15
mol_type = other DNA
organism = synthetic construct | 15 |
| SEQ ID NO: 40
FEATURE
misc_feature source SEQUENCE: 40
actaggtatg gccgg | moltype = DNA   length = 15
Location/Qualifiers
1..15
note = oligonucleotide barcode BC_40
1..15
mol_type = other DNA
organism = synthetic construct | 15 |
| SEQ ID NO: 41
FEATURE
misc_feature source SEQUENCE: 41
gtcctcgtct atcct | moltype = DNA   length = 15
Location/Qualifiers
1..15
note = oligonucleotide barcode BC_41
1..15
mol_type = other DNA
organism = synthetic construct | 15 |
| SEQ ID NO: 42
FEATURE
misc_feature source SEQUENCE: 42
taggattccg ttacc | moltype = DNA   length = 15
Location/Qualifiers
1..15
note = oligonucleotide barcode BC_42
1..15
mol_type = other DNA
organism = synthetic construct | 15 |
| SEQ ID NO: 43
FEATURE
misc_feature source SEQUENCE: 43
tctgaccacc ggaag | moltype = DNA   length = 15
Location/Qualifiers
1..15
note = oligonucleotide barcode BC_43
1..15
mol_type = other DNA
organism = synthetic construct | 15 |
| SEQ ID NO: 44
FEATURE
misc_feature source SEQUENCE: 44
agagtcacct cgtgg | moltype = DNA   length = 15
Location/Qualifiers
1..15
note = oligonucleotide barcode BC_44
1..15
mol_type = other DNA
organism = synthetic construct | 15 |
| SEQ ID NO: 45
FEATURE
misc_feature source SEQUENCE: 45
ctgatgtagt cgaag | moltype = DNA   length = 15
Location/Qualifiers
1..15
note = oligonucleotide barcode BC_45
1..15
mol_type = other DNA
organism = synthetic construct | 15 |

```
SEQ ID NO: 46           moltype = DNA   length = 15
FEATURE                 Location/Qualifiers
misc_feature            1..15
                        note = oligonucleotide barcode BC_46
source                  1..15
                        mol_type = other DNA
                        organism = synthetic construct
SEQUENCE: 46
gtcggttgcg gatag                                                          15

SEQ ID NO: 47           moltype = DNA   length = 15
FEATURE                 Location/Qualifiers
misc_feature            1..15
                        note = oligonucleotide barcode BC_47
source                  1..15
                        mol_type = other DNA
                        organism = synthetic construct
SEQUENCE: 47
tcctcctcct aagaa                                                          15

SEQ ID NO: 48           moltype = DNA   length = 15
FEATURE                 Location/Qualifiers
misc_feature            1..15
                        note = oligonucleotide barcode BC_48
source                  1..15
                        mol_type = other DNA
                        organism = synthetic construct
SEQUENCE: 48
attcggtcca cttca                                                          15

SEQ ID NO: 49           moltype = DNA   length = 15
FEATURE                 Location/Qualifiers
misc_feature            1..15
                        note = oligonucleotide barcode BC_49
source                  1..15
                        mol_type = other DNA
                        organism = synthetic construct
SEQUENCE: 49
ccttacaggt ctgcg                                                          15

SEQ ID NO: 50           moltype = DNA   length = 15
FEATURE                 Location/Qualifiers
misc_feature            1..15
                        note = oligonucleotide barcode BC_50
source                  1..15
                        mol_type = other DNA
                        organism = synthetic construct
SEQUENCE: 50
gatcattggc caatt                                                          15

SEQ ID NO: 51           moltype = DNA   length = 15
FEATURE                 Location/Qualifiers
misc_feature            1..15
                        note = oligonucleotide barcode BC_51
source                  1..15
                        mol_type = other DNA
                        organism = synthetic construct
SEQUENCE: 51
ttcaaggctg agttg                                                          15

SEQ ID NO: 52           moltype = DNA   length = 15
FEATURE                 Location/Qualifiers
misc_feature            1..15
                        note = oligonucleotide barcode BC_52
source                  1..15
                        mol_type = other DNA
                        organism = synthetic construct
SEQUENCE: 52
tggctcgatt gaatc                                                          15

SEQ ID NO: 53           moltype = DNA   length = 15
FEATURE                 Location/Qualifiers
misc_feature            1..15
                        note = oligonucleotide barcode BC_53
source                  1..15
                        mol_type = other DNA
                        organism = synthetic construct
SEQUENCE: 53
```

```
gtaagccatc cgctc                                                      15

SEQ ID NO: 54           moltype = DNA   length = 15
FEATURE                 Location/Qualifiers
misc_feature            1..15
                        note = oligonucleotide barcode BC_54
source                  1..15
                        mol_type = other DNA
                        organism = synthetic construct SEQUENCE: 54
acacatgcgt agaca                                                      15

SEQ ID NO: 55           moltype = DNA   length = 15
FEATURE                 Location/Qualifiers
misc_feature            1..15
                        note = oligonucleotide barcode BC_55
source                  1..15
                        mol_type = other DNA
                        organism = synthetic construct SEQUENCE: 55
tgctatggat tcaag                                                      15

SEQ ID NO: 56           moltype = DNA   length = 15
FEATURE                 Location/Qualifiers
misc_feature            1..15
                        note = oligonucleotide barcode BC_56
source                  1..15
                        mol_type = other DNA
                        organism = synthetic construct SEQUENCE: 56
ccacgaggct tagtt                                                      15

SEQ ID NO: 57           moltype = DNA   length = 15
FEATURE                 Location/Qualifiers
misc_feature            1..15
                        note = oligonucleotide barcode BC_57
source                  1..15
                        mol_type = other DNA
                        organism = synthetic construct SEQUENCE: 57
ggccaactaa ggtgc                                                      15

SEQ ID NO: 58           moltype = DNA   length = 15
FEATURE                 Location/Qualifiers
misc_feature            1..15
                        note = oligonucleotide barcode BC_58
source                  1..15
                        mol_type = other DNA
                        organism = synthetic construct SEQUENCE: 58
gcacctattc gacaa                                                      15

SEQ ID NO: 59           moltype = DNA   length = 15
FEATURE                 Location/Qualifiers
misc_feature            1..15
                        note = oligonucleotide barcode BC_59
source                  1..15
                        mol_type = other DNA
                        organism = synthetic construct SEQUENCE: 59
tggacacgat cggct                                                      15

SEQ ID NO: 60           moltype = DNA   length = 15
FEATURE                 Location/Qualifiers
misc_feature            1..15
                        note = oligonucleotide barcode BC_60
source                  1..15
                        mol_type = other DNA
                        organism = synthetic construct SEQUENCE: 60
ctataattcc aacgg                                                      15

SEQ ID NO: 61           moltype = DNA   length = 15
FEATURE                 Location/Qualifiers
misc_feature            1..15
                        note = oligonucleotide barcode BC_61
source                  1..15
                        mol_type = other DNA
                        organism = synthetic construct
```

```
SEQUENCE: 61
aacgtggtta gtaag                                                           15

SEQ ID NO: 62           moltype = DNA  length = 15
FEATURE                 Location/Qualifiers
misc_feature            1..15
                        note = oligonucleotide barcode BC_62
source                  1..15
                        mol_type = other DNA
                        organism = synthetic construct
SEQUENCE: 62
caaggaacga gtggc                                                           15

SEQ ID NO: 63           moltype = DNA  length = 15
FEATURE                 Location/Qualifiers
misc_feature            1..15
                        note = oligonucleotide barcode BC_63
source                  1..15
                        mol_type = other DNA
                        organism = synthetic construct
SEQUENCE: 63
caccagaacg gaaga                                                           15

SEQ ID NO: 64           moltype = DNA  length = 15
FEATURE                 Location/Qualifiers
misc_feature            1..15
                        note = oligonucleotide barcode BC_64
source                  1..15
                        mol_type = other DNA
                        organism = synthetic construct
SEQUENCE: 64
cgtacggtca agcaa                                                           15

SEQ ID NO: 65           moltype = DNA  length = 15
FEATURE                 Location/Qualifiers
misc_feature            1..15
                        note = oligonucleotide barcode BC_65
source                  1..15
                        mol_type = other DNA
                        organism = synthetic construct
SEQUENCE: 65
tcggtgacag gctaa                                                           15

SEQ ID NO: 66           moltype = DNA  length = 15
FEATURE                 Location/Qualifiers
misc_feature            1..15
                        note = oligonucleotide barcode BC_1 REV
source                  1..15
                        mol_type = other DNA
                        organism = synthetic construct
SEQUENCE: 66
cggcatgcta gacat                                                           15

SEQ ID NO: 67           moltype = DNA  length = 15
FEATURE                 Location/Qualifiers
misc_feature            1..15
                        note = oligonucleotide barcode BC_2REV
source                  1..15
                        mol_type = other DNA
                        organism = synthetic construct
SEQUENCE: 67
ttccacatga cacgg                                                           15

SEQ ID NO: 68           moltype = DNA  length = 15
FEATURE                 Location/Qualifiers
misc_feature            1..15
                        note = oligonucleotide barcode BC_3REV
source                  1..15
                        mol_type = other DNA
                        organism = synthetic construct
SEQUENCE: 68
tgatataccg gctta                                                           15

SEQ ID NO: 69           moltype = DNA  length = 15
FEATURE                 Location/Qualifiers
misc_feature            1..15
                        note = oligonucleotide barcode BC_4REV
source                  1..15
                        mol_type = other DNA
```

```
                    organism = synthetic construct
SEQUENCE: 69
ttccgtcata tcgaa                                                            15

SEQ ID NO: 70       moltype = DNA  length = 15
FEATURE             Location/Qualifiers
misc_feature        1..15
                    note = oligonucleotide barcode BC_5REV
source              1..15
                    mol_type = other DNA
                    organism = synthetic construct
SEQUENCE: 70
cctaacgcgt atacg                                                            15

SEQ ID NO: 71       moltype = DNA  length = 15
FEATURE             Location/Qualifiers
misc_feature        1..15
                    note = oligonucleotide barcode BC_6REV
source              1..15
                    mol_type = other DNA
                    organism = synthetic construct
SEQUENCE: 71
ggaatctcgg cagtt                                                            15

SEQ ID NO: 72       moltype = DNA  length = 15
FEATURE             Location/Qualifiers
misc_feature        1..15
                    note = oligonucleotide barcode BC_7REV
source              1..15
                    mol_type = other DNA
                    organism = synthetic construct
SEQUENCE: 72
gcacagctaa gatca                                                            15

SEQ ID NO: 73       moltype = DNA  length = 15
FEATURE             Location/Qualifiers
misc_feature        1..15
                    note = oligonucleotide barcode BC_8REV
source              1..15
                    mol_type = other DNA
                    organism = synthetic construct
SEQUENCE: 73
tcaaggtacc gactc                                                            15

SEQ ID NO: 74       moltype = DNA  length = 15
FEATURE             Location/Qualifiers
misc_feature        1..15
                    note = oligonucleotide barcode BC_9REV
source              1..15
                    mol_type = other DNA
                    organism = synthetic construct
SEQUENCE: 74
ccagatcaca agcgg                                                            15

SEQ ID NO: 75       moltype = DNA  length = 15
FEATURE             Location/Qualifiers
misc_feature        1..15
                    note = oligonucleotide barcode BC_10REV
source              1..15
                    mol_type = other DNA
                    organism = synthetic construct
SEQUENCE: 75
tccggtacgc tatct                                                            15

SEQ ID NO: 76       moltype = DNA  length = 15
FEATURE             Location/Qualifiers
misc_feature        1..15
                    note = oligonucleotide barcode BC_11REV
source              1..15
                    mol_type = other DNA
                    organism = synthetic construct
SEQUENCE: 76
gatgatgagc ctgga                                                            15

SEQ ID NO: 77       moltype = DNA  length = 15
FEATURE             Location/Qualifiers
misc_feature        1..15
                    note = oligonucleotide barcode BC_12REV
source              1..15
```

```
                                   mol_type = other DNA
                                   organism = synthetic construct
SEQUENCE: 77
ttggctctag tactc                                                              15

SEQ ID NO: 78              moltype = DNA  length = 15
FEATURE                    Location/Qualifiers
misc_feature               1..15
                           note = oligonucleotide barcode BC_13REV
source                     1..15
                           mol_type = other DNA
                           organism = synthetic construct
SEQUENCE: 78
ccgttattga cgctc                                                              15

SEQ ID NO: 79              moltype = DNA  length = 15
FEATURE                    Location/Qualifiers
misc_feature               1..15
                           note = oligonucleotide barcode BC_14REV
source                     1..15
                           mol_type = other DNA
                           organism = synthetic construct
SEQUENCE: 79
cagtgtagat accgc                                                              15

SEQ ID NO: 80              moltype = DNA  length = 15
FEATURE                    Location/Qualifiers
misc_feature               1..15
                           note = oligonucleotide barcode BC_15REV
source                     1..15
                           mol_type = other DNA
                           organism = synthetic construct
SEQUENCE: 80
ttctcttcgg agaag                                                              15

SEQ ID NO: 81              moltype = DNA  length = 15
FEATURE                    Location/Qualifiers
misc_feature               1..15
                           note = oligonucleotide barcode BC_16REV
source                     1..15
                           mol_type = other DNA
                           organism = synthetic construct
SEQUENCE: 81
ttaacacagg cttca                                                              15

SEQ ID NO: 82              moltype = DNA  length = 15
FEATURE                    Location/Qualifiers
misc_feature               1..15
                           note = oligonucleotide barcode BC_17REV
source                     1..15
                           mol_type = other DNA
                           organism = synthetic construct
SEQUENCE: 82
tcgacaacca tccag                                                              15

SEQ ID NO: 83              moltype = DNA  length = 15
FEATURE                    Location/Qualifiers
misc_feature               1..15
                           note = oligonucleotide barcode BC_18REV
source                     1..15
                           mol_type = other DNA
                           organism = synthetic construct
SEQUENCE: 83
ttggaaccgt gcagt                                                              15

SEQ ID NO: 84              moltype = DNA  length = 15
FEATURE                    Location/Qualifiers
misc_feature               1..15
                           note = oligonucleotide barcode BC_19 REV
source                     1..15
                           mol_type = other DNA
                           organism = synthetic construct
SEQUENCE: 84
aaggaccatc tctcg                                                              15

SEQ ID NO: 85              moltype = DNA  length = 15
FEATURE                    Location/Qualifiers
misc_feature               1..15
                           note = oligonucleotide barcode BC_20 REV
```

```
source                        1..15
                              mol_type = other DNA
                              organism = synthetic construct
SEQUENCE: 85
tcttgtctct caaga                                                        15

SEQ ID NO: 86                 moltype = DNA  length = 15
FEATURE                       Location/Qualifiers
misc_feature                  1..15
                              note = oligonucleotide barcode BC_21 REV
source                        1..15
                              mol_type = other DNA
                              organism = synthetic construct
SEQUENCE: 86
aacacagtgc gaatt                                                        15

SEQ ID NO: 87                 moltype = DNA  length = 15
FEATURE                       Location/Qualifiers
misc_feature                  1..15
                              note = oligonucleotide barcode BC_22 REV
source                        1..15
                              mol_type = other DNA
                              organism = synthetic construct
SEQUENCE: 87
tcttagcggc actac                                                        15

SEQ ID NO: 88                 moltype = DNA  length = 15
FEATURE                       Location/Qualifiers
misc_feature                  1..15
                              note = oligonucleotide barcode BC_23 REV
source                        1..15
                              mol_type = other DNA
                              organism = synthetic construct
SEQUENCE: 88
ggattgtgct atagg                                                        15

SEQ ID NO: 89                 moltype = DNA  length = 15
FEATURE                       Location/Qualifiers
misc_feature                  1..15
                              note = oligonucleotide barcode BC_24 REV
source                        1..15
                              mol_type = other DNA
                              organism = synthetic construct
SEQUENCE: 89
tccaacctcg gtgat                                                        15

SEQ ID NO: 90                 moltype = DNA  length = 15
FEATURE                       Location/Qualifiers
misc_feature                  1..15
                              note = oligonucleotide barcode BC_25 REV
source                        1..15
                              mol_type = other DNA
                              organism = synthetic construct
SEQUENCE: 90
cttctccgtt gaatc                                                        15

SEQ ID NO: 91                 moltype = DNA  length = 15
FEATURE                       Location/Qualifiers
misc_feature                  1..15
                              note = oligonucleotide barcode BC_26 REV
source                        1..15
                              mol_type = other DNA
                              organism = synthetic construct
SEQUENCE: 91
tggtgcgagg ttcgt                                                        15

SEQ ID NO: 92                 moltype = DNA  length = 15
FEATURE                       Location/Qualifiers
misc_feature                  1..15
                              note = oligonucleotide barcode BC_27 REV
source                        1..15
                              mol_type = other DNA
                              organism = synthetic construct
SEQUENCE: 92
tcttcttgaa gtcct                                                        15

SEQ ID NO: 93                 moltype = DNA  length = 15
FEATURE                       Location/Qualifiers
misc_feature                  1..15
```

```
                              note = oligonucleotide barcode BC_28 REV
source                        1..15
                              mol_type = other DNA
                              organism = synthetic construct
SEQUENCE: 93
tgcgaggatt caacc                                                                  15

SEQ ID NO: 94                 moltype = DNA   length = 15
FEATURE                       Location/Qualifiers
misc_feature                  1..15
                              note = oligonucleotide barcode BC_29 REV
source                        1..15
                              mol_type = other DNA
                              organism = synthetic construct
SEQUENCE: 94
cgctagaggt tggtt                                                                  15

SEQ ID NO: 95                 moltype = DNA   length = 15
FEATURE                       Location/Qualifiers
misc_feature                  1..15
                              note = oligonucleotide barcode BC_30 REV
source                        1..15
                              mol_type = other DNA
                              organism = synthetic construct
SEQUENCE: 95
gttagatatt cgcgt                                                                  15

SEQ ID NO: 96                 moltype = DNA   length = 15
FEATURE                       Location/Qualifiers
misc_feature                  1..15
                              note = oligonucleotide barcode BC_31 REV
source                        1..15
                              mol_type = other DNA
                              organism = synthetic construct
SEQUENCE: 96
ggtgtaattc tcaac                                                                  15

SEQ ID NO: 97                 moltype = DNA   length = 15
FEATURE                       Location/Qualifiers
misc_feature                  1..15
                              note = oligonucleotide barcode BC_32 REV
source                        1..15
                              mol_type = other DNA
                              organism = synthetic construct
SEQUENCE: 97
ggttcacaga gagag                                                                  15

SEQ ID NO: 98                 moltype = DNA   length = 15
FEATURE                       Location/Qualifiers
misc_feature                  1..15
                              note = oligonucleotide barcode BC_33 REV
source                        1..15
                              mol_type = other DNA
                              organism = synthetic construct
SEQUENCE: 98
tctcttactg atggc                                                                  15

SEQ ID NO: 99                 moltype = DNA   length = 15
FEATURE                       Location/Qualifiers
misc_feature                  1..15
                              note = oligonucleotide barcode BC_34 REV
source                        1..15
                              mol_type = other DNA
                              organism = synthetic construct
SEQUENCE: 99
ctcaattcac gttgc                                                                  15

SEQ ID NO: 100                moltype = DNA   length = 15
FEATURE                       Location/Qualifiers
misc_feature                  1..15
                              note = oligonucleotide barcode BC_35 REV
source                        1..15
                              mol_type = other DNA
                              organism = synthetic construct
SEQUENCE: 100
tgtggctcta cttag                                                                  15

SEQ ID NO: 101                moltype = DNA   length = 15
FEATURE                       Location/Qualifiers
```

```
misc_feature                 1..15
                             note = oligonucleotide barcode BC_36 REV
source                       1..15
                             mol_type = other DNA
                             organism = synthetic construct
SEQUENCE: 101
cgcttccaac agaca                                                              15

SEQ ID NO: 102               moltype = DNA  length = 15
FEATURE                      Location/Qualifiers
misc_feature                 1..15
                             note = oligonucleotide barcode BC_37 REV
source                       1..15
                             mol_type = other DNA
                             organism = synthetic construct
SEQUENCE: 102
cgcgctgtct attaa                                                              15

SEQ ID NO: 103               moltype = DNA  length = 15
FEATURE                      Location/Qualifiers
misc_feature                 1..15
                             note = oligonucleotide barcode BC_38 REV
source                       1..15
                             mol_type = other DNA
                             organism = synthetic construct
SEQUENCE: 103
cttgttagag cgtcg                                                              15

SEQ ID NO: 104               moltype = DNA  length = 15
FEATURE                      Location/Qualifiers
misc_feature                 1..15
                             note = oligonucleotide barcode BC_39 REV
source                       1..15
                             mol_type = other DNA
                             organism = synthetic construct
SEQUENCE: 104
tctcaataag ccatg                                                              15

SEQ ID NO: 105               moltype = DNA  length = 15
FEATURE                      Location/Qualifiers
misc_feature                 1..15
                             note = oligonucleotide barcode BC_40 REV
source                       1..15
                             mol_type = other DNA
                             organism = synthetic construct
SEQUENCE: 105
ccggccatac ctagt                                                              15

SEQ ID NO: 106               moltype = DNA  length = 15
FEATURE                      Location/Qualifiers
misc_feature                 1..15
                             note = oligonucleotide barcode BC_41 REV
source                       1..15
                             mol_type = other DNA
                             organism = synthetic construct
SEQUENCE: 106
aggatagacg aggac                                                              15

SEQ ID NO: 107               moltype = DNA  length = 15
FEATURE                      Location/Qualifiers
misc_feature                 1..15
                             note = oligonucleotide barcode BC_42 REV
source                       1..15
                             mol_type = other DNA
                             organism = synthetic construct
SEQUENCE: 107
ggtaacggaa tccta                                                              15

SEQ ID NO: 108               moltype = DNA  length = 15
FEATURE                      Location/Qualifiers
misc_feature                 1..15
                             note = oligonucleotide barcode BC_43 REV
source                       1..15
                             mol_type = other DNA
                             organism = synthetic construct
SEQUENCE: 108
cttccggtgg tcaga                                                              15

SEQ ID NO: 109               moltype = DNA  length = 15
```

```
                                  -continued

FEATURE                 Location/Qualifiers
misc_feature            1..15
                        note = oligonucleotide barcode BC_44 REV
source                  1..15
                        mol_type = other DNA
                        organism = synthetic construct SEQUENCE: 109
ccacgaggtg actct                                                            15

SEQ ID NO: 110          moltype = DNA   length = 15
FEATURE                 Location/Qualifiers
misc_feature            1..15
                        note = oligonucleotide barcode BC_45 REV
source                  1..15
                        mol_type = other DNA
                        organism = synthetic construct SEQUENCE: 110
cttcgactac atcag                                                            15

SEQ ID NO: 111          moltype = DNA   length = 15
FEATURE                 Location/Qualifiers
misc_feature            1..15
                        note = oligonucleotide barcode BC_46 REV
source                  1..15
                        mol_type = other DNA
                        organism = synthetic construct SEQUENCE: 111
ctatccgcaa ccgac                                                            15

SEQ ID NO: 112          moltype = DNA   length = 15
FEATURE                 Location/Qualifiers
misc_feature            1..15
                        note = oligonucleotide barcode BC_47 REV
source                  1..15
                        mol_type = other DNA
                        organism = synthetic construct SEQUENCE: 112
ttcttaggag gagga                                                            15

SEQ ID NO: 113          moltype = DNA   length = 15
FEATURE                 Location/Qualifiers
misc_feature            1..15
                        note = oligonucleotide barcode BC_48 REV
source                  1..15
                        mol_type = other DNA
                        organism = synthetic construct SEQUENCE: 113
tgaagtggac cgaat                                                            15

SEQ ID NO: 114          moltype = DNA   length = 15
FEATURE                 Location/Qualifiers
misc_feature            1..15
                        note = oligonucleotide barcode BC_49 REV
source                  1..15
                        mol_type = other DNA
                        organism = synthetic construct SEQUENCE: 114
cgcagacctg taagg                                                            15

SEQ ID NO: 115          moltype = DNA   length = 15
FEATURE                 Location/Qualifiers
misc_feature            1..15
                        note = oligonucleotide barcode BC_50 REV
source                  1..15
                        mol_type = other DNA
                        organism = synthetic construct SEQUENCE: 115
aattggccaa tgatc                                                            15

SEQ ID NO: 116          moltype = DNA   length = 15
FEATURE                 Location/Qualifiers
misc_feature            1..15
                        note = oligonucleotide barcode BC_51 REV
source                  1..15
                        mol_type = other DNA
                        organism = synthetic construct SEQUENCE: 116
caactcagcc ttgaa                                                            15
```

| | | |
|---|---|---|
| SEQ ID NO: 117<br>FEATURE<br>misc_feature<br>source | moltype = DNA   length = 15<br>Location/Qualifiers<br>1..15<br>note = oligonucleotide barcode BC_52 REV<br>1..15<br>mol_type = other DNA<br>organism = synthetic construct | |
| SEQUENCE: 117<br>gattcaatcg agcca | | 15 |
| SEQ ID NO: 118<br>FEATURE<br>misc_feature<br>source | moltype = DNA   length = 15<br>Location/Qualifiers<br>1..15<br>note = oligonucleotide barcode BC_53 REV<br>1..15<br>mol_type = other DNA<br>organism = synthetic construct | |
| SEQUENCE: 118<br>gagcggatgg cttac | | 15 |
| SEQ ID NO: 119<br>FEATURE<br>misc_feature<br>source | moltype = DNA   length = 15<br>Location/Qualifiers<br>1..15<br>note = oligonucleotide barcode BC_54 REV<br>1..15<br>mol_type = other DNA<br>organism = synthetic construct | |
| SEQUENCE: 119<br>tgtctacgca tgtgt | | 15 |
| SEQ ID NO: 120<br>FEATURE<br>misc_feature<br>source | moltype = DNA   length = 15<br>Location/Qualifiers<br>1..15<br>note = oligonucleotide barcode BC_55 REV<br>1..15<br>mol_type = other DNA<br>organism = synthetic construct | |
| SEQUENCE: 120<br>cttgaatcca tagca | | 15 |
| SEQ ID NO: 121<br>FEATURE<br>misc_feature<br>source | moltype = DNA   length = 15<br>Location/Qualifiers<br>1..15<br>note = oligonucleotide barcode BC_56 REV<br>1..15<br>mol_type = other DNA<br>organism = synthetic construct | |
| SEQUENCE: 121<br>aactaagcct cgtgg | | 15 |
| SEQ ID NO: 122<br>FEATURE<br>misc_feature<br>source | moltype = DNA   length = 15<br>Location/Qualifiers<br>1..15<br>note = oligonucleotide barcode BC_57 REV<br>1..15<br>mol_type = other DNA<br>organism = synthetic construct | |
| SEQUENCE: 122<br>gcaccttagt tggcc | | 15 |
| SEQ ID NO: 123<br>FEATURE<br>misc_feature<br>source | moltype = DNA   length = 15<br>Location/Qualifiers<br>1..15<br>note = oligonucleotide barcode BC_58 REV<br>1..15<br>mol_type = other DNA<br>organism = synthetic construct | |
| SEQUENCE: 123<br>ttgtcgaata ggtgc | | 15 |
| SEQ ID NO: 124<br>FEATURE<br>misc_feature<br>source | moltype = DNA   length = 15<br>Location/Qualifiers<br>1..15<br>note = oligonucleotide barcode BC_59 REV<br>1..15<br>mol_type = other DNA<br>organism = synthetic construct | |
| SEQUENCE: 124<br>agccgatcgt gtcca | | 15 |

```
SEQ ID NO: 125          moltype = DNA   length = 15
FEATURE                 Location/Qualifiers
misc_feature            1..15
                        note = oligonucleotide barcode BC_60 REV
source                  1..15
                        mol_type = other DNA
                        organism = synthetic construct
SEQUENCE: 125
ccgttggaat tatag                                                          15

SEQ ID NO: 126          moltype = DNA   length = 15
FEATURE                 Location/Qualifiers
misc_feature            1..15
                        note = oligonucleotide barcode BC_61 REV
source                  1..15
                        mol_type = other DNA
                        organism = synthetic construct
SEQUENCE: 126
cttactaacc acgtt                                                          15

SEQ ID NO: 127          moltype = DNA   length = 15
FEATURE                 Location/Qualifiers
misc_feature            1..15
                        note = oligonucleotide barcode BC_62 REV
source                  1..15
                        mol_type = other DNA
                        organism = synthetic construct
SEQUENCE: 127
gccactcgtt ccttg                                                          15

SEQ ID NO: 128          moltype = DNA   length = 15
FEATURE                 Location/Qualifiers
misc_feature            1..15
                        note = oligonucleotide barcode BC_63 REV
source                  1..15
                        mol_type = other DNA
                        organism = synthetic construct
SEQUENCE: 128
tcttccgttc tggtg                                                          15

SEQ ID NO: 129          moltype = DNA   length = 15
FEATURE                 Location/Qualifiers
misc_feature            1..15
                        note = oligonucleotide barcode BC_64 REV
source                  1..15
                        mol_type = other DNA
                        organism = synthetic construct
SEQUENCE: 129
ttgcttgacc gtacg                                                          15

SEQ ID NO: 130          moltype = DNA   length = 15
FEATURE                 Location/Qualifiers
misc_feature            1..15
                        note = oligonucleotide barcode BC_65 REV
source                  1..15
                        mol_type = other DNA
                        organism = synthetic construct
SEQUENCE: 130
ttagcctgtc accga                                                          15

SEQ ID NO: 131          moltype = AA   length = 16
FEATURE                 Location/Qualifiers
REGION                  1..16
                        note = synthetic peptide
MOD_RES                 1
                        note = formyl-Methionine
source                  1..16
                        mol_type = protein
                        organism = synthetic construct
SEQUENCE: 131
MDVEAWLGAR VPLVET                                                         16

SEQ ID NO: 132          moltype = AA   length = 10
FEATURE                 Location/Qualifiers
REGION                  1..10
                        note = synthetic peptide
source                  1..10
                        mol_type = protein
```

```
                                    organism = synthetic construct
SEQUENCE: 132
TENLYFQNHV                                                                      10

SEQ ID NO: 133          moltype = DNA  length = 20
FEATURE                 Location/Qualifiers
misc_feature            1..20
                        note = oligonucleotide primer
source                  1..20
                        mol_type = other DNA
                        organism = synthetic construct
SEQUENCE: 133
aatgatacgg cgaccaccga                                                           20

SEQ ID NO: 134          moltype = DNA  length = 24
FEATURE                 Location/Qualifiers
misc_feature            1..24
                        note = oligonucleotide primer
source                  1..24
                        mol_type = other DNA
                        organism = synthetic construct
SEQUENCE: 134
caagcagaag acggcatacg agat                                                      24

SEQ ID NO: 135          moltype =   length =
SEQUENCE: 135
000

SEQ ID NO: 136          moltype = AA  length = 8
FEATURE                 Location/Qualifiers
REGION                  1..8
                        note = synthetic peptide
source                  1..8
                        mol_type = protein
                        organism = synthetic construct
SEQUENCE: 136
DYKDDDDK                                                                        8

SEQ ID NO: 137          moltype = AA  length = 14
FEATURE                 Location/Qualifiers
REGION                  1..14
                        note = synthetic peptide
source                  1..14
                        mol_type = protein
                        organism = synthetic construct
SEQUENCE: 137
GKPIPNPLLG LDST                                                                 14

SEQ ID NO: 138          moltype = AA  length = 10
FEATURE                 Location/Qualifiers
REGION                  1..10
                        note = synthetic peptide
source                  1..10
                        mol_type = protein
                        organism = synthetic construct
SEQUENCE: 138
EQKLISEEDL                                                                      10

SEQ ID NO: 139          moltype = AA  length = 9
FEATURE                 Location/Qualifiers
REGION                  1..9
                        note = synthetic peptide
source                  1..9
                        mol_type = protein
                        organism = synthetic construct
SEQUENCE: 139
YPYDVPDYA                                                                       9

SEQ ID NO: 140          moltype = AA  length = 9
FEATURE                 Location/Qualifiers
REGION                  1..9
                        note = synthetic peptide
source                  1..9
                        mol_type = protein
                        organism = synthetic construct
SEQUENCE: 140
NWSHPQFEK                                                                       9

SEQ ID NO: 141          moltype = DNA  length = 82
```

```
FEATURE                 Location/Qualifiers
misc_feature            1..82
                        note = synthetic oligonucleotide
source                  1..82
                        mol_type = other DNA
                        organism = synthetic construct
misc_feature            1
                        note = biotin
SEQUENCE: 141
tttttgcaaa tggcattctg acatcccgta gtccgcgaca ctagatgtct agcatgccgc    60
cgtgtcatgt ggaaactgag tg                                             82

SEQ ID NO: 142          moltype = DNA  length = 72
FEATURE                 Location/Qualifiers
misc_feature            1..72
                        note = synthetic oligonucleotide
source                  1..72
                        mol_type = other DNA
                        organism = synthetic construct
misc_feature            1
                        note = biotin
SEQUENCE: 142
tttttttttt gactggttcc aattgacaag ccgtagtccg cgacactagt aagccggtat    60
atcaactgag tg                                                        72

SEQ ID NO: 143          moltype = DNA  length = 10
FEATURE                 Location/Qualifiers
misc_feature            1..10
                        note = synthetic oligonucleotide
source                  1..10
                        mol_type = other DNA
                        organism = synthetic construct
misc_feature            1
                        note = biotin
misc_feature            10
                        note = three carbon (3C) spacer
SEQUENCE: 143
tttttttttt                                                           10

SEQ ID NO: 144          moltype = DNA  length = 31
FEATURE                 Location/Qualifiers
misc_feature            1..31
                        note = synthetic oligonucleotide
source                  1..31
                        mol_type = other DNA
                        organism = synthetic construct
misc_feature            31
                        note = 18-atom hexa-ethyleneglycol spacer
SEQUENCE: 144
ggatgtcaga atgccatttg ctttttttttt t                                  31

SEQ ID NO: 145          moltype = DNA  length = 31
FEATURE                 Location/Qualifiers
misc_feature            1..31
                        note = synthetic oligonucleotide
source                  1..31
                        mol_type = other DNA
                        organism = synthetic construct
misc_feature            31
                        note = 18-atom hexa-ethyleneglycol spacer
SEQUENCE: 145
ggatgtcaga atgccatttg ctttttttttt t                                  31

SEQ ID NO: 146          moltype = DNA  length = 31
FEATURE                 Location/Qualifiers
misc_feature            1..31
                        note = synthetic oligonucleotide
source                  1..31
                        mol_type = other DNA
                        organism = synthetic construct
misc_feature            31
                        note = five 18-atom hexa-ethyleneglycol spacers
SEQUENCE: 146
ggatgtcaga atgccatttg ctttttttttt t                                  31

SEQ ID NO: 147          moltype = DNA  length = 25
FEATURE                 Location/Qualifiers
misc_feature            1..25
                        note = synthetic oligonucleotide
```

```
source                    1..25
                          mol_type = other DNA
                          organism = synthetic construct
misc_feature              25
                          note = 18-atom hexa-ethyleneglycol spacer
SEQUENCE: 147
gcttgtcaat tggaaccagt ctttt                                           25

SEQ ID NO: 148            moltype = DNA  length = 44
FEATURE                   Location/Qualifiers
misc_feature              1..44
                          note = synthetic oligonucleotide
source                    1..44
                          mol_type = other DNA
                          organism = synthetic construct
misc_feature              44
                          note = three carbon (3C) spacer
SEQUENCE: 148
cgatttgcaa ggatcactcg tcactcagtc ctaacgcgta tacg                      44

SEQ ID NO: 149            moltype =   length =
SEQUENCE: 149
000

SEQ ID NO: 150            moltype =   length =
SEQUENCE: 150
000

SEQ ID NO: 151            moltype = DNA  length = 18
FEATURE                   Location/Qualifiers
misc_feature              1..18
                          note = oligonucleotide primer
source                    1..18
                          mol_type = other DNA
                          organism = synthetic construct
SEQUENCE: 151
cgtagtccgc gacactag                                                   18

SEQ ID NO: 152            moltype = DNA  length = 20
FEATURE                   Location/Qualifiers
misc_feature              1..20
                          note = oligonucleotide primer
source                    1..20
                          mol_type = other DNA
                          organism = synthetic construct
SEQUENCE: 152
cgatttgcaa ggatcactcg                                                 20

SEQ ID NO: 153            moltype = DNA  length = 21
FEATURE                   Location/Qualifiers
misc_feature              1..21
                          note = synthetic oligonucleotide
source                    1..21
                          mol_type = other DNA
                          organism = synthetic construct
SEQUENCE: 153
gcaaatggca ttctgacatc c                                               21

SEQ ID NO: 154            moltype = DNA  length = 21
FEATURE                   Location/Qualifiers
misc_feature              1..21
                          note = synthetic oligonucleotide
source                    1..21
                          mol_type = other DNA
                          organism = synthetic construct
SEQUENCE: 154
gactggttcc aattgacaag c                                               21

SEQ ID NO: 155            moltype = DNA  length = 23
FEATURE                   Location/Qualifiers
misc_feature              1..23
                          note = synthetic oligonucleotide
source                    1..23
                          mol_type = other DNA
                          organism = synthetic construct
misc_feature              23
                          note = three carbon (3C) spacer
SEQUENCE: 155
cgtatacgcg ttaggactga gtg                                             23
```

```
SEQ ID NO: 156          moltype = DNA   length = 38
FEATURE                 Location/Qualifiers
misc_feature            1..38
                        note = synthetic oligonucleotide
source                  1..38
                        mol_type = other DNA
                        organism = synthetic construct
misc_feature            38
                        note = three carbon (3C) spacer
SEQUENCE: 156
aactgccgag attcccgtat acgcgttagg actgagtg                                 38

SEQ ID NO: 157          moltype = DNA   length = 46
FEATURE                 Location/Qualifiers
misc_feature            1..46
                        note = oligonucleotide primer
source                  1..46
                        mol_type = other DNA
                        organism = synthetic construct
SEQUENCE: 157
agtccgcgca atcagatgtc tagcatgccg gatccggatc gatctc                        46

SEQ ID NO: 158          moltype = DNA   length = 46
FEATURE                 Location/Qualifiers
misc_feature            1..46
                        note = oligonucleotide primer
source                  1..46
                        mol_type = other DNA
                        organism = synthetic construct
SEQUENCE: 158
agtccgcgca atcagccgtg tcatgtggaa gatccggatc gatctc                        46

SEQ ID NO: 159          moltype = DNA   length = 46
FEATURE                 Location/Qualifiers
misc_feature            1..46
                        note = oligonucleotide primer
source                  1..46
                        mol_type = other DNA
                        organism = synthetic construct
SEQUENCE: 159
agtccgcgca atcagtaagc cggtatatca gatccggatc gatctc                        46

SEQ ID NO: 160          moltype = DNA   length = 46
FEATURE                 Location/Qualifiers
misc_feature            1..46
                        note = oligonucleotide primer
source                  1..46
                        mol_type = other DNA
                        organism = synthetic construct
SEQUENCE: 160
agtccgcgca atcagttcga tatgacggaa gatccggatc gatctc                        46

SEQ ID NO: 161          moltype = DNA   length = 46
FEATURE                 Location/Qualifiers
misc_feature            1..46
                        note = oligonucleotide primer
source                  1..46
                        mol_type = other DNA
                        organism = synthetic construct
SEQUENCE: 161
tgcaaggatc actcgccaga tcacaagcgg gagatcgatc cggatc                        46

SEQ ID NO: 162          moltype = DNA   length = 46
FEATURE                 Location/Qualifiers
misc_feature            1..46
                        note = oligonucleotide primer
source                  1..46
                        mol_type = other DNA
                        organism = synthetic construct
SEQUENCE: 162
tgcaaggatc actcgtccgg tacgctatct gagatcgatc cggatc                        46

SEQ ID NO: 163          moltype = DNA   length = 46
FEATURE                 Location/Qualifiers
misc_feature            1..46
                        note = oligonucleotide primer
source                  1..46
                        mol_type = other DNA
```

```
                          organism = synthetic construct
SEQUENCE: 163
tgcaaggatc actcggatga tgagcctgga gagatcgatc cggatc           46

SEQ ID NO: 164            moltype = DNA   length = 46
FEATURE                   Location/Qualifiers
misc_feature              1..46
                          note = oligonucleotide primer
source                    1..46
                          mol_type = other DNA
                          organism = synthetic construct
SEQUENCE: 164
tgcaaggatc actcgttggc tctagtactc gagatcgatc cggatc           46

SEQ ID NO: 165            moltype = DNA   length = 21
FEATURE                   Location/Qualifiers
misc_feature              1..21
                          note = oligonucleotide primer
source                    1..21
                          mol_type = other DNA
                          organism = synthetic construct
SEQUENCE: 165
aatcgtagtc cgcgcaatca g                                      21

SEQ ID NO: 166            moltype = DNA   length = 21
FEATURE                   Location/Qualifiers
misc_feature              1..21
                          note = oligonucleotide primer
source                    1..21
                          mol_type = other DNA
                          organism = synthetic construct
SEQUENCE: 166
acgatttgca aggatcactc g                                      21

SEQ ID NO: 167            moltype = DNA   length = 16
FEATURE                   Location/Qualifiers
misc_feature              1..16
                          note = spacer sequence
source                    1..16
                          mol_type = other DNA
                          organism = synthetic construct
SEQUENCE: 167
gatccggatc gatctc                                            16

SEQ ID NO: 168            moltype = DNA   length = 734
FEATURE                   Location/Qualifiers
misc_feature              1..734
                          note = extended recording tag construct
source                    1..734
                          mol_type = other DNA
                          organism = synthetic construct
SEQUENCE: 168
aatcacggta caagtcactc atccgtacgc tatctgagaa tcgtccagat ccggcatgct   60
agtatctggt gcagactacg attgttacag atcactcaga tgatgagcac agaaaatcgt  120
cgaatcttcc atcaccatcg aacagttacg attaatgtag tccgcacaat cgaatgtcta  180
acatgccgaa tcccgacgt ctccagcttc taaaccaaca gtagtcgcac aaatcattgt  240
acggtacaag atctaacgag agatgatcgg atctgaccac tttaaacact gattacgcag  300
actacgatta cgatttaaga atcctcgtcc ggtacaatca tagtccgcac aatcaaccgt  360
gtcatgtgaa gatcagatcg atctcgaata gcgtaccaga cagtgatctt gcaaatcgta  420
atgtgtccgc gccaatcgat agccatgaat cccagtcgat ctcccgcttg tgatctggcg  480
atcgccttgt accgtcgtac gatttgagat cacctcgtta actcaagcta aagatcgtcc  540
ggatcgcttt ataaacatct gattgcgcgg tacgattatc gtagtccgca catatcgaac  600
ctgttgaaga tccggatcgt ctctccaggc tcatcatccg agtgatcctt gcaaataatc  660
atgtccgcac catcaggtgt ctaacgcttg ccggatccga atcgatctct ccaggctcat  720
catcgaagtg atgt                                                    734

SEQ ID NO: 169            moltype = AA   length = 10
FEATURE                   Location/Qualifiers
REGION                    1..10
                          note = synthetic peptide
source                    1..10
                          mol_type = protein
                          organism = synthetic construct
SEQUENCE: 169
CPVQLWVDST                                                   10

SEQ ID NO: 170            moltype = AA   length = 10
FEATURE                   Location/Qualifiers
REGION                    1..10
```

```
                        note = synthetic peptide
VARIANT                 1..10
                        note = Xaa = Any Amino Acid
source                  1..10
                        mol_type = protein
                        organism = synthetic construct
SEQUENCE: 170
CPXQXWXDXT                                                                  10

SEQ ID NO: 171          moltype = AA  length = 8
FEATURE                 Location/Qualifiers
REGION                  1..8
                        note = FLAG epitope peptide
source                  1..8
                        mol_type = protein
                        organism = synthetic construct
SEQUENCE: 171
DYKDDDDK                                                                    8

SEQ ID NO: 172          moltype = AA  length = 14
FEATURE                 Location/Qualifiers
REGION                  1..14
                        note = V5 epitope peptide
source                  1..14
                        mol_type = protein
                        organism = synthetic construct
SEQUENCE: 172
GKPIPNPLLG LDST                                                             14

SEQ ID NO: 173          moltype = AA  length = 10
FEATURE                 Location/Qualifiers
REGION                  1..10
                        note = c-Myc epitope peptide
source                  1..10
                        mol_type = protein
                        organism = synthetic construct
SEQUENCE: 173
EQKLISEEDL                                                                  10

SEQ ID NO: 174          moltype = AA  length = 9
FEATURE                 Location/Qualifiers
REGION                  1..9
                        note = HA epitope peptide
source                  1..9
                        mol_type = protein
                        organism = synthetic construct
SEQUENCE: 174
YPYDVPDYA                                                                   9

SEQ ID NO: 175          moltype = AA  length = 14
FEATURE                 Location/Qualifiers
REGION                  1..14
                        note = V5 epitope peptide
source                  1..14
                        mol_type = protein
                        organism = synthetic construct
SEQUENCE: 175
GKPIPNPLLG LDST                                                             14

SEQ ID NO: 176          moltype = AA  length = 9
FEATURE                 Location/Qualifiers
REGION                  1..9
                        note = StrepTag II peptide
source                  1..9
                        mol_type = protein
                        organism = synthetic construct
SEQUENCE: 176
NWSHPQFEK                                                                   9

SEQ ID NO: 177          moltype = DNA  length = 36
FEATURE                 Location/Qualifiers
misc_feature            1..36
                        note = synthetic nucleotide
misc_feature            11..22
                        note = compartment bar code n = A, C, T, or G
misc_feature            23..27
                        note = unique molecular identifier n = A, T, C or G
source                  1..36
                        mol_type = other DNA
```

```
                        organism = synthetic construct
SEQUENCE: 177
gcgcaatcag nnnnnnnnnn nnnnnnntgc aaggat                             36

SEQ ID NO: 178          moltype =    length =
SEQUENCE: 178
000

SEQ ID NO: 179          moltype =    length =
SEQUENCE: 179
000

SEQ ID NO: 180          moltype = AA  length = 10
FEATURE                 Location/Qualifiers
REGION                  1..10
                        note = butelase I peptide substrate
source                  1..10
                        mol_type = protein
                        organism = synthetic construct
SEQUENCE: 180
CGGSSGSNHV                                                          10

SEQ ID NO: 181          moltype = DNA  length = 47
FEATURE                 Location/Qualifiers
misc_feature            1..47
                        note = synthetic construct
misc_feature            1
                        note = 5'-phosphorylated
misc_feature            47
                        note = 3'-biotinylated
source                  1..47
                        mol_type = other DNA
                        organism = synthetic construct
SEQUENCE: 181
tgacatctag tgtcgcggac tacgtgcttg tcaattggaa ccagtct                 47

SEQ ID NO: 182          moltype = DNA  length = 49
FEATURE                 Location/Qualifiers
misc_feature            1..49
                        note = synthetic construct
misc_feature            1
                        note = 5'-phosphorylated
misc_feature            49
                        note = 3'-biotinylated
source                  1..49
                        mol_type = other DNA
                        organism = synthetic construct
SEQUENCE: 182
tgacatgtga aattgttatc cgctcatgga tgtcagaatg ccatttgct               49

SEQ ID NO: 183          moltype = DNA  length = 21
FEATURE                 Location/Qualifiers
misc_feature            1..21
                        note = synthetic construct
misc_feature            21
                        note = 3 18-atom hexa-ethyleneglycol spacers
source                  1..21
                        mol_type = other DNA
                        organism = synthetic construct
SEQUENCE: 183
gactggttcc aattgacaag c                                             21

SEQ ID NO: 184          moltype = DNA  length = 76
FEATURE                 Location/Qualifiers
misc_feature            1..76
                        note = synthetic construct
misc_feature            1
                        note = 5' Biotin
source                  1..76
                        mol_type = other DNA
                        organism = synthetic construct
SEQUENCE: 184
tttttgcaaa tggcattctg acatcccgta gtccgcgaca ctagatgtct agcatgccgc   60
cgtgtcatgt ggaaga                                                   76

SEQ ID NO: 185          moltype = DNA  length = 54
FEATURE                 Location/Qualifiers
misc_feature            1..54
                        note = synthetic construct
```

```
misc_feature            1
                        note = 5'-phosphorylated
misc_feature            54
                        note = 3' C3 (three carbon) spacer
source                  1..54
                        mol_type = other DNA
                        organism = synthetic construct
SEQUENCE: 185
ctcttcttcc acatgacacg gcggcatgct agacatctag tgtcgcggac tacg        54

SEQ ID NO: 186          moltype = DNA   length = 31
FEATURE                 Location/Qualifiers
misc_feature            1..31
                        note = synthetic construct
misc_feature            31
                        note = 18-atom hexa-ethyleneglycol spacer
source                  1..31
                        mol_type = other DNA
                        organism = synthetic construct
modified_base           6
                        mod_base = OTHER
                        note = uracil
modified_base           12
                        mod_base = OTHER
                        note = uracil
SEQUENCE: 186
ggatgtcaga atgccatttg ctttttttt t                                  31

SEQ ID NO: 187          moltype = DNA   length = 35
FEATURE                 Location/Qualifiers
misc_feature            1..35
                        note = synthetic construct
misc_feature            1
                        note = 5'-phosphorylated
misc_feature            35
                        note = 3' C3 (three carbon) spacer
source                  1..35
                        mol_type = other DNA
                        organism = synthetic construct
modified_base           24
                        mod_base = OTHER
                        note = uracil
SEQUENCE: 187
agagtccgta tacgcgttag ggatgagaga gaccg                             35

SEQ ID NO: 188          moltype = DNA   length = 31
FEATURE                 Location/Qualifiers
misc_feature            1..31
                        note = synthetic construct
misc_feature            31
                        note = 18-atom hexa-ethyleneglycol spacer
source                  1..31
                        mol_type = other DNA
                        organism = synthetic construct
modified_base           6
                        mod_base = OTHER
                        note = uracil
modified_base           12
                        mod_base = OTHER
                        note = uracil
SEQUENCE: 188
ggatgtcaga atgccatttg ctttttttt t                                  31

SEQ ID NO: 189          moltype = DNA   length = 49
FEATURE                 Location/Qualifiers
misc_feature            1..49
                        note = synthetic construct
misc_feature            1
                        note = 5'-phosphorylated
misc_feature            49
                        note = 3' C3 (three carbon) spacer
source                  1..49
                        mol_type = other DNA
                        organism = synthetic construct
SEQUENCE: 189
agagtcgagc gtcaataacg gcgagtgatc cttgcaaatc gagagaccg              49

SEQ ID NO: 190          moltype = DNA   length = 81
FEATURE                 Location/Qualifiers
```

```
misc_feature              1..81
                          note = synthetic construct
misc_feature              1
                          note = 5' amine group
variation                 23..24
                          note = 5'-Octadiynyl dU
source                    1..81
                          mol_type = other DNA
                          organism = synthetic construct
modified_base             28
                          mod_base = OTHER
                          note = uracil
modified_base             31
                          mod_base = OTHER
                          note = uracil
SEQUENCE: 190
gcaaatggca ttctgacatc cttttcgtag tccgcgacac tagatgtcta gcatgccgcc    60
gtgtcatgtg gaaactgagt g                                              81

SEQ ID NO: 191            moltype = DNA  length = 32
FEATURE                   Location/Qualifiers
misc_feature              1..32
                          note = synthetic construct
misc_feature              1
                          note = 5' amine group 18-atom hexa-ethyleneglycol spacer
misc_feature              32
                          note = 3' C3 (three carbon) spacer
source                    1..32
                          mol_type = other DNA
                          organism = synthetic construct
SEQUENCE: 191
cactcagtcc taacgcgtat acgtcactca gt                                  32

SEQ ID NO: 192            moltype = DNA  length = 31
FEATURE                   Location/Qualifiers
misc_feature              1..31
                          note = synthetic construct
misc_feature              31
                          note = 18-atom hexa-ethyleneglycol spacer
source                    1..31
                          mol_type = other DNA
                          organism = synthetic construct
SEQUENCE: 192
ggatgtcaga atgccatttg cttttttttt t                                   31

SEQ ID NO: 193            moltype = DNA  length = 24
FEATURE                   Location/Qualifiers
misc_feature              1..24
                          note = synthetic construct
source                    1..24
                          mol_type = other DNA
                          organism = synthetic construct
SEQUENCE: 193
cactcagttt ccacatgaca cggc                                           24

SEQ ID NO: 194            moltype = DNA  length = 21
FEATURE                   Location/Qualifiers
misc_feature              1..21
                          note = synthetic construct
source                    1..21
                          mol_type = other DNA
                          organism = synthetic construct
SEQUENCE: 194
cactcagtcc taacgcgtat a                                              21

SEQ ID NO: 195            moltype = AA  length = 18
FEATURE                   Location/Qualifiers
REGION                    1..18
                          note = synthetic construct
source                    1..18
                          mol_type = protein
                          organism = synthetic construct
SEQUENCE: 195
GVAMPGAEDD VVGGGGSC                                                  18

SEQ ID NO: 196            moltype = AA  length = 23
FEATURE                   Location/Qualifiers
REGION                    1..23
                          note = synthetic construct
```

```
MOD_RES                 1
                        note = FORMYLATION -
source                  1..23
                        mol_type = protein
                        organism = synthetic construct
SEQUENCE: 196
MDVEAWLGAR VPLVETGSGS GSC                                                  23

SEQ ID NO: 197          moltype = AA  length = 18
FEATURE                 Location/Qualifiers
REGION                  1..18
                        note = synthetic construct
source                  1..18
                        mol_type = protein
                        organism = synthetic construct
SEQUENCE: 197
HQKLVFFAED VGSGSGSC                                                        18

SEQ ID NO: 198          moltype = AA  length = 103
FEATURE                 Location/Qualifiers
source                  1..103
                        mol_type = protein
                        organism = Agrobacterium sp.
SEQUENCE: 198
MSDSPVDLKP KPKVKPKLER PKLYKVMLLN DDYTPREFVT VVLKAVFRMS EDTGRRVMMT           60
AHRFGSAVVV VCERDIAETK AKEATDLGKE AGFPLMFTTE PEE                            103

SEQ ID NO: 199          moltype = AA  length = 108
FEATURE                 Location/Qualifiers
source                  1..108
                        mol_type = protein
                        organism = Escherichia coli
SEQUENCE: 199
MGKTNDWLDF DQLAEEKVRD ALKPPSMYKV ILVNDDYTPM EFVIDVLQKF FSYDVERATQ           60
LMLAVHYQGK AICGVFTAEV AETKVAMVNK YARENEHPLL CTLEKAGA                      108

SEQ ID NO: 200          moltype = AA  length = 85
FEATURE                 Location/Qualifiers
source                  1..85
                        mol_type = protein
                        organism = Caulobacter sp.
SEQUENCE: 200
TQKPSLYRVL ILNDDYTPME FVVYVLERFF NKSREDATRI MLHVHQNGVG VCGVYTYEVA           60
ETKVAQVIDS ARRHQHPLQC TMEKD                                                85

SEQ ID NO: 201          moltype = AA  length = 19
FEATURE                 Location/Qualifiers
REGION                  1..19
                        note = Artificial Construct
source                  1..19
                        mol_type = protein
                        organism = synthetic construct
SEQUENCE: 201
FAGVAMPGAE DDVVGSGSK                                                       19

SEQ ID NO: 202          moltype = AA  length = 18
FEATURE                 Location/Qualifiers
REGION                  1..18
                        note = Artificial Construct
source                  1..18
                        mol_type = protein
                        organism = synthetic construct
SEQUENCE: 202
AGVAMPGAED DVVGSGSK                                                        18

SEQ ID NO: 203          moltype = AA  length = 20
FEATURE                 Location/Qualifiers
REGION                  1..20
                        note = Artificial Construct
source                  1..20
                        mol_type = protein
                        organism = synthetic construct
SEQUENCE: 203
AFAGVAMPGA EDDVVGSGSK                                                      20

SEQ ID NO: 204          moltype = DNA  length = 22
FEATURE                 Location/Qualifiers
source                  1..22
                        mol_type = other DNA
```

```
                        organism = synthetic construct
SEQUENCE: 204
gcttgtcaat tggaaccagt ct                                               22

SEQ ID NO: 205          moltype = DNA   length = 23
FEATURE                 Location/Qualifiers
misc_feature            1..23
                        note = Oligonucleotide
source                  1..23
                        mol_type = other DNA
                        organism = synthetic construct
SEQUENCE: 205
gacatctagt gtcgcggact acg                                              23

SEQ ID NO: 206          moltype = DNA   length = 21
FEATURE                 Location/Qualifiers
misc_feature            1..21
                        note = Oligonucleotide
source                  1..21
                        mol_type = other DNA
                        organism = synthetic construct
SEQUENCE: 206
gcttgtcaat tggaaccagt c                                                21

SEQ ID NO: 207          moltype = DNA   length = 24
FEATURE                 Location/Qualifiers
misc_feature            1..24
                        note = Oligonucleotide
source                  1..24
                        mol_type = other DNA
                        organism = synthetic construct
SEQUENCE: 207
cgatttgcaa ggatcactcg aggt                                             24

SEQ ID NO: 208          moltype = DNA   length = 22
FEATURE                 Location/Qualifiers
misc_feature            1..22
                        note = Oligonucleotide
source                  1..22
                        mol_type = other DNA
                        organism = synthetic construct
SEQUENCE: 208
gcttgtcaat tggaaccagt ct                                               22

SEQ ID NO: 209          moltype = DNA   length = 32
FEATURE                 Location/Qualifiers
misc_feature            1..32
                        note = Oligonucleotide
source                  1..32
                        mol_type = other DNA
                        organism = synthetic construct
SEQUENCE: 209
cactcagttt ccgtcatatc gaatcactca gt                                    32

SEQ ID NO: 210          moltype = DNA   length = 32
FEATURE                 Location/Qualifiers
misc_feature            1..32
                        note = Oligonucleotide
source                  1..32
                        mol_type = other DNA
                        organism = synthetic construct
SEQUENCE: 210
cactcagtcc taacgcgtat acgtcactca gt                                    32

SEQ ID NO: 211          moltype = DNA   length = 44
FEATURE                 Location/Qualifiers
misc_feature            1..44
                        note = Oligonucleotide
source                  1..44
                        mol_type = other DNA
                        organism = synthetic construct
SEQUENCE: 211
cgatttgcaa ggatcactcg ccgttattga cgctctcact cagt                       44

SEQ ID NO: 212          moltype = DNA   length = 153
FEATURE                 Location/Qualifiers
misc_feature            1..153
                        note = Oligonucleotide
source                  1..153
```

```
                         mol_type = other DNA
                         organism = synthetic construct
SEQUENCE: 212
cgtagtccgc gacactagaa taagccggta tatcaactga gtgattcgat atgacggaaa    60
ctgagtgacg tatacgcgtt aggactgagt gagagcgtca ataacggcga gtgatccttg   120
caaatcgccc tatagtgagt cgtattaatt cgc                                153

SEQ ID NO: 213           moltype = DNA   length = 199
FEATURE                  Location/Qualifiers
misc_feature             1..199
                         note = Oligonucleotide
source                   1..199
                         mol_type = other DNA
                         organism = synthetic construct
SEQUENCE: 213
cgtagtccgc gacactagcg tatacgcgtt aggactgagt gagagcgtca ataacggact    60
gagtgagagt cggtaccttg aactgagtga aactgccgag attccactga gtgattcgat   120
atgacggaaa ctgagtgata agccggtata tcacgagtga tccttgcaaa tcgccctata   180
gtgagtcgta ttaattcgc                                                199

SEQ ID NO: 214           moltype = DNA   length = 70
FEATURE                  Location/Qualifiers
misc_feature             1..70
                         note = Oligonucleotide
source                   1..70
                         mol_type = other DNA
                         organism = synthetic construct
SEQUENCE: 214
gactggttcc aattgacaag ctttttttc gtagtccgcg acactagtaa gccggtatat    60
caactgagtg                                                          70

SEQ ID NO: 215           moltype = DNA   length = 43
FEATURE                  Location/Qualifiers
misc_feature             1..43
                         note = Oligonucleotide
source                   1..43
                         mol_type = other DNA
                         organism = synthetic construct
SEQUENCE: 215
ttcgtagtcc gcgacactag taagccggta tatcaactga gtg                     43

SEQ ID NO: 216           moltype = DNA   length = 46
FEATURE                  Location/Qualifiers
misc_feature             1..46
                         note = Oligonucleotide
source                   1..46
                         mol_type = other DNA
                         organism = synthetic construct
misc_difference          21..30
                         note = n is a, c, g, or t
SEQUENCE: 216
ttcgtagtcc gcgacactag nnnnnnnnnn ttaagtcgac tgagtg                  46

SEQ ID NO: 217           moltype = DNA   length = 46
FEATURE                  Location/Qualifiers
misc_feature             1..46
                         note = Oligonucleotide
source                   1..46
                         mol_type = other DNA
                         organism = synthetic construct
misc_difference          21..30
                         note = n is a, c, g, or t
SEQUENCE: 217
ttcgtagtcc gcgacactag nnnnnnnnnn gttaatggac tgagtg                  46

SEQ ID NO: 218           moltype = DNA   length = 46
FEATURE                  Location/Qualifiers
misc_feature             1..46
                         note = Oligonucleotide
source                   1..46
                         mol_type = other DNA
                         organism = synthetic construct
misc_difference          21..30
                         note = n is a, c, g, or t
SEQUENCE: 218
ttcgtagtcc gcgacactag nnnnnnnnnn cagtaccgac tgagtg                  46

SEQ ID NO: 219           moltype = DNA   length = 46
FEATURE                  Location/Qualifiers
```

```
misc_feature            1..46
                        note = Oligonucleotide
source                  1..46
                        mol_type = other DNA
                        organism = synthetic construct
misc_difference         21..30
                        note = n is a, c, g, or t
SEQUENCE: 219
ttcgtagtcc gcgacactag nnnnnnnnnn gttggttaac tgagtg               46

SEQ ID NO: 220          moltype = DNA  length = 25
FEATURE                 Location/Qualifiers
misc_feature            1..25
                        note = Oligonucleotide
source                  1..25
                        mol_type = other DNA
                        organism = synthetic construct
SEQUENCE: 220
cactcagtca gactattcac tcagt                                      25

SEQ ID NO: 221          moltype = DNA  length = 31
FEATURE                 Location/Qualifiers
source                  1..31
                        mol_type = other DNA
                        organism = synthetic construct
misc_feature            1..31
                        note = synthetic oligonucleotide
misc_feature            1
                        note = 18-atom hexa-ethyleneglycol spacer
misc_feature            31
                        note = three carbon (3C) spacer
SEQUENCE: 221
cactcagtcc taacgcgtat acgcactcag t                               31

SEQ ID NO: 222          moltype = DNA  length = 32
FEATURE                 Location/Qualifiers
source                  1..32
                        mol_type = other DNA
                        organism = synthetic construct
misc_feature            1..32
                        note = synthetic oligonucleotide
misc_feature            1
                        note = 18-atom hexa-ethyleneglycol spacer
misc_feature            32
                        note = three carbon (3C) spacer
SEQUENCE: 222
cactcagtcc taacgcgtat acgtcactca gt                              32

SEQ ID NO: 223          moltype = DNA  length = 32
FEATURE                 Location/Qualifiers
source                  1..32
                        mol_type = other DNA
                        organism = synthetic construct
misc_feature            1..32
                        note = synthetic oligonucleotide
misc_feature            1
                        note = five 18-atom hexa-ethyleneglycol spacers
misc_feature            32
                        note = three carbon (3C) spacer
SEQUENCE: 223
cactcagtcc taacgcgtat acgtcactca gt                              32

SEQ ID NO: 224          moltype = DNA  length = 38
FEATURE                 Location/Qualifiers
source                  1..38
                        mol_type = other DNA
                        organism = synthetic construct
misc_feature            1..38
                        note = synthetic oligonucleotide
misc_feature            1
                        note = 18-atom hexa-ethyleneglycol spacer
misc_feature            38
                        note = three carbon (3C) spacer
SEQUENCE: 224
cactcagtcc taacgcgtat acgggaatct cggcagtt                        38

SEQ ID NO: 225          moltype = DNA  length = 44
FEATURE                 Location/Qualifiers
source                  1..44
```

```
                        mol_type = other DNA
                        organism = synthetic construct
misc_feature            1
                        note = 18-atom hexa-ethyleneglycol spacer
misc_feature            44
                        note = 3' C3 (three carbon) spacer
SEQUENCE: 225
cgatttgcaa ggatcactcg ccgttattga cgctctcact cagt            44

SEQ ID NO: 226          moltype = DNA  length = 28
FEATURE                 Location/Qualifiers
source                  1..28
                        mol_type = other DNA
                        organism = synthetic construct
modified_base           21
                        mod_base = OTHER
                        note = uracil
misc_feature            1
                        note = 3 18-atom hexa-ethyleneglycol spacers
misc_feature            1..28
                        note = synthetic construct
SEQUENCE: 226
cgatttgcaa ggatcactcg ttttaggt                              28

SEQ ID NO: 227          moltype = DNA  length = 31
FEATURE                 Location/Qualifiers
source                  1..31
                        mol_type = other DNA
                        organism = synthetic construct
misc_feature            1
                        note = 18-atom hexa-ethyleneglycol spacer
misc_feature            1..31
                        note = synthetic construct
modified_base           8
                        mod_base = OTHER
                        note = uracil
SEQUENCE: 227
cggtctctct cttccctaac gcgtatacgg a                          31

SEQ ID NO: 228          moltype = DNA  length = 45
FEATURE                 Location/Qualifiers
source                  1..45
                        mol_type = other DNA
                        organism = synthetic construct
misc_feature            1
                        note = 18-atom hexa-ethyleneglycol spacer
misc_feature            1..45
                        note = synthetic construct
modified_base           8
                        mod_base = OTHER
                        note = uracil
SEQUENCE: 228
cggtctctcg atttgcaagg atcactcgcc gttattgacg ctcga           45
```

KITS FOR ANALYSIS USING NUCLEIC ACID ENCODING AND/OR LABEL

CROSS-REFERENCE TO RELATED APPLICATIONS

This application is a continuation of U.S. patent application Ser. No. 17/819,263, filed Aug. 11, 2022, which is a continuation of U.S. patent application Ser. No. 16/760,028, filed Apr. 28, 2020, now U.S. Pat. No. 11,513,126 B2, which is a U.S. national phase of International Patent Application No. PCT/US2018/058565, having an international filing date of Oct. 31, 2018, which claims benefit of priority to U.S. Provisional Application No. 62/579,844, filed Oct. 31, 2017, entitled "KITS FOR ANALYSIS USING NUCLEIC ACID ENCODING AND/OR LABEL," and to U.S. Provisional Application No. 62/582,312, filed Nov. 6, 2017, entitled "KITS FOR ANALYSIS USING NUCLEIC ACID ENCODING AND/OR LABEL," and to U.S. Provisional Application No. 62/583,448, filed Nov. 8, 2017, entitled "KITS FOR ANALYSIS USING NUCLEIC ACID ENCODING AND/OR LABEL," the entire contents of each of these applications are incorporated herein by reference for all purposes. This application is related to U.S. Provisional Application No. 62/330,841, filed May 2, 2016, entitled "Macromolecule Analysis Employing Nucleic Acid Encoding"; U.S. Provisional Application No. 62/339,071, filed May 19, 2016, entitled "Macromolecule Analysis Employing Nucleic Acid Encoding"; U.S. Provisional Application No. 62/376,886, filed Aug. 18, 2016, entitled "Macromolecule Analysis Employing Nucleic Acid Encoding"; International Patent Application No. PCT/US2017/030702, filed May 2, 2017, entitled "Macromolecule Analysis Employing Nucleic Acid Encoding"; U.S. Provisional Application No. 62/579,844, filed Oct. 31, 2017, entitled "Kits for Analysis Using Nucleic Acid Encoding and/or Label"; U.S. Provisional Application No. 62/579,870, filed Oct. 31, 2017, entitled "Methods and Compositions for Polypeptide Analysis"; U.S. Provisional Application No. 62/579,840, filed Oct. 31, 2017, entitled "Methods and Kits Using Nucleic Acid Encoding and/or Label"; U.S. Provisional Application No. 62/582,312, filed Nov. 6, 2017, entitled "Kits for Analysis Using Nucleic Acid Encoding and/or Label"; and U.S. Provisional Application No. 62/582,916, filed Nov. 7, 2017, entitled "Methods and Kits Using Nucleic Acid Encoding and/or Label," the disclosures of which applications are incorporated herein by reference for all purposes.

SUBMISSION OF SEQUENCE LISTING

The contents of the electronic sequence listing (776532000504SEQLIST.xml; Size: 310,745 bytes; and Date of Creation: Jul. 26, 2024) is herein incorporated by reference in its entirety.

FIELD

The present disclosure generally relates to sample analysis kits employing nucleic acid encoding and/or nucleic acid recording of a molecular interaction and/or reaction, such as recognition events. In some embodiments, the kits may be used in high-throughput, multiplexed, and/or automated analysis, and are suitable for analysis of a proteome or subset thereof.

BACKGROUND

Proteins play an integral role in cell biology and physiology, performing and facilitating many different biological functions. The repertoire of different protein molecules is extensive, much more complex than the transcriptome, due to additional diversity introduced by post-translational modifications (PTMs). Additionally, proteins within a cell dynamically change (in expression level and modification state) in response to the environment, physiological state, and disease state. Thus, proteins contain a vast amount of relevant information that is largely unexplored, especially relative to genomic information. In general, innovation has been lagging in proteomics analysis relative to genomics analysis. In the field of genomics, next-generation sequencing (NGS) has transformed the field by enabling analysis of billions of DNA sequences in a single instrument run, whereas in protein analysis and peptide sequencing, throughput is still limited.

Yet this protein information is direly needed for a better understanding of proteome dynamics in health and disease and to help enable precision medicine. As such, there is great interest in developing "next-generation" tools to miniaturize and highly-parallelize collection of this proteomic information. The present disclosure addresses these and other needs.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In any of the embodiments in this summary herein, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with sequenceable polymer, such as a non-nucleic acid sequenceable polymer.

In one aspect, disclosed herein is a kit, comprising: (a) a recording tag configured to associate directly or indirectly with an analyte; (b) (i) a coding tag which comprises identifying information regarding a binding moiety capable of binding to the analyte, and which is configured to associate directly or indirectly with the binding moiety to form a binding agent, and/or (ii) a label, wherein the recording tag and the coding tag are configured to allow transfer of information between them, upon binding between the binding agent and the analyte; and optionally (c) the binding moiety. In one embodiment, the recording tag and/or the analyte are configured to be immobilized directly or indirectly to a support. In a further embodiment, the recording tag is configured to be immobilized to the support, thereby immobilizing the analyte associated with the recording tag. In another embodiment, the analyte is configured to be immobilized to the support, thereby immobilizing the recording tag associated with the analyte. In yet another embodiment, each of the recording tag and the analyte is configured to be immobilized to the support. In still another embodiment, the recording tag and the analyte are configured to co-localize when both are immobilized to the support. In some embodiments, the distance between (i) an analyte and (ii) a recording tag for information transfer between the recording tag and the coding tag of a binding agent bound to the analyte, is less than about $10^{-6}$ nm, about $10^{-6}$ nm, about $10^{-5}$ nm, about $10^{-4}$ nm, about 0.001 nm, about 0.01 nm, about 0.1 nm, about 0.5 nm, about 1 nm, about 2 nm, about 5 nm, or more than about 5 nm, or of any value in between the above ranges.

In any of the preceding embodiments, the kit can further comprise an immobilizing linker configured to: (i) be immobilized directly or indirectly to a support, and (ii) associate directly or indirectly with the recording tag and/or the analyte. In one embodiment, the immobilizing linker is configured to associate with the recording tag and the analyte.

In any of the preceding embodiments, the immobilizing linker can be configured to be immobilized directly to the support, thereby immobilizing the recording tag and/or the analyte which are associated with the immobilizing linker.

In any of the preceding embodiments, the kit can further comprise the support.

In any of the preceding embodiments, the kit can further comprise one or more reagents for transferring information between the coding tag and the recording tag, upon binding between the binding agent and the analyte. In one embodiment, the one or more reagents are configured to transfer information from the coding tag to the recording tag, thereby generating an extended recording tag. In another embodiment, the one or more reagents are configured to transfer information from the recording tag to the coding tag, thereby generating an extended coding tag. In yet another embodiment, the one or more reagents are configured to generate a di-tag construct comprising information from the coding tag and information from the recording tag.

In any of the preceding embodiments, the kit can comprise at least two of the recording tags. In any of the preceding embodiments, the kit can comprise at least two of the coding tags each comprising identifying information regarding its associated binding moiety. In particular embodiments, each analyte has a plurality of recording tags (e.g., at least about two, about five, about ten, about 20, about 50, about 100, about 200, about 500, about 1000, about 2000, about 5000, or more) available to a binding agent bound to that analyte. In particular embodiments, the kit comprises a plurality of recording tags, e.g., at least about two, about five, about ten, about 20, about 50, about 100, about 200, about 500, about 1000, about 2000, about 5000, or more.

In any of the preceding embodiments, the kit can comprise at least two of the binding agents. In one embodiment, the kit comprises: (i) one or more reagents for transferring information from a first coding tag of a first binding agent to the recording tag to generate a first order extended recording tag, upon binding between the first binding agent and the analyte, and/or (ii) one or more reagents for transferring information from a second coding tag of a second binding agent to the first order extended recording tag to generate a second order extended recording tag, upon binding between the second binding agent and the analyte, wherein the one or more reagents of (i) and the one or more reagents of (ii) can be the same or different. In particular embodiments, each analyte has a plurality of binding agents and/or coding tags, e.g., at least about two, about five, about ten, about 20, about 50, about 100, about 200, about 500, about 1000, about 2000, about 5000, or more, available to a recording tag for the analyte, and the plurality of binding agents may be added sequentially or in parallel. In particular embodiments, the kit comprises a plurality of binding agents and/or coding tags, e.g., at least about two, about five, about ten, about 20, about 50, about 100, about 200, about 500, about 1000, about 2000, about 5000, or more.

In any of the preceding embodiments, the kit can further comprise (iii) one or more reagents for transferring information from a third (or higher order) coding tag of a third (or higher order) binding agent to the second order extended recording tag to generate a third (or higher order) order extended recording tag, upon binding between the third (or higher order) binding agent and the analyte. In one embodiment, the kit comprises: (i) one or more reagents for transferring information from a first coding tag of a first binding agent to a first recording tag to generate a first extended recording tag, upon binding between the first binding agent and the analyte, (ii) one or more reagents for transferring information from a second coding tag of a second binding agent to a second recording tag to generate a second extended recording tag, upon binding between the second binding agent and the analyte, and/or (iii) one or more reagents for transferring information from a third (or higher order) coding tag of a third (or higher order) binding agent to a third (or higher order) recording tag to generate a third (or higher order) extended recording tag, upon binding between the third (or higher order) binding agent and the analyte, wherein the one or more reagents of (i), (ii), and/or (iii) can be the same or different.

In any of the preceding embodiments, the kit can further comprise (iii) one or more reagents for transferring information from a third (or higher order) coding tag of a third (or higher order) binding agent to a third (or higher order) recording tag to generate a third (or higher order) extended recording tag, upon binding between the third (or higher order) binding agent and the analyte.

In any of the preceding embodiments, the first recording tag, the second recording tag, and/or the third (or higher order) recording tag can be configured to associate directly or indirectly with the analyte.

In any of the preceding embodiments, the first recording tag, the second recording tag, and/or the third (or higher order) recording tag can be configured to be immobilized on a support.

In any of the preceding embodiments, the first recording tag, the second recording tag, and/or the third (or higher order) recording tag can be configured to co-localize with the analyte, for example, to allow transfer of information between the first, second, or third (or higher order) coding tag and the first, second, or third (or higher order) recording tag, respectively, upon binding between the first, second, or third (or higher order) binding agent and the analyte.

In any of the preceding embodiments, each of the first coding tag, the second coding tag, and/or the third (or higher order) coding tag can comprise a binding cycle specific barcode, such as a binding cycle specific spacer sequence $C_n$, and/or a coding tag specific spacer sequence $C_n$, wherein n is an integer and $C_n$ indicates binding between the $n^{th}$ binding agent and the polypeptide. Alternatively, a binding cycle tag $C_n$ may be added exogenously, for example, the binding cycle tag $C_n$ may be exogenous to the coding tag(s).

In any of the preceding embodiments, the analyte can comprise a polypeptide. In one embodiment, the binding moiety of the kit is capable of binding to one or more N-terminal, internal, or C-terminal amino acids of the polypeptide, or capable of binding to the one or more N-terminal, internal, or C-terminal amino acids modified by a functionalizing reagent.

In any of the preceding embodiments, the kit can further comprise one or more of the functionalizing reagent.

In any of the preceding embodiments, the kit can further comprise an eliminating reagent for removing (e.g., by chemical cleavage or enzymatic cleavage) the one or more N-terminal, internal, or C-terminal amino acids of the polypeptide, or removing the functionalized N-terminal, internal, or C-terminal amino acid(s), optionally wherein the eliminating reagent comprises a carboxypeptidase or an aminopeptidase or variant, mutant, or modified protein thereof, a hydrolase or variant, mutant, or modified protein thereof, a mild Edman degradation reagent; an Edmanase enzyme; anhydrous TFA, a base; or any combination thereof.

In any of the preceding embodiments, the one or more N-terminal, internal, or C-terminal amino acids can comprise: (i) an N-terminal amino acid (NTAA); (ii) an N-terminal dipeptide sequence; (iii) an N-terminal tripeptide sequence; (iv) an internal amino acid; (v) an internal dipeptide sequence; (vi) an internal tripeptide sequence; (vii) a C-terminal amino acid (CTAA); (viii) a C-terminal dipeptide sequence; or (ix) a C-terminal tripeptide sequence, or any combination thereof, optionally wherein any one or more of the amino acid residues in (i)-(ix) are modified or functionalized.

In another aspect, disclosed herein is a kit, comprising: at least (a) a first binding agent comprising (i) a first binding moiety capable of binding to an N-terminal amino acid (NTAA) or a functionalized NTAA of a polypeptide to be analyzed, and (ii) a first coding tag comprising identifying information regarding the first binding moiety, optionally (b) a recording tag configured to associate directly or indirectly with the polypeptide, and further optionally (c) a functionalizing reagent capable of modifying a first NTAA of the polypeptide to generate a first functionalized NTAA, wherein the recording tag and the first binding agent are configured to allow transfer of information between the first coding tag and the recording tag, upon binding between the first binding agent and the polypeptide. In one embodiment, the kit further comprises one or more reagents for transferring information from the first coding tag to the recording tag, thereby generating a first order extended recording tag.

In any of the preceding embodiments, the functionalizing reagent can comprise a chemical agent, an enzyme, and/or a biological agent, such as an isothiocyanate derivative, 2,4-dinitrobenzenesulfonic (DNBS), 4-sulfonyl-2-nitrofluorobenzene (SNFB) 1-fluoro-2,4-dinitrobenzene, dansyl chloride, 7-methoxycoumarin acetic acid, a thioacylation reagent, a thioacetylation reagent, or a thiobenzylation reagent.

In any of the preceding embodiments, the kit can further comprise an eliminating reagent for removing (e.g., by chemical cleavage or enzymatic cleavage) the first functionalized NTAA to expose the immediately adjacent amino acid residue, as a second NTAA. In one embodiment, the second NTAA is capable of being functionalized by the same or a different functionalizing reagent to generate a second functionalized NTAA, which may be the same as or different from the first functionalized NTAA. In another embodiment, the kit further comprises: (d) a second (or higher order) binding agent comprising (i) a second (or higher order) binding moiety capable of binding to the second functionalized NTAA, and (ii) a second (or higher order) coding tag comprising identifying information regarding the second (or higher order) binding moiety, wherein the first coding tag and the second (or higher order) coding tag can be the same or different. In yet another embodiment, the first functionalized NTAA and the second functionalized NTAA are selected, independent from each other, from the group consisting of a functionalized N-terminal Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

In any of the preceding embodiments, the kit can further comprise one or more reagents for transferring information from the second (or higher order) coding tag to the first order extended recording tag, thereby generating a second (or higher order) order extended recording tag.

In a further aspect, disclosed herein is a kit, comprising: at least (a) one or more binding agents each comprising (i) a binding moiety capable of binding to an N-terminal amino acid (NTAA) or a functionalized NTAA of a polypeptide to be analyzed, and (ii) a coding tag comprising identifying information regarding the binding moiety, and/or (b) one or more recording tags configured to associate directly or indirectly with the polypeptide, wherein the one or more recording tags and the one or more binding agents are configured to allow transfer of information between the coding tags and the recording tags, upon binding between each binding agent and the polypeptide, and optionally (c) a functionalizing reagent capable of modifying a first NTAA of the polypeptide to generate a first functionalized NTAA. In one embodiment, kit further comprises an eliminating reagent for removing (e.g., by chemical cleavage or enzymatic cleavage) the first functionalized NTAA to expose the immediately adjacent amino acid residue, as a second NTAA. In another embodiment, the second NTAA is capable of being functionalized by the same or a different functionalizing reagent to generate a second functionalized NTAA, which may be the same as or different from the first functionalized NTAA. In yet another embodiment, the first functionalized NTAA and the second functionalized NTAA are selected, independent from each other, from the group consisting of a functionalized N-terminal Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

In any of the preceding embodiments, the kit can comprise: (i) one or more reagents for transferring information from a first coding tag of a first binding agent to a first recording tag to generate a first extended recording tag, upon binding between the first binding agent and the polypeptide, and/or (ii) one or more reagents for transferring information from a second coding tag of a second binding agent to a second recording tag to generate a second extended recording tag, upon binding between the second binding agent and the polypeptide, wherein the one or more reagents of (i) and the one or more reagents of (ii) can be the same or different. In one aspect, the kit further comprises: (iii) one or more reagents for transferring information from a third (or higher order) coding tag of a third (or higher order) binding agent to a third (or higher order) recording tag to generate a third (or higher order) extended recording tag, upon binding between the third (or higher order) binding agent and the polypeptide.

In any of the preceding embodiments, the first recording tag, the second recording tag, and/or the third (or higher order) recording tag can be configured to associate directly or indirectly with the polypeptide.

In any of the preceding embodiments, the first recording tag, the second recording tag, and/or the third (or higher order) recording tag can be configured to be immobilized on a support.

In any of the preceding embodiments, the first recording tag, the second recording tag, and/or the third (or higher order) recording tag can be configured to co-localize with the polypeptide, for example, to allow transfer of information between the first, second, or third (or higher order) coding tag and the first, second, or third (or higher order) recording tag, respectively, upon binding between the first, second, or third (or higher order) binding agent and the polypeptide.

In any of the preceding embodiments, the distance between or among the first recording tag, the second recording tag, and/or the third (or higher order) recording tag on the support can be equal to or greater than about 10 nm, equal to or greater than about 15 nm, equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, or equal to or greater than about 500 nm, while each recording tag and its corresponding analyte is configured to co-localize when both are immobilized to the support, or while the distance between each recording tag and its corresponding analyte is less than about $10^{-6}$ nm, about $10^{-6}$ nm, about $10^{-5}$ nm, about $10^{-4}$ nm, about 0.001 nm, about 0.01 nm, about 0.1 nm, about 0.5 nm, about 1 nm, about 2 nm, about 5 nm, or more than about 5 nm, or of any value in between the above ranges.

In any of the preceding embodiments, each of the first coding tag, the second coding tag, and/or the third (or higher order) coding tag can comprise a binding cycle specific barcode, such as a binding cycle specific spacer sequence $C_n$, and/or a coding tag specific spacer sequence $C_n$, wherein n is an integer and $C_n$ indicates binding between the $n^{th}$ binding agent and the polypeptide. Alternatively, a binding cycle tag $C_n$ may be added exogenously, for example, the binding cycle tag $C_n$ may be exogenous to the coding tag(s).

In any of the preceding embodiments, the analyte or the polypeptide can comprise a protein or a polypeptide chain or a fragment thereof, a lipid, a carbohydrate, or a macrocycle, or a combination or complex thereof.

In any of the preceding embodiments, the analyte or the polypeptide can comprise a macromolecule or a complex thereof, such as a protein complex or subunit thereof.

In any of the preceding embodiments, the recording tag can comprise a nucleic acid, an oligonucleotide, a modified oligonucleotide, a DNA molecule, a DNA with pseudo-complementary bases, a DNA or RNA with one more protected bases, an RNA molecule, a BNA molecule, an XNA molecule, a LNA molecule, a PNA molecule, a γPNA molecule, or a morpholino, or a combination thereof.

In any of the preceding embodiments, the recording tag can comprise a universal priming site.

In any of the preceding embodiments, the recording tag can comprise a priming site for amplification, sequencing, or both, for example, the universal priming site comprises a priming site for amplification, sequencing, or both.

In any of the preceding embodiments, the recording tag and/or the coding tag can comprise a unique molecule identifier (UMI).

In any of the preceding embodiments, the recording tag and/or the coding tag can comprise a barcode and/or a nuclease site, such as a nicking endonuclease site (e.g., a dsDNA nicking endonuclease site).

In any of the preceding embodiments, the recording tag and/or the coding tag comprises a spacer at its 3'-terminus and/or at its 5'-terminus, for example, the recording tag comprises a spacer at its 3'-terminus.

In any of the preceding embodiments, the recording tag and/or the coding tag can comprise one or more nuclease sites, such as an endonuclease site, a homing endonuclease site, a restriction enzyme digestion site, a nicking endonuclease site, or a combination thereof. In some embodiments, a nuclease site can be provided in the coding tag, for example, within the spacer sequence or between the spacer sequence and the encoder sequence. In some embodiments, a nuclease site can be provided in the recording tag, for example, between the universal primer sequence and the support (e.g., for cleaving the recording tag off the support).

In any of the preceding embodiments, the kit can comprise a solid support, such as a rigid solid support, a flexible solid support, or a soft solid support, and including a porous support or a non-porous support.

In any of the preceding embodiments, the kit can comprise a support which comprises a bead, a porous bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof. In one embodiment, the support comprises a polystyrene bead, a polymer bead, an agarose bead, an acrylamide bead, a solid core bead, a porous bead, a paramagnetic bead, glass bead, or a controlled pore bead, or any combination thereof.

In any of the preceding embodiments, the kit can comprise a support and/or can be for analyzing a plurality of the analytes (such as polypeptides), in sequential reactions, in parallel reactions, or in a combination of sequential and parallel reactions. In one embodiment, the analytes are spaced apart on the support at an average distance equal to or greater than about 10 nm, equal to or greater than about 15 nm, equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, or equal to or greater than about 500 nm.

In any of the preceding embodiments, the binding moiety can comprise a polypeptide or fragment thereof, a protein or polypeptide chain or fragment thereof, or a protein complex or subunit thereof, such as an antibody or antigen binding fragment thereof.

In any of the preceding embodiments, the binding moiety can comprise a carboxypeptidase or an aminopeptidase or variant, mutant, or modified protein thereof, an aminoacyl tRNA synthetase or variant, mutant, or modified protein thereof, an anticalin or variant, mutant, or modified protein thereof, a ClpS or variant, mutant, or modified protein thereof, a UBR box protein or variant, mutant, or modified protein thereof, a modified small molecule that binds amino acid(s), i.e. vancomycin or a variant, mutant, or modified molecule thereof, or any combination thereof, or wherein in each binding agent, the binding moiety comprises a small molecule, the coding tag comprises a polynucleotide that identifies the small molecule, whereby a plurality of the binding agents form an encoded small molecule library, such as a DNA-encoded small molecule library.

In any of the preceding embodiments, the binding moiety can selectively and/or specifically bind to the analyte or the polypeptide.

In any of the preceding embodiments, the coding tag can comprise a nucleic acid, an oligonucleotide, a modified oligonucleotide, a DNA molecule, a DNA with pseudo-complementary bases, a DNA or RNA with one or more protected bases, an RNA molecule, a BNA molecule, an XNA molecule, a LNA molecule, a PNA molecule, a γPNA molecule, or a morpholino, or a combination thereof.

In any of the preceding embodiments, the coding tag can comprise a barcode sequence, such as an encoder sequence, e.g., one that identifies the binding moiety.

In any of the preceding embodiments, the coding tag can comprise a spacer, a binding cycle specific sequence, a unique molecular identifier (UMI), a universal priming site, or any combination thereof. In one embodiment, a binding cycle specific sequence is added to the recording tag after each binding cycle.

In any of the preceding embodiments, the binding moiety and the coding tag can be joined by a linker or a binding pair.

In any of the preceding embodiments, the binding moiety and the coding tag can be joined by a SpyTag/SpyCatcher, a SpyTag-KTag/SpyLigase (where two moieties to be joined have the SpyTag/KTag pair, and the SpyLigase joins SpyTag to KTag, thus joining the two moieties), a SnoopTag/Snoop-Catcher peptide-protein pair, a HaloTag/HaloTag ligand pair, or a sortase, such as a LPXTG Tag/Sortase (e.g., Sortase A5, ActiveMotif, San Diego, or as disclosed in U.S. Pat. No. 9,267,127 B2 which is incorporated herein by reference), or any combination thereof.

In any of the preceding embodiments, the kit can further comprise a reagent for transferring information between the coding tag and the recording tag in a templated or non-templated reaction, optionally wherein the reagent is (i) a chemical ligation reagent or a biological ligation reagent, for example, a ligase, such as a DNA ligase or RNA ligase for ligating single-stranded nucleic acid or double-stranded nucleic acid, or (ii) a reagent for primer extension of single-stranded nucleic acid or double-stranded nucleic acid, optionally wherein the kit further comprises a ligation reagent comprising at least two ligases or variants thereof (e.g., at least two DNA ligases, or at least two RNA ligases, or at least one DNA ligase and at least one RNA ligase), wherein the at least two ligases or variants thereof comprises an adenylated ligase and a constitutively non-adenylated ligase, or optionally wherein the kit further comprises a ligation reagent comprising a DNA or RNA ligase and a DNA/RNA deadenylase.

In any of the preceding embodiments, the kit can further comprise a polymerase, such as a DNA polymerase or RNA polymerase or a reverse transcriptase, for transferring information between the coding tag and the recording tag.

In any of the preceding embodiments, the kit can further comprise one or more reagents for nucleic acid sequence analysis. In one embodiment, the nucleic acid sequence analysis comprises sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy, or any combination thereof.

In any of the preceding embodiments, the kit can further comprise one or more reagents for nucleic acid amplification, for example, for amplifying one or more extended recording tags, optionally wherein the nucleic acid amplification comprises an exponential amplification reaction (e.g., polymerase chain reaction (PCR), such as an emulsion PCR to reduce or eliminate template switching) and/or a linear amplification reaction (e.g., isothermal amplification by in vitro transcription, or Isothermal Chimeric primer-initiated Amplification of Nucleic acids (ICAN)). See e.g., Uemori et al., (2007), "Investigation of the molecular mechanism of ICAN, a novel gene amplification method," *J Biochem* 142(2): 283-292; Mukai et al., (2007), "Highly efficient isothermal DNA amplification system using three elements of 5'-DNA-RNA-3' chimeric primers, RNaseH and strand-displacing DNA polymerase," *J Biochem* 142(2): 273-281; Ma et al., (2013), "Isothermal amplification method for next-generation sequencing," *Proc Natl Acad Sci USA*. 110(35): 14320-14323, all of which are incorporated herein by reference for all purposes.

In any of the preceding embodiments, the kit can comprise one or more reagents for transferring coding tag information to the recording tag to form an extended recording tag, wherein the order and/or frequency of coding tag information on the extended recording tag indicates the order and/or frequency in which the binding agent binds to the analyte or the polypeptide.

In any of the preceding embodiments, the kit can further comprise one or more reagents for target enrichment, for example, enrichment of one or more extended recording tags.

In any of the preceding embodiments, the kit can further comprise one or more reagents for subtraction, for example, subtraction of one or more extended recording tags.

In any of the preceding embodiments, the kit can further comprise one or more reagents for normalization, for example, to reduce highly abundant species such as one or more analytes or polypeptides.

In any of the preceding embodiments, at least one binding agent of the kit can bind to a terminal amino acid residue, terminal di-amino-acid residues, or terminal triple-amino-acid residues.

In any of the preceding embodiments, at least one binding agent of the kit can bind to a post-translationally modified amino acid.

In any of the preceding embodiments, the kit can further comprise one or more reagents or means for partitioning a plurality of the analytes or polypeptides in a sample into a plurality of compartments, wherein each compartment comprises a plurality of compartment tags optionally joined to a support (e.g., a solid support), wherein the plurality of compartment tags are the same within an individual compartment and are different from the compartment tags of other compartments. In one embodiment, the kit further comprises one or more reagents or means for fragmenting the plurality of the analytes or polypeptides (such as a plurality of protein complexes, proteins, and/or polypeptides) into a plurality of polypeptide fragments.

In any of the preceding embodiments, the kit can further comprise one or more reagents or means for annealing or joining of the plurality of polypeptide fragments with the compartment tag within each of the plurality of compartments, thereby generating a plurality of compartment tagged polypeptide fragments.

In any of the preceding embodiments, the plurality of compartments can comprise a microfluidic droplet, a microwell, or a separated region on a surface, or any combination thereof.

In any of the preceding embodiments, each of the plurality of compartments can comprise on average a single cell.

In any of the preceding embodiments, the kit can further comprise one or more universal DNA tags for labeling the plurality of the analytes or polypeptides in the sample.

In any of the preceding embodiments, the kit can further comprise one or more reagents for labeling the plurality of the analytes or polypeptides in the sample with one or more universal DNA tags.

In any of the preceding embodiments, the kit can further comprise one or more reagents for primer extension or ligation.

In any of the preceding embodiments, the support can comprise a bead, such as a polystyrene bead, a polymer bead, an agarose bead, an acrylamide bead, a solid core bead, a porous bead, a paramagnetic bead, glass bead, or a controlled pore bead, or any combination thereof.

In any of the preceding embodiments, the compartment tag can comprise a single stranded or double stranded nucleic acid molecule.

In any of the preceding embodiments, the compartment tag can comprise a barcode and optionally a UMI. In any of the preceding embodiments, the support can be a bead and the compartment tag can comprise a barcode.

In any of the preceding embodiments, the support can comprise a bead, and beads comprising the plurality of compartment tags joined thereto can be formed by split-and-pool synthesis, individual synthesis, or immobilization, or any combination thereof.

In any of the preceding embodiments, the kit can further comprise one or more reagents for split-and-pool synthesis, individual synthesis, or immobilization, or any combination thereof.

In any of the preceding embodiments, the compartment tag can be a component within a recording tag, wherein the recording tag optionally can further comprise a spacer, a barcode sequence, a unique molecular identifier, a universal priming site, or any combination thereof.

In any of the preceding embodiments, the compartment tags can further comprise a functional moiety capable of reacting with an internal amino acid, the peptide backbone, or N-terminal amino acid on the plurality of analytes or polypeptides (such as protein complexes, proteins, or polypeptides). In one embodiment, the functional moiety can comprise an aldehyde, an azide/alkyne, a malemide/thiol, an epoxy/nucleophile, an inverse Electron Demand Diels-Alder (iEDDA) group, a click reagent, or any combination thereof.

In any of the preceding embodiments, the compartment tag can further comprise a peptide, such as a protein ligase recognition sequence, and optionally the protein ligase can be butelase I or a homolog thereof.

In any of the preceding embodiments, the kit can further comprise a chemical or biological reagent, such as an enzyme, for example, a protease (e.g., a metalloprotease), for fragmenting the plurality of analytes or polypeptides.

In any of the preceding embodiments, the kit can further comprise one or more reagents for releasing the compartment tags from the support.

In any of the preceding embodiments, the kit can further comprise one or more reagents for forming an extended coding tag or a di-tag construct. In one embodiment, the 3'-terminus of the recording tag is blocked to prevent extension of the recording tag by a polymerase. In any of the preceding embodiments, the coding tag can comprise an encoder sequence, a UMI, a universal priming site, a spacer at its 3'-terminus, a binding cycle specific sequence, or any combination thereof.

In any of the preceding embodiments, the di-tag construct can be generated by gap fill, primer extension, or a combination thereof.

In any of the preceding embodiments, the di-tag molecule can comprise a universal priming site derived from the recording tag, a compartment tag derived from the recording tag, a unique molecular identifier derived from the recording tag, an optional spacer derived from the recording tag, an encoder sequence derived from the coding tag, a unique molecular identifier derived from the coding tag, an optional spacer derived from the coding tag, and a universal priming site derived from the coding tag.

In any of the preceding embodiments, the binding agent can be a polypeptide or protein.

In any of the preceding embodiments, the binding agent can comprise an aminopeptidase or variant, mutant, or modified protein thereof; an aminoacyl tRNA synthetase or variant, mutant, or modified protein thereof, an anticalin or variant, mutant, or modified protein thereof, a ClpS or variant, mutant, or modified protein thereof, or a modified small molecule that binds amino acid(s), i.e. vancomycin or a variant, mutant, or modified molecule thereof (such as a vancomycin that binds to D-alanyl-D-alanine); or an antibody or binding fragment thereof, or any combination thereof.

In any of the preceding embodiments, the binding agent can bind to a single amino acid residue (e.g., an N-terminal amino acid residue, a C-terminal amino acid residue, or an internal amino acid residue), a dipeptide (e.g., an N-terminal dipeptide, a C-terminal dipeptide, or an internal dipeptide), a tripeptide (e.g., an N-terminal tripeptide, a C-terminal tripeptide, or an internal tripeptide), or a post-translational modification of the analyte or polypeptide.

In any of the preceding embodiments, the binding agent can bind to an N-terminal polypeptide, a C-terminal polypeptide, or an internal polypeptide.

In any of the preceding embodiments, the coding tag and/or the recording tag can comprise one or more error correcting codes, one or more encoder sequences, one or more barcodes, one or more UMIs, one or more compartment tags, one or more cycle specific sequences, or any combination thereof. In some embodiments, the error correcting code is selected from Hamming code, Lee distance code, asymmetric Lee distance code, Reed-Solomon code, and Levenshtein-Tenengolts code.

In any of the preceding embodiments, the coding tag and/or the recording tag can comprise a cycle label.

In any of the preceding embodiments, the kit can further comprise a cycle label independent of the coding tag and/or the recording tag.

In any of the preceding embodiments, the kit can further comprise: (a) a reagent for generating a cell lysate or a protein sample; (b) a reagent for blocking an amino acid side chain, such as via alkylation of cysteine or blocking lysine; (c) a protease, such as trypsin, LysN, or LysC; (d) a reagent for immobilizing a nucleic acid-labeled polypeptide (such as a DNA-labeled protein) to a support; (e) a reagent for degradation-based polypeptide sequencing; and/or (f) a reagent for nucleic acid sequencing.

In any of the preceding embodiments, the kit can comprise: (a) a reagent for generating a cell lysate or a protein sample; (b) a reagent for blocking an amino acid side chain, such as via alkylation of cysteine or blocking lysine; (c) a protease, such as trypsin, LysN, or LysC; (d) a reagent for immobilizing a polypeptide (such as a protein) to a support comprising immobilized recording tags; (e) a reagent for degradation-based polypeptide sequencing; and/or (f) a reagent for nucleic acid sequencing.

In any of the preceding embodiments, the kit can comprise: (a) a reagent for generating a cell lysate or a protein sample; (b) a denaturing reagent; (c) a reagent for blocking an amino acid side chain, such as via alkylation of cysteine or blocking lysine; (d) a universal DNA primer sequence; (e) a reagent for labeling a polypeptide with a universal DNA primer sequence; (f) a barcoded bead for annealing the labeled polypeptide via a primer; (g) a reagent for polymerase extension for writing the barcode from the bead to the labeled polypeptide; (h) a protease, such as trypsin, LysN, or LysC; (i) a reagent for immobilizing a nucleic acid-labeled polypeptide (such as a DNA-labeled protein) to a support; (j) a reagent for degradation-based polypeptide sequencing; and/or (k) a reagent for nucleic acid sequencing.

In any of the preceding embodiments, the kit can comprise: (a) a cross-linking reagent; (b) a reagent for generating a cell lysate or a protein sample; (c) a reagent for blocking an amino acid side chain, such as via alkylation of cysteine or blocking lysine; (d) a universal DNA primer sequence; (e) a reagent for labeling a polypeptide with a universal DNA primer sequence; (f) a barcoded bead for annealing the labeled polypeptide via a primer; (g) a reagent for polymerase extension for writing the barcode from the bead to the labeled polypeptide; (h) a protease, such as trypsin, LysN, or LysC; (i) a reagent for immobilizing a nucleic acid-labeled polypeptide (such as a DNA-labeled protein) to a support; (j) a reagent for degradation-based polypeptide sequencing; and/or (k) a reagent for nucleic acid sequencing.

In any of the preceding embodiments of the kit, one or more components can be provided in a solution or on a support, for example, a solid support.

Kit components may also include any molecule, molecular complex or conjugate, reagent (e.g., chemical or biological), agent, structure (e.g., support, surface, particle, or bead), reaction intermediate, reaction product, binding complex, or any other article of manufacture disclosed and/or used in the following exemplary methods and/or aspects. The present kits can be used for analyzing any suitable analyte, e.g., a macromolecule or a polypeptide. In some embodiments, the present kits can be used for highly-parallel, high throughput digital analysis (e.g., a macromolecule analysis), particularly polypeptide analysis. In some embodiments, the present kits can be used in the following exemplary methods for analyzing an analyte, e.g., a macromolecule or a polypeptide.

In a first Example is a method for analyzing an analyte, e.g., a macromolecule or a polypeptide, comprising the steps of: (a) providing an analyte and an associated recording tag joined to a solid support; (b) contacting the an analyte with a first binding agent capable of binding to the analyte, wherein the first binding agent comprises a first coding tag with identifying information regarding the first binding agent; (c) transferring the information of the first coding tag to the recording tag to generate a first order extended recording tag; (d) contacting the analyte with a second binding agent capable of binding to the analyte, wherein the second binding agent comprises a second coding tag with identifying information regarding the second binding agent; (e) transferring the information of the second coding tag to the first order extended recording tag to generate a second order extended recording tag; and (f) analyzing the second order extended recording tag.

In a second Example is the method of the first Example, wherein contacting steps (b) and (d) are performed in sequential order.

In a third Example is the method of the first Example, where wherein contacting steps (b) and (d) are performed at the same time.

In a fourth Example is the method of the first Example, further comprising, between steps (e) and (f), the following steps: (x) repeating steps (d) and (e) one or more times by replacing the second binding agent with a third (or higher order) binding agent capable of binding to the analyte, wherein the third (or higher order) binding agent comprises a third (or higher order) coding tag with identifying information regarding the third (or higher order) bind agent; and (y) transferring the information of the third (or higher order) coding tag to the second (or higher order) extended recording tag to generate a third (or higher order) extended recording tag; and wherein the third (or higher order) extended recording tag is analyzed in step (f).

In a fifth Example is a method for analyzing an analyte, e.g., a macromolecule or a polypeptide, comprising the steps of: (a) providing an analyte, an associated first recording tag and an associated second recording tag joined to a solid support; (b) contacting the analyte with a first binding agent capable of binding to the analyte, wherein the first binding agent comprises a first coding tag with identifying information regarding the first binding agent; (c) transferring the information of the first coding tag to the first recording tag to generate a first extended recording tag; (d) contacting the analyte with a second binding agent capable of binding to the analyte, wherein the second binding agent comprises a second coding tag with identifying information regarding the second binding agent; (e) transferring the information of the second coding tag to the second recording tag to generate a second extended recording tag; and (f) analyzing the first and second extended recording tags.

In a sixth Example is the method of fifth Example, wherein contacting steps (b) and (d) are performed in sequential order.

In a seventh Example is the method of the fifth Example, wherein contacting steps (b) and (d) are performed at the same time.

In an eight Example is the method of fifth Example, wherein step (a) further comprises providing an associated third (or higher odder) recording tag joined to the solid support.

In a ninth Example is the method of the eighth Example, further comprising, between steps (e) and (f), the following steps: (x) repeating steps (d) and (e) one or more times by replacing the second binding agent with a third (or higher order) binding agent capable of binding to the analyte, wherein the third (or higher order) binding agent comprises a third (or higher order) coding tag with identifying information regarding the third (or higher order) bind agent; and (y) transferring the information of the third (or higher order) coding tag to the third (or higher order) recording tag to generate a third (or higher order) extended recording tag; and wherein the first, second and third (or higher order) extended recording tags are analyzed in step (f).

In a 10th Example is the method of any one of the fifth to ninth Examples, wherein the first coding tag, second coding tag, and any higher order coding tags comprise a binding cycle specific spacer sequence.

In an 11th Example is a method for analyzing a peptide, comprising the steps of: (a) providing a peptide and an associated recording tag joined to a solid support; (b) modifying the N-terminal amino acid (NTAA) of the peptide with a chemical agent; (c) contacting the peptide with a first binding agent capable of binding to the modified NTAA, wherein the first binding agent comprises a first coding tag with identifying information regarding the first binding agent; (d) transferring the information of the first coding tag to the recording tag to generate an extended recording tag; and (e) analyzing the extended recording tag.

In a 12$^{th}$ Example is the method of 11$^{th}$ Example, wherein step (c) further comprises contacting the peptide with a second (or higher order) binding agent comprising a second (or higher order) coding tag with identifying information regarding the second (or higher order) binding agent, wherein the second (or higher order) binding agent is capable of binding to a modified NTAA other than the modified NTAA of step (b).

In a 13$^{th}$ Example is the method of the 12$^{th}$ Example, wherein contacting the peptide with the second (or higher order) binding agent occurs in sequential order following the peptide being contacted with the first binding agent.

In a 14$^{th}$ Example is the method of 12$^{th}$ Example, wherein contacting the peptide with the second (or higher order) binding agent occurs simultaneously with the peptide being contacted with the first binding agent.

In a 15$^{th}$ Example is the method of any one the 11$^{th}$-14$^{th}$ Examples, wherein the chemical agent is an isothiocyanate derivative, 2,4-dinitrobenzenesulfonic (DNBS), 4-sulfonyl-2-nitrofluorobenzene (SNFB) 1-fluoro-2,4-dinitrobenzene, dansyl chloride, 7-methoxycoumarin acetic acid, a thioacylation reagent, a thioacetylation reagent, or a thiobenzylation reagent.

In a 16$^{th}$ Example is a method for analyzing a peptide, comprising the steps of: (a) providing a peptide and an associated recording tag joined to a solid support; (b) modifying the N-terminal amino acid (NTAA) of the peptide with a chemical agent to yield a modified NTAA; (c) contacting the peptide with a first binding agent capable of binding to the modified NTAA, wherein the first binding agent comprises a first coding tag with identifying information regarding the first binding agent; (d) transferring the information of the first coding tag to the recording tag to generate a first extended recording tag; (e) removing the modified NTAA to expose a new NTAA; (f) modifying the new NTAA of the peptide with a chemical agent to yield a newly modified NTAA; (g) contacting the peptide with a second binding agent capable of binding to the newly modified NTAA, wherein the second binding agent comprises a second coding tag with identifying information regarding the second binding agent; (h) transferring the information of the second coding tag to the first extended recording tag to generate a second extended recording tag; and (i) analyzing the second extended recording tag.

In a 17$^{th}$ Example is a method for analyzing a peptide, comprising the steps of: (a) providing a peptide and an associated recording tag joined to a solid support; (b) contacting the peptide with a first binding agent capable of binding to the N-terminal amino acid (NTAA) of the peptide, wherein the first binding agent comprises a first coding tag with identifying information regarding the first binding agent; (c) transferring the information of the first coding tag to the recording tag to generate an extended recording tag; and (d) analyzing the extended recording tag.

In an 18$^{th}$ Example is the method of the 17$^{th}$ Example, wherein step (b) further comprises contacting the peptide with a second (or higher order) binding agent comprising a second (or higher order) coding tag with identifying information regarding the second (or higher order) binding agent, wherein the second (or higher order) binding agent is capable of binding to a NTAA other than the NTAA of the peptide.

In a 19$^{th}$ Example is the method of the 18$^{th}$ Example, wherein contacting the peptide with the second (or higher order) binding agent occurs in sequential order following the peptide being contacted with the first binding agent.

In a 20$^{th}$ Example is the method of the 18$^{th}$ Example, wherein contacting the peptide with the second (or higher order) binding agent occurs simultaneously with the peptide being contacted with the first binding agent.

In a 21$^{st}$ Example is a method for analyzing a peptide, comprising the steps of: (a) providing a peptide and an associated recording tag joined to a solid support; (b) contacting the peptide with a first binding agent capable of binding to the N-terminal amino acid (NTAA) of the peptide, wherein the first binding agent comprises a first coding tag with identifying information regarding the first binding agent; (c) transferring the information of the first coding tag to the recording tag to generate a first extended recording tag; (d) removing the NTAA to expose a new NTAA of the peptide; (e) contacting the peptide with a second binding agent capable of binding to the new NTAA, wherein the second binding agent comprises a second coding tag with identifying information regarding the second binding agent; (f) transferring the information of the second coding tag to the first extended recording tag to generate a second extended recording tag; and (g) analyzing the second extended recording tag.

In a 22$^{nd}$ Example is the method of any one of the first-10$^{th}$ Examples, wherein the analyte is a protein, polypeptide or peptide.

In a 23$^{rd}$ Example is the method of any one of the first-10$^{th}$ Examples, wherein the analyte is a peptide.

In a 24$^{th}$ Example is the method of any one of the 11$^{th}$-23$^{rd}$ Examples, wherein the peptide is obtained by fragmenting a protein from a biological sample.

In a 25$^{th}$ Example is the method of any one of the first-10$^{th}$ Examples, wherein the analyte is a lipid, a carbohydrate, or a macrocycle.

In a 26$^{th}$ Example is the method of any one of the first-25$^{th}$ Examples, wherein the recording tag is a DNA molecule, DNA with pseudo-complementary bases, an RNA molecule, a BNA molecule, an XNA molecule, a LNA molecule, a PNA molecule, a γPNA molecule, or a combination thereof.

In a 27$^{th}$ Example is the method of any one of the first-26$^{th}$ Examples, wherein the recording tag comprises a universal priming site.

In a 28$^{th}$ Example is the method of the 27$^{th}$ Example, wherein the universal priming site comprises a priming site for amplification, sequencing, or both.

In a 29$^{th}$ Example is the method of the first-28$^{th}$ Examples, where the recording tag comprises a unique molecule identifier (UMI).

In a 30$^{th}$ Example is the method of any one of the first-29$^{th}$ Examples, wherein the recording tag comprises a barcode.

In a 31$^{st}$ Example is the method of any one of the first-30$^{th}$ Examples, wherein the recording tag comprises a spacer at its 3'-terminus.

In a 32$^{nd}$ Example is the method of any one of the first-31$^{st}$ Examples, wherein the analyte and the associated recording tag are covalently joined to the solid support.

In a 33$^{rd}$ Example is the method of any one of the first-32$^{nd}$ Examples, wherein the solid support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

In a $34^{rd}$ Example is the method of the $33^{rd}$ Example, wherein the solid support is a polystyrene bead, a polymer bead, an agarose bead, an acrylamide bead, a solid core bead, a porous bead, a paramagnetic bead, glass bead, or a controlled pore bead.

In a $35^{th}$ Example is the method of any one of the first-$34^{th}$ Examples, wherein a plurality of analytes (e.g., molecules of the same analyte or of different analytes) and associated recording tags are joined to a solid support.

In a $36^{th}$ Example is the method of the $35^{th}$ Example, wherein the plurality of analytes (e.g., molecules of the same analyte or of different analytes) are spaced apart on the solid support at an average distance >50 nm.

In a $37^{th}$ Example is the method of any one of first-$36^{th}$ Examples, wherein the binding agent is a polypeptide or protein.

In a $38^{th}$ Example is the method of the $37^{th}$ Example, wherein the binding agent is a modified aminopeptidase, a modified amino acyl tRNA synthetase, a modified anticalin, or a modified ClpS.

In a $39^{th}$ Example is the method of any one of the first-$38^{th}$ Examples, wherein the binding agent is capable of selectively binding to the analyte.

In a $40^{th}$ Example is the method of any one of the first-$39^{th}$ Examples, wherein the coding tag is DNA molecule, an RNA molecule, a BNA molecule, an XNA molecule, a LNA molecule, a PNA molecule, a γPNA molecule, or a combination thereof.

In a $41^{st}$ Example is the method of any one of the first-$40^{th}$ Examples, wherein the coding tag comprises an encoder sequence.

In a $42^{nd}$ Example is the method of any one of the first-$41^{st}$ Examples, wherein the coding tag further comprises a spacer, a binding cycle specific sequence, a unique molecular identifier, a universal priming site, or any combination thereof.

In a $43^{rd}$ Example is the method of any one of the first-$42^{nd}$ Examples, wherein the binding agent and the coding tag are joined by a linker.

In a $44^{th}$ Example is the method of any one of the first-$42^{nd}$ Examples, wherein the binding agent and the coding tag are joined by a SpyTag/SpyCatcher, a SpyTag-KTag/SpyLigase (where two moieties to be joined have the SpyTag/KTag pair, and the SpyLigase joins SpyTag to KTag, thus joining the two moieties), a sortase, or SnoopTag/SnoopCatcher peptide-protein pair.

In a $45^{th}$ Example is the method of any one of the first-$44^{th}$ Examples, wherein transferring the information of the coding tag to the recording tag is mediated by a DNA ligase.

In a $46^{th}$ Example is the method of any one of the first-$44^{th}$ Examples, wherein transferring the information of the coding tag to the recording tag is mediated by a DNA polymerase.

In a $47^{th}$ Example is the method of any one of the first-$44^{th}$ Examples, wherein transferring the information of the coding tag to the recording tag is mediated by chemical ligation.

In a $48^{th}$ Example is the method of any one of the first-$47^{th}$ Examples, wherein analyzing the extended recording tag comprises a nucleic acid sequencing method.

In a $49^{th}$ Example is the method of the $48^{th}$ Example, wherein the nucleic acid sequencing method is sequencing by synthesis, sequencing by ligation, sequencing by hybridization, polony sequencing, ion semiconductor sequencing, or pyrosequencing.

In a $50^{th}$ Example is the method of the $48^{th}$ Example, wherein the nucleic acid sequencing method is single molecule real-time sequencing, nanopore-based sequencing, or direct imaging of DNA using advanced microscopy.

In a $51^{st}$ Example is the method of any one of the first-$50^{th}$ Examples, wherein the extended recording tag is amplified prior to analysis.

In a $52^{nd}$ Example is the method of any one of the first-$51^{st}$ Examples, wherein the order of coding tag information contained on the extended recording tag provides information regarding the order of binding by the binding agents to the analyte.

In a $53^{rd}$ Example is the method of any one of the first-$52^{nd}$ Examples, wherein frequency of the coding tag information contained on the extended recording tag provides information regarding the frequency of binding by the binding agents to the analyte.

In a $54^{th}$ Example is the method of any one of the first-$53^{rd}$ Examples, wherein a plurality of extended recording tags representing a plurality of analytes (e.g., molecules of the same analyte or of different analytes) are analyzed in parallel.

In a $55^{th}$ Example is the method of the $54^{th}$ Example, wherein the plurality of extended recording tags representing a plurality of analytes (e.g., molecules of the same analyte or of different analytes) are analyzed in a multiplexed assay.

In a $56^{th}$ Example is the method of any one of the first-$55^{th}$ Examples, wherein the plurality of extended recording tags undergoes a target enrichment assay prior to analysis.

In a $57^{th}$ Example is the method of any one of the first-$56^{th}$ Examples, wherein the plurality of extended recording tags undergoes a subtraction assay prior to analysis.

In a $58^{th}$ Example is the method of any one of the first-$57^{th}$ Examples, wherein the plurality of extended recording tags undergoes a normalization assay to reduce highly abundant species prior to analysis.

In a $59^{th}$ Example is the method of any one of the first-$58^{th}$ Examples, wherein the NTAA is removed by a modified aminopeptidase, a modified amino acid tRNA synthetase, mild Edman degradation, Edmanase enzyme, or anhydrous TFA.

In a $60^{th}$ Example is the method of any one of the first-$59^{th}$ Examples, wherein at least one binding agent binds to a terminal amino acid residue.

In a $61^{st}$ Example is the method of any one of the first-$60^{th}$ Examples, wherein at least one binding agent binds to a post-translationally modified amino acid.

In a $62^{nd}$ Example is a method for analyzing one or more peptides from a sample comprising a plurality of protein complexes, proteins, or polypeptides, the method comprising: (a) partitioning the plurality of protein complexes, proteins, or polypeptides within the sample into a plurality of compartments, wherein each compartment comprises a plurality of compartment tags optionally joined to a solid support, wherein the plurality of compartment tags are the same within an individual compartment and are different from the compartment tags of other compartments; (b) fragmenting the plurality of protein complexes, proteins, and/or polypeptides into a plurality of peptides; (c) contacting the plurality of peptides to the plurality of compartment tags under conditions sufficient to permit annealing or joining of the plurality of peptides with the plurality of compartment tags within the plurality of compartments, thereby generating a plurality of compartment tagged peptides; (d) collecting the compartment tagged peptides from the plurality of compartments; and (e) analyzing one or more compartment tagged peptide according to a method of any one of the first-21$^{st}$ Examples and 26$^{th}$-61$^{st}$ Examples.

In a 63$^{rd}$ Example is the method of the 62$^{nd}$ Example, wherein the compartment is a microfluidic droplet.

In a 64$^{th}$ Example is the method of the 62$^{nd}$ Example, wherein the compartment is a microwell.

In a 65$^{th}$ Example is the method of the 62$^{nd}$ Example, wherein the compartment is a separated region on a surface.

In a 66$^{th}$ Example is the method of any one of the 62$^{nd}$-65$^{th}$ Examples, wherein each compartment comprises on average a single cell.

In a 67$^{th}$ Example is a method for analyzing one or more peptides from a sample comprising a plurality of protein complexes, proteins, or polypeptides, the method comprising: (a) labeling of the plurality of protein complexes, proteins, or polypeptides with a plurality of universal DNA tags; (b) partitioning the plurality of labeled protein complexes, proteins, or polypeptides within the sample into a plurality of compartments, wherein each compartment comprises a plurality of compartment tags, wherein the plurality of compartment tags are the same within an individual compartment and are different from the compartment tags of other compartments; (c) contacting the plurality of protein complexes, proteins, or polypeptides to the plurality of compartment tags under conditions sufficient to permit annealing or joining of the plurality of protein complexes, proteins, or polypeptides with the plurality of compartment tags within the plurality of compartments, thereby generating a plurality of compartment tagged protein complexes, proteins or polypeptides; (d) collecting the compartment tagged protein complexes, proteins, or polypeptides from the plurality of compartments; (e) optionally fragmenting the compartment tagged protein complexes, proteins, or polypeptides into a compartment tagged peptides; and (f) analyzing one or more compartment tagged peptide according to a method of any one of the first-21$^{st}$ Examples and 26$^{th}$-61$^{st}$ Examples.

In a 68$^{th}$ Example is the method of any one of the 62$^{nd}$-67$^{th}$ Examples, wherein compartment tag information is transferred to a recording tag associated with a peptide via primer extension or ligation.

In a 69$^{th}$ Example is the method of any one of the 62$^{nd}$-68$^{th}$ Examples, wherein the solid support comprises a bead.

In a 70$^{th}$ Example is the method of the 69$^{th}$ Example, wherein the bead is a polystyrene bead, a polymer bead, an agarose bead, an acrylamide bead, a solid core bead, a porous bead, a paramagnetic bead, glass bead, or a controlled pore bead.

In a 71$^{st}$ Example is the method of any one of the 62$^{nd}$-70$^{th}$ Examples, wherein the compartment tag comprises a single stranded or double stranded nucleic acid molecule.

In a 72$^{nd}$ Example is the method of any one of the 62$^{nd}$-71$^{st}$ Examples, wherein the compartment tag comprises a barcode and optionally a UMI.

In a 73$^{rd}$ Example is the method of the 72$^{nd}$ Example, wherein the solid support is a bead and the compartment tag comprises a barcode, further wherein beads comprising the plurality of compartment tags joined thereto are formed by split-and-pool synthesis.

In a 74$^{th}$ Example is the method of the 72$^{nd}$ Example, wherein the solid support is a bead and the compartment tag comprises a barcode, further wherein beads comprising a plurality of compartment tags joined thereto are formed by individual synthesis or immobilization.

In a 75$^{th}$ Example is the method of any one of the 62$^{nd}$-74$^{th}$ Examples, wherein the compartment tag is a component within a recording tag, wherein the recording tag optionally further comprises a spacer, a unique molecular identifier, a universal priming site, or any combination thereof.

In a 76$^{th}$ Example is the method of any one of the 62$^{nd}$-75$^{th}$ Examples, wherein the compartment tags further comprise a functional moiety capable of reacting with an internal amino acid or N-terminal amino acid on the plurality of protein complexes, proteins, or polypeptides.

In a 77$^{th}$ Example is the method of the 76$^{th}$ Example, wherein the functional moiety is an NHS group.

In a 78$^{th}$ Example is the method of the 76$^{th}$ Example, wherein the functional moiety is an aldehyde group.

In a 79$^{th}$ Example is the method of any one of the 62$^{nd}$-78$^{th}$ Examples, wherein the plurality of compartment tags is formed by: printing, spotting, ink-jetting the compartment tags into the compartment, or a combination thereof.

In an 80$^{th}$ Example is the method of any one of the 62$^{nd}$-79$^{th}$ Examples, wherein the compartment tag further comprises a peptide.

In an 81$^{st}$ Example is the method of the 80$^{th}$ Example, wherein the compartment tag peptide comprises a protein ligase recognition sequence.

In an 82$^{nd}$ Example is the method of the 81$^{st}$ Example, wherein the protein ligase is butelase I or a homolog thereof.

In an 83rd. Example is the method of any one of the 62$^{nd}$-82$^{nd}$ Examples, wherein the plurality of polypeptides is fragmented with a protease.

In an 84$^{th}$ Example is the method of the 83$^{rd}$ Example, wherein the protease is a metalloprotease.

In an 85$^{th}$ Example is the method of the 84$^{th}$ Example, wherein the activity of the metalloprotease is modulated by photo-activated release of metallic cations.

In an 86$^{th}$ Example is the method of any one of the 62$^{nd}$-85$^{th}$ Examples, further comprising subtraction of one or more abundant proteins from the sample prior to partitioning the plurality of polypeptides into the plurality of compartments.

In an 87$^{th}$ Example is the method of any one of the 62$^{nd}$-86$^{th}$ Examples, further comprising releasing the compartment tags from the solid support prior to joining of the plurality of peptides with the compartment tags.

In an 88$^{th}$ Example is the method of the 62$^{nd}$ Example, further comprising following step (d), joining the compartment tagged peptides to a solid support in association with recording tags.

In an 89$^{th}$ Example is the method of the 88$^{th}$ Example, further comprising transferring information of the compartment tag on the compartment tagged peptide to the associated recording tag.

In a 90$^{th}$ Example is the method of the 89$^{th}$ Example, further comprising removing the compartment tags from the compartment tagged peptides prior to step (e).

In a 91$^{st}$ Example is the method of any one of the 62$^{nd}$-90$^{th}$ Examples, further comprising determining the identity of the single cell from which the analyzed peptide derived based on the analyzed peptide's compartment tag sequence.

In a 92$^{nd}$ Example is the method of any one of the 62$^{nd}$-90$^{th}$ Examples, further comprising determining the identity of the protein or protein complex from which the analyzed peptide derived based on the analyzed peptide's compartment tag sequence.

In a 93rd Example is a method for analyzing a plurality of analytes (e.g., molecules of the same analyte or of different analytes), comprising the steps of: (a) providing a plurality of analytes and associated recording tags joined to a solid support; (b) contacting the plurality of analytes with a plurality of binding agents capable of binding to the plurality of analytes, wherein each binding agent comprises a coding tag with identifying information regarding the binding agent; (c) (i) transferring the information of the analyte associated recording tags to the coding tags of the binding agents that are bound to the analytes to generate extended coding tags; or (ii) transferring the information of analyte associated recording tags and coding tags of the binding agents that are bound to the analytes to a di-tag construct; (d) collecting the extended coding tags or di-tag constructs; (e) optionally repeating steps (b)-(d) for one or more binding cycles; (f) analyzing the collection of extended coding tags or di-tag constructs.

In a 94th Example is the method of the 93rd Example, wherein the analyte is a protein.

In a 95th Example is the method of the 93rd Example, wherein the analyte is a peptide.

In a 96th Example is the method of the 95th Example, wherein the peptide is obtained by fragmenting a protein from a biological sample.

In a 97th Example is the method of any one of the 93rd-96th Examples, wherein the recording tag is a DNA molecule, an RNA molecule, a PNA molecule, a BNA molecule, an XNA, molecule, an LNA molecule, a γPNA molecule, or a combination thereof.

In a 98th Example is the method of any one of the 93rd-97th Examples, wherein the recording tag comprises a unique molecular identifier (UMI).

In a 99th Example is the method of Examples 93-98, wherein the recording tag comprises a compartment tag.

In a 100th Example is the method of any one of Examples 93-99, wherein the recording tag comprises a universal priming site.

In a 101st Example is the method of any one of Examples 93-100, wherein the recording tag comprises a spacer at its 3'-terminus.

In a 102nd Example is the method of any one of Examples 93-101, wherein the 3'-terminus of the recording tag is blocked to prevent extension of the recording tag by a polymerase and the information of analyte associated recording tag and coding tag of the binding agent that is bound to the analyte is transferred to a di-tag construct.

In a 103rd Example is the method of any one of Examples 93-102, wherein the coding tag comprises an encoder sequence.

In a 104th Example is the method of any one of Examples 93-103, wherein the coding tag comprises a UMI.

In a 105th Example is the method of any one of Examples 93-104, wherein the coding tag comprises a universal priming site.

In a 106th Example is the method of any one of Examples 93-105, wherein the coding tag comprises a spacer at its 3'-terminus.

In a 107th Example is the method of any one of Examples 93-106, wherein the coding tag comprises a binding cycle specific sequence.

In a 108th Example is the method of any one of Examples 93-107, wherein the binding agent and the coding tag are joined by a linker.

In a 109th Example is the method of any one of Examples 93-108, wherein transferring information of the recording tag to the coding tag is effected by primer extension.

In a 110th Example is the method of any one of Examples 93-108, wherein transferring information of the recording tag to the coding tag is effected by ligation.

In an 111th Example is the method of any one of Examples 93-108, wherein the di-tag construct is generated by gap fill, primer extension, or both.

In a 112th Example is the method of any one of Examples 93-97, 107, 108, and 111, wherein the di-tag molecule comprises a universal priming site derived from the recording tag, a compartment tag derived from the recording tag, a unique molecular identifier derived from the recording tag, an optional spacer derived from the recording tag, an encoder sequence derived from the coding tag, a unique molecular identifier derived from the coding tag, an optional spacer derived from the coding tag, and a universal priming site derived from the coding tag.

In a 113th Example is the method of any one of Examples 93-112, wherein the analyte and the associated recording tag are covalently joined to the solid support.

In a 114th Example is the method of Example 113, wherein the solid support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

In a 115th Example is the method of Example 114, wherein the solid support is a polystyrene bead, a polymer bead, an agarose bead, an acrylamide bead, a solid core bead, a porous bead, a paramagnetic bead, glass bead, or a controlled pore bead.

In a 116th Example is the method of any one of Examples 93-115, wherein the binding agent is a polypeptide or protein.

In a 117th Example is the method of Example 116, wherein the binding agent is a modified aminopeptidase, a modified amino acyl tRNA synthetase, a modified anticalin, or an antibody or binding fragment thereof.

In an 118th Example is the method of any one of Example 95-117 wherein the binding agent binds to a single amino acid residue, a dipeptide, a tripeptide or a post-translational modification of the peptide.

In a 119th Example is the method of Example 118, wherein the binding agent binds to an N-terminal amino acid residue, a C-terminal amino acid residue, or an internal amino acid residue.

In a 120th Example is the method of Example 118, wherein the binding agent binds to an N-terminal peptide, a C-terminal peptide, or an internal peptide.

In a 121st Example is method of Example 119, wherein the binding agent binds to the N-terminal amino acid residue and the N-terminal amino acid residue is cleaved after each binding cycle.

In a 122nd Example is the method of Example 119, wherein the binding agent binds to the C-terminal amino acid residue and the C-terminal amino acid residue is cleaved after each binding cycle.

Example 123. The method of Example 121, wherein the N-terminal amino acid residue is cleaved via Edman degradation.

Example 124. The method of Example 93, wherein the binding agent is a site-specific covalent label of an amino acid or post-translational modification.

Example 125. The method of any one of Examples 93-124, wherein following step (b), complexes comprising the analyte and associated binding agents are dissociated from the solid support and partitioned into an emulsion of droplets or microfluidic droplets.

Example 126. The method of Example 125, wherein each microfluidic droplet, on average, comprises one complex comprising the analyte and the binding agents.

Example 127. The method of Example 125 or 126, wherein the recording tag is amplified prior to generating an extended coding tag or di-tag construct.

Example 128. The method of any one of Examples 125-127, wherein emulsion fusion PCR is used to transfer the recording tag information to the coding tag or to create a population of di-tag constructs.

Example 129. The method of any one of Examples 93-128, wherein the collection of extended coding tags or di-tag constructs are amplified prior to analysis.

Example 130. The method of any one of Examples 93-129, wherein analyzing the collection of extended coding tags or di-tag constructs comprises a nucleic acid sequencing method.

Example 131. The method of Example 130, wherein the nucleic acid sequencing method is sequencing by synthesis, sequencing by ligation, sequencing by hybridization, polony sequencing, ion semiconductor sequencing, or pyrosequencing.

Example 132. The method of Example 130, wherein the nucleic acid sequencing method is single molecule real-time sequencing, nanopore-based sequencing, or direct imaging of DNA using advanced microscopy.

Example 133. The method of Example 130, wherein a partial composition of the analyte is determined by analysis of a plurality of extended coding tags or di-tag constructs using unique compartment tags and optionally UMIs.

Example 134. The method of any one of Examples 1-133, wherein the analysis step is performed with a sequencing method having a per base error rate of >5%, >10%, >15%, >20%, >25%, or >30%.

Example 135. The method of any one of Examples 1-134, wherein the identifying components of a coding tag, recording tag, or both comprise error correcting codes.

Example 136. The method of Example 135, wherein the identifying components are selected from an encoder sequence, barcode, UMI, compartment tag, cycle specific sequence, or any combination thereof.

Example 137. The method of Example 135 or 136, wherein the error correcting code is selected from Hamming code, Lee distance code, asymmetric Lee distance code, Reed-Solomon code, and Levenshtein-Tenengolts code.

Example 138. The method of any one of Examples 1-134, wherein the identifying components of a coding tag, recording tag, or both are capable of generating a unique current or ionic flux or optical signature, wherein the analysis step comprises detection of the unique current or ionic flux or optical signature in order to identify the identifying components.

Example 139. The method of Example 138, wherein the identifying components are selected from an encoder sequence, barcode, UMI, compartment tag, cycle specific sequence, or any combination thereof.

Example 140. A method for analyzing a plurality of analytes (e.g., molecules of the same analyte or of different analytes), comprising the steps of: (a) providing a plurality of analytes and associated recording tags joined to a solid support; (b) contacting the plurality of analytes with a plurality of binding agents capable of binding to cognate analytes, wherein each binding agent comprises a coding tag with identifying information regarding the binding agent; (c) transferring the information of a first coding tag of a first binding agent to a first recording tag associated with the first analyte to generate a first order extended recording tag, wherein the first binding agent binds to the first analyte; (d) contacting the plurality of analytes with the plurality of binding agents capable of binding to cognate analytes; (e) transferring the information of a second coding tag of a second binding agent to the first order extended recording tag to generate a second order extended recording tag, wherein the second binding agent binds to the first analyte; (f) optionally repeating steps (d)-(e) for "n" binding cycles, wherein the information of each coding tag of each binding agent that binds to the first analyte is transferred to the extended recording tag generated from the previous binding cycle to generate an $n^{th}$ order extended recording tag that represents the first analyte; (g) analyzing the $n^{th}$ order extended recording tag.

Example 141. The method of Example 140, wherein a plurality of $n^{th}$ order extended recording tags that represent a plurality of analytes are generated and analyzed.

Example 142. The method of Example 140 or 141, wherein the analyte is a protein.

Example 143. The method of Example 142, wherein the analyte is a peptide.

Example 144. The method of Example 143, wherein the peptide is obtained by fragmenting proteins from a biological sample.

Example 145. The method of any one of Examples 140-144, wherein the plurality of analytes comprises analytes (e.g., macromolecules such as polypeptides, proteins, protein complexes) from multiple, pooled samples.

Example 146. The method of any one of Examples 140-145, wherein the recording tag is a DNA molecule, an RNA molecule, a PNA molecule, a BNA molecule, an XNA, molecule, an LNA molecule, a γPNA molecule, or a combination thereof.

Example 147. The method of any one of Examples 140-146, wherein the recording tag comprises a unique molecular identifier (UMI).

Example 148. The method of Examples 140-147, wherein the recording tag comprises a compartment tag.

Example 149. The method of any one of Examples 140-148, wherein the recording tag comprises a universal priming site.

Example 150. The method of any one of Examples 140-149, wherein the recording tag comprises a spacer at its 3'-terminus.

Example 151. The method of any one of Examples 140-150, wherein the coding tag comprises an encoder sequence.

Example 152. The method of any one of Examples 140-151, wherein the coding tag comprises a UMI.

Example 153. The method of any one of Examples 140-152, wherein the coding tag comprises a universal priming site.

Example 154. The method of any one of Examples 140-153, wherein the coding tag comprises a spacer at its 3'-terminus.

Example 155. The method of any one of Examples 140-154, wherein the coding tag comprises a binding cycle specific sequence.

Example 156. The method of any one of Examples 140-155, wherein the coding tag comprises a unique molecular identifier.

Example 157. The method of any one of Examples 140-156, wherein the binding agent and the coding tag are joined by a linker.

Example 158. The method of any one of Examples 140-157, wherein transferring information of the recording tag to the coding tag is mediated by primer extension.

Example 159. The method of any one of Examples 140-158, wherein transferring information of the recording tag to the coding tag is mediated by ligation.

Example 160. The method of any one of Examples 140-159, wherein the plurality of analytes, the associated recording tags, or both are covalently joined to the solid support.

Example 161. The method of any one of Examples 140-160, wherein the solid support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

Example 162. The method of Example 161, wherein the solid support is a polystyrene bead, a polymer bead, an agarose bead, an acrylamide bead, a solid core bead, a porous bead, a paramagnetic bead, glass bead, or a controlled pore bead.

Example 163. The method of any one of Examples 140-162, wherein the binding agent is a polypeptide or protein.

Example 164. The method of Example 163, wherein the binding agent is a modified aminopeptidase, a modified amino acyl tRNA synthetase, a modified anticalin, or an antibody or binding fragment thereof.

Example 165. The method of any one of Examples 142-164 wherein the binding agent binds to a single amino acid residue, a dipeptide, a tripeptide or a post-translational modification of the peptide.

Example 166. The method of Example 165, wherein the binding agent binds to an N-terminal amino acid residue, a C-terminal amino acid residue, or an internal amino acid residue.

Example 167. The method of Example 165, wherein the binding agent binds to an N-terminal peptide, a C-terminal peptide, or an internal peptide.

Example 168. The method of any one of Examples 142-164, wherein the binding agent binds to a chemical label of a modified N-terminal amino acid residue, a modified C-terminal amino acid residue, or a modified internal amino acid residue.

Example 169. The method of Example 166 or 168, wherein the binding agent binds to the N-terminal amino acid residue or the chemical label of the modified N-terminal amino acid residue, and the N-terminal amino acid residue is cleaved after each binding cycle.

Example 170. The method of Example 166 or 168, wherein the binding agent binds to the C-terminal amino acid residue or the chemical label of the modified C-terminal amino acid residue, and the C-terminal amino acid residue is cleaved after each binding cycle.

Example 171. The method of Example 169, wherein the N-terminal amino acid residue is cleaved via Edman degradation, Edmanase, a modified aminopeptidase, or a modified acylpeptide hydrolase.

Example 172. The method of Example 163, wherein the binding agent is a site-specific covalent label of an amino acid or post-translational modification.

Example 173. The method of any one of Examples 140-172, wherein the plurality of $n^{th}$ order extended recording tags are amplified prior to analysis.

Example 174. The method of any one of Examples 140-173, wherein analyzing the $n^{th}$ order extended recording tag comprises a nucleic acid sequencing method.

Example 175. The method of Example 174, wherein a plurality of $n^{th}$ order extended recording tags representing a plurality of analytes are analyzed in parallel.

Example 176. The method of Example 174 or 175, wherein the nucleic acid sequencing method is sequencing by synthesis, sequencing by ligation, sequencing by hybridization, polony sequencing, ion semiconductor sequencing, or pyrosequencing.

Example 177. The method of Example 174 or 175, wherein the nucleic acid sequencing method is single molecule real-time sequencing, nanopore-based sequencing, or direct imaging of DNA using advanced microscopy.

Example 1'. A method, comprising: (a) contacting a set of proteins, wherein each protein is associated directly or indirectly with a recording tag, with a library of agents, wherein each agent comprises (i) a small molecule, a peptide or peptide mimetic, a peptidomimetic (e.g., a peptoid, a β-peptide, or a D-peptide peptidomimetic), a polysaccharide, or an aptamer (e.g., a nucleic acid aptamer, such as a DNA aptamer, or a peptide aptamer), and (ii) a coding tag comprising identifying information regarding the small molecule, peptide or peptide mimetic, peptidomimetic (e.g., peptoid, β-peptide, or D-peptide peptidomimetic), polysaccharide, or aptamer, wherein each protein and/or its associated recording tag, or each agent, is immobilized directly or indirectly to a support; (b) allowing transfer of information between (i) the recording tag associated with each protein that binds and/or reacts with the small molecule(s), peptide(s) or peptide mimetic(s), peptidomimetic(s) (e.g., peptoid(s), β-peptide(s), or D-peptide peptidomimetic(s)), polysaccharide(s), or aptamer(s) of one or more agents, and (ii) the coding tag of the one or more agents, to generate an extended recording tag and/or an extended coding tag; and (c) analyzing the extended recording tag and/or the extended coding tag.

Example 2'. The method of Example 1', wherein each protein is spaced apart from other proteins on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 μm.

Example 3'. The method of Example 1' or 2', wherein each protein and its associated recording tag is spaced apart from other proteins and their associated recording tags on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 µm.

Example 4'. The method of any one of Examples 1'-3', wherein one or more of the proteins and/or their associated recording tags are covalently immobilized to the support (e.g., via a linker), or non-covalently immobilized to the support (e.g., via a binding pair).

Example 5'. The method of any one of Examples 1'-4', wherein a subset of the proteins and/or their associated recording tags are covalently immobilized to the support while another subset of the proteins and/or their associated recording tags are non-covalently immobilized to the support.

Example 6'. The method of any one of Examples 1'-5', wherein one or more of the recording tags are immobilized to the support, thereby immobilizing the associated protein(s).

Example 7'. The method of any one of Examples 1'-6', wherein one or more of the proteins are immobilized to the support, thereby immobilizing the associated recording tag(s).

Example 8'. The method of any one of Examples 1-7, wherein at least one protein co-localizes with its associated recording tag, while each is independently immobilized to the support.

Example 9'. The method of any one of Examples 1'-8', wherein at least one protein and/or its associated recording tag associates directly or indirectly with an immobilizing linker, and the immobilizing linker is immobilized directly or indirectly to the support, thereby immobilizing the at least one protein and/or its associated recording tag to the support.

Example 10'. The method of any one of Examples 1'-9', wherein the density of immobilized recording tags is equal to or greater than the density of immobilized proteins.

Example 11'. The method of Example 10', wherein the density of immobilized recording tags is at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 50-fold, at least about 100-fold, or more, of the density of immobilized proteins.

Example 12'. The method of Example 1', wherein each agent is spaced apart from other agents immobilized on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 µm.

Example 13'. The method of Example 12', wherein one or more of the agents are covalently immobilized to the support (e.g., via a linker), or non-covalently immobilized to the support (e.g., via a binding pair).

Example 14'. The method of Example 12' or 13', wherein a subset of the agents are covalently immobilized to the support while another subset of the agents are non-covalently immobilized to the support.

Example 15'. The method of any one of Examples 12'-14', wherein for one or more of the agents, the small molecule, peptide or peptide mimetic, peptidomimetic (e.g., peptoid, β-peptide, or D-peptide peptidomimetic), polysaccharide, or aptamer is immobilized to the support, thereby immobilizing the coding tag.

Example 16'. The method of any one of Examples 12'-15', wherein for one or more of the agents, the coding tag is immobilized to the support, thereby immobilizing the small molecule, peptide or peptide mimetic, peptidomimetic (e.g., peptoid, β-peptide, or D-peptide peptidomimetic), polysaccharide, or aptamer.

Example 17'. The method of any one of Examples 1'-16', wherein information is transferred from at least one coding tag to at least one recording tag, thereby generating at least one extended recording tag.

Example 18'. The method of any one of Examples 1'-17', wherein information is transferred from at least one recording tag to at least one coding tag, thereby generating at least one extended coding tag.

Example 19'. The method of any one of Examples 1'-18', wherein at least one di-tag construct is generated comprising information from the coding tag and information from the recording tag.

Example 20'. The method of any one of Examples 1'-19', wherein at least one of the proteins binds and/or reacts with the small molecules, peptides or peptide mimetics, peptidomimetics (e.g., peptoids, β-peptides, or D-peptide peptidomimetics), polysaccharides, or aptamers of two or more agents.

Example 21'. The method of Example 20', wherein the extended recording tag or the extended coding tag comprises identifying information regarding the small molecules, peptides or peptide mimetics, peptidomimetics (e.g., peptoids, β-peptides, or D-peptide peptidomimetics), polysaccharides, or aptamers of the two or more agents.

Example 22'. The method of any one of Examples 1'-21', wherein at least one of the proteins is associated with two or more recording tags, wherein the two or more recording tags can be the same or different.

Example 23'. The method of any one of Examples 1'-22', wherein at least one of the agents comprises two or more coding tags, wherein the two or more coding tags can be the same or different.

Example 24'. The method of any one of Examples 1'-23', wherein the transfer of information is accomplished by ligation (e.g., an enzymatic or chemical ligation, a splint ligation, a sticky end ligation, a single-strand (ss) ligation such as a ssDNA ligation, or any combination thereof), a polymerase-mediated reaction (e.g., primer extension of single-stranded nucleic acid or double-stranded nucleic acid), or any combination thereof.

Example 25'. The method of Example 24', wherein the ligation and/or polymerase-mediated reaction have faster kinetics relative to the binding occupancy time or reaction time between the protein and the small molecule, peptide or peptide mimetic, peptidomimetic (e.g., peptoid, β-peptide, or D-peptide peptidomimetic), polysaccharide, or aptamer, optionally wherein a reagent for the ligation and/or polymerase-mediated reaction is present in the same reaction volume as the binding or reaction between the protein and the small molecule, peptide or peptide mimetic, peptidomimetic (e.g., peptoid, β-peptide, or D-peptide peptidomimetic), polysaccharide, or aptamer, and further optionally wherein information transfer is effected by using a concomitant binding/encoding step, and/or by using a temperature of the encoding or information writing step that is decreased to slow the off rate of the binding agent.

Example 26'. The method of any one of Examples 1'-25', wherein each protein associates with its recording tag via individual attachment, and/or wherein each small molecule, peptide or peptide mimetic, peptidomimetic (e.g., peptoid, β-peptide, or D-peptide peptidomimetic), polysaccharide, or aptamer associates with its coding tag via individual attachment.

Example 27'. The method of Example 26', wherein the attachment occurs via ribosome or mRNA/cDNA display in which the recording tag and/or coding tag sequence information is contained in the mRNA sequence.

Example 28'. The method of Example 27', wherein the recording tag and/or coding tag comprise a universal primer sequence, a barcode, and/or a spacer sequence at the 3' end of the mRNA sequence.

Example 29'. The method of Example 28', wherein the recording tag and/or coding tag, at the 3' end, further comprise a restriction enzyme digestion site.

Example 30'. The method of any one of Examples 1'-29', wherein the set of proteins is a proteome or subset thereof, optionally wherein the set of proteins are produced using in vitro transcription of a genome or subset thereof followed by in vitro translation, or produced using in vitro translation of a transcriptome or subset thereof.

Example 31'. The method of Example 30', wherein the subset of the proteome comprises a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glycoproteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof.

Example 32'. The method of any one of Examples 1'-31', wherein the set of proteins are from a mammal such as human, a non-human animal, a fish, an invertebrate, an arthropod, an insect, or a plant, e.g., a yeast, a bacterium, e.g., E. coli, a virus, e.g., HIV or HCV, or a combination thereof.

Example 33'. The method of any one of Examples 1'-32', wherein the set of proteins comprise a protein complex or subunit thereof.

Example 34'. The method of any one of Examples 1'-33', wherein the recording tag comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, or a combination thereof.

Example 35'. The method of any one of Examples 1'-34', wherein the recording tag comprises a universal priming site.

Example 36'. The method of any one of Examples 1'-35', wherein the recording tag comprises a priming site for amplification, sequencing, or both, for example, the universal priming site comprises a priming site for amplification, sequencing, or both.

Example 37'. The method of any one of Examples 1'-36', wherein the recording tag comprises a unique molecule identifier (UMI).

Example 38'. The method of any one of Examples 1'-37', wherein the recording tag comprises a barcode.

Example 39'. The method of any one of Examples 1'-38', wherein the recording tag comprises a spacer at its 3'-terminus.

Example 40'. The method of any one of Examples 1'-39', wherein the support is a solid support, such as a rigid solid support, a flexible solid support, or a soft solid support, and including a porous support or a non-porous support.

Example 41'. The method of any one of Examples 1'-40', wherein the support comprises a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

Example 42'. The method of Example 41', wherein the support comprises a polystyrene bead, a polymer bead, an agarose bead, an acrylamide bead, a solid core bead, a porous bead, a magnetic bead, a paramagnetic bead, a glass bead, or a controlled pore bead, or any combination thereof.

Example 43'. The method of any one of Examples 1'-42', which is for parallel analysis of the interaction between the set of proteins and the library of small molecules, and/or peptides or peptide mimetics, and/or peptidomimetics (e.g., peptoids, β-peptides, or D-peptide peptidomimetics), and/or polysaccharides, and/or aptamers, in order to create a small molecule-protein binding matrix, and/or a peptide/peptide mimetic-protein binding matrix, and/or a peptidomimetic-protein binding matrix (e.g., a peptoid-protein binding matrix, a β-peptide-protein binding matrix, or a D-peptide peptidomimetic-protein binding matrix), and/or a polysaccharide-protein binding matrix, and/or an aptamer-protein binding matrix.

Example 44'. The method of Example 43', wherein the matrix size is of about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$, about $10^{14}$, or more, for example, of about $2 \times 10^{13}$.

Example 45'. The method of any one of Examples 1'-44', wherein the coding tag comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, or a combination thereof.

Example 46'. The method of any one of Examples 1'-45', wherein the coding tag comprises an encoder sequence that identifies the small molecule, peptide or peptide mimetic, peptidomimetic (e.g., peptoid, β-peptide, or D-peptide peptidomimetic), polysaccharide, or aptamer.

Example 47'. The method of any one of Examples 1'-46', wherein the coding tag comprises a spacer, a unique molecular identifier (UMI), a universal priming site, or any combination thereof.

Example 48'. The method of any one of Examples 1'-47', wherein the small molecule, peptide or peptide mimetic, peptidomimetic (e.g., peptoid, β-peptide, or D-peptide peptidomimetic), polysaccharide, or aptamer and the coding tag are joined by a linker or a binding pair.

Example 49'. The method of any one of Examples 1'-48', wherein the small molecule, peptide or peptide mimetic, peptidomimetic (e.g., peptoid, β-peptide, or D-peptide peptidomimetic), polysaccharide, or aptamer and the coding tag are joined by a SpyTag-KTag/SpyLigase (where two moieties to be joined have the SpyTag/KTag pair, and the SpyLigase joins SpyTag to KTag, thus joining the two moieties), a SpyTag/SpyCatcher, a SnoopTag/SnoopCatcher peptide-protein pair, a sortase, or a HaloTag/HaloTag ligand pair, or any combination thereof.

Example 50'. A method for analyzing a polypeptide, comprising: (a) contacting (i) a set of fragments of a polypeptide, wherein each fragment is associated directly or indirectly with a recording tag, with (ii) a library of binding agents, wherein each binding agent comprises a binding moiety and a coding tag comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent, and wherein each fragment and/or its associated recording tag, or each binding agent, is immobilized directly or indirectly to a support; (b) allowing transfer of information between (i) the recording tag associated with each fragment and (ii) the coding tag, upon binding between the binding moiety and the one or more N-terminal, internal, or C-terminal amino acids of the fragment, to generate an extended recording tag and/or an extended coding tag; and (c) analyzing the extended recording tag and/or the extended coding tag.

Example 51'. The method of Example 50', wherein the one or more N-terminal, internal, or C-terminal amino acids comprise: (i) an N-terminal amino acid (NTAA); (ii) an N-terminal dipeptide sequence; (iii) an N-terminal tripeptide sequence; (iv) an internal amino acid; (v) an internal dipeptide sequence; (vi) an internal tripeptide sequence; (vii) a C-terminal amino acid (CTAA); (viii) a C-terminal dipeptide sequence; or (ix) a C-terminal tripeptide sequence, or any combination thereof, optionally wherein any one or more of the amino acid residues in (i)-(ix) are modified or functionalized.

Example 52'. The method of Example 51', wherein the one or more N-terminal, internal, or C-terminal amino acids are selected, independently at each residue, from the group consisting of Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

Example 53'. The method of any one of Examples 50'-52', wherein the binding moiety comprises a polypeptide or fragment thereof, a protein or polypeptide chain or fragment thereof, or a protein complex or subunit thereof, such as an antibody or antigen binding fragment thereof.

Example 54'. The method of any one of Examples 50'-53', wherein the binding moiety comprises an anticalin or variant, mutant, or modified protein thereof, an aminoacyl tRNA synthetase or variant, mutant, or modified protein thereof, an anticalin or variant, mutant, or modified protein thereof, a ClpS or variant, mutant, or modified protein thereof, a UBR box protein or variant, mutant, or modified protein thereof; or a modified small molecule that binds amino acid(s), i.e. vancomycin or a variant, mutant, or modified molecule thereof; or any combination thereof.

Example 55'. The method of any one of Examples 50'-54', wherein the binding moiety is capable of selectively and/or specifically binding to a functionalized N-terminal amino acid (NTAA), an N-terminal dipeptide sequence, or an N-terminal tripeptide sequence, or any combination thereof.

Example 56'. A method for analyzing a plurality of polypeptides, comprising: (a) labeling each molecule of a plurality of polypeptides with a plurality of universal tags; (b) contacting the plurality of polypeptides with a plurality of compartment tags, under a condition suitable for annealing or joining of the plurality of universal tags with the plurality of compartment tags, thereby partitioning the plurality of polypeptides into a plurality of compartments (e.g., a bead surface, a microfluidic droplet, a microwell, or a separated region on a surface, or any combination thereof), wherein the plurality of compartment tags are the same within each compartment and are different from the compartment tags of other compartments; (c) fragmenting the polypeptide(s) in each compartment, thereby generating a set of polypeptide fragments each associated with a recording tag comprising at least one universal polynucleotide tag and at least one compartment tag; (d) immobilizing the set of polypeptide fragments, directly or indirectly, to a support; (e) contacting the immobilized set of polypeptide fragments with a library of binding agents, wherein each binding agent comprises a binding moiety and a coding tag comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent; (f) allowing transfer of information between (i) the recording tag associated with each fragment and (ii) the coding tag, upon binding between the binding moiety and the one or more N-terminal, internal, or C-terminal amino acids of the fragment, to generate an extended recording tag and/or an extended coding tag; and (g) analyzing the extended recording tag and/or the extended coding tag.

Example 57'. The method of Example 56', wherein the plurality of polypeptides with the same compartment tag belong to the same protein.

Example 58'. The method of Example 56', wherein the plurality of polypeptides with the same compartment tag belong to different proteins, for example, two, three, four, five, six, seven, eight, nine, ten, or more proteins.

Example 59'. The method of any one of Examples 56'-58', wherein the plurality of compartment tags are immobilized to a plurality of substrates, with each substrate defining a compartment.

Example 60'. The method of Example 59', wherein the plurality of substrates are selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

Example 61'. The method of Example 59' or 60', wherein each of the plurality of substrates comprises a bar-coded particle, such as a bar-coded bead, e.g., a polystyrene bead, a polymer bead, an agarose bead, an acrylamide bead, a solid core bead, a porous bead, a magnetic bead, a paramagnetic bead, a glass bead, or a controlled pore bead, or any combination thereof.

Example 62'. The method of any one of Examples 59'-61', wherein the support is selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

Example 63'. The method of Example 62', wherein the support comprises a sequencing bead, e.g., a polystyrene bead, a polymer bead, an agarose bead, an acrylamide bead, a solid core bead, a porous bead, a magnetic bead, a paramagnetic bead, a glass bead, or a controlled pore bead, or any combination thereof.

Example 64'. The method of any one of Examples 56'-63', wherein each fragment and its associated recording tag is spaced apart from other fragments and their associated recording tags on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 μm.

Example 65'. A method for analyzing a plurality of polypeptides, comprising: (a) immobilizing a plurality of polypeptides to a plurality of substrates, wherein each substrate comprises a plurality of recording tags each comprising a compartment tag, optionally wherein each compartment is a bead, a microfluidic droplet, a microwell, or a separated region on a surface, or any combination thereof; (b) fragmenting (e.g., by a protease digestion) the polypeptide(s) immobilized on each substrate, thereby generating a set of polypeptide fragments immobilized to the substrate; (c) contacting the immobilized set of polypeptide fragments with a library of binding agents, wherein each binding agent comprises a binding moiety and a coding tag comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent; (d) allowing transfer of information between (i) the recording tag and (ii) the coding tag, upon binding between the binding moiety and the one or more N-terminal, internal, or C-terminal amino acids of each fragment, to generate an extended recording tag and/or an extended coding tag; and (e) analyzing the extended recording tag and/or the extended coding tag.

Example 66'. The method of Example 65', wherein the plurality of polypeptides with the same compartment tag belong to the same protein.

Example 67'. The method of Example 65', wherein the plurality of polypeptides with the same compartment tag belong to different proteins, for example, two, three, four, five, six, seven, eight, nine, ten, or more proteins.

Example 68'. The method of any one of Examples 65'-67', wherein each substrate defines a compartment.

Example 69'. The method of any one of Examples 65'-68', wherein the plurality of substrates are selected from the group consisting of a bead, a porous bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

Example 70'. The method of any one of Examples 65'-69', wherein each of the plurality of substrates comprises a bar-coded particle, such as a bar-coded bead, e.g., a polystyrene bead, a polymer bead, an agarose bead, an acrylamide bead, a solid core bead, a porous bead, a magnetic bead, a paramagnetic bead, a glass bead, or a controlled pore bead, or any combination thereof.

Example 71'. The method of any one of Examples 50'-70', wherein the functionalizing reagent comprises a chemical agent, an enzyme, and/or a biological agent, such as an isothiocyanate derivative, 2,4-dinitrobenzenesulfonic (DNBS), 4-sulfonyl-2-nitrofluorobenzene (SNFB) 1-fluoro-2,4-dinitrobenzene, dansyl chloride, 7-methoxycoumarin acetic acid, a thioacylation reagent, a thioacetylation reagent, or a thiobenzylation reagent.

Example 72'. The method of any one of Examples 50'-71', wherein the recording tag comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, or a combination thereof.

Example 73'. The method of any one of Examples 50'-72', wherein the recording tag comprises a universal priming site; a priming site for amplification, sequencing, or both; optionally, a unique molecule identifier (UMI); a barcode; optionally, a spacer at its 3'-terminus; or a combination thereof.

Example 74'. The method of any one of Examples 50'-73', which is for determining the sequence(s) of the polypeptide or plurality of polypeptides.

Example 75'. The method of any one of Examples 50'-74', wherein the coding tag comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, or a combination thereof.

Example 76'. The method of any one of Examples 50'-75', wherein the coding tag comprises an encoder sequence, an optional spacer, an optional unique molecular identifier (UMI), a universal priming site, or any combination thereof.

Example 77'. The method of any one of Examples 50'-76', wherein the binding moiety and the coding tag are joined by a linker or a binding pair.

Example 78'. The method of any one of Examples 50'-77', wherein the binding moiety and the coding tag are joined by a SpyTag-KTag/SpyLigase (where two moieties to be joined have the SpyTag/KTag pair, and the SpyLigase joins SpyTag to KTag, thus joining the two moieties), a SpyTag/SpyCatcher, a SnoopTag/SnoopCatcher peptide-protein pair, a sortase, or a HaloTag/HaloTag ligand pair, or any combination thereof.

Example 79'. The method of any one of Examples 1'-78', wherein the coding tag and/or the recording tag comprise one or more error correcting codes, one or more encoder sequences, one or more barcodes, one or more UMIs, one or more compartment tags, or any combination thereof.

Example 80'. The method of Example 79', wherein the error correcting code is selected from Hamming code, Lee distance code, asymmetric Lee distance code, Reed-Solomon code, and Levenshtein-Tenengolts code.

Example 81'. The method of any one of Examples 1'-80', wherein analyzing the extended recording tag and/or extended coding tag comprises a nucleic acid sequence analysis.

Example 82'. The method of Example 81', wherein the nucleic acid sequence analysis comprises a nucleic acid sequencing method, such as sequencing by synthesis, sequencing by ligation, sequencing by hybridization, polony sequencing, ion semiconductor sequencing, or pyrosequencing, or any combination thereof.

Example 83'. The method of Example 82', wherein the nucleic acid sequencing method is single molecule real-time sequencing, nanopore-based sequencing, or direct imaging of DNA using advanced microscopy.

Example 84'. The method of any one of Examples 1'-83', further comprising one or more washing steps.

Example 85'. The method of any one of Examples 1'-84', wherein the extended recording tag and/or extended coding tag are amplified prior to analysis.

Example 86'. The method of any one of Examples 1'-85', wherein the extended recording tag and/or extended coding tag undergo a target enrichment assay prior to analysis.

Example 87'. The method of any one of Examples 1'-86', wherein the extended recording tag and/or extended coding tag undergo a subtraction assay prior to analysis.

In one aspect, disclosed herein is a kit, comprising: (a) a library of agents, wherein each agent comprises (i) a small molecule, peptide or peptide mimetic, peptidomimetic (e.g., peptoid, 3-peptide, or D-peptide peptidomimetic), polysaccharide, and/or aptamer, and (ii) a coding tag comprising identifying information regarding the small molecule, peptide or peptide mimetic, peptidomimetic (e.g., peptoid, β-peptide, or D-peptide peptidomimetic), polysaccharide, or aptamer; and optionally (b) a set of proteins, wherein each protein is associated directly or indirectly with a recording tag, wherein each protein and/or its associated recording tag, or each agent, is immobilized directly or indirectly to a support, and wherein the set of proteins, the recording tags, and the library of agents are configured to allow information transfer between (i) the recording tag associated with each protein that binds and/or reacts with the small molecule(s), peptide(s) or peptide mimetic(s), peptidomimetic(s) (e.g., peptoid(s), 0-peptide(s), or D-peptide peptidomimetic(s)), polysaccharide(s), or aptamer(s) of one or more agents, and (ii) the coding tag of the one or more agents, to generate an extended recording tag and/or an extended coding tag.

In one aspect, disclosed herein is a kit for analyzing a polypeptide, comprising: (a) a library of binding agents, wherein each binding agent comprises a binding moiety and a coding tag comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent; and optionally (b) a set of fragments of a polypeptide, wherein each fragment is associated directly or indirectly with a recording tag, or (b') a means for fragmenting a polypeptide, such as a protease, wherein each fragment and/or its associated recording tag, or each binding agent, is immobilized directly or indirectly to a support, and wherein the set of fragments of a polypeptide, the recording tags, and the library of binding agents are configured to allow transfer of information between (i) the recording tag associated with each fragment and (ii) the coding tag, upon binding between the binding moiety and the one or more N-terminal, internal, or C-terminal amino acids of the fragment, to generate an extended recording tag and/or an extended coding tag.

In one aspect, disclosed herein is a kit for analyzing a plurality of polypeptides, comprising: (a) a library of binding agents, wherein each binding agent comprises a binding moiety and a coding tag comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent; and (b) a plurality of substrates, optionally with a plurality of polypeptides immobilized thereto, wherein each substrate comprises a plurality of recording tags each comprising a compartment tag, optionally wherein each compartment is a bead, a microfluidic droplet, a microwell, or a separated region on a surface, or any combination thereof, wherein the polypeptide(s) immobilized on each substrate are configured to be fragmented (e.g., by a protease cleavage) to generate a set of polypeptide fragments immobilized to the substrate, wherein the plurality of polypeptides, the recording tags, and the library of binding agents are configured to allow transfer of information between (i) the recording tag and (ii) the coding tag, upon binding between the binding moiety and the one or more N-terminal, internal, or C-terminal amino acids of each fragment, to generate an extended recording tag and/or an extended coding tag.

The following aspects provide additional illustrations of the present disclosure.

Aspect 1. A method for analyzing a polypeptide, comprising the steps of: (a) providing the polypeptide optionally associated directly or indirectly with a recording tag; (b) functionalizing the N-terminal amino acid (NTAA) of the polypeptide with a chemical reagent, wherein the chemical reagent comprises a compound selected from the group consisting of (i) a compound of Formula (I):

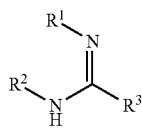

(I)

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2R^c$;
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
$R^3$ is heteroaryl, —NR$^d$C(O)OR$^e$, or —SR$^f$, wherein the heteroaryl is unsubstituted or substituted;
$R^d$, $R^e$, and $R^f$ are each independently H or $C_{1-6}$alkyl; and
optionally wherein when $R^3$ is

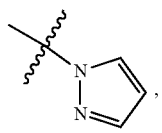

, $R^1$ and $R^2$ are not both H;
(ii) a compound of Formula (II):

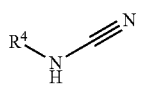

(II)

or a salt or conjugate thereof,
wherein
$R^4$ is H, $C_{1-6}$alkyl, cycloalkyl, —C(O)$R^g$, or —C(O)O$R^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;
(iii) a compound of Formula (III):

 (III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;
$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

(iv) a compound of Formula (IV):

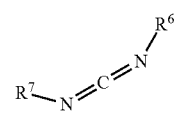

(IV)

or a salt or conjugate thereof,
wherein
$R^6$ and $R^7$ are each independently H, $C_{1-6}$alkyl, —CO$_2$C$_{1-4}$ alkyl, —OR$^k$, aryl, or cycloalkyl, wherein the $C_{1-6}$alkyl, —CO$_2$C$_{1-4}$alkyl, —OR$^k$, aryl, and cycloalkyl are each unsubstituted or substituted; and
$R^k$ is H, $C_{1-6}$alkyl, or heterocyclyl, wherein the $C_{1-6}$alkyl and heterocyclyl are each unsubstituted or substituted;
(v) a compound of Formula (V):

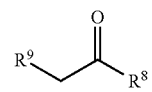

(V)

or a salt or conjugate thereof,
wherein
$R^8$ is halo or —OR$^m$;
$R^m$ is H, $C_{1-6}$alkyl, or heterocyclyl; and
$R^9$ is hydrogen, halo, or $C_{1-6}$haloalkyl;
(vi) a metal complex of Formula (VI):

 ML$_n$ (VI)

or a salt or conjugate thereof,
wherein
M is a metal selected from the group consisting of Co, Cu, Pd, Pt, Zn, and Ni;
L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and
(vii) a compound of Formula (VII):

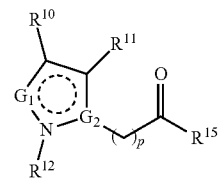

(VII)

or a salt or conjugate thereof,
wherein
$G^1$ is N, NR$^{13}$, or CR$^{13}$R$^{14}$;
$G^2$ is N or CH;
p is 0 or 1;
$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and
$R^{15}$ is H or OH, (c) contacting the polypeptide with a first binding agent comprising a first binding portion capable of binding to the functionalized NTAA and
  (c1) a first coding tag with identifying information regarding the first binding agent, or
  (c2) a first detectable label;
(d) (d1) transferring the information of the first coding tag to the recording tag to generate an extended recording tag and analyzing the extended recording tag, or
  (d2) detecting the first detectable label;
wherein step (b) is conducted before step (c), after step (c) and before step (d), or after step (d).

In some embodiments, this method of sequencing employs an "Edman-like" N-terminal amino acid degradation process. Edman-like degradation consists of two key steps: 1) Functionalization of the -amine on the NTAA of the peptide, and 2) Elimination of the functionalized NTAA. Standard Edman functionalization chemistry as well as the Edman-like functionalization chemistry described herein exhibits poorer functionalization and elimination of N-terminal proline residues. As such, the presence of an N-terminal proline may lead to "stalling" of the cyclic sequencing reaction. Thus, in some embodiments of the methods described herein, it is beneficial to remove any N-terminal prolines at the start of each Edman-like degradation cycle by exposing the target polypeptide to a proline aminopeptidase (proline iminopeptidase) which specifically cleaves just N terminal prolines. Accordingly, in some embodiments, each of the methods and assays described herein can optionally include an additional step of contacting the polypeptide being analyzed with a proline aminopeptidase. Likewise, kits for performing these methods can, optionally, include at least one proline aminopeptidase.

There are several proline aminopeptidases (PAPs) known in the literature that can be used for this purpose. In a preferred embodiment, small monomeric PAPs (~25-35 kDa) are employed for removal of NTAA prolines. Suitable monomeric PAPs for use in the methods and kits described herein include family members from *B. coagulans, L. delbrueckii, N. gonorrhoeae, F. meningosepticum, S. marcescens, T. acidophilum,* and *L. plantarum* (MEROPS S33.001) (Nakajima, Ito et al. 2006) (Kitazono, Yoshimoto et al. 1992). Suitable multimeric PAPs are also known, and include enzyme from *D. hansenii* (Bolumar, Sanz et al. 2003). Either native or engineered PAPs may be employed. Effective mapping of peptide sequences generated by the methods and assays herein that are devoid of proline residues can be accomplished by mapping peptide reads back to a "proline minus" proteome. At the bioinformatic level, this essentially translates to proteins comprised of 19 amino acid residues rather than 20.

Alternatively, to retain proline information, two steps of binding can be employed both before and after proline removal to enable detection of proline residues, but this comes at the extra cost of an extra binding/encoding cycle for each sequencing cycle. Furthermore, this concept of combining Edman-like chemistry with R-group specific aminopeptidases can be used to remove any NTF/NTE recalcitrant amino acid; however, in the preferred embodiments, only a single recalcitrant amino residue, typically proline, is removed by an aminopeptidase. Removal of multiple residues leads to a combinatoric explosion of removed sequences (i.e. removal of P and W leads to removal of sequences with runs of Ps, runs of Ws, and runs of P and W.)

Aspect 2. The method of Aspect 1, wherein step (a) comprises providing the polypeptide and an associated recording tag joined to a support (e.g., a solid support).
Aspect 3. The method of Aspect 1, wherein step (a) comprises providing the polypeptide joined to an associated recording tag in a solution.
Aspect 4. The method of Aspect 1, wherein step (a) comprises providing the polypeptide associated indirectly with a recording tag.
Aspect 5. The method of Aspect 1, wherein the polypeptide is not associated with a recording tag in step (a).
Aspect 6. The method of any one of Aspects 1-5, wherein step (b) is conducted before step (c).
Aspect 7. The method of any one of Aspects 1-5, wherein step (b) is conducted after step (c) and before step (d).
Aspect 8. The method of any one of Aspects 1-5, wherein step (b) is conducted after both step (c) and step (d).
Aspect 9. The method of any one of Aspects 1-5, wherein steps (a), (b), (c1), and (d1) occur in sequential order.
Aspect 10. The method of any one of Aspects 1-5, wherein steps (a), (c1), (b), and (d1) occur in sequential order.
Aspect 11. The method of any one of Aspects 1-5, wherein steps (a), (c1), (d1), and (b) occur in sequential order.
Aspect 12. The method of any one of Aspects 1-5, wherein steps (a), (b), (c2), and (d2) occur in sequential order.
Aspect 13. The method of any one of Aspects 1-5, wherein steps (a), (c2), (b), and (d2) occur in sequential order.
Aspect 14. The method of any one of Aspects 1-5, wherein steps (a), (c2), (d2), and (b) occur in sequential order.
Aspect 15. The method of any one of Aspects 1-14, wherein step (c) further comprises contacting the polypeptide with a second (or higher order) binding agent comprising a second (or higher order) binding portion capable of binding to a functionalized NTAA other than the functionalized NTAA of step (b) and a coding tag with identifying information regarding the second (or higher order) binding agent.
Aspect 16. The method of Aspect 15, wherein contacting the polypeptide with the second (or higher order) binding agent occurs in sequential order following the polypeptide being contacted with the first binding agent.
Aspect 17. The method of Aspect 15, wherein contacting the polypeptide with the second (or higher order) binding agent occurs simultaneously with the polypeptide being contacted with the first binding agent.
Aspect 18. A method for analyzing a polypeptide, comprising the steps of:
(a) providing the polypeptide optionally associated directly or indirectly with a recording tag;
(b) functionalizing the N-terminal amino acid (NTAA) of the polypeptide with a chemical reagent to yield a functionalized NTAA, wherein the chemical reagent comprises a compound selected from the group consisting of
(i) a compound of Formula (I):

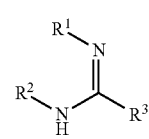

(I)

or a salt or conjugate thereof, wherein

R¹ and R² are each independently H, C₁₋₆alkyl, cycloalkyl, —C(O)Rᵃ, —C(O)ORᵇ, or —S(O)₂Rᶜ;

Rᵃ, Rᵇ, and Rᶜ are each independently H, C₁₋₆alkyl, C₁₋₆haloalkyl, arylalkyl, aryl, or heteroaryl, wherein the C₁₋₆alkyl, C₁₋₆haloalkyl, arylalkyl, aryl, and heteroaryl are each unsubstituted or substituted;

R³ is heteroaryl, —NRᵈC(O)ORᵉ, or —SRᶠ, wherein the heteroaryl is unsubstituted or substituted;

Rᵈ, Rᵉ, and Rᶠ are each independently H or C₁₋₆alkyl; and optionally wherein when R³ is

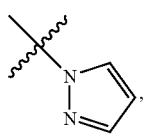

R¹ and R² are not both H;

(ii) a compound of Formula (II):

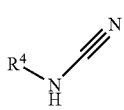

(II)

or a salt or conjugate thereof,
wherein

R⁴ is H, C₁₋₆alkyl, cycloalkyl, —C(O)Rᵍ, or —C(O)ORᵍ; and

Rᵍ is H, C₁₋₆alkyl, C₂₋₆alkenyl, C₁₋₆haloalkyl, or arylalkyl, wherein the C₁₋₆alkyl, C₂₋₆alkenyl, C₁₋₆haloalkyl, and arylalkyl are each unsubstituted or substituted;

(iii) a compound of Formula (III):

R⁵—N═C═S         (III)

or a salt or conjugate thereof,
wherein

R⁵ is C₁₋₆alkyl, C₂₋₆alkenyl, cycloalkyl, heterocycloalkyl, aryl or heteroaryl;

wherein the C₁₋₆alkyl, C₂₋₆alkenyl, cycloalkyl, heterocycloalkyl, aryl or heteroaryl are each unsubstituted or substituted with one or more groups selected from the group consisting of halo, —NRʰRⁱ, —S(O)₂Rʲ, or heterocyclyl;

Rʰ, Rⁱ, and Rʲ are each independently H, C₁₋₆alkyl, C₁₋₆haloalkyl, arylalkyl, aryl, or heteroaryl, wherein the C₁₋₆alkyl, C₁₋₆haloalkyl, arylalkyl, aryl, and heteroaryl are each unsubstituted or substituted;

(iv) a compound of Formula (IV):

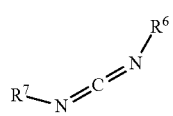

(IV)

or a salt or conjugate thereof, wherein

R⁶ and R⁷ are each independently H, C₁₋₆alkyl, —CO₂C₁₋₄ alkyl, —ORᵏ, aryl, or cycloalkyl, wherein the C₁₋₆alkyl, —CO₂C₁₋₄alkyl, —ORᵏ, aryl, and cycloalkyl are each unsubstituted or substituted; and Rᵏ is H, C₁₋₆alkyl, or heterocyclyl, wherein the C₁₋₆alkyl and heterocyclyl are each unsubstituted or substituted; and (v) a compound of Formula (V):

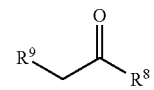

(V)

or a salt or conjugate thereof,
wherein

R⁸ is halo or —ORᵐ;

Rᵐ is H, C₁₋₆alkyl, or heterocyclyl; and

R⁹ is hydrogen, halo, or C₁₋₆haloalkyl; and (vi) a metal complex of Formula (VI):

MLₙ         (VI)

or a salt or conjugate thereof,
wherein

M is a metal selected from the group consisting of Co, Cu, Pd, Pt, Zn, and Ni; L is a ligand selected from the group consisting of —OH, —OH₂, 2,2'-bipyridine (bpy), 1,5dithiacyclooctane (dtco), 1,2-bis(diphenylphosphino)ethane (dppe), ethylenediamine (en), and triethylenetetramine (trien); and n is an integer from 1-8, inclusive;

wherein each L can be the same or different; and (vii) a compound of Formula (VII):

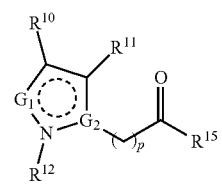

(VII)

or a salt or conjugate thereof,
wherein

G¹ is N, NR¹³, or CR¹³R¹⁴;

G² is N or CH;

p is 0 or 1;

R¹⁰, R¹¹, R¹², R¹³, and R¹⁴ are each independently selected from the group consisting of H, C₁₋₆alkyl, C₁₋₆haloalkyl, C₁₋₆alkylamine, and C₁₋₆alkylhydroxylamine, wherein the C₁₋₆alkyl, C₁₋₆haloalkyl, C₁₋₆alkylamine, and C₁₋₆alkylhydroxylamine are each unsubstituted or substituted, and R¹⁰ and R¹¹ can optionally come together to form a ring; and R¹⁵ is H or OH, (c) contacting the polypeptide with a first binding agent comprising a first binding portion capable of binding to the functionalized NTAA and (c1) a first coding tag with identifying information regarding the first binding agent, or (c2) a first detectable label;

(d) (d1) transferring the information of the first coding tag to the recording tag to generate a first extended recording tag and analyzing the extended recording tag, or (d2) detecting the first detectable label, and (e) eliminating the functionalized NTAA to expose a new NTAA;

wherein step (b) is conducted before step (c), after step (c) and before step (d), or after step (d).

In some embodiments of the compound of Formula (I) for use in any of the methods and kits disclosed herein, $R^3$ is a monocyclic heteroaryl group. In some embodiments of Formula (I), $R^3$ is a 5- or 6-membered monocyclic heteroaryl group. In some embodiments of Formula (I), $R^3$ is a 5- or 6-membered monocyclic heteroaryl group containing one or more N. Preferably, $R^3$ is selected from pyrazole, imidazole, triazole and tetrazole, and is linked to the amidine of Formula (I) via a nitrogen atom of the pyrazole, imidazole, triazole or tetrazole ring, and $R^3$ is optionally substituted by a group selected from halo, $C_{1-3}$ alkyl, $C_{1-3}$ haloalkyl, and nitro. In some embodiments, $R^3$ is

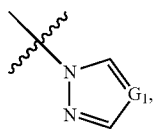

wherein $G_1$ is N, CH, or CX where X is halo, $C_{1-3}$ alkyl, $C_{1-3}$ haloalkyl, or nitro. In some embodiments, $R^3$ is

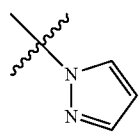 [SMILES: *n1cccn1]

or, where X is Me, F, Cl, $CF_3$, or $NO_2$. In some embodiments, $R^3$ is N

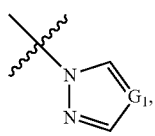

wherein $G_1$ is N or CH. In some embodiments, $R^3$ is

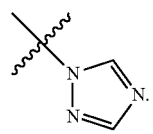

In some embodiments, $R^3$ is a bicyclic heteroaryl group. In some embodiments, $R^3$ is a 9- or 10-membered bicyclic heteroaryl group. In some embodiments, $R^3$ is

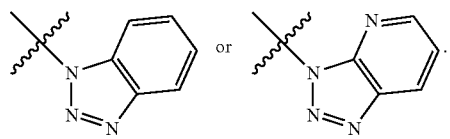 [SMILES: *n1nnc2ccccc21 ; *n1nnc2cccnc21]

Aspect 19. The method of Aspect 18, wherein step (a) comprises providing the polypeptide and an associated recording tag joined to a support (e.g., a solid support).

Aspect 20. The method of Aspect 18, wherein step (a) comprises providing the polypeptide joined to an associated recording tag in a solution.

Aspect 21. The method of Aspect 18, wherein step (a) comprises providing the polypeptide associated indirectly with a recording tag.

Aspect 22. The method of Aspect 18, wherein the polypeptide is not associated with a recording tag in step (a).

Aspect 23. The method of any one of Aspects 18-22, wherein step (b) is conducted before step (c).

Aspect 24. The method of any one of Aspects 18-22, wherein step (b) is conducted after step (c) and before step (d).

Aspect 25. The method of any one of Aspects 18-22, wherein step (b) is conducted after both step (c) and step (d).

Aspect 26. The method of any one of Aspects 18-22, wherein steps (a), (b), (c1), and (d1) occur in sequential order.

Aspect 27. The method of any one of Aspects 18-22, wherein steps (a), (c1), (b), and (d1) occur in sequential order.

Aspect 28. The method of any one of Aspects 18-22, wherein steps (a), (c1), (d1), and (b) occur in sequential order.

Aspect 29. The method of any one of Aspects 18-22, wherein steps (a), (b), (c2), and (d2) occur in sequential order.

Aspect 30. The method of any one of Aspects 18-22, wherein steps (a), (c2), (b), and (d2) occur in sequential order.

Aspect 31. The method of any one of Aspects 18-22, wherein steps (a), (c2), (d2), and (b) occur in sequential order.

Aspect 32. The method of any one of Aspects 18-31, further comprising the steps of:

(f) functionalizing the new NTAA of the polypeptide with a chemical reagent to yield a newly functionalized NTAA;

(g) contacting the polypeptide with a second (or higher order) binding agent comprising a second (or higher order) binding portion capable of binding to the newly functionalized NTAA and (g1) a second coding tag with identifying information regarding the second (or higher order) binding agent, or (g2) a second detectable label;

(h) (h1) transferring the information of the second coding tag to the first extended recording tag to generate a second extended recording tag and analyzing the second extended recording tag, or (h2) detecting the second detectable label, and (i) eliminating the functionalized NTAA to expose a new NTAA;

wherein step (f) is conducted before step (g), after step (g) and before step (h), or after step (h).

In any of the aspects 1-32, the method optionally further includes a step of contacting the polypeptide with a proline aminopeptidase, typically before the recited method steps, under conditions suitable to cleave any N-terminal proline present.

Aspect 33. The method of Aspect 32, wherein the chemical reagent comprises a compound selected from the group consisting of (i) a compound of Formula (I):

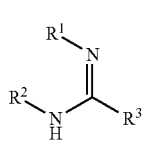
(I)

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2$$R^c$;
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
$R^3$ is heteroaryl, —N$R^d$C(O)O$R^e$, or —S$R^f$, wherein the heteroaryl is unsubstituted or substituted;
$R^d$, $R^e$, and $R^f$ are each independently H or $C_{1-6}$alkyl; and
optionally wherein when $R^3$ is

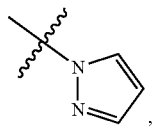

$R^1$ and $R^2$ are not both H;
(ii) a compound of Formula (II):

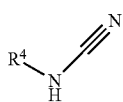
(II)

or a salt or conjugate thereof,
wherein
$R^4$ is H, $C_{1-6}$alkyl, cycloalkyl, —C(O)$R^g$, or —C(O)O$R^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;
(iii) a compound of Formula (III):

(III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —N$R^h$$R^i$, —S(O)$_2$$R^j$, or heterocyclyl;
$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

(iv) a compound of Formula (IV):

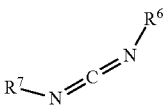
(IV)

or a salt or conjugate thereof,
wherein
$R^6$ and $R^7$ are each independently H, $C_{1-6}$alkyl, —CO$_2$$C_{1-4}$ alkyl, —O$R^k$, aryl, or cycloalkyl, wherein the $C_{1-6}$alkyl, —CO$_2$$C_{1-4}$alkyl, —O$R^k$, aryl, and cycloalkyl are each unsubstituted or substituted; and
$R^k$ is H, $C_{1-6}$alkyl, or heterocycle, wherein the $C_{1-6}$alkyl and heterocyclyl are each unsubstituted or substituted; and
(v) a compound of Formula (V):

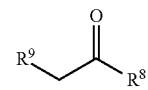
(V)

or a salt or conjugate thereof,
wherein
$R^8$ is halo or —O$R^m$;
$R^m$ is H, $C_{1-6}$alkyl, or heterocyclyl; and
$R^9$ is hydrogen, halo, or $C_{1-6}$haloalkyl; and
(vi) a metal complex of Formula (VI):

(VI)

or a salt or conjugate thereof,
wherein
M is a metal selected from the group consisting of Co, Cu, Pd, Pt, Zn, and Ni;
L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and
(vii) a compound of Formula (VII):

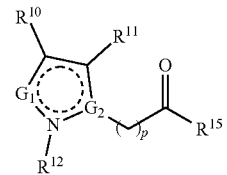
(VII)

or a salt or conjugate thereof,
wherein
$G^1$ is N, N$R^{13}$, or C$R^{13}$$R^{14}$;
$G^2$ is N or CH;
p is 0 or 1;
$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and
$R^{15}$ is H or OH.

Aspect 34. The method of Aspect 32 or Aspect 33, wherein step (f) is conducted before step (g).

Aspect 35. The method of Aspect 32 or Aspect 33, wherein step (f) is conducted after step (g) and before step (h).

Aspect 36. The method of Aspect 32 or Aspect 33, wherein step (f) is conducted after both step (g) and step (h).

Aspect 37. The method of Aspect 32 or Aspect 33, wherein steps (f), (g1), and (h1) occur in sequential order.

Aspect 38. The method of Aspect 32 or Aspect 33, wherein steps (g1), (f), and (h1) occur in sequential order.

Aspect 39. The method of Aspect 32 or Aspect 33, wherein steps (g1), (h1), and (f) occur in sequential order.

Aspect 40. The method of Aspect 32 or Aspect 33, wherein steps (f), (g2), and (h2) occur in sequential order.

Aspect 41. The method of Aspect 32 or Aspect 33, wherein steps (g2), (f), and (h2) occur in sequential order.

Aspect 42. The method of Aspect 32 or Aspect 33, wherein steps (g2), (h2), and (f) occur in sequential order.

Aspect 43. The method of any one of Aspects 32-42, wherein contacting the polypeptide with the second (or higher order) binding agent occurs in sequential order following the polypeptide being contacted with the first binding agent.

Aspect 44. The method of any one of Aspects 32-42, wherein contacting the polypeptide with the second (or higher order) binding agent occurs simultaneously with the polypeptide being contacted with the first binding agent.

Aspect 45. The method of any one of Aspects 1-44, wherein the polypeptide is obtained by fragmenting a protein from a biological sample.

Aspect 46. The method of any one of Aspects 1-45, wherein the recording tag comprises a nucleic acid, an oligonucleotide, a modified oligonucleotide, a DNA molecule, a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof.

Aspect 47. The method of Aspect 46, wherein the DNA molecule is backbone modified, sugar modified, or nucleobase modified.

Aspect 48. The method of Aspect 46, wherein the DNA molecule has nucleobase protecting groups such as Alloc, electrophilic protecting groups such as thiaranes, acetyl protecting groups, nitrobenzyl protecting groups, sulfonate protecting groups, or traditional base-labile protecting groups including Ultramild reagents.

Aspect 49. The method of any one of Aspects 1-48, wherein the recording tag comprises a universal priming site.

Aspect 50. The method of Aspect 49, wherein the universal priming site comprises a priming site for amplification, sequencing, or both.

Aspect 51. The method of Aspects 1-50, where the recording tag comprises a unique molecule identifier (UMI).

Aspect 52. The method of any one of Aspects 1-51, wherein the recording tag comprises a barcode.

Aspect 53. The method of any one of Aspects 1-52, wherein the recording tag comprises a spacer at its 3'-terminus.

Aspect 54. The method of Aspect any one of Aspects 1-53, wherein the polypeptide and the associated recording tag are covalently joined to the support.

Aspect 55. The method of any one of Aspects 1-54, wherein the support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

Aspect 56. The method of Aspect 55, wherein the support comprises gold, silver, a semiconductor or quantum dots.

Aspect 57. The method of Aspect 55, wherein the nanoparticle comprises gold, silver, or quantum dots.

Aspect 58. The method of Aspect 55, wherein the support is a polystyrene bead, a polymer bead, an agarose bead, an acrylamide bead, a solid core bead, a porous bead, a paramagnetic bead, glass bead, or a controlled pore bead.

Aspect 59. The method of any one of Aspects 1-58, wherein a plurality of polypeptides and associated recording tags are joined to a support.

Aspect 60. The method of Aspect 59, wherein the plurality of polypeptides are spaced apart on the support, wherein the average distance between the polypeptides is about >20 nm.

Aspect 61. The method of any one of Aspects 1-60, wherein the binding portion of the binding agent comprises a peptide or protein.

Aspect 62. The method of any one of Aspects 1-61, wherein the binding portion of the binding agent comprises an aminopeptidase or variant, mutant, or modified protein thereof, an aminoacyl tRNA synthetase or variant, mutant, or modified protein thereof, an anticalin or variant, mutant, or modified protein thereof, a ClpS (such as ClpS2) or variant, mutant, or modified protein thereof, a UBR box protein or variant, mutant, or modified protein thereof, or a modified small molecule that binds amino acid(s), i.e. vancomycin or a variant, mutant, or modified molecule thereof, or an antibody or binding fragment thereof, or any combination thereof.

Aspect 63. The method of any one of Aspects 1-62, wherein the binding agent binds to a single amino acid residue (e.g., an N-terminal amino acid residue, a C-terminal amino acid residue, or an internal amino acid residue), a dipeptide (e.g., an N-terminal dipeptide, a C-terminal dipeptide, or an internal dipeptide), a tripeptide (e.g., an N-terminal tripeptide, a C-terminal tripeptide, or an internal tripeptide), or a post-translational modification of the polypeptide.

Aspect 64. The method of any one of Aspects 1-62, wherein the binding agent binds to a NTAA-functionalized single amino acid residue, a NTAA-functionalized dipeptide, a NTAA-functionalized tripeptide, or a NTAA-functionalized polypeptide.

Aspect 65. The method of any one of Aspects 1-64, wherein the binding portion of the binding agent is capable of selectively binding to the polypeptide.

Aspect 66. The method of any one of Aspects 1-65, wherein the coding tag is DNA molecule, an RNA molecule, a BNA molecule, an XNA molecule, a LNA molecule, a PNA molecule, a γPNA molecule, or a combination thereof.

Aspect 67. The method of any one of Aspects 1-66, wherein the coding tag comprises an encoder or barcode sequence.

Aspect 68. The method of any one of Aspects 1-67, wherein the coding tag further comprises a spacer, a binding cycle specific sequence, a unique molecular identifier, a universal priming site, or any combination thereof.

Aspect 69. The method of any one of Aspects 1-68, wherein the binding portion and the coding tag are joined by a linker.

Aspect 70. The method of Aspects 1-69, wherein the binding portion and the coding tag are joined by a SpyTag/SpyCatcher peptide-protein pair, a SnoopTag/SnoopCatcher peptide-protein pair, or a HaloTag/HaloTag ligand pair.

Aspect 71. The method of any one of Aspects 1-70, wherein transferring the information of the coding tag to the recording tag is mediated by a DNA ligase or an RNA ligase.

Aspect 72. The method of any one of Aspects 1-70, wherein transferring the information of the coding tag to the recording tag is mediated by a DNA polymerase, an RNA polymerase, or a reverse transcriptase.

Aspect 73. The method of any one of Aspects 1-70, wherein transferring the information of the coding tag to the recording tag is mediated by chemical ligation.

Aspect 74. The method of Aspect 73, wherein the chemical ligation is performed using single-stranded DNA.

75. The method of Aspect 74, wherein the chemical ligation is performed using double-stranded DNA.

76. The method of any one of Aspects 1-72, wherein analyzing the extended recording tag comprises a nucleic acid sequencing method.

77. The method of Aspect 76, wherein the nucleic acid sequencing method is sequencing by synthesis, sequencing by ligation, sequencing by hybridization, polony sequencing, ion semiconductor sequencing, or pyrosequencing.

78. The method of Aspect 76, wherein the nucleic acid sequencing method is single molecule real-time sequencing, nanopore-based sequencing, or direct imaging of DNA using advanced microscopy.

79. The method of any one of Aspects 1-78, wherein the extended recording tag is amplified prior to analysis 80. The method of any one of Aspects 1-79, further comprising the step of adding a cycle label.

81. The method of Aspect 80, wherein the cycle label provides information regarding the order of binding by the binding agents to the polypeptide.

82. The method of Aspect 80 or Aspect 81, wherein the cycle label is added to the coding tag.

83. The method of Aspect 80 or Aspect 81, wherein the cycle label is added to the recording tag.

84. The method of Aspect 80 or Aspect 81, wherein the cycle label is added to the binding agent.

85. The method of Aspect 80 or Aspect 81, wherein the cycle label is added independent of the coding tag, recording tab, and binding agent.

86. The method of any one of Aspects 1-85, wherein the order of coding tag information contained on the extended recording tag provides information regarding the order of binding by the binding agents to the polypeptide.

87. The method of any one of Aspects 1-86, wherein frequency of the coding tag information contained on the extended recording tag provides information regarding the frequency of binding by the binding agents to the polypeptide.

88. The method of any one of Aspects 1-87, wherein a plurality of extended recording tags representing a plurality of polypeptides is analyzed in parallel.

89. The method of Aspect 88, wherein the plurality of extended recording tags representing a plurality of polypeptides is analyzed in a multiplexed assay.

90. The method of Aspect 88 or 89, wherein the plurality of extended recording tags undergoes a target enrichment assay prior to analysis.

91. The method of any one of Aspects 88-90, wherein the plurality of extended recording tags undergoes a subtraction assay prior to analysis.

92. The method of any one of Aspects 88-91, wherein the plurality of extended recording tags undergoes a normalization assay to reduce highly abundant species prior to analysis.

93. The method of any one of Aspects 1-92, wherein the NTAA is eliminated by chemical cleavage or enzymatic cleavage from the polypeptide.

94. The method of Aspect 93, wherein the NTAA is eliminated by a carboxypeptidase or aminopeptidase or variant, mutant, or modified protein thereof, a hydrolase or variant, mutant, or modified protein thereof, mild Edman degradation; Edmanase enzyme; TFA, a base; or any combination thereof.

95. The method of Aspect 94, wherein the mild Edman degradation uses a dichloro or monochloro acid 96. The method of Aspect 94, wherein the mild Edman degradation uses TFA, TCA, or DCA.

97. The method of Aspect 94, wherein the mild Edman degradation uses triethylammonium acetate (Et3NHOAc).

98. The method of Aspect 94, wherein the base is a hydroxide, an alkylated amine, a cyclic amine, a carbonate buffer, or a metal salt.

99. The method of Aspect 98, wherein the hydroxide is sodium hydroxide

100. The method of Aspect 98, wherein the alkylated amine is selected from methylamine, ethylamine, propylamine, dimethylamine, diethylamine, dipropylamine, trimethylamine, triethylamine, tripropylamine, cyclohexylamine, benzylamine, aniline, diphenylamine, N,N-Diisopropylethylamine (DIPEA), and lithium diisopropylamide (LDA).

101. The method of Aspect 98, wherein the cyclic amine is selected from pyridine, pyrimidine, imidazole, pyrrole, indole, piperidine, pyrolidine, 1,8-diazabicyclo[5.4.0]undec-7-ene (DBU), and 1,5-diazabicyclo[4.3.0]non-5-ene (DBN).

102. The method of Aspect 98, wherein the carbonate buffer comprises sodium carbonate, potassium carbonate, calcium carbonate, sodium bicarbonate, potassium bicarbonate, or calcium bicarbonate.

103. The method of Aspect 98, wherein the metal salt comprises silver.

104. The method of Aspect 103, wherein the metal salt is $AgClO_4$.

105. The method of any one of Aspects 1-104, wherein at least one binding agent binds to a terminal amino acid residue, terminal di-amino-acid residues, or terminal tri-amino-acid residues.

106. The method of any one of Aspects 1-105, wherein at least one binding agent binds to a post-translationally modified amino acid.

107. The method of any one of Aspects 1-106, wherein the chemical reagent comprises a compound selected from the group consisting of a compound of Formula (I):

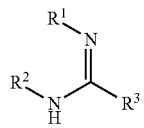
(I)

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2$$R^c$;
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
$R^3$ is heteroaryl, —N$R^d$C(O)O$R^e$, or —S$R^f$, wherein the heteroaryl is unsubstituted or substituted;
$R^d$, $R^e$, and $R^f$ are each independently H or $C_{1-6}$alkyl; and
optionally wherein when $R^3$ is

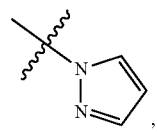, $R^1$ and $R^2$ are not both H.

108. The method of Aspect 107, wherein $R^1$ is

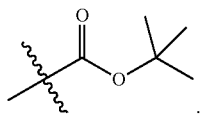 [SMILES: *C(=O)OC(C)(C)C].

109. The method of Aspect 107 or 108, wherein $R^2$ is

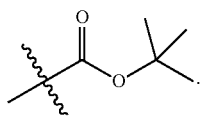 [SMILES: *C(=O)OC(C)(C)C].

110. The method of any one of Aspects 107-109, wherein $R^1$ or $R^2$ is

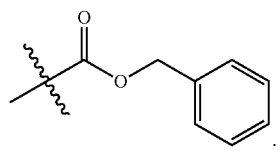 [SMILES: *C(=O)OCc1ccccc1].

111. The method of any one of Aspects 107-110, wherein $R^3$ is

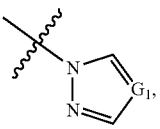, wherein $G_1$ is N or CH.

112. The method of any one of Aspects 107-110, wherein $R^3$ is

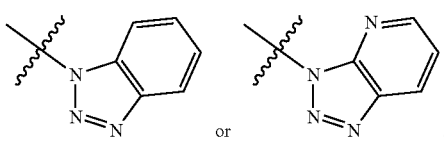.

113. The method of Aspect 107, wherein the compound of Formula (I) is selected from the group consisting of

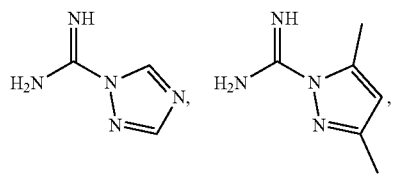

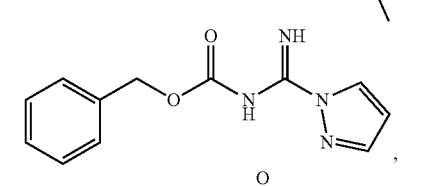

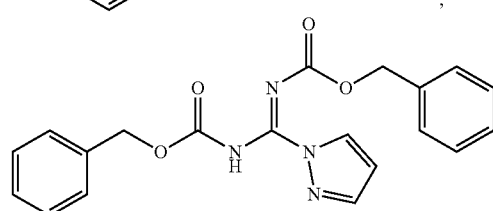

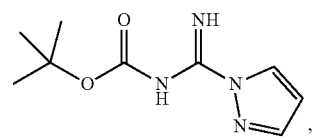

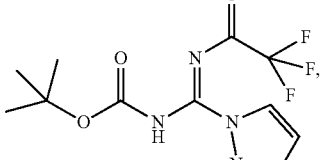

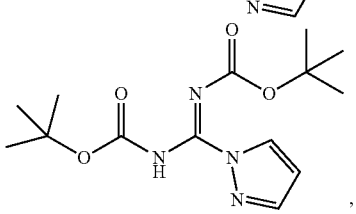

-continued

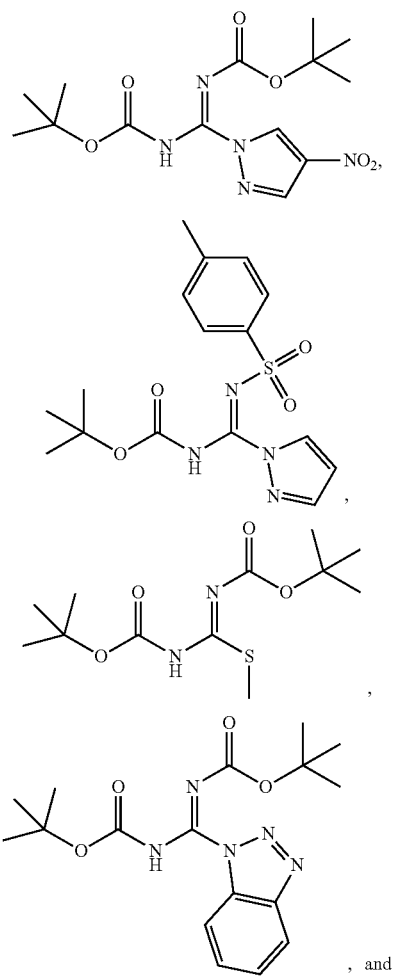

and optionally further including a compound selected from the following:

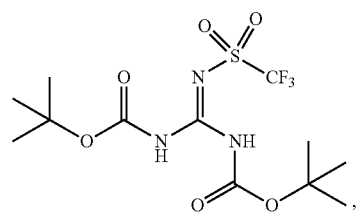

-continued

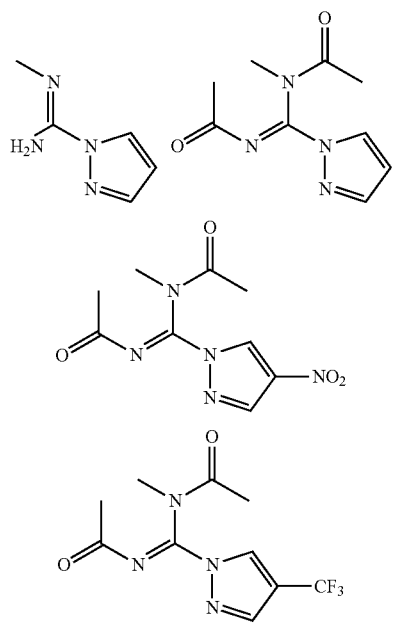

(N-Boc,N'-trifluoroacetyl-pyrazolecarboxamidine, N,N'-bisacetyl-pyrazolecarboxamidine, N-methyl-pyrazolecarboxamidine, N,N'-bisacetyl-N-methyl-pyrazolecarboxamidine, N,N'-bisacetyl-N-methyl-4-nitro-pyrazolecarboxamidine, and N,N'-bisacetyl-N-methyl-4-trifluoromethyl-pyrazolecarboxamidine), or a salt or conjugate thereof.

114 The method of any one of Aspects 107-113, wherein the chemical reagent additionally comprises Mukaiyama's reagent (2-chloro-1-methylpyridinium iodide).

115. The method of any one of Aspects 1-106, wherein the chemical reagent comprises a compound selected from the group consisting of a compound of Formula (II):

or a salt or conjugate thereof, wherein $R^4$ is H, $C_{1-6}$alkyl, cycloalkyl, —C(O)$R^g$, or —C(O)O$R^g$; and $R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted.

116. The method of Aspect 115, wherein $R^4$ is carboxybenzyl.

117. The method of Aspect 115, wherein $R^4$ is —C(O)$R^g$ and $R^g$ is $C_{2-6}$alkenyl, optionally substituted with aryl, heteroaryl, or heterocycloalkyl.

118. The method of Aspect 115, wherein the compound is selected from the group consisting of

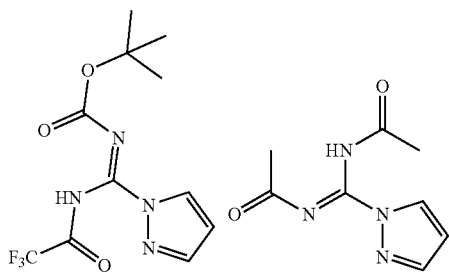

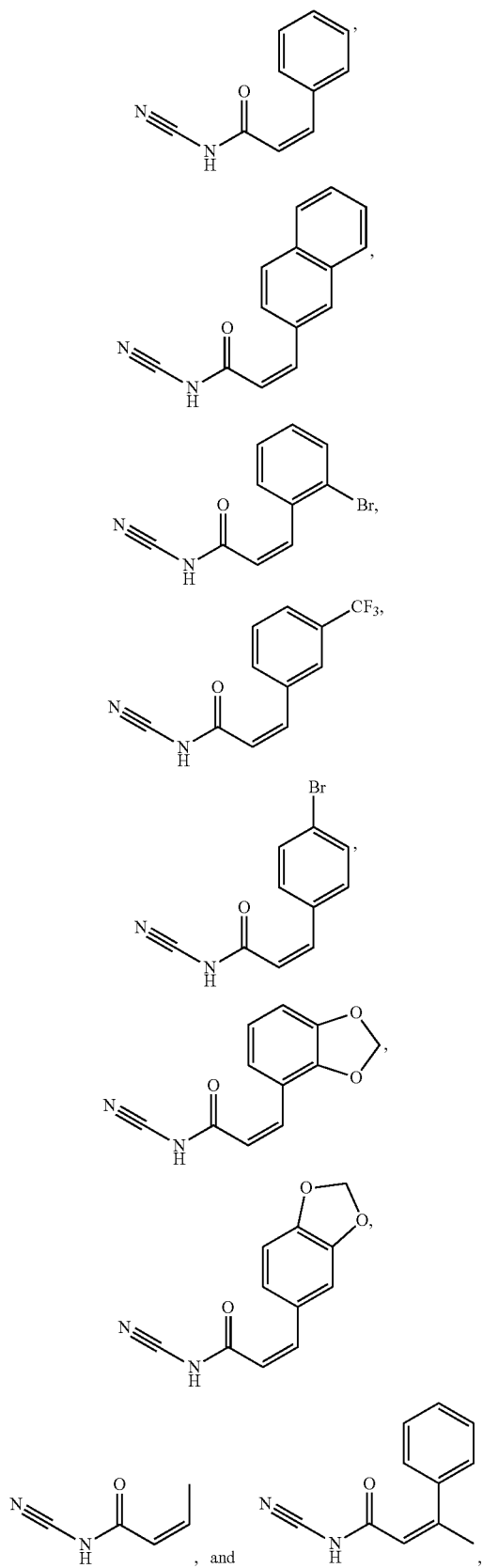

or a salt or conjugate thereof.

119. The method of any one of Aspects 115-118, wherein the chemical reagent additionally comprises TMS-Cl, Sc(OTf)$_2$, Zn(OTf)$_2$, or a lanthanide-containing reagent.

120. The method of any one of Aspects 1-106, wherein the chemical reagent comprises a compound selected from the group consisting of a compound of Formula (III):

$$R^5-N=C=S \qquad (III)$$

or a salt or conjugate thereof,
wherein
R$^5$ is C$_{1-6}$alkyl, C$_{2-6}$alkenyl, cycloalkyl, heterocycloalkyl, aryl or heteroaryl;
wherein the C$_{1-6}$alkyl, C$_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;
R$^h$, R$^i$, and R$^j$ are each independently H, C$_{1-6}$alkyl, C$_{1-6}$haloalkyl, arylalkyl, aryl, or heteroaryl, wherein the C$_{1-6}$alkyl, C$_{1-6}$haloalkyl, arylalkyl, aryl, and heteroaryl are each unsubstituted or substituted.

121. The method of Aspect 120, wherein R$^5$ is substituted phenyl.

122. The method of Aspect 120 or Aspect 121, wherein R$^5$ is phenyl, substituted with one or more groups selected from the group consisting of halo, —NR$^h$R$^i$, —S(O)$_2$R$^j$, and heterocyclyl.

123. The method of Aspect 120, wherein the compound of Formula (III) is trimethylsilyl isothiocyanate (TMSITC) or pentafluorophenyl isothiocyanate (PFPITC).

124. The method of any one of Aspects 120-123, wherein the chemical reagent additionally comprises a carbodiimide compound.

125. The method of any one of Aspects 120-124, wherein the NTAA is eliminated using trifluoroacetic acid or hydrochloric acid.

126. The method of any one of Aspects 120-124, wherein the NTAA is eliminated using mild Edman degradation.

127. The method of any one of Aspects 120-124, wherein the NTAA is eliminated using Edmanase or an engineered hydrolase, aminopeptidase, or carboxypeptidase.

128. The method of any one of Aspects 1-106, wherein the chemical reagent comprises a compound selected from the group consisting of a compound of Formula (IV):

$$R^7-N\underset{N}{\overset{N-R^6}{=}}C=N \qquad (IV)$$

or a salt or conjugate thereof,
wherein
R$^6$ and R$^7$ are each independently H, C$_{1-6}$alkyl, —CO$_2$C$_{1-4}$alkyl, —OR$^k$, aryl, or cycloalkyl, wherein the C$_{1-6}$alkyl, —CO$_2$C$_{1-4}$alkyl, —OR$^k$, aryl, and cycloalkyl are each unsubstituted or substituted; and
R$^k$ is H, C$_{1-6}$alkyl, or heterocyclyl, wherein the C$_{1-6}$alkyl and heterocyclyl are each unsubstituted or substituted.

129. The method of Aspect 128, wherein R$^6$ and R$^7$ are each independently H, C$_{1-6}$alkyl or cycloalkyl.

130. The method of Aspect 128, wherein the compound is selected from the group consisting of

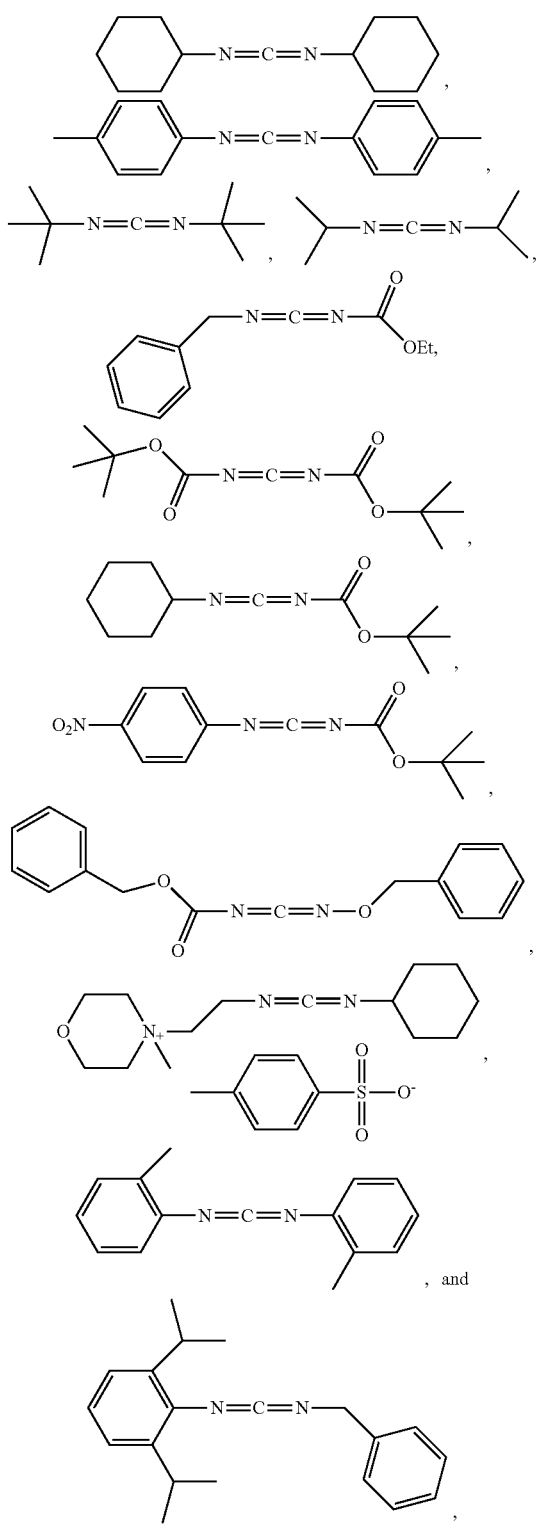

or a salt or conjugate thereof.

131. The method of any one of Aspects 128-130, wherein the compound of Formula (IV) is prepared by desulfurization of the corresponding thiourea.

132. The method of any one of Aspects 128-131, wherein the chemical reagent additionally comprises Mukaiyama's reagent (2-chloro-1-methylpyridinium iodide).

133. The method of any one of Aspects 128-131, wherein the chemical reagent additionally comprises a Lewis acid.

134. The method of Aspect 133, wherein the Lewis acid selected from N-((aryl)imino-acenapthenone)ZnCl$_2$, Zn(OTf)$_2$, ZnCl$_2$, PdCl$_2$, CuCl, and CuCl$_2$.

135. The method of any one of Aspects 1-106, wherein the chemical reagent comprises a compound selected from the group consisting of a compound of Formula (V):

(V)

or a salt or conjugate thereof,
wherein
  $R^8$ is halo or —$OR^m$;
  $R^m$ is H, $C_{1-6}$alkyl, or heterocyclyl; and
  $R^9$ is hydrogen, halo, or $C_{1-6}$haloalkyl.

136. The method of Aspect 135, wherein $R^8$ is chloro.

137. The method of Aspect 135 or Aspect 136, wherein $R^9$ is hydrogen or bromo.

138. The method of any one of Aspects 135-137, wherein the chemical reagent additionally comprises a peptide coupling reagent.

139. The method of Aspect 138, wherein the peptide coupling reagent is a carbodiimide compound.

140. The method of Aspect 139, wherein the carbodiimide compound is diisopropylcarbodiimide (DIC) or 1-ethyl-3-(3-dimethylaminopropyl)carbodiimide (EDC).

141. The method of any one of Aspects 135-140, wherein the NTAA is eliminated using acylpeptide hydrolase (APH).

142. The method of any one of Aspects 1-106, wherein the chemical reagent comprises a metal complex of Formula (VI):

$$ML_n \qquad (VI)$$

or a salt or conjugate thereof,
wherein
  M is a metal selected from the group consisting of Co, Cu, Pd, Pt, Zn, and Ni;
  L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
  n is an integer from 1-8, inclusive;
wherein each L can be the same or different.

143. The method of Aspect 142, wherein M is Co.

144. The method of Aspect 142 or Aspect 143, wherein the chemical reagent comprises a cis-β-hydroxyaquo (triethylenetetramine)cobalt(III) complex.

145. The method of Aspect 142, wherein the chemical reagent comprises β-[Co(trien)(OH)(OH$_2$)]$^{2+}$.

146. The method of any one of Aspects 1-106, wherein the chemical reagent comprises a compound selected from the group consisting of a compound of Formula (VII):

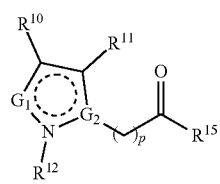

(VII)

or a salt or conjugate thereof,
wherein
G$^1$ is N, NR$^{13}$, or CR$^{13}$R$^{14}$;
G$^2$ is N or CH;
p is 0 or 1;
R$^{10}$, R$^{11}$, R$^{12}$, R$^{13}$, and R$^{14}$ are each independently selected from the group consisting of H, C$_{1-6}$alkyl, C$_{1-6}$haloalkyl, C$_{1-6}$alkylamine, and C$_{1-6}$alkylhydroxylamine, wherein the C$_{1-6}$alkyl, C$_{1-6}$haloalkyl, C$_{1-6}$alkylamine, and C$_{1-6}$alkylhydroxylamine are each unsubstituted or substituted, and R$^{10}$ and R$^{11}$ can optionally come together to form a ring; and
R$^{15}$ is H or OH.

147. The method of Aspect 146, wherein G$^1$ is CH$_2$ and G$^2$ is CH or G$^1$ is NH and G$^2$ is N.
148. The method of Aspect 146 or 147, wherein R$^{12}$ is H.
149. The method of any one of Aspects 146-148, wherein R$^{10}$ and R$^{11}$ are each H.
150. The method of Aspect 146, wherein the compound of Formula (VII) is selected from the group consisting of

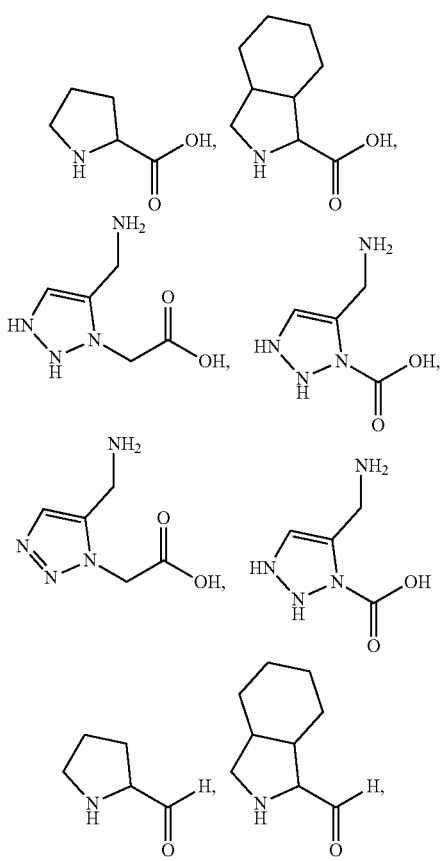

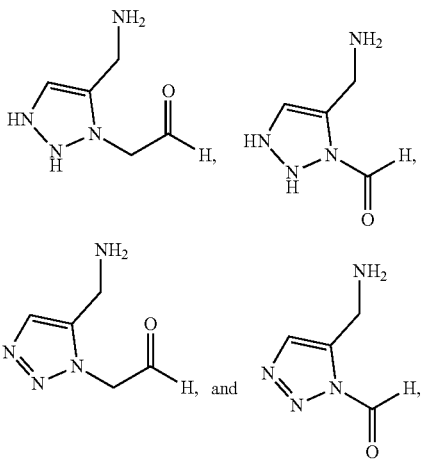

or a salt or conjugate thereof.

151. The method of any one of Aspects 107-150, wherein the NTAA is eliminated using a base.
152. The method of Aspect 151, wherein the base is a hydroxide, an alkylated amine, a cyclic amine, a carbonate buffer, or a metal salt.
153. The method of Aspect 152, wherein the hydroxide is sodium hydroxide.
154. The method of Aspect 152, wherein the alkylated amine is selected from methylamine, ethylamine, propylamine, dimethylamine, diethylamine, dipropylamine, trimethylamine, triethylamine, tripropylamine, cyclohexylamine, benzylamine, aniline, diphenylamine, N,N-diisopropylethylamine (DIPEA), and lithium diisopropylamide (LDA).
155. The method of Aspect 152, wherein the cyclic amine is selected from pyridine, pyrimidine, imidazole, pyrrole, indole, piperidine, pyrolidine, 1,8-diazabicyclo[5.4.0]undec-7-ene (DBU), and 1,5-diazabicyclo[4.3.0]non-5-ene (DBN).
156. The method of Aspect 152, wherein the carbonate buffer comprises sodium carbonate, potassium carbonate, calcium carbonate, sodium bicarbonate, potassium bicarbonate, or calcium bicarbonate.
157. The method of Aspect 152, wherein the metal salt comprises silver.
158. The method of Aspect 152, wherein the metal salt is AgClO$_4$.
159. The method of any one of Aspects 1-158, wherein the chemical reagent comprises a conjugate selected from the group consisting of

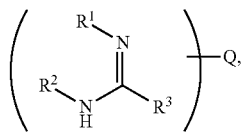

Formula (I)-Q wherein R$^1$, R$^2$, and R$^3$ are as defined for Formula (I) in Aspect 1, and Q is a ligand;

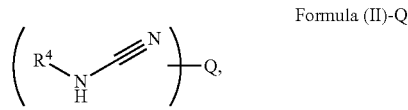

Formula (II)-Q wherein R⁴ is as defined for Formula (II) in Aspect 1, and Q is a ligand;

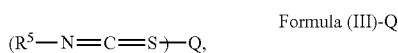

Formula (III)-Q wherein R⁵ is as defined for Formula (III) in Aspect 1, and Q is a ligand;

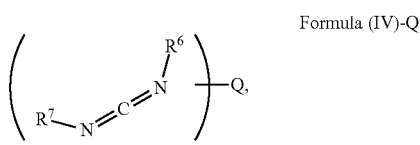

Formula (IV)-Q wherein $R^6$ and $R^7$ are as defined for Formula (IV) in Aspect 1, and Q is a ligand;

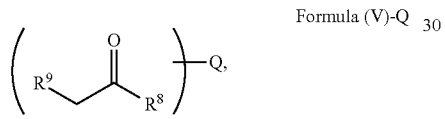

Formula (V)-Q wherein $R^8$ and $R^9$ are as defined for Formula (V) in Aspect 1, and Q is a ligand;

(ML$_n$)-Q       Formula (VI)-Q, wherein M, L, and n are as defined for Formula (VI) in Aspect 1, and Q is a ligand;

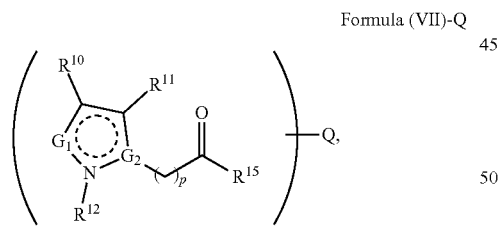

Formula (VII)-Q wherein $R^{10}$, $R^{11}$, $R^{12}$, $R^{15}$, $G^1$, $G^2$, and p are as defined for Formula (VII) in Aspect 1, and Q is a ligand.

160. The method of Aspect 159, wherein the Q is selected from the group consisting of —C$_{1-6}$alkyl, —C$_{2-6}$alkenyl, —C$_{2-6}$alkynyl, aryl, heteroaryl, heterocyclyl, —N=C=S, —CN, —C(O)R$^n$, —C(O)OR$^o$, —SR$^p$ or —S(O)$_2$R$^q$; wherein the —C$_{1-6}$alkyl, —C$_{2-6}$alkenyl, —C$_{2-6}$alkynyl, aryl, heteroaryl, and heterocyclyl are each unsubstituted or substituted, and R$^n$, R$^o$, R$^p$, and R$^q$ are each independently selected from the group consisting of —C$_{1-6}$alkyl, —C$_{1-6}$haloalkyl, —C$_{2-6}$alkenyl, —C$_{2-6}$alkynyl, aryl, heteroaryl, and heterocyclyl.

161. The method of Aspect 159, wherein the Q is selected from the group consisting of

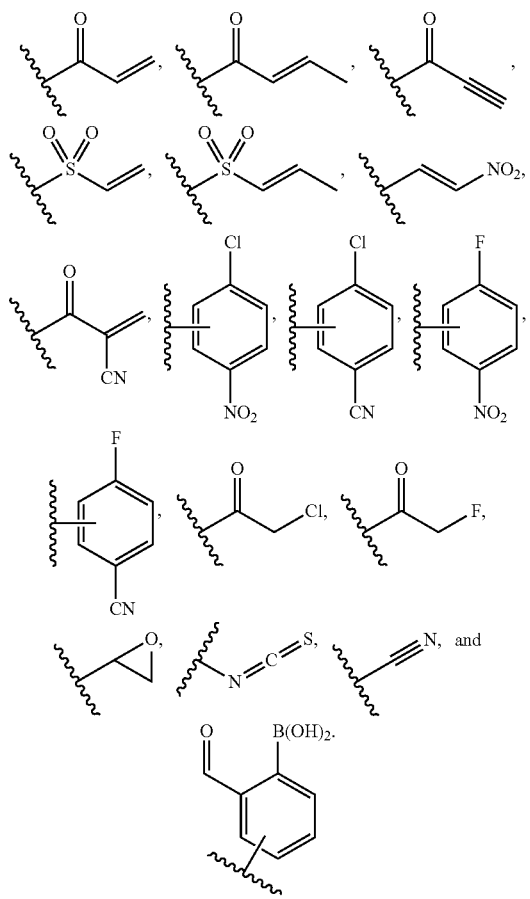

162. The method of Aspect 159, wherein Q is a fluorophore.

163. The method of any one of Aspects 1-162, wherein step (b) of Aspect 1 or Aspect 5 comprises difunctionalization of the NTAA.

164. The method of Aspect 163, wherein step (b) of Aspect 1 or Aspect 5 comprises difunctionalizing the NTAA with (1) a first chemical reagent comprising a compound selected from the group consisting of a compound of Formula (I), (II), (III), (IV), (V), (VI), and (VII), or a salt or conjugate thereof, and (2) a second chemical reagent.

165. The method of Aspect 164, wherein the second chemical reagent comprises a compound of Formula (VIIIa) or (VIIIb):

(VIIIa)

or a salt or conjugate thereof,
wherein
$R^{13}$ is H, C$_{1-6}$alkyl, aryl, heteroaryl, cycloalkyl, or heterocycloalkyl, wherein the C$_{1-6}$alkyl, aryl, heteroaryl, cycloalkyl, and heterocycloalkyl are each unsubstituted or substituted; or $R^1$—X   (VIIIb)

wherein
R$^{13}$ is C$_{1-6}$alkyl, aryl, heteroaryl, cycloalkyl, or heterocycloalkyl, each of which is unsubstituted or substituted; and X is a halogen.

166. The method of 164 or 165, wherein step (b) of Aspect 1 or Aspect 5 comprises functionalizing the NTAA with the second chemical reagent prior to functionalizing with the first chemical reagent.

167. The method of 164 or 165, wherein step (b) of Aspect 1 or Aspect 5 comprises functionalizing the NTAA with the first chemical reagent prior to functionalizing with the second chemical reagent.

168. The method of any one of Aspects 32-167, wherein step (f) of Aspect 6 comprises difunctionalization of the NTAA.

169. The method of Aspect 168, wherein the step (f) of Aspect 6 comprises difunctionalizing the NTAA with (1) a first chemical reagent comprising a compound selected from the group consisting of a compound of Formula (I), (II), (III), (IV), (V), (VI), and (VII) and (2) a second chemical reagent.

170. The method of Aspect 169, wherein the second chemical reagent comprises a compound of Formula (VIIIa) or (VIIIb):

(VIIIa)

or a salt or conjugate thereof,
wherein
R$^{13}$ is H, C$_{1-6}$alkyl, aryl, heteroaryl, cycloalkyl, or heterocycloalkyl, wherein the C$_{1-6}$alkyl, aryl, heteroaryl, cycloalkyl, and heterocycloalkyl are each unsubstituted or substituted; or

(VIIIb)

wherein
R$^{13}$ is C$_{1-6}$alkyl, aryl, heteroaryl, cycloalkyl, or heterocycloalkyl, each of which is unsubstituted or substituted; and X is a halogen.

171. The method of 169 or 170, wherein step (b) of Aspect 1 or Aspect 5 comprises functionalizing the NTAA with the second chemical reagent prior to functionalizing with the first chemical reagent.

172. The method of 169 or 170, wherein step (b) of Aspect 1 or Aspect 5 comprises functionalizing the NTAA with the first chemical reagent prior to functionalizing with the second chemical reagent.

173. The method of any one of Aspects 165-167 and 170-172, wherein the compound of Formula (VIIIa) is formaldehyde.

174. The method of any one of Aspects 165-167 and 170-172, wherein the compound of Formula (VIIIb) is methyl iodide.

175. A method for analyzing one or more polypeptides from a sample comprising a plurality of protein complexes, proteins, or polypeptides, the method comprising:

(a) partitioning the plurality of protein complexes, proteins, or polypeptides within the sample into a plurality of compartments, wherein each compartment comprises a plurality of compartment tags optionally joined to a support (e.g., a solid support), wherein the plurality of compartment tags are the same within an individual compartment and are different from the compartment tags of other compartments;

(b) fragmenting the plurality of protein complexes, proteins, and/or polypeptides into a plurality of polypeptides;

(c) contacting the plurality of polypeptides to the plurality of compartment tags under conditions sufficient to permit annealing or joining of the plurality of polypeptides with the plurality of compartment tags within the plurality of compartments, thereby generating a plurality of compartment tagged polypeptides;

(d) collecting the compartment tagged polypeptides from the plurality of compartments; and (e) analyzing one or more compartment tagged polypeptide according to a method of any one of Aspects 1-174.

176. The method of Aspect 175, wherein the compartment is a microfluidic droplet.

177. The method of Aspect 175, wherein the compartment is a microwell.

178. The method of Aspect 175, wherein the compartment is a separated region on a surface.

179. The method of any one of Aspects 175-178, wherein each compartment comprises on average a single cell.

180. A method for analyzing one or more polypeptides from a sample comprising a plurality of protein complexes, proteins, or polypeptides, the method comprising:

(a) labeling of the plurality of protein complexes, proteins, or polypeptides with a plurality of universal DNA tags;

(b) partitioning the plurality of labeled protein complexes, proteins, or polypeptides within the sample into a plurality of compartments, wherein each compartment comprises a plurality of compartment tags, wherein the plurality of compartment tags are the same within an individual compartment and are different from the compartment tags of other compartments;

(c) contacting the plurality of protein complexes, proteins, or polypeptides to the plurality of compartment tags under conditions sufficient to permit annealing or joining of the plurality of protein complexes, proteins, or polypeptides with the plurality of compartment tags within the plurality of compartments, thereby generating a plurality of compartment tagged protein complexes, proteins or polypeptides;

(d) collecting the compartment tagged protein complexes, proteins, or polypeptides from the plurality of compartments;

(e) optionally fragmenting the compartment tagged protein complexes, proteins, or polypeptides into a compartment tagged polypeptides; and (f) analyzing one or more compartment tagged polypeptide according to a method of any one of Aspects 1-174.

181. The method of any one of Aspects 175-180, wherein compartment tag information is transferred to a recording tag associated with a polypeptide via primer extension or ligation.

182. The method of any one of Aspects 175-181, wherein the support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

183. The method of any one of Aspects 175-181, wherein the support comprises a bead.

184. The method of Aspect 183, wherein the bead is a polystyrene bead, a polymer bead, an agarose bead, an acrylamide bead, a solid core bead, a porous bead, a paramagnetic bead, glass bead, or a controlled pore bead.

185. The method of any one of Aspects 175-184, wherein the compartment tag comprises a single stranded or double stranded nucleic acid molecule.

186. The method of any one of Aspects 175-185, wherein the compartment tag comprises a barcode and optionally a UMI.

187. The method of Aspect 186, wherein the support is a bead and the compartment tag comprises a barcode, further wherein beads comprising the plurality of compartment tags joined thereto are formed by split-and-pool synthesis.

188. The method of Aspect 186, wherein the support is a bead and the compartment tag comprises a barcode, further wherein beads comprising a plurality of compartment tags joined thereto are formed by individual synthesis or immobilization.

189. The method of any one of Aspects 175-188, wherein the compartment tag is a component within a recording tag, wherein the recording tag optionally further comprises a spacer, a barcode sequence, a unique molecular identifier, a universal priming site, or any combination thereof.

190. The method of any one of Aspects 175-189, wherein the compartment tags further comprise a functional moiety capable of reacting with an internal amino acid, the peptide backbone, or N-terminal amino acid on the plurality of protein complexes, proteins, or polypeptides.

191. The method of Aspect 190, wherein the functional moiety is an aldehyde, an azide/alkyne, or a maleimide/thiol, or an epoxide/nucleophile, or an inverse electron demand Diels-Alder (iEDDA) group.

192. The method of Aspect 190, wherein the functional moiety is an aldehyde group.

193. The method of any one of Aspects 175-192, wherein the plurality of compartment tags is formed by: printing, spotting, ink-jetting the compartment tags into the compartment, or a combination thereof.

194. The method of any one of Aspects 175-193, wherein the compartment tag further comprises a polypeptide.

195. The method of Aspect 194, wherein the compartment tag polypeptide comprises a protein ligase recognition sequence.

196. The method of Aspect 195, wherein the protein ligase is butelase I or a homolog thereof.

197. The method of any one of Aspects 175-196, wherein the plurality of polypeptides is fragmented with a protease.

198. The method of Aspect 197, wherein the protease is a metalloprotease.

199. The method of Aspect 198, wherein the activity of the metalloprotease is modulated by photo-activated release of metallic cations.

200. The method of any one of Aspects 175-199, further comprising subtraction of one or more abundant proteins from the sample prior to partitioning the plurality of polypeptides into the plurality of compartments.

201. The method of Aspect 175-200, further comprising releasing the compartment tags from the support prior to joining of the plurality of polypeptides with the compartment tags.

202. The method of Aspect 175, further comprising following step (d), joining the compartment tagged polypeptides to a support in association with recording tags.

203. The method of Aspect 202, further comprising transferring information of the compartment tag on the compartment tagged polypeptide to the associated recording tag.

204. The method of Aspect 203, further comprising removing the compartment tags from the compartment tagged polypeptides prior to step (e).

205. The method of any one of Aspects 175-204, further comprising determining the identity of the single cell from which the analyzed polypeptide derived based on the analyzed polypeptide's compartment tag sequence.

206. The method of any one of Aspects 175-204, further comprising determining the identity of the protein or protein complex from which the analyzed polypeptide derived based on the analyzed polypeptide's compartment tag sequence.

207. The method of any one of Aspects 32-206, wherein steps (f), (g), (h), and (i) are repeated with multiple amino acids.

208. The method of Aspect 207, wherein steps (f), (g), (h), and (i) are repeated with two or more amino acids.

209. The method of Aspect 207, wherein steps (f), (g), and (h) are repeated with up to about 100 amino acids.

210. A kit for analyzing a polypeptide, comprising:
(a) a reagent for providing the polypeptide optionally associated directly or indirectly with a recording tag;
(b) a reagent for functionalizing the N-terminal amino acid (NTAA) of the polypeptide, wherein the reagent comprises a compound selected from the group consisting of:
(i) a compound of Formula (I):

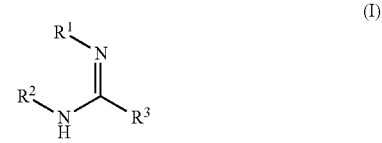

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2R^c$;
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
$R^3$ is heteroaryl, —NR$^d$C(O)OR$^e$, or —SR$^f$, wherein the heteroaryl is unsubstituted or substituted;
$R^d$, $R^e$, and $R^f$ are each independently H or $C_{1-6}$alkyl; and
optionally wherein when $R^3$ is

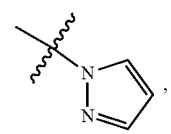 [SMILES: *n1cccn1]

$R^1$ and $R^2$ are not both H;

(ii) a compound of Formula (II):

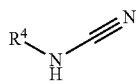

(II)

or a salt or conjugate thereof,
wherein
$R^4$ is H, $C_{1-6}$alkyl, cycloalkyl, —C(O)$R^g$, or —C(O)O$R^g$; and
  $R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;
(iii) a compound of Formula (III):

(III)

or a salt or conjugate thereof,
wherein
$R^5$ is $C_{1-6}$alkyl, $C_{2-6}$alkenyl, cycloalkyl, heterocycloalkyl, aryl or heteroaryl;
  wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —N$R^h R^i$, —S(O)$_2 R^j$, or heterocyclyl;
  $R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
(iv) a compound of Formula (IV):

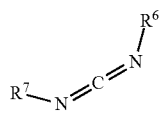

(IV)

or a salt or conjugate thereof,
wherein
$R^6$ and $R^7$ are each independently H, $C_{1-6}$alkyl, —CO$_2 C_{1-4}$ alkyl, —O$R^k$, aryl, or cycloalkyl, wherein the $C_{1-6}$alkyl, —CO$_2 C_{1-4}$alkyl, —O$R^k$, aryl, and cycloalkyl are each unsubstituted or substituted; and
  $R^k$ is H, $C_{1-6}$alkyl, or heterocyclyl, wherein the $C_{1-6}$alkyl and heterocyclyl are each unsubstituted or substituted;
(v) a compound of Formula (V):

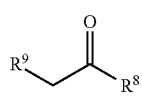

(V)

or a salt or conjugate thereof,
wherein
$R^8$ is halo or —O$R^m$;
  $R^m$ is H, $C_{1-6}$alkyl, or heterocyclyl; and
  $R^9$ is hydrogen, halo, or $C_{1-6}$haloalkyl;
(vi) a metal complex of Formula (VI):

(VI)

or a salt or conjugate thereof, wherein
M is a metal selected from the group consisting of Co, Cu, Pd, Pt, Zn, and Ni;
L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and
(vii) a compound of Formula (VII):

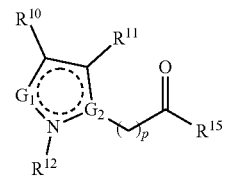

(VII)

or a salt or conjugate thereof,
wherein
$G^1$ is N, N$R^{13}$, or C$R^{13}R^{14}$;
$G^2$ is N or CH;
p is 0 or 1;
$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and
$R^{15}$ is H or OH;
(c) a first binding agent comprising a first binding portion capable of binding to the functionalized NTAA and (c1) a first coding tag with identifying information regarding the first binding agent, or (c2) a first detectable label; and
(d) a reagent for transferring the information of the first coding tag to the recording tag to generate an extended recording tag; and optionally
(e) a reagent for analyzing the extended recording tag or a reagent for detecting the first detectable label.
211. The kit of Aspect 210, wherein the reagent of (a) is configured to provide the polypeptide and an associated recording tag joined to a support (e.g., a solid support).
212. The kit of Aspect 210, wherein the reagent of (a) is configured to provide the polypeptide associated directly with a recording tag in a solution.
213. The kit of Aspect 210, wherein the reagent of (a) is configured to provide the polypeptide associated indirectly with a recording tag.
214. The kit of Aspect 210, wherein the reagent of (a) is configured to provide the polypeptide which is not associated with a recording tag.
215. The kit of any one of Aspects 210-214, wherein the kit comprises two or more different reagents for functionalizing the NTAA of the polypeptide.
216. The kit of Aspect 215, wherein the kit comprises a first reagent comprising a compound selected from the group consisting of a compound of Formula (I), (II), (III), (IV), (V), (VI), and (VII), or a salt or conjugate thereof, as described in Aspect 125, and a second reagent.

217. The kit of Aspect 216, wherein the second reagent comprises a compound of Formula (VIIIa) or (VIIIb):

 (VIIIa)

or a salt or conjugate thereof,
wherein
R$^{13}$ is H, C$_{1-6}$alkyl, aryl, heteroaryl, cycloalkyl, or heterocycloalkyl, wherein the C$_{1-6}$alkyl, aryl, heteroaryl, cycloalkyl, and heterocycloalkyl are each unsubstituted or substituted; or R$^{13}$—X (VIIIb)

wherein
R$^{13}$ is C$_{1-6}$alkyl, aryl, heteroaryl, cycloalkyl, or heterocycloalkyl, each of which is unsubstituted or substituted; and
X is a halogen.
218. The kit of Aspect 217, wherein the compound of Formula (VIIIa) is formaldehyde.
219. The kit of Aspect 217, wherein the compound of Formula (VIIIb) is methyl iodide.
220. The kit of any one of Aspects 210-219, wherein the kit comprises two or more different binding agents.
221. The kit of any one of Aspects 210-220, further comprising a reagent for eliminating the functionalized NTAA to expose a new NTAA.
222. The kit of any one of Aspects 211-221, wherein the kit comprises two or more different reagents for eliminating the functionalized NTAA.
223. The kit of Aspect 221 or Aspect 222, wherein the reagent for eliminating the functionalized NTAA comprises a chemical cleavage reagent or an enzymatic cleavage reagent.
224. The kit of Aspect 221 or Aspect 222, wherein the reagent for eliminating the functionalized NTAA comprises a carboxypeptidase or aminopeptidase or variant, mutant, or modified protein thereof, a hydrolase or variant, mutant, or modified protein thereof, a mild Edman degradation reagent; an Edmanase enzyme; TFA; a base; or any combination thereof.
225. The kit of any one of Aspects 210-224, wherein the chemical reagent comprises a compound selected from the group consisting of a compound of Formula (I):

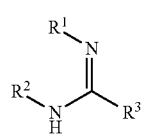 (I)

or a salt or conjugate thereof,
wherein
R$^1$ and R$^2$ are each independently H, C$_{1-6}$alkyl, cycloalkyl, —C(O)R$^a$, —C(O)OR$^b$, or —S(O)$_2$R$^c$;
R$^a$, R$^b$, and R$^c$ are each independently H, C$_{1-6}$alkyl, C$_{1-6}$haloalkyl, arylalkyl, aryl, or heteroaryl, wherein the C$_{1-6}$alkyl, C$_{1-6}$haloalkyl, arylalkyl, aryl, and heteroaryl are each unsubstituted or substituted;
R$^3$ is heteroaryl, —NR$^d$C(O)OR$^e$, or —SR$^f$, wherein the heteroaryl is unsubstituted or substituted;

R$^d$, R$^e$, and R$^f$ are each independently H or C$_{1-6}$alkyl; and optionally wherein when R$^3$ is

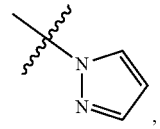

R$^1$ and R$^2$ are not both H.
226. The kit of Aspect 225, wherein R$^1$ is

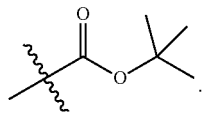

227. The kit of Aspect 225 or Aspect 226, wherein R$^2$ is

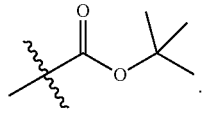

228. The kit of any one of Aspects 225-227, wherein R$^1$ or R$^2$ is

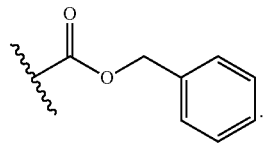

229. The kit of any one of Aspects 225-228, wherein R$^3$ is

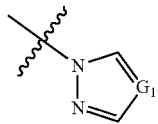

wherein G$_1$ is N or CH.
230. The kit of any one of Aspects 225-228, wherein R$^3$ is

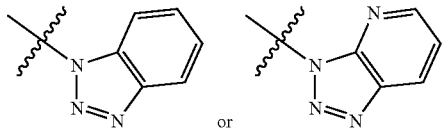

231. The kit of Aspect 225, wherein the compound of Formula (I) is selected from the group consisting of

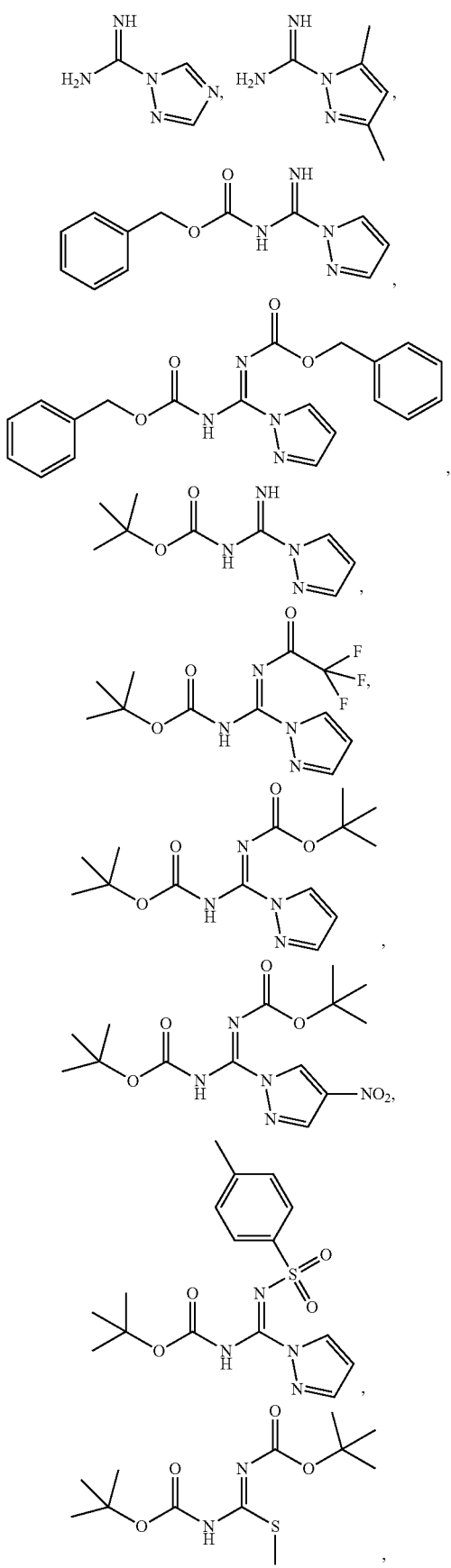

or a salt or conjugate thereof.

232. The kit of any one of Aspects 225-231, wherein the chemical reagent additionally comprises Mukaiyama's reagent (2-chloro-1-methylpyridinium iodide).

233. The kit of any one of Aspects 210-224, wherein the chemical reagent comprises a compound selected from the group consisting of a compound of Formula (II):

$$\text{(II)}$$

or a salt or conjugate thereof,
wherein
R$^4$ is H, C$_{1-6}$alkyl, cycloalkyl, —C(O)R$^g$, or —C(O)OR$^g$; and
R$^g$ is H, C$_{1-6}$alkyl, C$_{2-6}$alkenyl, C$_{1-6}$haloalkyl, or arylalkyl, wherein the C$_{1-6}$alkyl, C$_{2-6}$alkenyl, C$_{1-6}$haloalkyl, and arylalkyl are each unsubstituted or substituted.

234. The kit of Aspect 142, wherein R$^4$ is carboxybenzyl.

235. The kit of Aspect 142, wherein R$^4$ is —C(O)R$^g$ and R$^g$ is C$_{2-6}$alkenyl, optionally substituted with aryl, heteroaryl, or heterocycloalkyl.

236. The kit of Aspect 142, wherein the compound is selected from the group consisting of -continued

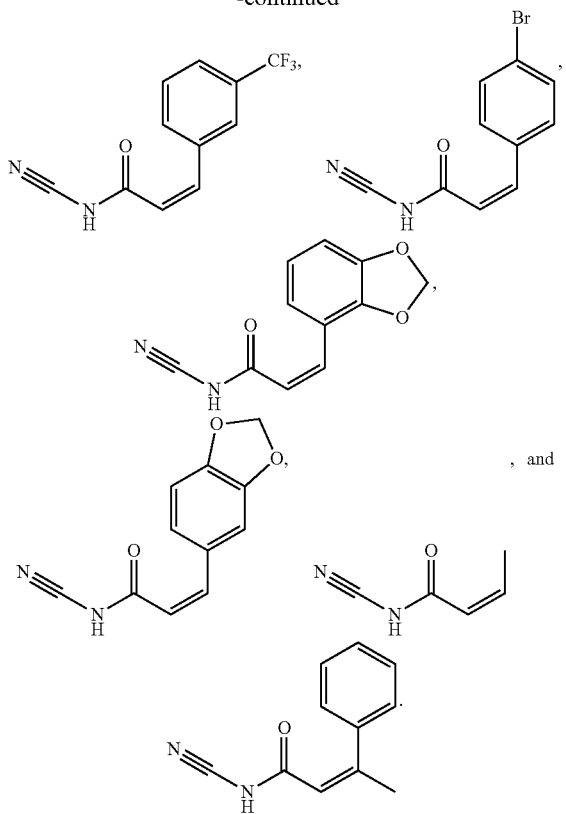

or a salt or conjugate thereof

237. The kit of any one of Aspects 142-145, wherein the chemical reagent additionally comprises TMS-Cl, Sc(OTf)$_2$, Zn(OTf)$_2$, or a lanthanide-containing reagent.

238. The kit of any one of Aspects 210-224, wherein the chemical reagent comprises a compound selected from the group consisting of a compound of Formula (III):

$$R^5-N=C=S \quad (III)$$

or a salt or conjugate thereof,
wherein
R$^5$ is C$_{1-6}$alkyl, C$_{2-6}$alkenyl, cycloalkyl, heterocycloalkyl, aryl or heteroaryl;
  wherein the C$_{1-6}$alkyl, C$_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;
R$^h$, R$^i$, and R$^j$ are each independently H, C$_{1-6}$alkyl, C$_{1-6}$haloalkyl, arylalkyl, aryl, or heteroaryl, wherein the C$_{1-6}$alkyl, C$_{1-6}$haloalkyl, arylalkyl, aryl, and heteroaryl are each unsubstituted or substituted.

239. The kit of Aspect 238, wherein R$^5$ is substituted phenyl.

240. The kit of Aspect 238 or Aspect 239, wherein R$^5$ is phenyl, substituted with one or more groups selected from the group consisting of halo, —NR$^h$R$^i$, —S(O)$_2$R$^j$, and heterocyclyl.

241. The kit of Aspect 238, wherein the compound of Formula (III) is trimethylsilyl isothiocyanate (TM-SITC) or pentafluorophenyl isothiocyanate (PFPITC).

242. The kit of any one of Aspects 238-240, wherein the chemical reagent additionally comprises a carbodiimide compound.

243. The kit of any one of Aspects 238-242, wherein the reagent for eliminating the functionalized NTAA comprises trifluoroacetic acid or hydrochloric acid.

244. The kit of any one of Aspects 238-243, wherein the reagent for eliminating the functionalized NTAA comprises a mild Edman degradation reagent.

245. The kit of any one of Aspects 238-243, wherein the reagent for eliminating the functionalized NTAA comprises an Edmanase or an engineered hydrolase, aminopeptidase, or carboxypeptidase.

246. The kit of any one of Aspects 210-224, wherein the chemical reagent comprises a compound selected from the group consisting of a compound of Formula (IV):

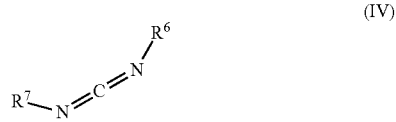

(IV)

or a salt or conjugate thereof,
wherein
R$^6$ and R$^7$ are each independently H, C$_{1-6}$alkyl, —CO$_2$C$_{1-4}$ alkyl, —OR$^k$, aryl, or cycloalkyl, wherein the C$_{1-6}$alkyl, —CO$_2$C$_{1-4}$alkyl, —OR$^k$, aryl, and cycloalkyl are each unsubstituted or substituted; and
R$^k$ is H, C$_{1-6}$alkyl, or heterocyclyl, wherein the C$_{1-6}$alkyl and heterocyclyl are each unsubstituted or substituted.

247. The kit of Aspect 246 wherein R$^6$ and R$^7$ are each independently H, C$_{1-6}$alkyl or cycloalkyl.

248. The kit of Aspect 246, wherein the compound is selected from the group consisting of

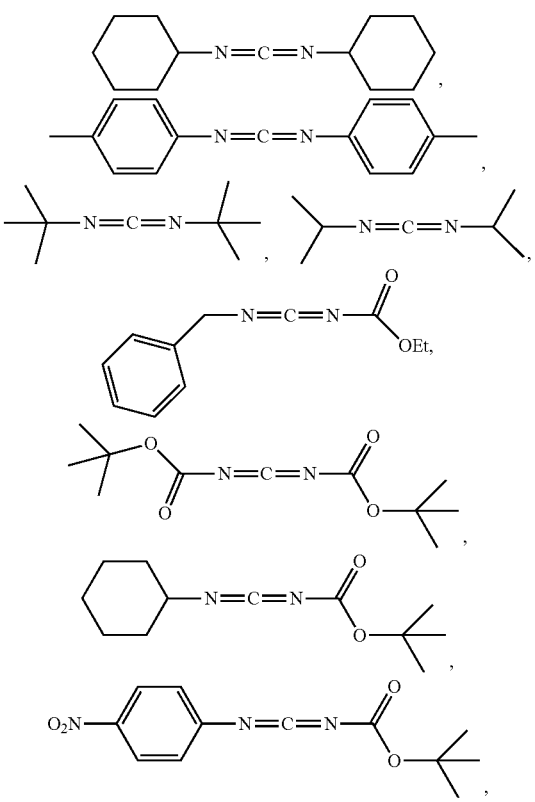

-continued

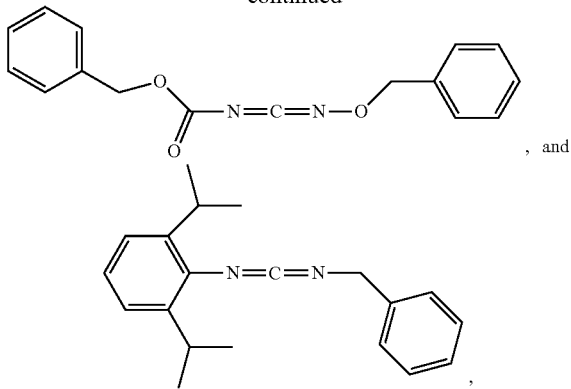

, and or a salt or conjugate thereof.

249. The kit of any one of Aspects 246-248, wherein the compound of Formula (IV) is prepared by desulfurization of the corresponding thiourea.
250. The kit of any one of Aspects 246-249, wherein the chemical reagent additionally comprises Mukaiyama's reagent (2-chloro-1-methylpyridinium iodide).
251. The kit of any one of Aspects 246-249, wherein the chemical reagent additionally comprises a Lewis acid.
252. The kit of Aspect 251, wherein the Lewis acid selected from N-((aryl)imino-acenapthenone)$ZnCl_2$, $Zn(OTf)_2$, $ZnCl_2$, $PdCl_2$, CuCl, and $CuCl_2$.
253. The kit of any one of Aspects 210-224, wherein the chemical reagent comprises a compound selected from the group consisting of a compound of Formula (V):

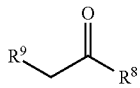

(V)

or a salt or conjugate thereof,
wherein
$R^8$ is halo or —$OR^m$;
$R^m$ is H, $C_{1-6}$alkyl, or heterocyclyl; and
$R^9$ is hydrogen, halo, or $C_{1-6}$haloalkyl.

254. The kit of Aspect 253, wherein $R^8$ is chloro.
255. The kit of Aspect 253 or Aspect 254, wherein $R^9$ is hydrogen or bromo.
256. The kit of any one of Aspects 253-255, wherein the chemical reagent additionally comprises a peptide coupling reagent.
257. The kit of Aspect 256, wherein the peptide coupling reagent is a carbodiimide compound.
258. The kit of Aspect 257, wherein the carbodiimide compound is diisopropylcarbodiimide (DIC) or 1-ethyl-3-(3-dimethylaminopropyl)carbodiimide (EDC).
259. The kit of any one of Aspects 253-258, wherein the reagent for eliminating the functionalized NTAA comprises acylpeptide hydrolase (APH).
260. The kit of any one of Aspects 210-224, wherein the chemical reagent comprises a metal complex of Formula (VI):

$ML_n$ (VI)

or a salt or conjugate thereof, wherein
M is a metal selected from the group consisting of Co, Cu, Pd, Pt, Zn, and Ni;
L is a ligand selected from the group consisting of —OH, —$OH_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different.

261. The kit of Aspect 260, wherein M is Co.
262. The kit of Aspect 260 or 261, wherein the chemical reagent comprises a cis-β-hydroxyaquo(triethylenetetramine)cobalt(III) complex.
263. The kit of Aspect 260 or 261, wherein the chemical reagent comprises β-[Co(trien)(OH)($OH_2$)]$^{2+}$.
264. The kit of any one of Aspects 210-224, wherein the chemical reagent comprises a compound selected from the group consisting of a compound of Formula (VII):

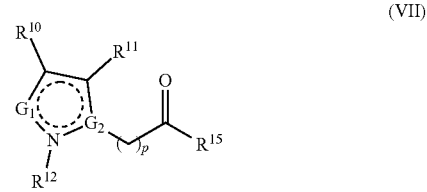

(VII)

or a salt or conjugate thereof,
wherein
$G^1$ is N, $NR^{13}$, or $CR^{13}R^{14}$;
$G^2$ is N or CH;
p is 0 or 1;
$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and
$R^{15}$ is H or OH.

265. The kit of Aspect 264, wherein $G^1$ is $CH_2$ and $G^2$ is CH or $G^1$ is NH and $G^2$ is N.
266. The kit of Aspect 264 or 265, wherein $R^{12}$ is H.
267. The kit of any one of Aspects 264-266, wherein $R^{10}$ and $R^{11}$ are each H.
268. The kit of Aspect 264, wherein the compound of Formula (VII) is selected from the group consisting of

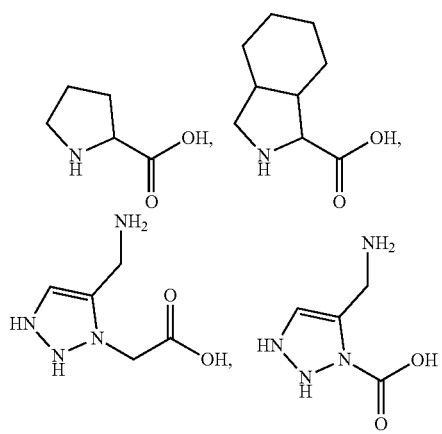

-continued

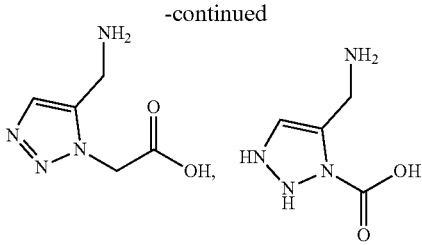

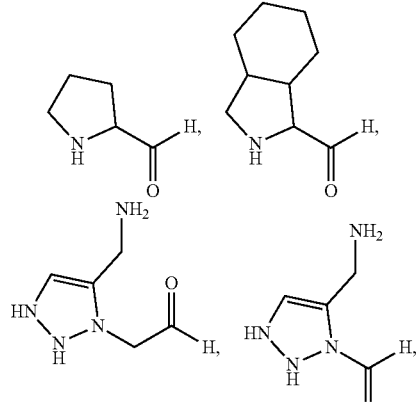

or a salt or conjugate thereof.

269. The kit of any one of Aspects 225-268, wherein the reagent for eliminating the functionalized NTAA comprises a base.
270. The kit of Aspect 269, wherein the base is a hydroxide, an alkylated amine, a cyclic amine, a carbonate buffer, or a metal salt.
271. The kit of Aspect 270, wherein the hydroxide is sodium hydroxide.
272. The kit of Aspect 270, wherein the alkylated amine is selected from methylamine, ethylamine, propylamine, dimethylamine, diethylamine, dipropylamine, trimethylamine, triethylamine, tripropylamine, cyclohexylamine, benzylamine, aniline, diphenylamine, N,N-diisopropylethylamine (DIPEA), and lithium diisopropylamide (LDA).
273. The kit of Aspect 270, wherein the cyclic amine is selected from pyridine, pyrimidine, imidazole, pyrrole, indole, piperidine, pyrolidine, 1,8-diazabicyclo[5.4.0]undec-7-ene (DBU), and 1,5-diazabicyclo[4.3.0]non-5-ene (DBN).
274. The kit of Aspect 270, wherein the carbonate buffer comprises sodium carbonate, potassium carbonate, calcium carbonate, sodium bicarbonate, potassium bicarbonate, or calcium bicarbonate.
275. The kit of Aspect 270, wherein the metal salt comprises silver.
276. The kit of Aspect 270, wherein the metal salt is $AgClO_4$.
277. The kit of any one of Aspects 210-276, wherein the chemical reagent comprises a conjugate selected from the group consisting of

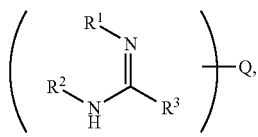

Formula (I)-Q wherein $R^1$, $R^2$, and $R^3$ are as defined for Formula (I) in Aspect 1, and Q is a ligand;

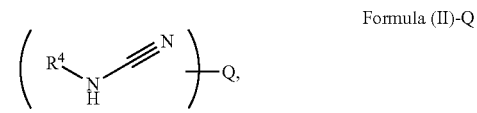

Formula (II)-Q wherein $R^4$ is as defined for Formula (II) in Aspect 1, and Q is a ligand;

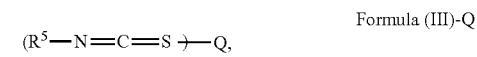

Formula (III)-Q wherein $R^5$ is as defined for Formula (III) in Aspect 1, and Q is a ligand;

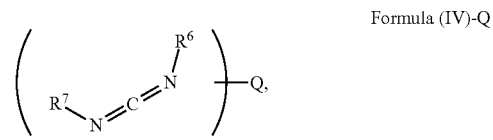

Formula (IV)-Q wherein $R^6$ and $R^7$ are as defined for Formula (IV) in Aspect 1, and Q is a ligand;

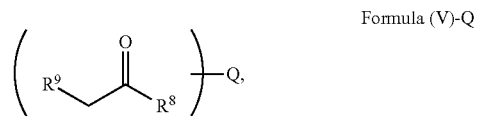

Formula (V)-Q wherein $R^8$ and $R^9$ are as defined for Formula (V) in Aspect 1, and Q is a ligand;

$(ML_n)$-Q  Formula (VI)-Q, wherein M, L, and n are as defined for Formula (VI) in Aspect 1, and Q is a ligand;

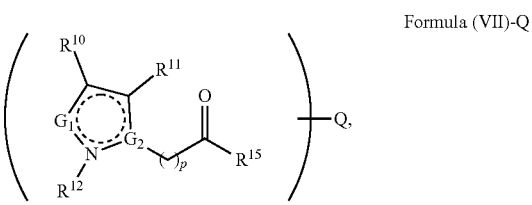

Formula (VII)-Q wherein $R^{10}$, $R^{11}$, $R^{12}$, $R^{15}$, $G^1$, $G^2$, and p are as defined for Formula (VII) in Aspect 1, and Q is a ligand.

278. The kit of Aspect 277, wherein the Q is selected from the group consisting of —$C_{1-6}$alkyl, —$C_{2-6}$alkenyl, —$C_{2-6}$alkynyl, aryl, heteroaryl, heterocyclyl, —N=C=S, —CN, —C(O)R$^n$, —C(O)OR$^o$, —SR$^p$ or —S(O)$_2$R$^q$; wherein the —C$_{1-6}$alkyl, —C$_{2-6}$alkenyl, —C$_{2-6}$alkynyl, aryl, heteroaryl, and heterocyclyl are each unsubstituted or substituted, and R$^n$, R$^o$, R$^p$, and R$^q$ are each independently selected from the group consisting of —C$_{1-6}$alkyl, —C$_{1-6}$haloalkyl, —C$_{2-6}$alkenyl, —C$_{2-6}$alkynyl, aryl, heteroaryl, and heterocyclyl.

279. The kit of Aspect 277, wherein the Q is selected from the group consisting of

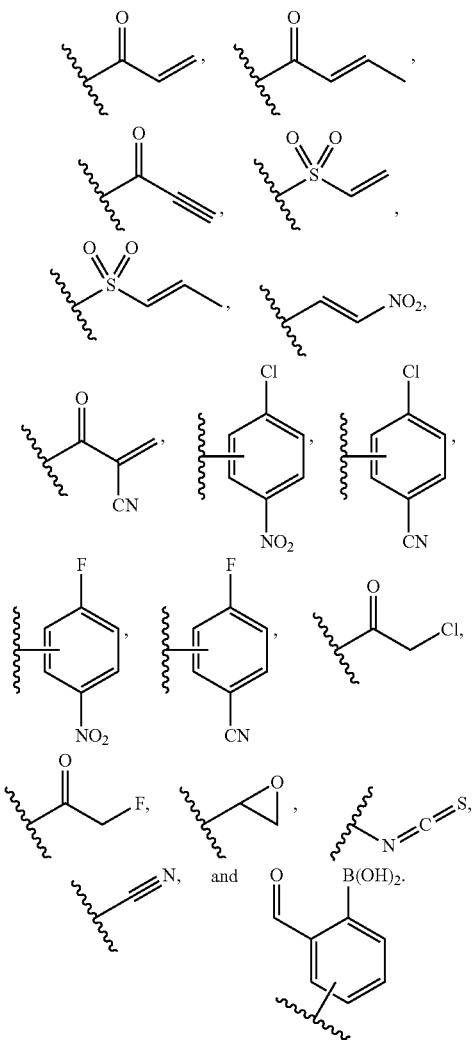

280. The kit of Aspect 277, wherein Q is a fluorophore.
281. The kit of any one of Aspects 210-280, wherein the binding agent binds to a terminal amino acid residue, terminal di-amino-acid residues, or terminal tri-amino-acid residues.
282. The kit of any one of Aspects 210-280, wherein the binding agent binds to a post-translationally modified amino acid.
283. The kit of any one of Aspects 210-282, wherein the recording tag comprises a nucleic acid, an oligonucleotide, a modified oligonucleotide, a DNA molecule, a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof.

284. The kit of Aspect 283, wherein the DNA molecule is backbone modified, sugar modified, or nucleobase modified.
285. The kit of Aspect 283, wherein the DNA molecule has nucleobase protecting groups such as Alloc, electrophilic protecting groups such as thiranes, acetyl protecting groups, nitrobenzyl protecting groups, sulfonate protecting groups, or traditional base-labile protecting groups including Ultramild reagents.
286. The kit of any one of Aspects 210-285, wherein the recording tag comprises a universal priming site.
287. The kit of Aspect 286, wherein the universal priming site comprises a priming site for amplification, sequencing, or both.
288. The kit of any one of Aspects 210-287, where the recording tag comprises a unique molecule identifier (UMI).
289. The kit of any one of Aspects 210-288, wherein the recording tag comprises a barcode.
290. The kit of any one of Aspects 210-288, wherein the recording tag comprises a spacer at its 3'-terminus.
291. The kit of any one of Aspects 210-290, wherein the reagents for providing the polypeptide and an associated recording tag joined to a support provide for covalent linkage of the polypeptide and the associated recording tag on the support.
292. The kit of any one of Aspects 210-291, wherein the support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere
293. The kit of Aspect 292, wherein the support comprises gold, silver, a semiconductor or quantum dots.
294. The kit of Aspect 292, wherein the nanoparticle comprises gold, silver, or quantum dots.
295. The kit of Aspect 292, wherein the support is a polystyrene bead, a polymer bead, an agarose bead, an acrylamide bead, a solid core bead, a porous bead, a paramagnetic bead, glass bead, or a controlled pore bead.
296. The kit of any one of Aspects 210-295, wherein the reagents for providing the polypeptide and an associated recording tag joined to a support provide for a plurality of polypeptides and associated recording tags that are joined to a support.
297. The kit of Aspect 296, wherein the plurality of polypeptides are spaced apart on the support, wherein the average distance between the polypeptides is about >20 nm.
298. The kit of any one of Aspects 210-297, wherein the binding agent is a peptide or protein.
299. The kit of any one of Aspects 210-298, wherein the binding agent comprises an aminopeptidase or variant, mutant, or modified protein thereof; an aminoacyl tRNA synthetase or variant, mutant, or modified protein thereof; an anticalin or variant, mutant, or modified protein thereof, a ClpS or variant, mutant, or modified protein thereof, or a modified small molecule that binds amino acid(s), i.e. vancomycin or a variant, mutant, or modified molecule thereof; or an antibody or binding fragment thereof, or any combination thereof.
300. The kit of any one of Aspects 210-299, wherein the binding agent binds to a single amino acid residue (e.g., an N-terminal amino acid residue, a C-terminal amino acid residue, or an internal amino acid residue), a dipeptide (e.g., an N-terminal dipeptide, a C-terminal dipeptide, or an internal dipeptide), a tripeptide (e.g., an N-terminal tripeptide, a C-terminal tripeptide, or an internal tripeptide), or a post-translational modification of the analyte or polypeptide.
301. The kit of any one of Aspects 210-300, wherein the binding agent binds to a NTAA-functionalized single amino acid residue, a NTAA-functionalized dipeptide, a NTAA-functionalized tripeptide, or a NTAA-functionalized polypeptide.
302. The kit of any one of Aspects 210-301, wherein the binding agent is capable of selectively binding to the polypeptide.
303. The kit of any one of Aspects 210-302, wherein the coding tag is DNA molecule, an RNA molecule, a BNA molecule, an XNA molecule, a LNA molecule, a PNA molecule, a γPNA molecule, or a combination thereof.
304. The kit of any one of Aspects 210-303, wherein the coding tag comprises an encoder or barcode sequence.
305. The kit of any one of Aspects 210-304, wherein the coding tag further comprises a spacer, a binding cycle specific sequence, a unique molecular identifier, a universal priming site, or any combination thereof.
306. The kit of any one of Aspects 210-305, wherein the binding portion and the coding tag in the binding agent are joined by a linker.
307. The kit of any one of Aspects 210-305, wherein the binding portion and the coding tag are joined by a SpyTag/SpyCatcher peptide-protein pair, a SnoopTag/SnoopCatcher peptide-protein pair, or a HaloTag/HaloTag ligand pair.
308. The kit of any one of Aspects 210-307, wherein the reagent for transferring the information of the coding tag to the recording tag comprises a DNA ligase or an RNA ligase.
309. The kit of any one of Aspects 210-307, wherein the reagent for transferring the information of the coding tag to the recording tag comprises a DNA polymerase, an RNA polymerase, or a reverse transcriptase.
310. The kit of any one of Aspects 210-307, wherein the reagent for transferring the information of the coding tag to the recording tag comprises a chemical ligation reagent.
311. The kit of Aspect 310, wherein the chemical ligation reagent is for use with single-stranded DNA.
312. The kit of Aspect 310, wherein the chemical ligation reagent is for use with double-stranded DNA.
313. The kit of any one of Aspects 210-312, further comprising a ligation reagent comprised of two DNA or RNA ligase variants, an adenylated variant and a constitutively non-adenylated variant.
314. The kit of any one of Aspects 210-312, further comprising a ligation reagent comprised of a DNA or RNA ligase and a DNA/RNA deadenylase.
315. The kit of any one of Aspects 210-314, wherein the kit additionally comprises reagents for nucleic acid sequencing methods.
316. The kit of Aspect 315, wherein the nucleic acid sequencing method is sequencing by synthesis, sequencing by ligation, sequencing by hybridization, polony sequencing, ion semiconductor sequencing, or pyrosequencing.
317. The kit of Aspect 315, wherein the nucleic acid sequencing method is single molecule real-time sequencing, nanopore-based sequencing, or direct imaging of DNA using advanced microscopy.
318. The kit of any one of Aspects 210-317, wherein the kit additionally comprises reagents for amplifying the extended recording tag.
319. The kit of any one of Aspects 210-318, further comprising reagents for adding a cycle label.
320. The kit of Aspect 319, wherein the cycle label provides information regarding the order of binding by the binding agents to the polypeptide.
321. The kit of Aspect 319 or Aspect 320, wherein the cycle label can be added to the coding tag.
322. The kit of Aspect 319 or Aspect 320, wherein the cycle label can be added to the recording tag.
323. The kit of Aspect 319 or Aspect 320, wherein the cycle label can be added to the binding agent.
324. The kit of Aspect 319 or Aspect 320, wherein the cycle label can be added independent of the coding tag, recording tab, and binding agent.
325. The kit of any one of Aspects 210-324, wherein the order of coding tag information contained on the extended recording tag provides information regarding the order of binding by the binding agents to the polypeptide.
326. The kit of any one of Aspects 210-325, wherein frequency of the coding tag information contained on the extended recording tag provides information regarding the frequency of binding by the binding agents to the polypeptide.
327. The kit of any one of Aspects 210-326, which is configured for analyzing one or more polypeptides from a sample comprising a plurality of protein complexes, proteins, or polypeptides.
328. The kit of Aspect 327, further comprising means for partitioning the plurality of protein complexes, proteins, or polypeptides within the sample into a plurality of compartments, wherein each compartment comprises a plurality of compartment tags optionally joined to a support (e.g., a solid support), wherein the plurality of compartment tags are the same within an individual compartment and are different from the compartment tags of other compartments.
329. The kit of Aspect 327 or 328, further comprising a reagent for fragmenting the plurality of protein complexes, proteins, and/or polypeptides into a plurality of polypeptides.
330. The kit of Aspect 328, wherein the compartment is a microfluidic droplet.
331. The kit of Aspect 328, wherein the compartment is a microwell.
332. The kit of Aspect 328, wherein the compartment is a separated region on a surface.
333. The kit of any one of Aspects 328-332, wherein each compartment comprises on average a single cell.
334. A kit of any one of Aspects 327-333, further comprising a reagent for labeling the plurality of protein complexes, proteins, or polypeptides with a plurality of universal DNA tags.
335. The kit of any one of Aspects 328-334, wherein the reagent for transferring the compartment tag information to the recording tag associated with a polypeptide comprises a primer extension or ligation reagent.
336. The kit of any one of Aspects 328-335, wherein the support is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

337. The kit of any one of Aspects 328-335, wherein the support comprises a bead.

338. The kit of Aspect 337, wherein the bead is a polystyrene bead, a polymer bead, an agarose bead, an acrylamide bead, a solid core bead, a porous bead, a paramagnetic bead, glass bead, or a controlled pore bead.

339. The kit of any one of Aspects 328-338, wherein the compartment tag comprises a single stranded or double stranded nucleic acid molecule.

340. The kit of any one of Aspects 328-339, wherein the compartment tag comprises a barcode and optionally a UMI.

341. The kit of Aspect 340, wherein the support is a bead and the compartment tag comprises a barcode, further wherein beads comprising the plurality of compartment tags joined thereto are formed by split-and-pool synthesis.

342. The kit of Aspect 340, wherein the support is a bead and the compartment tag comprises a barcode, further wherein beads comprising a plurality of compartment tags joined thereto are formed by individual synthesis or immobilization.

343. The kit of any one of Aspects 328-342, wherein the compartment tag is a component within a recording tag, wherein the recording tag optionally further comprises a spacer, a barcode sequence, a unique molecular identifier, a universal priming site, or any combination thereof.

344. The kit of any one of Aspects 328-343, wherein the compartment tags further comprise a functional moiety capable of reacting with an internal amino acid, the peptide backbone, or N-terminal amino acid on the plurality of protein complexes, proteins, or polypeptides.

345. The kit of Aspect 344, wherein the functional moiety is an aldehyde, an azide/alkyne, or a malemide/thiol, or an epoxide/nucleophile, or an inverse electron domain Diels-Alder (iEDDA) group.

346. The kit of Aspect 344, wherein the functional moiety is an aldehyde group.

347. The kit of any one of Aspects 328-346, wherein the plurality of compartment tags is formed by: printing, spotting, ink-jetting the compartment tags into the compartment, or a combination thereof.

348. The kit of any one of Aspects 328-347, wherein the compartment tag further comprises a polypeptide.

349. The kit of Aspect 348, wherein the compartment tag polypeptide comprises a protein ligase recognition sequence.

350. The kit of Aspect 349, wherein the protein ligase is butelase I or a homolog thereof.

351. The kit of any one of Aspects 328-350, wherein the reagent for fragmenting the plurality of polypeptides comprises a protease.

352. The kit of Aspect 351, wherein the protease is a metalloprotease.

353. The kit of Aspect 352, further comprising a reagent for modulating the activity of the metalloprotease, e.g., a reagent for photo-activated release of metallic cations of the metalloprotease.

354. The kit of any one of Aspects 328-353, further comprising a reagent for subtracting one or more abundant proteins from the sample prior to partitioning the plurality of polypeptides into the plurality of compartments.

355. The kit of any one of Aspect 328-354, further comprising a reagent for releasing the compartment tags from the support prior to joining of the plurality of polypeptides with the compartment tags.

356. The kit of Aspect 328, further comprising a reagent for joining the compartment tagged polypeptides to a support in association with recording tags.

357. A method for screening for a polypeptide functionalizing reagent, an amino acid eliminating reagent and/or a reaction condition, which method comprises the steps of:
(a) contacting a polynucleotide with a polypeptide functionalizing reagent and/or an amino acid eliminating reagent under a reaction condition; and
(b) assessing the effect of step (a) on said polynucleotide, optionally to identify a polypeptide functionalizing reagent, an amino acid eliminating reagent and/or a reaction condition that has no or minimal effect on said polynucleotide.

358. The method of Aspect 357, wherein the polynucleotide comprises at least about 4 nucleotides.

359. The method of Aspect 357, wherein the polynucleotide comprises at most about 10 kb nucleotides.

360. The method of any one of Aspects 357-359, wherein the polynucleotide is a DNA polynucleotide.

361. The method of any one of Aspects 357-360, wherein the polynucleotide is genomic DNA or the method is conducted in the presence of genomic DNA.

362. The method of any one of Aspects 357-360, wherein the polynucleotide is an isolated polynucleotide.

363. The method of any one of Aspects 357-360, wherein the polynucleotide is a part of a binding agent for the polypeptide.

364. The method of any one of Aspects 357-363, wherein the polynucleotide is contacted with the polypeptide functionalizing reagent and/or the amino acid eliminating reagent under a reaction condition in the absence of the polypeptide.

365. The method of any one of Aspects 357-363, wherein the polynucleotide is contacted with the polypeptide functionalizing reagent and/or the amino acid eliminating reagent under a reaction condition in the presence of the polypeptide.

366. The method of Aspect 365, wherein the polynucleotide is a part of a binding agent for the polypeptide.

367. The method of any one of Aspects 357-366, wherein the polypeptide functionalizing reagent comprises a compound selected from the group consisting of
(i) a compound of Formula (I):

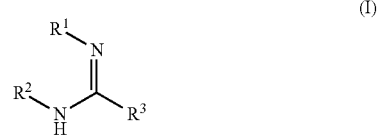

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2R^c$,
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

$R^3$ is heteroaryl, $-NR^dC(O)OR^e$, or $-SR^f$, wherein the heteroaryl is unsubstituted or substituted;

$R^d$, $R^e$, and $R^f$ are each independently H or $C_{1-6}$alkyl; and optionally wherein when $R^3$ is

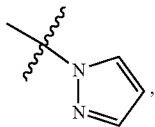

$R^1$ and $R^2$ are not both H;

(ii) a compound of Formula (II):

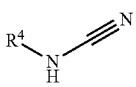

(II)

or a salt or conjugate thereof,
wherein
$R^4$ is H, $C_{1-6}$alkyl, cycloalkyl, $-C(O)R^g$, or $-C(O)OR^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;

(iii) a compound of Formula (III):

 (III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, $-NR^hR^i$, $-S(O)_2R^j$, or heterocyclyl;
$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

(iv) a compound of Formula (IV):

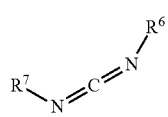 (IV)

or a salt or conjugate thereof,
wherein
$R^6$ and $R^7$ are each independently H, $C_{1-6}$alkyl, $-CO_2C_{1-4}$alkyl, $-OR^k$, aryl, or cycloalkyl, wherein the $C_{1-6}$alkyl, $-CO_2C_{1-4}$alkyl, $-OR^k$, aryl, and cycloalkyl are each unsubstituted or substituted; and
$R^k$ is H, $C_{1-6}$alkyl, or heterocyclyl, wherein the $C_{1-6}$alkyl and heterocyclyl are each unsubstituted or substituted;

(v) a compound of Formula (V):

 (V)

or a salt or conjugate thereof,
wherein
$R^8$ is halo or $-OR^m$;
$R^m$ is H, $C_{1-6}$alkyl, or heterocyclyl; and
$R^9$ is hydrogen, halo, or $C_{1-6}$haloalkyl;

(vi) a metal complex of Formula (VI):

$$ML_n \quad (VI)$$

or a salt or conjugate thereof,
wherein
M is a metal selected from the group consisting of Co, Cu, Pd, Pt, Zn, and Ni;
L is a ligand selected from the group consisting of $-OH$, $-OH_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and (vii) a compound of Formula (VII):

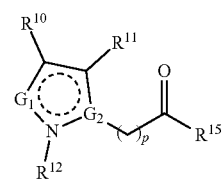 (VII)

or a salt or conjugate thereof,
wherein
$G^1$ is N, $NR^{13}$, or $CR^{13}R^{14}$;
$G^2$ is N or CH;
p is 0 or 1;
$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and
$R^{15}$ is H or OH 368. The method of any one of Aspects 357-367, wherein the amino acid eliminating reagent is a chemical cleavage reagent or an enzymatic cleavage reagent.

369. The method of Aspect 368, wherein the amino acid eliminating reagent is a carboxypeptidase or aminopeptidase or variant, mutant, or modified protein thereof, a hydrolase or variant, mutant, or modified protein thereof; a mild Edman degradation reagent; an Edmanase enzyme; TFA; a base; or any combination thereof.

370. The method of any one of Aspects 357-369, wherein the reaction condition comprises reaction time, reaction temperature, reaction pH, solvent type, co-solvent, catalysts, and ionic liquids, and electrochemical potential.

371. The method of any one of Aspects 357-370, wherein step (a) is conducted in a solution.

372. The method of any one of Aspects 357-370, wherein step (a) is conducted on a solid phase.

373. The method of any one of Aspects 357-372, wherein the effect of step (a) on the polynucleotide is assessed by assessing the presence, absence or quantity of modification of the polynucleotide by the polypeptide functionalizing reagent, the amino acid eliminating reagent and/or the reaction condition.

374. The method of any one of Aspects 357-373, wherein less than 50% modification of the polynucleotide, as compared to a corresponding polynucleotide not contacted with a polypeptide functionalizing reagent and/or an amino acid eliminating reagent under a reaction condition, identifies the polypeptide functionalizing reagent, the amino acid eliminating reagent and/or the reaction condition that has no or minimal effect on the polynucleotide.

375. A kit for screening for a polypeptide functionalizing reagent, an amino acid eliminating reagent and/or a reaction condition, comprising: (a) a polynucleotide; (b) a polypeptide functionalizing reagent and/or an amino acid eliminating reagent; (c) means for assessing the effect of said polypeptide functionalizing reagent, said amino acid eliminating reagent and/or a reaction condition for polypeptide functionalization or elimination on said polynucleotide.

376. The kit of Aspect 375, wherein the polypeptide functionalizing reagent comprises a compound selected from the group consisting of (i) a compound of Formula (I):

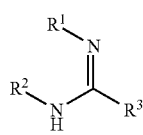

(I)

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2R^c$;

$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

$R^3$ is heteroaryl, —NR$^d$C(O)OR$^e$, or —SR$^f$, wherein the heteroaryl is unsubstituted or substituted;

$R^d$, $R^e$, and $R^f$ are each independently H or $C_{1-6}$alkyl; and
optionally wherein when $R^3$ is

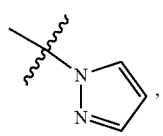 [SMILES: *n1cccn1]

, $R^1$ and $R^2$ are not both H;

(ii) a compound of Formula (II):

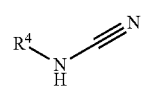

(II)

or a salt or conjugate thereof,
wherein
$R^4$ is H, $C_{1-6}$alkyl, cycloalkyl, —C(O)$R^g$, or —C(O)O$R^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;

(iii) a compound of Formula (III):

$R^5$—N=C=S  (III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;
$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

(iv) a compound of Formula (IV):

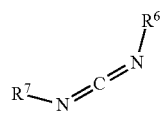

(IV)

or a salt or conjugate thereof,
wherein
$R^6$ and $R^7$ are each independently H, $C_{1-6}$alkyl, —CO$_2$C$_{1-4}$ alkyl, —OR$^k$, aryl, or cycloalkyl, wherein the $C_{1-6}$alkyl, —CO$_2$C$_{1-4}$alkyl, —OR$^k$, aryl, and cycloalkyl are each unsubstituted or substituted; and
$R^k$ is H, $C_{1-6}$alkyl, or heterocyclyl, wherein the $C_{1-6}$alkyl and heterocyclyl are each unsubstituted or substituted;

(v) a compound of Formula (V):

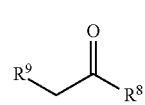

(V)

or a salt or conjugate thereof,
wherein
$R^8$ is halo or —OR$^m$;
$R^m$ is H, $C_{1-6}$alkyl, or heterocyclyl; and
$R^9$ is hydrogen, halo, or $C_{1-6}$haloalkyl;

(vi) a metal complex of Formula (VI):

ML$_n$  (VI)

or a salt or conjugate thereof, wherein

M is a metal selected from the group consisting of Co, Cu, Pd, Pt, Zn, and Ni;

L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and n is an integer from 1-8, inclusive;

wherein each L can be the same or different; and
(vii) a compound of Formula (VII):

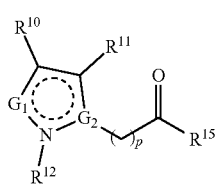
(VII)

or a salt or conjugate thereof,
wherein
$G^1$ is N, NR$^{13}$, or CR$^{13}$R$^{14}$;
$G^2$ is N or CH;
p is 0 or 1;
$R^{10}$, $R^{11}$, $R^{12}$, $R^{13}$, and $R^{14}$ are each independently selected from the group consisting of H, C$_{1-6}$alkyl, C$_{1-6}$haloalkyl, C$_{1-6}$alkylamine, and C$_{1-6}$alkylhydroxylamine, wherein the C$_{1-6}$alkyl, C$_{1-6}$haloalkyl, C$_{1-6}$alkylamine, and C$_{1-6}$alkylhydroxylamine are each unsubstituted or substituted, and $R^{10}$ and $R^{11}$ can optionally come together to form a ring; and
$R^{15}$ is H or OH.

377. The kit of Aspect 375 or Aspect 376, which comprises a polypeptide functionalizing reagent and an amino acid eliminating reagent.

378. A method of sequencing a polypeptide comprising:
(a) affixing the polypeptide to a support or substrate, or providing the polypeptide in a solution;
(b) functionalizing the N-terminal amino acid (NTAA) of the polypeptide with a chemical reagent, wherein the chemical reagent comprises a compound selected from the group consisting of
(i) a compound of Formula (I):

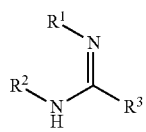
(I)

or a salt or conjugate thereof,
wherein
$R^1$ and $R^2$ are each independently H, C$_{1-6}$alkyl, cycloalkyl, —C(O)R$^a$, —C(O)OR$^b$, or —S(O)$_2$R$^c$;
$R^a$, $R^b$, and $R^c$ are each independently H, C$_{1-6}$alkyl, C$_{1-6}$haloalkyl, arylalkyl, aryl, or heteroaryl, wherein the C$_{1-6}$alkyl, C$_{1-6}$haloalkyl, arylalkyl, aryl, and heteroaryl are each unsubstituted or substituted;
$R^3$ is heteroaryl, —NR$^d$C(O)OR$^e$, or —SR$^f$, wherein the heteroaryl is unsubstituted or substituted;
$R^d$, $R^e$, and $R^f$ are each independently H or C$_{1-6}$alkyl; and optionally wherein when $R^3$ is

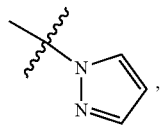 [SMILES: *n1cccn1]

$R^1$ and $R^2$ are not both H;
(ii) a compound of Formula (II):

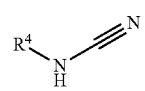
(II)

or a salt or conjugate thereof,
wherein
$R^4$ is H, C$_{1-6}$alkyl, cycloalkyl, —C(O)R$^g$, or —C(O)OR$^g$; and
$R^g$ is H, C$_{1-6}$alkyl, C$_{2-6}$alkenyl, C$_{1-6}$haloalkyl, or arylalkyl, wherein the C$_{1-6}$alkyl, C$_{2-6}$alkenyl, C$_{1-6}$haloalkyl, and arylalkyl are each unsubstituted or substituted;
(iii) a compound of Formula (III):

$R^5$—N=C=S  (III)

or a salt or conjugate thereof,
wherein
$R^5$ is C$_{1-6}$alkyl, C$_{2-6}$alkenyl, cycloalkyl, heterocycloalkyl, aryl or heteroaryl;
wherein the C$_{1-6}$alkyl, C$_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;
$R^h$, $R^i$, and $R^j$ are each independently H, C$_{1-6}$alkyl, C$_{1-6}$haloalkyl, arylalkyl, aryl, or heteroaryl, wherein the C$_{1-6}$alkyl, C$_{1-6}$haloalkyl, arylalkyl, aryl, and heteroaryl are each unsubstituted or substituted;
(iv) a compound of Formula (IV):

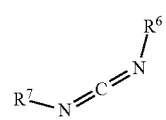
(IV)

or a salt or conjugate thereof,
wherein
$R^6$ and $R^7$ are each independently H, C$_{1-6}$alkyl, —CO$_2$C$_{1-4}$ alkyl, —OR$^k$, aryl, or cycloalkyl, wherein the C$_{1-6}$alkyl, —CO$_2$C$_{1-4}$alkyl, —OR$^k$, aryl, and cycloalkyl are each unsubstituted or substituted; and
$R^k$ is H, C$_{1-6}$alkyl, or heterocyclyl, wherein the C$_{1-6}$alkyl and heterocyclyl are each unsubstituted or substituted;
(v) a compound of Formula (V):

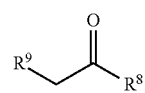
(V)

or a salt or conjugate thereof, wherein
R$^8$ is halo or —OR$^m$;
R$^m$ is H, C$_{1-6}$alkyl, or heterocyclyl; and
R$^9$ is hydrogen, halo, or C$_{1-6}$haloalkyl;
(vi) a metal complex of Formula (VI):

or a salt or conjugate thereof,
wherein
M is a metal selected from the group consisting of Co, Cu, Pd, Pt, Zn, and Ni;
L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and
(vii) a compound of Formula (VII):

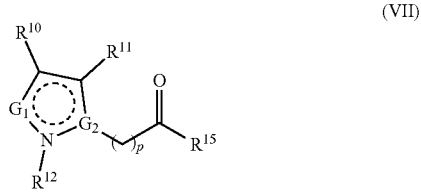

or a salt or conjugate thereof,
wherein
G$^1$ is N, NR$^{13}$, or CR$^{13}$R$^{14}$;
G$^2$ is N or CH;
p is 0 or 1;
R$^{10}$, R$^{11}$, R$^{12}$, R$^{13}$, and R$^{14}$ are each independently selected from the group consisting of H, C$_{1-6}$alkyl, C$_{1-6}$haloalkyl, C$_{1-6}$alkylamine, and C$_{1-6}$alkylhydroxylamine, wherein the C$_{1-6}$alkyl, C$_{1-6}$haloalkyl, C$_{1-6}$alkylamine, and C$_{1-6}$alkylhydroxylamine are each unsubstituted or substituted, and R$^{10}$ and R$^{11}$ can optionally come together to form a ring; and
R$^{15}$ is H or OH;
(c) contacting the polypeptide with a plurality of binding agents each comprising a binding portion capable of binding to the functionalized NTAA and a detectable label;
(d) detecting the detectable label of the binding agent bound to the polypeptide, thereby identifying the N-terminal amino acid of the polypeptide;
(e) eliminating the functionalized NTAA to expose a new NTAA; and
(f) repeating steps (b) to (d) to determine the sequence of at least a portion of the polypeptide.
379. The method of Aspect 378, wherein step (b) is conducted before step (c).
380. The method of Aspect 378, wherein step (b) is conducted after step (c) and before step (d).
381. The method of Aspect 378, wherein step (b) is conducted after both step (c) and step (d).
382. The method of any one of Aspects 378-381, wherein the polypeptide is obtained by fragmenting a protein from a biological sample.
383. The method of any one of Aspects 378-382, wherein the support or substrate is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.
384. The method of any one of Aspects 378-383, wherein the NTAA is eliminated by chemical cleavage or enzymatic cleavage from the polypeptide.
385. The method of any one of Aspects 378-384, wherein the NTAA is eliminated by a carboxypeptidase or aminopeptidase or variant, mutant, or modified protein thereof; a hydrolase or variant, mutant, or modified protein thereof, mild Edman degradation; Edmanase enzyme; TFA, a base; or any combination thereof.
386. The method of any one of Aspects 378-385, wherein the polypeptide is covalently affixed to the support or substrate.
387. The method of any one of Aspects 378-386, wherein the support or substrate is optically transparent.
388. The method of any one of Aspects 378-387, wherein the support or substrate comprises a plurality of spatially resolved attachment points and step a) comprises affixing the polypeptide to a spatially resolved attachment point.
389. The method of Aspect any one of Aspects 378-388, wherein the binding portion of the binding agent comprises a peptide or protein.
390. The method of any one of Aspects 378-389, wherein the binding portion of the binding agent comprises an aminopeptidase or variant, mutant, or modified protein thereof, an aminoacyl tRNA synthetase or variant, mutant, or modified protein thereof, an anticalin or variant, mutant, or modified protein thereof, a ClpS (such as ClpS2) or variant, mutant, or modified protein thereof, a UBR box protein or variant, mutant, or modified protein thereof, or a modified small molecule that binds amino acid(s), i.e. vancomycin or a variant, mutant, or modified molecule thereof, or an antibody or binding fragment thereof, or any combination thereof.
391. The method of any one of Aspects 378-390, wherein the chemical reagent comprises a conjugate selected from the group consisting of

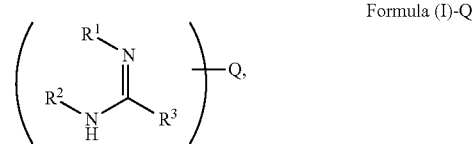

Formula (I)-Q wherein R$^i$, R$^2$, and R$^3$ are as defined for Formula (I) in Aspect 1, and Q is a ligand;

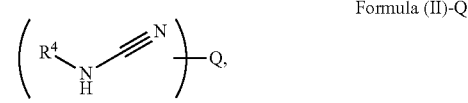

Formula (II)-Q wherein R$^4$ is as defined for Formula (II) in Aspect 1, and Q is a ligand;

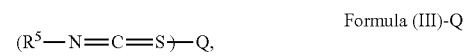

Formula (III)-Q wherein $R^5$ is as defined for Formula (III) in Aspect 1, and Q is a ligand;

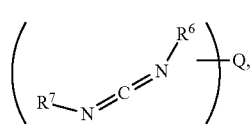

Formula (IV)-Q wherein $R^6$ and $R^7$ are as defined for Formula (IV) in Aspect 1, and Q is a ligand;

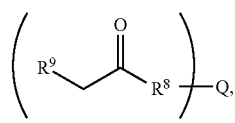

Formula (V)-Q wherein $R^8$ and $R^9$ are as defined for Formula (V) in Aspect 1, and Q is a ligand;

$(ML_n)$-Q  Formula (VI)-Q, wherein M, L, and n are as defined for Formula (VI) in Aspect 1, and Q is a ligand;

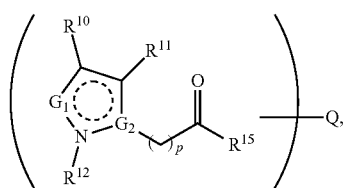

Formula (VII)-Q wherein $R^{10}$, $R^{11}$, $R^{12}$, $R^{15}$, $G^1$, $G^2$, and p are as defined for Formula (VII) in Aspect 1, and Q is a ligand.

392. The method of any one of Aspects 378-391, wherein step (b) comprises functionalizing the NTAA with a second chemical reagent selected from Formula (VIIIa) and (VIIIb):

(VIIIa)

or a salt or conjugate thereof,
wherein
$R^{13}$ is H, $C_{1-6}$alkyl, aryl, heteroaryl, cycloalkyl, or heterocycloalkyl, wherein the $C_{1-6}$alkyl, aryl, heteroaryl, cycloalkyl, and heterocycloalkyl are each unsubstituted or substituted; and $R^{13}$—X  (VIIIb)

wherein
$R^{13}$ is $C_{1-6}$alkyl, aryl, heteroaryl, cycloalkyl, or heterocycloalkyl, each of which is unsubstituted or substituted; and
X is a halogen.

393. The method of any one of Aspects 378-392, wherein the polypeptide is a partially or completely digested protein.

394. A method of sequencing a plurality of polypeptide molecules in a sample comprising:
(a) affixing the polypeptide molecules in the sample to a plurality of spatially resolved attachment points on a support or substrate;
(b) functionalizing the N-terminal amino acid (NTAA) of the polypeptide molecules with a chemical reagent, wherein the chemical reagent comprises a compound selected from the group consisting of
(i) a compound of Formula (I):

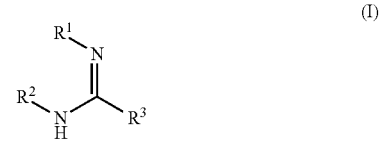

(I)

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2R^c$;
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
$R^3$ is heteroaryl, —NR$^d$C(O)OR$^e$, or —SR$^f$, wherein the heteroaryl is unsubstituted or substituted;
$R^d$, $R^e$, and $R^f$ are each independently H or $C_{1-6}$alkyl; and
optionally wherein when $R^3$ is

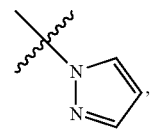

$R^1$ and $R^2$ are not both H;
(ii) a compound of Formula (II):

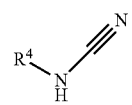

(II)

or a salt or conjugate thereof,
wherein
$R^4$ is H, $C_{1-6}$alkyl, cycloalkyl, —C(O)$R^g$, or —C(O)O$R^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;
(iii) a compound of Formula (III):

$R^5$—N=C=S  (III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;

R$^h$, R$^i$, and R$^j$ are each independently H, C$_{1-6}$alkyl, C$_{1-6}$haloalkyl, arylalkyl, aryl, or heteroaryl, wherein the C$_{1-6}$alkyl, C$_{1-6}$haloalkyl, arylalkyl, aryl, and heteroaryl are each unsubstituted or substituted;

(iv) a compound of Formula (IV):

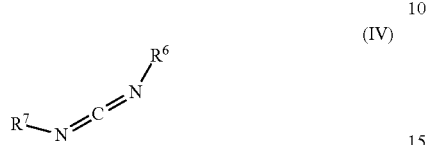

or a salt or conjugate thereof,
wherein
R$^6$ and R$^7$ are each independently H, C$_{1-6}$alkyl, —CO$_2$C$_{1-4}$ alkyl, —OR$^k$, aryl, or cycloalkyl, wherein the C$_{1-6}$alkyl, —CO$_2$C$_{1-4}$alkyl, —OR$^k$, aryl, and cycloalkyl are each unsubstituted or substituted; and
R$^k$ is H, C$_{1-6}$alkyl, or heterocyclyl, wherein the C$_{1-6}$alkyl and heterocyclyl are each unsubstituted or substituted;

(v) a compound of Formula (V):

or a salt or conjugate thereof,
wherein
R$^8$ is halo or —OR$^m$;
R$^m$ is H, C$_{1-6}$alkyl, or heterocyclyl; and
R$^9$ is hydrogen, halo, or C$_{1-6}$haloalkyl;

(vi) a metal complex of Formula (VI):

or a salt or conjugate thereof,
wherein
M is a metal selected from the group consisting of Co, Cu, Pd, Pt, Zn, and Ni;
L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and (vii) a compound of Formula (VII):

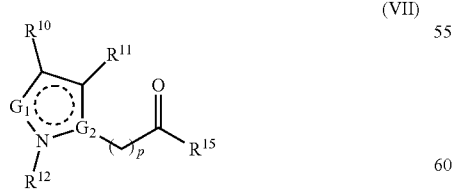

or a salt or conjugate thereof,
wherein
G$^1$ is N, NR$^{13}$, or CR$^{13}$R$^{14}$;
G$^2$ is N or CH;
p is 0 or 1;

R$^{10}$, R$^{11}$, R$^{12}$, R$^{13}$, and R$^{14}$ are each independently selected from the group consisting of H, C$_{1-6}$alkyl, C$_{1-6}$haloalkyl, C$_{1-6}$alkylamine, and C$_{1-6}$alkylhydroxylamine, wherein the C$_{1-6}$alkyl, C$_{1-6}$haloalkyl, C$_{1-6}$alkylamine, and C$_{1-6}$alkylhydroxylamine are each unsubstituted or substituted, and R$^{10}$ and R$^{11}$ can optionally come together to form a ring; and R$^{15}$ is H or OH;

(c) contacting the polypeptides with a plurality of binding agents each comprising a binding portion capable of binding to the functionalized NTAA and a detectable label;

(d) for a plurality of polypeptides molecule that are spatially resolved and affixed to the support or substrate, optically detecting the fluorescent label of the probe bound to each polypeptide;

(e) eliminating the functionalized NTAA of each of the polypeptides; and (f) repeating steps b) to d) to determine the sequence of at least a portion of one or more of the plurality of polypeptide molecules that are spatially resolved and affixed to the support or substrate.

395. The method of Aspect 394, wherein step (b) is conducted before step (c).

396. The method of Aspect 394, wherein step (b) is conducted after step (c) and before step (d).

397. The method of Aspect 394, wherein step (b) is conducted after both step (c) and step (d).

398. The method of any one of Aspects 394-397, wherein the sample comprises a biological fluid, cell extract or tissue extract.

399. The method of any one of Aspects 394-398, further comprising comparing the sequence of at least one polypeptide molecule determined in step e) to a reference protein sequence database.

400. The method of any one of Aspects 394-399, further comprising comparing the sequences of each polypeptide determined in step e), grouping similar polypeptide sequences and counting the number of instances of each similar polypeptide sequence.

401. The method of any one of Aspects 394-400, wherein the fluorescent label is a fluorescent moiety, color-coded nanoparticle or quantum dot.

402. A kit for sequencing a polypeptide comprising:
(a) a reagent for affixing the polypeptide to a support or substrate, or a reagent for providing the polypeptide in a solution;
(b) a reagent for functionalizing the N-terminal amino acid (NTAA) of the polypeptide, wherein the reagent comprises a compound selected from the group consisting of
(i) a compound of Formula (I):

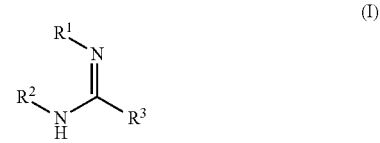

or a salt or conjugate thereof,
wherein
R$^1$ and R$^2$ are each independently H, C$_{1-6}$alkyl, cycloalkyl, —C(O)R$^a$, —C(O)OR$^b$, or —S(O)$_2$R$^c$;
R$^a$, R$^b$, and R$^c$ are each independently H, C$_{1-6}$alkyl, C$_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

$R^3$ is heteroaryl, —$NR^dC(O)OR^e$, or —$SR^f$, wherein the heteroaryl is unsubstituted or substituted;

$R^d$, $R^e$, and $R^f$ are each independently H or $C_{1-6}$alkyl; and optionally wherein when $R^3$ is

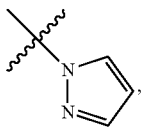

$R^1$ and $R^2$ are not both H;

(ii) a compound of Formula (II):

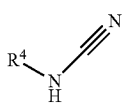 (II)

or a salt or conjugate thereof,
wherein
$R^4$ is H, $C_{1-6}$alkyl, cycloalkyl, —$C(O)R^g$, or —$C(O)OR^g$; and $R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;

(iii) a compound of Formula (III):

 (III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —$NR^hR^i$, —$S(O)_2R^j$, or heterocyclyl;

$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;

(iv) a compound of Formula (IV):

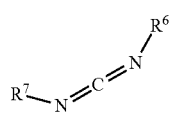 (IV)

or a salt or conjugate thereof,
wherein
$R^6$ and $R^7$ are each independently H, $C_{1-6}$alkyl, —$CO_2C_{1-4}$ alkyl, —$OR^k$, aryl, or cycloalkyl, wherein the $C_{1-6}$alkyl, —$CO_2C_{1-4}$alkyl, —$OR^k$, aryl, and cycloalkyl are each unsubstituted or substituted; and $R^k$ is H, $C_{1-6}$alkyl, or heterocyclyl, wherein the $C_{1-6}$alkyl and heterocyclyl are each unsubstituted or substituted;

(v) a compound of Formula (V):

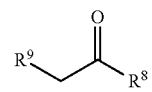 (V)

or a salt or conjugate thereof,
wherein
$R^8$ is halo or —$OR^m$;
$R^m$ is H, $C_{1-6}$alkyl, or heterocyclyl; and
$R^9$ is hydrogen, halo, or $C_{1-6}$haloalkyl;

(vi) a metal complex of Formula (VI):

$ML_n$ (VI)

or a salt or conjugate thereof,
wherein
M is a metal selected from the group consisting of Co, Cu, Pd, Pt, Zn, and Ni;
L is a ligand selected from the group consisting of —OH, —$OH_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and (vii) a compound of Formula VII):

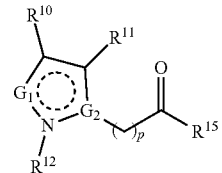 (VII)

or a salt or conjugate thereof,
wherein
$G^1$ is N, $NR^{13}$, or $CR^{13}R^{14}$;
$G^2$ is N or CH;
p is 0 or 1;
$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and
$R^{15}$ is H or OH; and (c) a binding agent comprising a binding portion capable of binding to the functionalized NTAA and a detectable label.

403. The kit of Aspect 402, wherein the kit additionally comprises a reagent for eliminating the functionalized NTAA to expose a new NTAA.

404. The kit of Aspect 402 or Aspect 403, wherein the polypeptide is obtained by fragmenting a protein from a biological sample.

405. The kit of any one of Aspects 402-404, wherein the support or substrate is a bead, a porous bead, a porous matrix, an array, a glass surface, a silicon surface, a plastic surface, a filter, a membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

406. The kit of any one of Aspects 403-405, wherein the reagent for eliminating the functionalized NTAA is a carboxypeptidase or aminopeptidase or variant, mutant, or modified protein thereof, a hydrolase or variant, mutant, or modified protein thereof, mild Edman degradation; Edmanase enzyme; TFA, a base; or any combination thereof.

407. The kit of any one of Aspects 402-406, wherein the polypeptide is covalently affixed to the support or substrate.

408. The kit of any one of Aspects 402-407, wherein the support or substrate is optically transparent.

409. The kit of any one of Aspects 402-408, wherein the support or substrate comprises a plurality of spatially resolved attachment points and step a) comprises affixing the polypeptide to a spatially resolved attachment point.

410. The kit of Aspect any one of Aspects 402-409, wherein the binding portion of the binding agent comprises a peptide or protein.

411. The kit of any one of Aspects 402-410, wherein the binding portion of the binding agent comprises an aminopeptidase or variant, mutant, or modified protein thereof, an aminoacyl tRNA synthetase or variant, mutant, or modified protein thereof, an anticalin or variant, mutant, or modified protein thereof, a ClpS (such as ClpS2) or variant, mutant, or modified protein thereof, a UBR box protein or variant, mutant, or modified protein thereof, or a modified small molecule that binds amino acid(s), i.e. vancomycin or a variant, mutant, or modified molecule thereof, or an antibody or binding fragment thereof, or any combination thereof.

412. The kit of any one of Aspects 402-411, wherein the chemical reagent comprises a conjugate selected from the group consisting of

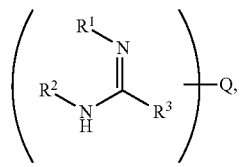

Formula (I)-Q wherein $R^1$, $R^2$, and $R^3$ are as defined for Formula (I) in Aspect 1, and Q is a ligand;

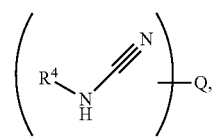

Formula (II)-Q wherein $R^4$ is as defined for Formula (II) in Aspect 1, and Q is a ligand;

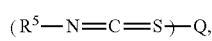

Formula (III)-Q wherein $R^5$ is as defined for Formula (III) in Aspect 1, and Q is a ligand;

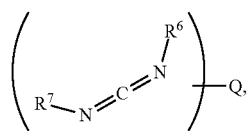

Formula (IV)-Q wherein $R^6$ and $R^7$ are as defined for Formula (IV) in Aspect 1, and Q is a ligand;

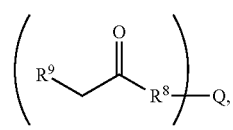

Formula (V)-Q wherein $R^8$ and $R^9$ are as defined for Formula (V) in Aspect 1, and Q is a ligand;

Formula (VI)-Q, wherein M, L, and n are as defined for Formula (VI) in Aspect 1, and Q is a ligand;

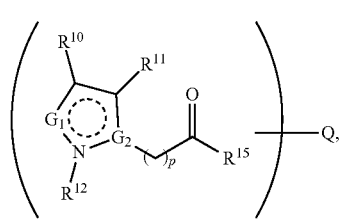

Formula (VII)-Q wherein $R^{10}$, $R^{11}$, $R^{12}$, $R^{15}$, $G^1$, $G^2$, and p are as defined for Formula (VII) in Aspect 1, and Q is a ligand.

Aspect 413. The kit of any one of Aspects 402-412, the kit includes a second chemical reagent selected from Formula (VIIIa) and (VIIIb):

(VIIIa)

or a salt or conjugate thereof,
wherein
$R^{13}$ is H, $C_{1-6}$alkyl, aryl, heteroaryl, cycloalkyl, or heterocycloalkyl, wherein the $C_{1-6}$alkyl, aryl, heteroaryl, cycloalkyl, and heterocycloalkyl are each unsubstituted or substituted; and

(VIIIb)

wherein
$R^{13}$ is $C_{1-6}$alkyl, aryl, heteroaryl, cycloalkyl, or heterocycloalkyl, each of which is unsubstituted or substituted; and
X is a halogen.

414. The method of any one of Aspects 402-413, wherein the polypeptide is a partially or completely digested protein.

415. A kit for sequencing a plurality of polypeptide molecules in a sample comprising:

(a) a reagent for affixing the polypeptide molecules in the sample to a plurality of spatially resolved attachment points on a support or substrate;
(b) a reagent for functionalizing the N-terminal amino acid (NTAA) of the polypeptide molecules, wherein the reagent comprises a compound selected from the group consisting of
(i) a compound of Formula (I):

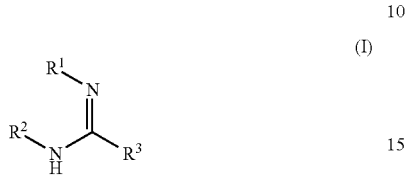

or a salt or conjugate thereof,
wherein
$R^1$ and $R^2$ are each independently H, $C_{1-6}$alkyl, cycloalkyl, —C(O)$R^a$, —C(O)O$R^b$, or —S(O)$_2R^c$;
$R^a$, $R^b$, and $R^c$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
$R^3$ is heteroaryl, —NR$^d$C(O)O$R^e$, or —S$R^f$, wherein the heteroaryl is unsubstituted or substituted;
$R^d$, $R^e$, and $R^f$ are each independently H or $C_{1-6}$alkyl; and
optionally wherein when $R^3$ is

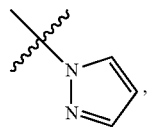

$R^1$ and $R^2$ are not both H;
(ii) a compound of Formula (II):

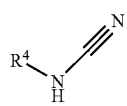

or a salt or conjugate thereof,
wherein
$R^4$ is H, $C_{1-6}$alkyl, cycloalkyl, —C(O)$R^g$, or —C(O)O$R^g$; and
$R^g$ is H, $C_{1-6}$alkyl, $C_{2-6}$alkenyl, $C_{1-6}$haloalkyl, or arylalkyl, wherein the $C_{1-6}$alkyl, $C_{2-6}$alkenyl, $C_{1-6}$haloalkyl, and arylalkyl are each unsubstituted or substituted;
(iii) a compound of Formula (III):

 (III)

or a salt or conjugate thereof,
wherein
$R^5$ is $C_{1-6}$alkyl, $C_{2-6}$alkenyl, cycloalkyl, heterocycloalkyl, aryl or heteroaryl;
wherein the $C_{1-6}$alkyl, $C_{2-6}$alkenyl, cycloalkyl, heterocycloalkyl, aryl or heteroaryl are each unsubstituted or substituted with one or more groups selected from the group consisting of halo, —NR$^h$R$^i$, —S(O)$_2$R$^j$, or heterocyclyl;
$R^h$, $R^i$, and $R^j$ are each independently H, $C_{1-6}$alkyl, $C_{1-6}$haloalkyl, arylalkyl, aryl, or heteroaryl, wherein the $C_{1-6}$alkyl, $C_{1-6}$haloalkyl, arylalkyl, aryl, and heteroaryl are each unsubstituted or substituted;
(iv) a compound of Formula (IV):

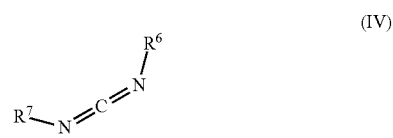

or a salt or conjugate thereof,
wherein
$R^6$ and $R^7$ are each independently H, $C_{1-6}$alkyl, —CO$_2$C$_{1-4}$ alkyl, —OR$^k$, aryl, or cycloalkyl, wherein the $C_{1-6}$alkyl, —CO$_2$C$_{1-4}$alkyl, —OR$^k$, aryl, and cycloalkyl are each unsubstituted or substituted; and
$R^k$ is H, $C_{1-6}$alkyl, or heterocyclyl, wherein the $C_{1-6}$alkyl and heterocyclyl are each unsubstituted or substituted;
(v) a compound of Formula (V):

or a salt or conjugate thereof,
wherein
$R^8$ is halo or —OR$^m$;
$R^m$ is H, $C_{1-6}$alkyl, or heterocyclyl; and
$R^9$ is hydrogen, halo, or $C_{1-6}$haloalkyl;
(vi) a metal complex of Formula (VI):

$ML_n$ (VI)

or a salt or conjugate thereof,
wherein
M is a metal selected from the group consisting of Co, Cu, Pd, Pt, Zn, and Ni;
L is a ligand selected from the group consisting of —OH, —OH$_2$, 2,2'-bipyridine (bpy), 1,5dithiacyclooctane (dtco), 1,2-bis(diphenylphosphino)ethane (dppe), ethylenediamine (en), and triethylenetetramine (trien); and
n is an integer from 1-8, inclusive;
wherein each L can be the same or different; and
(vii) a compound of Formula (VII):

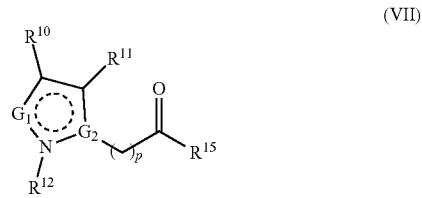

or a salt or conjugate thereof,
wherein
$G^1$ is N, NR$^{13}$, or CR$^{13}$R$^{14}$;
$G^2$ is N or CH;

p is 0 or 1;

$R^{10}$, $R^{11}$, $R^{12}$, $R^{13}$, and $R^{14}$ are each independently selected from the group consisting of H, $C_{1-6}$alkyl, $C_{1-6}$haloalkyl, $C_{1-6}$alkylamine, and $C_{1-6}$alkylhydroxylamine, wherein the $C_{1-6}$alkyl, $C_{1-6}$haloalkyl, $C_{1-6}$alkylamine, and $C_{1-6}$alkylhydroxylamine are each unsubstituted or substituted, and $R^{10}$ and $R^{11}$ can optionally come together to form a ring; and $R^{15}$ is H or OH; and (c) a binding agent comprising a binding portion capable of binding to the functionalized NTAA and a detectable label.

416. The kit of Aspect 415, wherein the kit additionally comprises a reagent for eliminating the functionalized NTAA to expose a new NTAA.

Aspect 417. The kit of Aspect 415 or 416, wherein the sample comprises a biological fluid, cell extract or tissue extract.

Aspect 418. The kit of any one of Aspects 415-417, wherein the fluorescent label is a fluorescent moiety, color-coded nanoparticle or quantum dot.

In any of the preceding embodiments, the recording tag and/or the coding tag can be a small molecule, or a subunit, monomer, residue, or building block of a sequenceable polymer, such as a polynucleotide or a non-nucleic acid sequenceable polymer.

In any of the preceding embodiments, the recording tag and/or the coding tag can be a sequenceable polymer, such as a polynucleotide or a non-nucleic acid sequenceable polymer.

In any of the preceding embodiments, the recording tag and/or the coding tag can comprise a small molecule, or a subunit, monomer, residue, or building block of a sequenceable polymer, such as a polynucleotide or a non-nucleic acid sequenceable polymer.

In any of the preceding embodiments, the coding tag can be a small molecule, or a subunit, monomer, residue, or building block of a sequenceable polymer, such as a polynucleotide or a non-nucleic acid sequenceable polymer, while the recording tag is a sequenceable polymer. In some embodiments, the coding tag (a small molecule, subunit, or monomer etc.) can be added to the recording tag in order to form a sequenceable polymer, akin to beads (e.g., various coding tags) on a string (e.g., the extended recording tag).

In any of the preceding embodiments, the extended recording tag and/or the extended coding tag can be a sequenceable polymer, such as a polynucleotide or a non-nucleic acid sequenceable polymer.

In one aspect, disclosed herein is a method, comprising: (a) contacting an analyte with a first binding agent capable of binding to the analyte, wherein the first binding agent comprises a first coding portion with identifying information regarding the first binding agent, the analyte is associated with a recording portion joined to a support, and the analyte and/or the recording portion is immobilized to a support; (b) transferring the information of the first coding portion to the recording portion to generate a first order extended recording portion; (c) contacting the analyte with a second binding agent capable of binding to the analyte, wherein the second binding agent comprises a second coding portion with identifying information regarding the second binding agent; (d) transferring the information of the second coding portion to the first order extended recording portion to generate a second order extended recording portion; and (e) analyzing the second order extended recording portion. In one embodiment, the method further comprises between steps (d) and (e), the following steps: (x) repeating steps (c) and (d) one or more times by replacing the second binding agent with a third (or higher order) binding agent capable of binding to the analyte, wherein the third (or higher order) binding agent comprises a third (or higher order) coding portion with identifying information regarding the third (or higher order) bind agent; and (y) transferring the information of the third (or higher order) coding portion to the second (or higher order) extended recording portion to generate a third (or higher order) extended recording portion, wherein the third (or higher order) extended recording portion is analyzed in step (e).

In any of the preceding embodiments, the recording portion can be a small molecule, or a subunit, monomer, residue, or building block of a sequenceable polymer, such as a polynucleotide or a non-nucleic acid sequenceable polymer.

In any of the preceding embodiments, the recording portion can be a sequenceable polymer, such as a polynucleotide or a non-nucleic acid sequenceable polymer. In some embodiments, the first, second, third, and/or higher order coding portion comprises a small molecule, and/or a subunit, monomer, residue, or building block of a sequenceable polymer, such as a polynucleotide or a non-nucleic acid sequenceable polymer.

In any of the preceding embodiments, the first, second, third, and/or higher order coding portion can be a small molecule, or a subunit, monomer, residue, or building block of a sequenceable polymer, such as a polynucleotide or a non-nucleic acid sequenceable polymer.

In any of the preceding embodiments, the first order extended recording portion, second order extended recording portion, third order extended recording portion, and/or higher order extended recording portion can be a sequenceable polymer, such as a polynucleotide or a non-nucleic acid sequenceable polymer.

In another aspect, disclosed herein is a method, comprising: (a) contacting a polypeptide with a first binding agent capable of binding to one or more N-terminal, internal, or C-terminal amino acid of the polypeptide, wherein the first binding agent comprises a first coding portion with identifying information regarding the first binding agent, the polypeptide is associated with a recording portion joined to a support, and the polypeptide and/or the recording portion is immobilized to a support; (b) transferring the information of the first coding portion to the recording portion to generate a first order extended recording portion; (c) contacting the analyte with a second binding agent capable of binding to a different one or more N-terminal, internal, or C-terminal amino acid of the polypeptide, wherein the second binding agent comprises a second coding portion with identifying information regarding the second binding agent; (d) transferring the information of the second coding portion to the first order extended recording portion to generate a second order extended recording portion; and (e) analyzing the second order extended recording portion. In one embodiment, the one or more N-terminal, internal, or C-terminal amino acid and/or the different one or more N-terminal, internal, or C-terminal amino acid of the polypeptide is a modified amino acid, such as a modified N-terminal amino acid (NTAA).

In another aspect, disclosed herein is a method, comprising: (a) contacting a polypeptide with a first binding agent capable of binding to one or more N-terminal or C-terminal amino acid of the polypeptide, wherein the first binding agent comprises a first coding portion with identifying information regarding the first binding agent, the polypeptide is associated with a recording portion joined to a support, and the polypeptide and/or the recording portion is immobilized to a support; (b) transferring the information of the first coding portion to the recording portion to generate a first order extended recording portion; (c) eliminating the one or more N-terminal or C-terminal amino acid of the polypeptide, to expose a different one or more N-terminal or C-terminal amino acid of the polypeptide; (d) contacting the analyte with a second binding agent capable of binding to the different one or more N-terminal or C-terminal amino acid of the polypeptide, wherein the second binding agent comprises a second coding portion with identifying information regarding the second binding agent; (e) transferring the information of the second coding portion to the first order extended recording portion to generate a second order extended recording portion; and (f) analyzing the second order extended recording portion. In one embodiment, the one or more N-terminal or C-terminal amino acid and/or the different one or more N-terminal or C-terminal amino acid of the polypeptide is a modified amino acid, such as a modified N-terminal amino acid (NTAA).

In any of the preceding embodiments, the recording portion of step (a) can be a small molecule, or a subunit, monomer, residue, or building block of a sequenceable polymer, such as a polynucleotide or a non-nucleic acid sequenceable polymer.

In any of the preceding embodiments, the recording portion of step (a) can be a sequenceable polymer, such as a polynucleotide or a non-nucleic acid sequenceable polymer. In some embodiments, the first or second order coding portion comprises a small molecule, and/or a subunit, monomer, residue, or building block of a sequenceable polymer, such as a polynucleotide or a non-nucleic acid sequenceable polymer.

In any of the preceding embodiments, the first or second order coding portion can be a small molecule, or a subunit, monomer, residue, or building block of a sequenceable polymer, such as a polynucleotide or a non-nucleic acid sequenceable polymer.

In any of the preceding embodiments, the first order extended recording portion or second order extended recording portion can be a sequenceable polymer, such as a polynucleotide or a non-nucleic acid sequenceable polymer.

In any of the preceding embodiments, the sequenceable polymer can comprise one or more blockade group. In one embodiment, the one or more blockade group is capable of generating a signature current blockade signal when the sequenceable polymer passes through a nanopore.

In any of the preceding embodiments, the sequenceable polymer can comprise one or more binding moiety capable of binding to a binding agent that stalls the sequenceable polymer when passing through a nanopore.

In any of the preceding embodiments, the sequenceable polymer can comprise one or more structure capable of stalling the sequenceable polymer when passing through a nanopore. In one embodiment, the one or more structure comprises a secondary structure, such as an intrinsic metastable secondary structure.

In any of the preceding embodiments, the sequenceable polymer can comprise a polymer built using phosphoramidite chemistry, or a peptoid polymer, or a combination thereof.

In another aspect, disclosed herein is a kit, comprising any molecule, molecular complex or conjugate, reagent (e.g., chemical or biological agent), agent, structure (e.g., support, surface, particle, or bead), reaction intermediate, reaction product, binding complex, or any other article of manufacture disclosed and/or used in the method of any of the preceding embodiments, or any combination thereof.

Any of the above-mentioned kit components, and any molecule, molecular complex or conjugate, reagent (e.g., chemical or biological reagents), agent, structure (e.g., support, surface, particle, or bead), reaction intermediate, reaction product, binding complex, or any other article of manufacture disclosed and/or used in the exemplary kits and methods, may be provided separately or in any suitable combination in order to form a kit. The kit may optionally comprise instruction for use, for example, in highly-parallel, high throughput digital analysis (such as macromolecule analysis), particularly polypeptide analysis.

BRIEF DESCRIPTION OF THE DRAWINGS

Non-limiting embodiments of the present disclosure will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the present disclosure.

FIG. 1A illustrates key for functional elements shown in the figures. Thus in one embodiment, provided herein is a recording tag or an extended recording tag, comprising one or more universal primer sequences (or one or more pairs of universal primer sequences, for example, one universal prime of the pair at the 5' end and the other of the pair at the 3' end of the recording tag or extended recording tag), one or more barcode sequences that can identify the recording tag or extended recording tag among a plurality of recording tags or extended recording tags, one or more UMI sequences, one or more spacer sequences, and/or one or more encoder sequences (also referred to as the coding sequence, e.g., of a coding tag). In certain embodiments, the extended recording tag comprises (i) one universal primer sequence, one barcode sequence, one UMI sequence, and one spacer (all from the unextended recording tag), (ii) one or more "cassettes" arranged in tandem, each cassette comprising an encoder sequence for a binding agent, a UMI sequence, and a spacer, and each cassette comprises sequence information from a coding tag, and (iii) another universal primer sequence, which may be provided by the coding tag of the coding agent in the $n^{th}$ binding cycle, where n is an integer representing the number of binding cycle after which assay read out is desired. In one embodiment, after a universal primer sequence is introduced into an extended recoding tag, the binding cycles may continue, the extended recording tag may be further extended, and one or more additional universal primer sequences may be introduced. In that case, amplification and/or sequencing of the extended recording tag may be done using any combination of the universal primer sequences. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 1B illustrates a general overview of transducing or converting a protein code to a nucleic acid (e.g., DNA) code where a plurality of proteins or polypeptides are fragmented into a plurality of peptides, which are then converted into a library of extended recording tags, representing the plurality of peptides. The extended recording tags constitute a DNA Encoded Library (DEL) representing the peptide sequences. The library can be appropriately modified to sequence on any Next Generation Sequencing (NGS) platform. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 2A illustrates a process of creating an extended recording tag through the cyclic binding of cognate binding agents to a analyte (such as a protein or protein complex), and corresponding information transfer from the binding agent's coding tag to the analyte's recording tag. After a series of sequential binding and coding tag information transfer steps, the final extended recording tag is produced, containing binding agent coding tag information including encoder sequences from "n" binding cycles providing identifying information for the binding agents (e.g., antibody 1 (Ab1), antibody 2 (Ab2), antibody 3 (Ab3), ... antibody "n" (Abn)), a barcode/optional UMI sequence from the recording tag, an optional UMI sequence from the binding agent's coding tag, and flanking universal priming sequences at each end of the library construct to facilitate amplification and/or analysis by digital next-generation sequencing. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 2B illustrates an example of a scheme for labeling a protein with DNA barcoded recording tags. In the top panel, N-hydroxysuccinimide (NHS) is an amine reactive coupling agent, and Dibenzocyclooctyl (DBCO) is a strained alkyne useful in "click" coupling to the surface of a solid substrate. In this scheme, the recording tags are coupled to e amines of lysine (K) residues (and optionally N-terminal amino acids) of the protein via NHS moieties. In the bottom panel, a heterobifunctional linker, NHS-alkyne, is used to label the e amines of lysine (K) residues to create an alkyne "click" moiety. Azide-labeled DNA recording tags can then easily be attached to these reactive alkyne groups via standard click chemistry. Moreover, the DNA recording tag can also be designed with an orthogonal methyltetrazine (mTet) moiety for downstream coupling to a trans-cyclooctene (TCO)-derivatized sequencing substrate via an inverse Electron Demand Diels-Alder (iEDDA) reaction. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 2C illustrates two examples of the protein analysis methods using recording tags. In the top panel, analytes such as protein macromolecules are immobilized on a solid support via a capture agent and optionally cross-linked. Either the protein or capture agent may co-localize or be labeled with a recording tag. In the bottom panel, proteins with associated recording tags are directly immobilized on a solid support. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 2D illustrates an example of an overall workflow for a simple protein immunoassay using DNA encoding of cognate binders and sequencing of the resultant extended recording tag. The proteins can be sample barcoded (i.e., indexed) via recording tags and pooled prior to cyclic binding analysis, greatly increasing sample throughput and economizing on binding reagents. This approach is effectively a digital, simpler, and more scalable approach to performing reverse phase protein assays (RPPA), allowing measurement of protein levels (such as expression levels) in a large number of biological samples simultaneously in a quantitative manner. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 4A illustrates exemplary work flows with alternative modes outlined in light grey dashed lines, with a particular embodiment shown in boxes linked by arrows. Alternative modes for each step of the workflow are shown in boxes below the arrows. FIG. 4B illustrates options in conducting a cyclic binding and coding tag information transfer step to improve the efficiency of information transfer. Multiple recording tags per molecule can be employed. Moreover, for a given binding event, the transfer of coding tag information to the recording tag can be conducted multiples times, or alternatively, a surface amplification step can be employed to create copies of the extended recording tag library, etc. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 9A illustrates on a solid support a plurality of recording tags (e.g., comprising universal forward priming sequence and a UMI) which are available to a binding agent bound to the analyte. Individual recording tags possess a common spacer sequence (Sp) complementary to a common spacer sequence within coding tags of binding agents, which can be used to prime an extension reaction to transfer coding tag information to a recording tag. For example, the plurality of recording tags may co-localize with the analyte on the support, and some of the recording tags may be closer to the analyte than others. In one aspect, the density of recording tags relative to the analyte density on the support may be controlled, so that statistically each analyte will have a plurality of recording tags (e.g., at least about two, about five, about ten, about 20, about 50, about 100, about 200, about 500, about 1000, about 2000, about 5000, or more) available to a binding agent bound to that analyte. This mode may be particularly useful for analyzing low abundance proteins or polypeptides in a sample. Although FIG. 9A shows a different recording tag is extended in each of Cycles 1-3 (e.g., a cycle-specific barcode in the binding agent or separately added in each binding/reaction cycle may be used to "clock" the binding/reactions), it is envisaged that an extended recording tag may be further extended in any one or more of subsequent binding cycles, and the resultant pool of extended recording tags may be a mix of recording tags that are extended only once, twice, three times, or more. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 9B illustrates different pools of cycle-specific NTAA binding agents that are used for each successive cycle of binding, each pool having a cycle specific sequence, such as a cycle specific spacer sequence. Alternatively, the cycle specific sequence may be provided in a reagent separate from the binding agents. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 10A-10C illustrate an exemplary mode comprising multiple cycles of transferring information of a coding tag that is attached to a binding agent to a recording tag among a plurality of recording tags co-localized at a site of a single analyte (e.g., a macromolecule such as a polypeptide) attached to a solid support (e.g., a bead), thereby generating multiple extended recording tags that collectively represent the analyte. In this figure, for purposes of example only, the analyte is a polypeptide and each round of processing involves binding to an NTAA, recording the binding event, followed by removal of the NTAA to expose a new NTAA. FIG. 10A illustrates a plurality of recording tags (e.g., comprising a universal forward priming sequence and a UMI) on a solid support for the analyte, for example, a single molecule per bead. Individual recording tags possess different spacer sequences at their 3'-end with different "cycle specific" sequences (e.g., $C_1$, $C_2$, $C_3$, . . . $C_n$). For example, the recording tags on each bead share the same compartment barcode and/or UMI sequence. In a first cycle of binding (Cycle 1), a plurality of NTAA binding agents is contacted with the analyte. The binding agents used in Cycle 1 possess a common 5'-spacer sequence (C'1) that is complementary to the Cycle 1 $C_1$ spacer sequence of the recording tag. The binding agents used in Cycle 1 also possess a 3'-spacer sequence ($C'_2$) that is complementary to the Cycle 2 spacer $C_2$. During binding Cycle 1, a first NTAA binding agent binds to the free N-terminus of the analyte, and the information of a first coding tag is transferred to a cognate recording tag via primer extension from the $C_1$ sequence hybridized to the complementary $C'_1$ spacer sequence. Following removal of the NTAA to expose a new NTAA, binding Cycle 2 contacts a plurality of NTAA binding agents that possess a Cycle 2 5'-spacer sequence ($C'_2$) that is identical to the 3'-spacer sequence of the Cycle 1 binding agents and a common Cycle 3 3'-spacer sequence ($C'_3$), with the analyte. A second NTAA binding agent binds to the NTAA of the analyte, and the information of a second coding tag is transferred to a cognate recording tag via primer extension from the complementary $C_2$ and $C'_2$ spacer sequences. These cycles are repeated up to "n" binding cycles, wherein the last extended recording tag is capped with a universal reverse priming sequence, generating a plurality of extended recording tags co-localized with the single analyte, wherein each extended recording tag possesses coding tag information from one binding cycle. Because each set of binding agents used in each successive binding cycle possess cycle specific spacer sequences in the coding tags, binding cycle information can be associated with binding agent information in the resulting extended recording tags. FIG. 10B illustrates different pools of cycle-specific binding agents that are used for each successive cycle of binding, each pool having cycle specific spacer sequences. FIG. 10C illustrates how the collection of extended recording tags (e.g., that are co-localized at the site of the analyte) can be assembled in a sequential order based on PCR assembly of the extended recording tags using cycle specific spacer sequences, thereby providing an ordered sequence of the analyte such as a macromolecule. In a preferred mode, multiple copies of each extended recording tag are generated via amplification prior to concatenation. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In FIG. 12A, the construction of a combinatorial PNA barcode/UMI via chemical ligation of four elementary PNA word sequences (A, A'-B, B'-C, and C') is illustrated. Hybridizing DNA arms are included to create a spacer-less combinatorial template for combinatorial assembly of a PNA barcode/UMI. Chemical ligation is used to stitch the annealed PNA "words" together. FIG. 12B shows a method to transfer the PNA information of the recording tag to a DNA intermediate. The DNA intermediate is capable of transferring information to the coding tag. Namely, complementary DNA word sequences are annealed to the PNA and chemically ligated (optionally enzymatically ligated if a ligase is discovered that uses a PNA template). In FIG. 12C, the DNA intermediate is designed to interact with the coding tag via a spacer sequence, Sp. A strand-displacing primer extension step displaces the ligated DNA and transfers the recording tag information from the DNA intermediate to the coding tag to generate an extended coding tag. A terminator nucleotide may be incorporated into the end of the DNA intermediate to prevent transfer of coding tag information to the DNA intermediate via primer extension. FIG. 12D: Alternatively, information can be transferred from the coding tag to the DNA intermediate to generate a di-tag construct. A terminator nucleotide may be incorporated into the end of the coding tag to prevent transfer of recording tag information from the DNA intermediate to the coding tag. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

(FIG. 17A) a plurality of extended recording tags representing a plurality of peptides; and (FIG. 17B) an exemplary method of target peptide enrichment via standard hybrid capture techniques. For example, hybrid capture enrichment may use one or more biotinylated "bait" oligonucleotides that hybridize to extended recording tags representing one or more peptides of interest ("target peptides") from a library of extended recording tags representing a library of peptides. The bait oligonucleotide:target extended recording tag hybridization pairs are pulled down from solution via the biotin tag after hybridization to generate an enriched fraction of extended recording tags representing the peptide or peptides of interest. The separation ("pull down") of extended recording tags can be accomplished, for example, using streptavidin-coated magnetic beads. The biotin moieties bind to streptavidin on the beads, and separation is accomplished by localizing the beads using a magnet while solution is removed or exchanged. A non-biotinylated competitor enrichment oligonucleotide that competitively hybridizes to extended recording tags representing undesirable or over-abundant peptides can optionally be included in the hybridization step of a hybrid capture assay to modulate the amount of the enriched target peptide. The non-biotinylated competitor oligonucleotide competes for hybridization to the target peptide, but the hybridization duplex is not captured during the capture step due to the absence of a biotin moiety. Therefore, the enriched extended recording tag fraction can be modulated by adjusting the ratio of the competitor oligonucleotide to the biotinylated "bait" oligonucleotide over a large dynamic range. This step will be important to address the dynamic range issue of protein abundance within the sample. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 20A-20L illustrate generation of compartment barcoded recording tags attached to peptides. Compartment barcoding technology (e.g., barcoded beads in microfluidic droplets, etc.) can be used to transfer a compartment-specific barcode to molecular contents encapsulated within a particular compartment. FIG. 20A. In a particular embodiment, the protein molecule is denatured, and the ε-amine group of lysine residues (K) is chemically conjugated to an activated universal DNA tag molecule (comprising a universal priming sequence (U1)), shown with NHS moiety at the 5' end, but any other bioconjugation moiety can also be employed). After conjugation of universal DNA tags to the polypeptide, excess universal DNA tags are removed. FIG. 20B. The universal DNA tagged-polypeptides are hybridized to nucleic acid molecules bound to beads, wherein the nucleic acid molecules bound to an individual bead comprise a unique population of compartment tag (barcode) sequences. The compartmentalization can occur by separating the sample into different physical compartments, such as droplets (illustrated by the dashed oval). Alternatively, compartmentalization can be directly accomplished by the immobilization of the labeled polypeptides on the bead surface, e.g., via annealing of the universal DNA tags on the polypeptide to the compartment DNA tags on the bead, without the need for additional physical separation. A single polypeptide molecule interacts with only a single bead (e.g., a single polypeptide does not span multiple beads). Multiple polypeptides, however, may interact with the same bead. In addition to the compartment barcode sequence (BC), the nucleic acid molecules bound to the bead may be comprised of a common Sp (spacer) sequence, a unique molecular identifier (UMI), and a sequence complementary to the polypeptide DNA tag, U1'. FIG. 20C. After annealing of the universal DNA tagged polypeptides to the compartment tags bound to the bead, the compartment tags are released from the beads via cleavage of the attachment linkers. FIG. 20D. The annealed U1 DNA tag primers are extended via polymerase-based primer extension using the compartment tag nucleic acid molecule originating from the bead as template. The primer extension step may be carried out after release of the compartment tags from the bead as shown in FIG. 20C or, optionally, while the compartment tags are still attached to the bead (not shown). This effectively writes the barcode sequence from the compartment tags on the bead onto the U1 DNA-tag sequence on the polypeptide. This new sequence constitutes a recording tag. After primer extension, a protease, e.g., Lys-C (cleaves on C-terminal side of lysine residues), Glu-C (cleaves on C-terminal side of glutamic acid residues and to a lower extent glutamic acid residues), or random protease such as Proteinase K, is used to cleave the polypeptide into peptide fragments. FIG. 20E. Each peptide fragment is labeled with an extended DNA tag sequence constituting a recording tag on its C-terminal lysine for downstream peptide sequencing as disclosed herein. FIG. 20F. The recording tagged peptides are coupled to azide beads through a strained alkyne label, DBCO. The azide beads optionally also contain a capture sequence complementary to the recording tag to facilitate the efficiency of DBCO-azide immobilization. It should be noted that removing the peptides from the original beads and re-immobilizing to a new solid support (e.g., beads) permits optimal intermolecular spacing between peptides to facilitate peptide sequencing methods as disclosed herein. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 20G-L illustrates a similar concept as illustrated in FIG. 20A-F except using click chemistry conjugation of DNA tags to an alkyne pre-labeled polypeptide (as described in FIG. 2B). The Azide and mTet chemistries are orthogonal allowing click conjugation to DNA tags and click iEDDA conjugation (mTet and TCO) to the sequencing substrate. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 22A. A compartment tag (DNA-peptide chimera) is attached onto the peptide using peptide ligation with Butelase I. FIG. 22B. Compartment tag information is transferred to an associated recording tag prior to commencement of peptide sequencing. Optionally, an endopeptidase AspN, which selectively cleaves peptide bonds N-terminal to aspartic acid residues, can be used to cleave the compartment tag after information transfer to the recording tag. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 23A-23C: Array-based barcodes for a spatial proteomics-based analysis of a tissue slice. FIG. 23A. An array of spatially-encoded DNA barcodes (feature barcodes denoted by $BC_{ij}$), is combined with a tissue slice (e.g., FFPE or frozen). In one embodiment, the tissue slice is fixed and permeabilized. In a preferred embodiment, the array feature size is smaller than the cell size (~10 μm for human cells). FIG. 23B. The array-mounted tissue slice is treated with reagents to reverse cross-linking (e.g., antigen retrieval protocol w/ citraconic anhydride (Namimatsu, Ghazizadeh et al. 2005), and then the proteins therein are labeled with site-reactive DNA labels, that effectively label all protein molecules with DNA recording tags (e.g., lysine labeling, liberated after antigen retrieval). After labeling and washing, the array bound DNA barcode sequences are cleaved and allowed to diffuse into the mounted tissue slice and hybridize to DNA recording tags attached to the proteins therein. FIG. 23C. The array-mounted tissue is now subjected to polymerase extension to transfer information of the hybridized barcodes to the DNA recording tags labeling the proteins. After transfer of the barcode information, the array-mounted tissue is scraped from the slides, optionally digested with a protease, and the proteins or peptides extracted into solution. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 24A illustrates the interaction of an AB macromolecule with an A-specific binding agent ("A'", an oligonucleotide sequence complementary to the "A" component of the AB macromolecule) and transfer of information of an associated coding tag to a recording tag via primer extension, and a B-specific binding agent ("B'", an oligonucleotide sequence complementary to the "B" component of the AB macromolecule) and transfer of information of an associated coding tag to a recoding tag via primer extension. Coding tags A and B are of different sequence, and for ease of identification in this illustration, are also of different length. The different lengths facilitate analysis of coding tag transfer by gel electrophoresis, but are not required for analysis by next generation sequencing. The binding of A' and B' binding agents are illustrated as alternative possibilities for a single binding cycle. If a second cycle is added, the extended recording tag would be further extended. Depending on which of A' or B' binding agents are added in the first and second cycles, the extended recording tags can contain coding tag information of the form AA, AB, BA, and BB. Thus, the extended recording tag contains information on the order of binding events as well as the identity of binders. Similarly, FIG. 24B illustrates the interaction of a CD macromolecule with a C-specific binding agent ("C'", an oligonucleotide sequence complementary to the "C" component of the CD macromolecule) and transfer of information of an associated coding tag to a recording tag via primer extension, and a D-specific binding agent ("D'", an oligonucleotide sequence complementary to the "D" component of the CD macromolecule) and transfer of information of an associated coding tag to a recording tag via primer extension. Coding tags C and D are of different sequence and for ease of identification in this illustration are also of different length. The different lengths facilitate analysis of coding tag transfer by gel electrophoresis, but are not required for analysis by next generation sequencing. The binding of C' and D' binding agents are illustrated as alternative possibilities for a single binding cycle. If a second cycle is added, the extended recording tag would be further extended. Depending on which of C' or D' binding agents are added in the first and second cycles, the extended recording tags can contain coding tag information of the form CC, CD, DC, and DD. Coding tags may optionally comprise a UMI. The inclusion of UMIs in coding tags allows additional information to be recorded about a binding event; it allows binding events to be distinguished at the level of individual binding agents. This can be useful if an individual binding agent can participate in more than one binding event (e.g. its binding affinity is such that it can disengage and re-bind sufficiently frequently to participate in more than one event). It can also be useful for error-correction. For example, under some circumstances a coding tag might transfer information to the recording tag twice or more in the same binding cycle. The use of a UMI would reveal that these were likely repeated information transfer events all linked to a single binding event. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 26A illustrates an exemplary oligonucleotide-peptide target macromolecule ("A" oligonucleotide-cMyc peptide) immobilized on beads. A cMyc-specific binding agent (e.g. antibody) interacts with the cMyc peptide portion of the macromolecule and information of an associated coding tag is transferred to a recording tag. The transfer of information of the cMyc coding tag to a recording tag may be analyzed by gel electrophoresis. FIG. 26B illustrates an exemplary oligonucleotide-peptide target macromolecule ("C" oligonucleotide-hemagglutinin (HA) peptide) immobilized on beads. An HA-specific binding agent (e.g., antibody) interacts with the HA peptide portion of the macromolecule and information of an associated coding tag is transferred to a recording tag. The transfer of information of the coding tag to a recording tag may be analyzed by gel electrophoresis. The binding of cMyc antibody-coding tag and HA antibody-coding tag are illustrated as alternative possibilities for a single binding cycle. If a second binding cycle is performed, the extended recording tag would be further extended. Depending on which of cMyc antibody-coding tag or HA antibody-coding tag are added in the first and second binding cycles, the extended recording tags can contain coding tag information of the form cMyc-HA, HA-cMyc, cMyc-cMyc, and HA-HA. Although not illustrated, additional binding agents can also be introduced to enable detection of the A and C oligonucleotide components of the macromolecules. Thus, hybrid macromolecules comprising different types of backbone can be analyzed via transfer of information to a recording tag and readout of the extended recording tag, which contains information on the order of binding events as well as the identity of the binding agents. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 27A-27D illustrate examples for the generation of Error-Correcting Barcodes. (FIG. 27A) A subset of 65 error-correcting barcodes (SEQ ID NOs: 1-65) were selected from a set of 77 barcodes derived from the R software package 'DNABarcodes' (bioconductor.riken.jp/packages/3.3/bioc/manuals/DNABarcodes/man/DNABarcodes.pdf) using the command parameters [create.dnabarcodes(n=15, dist=10)]. This algorithm generates 15-mer "Hamming" barcodes that can correct substitution errors out to a distance of four substitutions, and detect errors out to nine substitutions. The subset of 65 barcodes was created by filtering out barcodes that didn't exhibit a variety of nanopore current levels (for nanopore-based sequencing) or that were too correlated with other members of the set. (FIG. 27B) A plot of the predicted nanopore current levels for the 15-mer barcodes passing through the pore. The predicted currents were computed by splitting each 15-mer barcode word into composite sets of 11 overlapping 5-mer words, and using a 5-mer R9 nanopore current level look-up table (template_median68pA.5mers.model, available at github.com/jts/nanopolish/tree/master/etc/r9-models) to predict the corresponding current level as the barcode passes through the nanopore, one base at a time. As can be appreciated from (B), this set of 65 barcodes exhibit unique current signatures for each of its members. (FIG. 27C) Generation of PCR products as model extended recording tags for nanopore sequencing is shown using overlapping sets of DTR and DTR primers. PCR amplicons are then ligated to form a concatenated extended recording tag model. (FIG. 27D) Nanopore sequencing read of exemplary "extended recording tag" model (read length 734 bases) generated as shown in FIG. 27C. The MinIon R9.4 Read has a quality score of 7.2 (poor read quality). However, barcode sequences can easily be identified using lalign even with a poor quality read (Qscore=7.2). A 15-mer spacer element is underlined. Barcodes can align in either forward or reverse orientation, denoted by BC or BC' designation. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 28A. A binding agent targeting a protein analyte of interest in its native conformation comprises an analyte-specific barcode ($BC_A'$) that hybridizes to a complementary analyte-specific barcode ($BC_A$) on a DNA recording tag. Alternatively, the DNA recording tag could be attached to the binding agent via a cleavable linker, and the DNA recording tag is "clicked" to the protein directly and is subsequently cleaved from the binding agent (via the cleavable linker). The DNA recording tag comprises a reactive coupling moiety (such as a click chemistry reagent (e.g., azide, mTet, etc.) for coupling to the protein of interest, and other functional components (e.g., universal priming sequence (P1), sample barcode (BCs), analyte specific barcode ($BC_A$), and spacer sequence (Sp)). A sample barcode (BCs) can also be used to label and distinguish proteins from different samples. The DNA recording tag may also comprise an orthogonal coupling moiety (e.g., mTet) for subsequent coupling to a substrate surface. For click chemistry coupling of the recording tag to the protein of interest, the protein is pre-labeled with a click chemistry coupling moiety cognate for the click chemistry coupling moiety on the DNA recording tag (e.g., alkyne moiety on protein is cognate for azide moiety on DNA recording tag). Examples of reagents for labeling the DNA recording tag with coupling moieties for click chemistry coupling include alkyne-NHS reagents for lysine labeling, alkyne-benzophenone reagents for photoaffinity labeling, etc. FIG. 28B. After the binding agent binds to a proximal target protein, the reactive coupling moiety on the recording tag (e.g., azide) covalently attaches to the cognate click chemistry coupling moiety (shown as a triple line symbol) on the proximal protein. FIG. 28C. After the target protein analyte is labeled with the recording tag, the attached binding agent is removed by digestion of uracils (U) using a uracil-specific excision reagent (e.g., USER™). Thus, the presently claimed kit may also comprise a nicking reagent, such as a nicking endonuclease. FIG. 28D. The DNA recording tag labeled target protein analyte is immobilized to a substrate surface using a suitable bioconjugate chemistry reaction, such as click chemistry (alkyne-azide binding pair, methyl tetrazine (mTET)-trans-cyclooctene (TCO) binding pair, etc.). In certain embodiments, the entire target protein-recording tag labeling assay is performed in a single tube comprising many different target protein analytes using a pool of binding agents and a pool of recording tags. After targeted labeling of protein analytes within a sample with recording tags comprising a sample barcode (BCs), multiple protein analyte samples can be pooled before the immobilization step in FIG. 28D. Accordingly, in certain embodiments, up to thousands of protein analytes across hundreds of samples can be labeled and immobilized in a single tube next generation protein assay (NGPA), greatly economizing on expensive affinity reagents (e.g., antibodies). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 29A. A denatured polypeptide is labeled with a bifunctional click chemistry reagent, such as alkyne-NHS ester (acetylene-PEG-NHS ester) reagent or alkyne-benzophenone to generate an alkyne-labeled (triple line symbol) polypeptide. An alkyne can also be a strained alkyne, such as cyclooctynes including Dibenzocyclooctyl (DBCO), etc. FIG. 29B. An example of a DNA recording tag design that is chemically coupled to the alkyne-labeled polypeptide is shown. The recording tag comprises a universal priming sequence (P1), a barcode (BC), and a spacer sequence (Sp). The recording tag is labeled with a mTet moiety for coupling to a substrate surface and an azide moiety for coupling with the alkyne moiety of the labeled polypeptide. FIG. 29C. A denatured, alkyne-labeled protein or polypeptide is labeled with a recording tag via the alkyne and azide moieties. Optionally, the recording tag-labeled polypeptide can be further labeled with a compartment barcode, e.g., via annealing to complementary sequences attached to a compartment bead and primer extension (also referred to as polymerase extension), or a shown in FIG. 20H-J. FIG. 29D. Protease digestion of the recording tag-labeled polypeptide creates a population of recording tag-labeled peptides. In some embodiments, some peptides will not be labeled with any recording tags. In other embodiments, some peptides may have one or more recording tags attached. FIG. 29E. Recording tag-labeled peptides are immobilized onto a substrate surface using an inverse electron demand Diels-Alder (iEDDA) click chemistry reaction between the substrate surface functionalized with TCO groups and the mTet moieties of the recording tags attached to the peptides. In certain embodiments, clean-up steps may be employed between the different stages shown. The use of orthogonal click chemistries (e.g., azide-alkyne and mTet-TCO) allows both click chemistry labeling of the polypeptides with recording tags, and click chemistry immobilization of the recording tag-labeled peptides onto a substrate surface (see, McKay et al., 2014, *Chem. Biol.* 21:1075-1101, incorporated by reference in its entirety). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 30A-30E illustrate an exemplary process of writing sample barcodes into recording tags after initial DNA tag labeling of polypeptides. FIG. 30A. A denatured polypeptide is labeled with a bifunctional click chemistry reagent such as an alkyne-NHS reagent or alkyne-benzophenone to generate an alkyne-labeled polypeptide. FIG. 30B. After alkyne (or alternative click chemistry moiety) labeling of the polypeptide, DNA tags comprising a universal priming sequence (P1) and labeled with an azide moiety and an mTet moiety are coupled to the polypeptide via the azide-alkyne interaction. It is understood that other click chemistry interactions may be employed. FIG. 30C. A recording tag DNA construct comprising a sample barcode information (BCs') and other recording tag functional components (e.g., universal priming sequence (P1'), spacer sequence (Sp')) anneals to the DNA tag-labeled polypeptide via complementary universal priming sequences (P1-P1'). Recording tag information is transferred to the DNA tag by polymerase extension. FIG. 30D. Protease digestion of the recording tag-labeled polypeptide creates a population of recording tag-labeled peptides. FIG. 30E. Recording tag-labeled peptides are immobilized onto a substrate surface using an inverse electron demand Diels-Alder (iEDDA) click chemistry reaction between a surface functionalized with TCO groups and the mTet moieties of the recording tags attached to the peptides. In certain embodiments, clean-up steps may be employed between the different stages shown. The use of orthogonal click chemistries (e.g., azide-alkyne and mTet-TCO) allows both click chemistry labeling of the polypeptides with recording tags, and click chemistry immobilization of the recording tag-labeled polypeptides onto a substrate surface (see, McKay et al., 2014, *Chem. Biol.* 21:1075-1101, incorporated by reference in its entirety). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 31A-31E illustrate examples for bead compartmentalization for barcoding polypeptides. FIG. 31A. A polypeptide is labeled in solution with a heterobifunctional click chemistry reagent using standard bioconjugation or photoaffinity labeling techniques. Possible labeling sites include F-amine of lysine residues (e.g., with NHS-alkyne as shown) or the carbon backbone of the peptide (e.g., with benzophenone-alkyne). FIG. 31B. Azide-labeled DNA tags comprising a universal priming sequence (P1) are coupled to the alkyne moieties of the labeled polypeptide. FIG. 31C. The DNA tag-labeled polypeptide is annealed to DNA recording tag labeled beads via complementary DNA sequences (P1 and P1'). The DNA recording tags on the bead comprises a spacer sequence (Sp'), a compartment barcode sequence (BCr'), an optional unique molecular identifier (UMI), and a universal sequence (P1'). The DNA recording tag information is transferred to the DNA tags on the polypeptide via polymerase extension (alternatively, ligation could be employed). After information transfer, the resulting polypeptide comprises multiple recording tags containing several functional elements including compartment barcodes. FIG. 31D. Protease digestion of the recording tag-labeled polypeptide creates a population of recording tag-labeled peptides. The recording tag-labeled peptides are dissociated from the beads, and (FIG. 31E) re-immobilized onto a sequencing substrate (e.g., using iEDDA click chemistry between mTet and TCO moieties as shown). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 32A-32H illustrate examples for the workflow for Next Generation Protein Assay (NGPA). A protein sample is labeled with a DNA recording tag comprised of several functional units, e.g., a universal priming sequence (P1), a barcode sequence (BC), an optional UMI sequence, and a spacer sequence (Sp) (enables information transfer with a binding agent coding tag). FIG. 32A. The labeled proteins are immobilized (passively or covalently) to a substrate (e.g., bead, porous bead or porous matrix). FIG. 32B. The substrate is blocked with protein and, optionally, competitor oligonucleotides (Sp') complementary to the spacer sequence are added to minimize non-specific interaction of the analyte recording tag sequence. FIG. 32C. Analyte-specific antibodies (with associated coding tags) are incubated with substrate-bound protein. The coding tag may comprise a uracil base for subsequent uracil specific cleavage. FIG. 32D. After antibody binding, excess competitor oligonucleotides (Sp'), if added, are washed away. The coding tag transiently anneals to the recording tag via complementary spacer sequences, and the coding tag information is transferred to the recording tag in a primer extension reaction to generate an extended recording tag. If the immobilized protein is denatured, the bound antibody and annealed coding tag can be removed under alkaline wash conditions such as with 0.1N NaOH. If the immobilized protein is in a native conformation, then milder conditions may be needed to remove the bound antibody and coding tag. An example of milder antibody removal conditions is outlined in panels E-H. FIG. 32E. After information transfer from the coding tag to the recording tag, the coding tag is nicked (cleaved) at its uracil site using a uracil-specific excision reagent (e.g., USER™) enzyme mix. FIG. 32F. The bound antibody is removed from the protein using a high-salt, low/high pH wash. The truncated DNA coding tag remaining attached to the antibody is short and rapidly elutes off as well. The longer DNA coding tag fragment may or may not remain annealed to the recording tag. FIG. 32G. A second binding cycle commences as in steps (B)-(D) and a second primer extension step transfers the coding tag information from the second antibody to the extended recording tag via primer extension. FIG. 32H. The result of two binding cycles is a concatenate of binding information from the first antibody and second antibody attached to the recording tag. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In FIG. 33A, the coding tag of the antibody bound to epitope 1 (Epi #1) of a protein transfers coding tag information (e.g., encoder sequence) to the recording tag in a primer extension step following hybridization of complementary spacer sequences. In FIG. 33B, once the double stranded DNA duplex between the extended recording tag and coding tag is formed, a nicking endonuclease that cleaves only one strand of DNA on a double-stranded DNA substrate, such as Nt.BsmAI, which is active at 37° C., is used to cleave the coding tag. Following the nicking step, the duplex formed from the truncated coding tag-binding agent and extended recording tag is thermodynamically unstable and dissociates. The longer coding tag fragment may or may not remain annealed to the recording tag. In FIG. 33C, this allows the coding tag from the antibody bound to epitope #2 (Epi #2) of the protein to anneal to the extended recording tag via complementary spacer sequences, and the extended recording tag to be further extended by transferring information from the coding tag of Epi #2 antibody to the extended recording tag via primer extension. In FIG. 33D, once again, after a double stranded DNA duplex is formed between the extended recording tag and coding tag of Epi #2 antibody, the coding tag is nicked by a nicking endonuclease, such Nb.BssSI. In certain embodiments, use of a non-strand displacing polymerase during primer extension (also referred to as polymerase extension) is preferred. A non-strand displacing polymerase prevents extension of the cleaved coding tag stub that remains annealed to the recording tag by more than a single base. The process of FIG. 33A-D can repeat itself until all the coding tags of proximal bound binding agents are "consumed" by the hybridization, information transfer to the extended recording tag, and nicking steps. The coding tag can comprise an encoder sequence identical for all binding agents (e.g., antibodies) specific for a given analyte (e.g., cognate protein), can comprise an epitope-specific encoder sequence, or can comprise a unique molecular identifier (UMI) to distinguish between different molecular events. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 34A-34C illustrate examples for controlled density of recording tag-peptide immobilization using titration of reactive moieties on substrate surface. In FIG. 34A, peptide density on a substrate surface may be titrated by controlling the density of functional coupling moieties on the surface of the substrate. This can be accomplished by derivitizing the surface of the substrate with an appropriate ratio of active coupling molecules to "dummy" coupling molecules. In the example shown, NHS-PEG-TCO reagent (active coupling molecule) is combined with NHS-mPEG (dummy molecule) in a defined ratio to derivitize an amine surface with TCO. Functionalized PEGs come in various molecular weights from 300 to over 40,000. In FIG. 34B, a bifunctional 5' amine DNA recording tag (mTet is other functional moiety) is coupled to a N-terminal Cys residue of a peptide using a succinimidyl 4-(N-maleimidomethyl)cyclohexane-1 (SMCC) bifunctional cross-linker. The internal mTet-dT group on the recording tag is created from an azide-dT group using mTetrazine-Azide. In FIG. 34C, the recording tag labeled peptides are immobilized to the activated substrate surface from FIG. 34A using the iEDDA click chemistry reaction with mTet and TCO. The mTet-TCO iEDDA coupling reaction is extremely fast, efficient, and stable (mTet-TCO is more stable than Tet-TCO). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 35A. Design of NGPS assay (also referred to herein as ProteoCode) with a cycle-specific N-terminal amino acid (NTAA) binding agent coding tags. An NTAA binding agent (e.g., antibody specific for N-terminal DNP-labeled tyrosine) binds to a DNP-labeled NTAA of a peptide associated with a recording tag comprising a universal priming sequence (P1), barcode (BC) and spacer sequence (Sp). When the binding agent binds to a cognate NTAA of the peptide, the coding tag associated with the NTAA binding agent comes into proximity of the recording tag and anneals to the recording tag via complementary spacer sequences. Coding tag information is transferred to the recording tag via primer extension. To keep track of which binding cycle a coding tag represents, the coding tag can comprise of a cycle-specific barcode. In certain embodiments, coding tags of binding agents that bind to an analyte have the same encoder barcode independent of cycle number, which is combined with a unique binding cycle-specific barcode. In other embodiments, a coding tag for a binding agent to an analyte comprises a unique encoder barcode for the combined analyte-binding cycle information. In either approach, a common spacer sequence can be used for binding agents' coding tags in each binding cycle. FIG. 35B. In this example, binding agents from each binding cycle have a short binding cycle-specific barcode to identify the binding cycle, which together with the encoder barcode that identifies the binding agent, provides a unique combination barcode that identifies a particular binding agent-binding cycle combination. FIG. 35C. After completion of the binding cycles, the extended recording tag can be converted into an amplifiable library using a capping cycle step where, for example, a cap comprising a universal priming sequence P1' linked to a universal priming sequence P2 and spacer sequence Sp' initially anneals to the extended recording tag via complementary P1 and P1' sequences to bring the cap in proximity to the extended recording tag. The complementary Sp and Sp' sequences in the extended recording tag and cap anneal and primer extension adds the second universal primer sequence (P2) to the extended recording tag. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 36A-36F illustrate examples for DNA based model system for demonstrating information transfer from coding tags to recording tags. Exemplary binding and intra-molecular writing was demonstrated by an oligonucleotide model system. The targeting agent A' and B' in coding tags were designed to hybridize to target binding regions A and B in recording tags. Recording tag (RT) mix was prepared by pooling two recoding tags, saRT_Abc_v2 (A target) and saRT_Bbc_V2 (B target), at equal concentrations. Recording tags are biotinylated at their 5' end and contain a unique target binding region, a universal forward primer sequence, a unique DNA barcode, and an 8 base common spacer sequence (Sp). The coding tags contain unique encoder barcodes base flanked by 8 base common spacer sequences (Sp'), one of which is covalently linked to A or B target agents via polyethylene glycol linker. In FIG. 36A, biotinylated recording tag oligonucleotides (saRT_Abc_v2 and saRT_Bbc_V2) along with a biotinylated Dummy-T10 oligonucleotide were immobilized to streptavidin beads. The recording tags were designed with A or B capture sequences (recognized by cognate binding agents—A' and B', respectively), and corresponding barcodes (rtA_BC and rtB_BC) to identify the binding target. All barcodes in this model system were chosen from the set of 65 15-mer barcodes (SEQ ID NOs: 1-65). In some cases, 15-mer barcodes were combined to constitute a longer barcode for ease of gel analysis. In particular, rtA_BC=BC_1+BC_2; rtB_BC=BC_3. Two coding tags for binding agents cognate to the A and B sequences of the recording tags, namely CT_A'-bc (encoder barcode=BC_5) and CT_B'-bc (encoder barcode=BC_5+BC_6) were also synthesized. Complementary blocking oligos (DupCT_A'BC and DupCT_AB'BC) to a portion of the coding tag sequence (leaving a single stranded Sp' sequence) were optionally pre-annealed to the coding tags prior to annealing of coding tags to the bead-immobilized recording tags. A strand displacing polymerase removes the blocking oligo during polymerase extension. A barcode key (inset) indicates the assignment of 15-mer barcodes to the functional barcodes in the recording tags and coding tags. In FIG. 36B, the recording tag barcode design and coding tag encoder barcode design provide an easy gel analysis of "intra-molecular" vs. "inter-molecular" interactions between recording tags and coding tags. In this design, undesired "inter-molecular" interactions (A recording tag with B' coding tag, and B recording tag with A' coding tag) generate gel products that are wither 15 bases longer or shorter than the desired "intra-molecular" (A recording tag with A' coding tag; B recording tag with B' coding tag) interaction products. The primer extension step changes the A' and B' coding tag barcodes (ctA'_BC, ctB'_BC) to the reverse complement barcodes (ctA_BC and ctB_BC). In FIG. 36C, a primer extension assay demonstrated information transfer from coding tags to recording tags, and addition of adapter sequences via primer extension on annealed EndCap oligo for PCR analysis. FIG. 36D shows optimization of "intra-molecular" information transfer via titration of surface density of recording tags via use of Dummy-T20 oligo. Biotinylated recording tag oligos were mixed with biotinylated Dummy-T20 oligo at various ratios from 1:0, 1:10, all the way down to 1:10000. At reduced recording tag density ($1:10^3$ and $1:10^4$), "intra-molecular" interactions predominate over "inter-molecular" interactions. In FIG. 36E, as a simple extension of the DNA model system, a simple protein binding system comprising Nano-Tag$_{15}$ peptide-Streptavidin binding pair is illustrated ($K_D$~4 nM) (Perbandt et al., 2007, *Proteins* 67:1147-1153), but any number of peptide-binding agent model systems can be employed. Nano-Tag$_{15}$ peptide sequence is (fM)DVEAWLGARVPLVET (SEQ ID NO: 131) (fM=formyl-Met). Nano-Tag$_{15}$ peptide further comprises a short, flexible linker peptide (GGGGS) and a cysteine residue for coupling to the DNA recording tag. Other examples peptide tag—cognate binding agent pairs include: calmodulin binding peptide (CBP)-calmodulin ($K_D$~2 pM) (Mukherjee et al., 2015, *J. Mol. Biol.* 427: 2707-2725), amyloid-beta (AP16-27) peptide-US7/Lcn2 anticalin (0.2 nM) (Rauth et al., 2016, *Biochem. J.* 473: 1563-1578), PA tag/NZ-1 antibody ($K_D$~400 pM), FLAG-M2 Ab (28 nM), HA-4B2 Ab (1.6 nM), and Myc-9E10 Ab (2.2 nM) (Fujii et al., 2014, *Protein Expr. Purif* 95:240-247). FIG. 36F. As a test of intra-molecular information transfer from the binding agent's coding tag to the recording tag via primer extension, an oligonucleotide "binding agent" that binds to complementary DNA sequence "A" can be used in testing and development. This hybridization event has essentially greater than fM affinity. Streptavidin may be used as a test binding agent for the Nano-tag$_{15}$ peptide epitope. The peptide tag-binding agent interaction is high affinity, but can easily be disrupted with an acidic and/or high salt washes (Perbandt et al., supra). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In FIG. 37A, a polypeptide is labeled, at its N- or C-terminus with a nucleic acid molecule comprising a unique molecular identifier (UMI). The UMI may be flanked by sequences that are used to prime subsequent PCR. The polypeptide is then "body labeled" at internal sites with a separate DNA tag comprising sequence complementary to a priming sequence flanking the UMI. In FIG. 37B, the resultant labeled polypeptides are emulsified and undergo an emulsion PCR (ePCR) (alternatively, an emulsion in vitro transcription-RT-PCR (IVT-RT-PCR) reaction or other suitable amplification reaction can be performed) to amplify the N- or C-terminal UMI. A microemulsion or nanoemulsion is formed such that the average droplet diameter is 50-1000 nm, and that on average there is fewer than one polypeptide per droplet. A snapshot of a droplet content pre- and post PCR is shown in the left panel and right panel, respectively. The UMI amplicons hybridize to the internal polypeptide body DNA tags via complementary priming sequences and the UMI information is transferred from the amplicons to the internal polypeptide body DNA tags via primer extension. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 40A-40I illustrate examples for generation of C-terminal recording tag-labeled peptides from protein lysate (may be encapsulated in a gel bead). FIG. 40A. A denatured polypeptide is reacted with an acid anhydride to label lysine residues. In one embodiment, a mix of alkyne (mTet)-substituted citraconic anhydride+propionic anhydride is used to label the lysines with mTet (shown as striped rectangles). FIG. 40B. The result is an alkyne (mTet)-labeled polypeptide, with a fraction of lysines blocked with a propionic group (shown as squares on the polypeptide chain). The alkyne (mTet) moiety is useful in click-chemistry based DNA labeling. FIG. 40C. DNA tags (shown as solid rectangles) are attached by click chemistry using azide or trans-cyclooctene (TCO) labels for alkyne or mTet moieties, respectively. FIG. 40D. Barcodes and functional elements such as a spacer (Sp) sequence and universal priming sequence are appended to the DNA tags using a primer extension step as shown in FIG. 31C to produce recording tag-labeled polypeptide. The barcodes may be a sample barcode, a partition barcode, a compartment barcode, a spatial location barcode, etc., or any combination thereof. FIG. 40E. The resulting recording tag-labeled polypeptide is fragmented into recording tag-labeled peptides with a protease or chemically. FIG. 40F. For illustration, a peptide fragment labeled with two recording tags is shown. FIG. 40G. A DNA tag comprising universal priming sequence that is complementary to the universal priming sequence in the recording tag is ligated to the C-terminal end of the peptide. The C-terminal DNA tag also comprises a moiety for conjugating the peptide to a surface. FIG. 40H. The complementary universal priming sequences in the C-terminal DNA tag and a stochastically selected recording tag anneal. An intra-molecular primer extension reaction is used to transfer information from the recording tag to the C-terminal DNA tag. FIG. 40I. The internal recording tags on the peptide are coupled to lysine residues via maleic anhydride, which coupling is reversible at acidic pH. The internal recording tags are cleaved from the peptide's lysine residues at acidic pH, leaving the C-terminal recording tag. The newly exposed lysine residues can optionally be blocked with a non-hydrolyzable anhydride, such as proprionic anhydride. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 43A. Structure of an exemplary recording tag associated protein (or peptide) and bound binding agent (e.g., anticalin) with associated coding tag. A thymidine (T) base is inserted between the spacer (Sp') and barcode (BC') sequence on the coding tag to accommodate a stochastic non-templated 3' terminal adenosine (A) addition in the primer extension reaction. FIG. 43B. DNA coding tag is attached to a binding agent (e.g., anticalin) via SpyCatcher-SpyTag protein-peptide interaction. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In FIG. 44A-B, a recording tag-labeled peptide attached to a solid-phase substrate (e.g., bead) is modified or labeled at the NTAA (Mod), e.g., with PITC, DNP, SNP, an acetyl modifier, guanidinylation, etc. In FIG. 44C, a cleavage enzyme (e.g., acylpeptide hydrolase (APH), aminopeptidase (AP), Edmanase, etc.) is attached to a DNA tag comprising a universal priming sequence complementary to the universal priming sequence on the recording tag. The cleavage enzyme is recruited to the modified NTAA via hybridization of complementary universal priming sequences on the cleavage enzyme's DNA tag and the recording tag. In FIG. 44D, the hybridization step greatly improves the effective affinity of the cleavage enzyme for the NTAA. In FIG. 44E, the cleaved NTAA diffuses away and associated cleavage enzyme can be removed by stripping the hybridized DNA tag. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 46A-46C illustrate an exemplary "spacer-less" coding tag transfer via ligation of single strand DNA coding tag to single strand DNA recording tag. A single strand DNA coding tag is transferred directly by ligating the coding tag to a recording tag to generate an extended recording tag. FIG. 46A. Overview of DNA based model system via single strand DNA ligation. The targeting agent B' sequence conjugated to a coding tag was designed for detecting the B DNA target in the recording tag. The ssDNA recording tag, saRT_Bbca_ssLig is 5' phosphorylated and 3' biotinylated, and comprised of a 6 base DNA barcode BCa, a universal forward primer sequence, and a target DNA B sequence. The coding tag, CT_B'bcb_ssLig contains a universal reverse primer sequence, a uracil base, and a unique 6 bases encoder barcode BCb. The coding tag is covalently liked to B'DNA sequence via polyethylene glycol linker. Hybridization of the B' sequence attached to the coding tag to the B sequence attached to the recording tag brings the 5' phosphate group of the recording tag and 3' hydroxyl group of the coding tag into close proximity on the solid surface, resulting in the information transfer via single strand DNA ligation with a ligase, such as CircLigase II. FIG. 46B. Gel analysis to confirm single strand DNA ligation. Single strand DNA ligation assay demonstrated binding information transfer from coding tags to recording tags. The size of ligated products of 47 bases recording tags with 49 bases coding tag is 96 bases. Specificity is demonstrated given that a ligated product band was observed in the presence of the cognate saRT_Bbca_ssLig recording tag, while no product bands were observed in the presence of the non-cognate saRT_Abcb_ssLig recording tag. FIG. 46C. Multiple cycles information transfer of coding tag. The first cycle ligated product was treated with USER enzyme to generate a free 5' phosphorylated terminus for use in the second cycle of information transfer. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 47A. Overview of DNA based model system via double strand DNA ligation. The targeting agent A' sequence conjugated to coding tag was prepared for detection of target binding agent A in recording tag. Both of recording tag and coding tag are composed of two strands with 4 bases overhangs. The proximity overhang ends of both tags hybridize when targeting agent A' in coding tag hybridizes to target binding agent A in recording tag immobilized on solid surface, resulting in the information transfer via double strand DNA ligation by a ligase, such as a T4 DNA ligase. FIG. 47B. Gel analysis to confirm double strand DNA ligation. Double strand DNA ligation assay demonstrated A/A' binding information transfer from coding tags to recording tags. The size of ligated products of 76 and 54 bases recording tags with double strand coding tag is 116 and 111 bases, respectively. The first cycle ligated products were digested by USER Enzyme (NEB), and used in the second cycle assay. The second cycle ligated product bands were observed at around 150 bases. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 48A-48E illustrate an exemplary peptide-based and DNA-based model system for demonstrating information transfer from coding tags to recording tags with multiple cycles. Multiple information transfer was demonstrated by sequential peptide and DNA model systems. FIG. 48A. Overview of the first cycle in the peptide based model system. The targeting agent anti-PA antibody conjugated to coding tag was prepared for detecting the PA-peptide tag in recording tag at the first cycle information transfer. In addition, peptide-recording tag complex negative controls were also generated, using a Nanotag peptide or an amyloid beta (A3) peptide. Recording tag, amRT_Abc that contains A sequence target agents, poly-dT, a universal forward primer sequence, unique DNA barcodes BC1 and BC2, and an 8 bases common spacer sequence (Sp) is covalently attached to peptide and solid support via amine group at 5' end and internal alkyne group, respectively. The coding tag, amCT_bc5 that contains unique encoder barcode BC5' flanked by 8 base common spacer sequences (Sp') is covalently liked to antibody and $C_3$ linker at the 5' end and 3' end, respectively. The information transfer from coding tags to recording tags is done by polymerase extension when anti-PA antibody binds to PA-tag peptide-recording tag (RT)

complex. FIG. 48B. Overview of the second cycle in the DNA based model assay. The targeting agent A' sequence linked to coding tag was prepared for detecting the A sequence target agent in recording tag. The coding tag, CT_A'_bcl3 that contains an 8 bases common spacer sequence (Sp'), a unique encoder barcode BC13', a universal reverse primer sequence. The information transfer from coding tags to recording tags are done by polymerase extension when A' sequence hybridizes to A sequence. FIG. 48C. Recording tag amplification for PCR analysis. The immobilized recording tags were amplified by 18 cycles PCR using P1_F2 and Sp/BC2 primer sets. The recording tag density dependent PCR products were observed at around 56 bp. FIG. 48D. PCR analysis to confirm the first cycle extension assay. The first cycle extended recording tags were amplified by 21 cycles PCR using P1_F2 and Sp/BC5 primer sets. The strong bands of PCR products from the first cycle extended products were observed at around 80 bp for the PA-peptide RT complex across the different density titration of the complexes. A small background band is observed at the highest complex density for Nano and A3 peptide complexes as well, ostensibly due to non-specific binding. FIG. 48E. PCR analysis to confirm the second cycle extension assay. The second extended recording tags were amplified by 21 cycles PCR using P1_F2 and P2_R1 primer sets. Relatively strong bands of PCR products were observed at 117 base pairs for all peptides immobilized beads, which correspond to only the second cycle extended products on original recording tags (BC1+BC2+BC13). The bands corresponding to the second cycle extended products on the first cycle extended recording tags (BC1+BC2+BC5+ BC13) were observed at 93 base pairs only when PA-tag immobilized beads were used in the assay. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 49A-49B use p53 protein sequencing as an example to illustrate the importance of proteoform and the robust mappability of the sequencing reads, e.g., those obtained using a single molecule approach. FIG. 49A at the left panel shows the intact proteoform may be digested to fragments, each of which may comprise one or more methylated amino acids, one or more phosphorylated amino acids, or no post-translational modification. The post-translational modification information may be analyzed together with sequencing reads. The right panel shows various post-translational modifications along the protein. FIG. 49B shows mapping reads using partitions, for example, the read "CPXQXWXDXT" (SEQ ID NO: 170, where X=any amino acid) maps uniquely back to p53 (at the CPVQLWVDST sequence, SEQ ID NO: 169) after blasting the entire human proteome. The sequencing reads do not have to be long—for example, about 10-15 amino acid sequences may give sufficient information to identify the protein within the proteome. The sequencing reads may overlap and the redundancy of sequence information at the overlapping sequences may be used to deduce and/or validate the entire polypeptide sequence.

FIG. 51A-51E illustrate a single cycle protein identification via N-terminal dipeptide binding to partition barcode-labeled peptides. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

FIG. 52A-52E illustrate a single cycle protein identification via N-terminal dipeptide binders to peptides immobilized partition barcoded beads. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

(SEQ ID NO: 198)
MSDSPVDLKPKPKVKPKLERPKLYKVMLLNDDYTPREFV

TVVLKAVFRMSEDTGRRVMMTAHRFGSAVVVVCERDIAE

TKAKEATDLGKEAGFPLMFTTEPEE;

ClpS from Accession No. 2W9R, *E. coli*:

(SEQ ID NO: 199)
MGKTNDWLDFDQLAEEKVRDALKPPSMYKVILVNDDYTP

MEFVIDVLQKFFSYDVERATQLMLAVHYQGKAICGVFTA

EVAETKVAMVNKYARENEHPLLCTLEKAGA;

and ClpS from Accession No. 3DNJ, *C. crescentus*:

(SEQ ID NO: 200)
TQKPSLYRVLILNDDYTPMEFVVYVLERFFNKSREDATRI

MLHVHQNGVGVCGVYTYEVAETKVAQVIDSARRHQHPLQ

CTMEKD.

Figures 53A, 53B:
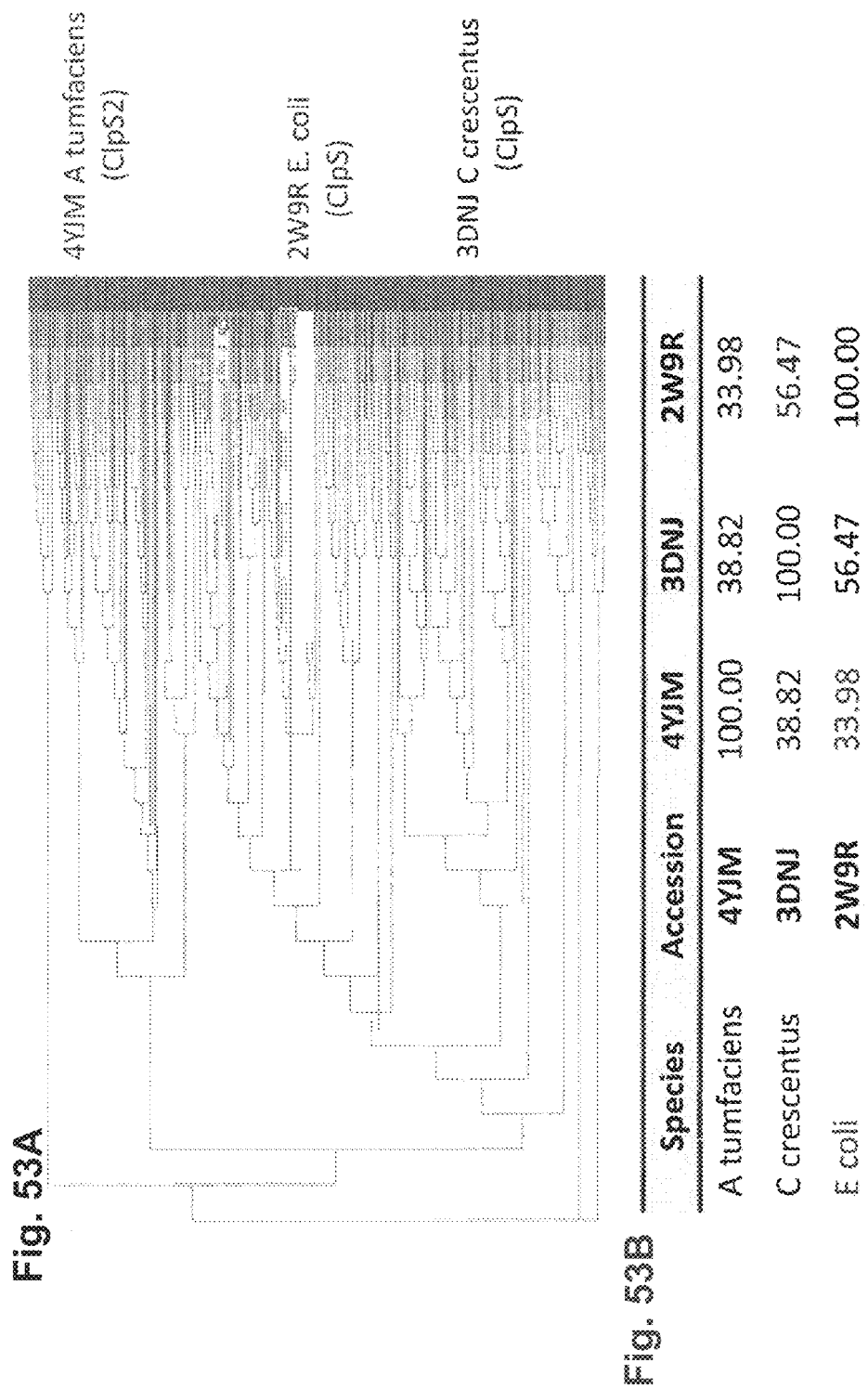
FIG. 53A-53B illustrate ClpS homologues/variants across different species of bacteria, and exemplary ClpS proteins for use in the present disclosure, e.g., ClpS2 from Accession No. 4YJM, *A. tumefaciens*.

FIG. 53A shows dendogram of hierarchical clustering of ClpS amino acid sequences from 612 different bacterial species clustered to 99% identity. FIG. 53B is a table of amino acid sequence identity between ClpSs from the three species in FIG. 53A. *A. tumefaciens* ClpS2 has less than 35% sequence identity to *E. coli* ClpS, and less than 40% sequence identity to *C. crescentus* ClpS.

Figure 54:
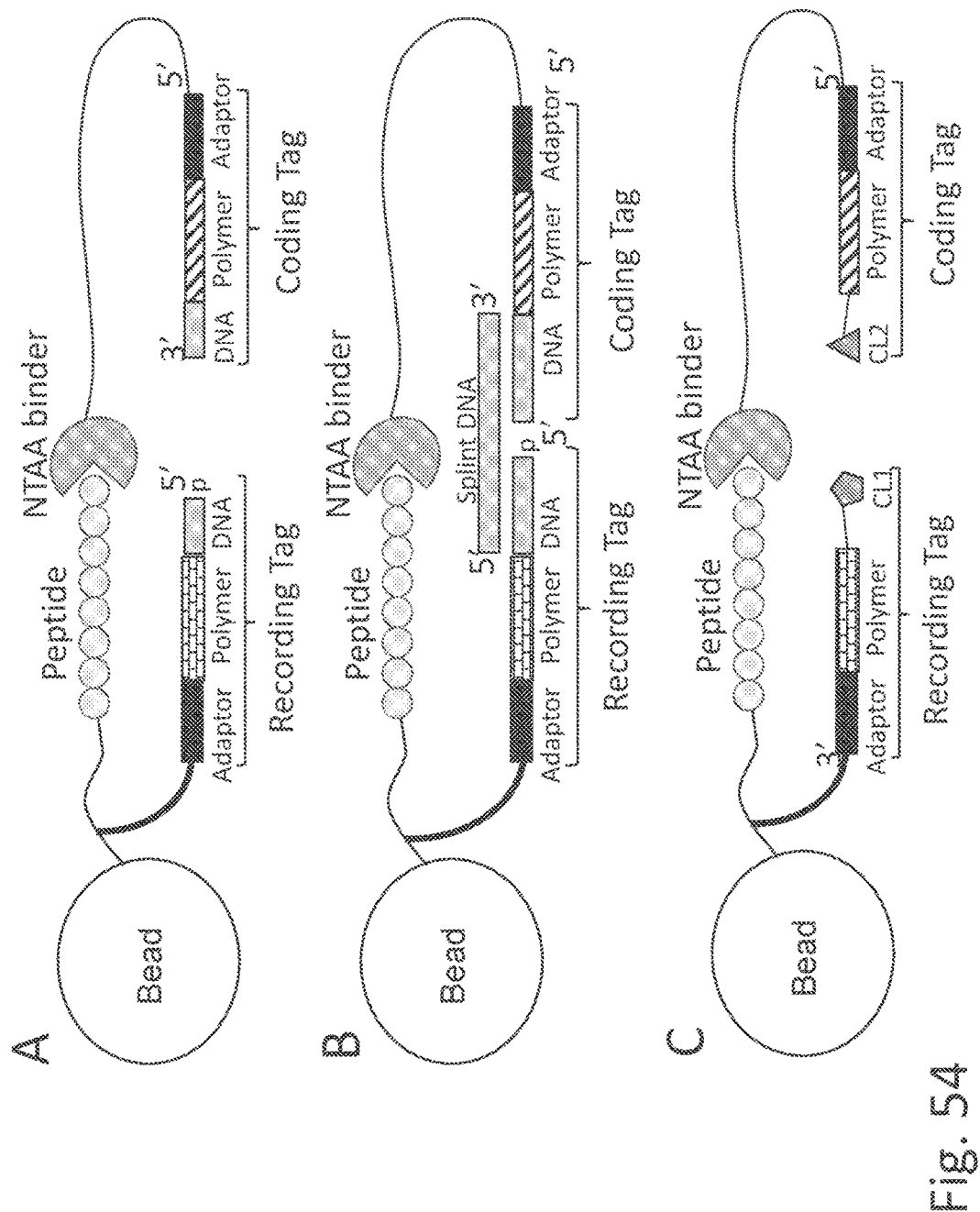

FIG. 54 illustrates an example of polymer coding tag transfer via ligation of single strand DNA/polymer chimera coding tag to single strand DNA/polymer chimera recording tag. A single strand polymer coding tag is transferred directly by ligating the coding tag to a recording tag via DNA spacer to generate an extended recording tag. Part (A). Overview of NTAA detection system via single strand DNA spacer ligation. The N-terminus amino acid (NTAA) binder conjugated to a coding tag is designed for detecting the NTAA of peptide in the recording tag. The single strand DNA/Polymer chimera recording tag is 5' phosphorylated, and comprised of a DNA spacer, a polymer barcode (e.g. protected DNA, PNA, peptoid, etc.), universal polymer adaptor (e.g. cholesterol, biotin, tether DNA sequence, etc.) for nanopore sequencing. The length of spacer could be 1-6 bases to initiate enzymatic ligation. The DNA/Polymer chimera coding tag contains a universal polymer adapter, a polymer barcode (e.g. protected DNA, PNA, peptoid, etc.), and a DNA spacer. The coding tag is covalently liked to NTAA binder via polyethylene glycol linker. Binding of the NTAA binder attached to the coding tag to the NTAA of peptide attached to the recording tag brings the 5' phosphate group of the recording tag and 3' hydroxyl group of the coding tag into close proximity on the solid surface, resulting in the information transfer via single strand DNA ligation with CircLigase II. Part (B). Overview of NTAA detection system via double strand DNA spacer ligation. The NTAA binder conjugated to DNA/Polymer chimera coding tag is prepared for detection of the NTAA of peptide in recording tag. The single strand DNA/Polymer chimera recording tag is 5' phosphorylated, and comprised of a DNA spacer, a polymer barcode (e.g. protected DNA, PNA, peptoid, etc.), universal polymer adaptor (e.g. cholesterol, biotin, tether DNA sequence, etc.) for nanopore sequencing. The length of spacer could be 5-20 bases to initiate enzymatic ligation. The DNA/Polymer chimera coding tag contains a universal polymer adapter, a polymer barcode (e.g. protected DNA, PNA, peptoid, etc.), and a DNA spacer. The coding tag is covalently liked to NTAA binder via polyethylene glycol linker. Binding of the NTAA binder attached to the coding tag to the NTAA of peptide attached to the recording tag brings the 5' phosphate group of the recording tag and 3' hydroxyl group of the coding tag into close proximity on the solid surface, resulting in the information transfer via split DNA hybridization followed by double strand DNA ligation with T4 DNA ligase.

Figure 55:
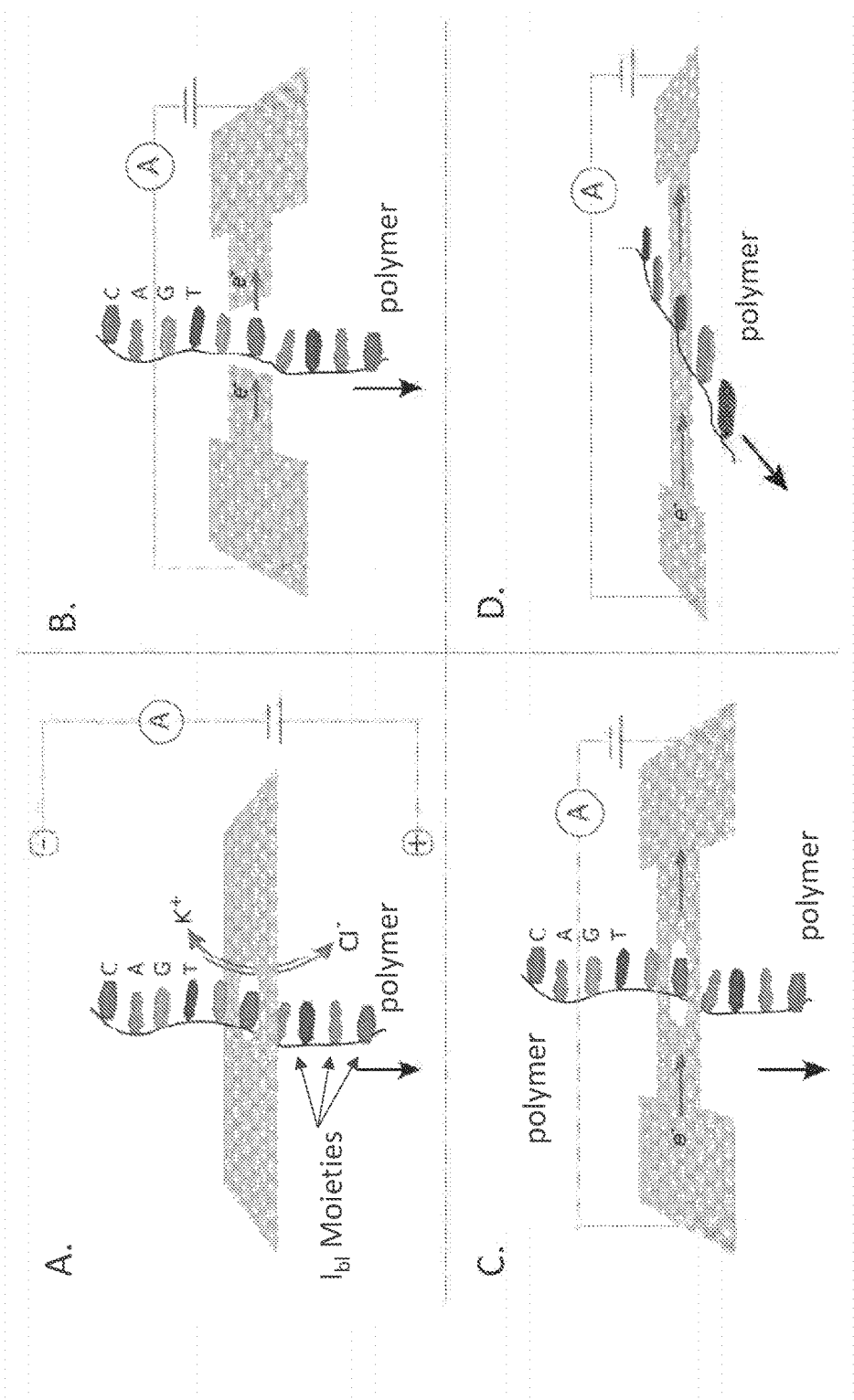

FIG. 55 illustrates an exemplary method of single molecule electronic sequencing. Part (A) Ionic current blockade; Part (B) Tunneling current; Part (C) Inplane transconductance with NP/nanoribbon; Part (D) Inplane transconductance with nanoribbon. The current blockade moieties can block ionic current, or can mediate tunneling current, or can modulate transconductance depend on the mode of electronic readout (Heerema et al., 2016, Nat Nanotechnol, 11(2): 127-136).

Figure 56:
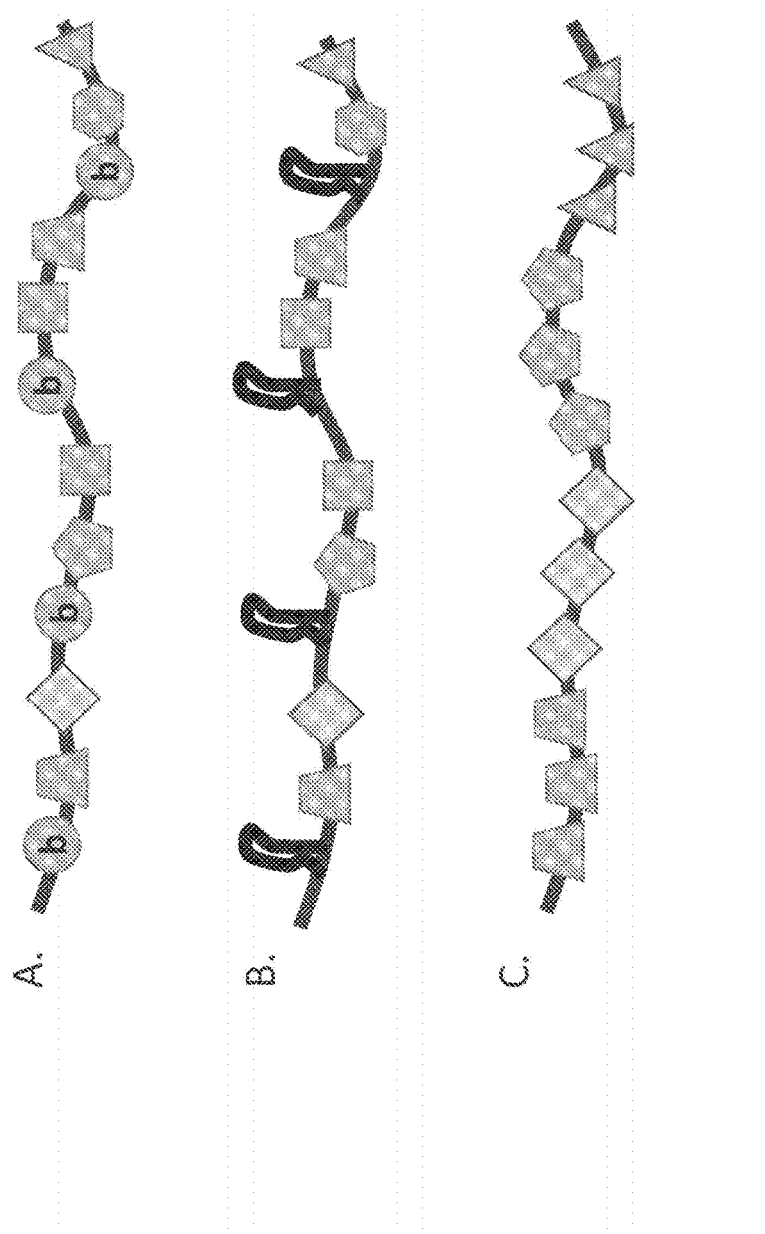

FIG. 56 illustrates an exemplary design of encoded polymer sequences for Nanopore/Nanogap analysis. Part (A) The encoded polymer is comprised of combinatorial current blockade groups (denoted by the shaded polygons) which comprise a code. As the current blockade groups pass through the nanopore, they generate a signature current blockade signal which can be associated with the polymer code using a number of computational and machine learning approaches. The "biotin" circle constitutes a binding moiety that can be bound by a binding agent that "stalls" the DNA in the nanopore allowing more accurate readout of downstream polymer blockade groups. Without this feature to stall the translocation, the polymer may transit too quickly through the pore. In the example shown, biotin can be bound by streptavidin (SA), monomeric streptavidin (mSA2), avidin, etc. The binder and binding conditions should be chosen such that the binding is metastable and the binder will dissociate within msecs of binding, or alternatively can be removed with an increase in trans-membrane voltage. Part (B) As an alternative to an exogenous binding agent to "stall" translocation through the pore, an intrinsic metastable secondary structure of the polymer can be used to stall the transit of the polymer through the pore. Again, the energetics of the secondary structure should be chosen so that the stall time is on the order of msecs. Part (C) If nanopore readout electronics is fast enough and the noise low enough, the polymer can be readout directly via translocation through the pore.

Figure 57:
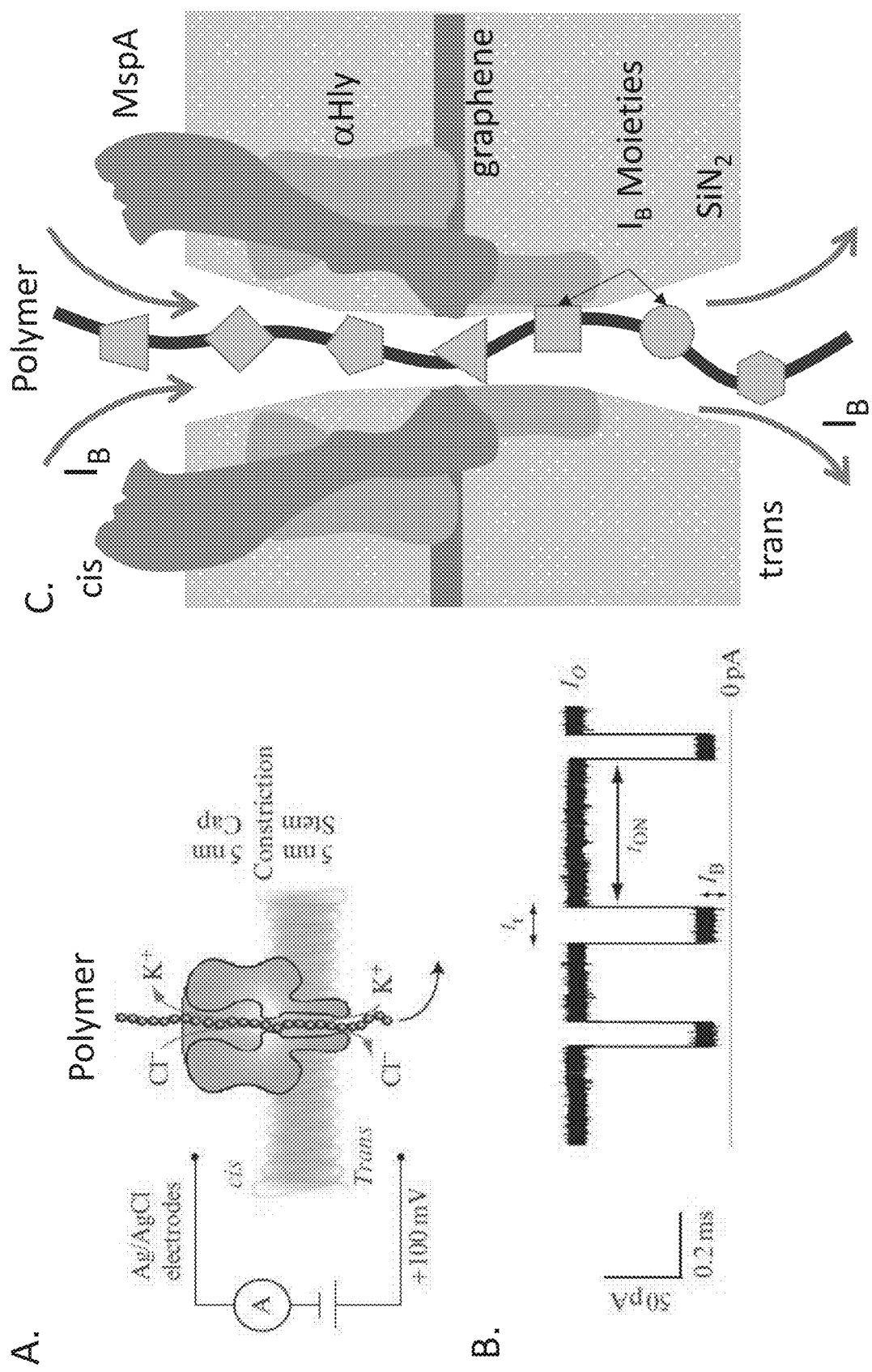

FIG. 57 illustrates an example of polymer readout using nanopore technology. Part (A) Illustration of basic nanopore set-up with alpha haemolysin (aHly) pore inserted into lipid bilayer membrane held at a +100 mV trans relative to cis membrane voltage. This membrane voltage polarity translocates negatively charged polymers from the cis to the trans side. The membrane voltage can be reversed for positively-charged polymers. Part (B) Exampler blockade current signature for a single blockade moiety. Part (C) Comparative structure of different nanopore types: biological nanopores MspA and aHly, synthetic nanopores graphene and $SiN_2$. Blockade currents can be measured with all pore types with the proviso that the dimensionality of the blocking group (shaded polygons) should be on the order of the pore diameter. (Laszlo et al., 2014, Nature Biotech., 32, 829-833; Ying et al., 2014, The Analyst, 139, 3826-3835.)

Figure 58:
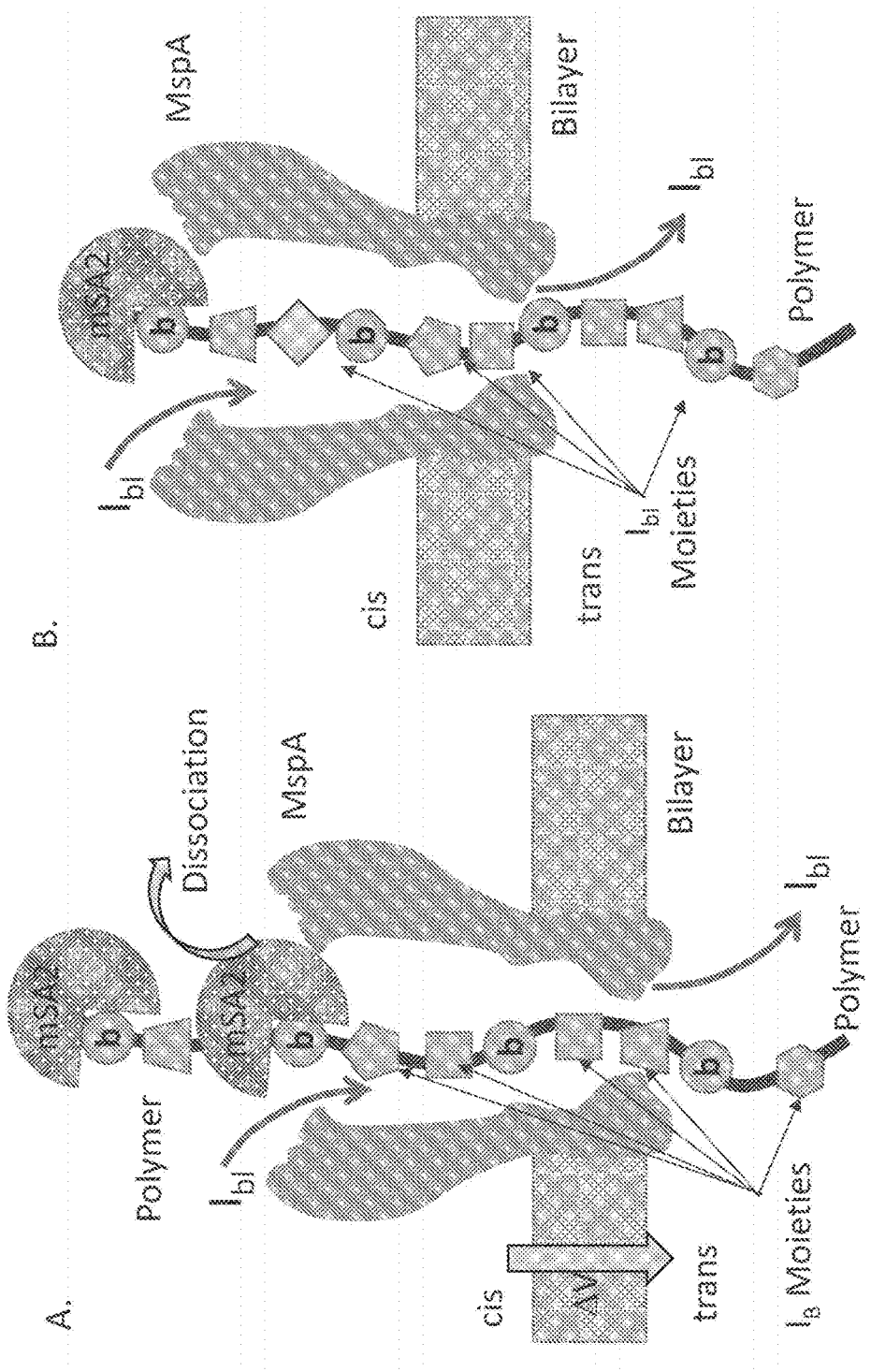

FIG. 58 illustrates an exemplary method of controlling polymer transit through nanopore by stalling transit with a binding feature. Part (A) The sequenceable polymer, in this example, is designed to have current blockade moieties (IB Moieties), interspersed with polymer "catches" (e.g. monomeric streptavidin (mSA2) binding to biotin (b)) which are binding elements or intrinsic secondary structural elements that transiently stall the transits of the polymer in the pore to allow ample time to make an accurate current blockade (IB) measurement. Part (B) The binding agent, mSA2 abut against the pore eventually dissociates under a membrane potential (i.e. 180 mV). Ideally the metastable binding dissociates on a msec time scale.

Figure 59:
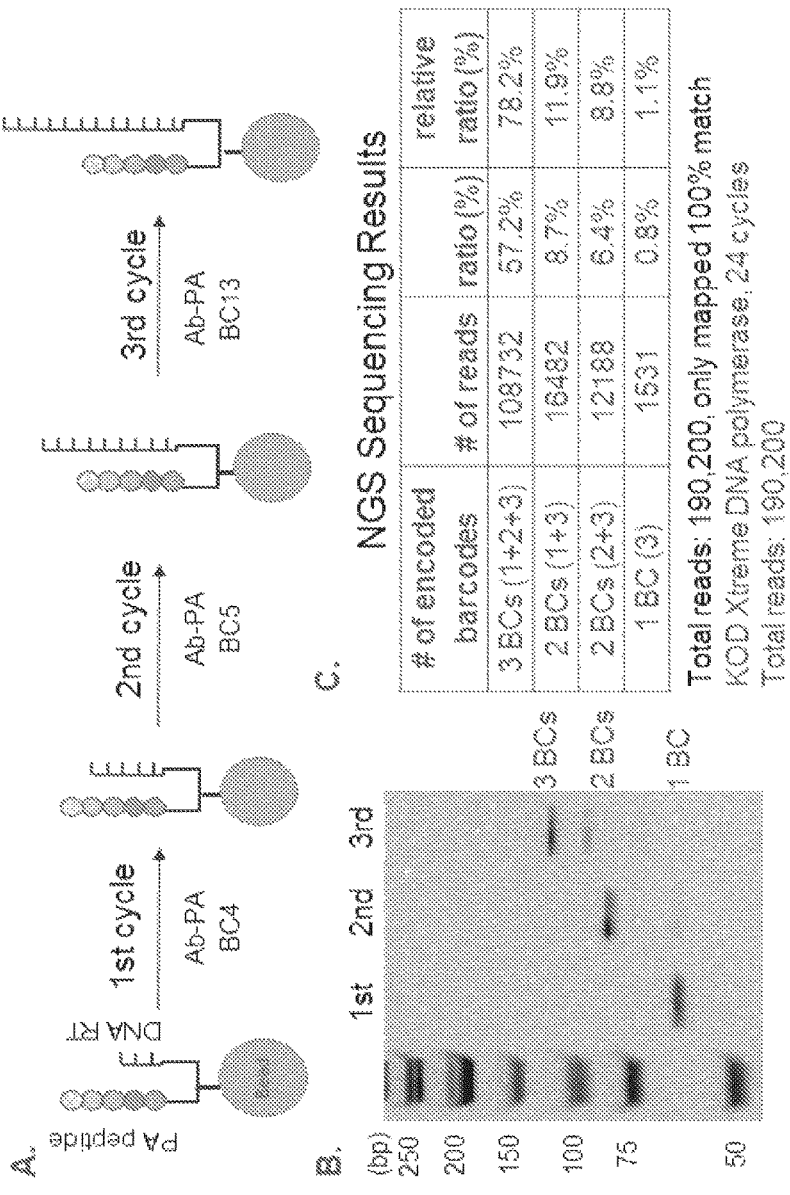

FIG. 59. Three cycle binding/encoding and NGS readout. Part (A) Three sequential encoding steps are illustrated. A peptide is shown conjugated to a recording tag (DNA RT) and immobilized on a magnetic bead. The peptide contains a PA epitope. An anti-PA antibody labeled with three different cycle-specific barcodes (BC4, BC5, BC13) was used to carry out three sequential cycles of the assay, with each barcode used for a different cycle (1st, 2nd and 3rd cycle respectively). Each cycle results in the recording tag being extended with the respective cycle barcode. Part (B) Agarose gel showing analysis of PCR products of the extended recording tag after each cycle. Lane 1=size standards, Lane 2 to 4 correspond to 1st, 2nd and 3rd cycle products respectively. The gel clearly shows high yield encoding. PCR employed KOD polymerase with 24 cycles of amplification. Part (C) In addition to gel analysis, the final "three cycle" product (3rd lane in gel) was analyzed by NGS sequencing. The primary product (over 78% of products), corresponding to largest band on the gel, consisted of library elements with all three barcodes. Single and double barcode products were also observed at a lower proportion (2 BCs at 20.7% and 1 BC at 1.1%).

Figure 60:
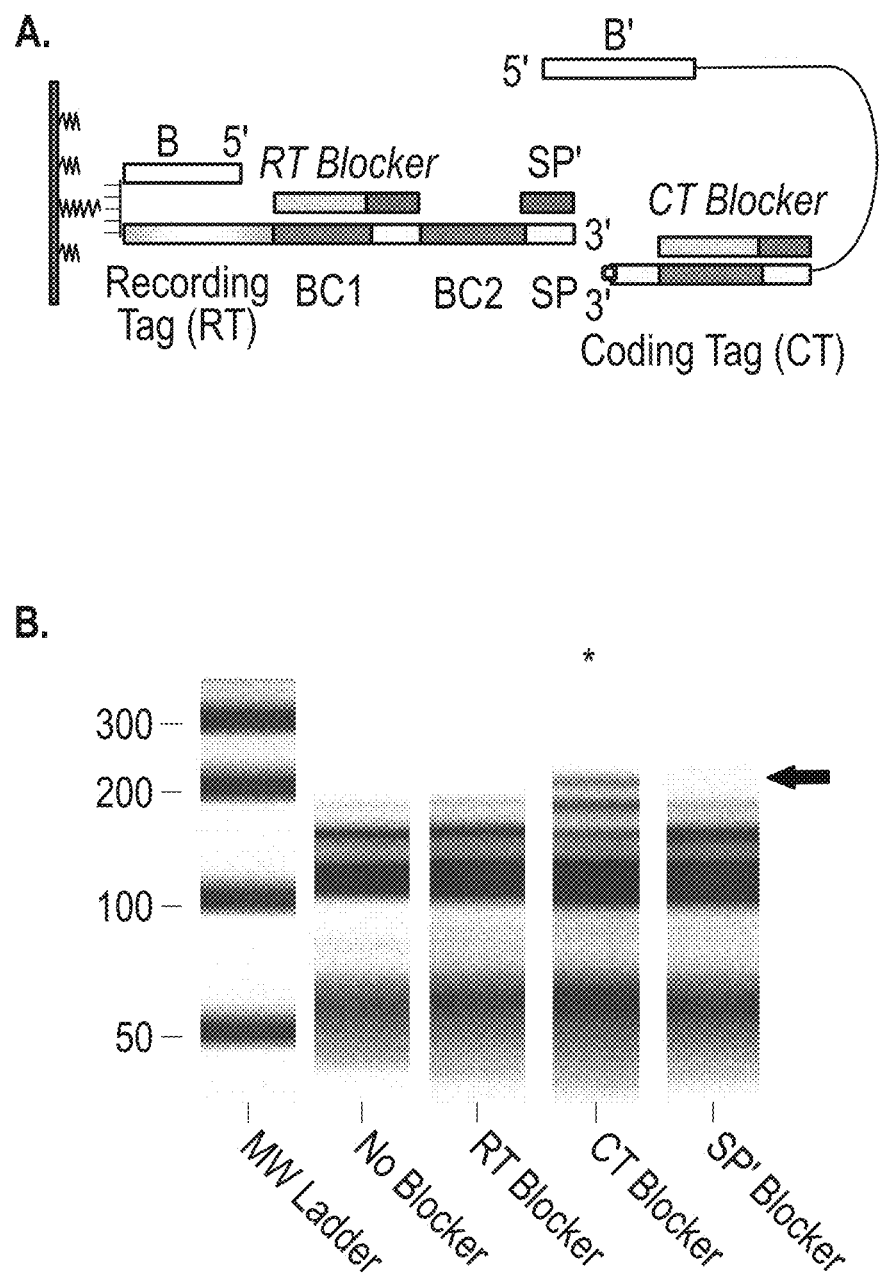

FIG. 60. Use of Blocking Oligonucleotides in Primer Extension Encoding Assay. Several types of blocking oligonucleotide were tested in a primer extension-based encoding assay. Part (A) illustrates the design of a DNA "binder" model system and three types of blocking oligonucleotide used to block components of an encoding assay: RT Blocker, CT Blocker, and Sp' Blocker. Coding tag barcodes for each cycle were designed to be cycle-specific and orthogonal (non-interacting) between cycles. Part (B) Gel analysis of encoding results after three cycles of encoding and PCR amplification. In the example shown, a CT Blocker cognate (lane marked with *) to the incoming coding tag on each cycle provided the highest encoding efficiency as indicated by the upper band denoted by the arrow.

Figure 61:
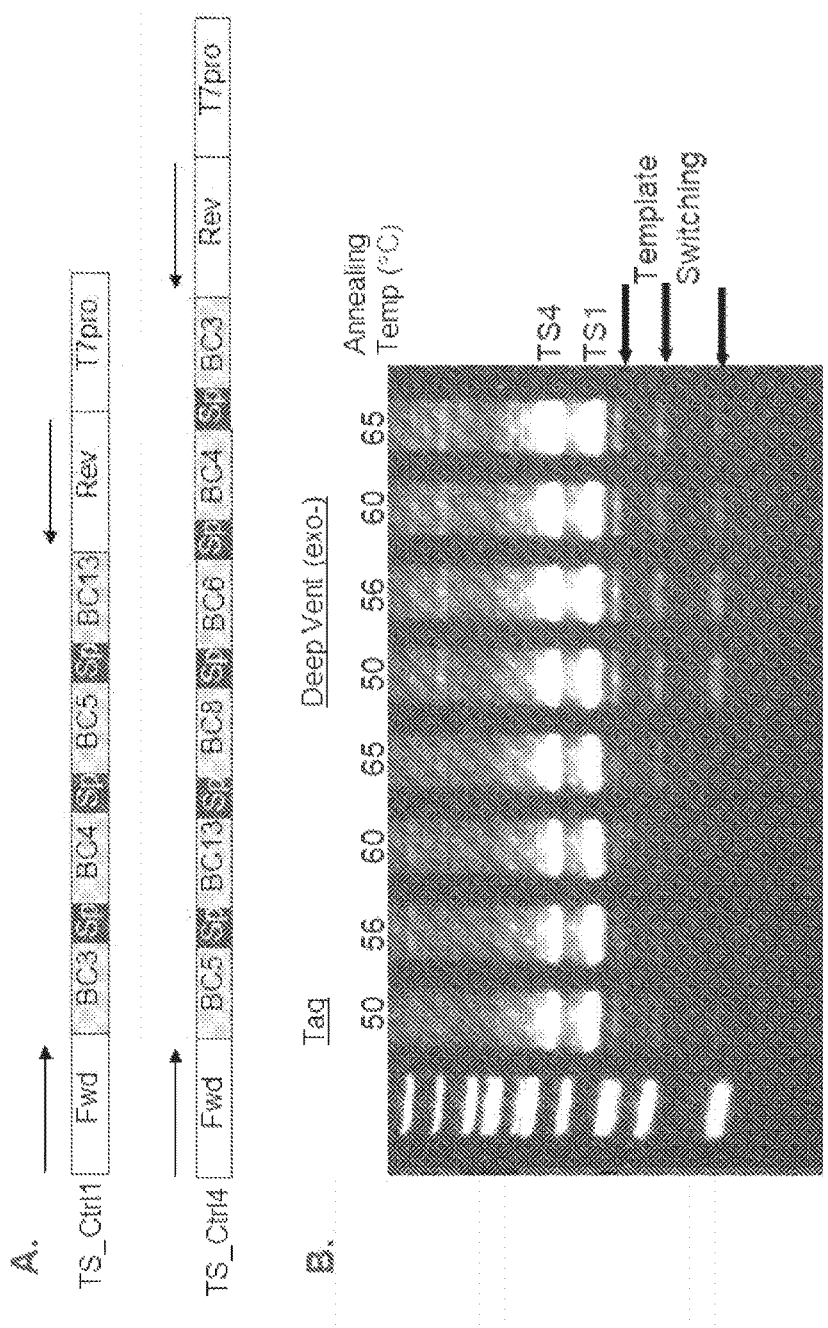

FIG. 61. Minimizing template switching during Proteo-Code library amplification. Part (A) Thermophilic polymerases were screened for propensity for template switching during PCR. Two synthetic mock templates of differing lengths (TS_Ctrl1 and TS_Ctrl4) containing shared barcodes (BC3, BC4, BC5 and BC13) and spacer (Sp) sequences are shown. Following co-amplification by PCR, the presence of bands by PAGE in addition to the two original template bands is indicative of template switching. Part (B) PCR products were analyzed by PAGE. Template switching was a function of PCR conditions and polymerase type. Taq polymerase (lanes 2-5; lane 1=size markers) exhibited much lower template switching than Deep Vent exo- (lanes 6-9) especially at 60° C. annealing.

Figure 62:
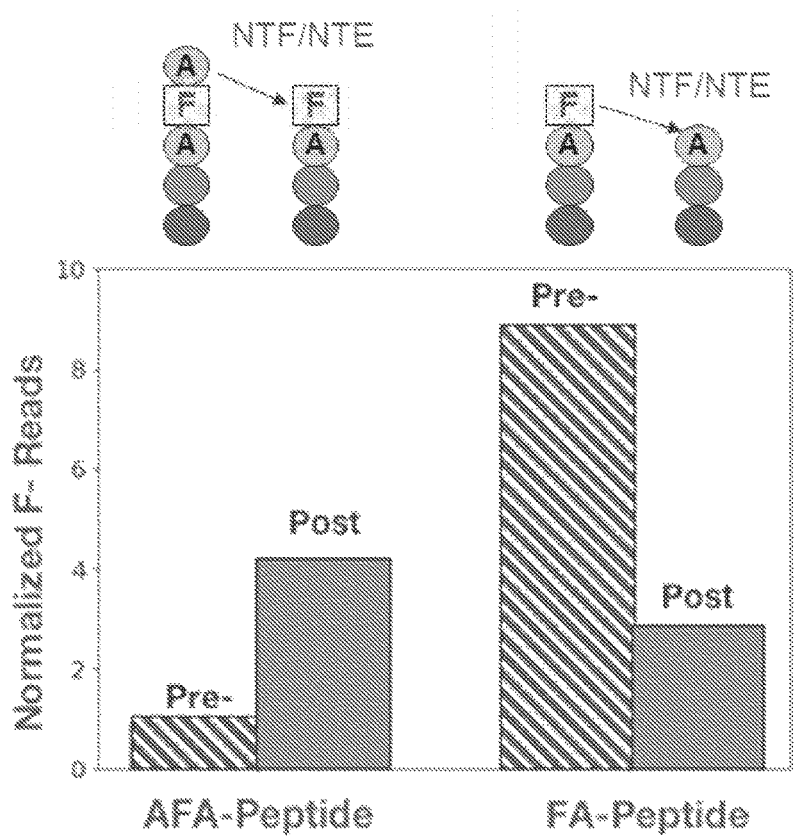

FIG. 62. Single Cycle ProteoCode Assay. Two different bead types (one with an amino A-terminal peptide (AFA-peptide), and the other with an amino F-terminal peptide (FA-peptide) were used in the assay. AFA-peptide and FA-peptide beads were used in a full cycle ProteoCode assay consisting of one cycle of NTF/NTE chemistry and two cycles of encoding comprised of pre- and post-chemistry encoding steps employing an engineered phenylalanine (F) binder. A different barcode for the F-binder was used in the pre-chemistry encoding assay vs. post-chemistry encoding assay. After two cycles of encoding (pre and post), the extended recording tags were subjected to PCR and NGS library preparation followed by NGS sequencing readout on an Illumina MiSeq instrument. The normalized number of reads of the AFA and FA recording tags containing "Pre" and "Post" barcoded coding tags are shown. For the FA peptide incubated with F-binder, higher "pre-chemistry" coding tag read counts were observed compared to post-chemistry cycle tags indicating successful removal of the F residue. Conversely, for the AFA peptide incubated with F-binder, lower read counts of the pre-chemistry cycle tags compared to post-chemistry cycle tags were observed indicating successful removal of the A residue.

Figure 63:
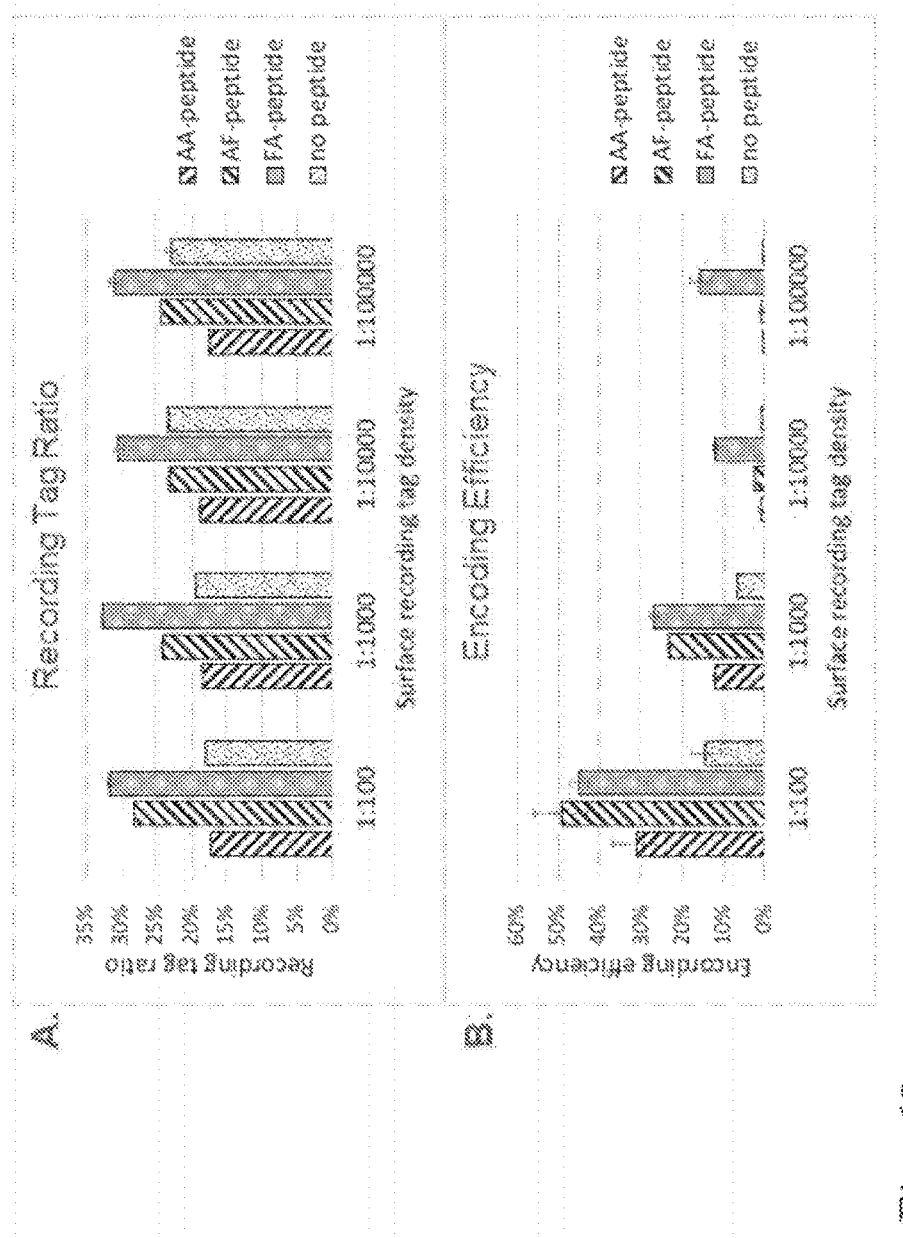

FIG. 63. Inter-molecular cross-talk as a function of peptide chimera surface density. F-binder assay crosstalk measurement on 4-plex peptide-recording tag chimeras (AA-peptide, AF-peptide, FA-peptide, and no peptide) immobilized on the same bead at different surface chimera densities. Part (A) Uniformity of chimera immobilization across four chimera type assessed by PA antibody binding/encoding. Each chimera (as measured by sequencing or recording tags) represented roughly 20-30% of total chimera. Part (B) Encoding efficiency of a single cycle of binding and encoding with an F-binder across four chimera types. At chimera surface dilutions of 1:10,000 and 1:100,000, the intra-molecular encoding efficiency of the FA-peptide is much greater than the inter-molecular encoding of the off-target peptide chimeras (AF, AA, and no peptide).

Figure 64:
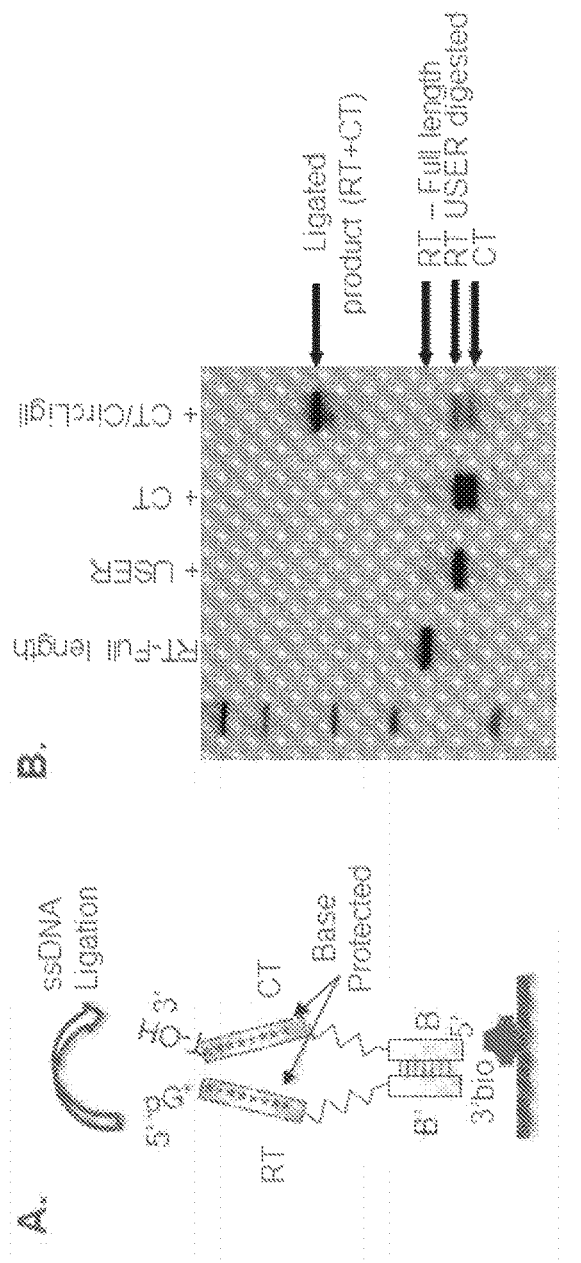

FIG. 64. DNA encoding with base protected DNA using ssDNA ligase. Part (A) Design of base protected recording tag (RT) and coding tag (CT) for ssDNA ligation assay. The base protection groups employed were the standard phosphoramidite protection groups used in oligonucleotide synthesis: Bz-dA, ibu-dG, Ac-dC. These protecting groups were left in place after synthesis. CircLigase II was used to ligate the 5' phosphorylated terminus of the RT oligo with the 3' OH of the CT oligo. Part (B) PAGE gel analysis of ssDNA ligase ligation reaction components and products. Lane 1=RT Full length oligo; Lane 2=after USER enzyme treatment to generate a phosphorylated RT sequence from an RT full length comprised of a 5' U; Lane 3=after annealing of CT oligo to RT oligo immobilized on beads; Lane 4=after ligation of the 3' terminus of CT to the 5' terminus of RT via the B-B' interaction, using CircLigase II. The ligation of "base protected" DNA is relatively efficient as indicated by formation of a higher molecular weight ligation product as seen in Lane 5 using CircLigase II.

Figure 65:
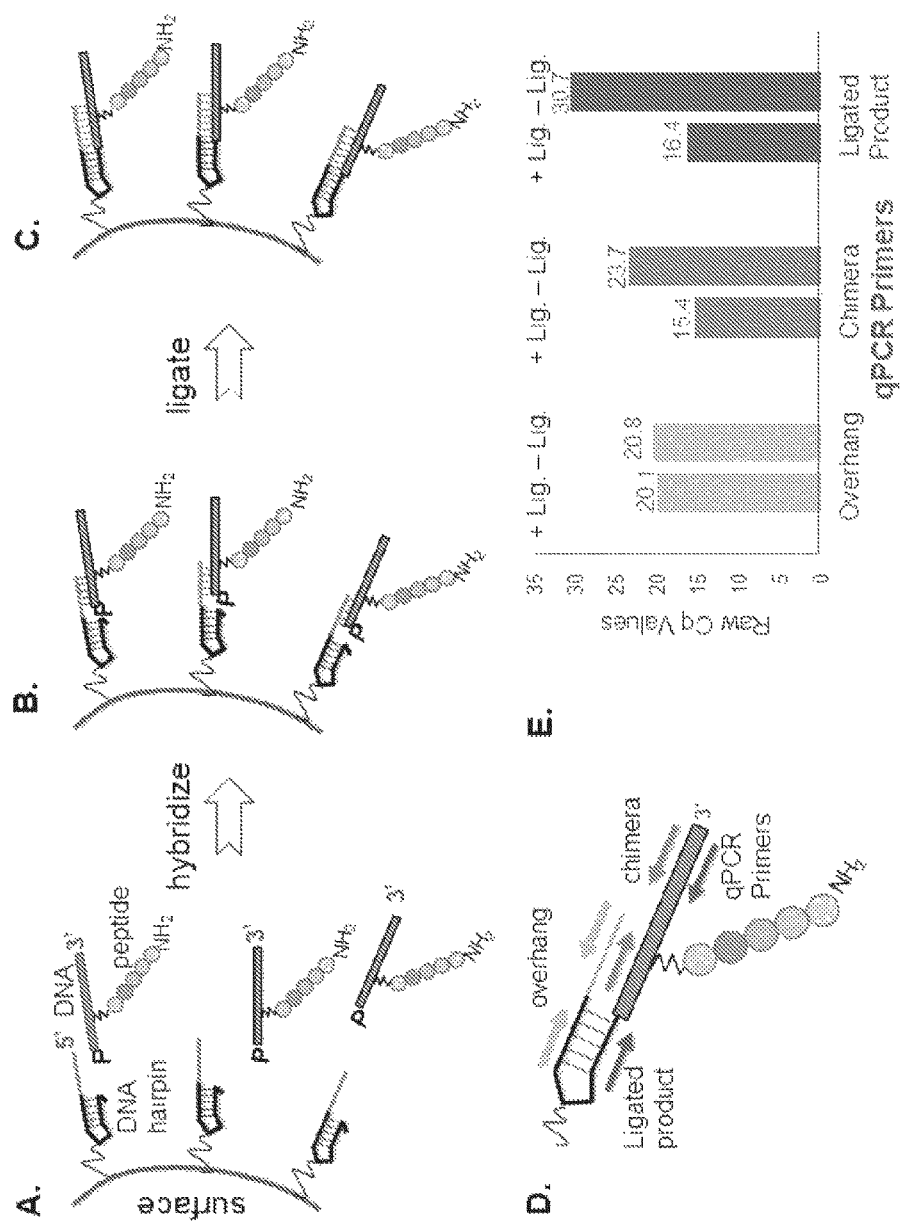

FIG. 65. Immobilization of DNA tagged peptides using hybridization and ligation to DNA beads. Part (A) Design of DNA hairpin beads in which the 5' overhang on the DNA hairpin is used to capture the DNA-peptide chimeras. Part (B) DNA-peptide chimera hybridized to the hairpins on the bead. Part (C) DNA ligase is used to covalently join the 5' end of the phosphorylated DNA tags on the peptides to the hairpin. The DNA tag on the peptide is designed such that the peptide is chemically conjugated to an internal nucleotide. The DNA tag on the peptide constitutes a recording tag with a free 3' end to which information from the coding tag can be transferred. Part (D) Design of qPCR primers to assess efficiency of immobilization of DNA tagged peptides on beads. Part (E) qPCR quantitation using three different primer sets to assess hairpin (Overhang) and DNA tagged peptide immobilization (chimera and ligated product). Lower Cq values indicate higher abundance of the amplified product.

DETAILED DESCRIPTION

Terms not specifically defined herein should be given the meanings that would be given to them by one of skill in the art in light of the disclosure and the context. As used in the specification, however, unless specified to the contrary, the terms have the meaning indicated.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

I. Introduction and Overview

Highly-parallel macromolecular characterization and recognition of polypeptides (such as proteins) is challenging for several reasons. The use of affinity-based assays is often difficult due to several key challenges. One significant challenge is multiplexing the readout of a collection of affinity agents to a collection of cognate macromolecules; another challenge is minimizing cross-reactivity between the affinity agents and off-target macromolecules; a third challenge is developing an efficient high-throughput read out platform. An example of this problem occurs in proteomics in which one goal is to identify and quantitate most or all the proteins in a sample. Additionally, it is desirable to characterize various post-translational modifications (PTMs) on the proteins at a single molecule level. Currently this is a formidable task to accomplish in a high-throughput way.

Molecular recognition and characterization of a protein or polypeptide analyte is typically performed using an immunoassay. There are many different immunoassay formats including ELISA, multiplex ELISA (e.g., spotted antibody arrays, liquid particle ELISA arrays), digital ELISA (e.g., Quanterix, Singulex), reverse phase protein arrays (RPPA), and many others. These different immunoassay platforms all face similar challenges including the development of high affinity and highly-specific (or selective) antibodies (binding agents), limited ability to multiplex at both the sample level and the analyte level, limited sensitivity and dynamic range, and cross-reactivity and background signals. Binding agent agnostic approaches such as direct protein characterization via peptide sequencing (Edman degradation or Mass Spectroscopy) provide useful alternative approaches. However, neither of these approaches is very parallel or high-throughput.

Peptide sequencing based on Edman degradation was first proposed by Pehr Edman in 1950; namely, stepwise degradation of the N-terminal amino acid on a peptide through a series of chemical modifications and downstream HPLC analysis (later replaced by mass spectrometry analysis). In a first step, the N-terminal amino acid is modified with phenyl isothiocyanate (PITC) under mildly basic conditions (NMP/methanol/$H_2O$) to form a phenylthiocarbamoyl (PTC) derivative. In a second step, the PTC-modified amino group is treated with acid (anhydrous trifluoroacetic acid, TFA) to create a cleaved cyclic ATZ (2-anilino-5(4)-thiozolinone) modified amino acid, leaving a new N-terminus on the peptide. The cleaved cyclic ATZ-amino acid is converted to a phenylthiohydantoin (PTH)-amino acid derivative and analyzed by reverse phase HPLC. This process is continued in an iterative fashion until all or a partial number of the amino acids comprising a peptide sequence has been removed from the N-terminal end and identified. In general, the art Edman degradation peptide sequencing method is slow and has a limited throughput of only a few peptides per day.

In the last 10-15 years, peptide analysis using MALDI, electrospray mass spectroscopy (MS), and LC-MS/MS has largely replaced Edman degradation. Despite the recent advances in MS instrumentation (Riley et al., 2016, *Cell Syst* 2:142-143), MS still suffers from several drawbacks including high instrument cost, requirement for a sophisticated user, poor quantification ability, and limited ability to make measurements spanning the entire dynamic range of a proteome. For example, since proteins ionize at different levels of efficiencies, absolute quantitation and even relative quantitation between sample is challenging. The implementation of mass tags has helped improve relative quantitation, but requires labeling of the proteome. Dynamic range is an additional complication in which concentrations of proteins within a sample can vary over a very large range (over 10 orders for plasma). MS typically only analyzes the more abundant species, making characterization of low abundance proteins challenging. Finally, sample throughput is typically limited to a few thousand peptides per run, and for data independent analysis (DIA), this throughput is inadequate for true bottoms-up high-throughput proteome analysis. Furthermore, there is a significant compute requirement to de-convolute thousands of complex MS spectra recorded for each sample.

Accordingly, there remains a need in the art for improved techniques relating to macromolecule sequencing and/or analysis, with applications to protein sequencing and/or analysis, as well as to products, methods and kits for accomplishing the same. There is a need for proteomics technology that is highly-parallelized, accurate, sensitive, and high-throughput. These and other aspects of the invention will be apparent upon reference to the following detailed description. To this end, various references are set forth herein which describe in more detail certain background information, procedures, compounds and/or compositions, and are each hereby incorporated by reference in their entirety.

Figure 1A:
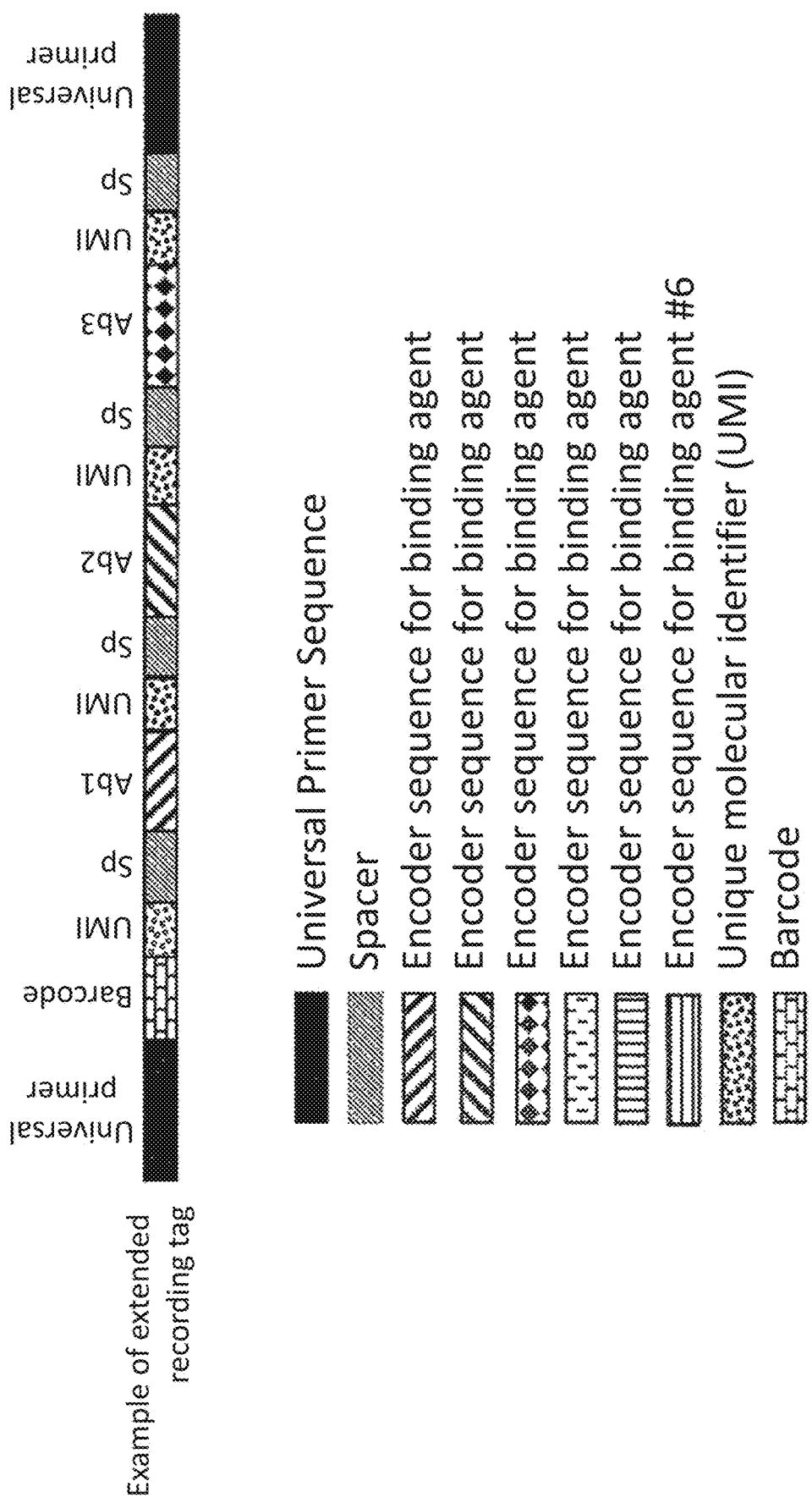
FIG. 1A-1B.
Figure 1B:
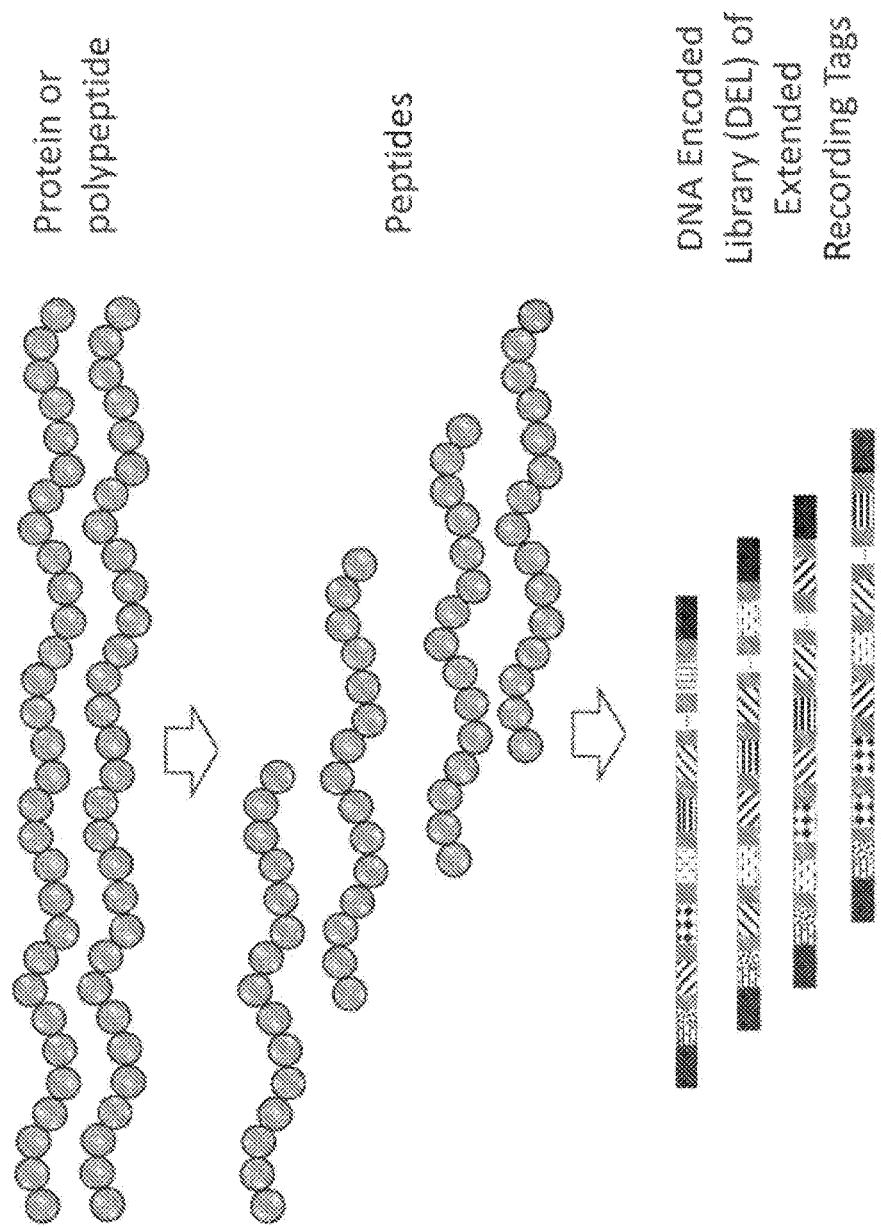
Figure 2A:
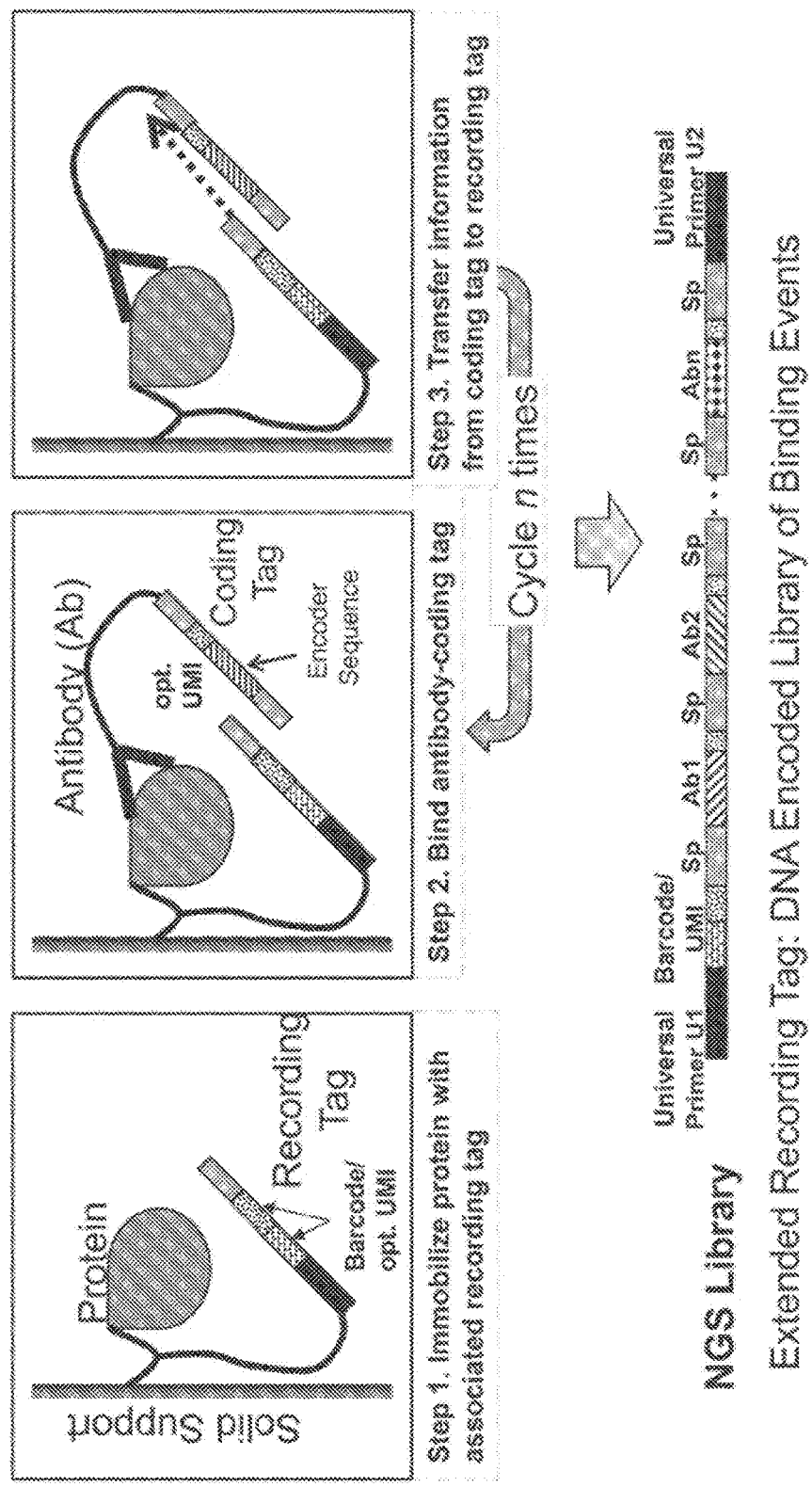
FIG. 2A-2D illustrate an example of polypeptide (e.g., protein) analysis according to the methods disclosed herein, using multiple cycles of binding agents (e.g., antibodies, anticalins, N-recognins proteins (e.g., ClpSs, or UBR box proteins, etc.), and variants/homologues thereof, and aptamers etc.) comprising coding tags interacting with an immobilized protein that is co-localized or co-labeled with a single or multiple recording tags. In this example, the recording tag comprises a universal priming site, a barcode (e.g., partition barcode, compartment barcode, and/or fraction barcode), an optional unique molecular identifier (UMI) sequence, and optionally a spacer sequence (Sp) used in information transfer between the coding tag and the recording tag (or an extended recording tag). The spacer sequence (Sp) can be constant across all binding cycles, be binding agent specific, and/or be binding cycle number specific (e.g., used for "clocking" the binding cycles). In this example, the coding tag comprises an encoder sequence providing identifying information for the binding agent (or a class of binding agents, for example, a class of binders that all specifically bind to a terminal amino acid, such as a modified N-terminal Q as shown in FIG. 3), an optional UMI, and a spacer sequence that hybridizes to the complementary spacer sequence on the recording tag, facilitating transfer of coding tag information to the recording tag (e.g., by primer extension, also referred to herein as polymerase extension). Ligation may also be used to transfer sequence information and in that case, a spacer sequence may be used but is not necessary. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

The present disclosure provides, in part, methods of highly-parallel, high throughput digital macromolecule characterization and quantitation, with direct applications to protein and peptide characterization and sequencing (see, e.g., FIG. 1B, FIG. 2A). The methods described herein use binding agents comprising a coding tag with identifying information in the form of a nucleic acid molecule or sequenceable polymer, wherein the binding agents interact with a macromolecule of interest. Multiple, successive binding cycles, each cycle comprising exposing a plurality of macromolecules, for example, representing pooled samples, immobilized on a solid support to a plurality of binding agents, are performed. During each binding cycle, the identity of each binding agent that binds to the macromolecule, and optionally binding cycle number, is recorded by transferring information from the binding agent coding tag to a recording tag co-localized with the macromolecule. In an alternative embodiment, information from the recording tag comprising identifying information for the associated macromolecule may be transferred to the coding tag of the bound binding agent (e.g., to form an extended coding tag) or to a third "di-tag" construct. Multiple cycles of binding events build historical binding information on the recording tag co-localized with the macromolecule, thereby producing an extended recording tag comprising multiple coding tags in co-linear order representing the temporal binding history for a given macromolecule. In addition, cycle-specific coding tags can be employed to track information from each cycle, such that if a cycle is skipped for some reason, the extended recording tag can continue to collect information in subsequent cycles, and identify the cycle with missing information.

Alternatively, instead of writing or transferring information from the coding tag to recording tag, information can be transferred from a recording tag comprising identifying information for the associated macromolecule to the coding tag forming an extended coding tag or to a third di-tag construct. The resulting extended coding tags or di-tags can be collected after each binding cycle for subsequent sequence analysis. The identifying information on the recording tags comprising barcodes (e.g., partition tags, compartment tags, sample tags, fraction tags, UMIs, or any combination thereof) can be used to map the extended coding tag or di-tag sequence reads back to the originating macromolecule. In this manner, a nucleic acid encoded library representation of the binding history of the macromolecule is generated. This nucleic acid encoded library can be amplified, and analyzed using very high-throughput next generation digital sequencing methods, enabling millions to billions of molecules to be analyzed per run. The creation of a nucleic acid encoded library of binding information is useful in another way in that it enables enrichment, subtraction, and normalization by DNA-based techniques that make use of hybridization. These DNA-based methods are easily and rapidly scalable and customizable, and more cost-effective than those available for direct manipulation of other types of macromolecule libraries, such as protein libraries. Thus, nucleic acid encoded libraries of binding information can be processed prior to sequencing by one or more techniques to enrich and/or subtract and/or normalize the representation of sequences. This enables information of maximum interest to be extracted much more efficiently, rapidly and cost-effectively from very large libraries whose individual members may initially vary in abundance over many orders of magnitude. Importantly, these nucleic-acid based techniques for manipulating library representation are orthogonal to more conventional methods, and can be used in combination with them. For example, common, highly abundant proteins, such as albumin, can be subtracted using protein-based methods, which may remove the majority but not all the undesired protein. Subsequently, the albumin-specific members of an extended recording tag library can also be subtracted, thus achieving a more complete overall subtraction.

In one aspect, the present disclosure provides a highly-parallelized approach for peptide sequencing using an Edman-like degradation approach, allowing the sequencing from a large collection of DNA recording tag-labeled peptides (e.g., millions to billions). These recording tag labeled peptides are derived from a proteolytic digest or limited hydrolysis of a protein sample, and the recording tag labeled peptides are immobilized randomly on a sequencing substrate (e.g., porous beads) at an appropriate inter-molecular spacing on the substrate. Modification of N-terminal amino acid (NTAA) residues of the peptides with small chemical moieties, such as phenylthiocarbamoyl (PTC), dinitrophenol (DNP), sulfonyl nitrophenol (SNP), dansyl, 7-methoxy coumarin, acetyl, or guanidinyl, that catalyze or recruit an NTAA cleavage reaction allows for cyclic control of the Edman-like degradation process. The modifying chemical moieties may also provide enhanced binding affinity to cognate NTAA binding agents. The modified NTAA of each immobilized peptide is identified by the binding of a cognate NTAA binding agent comprising a coding tag, and transferring coding tag information (e.g., encoder sequence providing identifying information for the binding agent) from the coding tag to the recording tag of the peptide (e.g., primer extension or ligation). Subsequently, the modified NTAA is removed by chemical methods or enzymatic means. In certain embodiments, enzymes (e.g., Edmanase) are engineered to catalyze the removal of the modified NTAA. In other embodiments, naturally occurring exopeptidases, such as aminopeptidases or acyl peptide hydrolases, can be engineered to cleave a terminal amino acid only in the presence of a suitable chemical modification. Optionally, the methods include a step of contacting the polypeptide with a proline aminopeptidase before and/or after each NTAA removal step, since the steps may not cleave a terminal proline otherwise.

II. Definitions

In the following description, certain specific details are set forth in order to provide a thorough understanding of various embodiments. However, one skilled in the art will understand that the present compounds may be made and used without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising," are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the singular forms "a," "an," and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

As used herein, the term "macromolecule" encompasses large molecules composed of smaller subunits. Examples of macromolecules include, but are not limited to peptides, polypeptides, proteins, nucleic acids, carbohydrates, lipids, macrocycles. A macromolecule also includes a chimeric macromolecule composed of a combination of two or more types of macromolecules, covalently linked together (e.g., a peptide linked to a nucleic acid). A macromolecule may also include a "macromolecule assembly", which is composed of non-covalent complexes of two or more macromolecules. A macromolecule assembly may be composed of the same type of macromolecule (e.g., protein-protein) or of two more different types of macromolecules (e.g., protein-DNA).

As used herein, the term "polypeptide" encompasses peptides and proteins, and refers to a molecule comprising a chain of two or more amino acids joined by peptide bonds. In some embodiments, a polypeptide comprises 2 to 50 amino acids, e.g., having more than 20-30 amino acids. In some embodiments, a peptide does not comprise a secondary, territory, or higher structure. In some embodiments, a protein comprises 30 or more amino acids, e.g. having more than 50 amino acids. In some embodiments, in addition to a primary structure, a protein comprises a secondary, territory, or higher structure. The amino acids of the polypeptide are most typically L-amino acids, but may also be D-amino acids, unnatural amino acids, modified amino acids, amino acid analogs, amino acid mimetics, or any combination thereof. Polypeptides may be naturally occurring, synthetically produced, or recombinantly expressed. Polypeptide may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, 3-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids.

As used herein, the term "post-translational modification" refers to modifications that occur on a peptide after its translation by ribosomes is complete. A post-translational modification may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini. The term post-translational modification can also include peptide modifications that include one or more detectable labels.

As used herein, the term "binding agent" refers to a nucleic acid molecule, a peptide, a polypeptide, a protein, carbohydrate, or a small molecule that binds to, associates, unites with, recognizes, or combines with an analyte, e.g., a macromolecule or a component or feature of a macromolecule. A binding agent may form a covalent association or non-covalent association with the analyte, e.g., a macromolecule or component or feature of a macromolecule. A binding agent may also be a chimeric binding agent, composed of two or more types of molecules, such as a nucleic acid molecule-peptide chimeric binding agent or a carbohydrate-peptide chimeric binding agent. A binding agent may be a naturally occurring, synthetically produced, or recombinantly expressed molecule. A binding agent may bind to a single monomer or subunit of a macromolecule (e.g., a single amino acid of a peptide) or bind to a plurality of linked subunits of a macromolecule (e.g., a di-peptide, tri-peptide, or higher order peptide of a longer peptide, polypeptide, or protein molecule). A binding agent may bind to a linear molecule or a molecule having a three-dimensional structure (also referred to as conformation). For example, an antibody binding agent may bind to linear peptide, polypeptide, or protein, or bind to a conformational peptide, polypeptide, or protein. A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may for example bind to a chemically modified or labeled amino acid over a non-modified or unlabeled amino acid. For example, a binding agent may for example bind to an amino acid that has been modified with an acetyl moiety, guanyl moiety, dansyl moiety, PTC moiety, DNP moiety, SNP moiety, etc., over an amino acid that does not possess said moiety. A binding agent may bind to a post-translational modification of a polypeptide molecule. A binding agent may exhibit selective binding to a component or feature of an analyte, such as a macromolecule (e.g., a binding agent may selectively bind to one of the 20 possible natural amino acid residues and bind with very low affinity or not at all to the other 19 natural amino acid residues). A binding agent may exhibit less selective binding, where the binding agent is capable of binding a plurality of components or features of an analyte, such as a macromolecule (e.g., a binding agent may bind with similar affinity to two or more different amino acid residues). A binding agent comprises a coding tag, which may be joined to the binding agent by a linker.

In some embodiments, the term "agent" and "reagent" are used interchangeably. For example, while a binding agent is referred to as an agent, its coding tag can have a reactive portion, e.g., a spacer sequence or a reactive end, to react with a spacer sequence or reactive end on the recording tag in order to transfer information. The reactions may include ligation and/or annealing followed by primer extension.

As used herein, the term "linker" refers to one or more of a nucleotide, a nucleotide analog, an amino acid, a peptide, a polypeptide, or a non-nucleotide chemical moiety that is used to join two molecules. A linker may be used to join a binding agent with a coding tag, a recording tag with a macromolecule (e.g., peptide), a macromolecule with a solid support, a recording tag with a solid support, etc. In certain embodiments, a linker joins two molecules via enzymatic reaction or chemistry reaction (e.g., click chemistry).

As used herein, the term "proteomics" refers to analysis (e.g., quantitative analysis) of a proteome, e.g., the proteome within cell(s), tissue(s), and bodily fluid(s), and the corresponding spatial distribution of the proteome within the cell and within tissues. Additionally, proteomics studies include the dynamic state of a proteome, continually changing in time as a function of biology and defined biological or chemical stimuli.

As used herein, the term "proteome" can include the entire set of proteins, polypeptides, or peptides (including conjugates or complexes thereof) expressed by a target, e.g., a genome, cell, tissue, or organism at a certain time, of any organism. In one aspect, it is the set of expressed proteins in a given type of cell or organism, at a given time, under defined conditions. Proteomics is the study of a proteome. For example, a "cellular proteome" may include the collection of proteins found in a particular cell type under a particular set of environmental conditions, such as exposure to hormone stimulation. An organism's complete proteome may include the complete set of proteins from all of the various cellular proteomes. A proteome may also include the collection of proteins in certain sub-cellular biological systems. For example, all of the proteins in a virus can be called a viral proteome. As used herein, the term "proteome" include subsets of a proteome, including but not limited to a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glycoproteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof.

As used herein, the term "non-cognate binding agent" refers to a binding agent that is not capable of binding or binds with low affinity to a macromolecule feature, component, or subunit being interrogated in a particular binding cycle reaction as compared to a "cognate binding agent", which binds with high affinity to the corresponding macromolecule feature, component, or subunit. For example, if a tyrosine residue of a peptide molecule is being interrogated in a binding reaction, non-cognate binding agents are those that bind with low affinity or not at all to the tyrosine residue, such that the non-cognate binding agent does not efficiently transfer coding tag information to the recording tag under conditions that are suitable for transferring coding tag information from cognate binding agents to the recording tag. Alternatively, if a tyrosine residue of a peptide molecule is being interrogated in a binding reaction, non-cognate binding agents are those that bind with low affinity or not at all to the tyrosine residue, such that recording tag information does not efficiently transfer to the coding tag under suitable conditions for those embodiments involving extended coding tags rather than extended recording tags.

As used herein, the term 'proline aminopeptidase' refers to an enzyme that is capable of specifically cleaving an N-terminal proline from a polypeptide. Enzymes with this activity are well known in the art, and may also be referred to as proline iminopeptidases or as PAPs. Known monomeric PAPs include family members from *B. coagulans, L. delbrueckii, N. gonorrhoeae, F. meningosepticum, S. marcescens, T. acidophilum, L. plantarum* (MEROPS 533.001) (Nakajima, Ito et al. 2006) (Kitazono, Yoshimoto et al. 1992). Known multimeric PAPs include *D. hansenii* (Bolumar, Sanz et al. 2003). Either native or engineered PAPs may be employed.

As used herein, the term "specific binding" refers to the specificity of a binder, e.g., an antibody, a ClpS protein, or an anticalin, such that it preferentially binds to a target, such as a polypeptide antigen. When referring to a binding partner, e.g., protein, nucleic acid, antibody or other affinity capture agent, etc., "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. For example, binders, antibodies or antibody fragments that are specific for or bind specifically to a target bind to the target with higher affinity than binding to other non-target substances. For example, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

As used herein, a polynucleotide, protein or polypeptide variant, mutant, homologue, or modified version include proteins or polypeptides that share nucleic acid or amino acid sequence identity with a reference polynucleotide, protein or polypeptide, for example, about 10% sequence identity, about 15% sequence identity, about 20% sequence identity, about 25% sequence identity, about 30% sequence identity, about 35% sequence identity, about 40% sequence identity, about 45% sequence identity, about 50% sequence identity, about 55% sequence identity, about 60% sequence identity, about 65% sequence identity, about 70% sequence identity, about 75% sequence identity, about 80% sequence identity, about 85% sequence identity, about 90%, 91%, 92%, 93%, 94%, 95%, 96%, 97%, 98%, or 99% sequence identity, or about 100% sequence identity.

"Percent (%) nucleic acid sequence identity" with respect to a reference polynucleotide sequence is defined as the percentage of nucleic acid residues in a candidate sequence that are identical with the nucleic acid residues in the reference polynucleotide sequence, after aligning the sequences and introducing gaps, if necessary, to achieve the maximum percent sequence identity, and not considering any conservative substitutions as part of the sequence identity. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity and/or percent nucleic acid sequence can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

For example, a ClpS protein or polypeptide disclosed herein include a variant, mutant, homologue, or modified version that shares sequence identity with a reference ClpS protein or polypeptide, such as *A. tumefaciens* ClpS2 (e.g., SEQ ID NO: 198), *E. coli* ClpS (e.g., SEQ ID NO: 199), and/or *C. crescentus* ClpS (e.g., SEQ ID NO: 200), with about 10% sequence identity, about 15% sequence identity, about 20% sequence identity, about 25% sequence identity, about 30% sequence identity, about 35% sequence identity, about 40% sequence identity, about 45% sequence identity, about 50% sequence identity, about 55% sequence identity, about 60% sequence identity, about 65% sequence identity, about 70% sequence identity, about 75% sequence identity, about 80% sequence identity, about 85% sequence identity, about 90%, 91%, 92%, 93%, 94%, 95%, 96%, 97%, 98%, or 99% sequence identity, or about 100% sequence identity.

The terminal amino acid at one end of the peptide chain that has a free amino group is referred to herein as the "N-terminal amino acid" (NTAA). The terminal amino acid at the other end of the chain that has a free carboxyl group is referred to herein as the "C-terminal amino acid" (CTAA). The amino acids making up a peptide may be numbered in order, with the peptide being "n" amino acids in length. As used herein, NTAA is considered the $n^{th}$ amino acid (also referred to herein as the "$n^{th}$ NTAA"). Using this nomenclature, the next amino acid is the $(n-1)^{th}$ amino acid, then the $(n-2)^{th}$ amino acid, and so on down the length of the peptide from the N-terminal end to C-terminal end. In certain embodiments, an NTAA, CTAA, or both may be modified or labeled with a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a macromolecule (e.g., protein, polypeptide, peptide), a binding agent, a set of binding agents from a binding cycle, a sample macromolecules, a set of samples, macromolecules within a compartment (e.g., droplet, bead, or separated location), macromolecules within a set of compartments, a fraction of macromolecules, a set of macromolecule fractions, a spatial region or set of spatial regions, a library of macromolecules, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error correcting barcodes. Barcodes can be used to computationally deconvolute the multiplexed sequencing data and identify sequence reads derived from an individual macromolecule, sample, library, etc. A barcode can also be used for deconvolution of a collection of macromolecules that have been distributed into small compartments for enhanced mapping. For example, rather than mapping a peptide back to the proteome, the peptide is mapped back to its originating protein molecule or protein complex.

A "sample barcode", also referred to as "sample tag" identifies from which sample a macromolecule derives.

A "spatial barcode" which region of a 2-D or 3-D tissue section from which a macromolecule derives. Spatial barcodes may be used for molecular pathology on tissue sections. A spatial barcode allows for multiplex sequencing of a plurality of samples or libraries from tissue section(s).

As used herein, the term "coding tag" refers to a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequencable polymer" (see, e.g., Niu et al., 2013, *Nat. Chem.* 5:282-292; Roy et al., 2015, *Nat. Commun.* 6:7237; Lutz, 2015, *Macromolecules* 48:4759-4767; each of which are incorporated by reference in its entirety). A coding tag may comprise an encoder sequence (e.g., a barcode identifier), which is optionally flanked by one spacer on one side or flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

As used herein, the term "encoder sequence" or "encoder barcode" refers to a nucleic acid molecule of about 2 bases to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) in length that provides identifying information for its associated binding agent. The encoder sequence may uniquely identify its associated binding agent. In certain embodiments, an encoder sequence is provides identifying information for its associated binding agent and for the binding cycle in which the binding agent is used. In other embodiments, an encoder sequence is combined with a separate binding cycle-specific barcode within a coding tag. Alternatively, the encoder sequence may identify its associated binding agent as belonging to a member of a set of two or more different binding agents. In some embodiments, this level of identification is sufficient for the purposes of analysis. For example, in some embodiments involving a binding agent that binds to an amino acid, it may be sufficient to know that a peptide comprises one of two possible amino acids at a particular position, rather than definitively identify the amino acid residue at that position. In another example, a common encoder sequence is used for polyclonal antibodies, which comprises a mixture of antibodies that recognize more than one epitope of a protein target, and have varying specificities. In other embodiments, where an encoder sequence identifies a set of possible binding agents, a sequential decoding approach can be used to produce unique identification of each binding agent. This is accomplished by varying encoder sequences for a given binding agent in repeated cycles of binding (see, Gunderson et al., 2004, *Genome Res.* 14:870-7). The partially identifying coding tag information from each binding cycle, when combined with coding information from other cycles, produces a unique identifier for the binding agent, e.g., the particular combination of coding tags rather than an individual coding tag (or encoder sequence) provides the uniquely identifying information for the binding agent. For example, the encoder sequences within a library of binding agents possess the same or a similar number of bases.

As used herein the term "binding cycle specific tag," "binding cycle specific barcode," or "binding cycle specific sequence" refers to a unique sequence used to identify a library of binding agents used within a particular binding cycle. A binding cycle specific tag may comprise about 2 bases to about 8 bases (e.g., 2, 3, 4, 5, 6, 7, or 8 bases) in length. A binding cycle specific tag may be incorporated within a binding agent's coding tag as part of a spacer sequence, part of an encoder sequence, part of a UMI, or as a separate component within the coding tag.

As used herein, the term "spacer" (Sp) refers to a nucleic acid molecule of about 0 base to about 20 bases (e.g., 0, 1, 2, 3, 4, 5, 6, 7, 8, 9, 10, 11, 12, 13, 14, 15, 16, 17, 18, 19, or 20 bases) in length that is present on a terminus of a recording tag or coding tag. When the spacer is 0 base, the assay is sometimes referred to as of a "spacer-less" format, for example, as shown in FIG. 7 and FIG. 46A-C. In certain embodiments, a spacer sequence flanks an encoder sequence of a coding tag on one end or both ends. Following binding of a binding agent to a macromolecule, annealing between complementary spacer sequences on their associated coding tag and recording tag, respectively, allows transfer of binding information through a primer extension reaction or ligation to the recording tag, coding tag, or a di-tag construct. Sp' refers to spacer sequence complementary to Sp. For example, spacer sequences within a library of binding agents possess the same number of bases. A common (shared or identical) spacer may be used in a library of binding agents. A spacer sequence may have a "cycle specific" sequence in order to track binding agents used in a particular binding cycle. The spacer sequence (Sp) can be constant across all binding cycles, be specific for a particular class of macromolecules, or be binding cycle number specific. Macromolecule class-specific spacers permit annealing of a cognate binding agent's coding tag information present in an extended recording tag from a completed binding/extension cycle to the coding tag of another binding agent recognizing the same class of macromolecules in a subsequent binding cycle via the class-specific spacers. Only the sequential binding of correct cognate pairs results in interacting spacer elements and effective primer extension. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction. A spacer sequence may comprise a fewer number of bases than the encoder sequence within a coding tag.

As used herein, the term "recording tag" refers to a moiety, e.g., a chemical coupling moiety, a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred, or from which identifying information about the macromolecule (e.g., UMI information) associated with the recording tag can be transferred to the coding tag. Identifying information can comprise any information characterizing a molecule such as information pertaining to sample, fraction, partition, spatial location, interacting neighboring molecule(s), cycle number, etc. Additionally, the presence of UMI information can also be classified as identifying information. In certain embodiments, after a binding agent binds a polypeptide, information from a coding tag linked to a binding agent can be transferred to the recording tag associated with the polypeptide while the binding agent is bound to the polypeptide. In other embodiments, after a binding agent binds a polypeptide, information from a recording tag associated with the polypeptide can be transferred to the coding tag linked to the binding agent while the binding agent is bound to the polypeptide. A recoding tag may be directly linked to a polypeptide, linked to a polypeptide via a multifunctional linker, or associated with a polypeptide by virtue of its proximity (or co-localization) on a solid support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

As used herein, the term "primer extension", also referred to as "polymerase extension," refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases in length providing a unique identifier tag for each macromolecule (e.g., peptide) or binding agent to which the UMI is linked. A macromolecule UMI can be used to computationally deconvolute sequencing data from a plurality of extended recording tags to identify extended recording tags that originated from an individual macromolecule. A binding agent UMI can be used to identify each individual binding agent that binds to a particular macromolecule. For example, a UMI can be used to identify the number of individual binding events for a binding agent specific for a single amino acid that occurs for a particular peptide molecule. It is understood that when UMI and barcode are both referenced in the context of a binding agent or macromolecule, that the barcode refers to identifying information other that the UMI for the individual binding agent or macromolecule (e.g., sample barcode, compartment barcode, binding cycle barcode).

As used herein, the term "universal priming site" or "universal primer" or "universal priming sequence" refers to a nucleic acid molecule, which may be used for library amplification and/or for sequencing reactions. A universal priming site may include, but is not limited to, a priming site (primer sequence) for PCR amplification, flow cell adaptor sequences that anneal to complementary oligonucleotides on flow cell surfaces enabling bridge amplification in some next generation sequencing platforms, a sequencing priming site, or a combination thereof. Universal priming sites can be used for other types of amplification, including those commonly used in conjunction with next generation digital sequencing. For example, extended recording tag molecules may be circularized and a universal priming site used for rolling circle amplification to form DNA nanoballs that can be used as sequencing templates (Drmanac et al., 2009, *Science* 327:78-81). Alternatively, recording tag molecules may be circularized and sequenced directly by polymerase extension from universal priming sites (Korlach et al., 2008, Proc. Natl. Acad. Sci. 105:1176-1181). The term "forward" when used in context with a "universal priming site" or "universal primer" may also be referred to as "5'" or "sense." The term "reverse" when used in context with a "universal priming site" or "universal primer" may also be referred to as "3'" or "antisense."

As used herein, the term "extended recording tag" refers to a recording tag to which information of at least one binding agent's coding tag (or its complementary sequence) has been transferred following binding of the binding agent to an analyte, e.g., a macromolecule. Information of the coding tag may be transferred to the recording tag directly (e.g., ligation) or indirectly (e.g., primer extension). Information of a coding tag may be transferred to the recording tag enzymatically or chemically. An extended recording tag may comprise binding agent information of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 125, 150, 175, 200 or more coding tags. The base sequence of an extended recording tag may reflect the temporal and sequential order of binding of the binding agents identified by their coding tags, may reflect a partial sequential order of binding of the binding agents identified by the coding tags, or may not reflect any order of binding of the binding agents identified by the coding tags. In certain embodiments, the coding tag information present in the extended recording tag represents with at least 25%, 30%, 35%, 40%, 45%, 50%, 55%, 60%, 65%, 70%, 75%, 80%, 85%, 90%, 91%, 92%, 93%, 94%, 95%, 96%, 97% 98%, 99%, or 100% identity the macromolecule sequence being analyzed. In certain embodiments where the extended recording tag does not represent the macromolecule sequence being analyzed with 100% identity, errors may be due to off-target binding by a binding agent, or to a "missed" binding cycle (e.g., because a binding agent fails to bind to a macromolecule during a binding cycle, because of a failed primer extension reaction), or both.

As used herein, the term "extended coding tag" refers to a coding tag to which information of at least one recording tag (or its complementary sequence) has been transferred following binding of a binding agent, to which the coding tag is joined, to a macromolecule, to which the recording tag is associated. Information of a recording tag may be transferred to the coding tag directly (e.g., ligation), or indirectly (e.g., primer extension). Information of a recording tag may be transferred enzymatically or chemically. In certain embodiments, an extended coding tag comprises information of one recording tag, reflecting one binding event. As used herein, the term "di-tag" or "di-tag construct" or "di-tag molecule" refers to a nucleic acid molecule to which information of at least one recording tag (or its complementary sequence) and at least one coding tag (or its complementary sequence) has been transferred following binding of a binding agent, to which the coding tag is joined, to a macromolecule, to which the recording tag is associated (see, e.g., FIG. 11B). Information of a recording tag and coding tag may be transferred to the di-tag indirectly (e.g., primer extension). Information of a recording tag may be transferred enzymatically or chemically. In certain embodiments, a di-tag comprises a UMI of a recording tag, a compartment tag of a recording tag, a universal priming site of a recording tag, a UMI of a coding tag, an encoder sequence of a coding tag, a binding cycle specific barcode, a universal priming site of a coding tag, or any combination thereof.

As used herein, the term "solid support," "solid surface," or "solid substrate" or "substrate" refers to any solid material, including porous and non-porous materials, to which a macromolecule (e.g., peptide) can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, nylon, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, nitrocellulose, glass, gold, quartz, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polyactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, polystyrene bead, a polymer bead, a methylstyrene bead, an agarose bead, an acrylamide bead, a solid core bead, a porous bead, a paramagnetic bead, a glass bead, or a controlled pore bead. A bead may be spherical or an irregularly shaped. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 µm in diameter. In certain embodiments, "a bead" solid support may refer to an individual bead or a plurality of beads. As used herein, the term "substrate" includes a mechanical support upon which material may be disposed to provide functionality, whether mechanical, biological, optical, chemical or other functionality. A substrate may be unpatterned or patterned, partitioned or unpartitioned. Molecules on a substrate may be disposed in features or may be uniformly disposed on the substrate surface.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding.

As used herein, "nucleic acid sequencing" means the determination of the order of nucleotides in a nucleic acid molecule or a sample of nucleic acid molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays, as reviewed by Service (*Science* 311:1544-1546, 2006).

As used herein, "single molecule sequencing" or "third generation sequencing" refers to next-generation sequencing methods wherein reads from single molecule sequencing instruments are generated by sequencing of a single molecule of DNA. Unlike next generation sequencing methods that rely on amplification to clone many DNA molecules in parallel for sequencing in a phased approach, single molecule sequencing interrogates single molecules of DNA and does not require amplification or synchronization. Single molecule sequencing includes methods that need to pause the sequencing reaction after each base incorporation ('wash-and-scan' cycle) and methods which do not need to halt between read steps. Examples of single molecule sequencing methods include single molecule real-time sequencing (Pacific Biosciences), nanopore-based sequencing (Oxford Nanopore), duplex interrupted nanopore sequencing, and direct imaging of DNA using advanced microscopy.

As used herein, "analyzing" an analyte, e.g., a macromolecule, means to quantify, characterize, distinguish, or a combination thereof, all or a portion of the components of the analyte or macromolecule. For example, analyzing a peptide, polypeptide, or protein includes determining all or a portion of the amino acid sequence (contiguous or non-continuous) of the peptide. Analyzing a macromolecule also includes partial identification of a component of the macromolecule. For example, partial identification of amino acids in the macromolecule protein sequence can identify an amino acid in the protein as belonging to a subset of possible amino acids. Analysis typically begins with analysis of the $n^{th}$ NTAA, and then proceeds to the next amino acid of the peptide (i.e., n−1, n−2, n−3, and so forth). This is accomplished by cleavage of the $n^{th}$ NTAA, thereby converting the $(n-1)^{th}$ amino acid of the peptide to an N-terminal amino acid (referred to herein as the "(n−1)th NTAA"). Analyzing the peptide may also include determining the presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

As used herein, the term "compartment" refers to a physical area or volume that separates or isolates a subset of macromolecules from a sample of macromolecules. For example, a compartment may separate an individual cell from other cells, or a subset of a sample's proteome from the rest of the sample's proteome. A compartment may be an aqueous compartment (e.g., microfluidic droplet), a solid compartment (e.g., picotiter well or microtiter well on a plate, tube, vial, gel bead), or a separated region on a surface. A compartment may comprise one or more beads to which macromolecules may be immobilized.

As used herein, the term "compartment tag" or "compartment barcode" refers to a single or double stranded nucleic acid molecule of about 4 bases to about 100 bases (including 4 bases, 100 bases, and any integer between) that comprises identifying information for the constituents (e.g., a single cell's proteome), within one or more compartments (e.g., microfluidic droplet). A compartment barcode identifies a subset of macromolecules in a sample, e.g., a subset of protein sample, that have been separated into the same physical compartment or group of compartments from a plurality (e.g., millions to billions) of compartments. Thus, a compartment tag can be used to distinguish constituents derived from one or more compartments having the same compartment tag from those in another compartment having a different compartment tag, even after the constituents are pooled together. By labeling the proteins and/or peptides within each compartment or within a group of two or more compartments with a unique compartment tag, peptides derived from the same protein, protein complex, or cell within an individual compartment or group of compartments can be identified. A compartment tag comprises a barcode, which is optionally flanked by a spacer sequence on one or both sides, and an optional universal primer. The spacer sequence can be complementary to the spacer sequence of a recording tag, enabling transfer of compartment tag information to the recording tag. A compartment tag may also comprise a universal priming site, a unique molecular identifier (for providing identifying information for the peptide attached thereto), or both, particularly for embodiments where a compartment tag comprises a recording tag to be used in downstream peptide analysis methods described herein. A compartment tag can comprise a functional moiety (e.g., aldehyde, NHS, mTet, alkyne, etc.) for coupling to a peptide. Alternatively, a compartment tag can comprise a peptide comprising a recognition sequence for a protein ligase to allow ligation of the compartment tag to a peptide of interest. A compartment can comprise a single compartment tag, a plurality of identical compartment tags save for an optional UMI sequence, or two or more different compartment tags. In certain embodiments each compartment comprises a unique compartment tag (one-to-one mapping). In other embodiments, multiple compartments from a larger population of compartments comprise the same compartment tag (many-to-one mapping). A compartment tag may be joined to a solid support within a compartment (e.g., bead) or joined to the surface of the compartment itself (e.g., surface of a picotiter well). Alternatively, a compartment tag may be free in solution within a compartment.

As used herein, the term "partition" refers to random assignment of a unique barcode to a subpopulation of macromolecules from a population of macromolecules within a sample. In certain embodiments, partitioning may be achieved by distributing macromolecules into compartments. A partition may be comprised of the macromolecules within a single compartment or the macromolecules within multiple compartments from a population of compartments.

As used herein, a "partition tag" or "partition barcode" refers to a single or double stranded nucleic acid molecule of about 4 bases to about 100 bases (including 4 bases, 100 bases, and any integer between) that comprises identifying information for a partition. In certain embodiments, a partition tag for a macromolecule refers to identical compartment tags arising from the partitioning of macromolecules into compartment(s) labeled with the same barcode.

As used herein, the term "fraction" refers to a subset of macromolecules (e.g., proteins) within a sample that have been sorted from the rest of the sample or organelles using physical or chemical separation methods, such as fractionating by size, hydrophobicity, isoelectric point, affinity, and so on. Separation methods include HPLC separation, gel separation, affinity separation, cellular fractionation, cellular organelle fractionation, tissue fractionation, etc. Physical properties such as fluid flow, magnetism, electrical current, mass, density, or the like can also be used for separation.

As used herein, the term "fraction barcode" refers to a single or double stranded nucleic acid molecule of about 4 bases to about 100 bases (including 4 bases, 100 bases, and any integer therebetween) that comprises identifying information for the macromolecules within a fraction.

As used herein, the term "multiplexing" or "multiplex assay" herein may include an assay or other analytical method in which the presence and/or amount of multiple targets, e.g., multiple nucleic acid sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

III. Kits for Analyzing Analytes Including Macromolecules

A. Overview of the Articles of Manufacture and Kits

The kits and kit components described herein provide a highly-parallelized approach for analyte, e.g., macromolecule, analysis. Highly multiplexed analyte macromolecule binding assays are converted into a nucleic acid molecule library for readout by next generation sequencing. The kits and kit components provided herein are particularly useful for protein or peptide sequencing.

In a preferred embodiment, protein samples are labeled at the single molecule level with at least one nucleic acid recording tag that includes a barcode (e.g., sample barcode, compartment barcode) and an optional unique molecular identifier. The protein samples undergo proteolytic digest to produce a population of recording tag labeled peptides (e.g., millions to billions). These recording tag labeled peptides are pooled and immobilized randomly on a solid support (e.g., porous beads). The pooled, immobilized, recording tag labeled peptides are subjected to multiple, successive binding cycles, each binding cycle comprising exposure to a plurality of binding agents (e.g., binding agents for all twenty of the naturally occurring amino acids) that are labeled with coding tags comprising an encoder sequence that identifies the associated binding agent. During each binding cycle, information about the binding of a binding agent to the peptide is captured by transferring a binding agent's coding tag information to the recording tag (or transferring the recording tag information to the coding tag or transferring both recording tag information and coding tag information to a separate di-tag construct). Upon completion of binding cycles, a library of extended recording tags (or extended coding tags or di-tag constructs) is generated that represents the binding histories of the assayed peptides, which can be analyzed using very high-throughput next generation digital sequencing methods. The use of nucleic acid barcodes in the recording tag allows deconvolution of a massive amount of peptide sequencing data, e.g., to identify which sample, cell, subset of proteome, or protein, a peptide sequence originated from.

In one aspect, provided herein are a kit and kit components for use in a method for analysing a macromolecule, the method comprising: (a) providing a macromolecule and an associated or co-localized recording tag joined to a solid support; (b) contacting the macromolecule with a first binding agent capable of binding to the macromolecule, wherein the first binding agent comprises a first coding tag with identifying information regarding the first binding agent; (c) transferring the information of the first coding tag to the recording tag to generate a first order extended recording tag; (d) contacting the macromolecule with a second binding agent capable of binding to the macromolecule, wherein the second binding agent comprises a second coding tag with identifying information regarding the second binding agent; (e) transferring the information of the second coding tag is transferred to the first order extended recording tag to generate a second order extended recording tag; and (f) analysing the second order extended tag (see, e.g., FIG. 2A-D).

In certain embodiments, the contacting steps (b) and (d) are performed in sequential order, e.g., the first binding agent and the second binding agent are contacted with the macromolecule in separate binding cycle reactions. In other embodiments, the contacting steps (b) and (d) are performed at the same time, e.g., as in a single binding cycle reaction comprising the first binding agent, the second binding agent, and optionally additional binding agents. In a preferred embodiment, the contacting steps (b) and (d) each comprise contacting the macromolecule with a plurality of binding agents. Kit components are provided to perform these steps.

In certain embodiments, the method further comprises between steps (e) and (f) the following steps: (x) repeating steps (d) and (e) one or more times by replacing the second binding agent with a third (or higher order) binding agent capable of binding to the macromolecule, wherein the third (or higher order) binding agent comprises a third (or higher order) coding tag with identifying information regarding the third (or higher order) bind agent; and (y) transferring the information of the third (or higher order) coding tag to the second (or higher order) extended recording tag to generate a third (or higher order) extended recording tag; and (z) analysing the third (or higher order) extended recording tag. Kit components are provided to perform these steps.

The third (or higher order) binding agent may be contacted with the macromolecule in a separate binding cycle reaction from the first binding agent and the second binding agent. In one embodiment, a $n^{th}$ binding agent is contacted with the analyte (such as a macromolecule) at the $n^{th}$ binding cycle, and information is transferred from the $n^{th}$ coding tag (of the $n^{th}$ binding agent) to the extended recording tag formed in the $(n-1)^{th}$ binding cycle in order to form a further extended recording tag (the $n^{th}$ extended recording tag), wherein n is an integer of 2, 3, 4, 5, 6, 7, 8, 9, 10, 11, 12, 13, 14, 15, 16, 17, 18, 19, 20, 21, 22, 23, 24, 25, 26, 27, 28, 29, 30, or about 50, about 100, about 150, about 200, or more. Similarly, a $(n+1)^{th}$ binding agent is contacted with the analyte at the $(n+1)^{th}$ binding cycle, and so on.

Alternatively, the third (or higher order) binding agent may be contacted with the macromolecule in a single binding cycle reaction with the first binding agent, and the second binding agent. In this case, binding cycle specific sequences such as binding cycle specific coding tags may be used. For example, the coding tags may comprise binding cycle specific spacer sequences, such that only after information is transferred from the $n^{th}$ coding tag to the $(n-1)^{th}$ extended recording tag to form the $n^{th}$ extended recording tag, will then the $(n+1)^{th}$ binding agent (which may or may not already be bound to the analyte) be able to transfer information of the $(n+1)^{th}$ binding tag to the $n^{th}$ extended recording tag.

In a second aspect, provided herein are a kit and kit components for use in a method, the method comprising the steps of: (a) providing a macromolecule, an associated first recording tag and an associated second recording tag joined to a solid support; (b) contacting the macromolecule with a first binding agent capable of binding to the macromolecule, wherein the first binding agent comprises a first coding tag with identifying information regarding the first binding agent; (c) transferring the information of the first coding tag to the first recording tag to generate a first extended recording tag; (d) contacting the macromolecule with a second binding agent capable of binding to the macromolecule, wherein the second binding agent comprises a second coding tag with identifying information regarding the second binding agent; (e) transferring the information of the second coding tag to the second recording tag to generate a second extended recording tag; and (f) analyzing the first and second extended recording tags.

In certain embodiments, contacting steps (b) and (d) are performed in sequential order, e.g., the first binding agent and the second binding agent are contacted with the macromolecule in separate binding cycle reactions. In other embodiments, contacting steps (b) and (d) are performed at the same time, e.g., as in a single binding cycle reaction comprising the first binding agent, the second binding agent, and optionally additional binding agents. Kit components are provided to perform these steps.

In certain embodiments, step (a) further comprises providing an associated third (or higher order) recording tag joined to the solid support. In further embodiments, the method further comprises, between steps (e) and (f), the following steps: (x) repeating steps (d) and (e) one or more times by replacing the second binding agent with a third (or higher order) binding agent capable of binding to the macromolecule, wherein the third (or higher order) binding agent comprises a third (or higher order) coding tag with identifying information regarding the third (or higher order) bind agent; and (y) transferring the information of the third (or higher order) coding tag to the third (or higher order) recording tag to generate a third (or higher order) extended recording tag; and (z) analysing the first, second and third (or higher order) extended recording tags. Kit components are provided to perform these steps.

The third (or higher order) binding agent may be contacted with the macromolecule in a separate binding cycle reaction from the first binding agent and the second binding agent. Alternatively, the third (or higher order) binding agent may be contacted with the macromolecule in a single binding cycle reaction with the first binding agent, and the second binding agent.

In certain embodiments of the kit, the first coding tag, second coding tag, and any higher order coding tags each have a binding cycle specific sequence.

Figure 3:
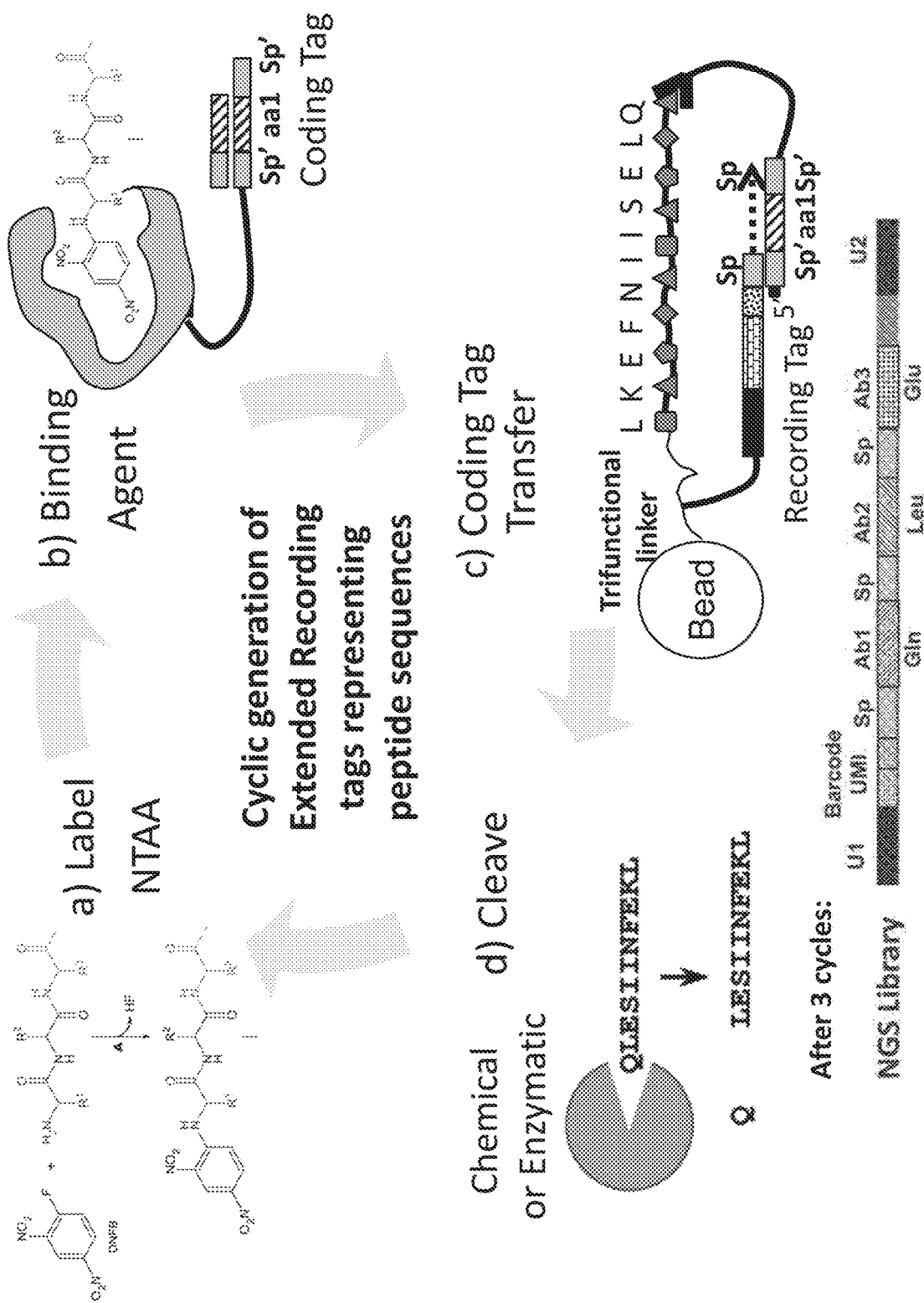
FIG. 3 illustrates a process for a degradation-based polypeptide sequencing assay by construction of an extended recording tag (e.g., DNA sequence) representing the polypeptide sequence. This is accomplished through an Edman degradation-like approach using a cyclic process, such as N-terminal amino acid (NTAA) binding, coding tag information transfer to a recording tag attached to the polypeptide, terminal amino acid(s) cleavage (such as NTAA cleavage), and repeating the process in a cyclic manner, for example, all on a solid support. Provided is an overview of an exemplary construction of an extended recording tag from N-terminal degradation of a peptide: (Step a) N-terminal amino acid of a peptide is labeled (e.g., with a phenylthiocarbamoyl (PTC), dinitrophenyl (DNP), sulfonyl nitrophenyl (SNP), acetyl, or guanidindyl moiety); (Step b) shows a binding agent and an associated coding tag bound to the labeled NTAA; (Step c) shows the polypeptide bound to a solid support (e.g., bead) and associated with a recording tag (e.g., via a trifunctional linker), wherein upon binding of the binding agent to the NTAA of the polypeptide, information of the coding tag is transferred to the recording tag (e.g., via primer extension or ligation, including single strand ligation or double strand ligation or blunt end ligation or sticky end ligation) to generate an extended recording tag; (Step d) the labeled NTAA is cleaved via chemical or biological (e.g., enzymatic) means to expose a new NTAA. As illustrated by the arrows, the cycle is repeated "n" times to generate a final extended recording tag. The final extended recording tag is optionally flanked by universal priming sites to facilitate downstream amplification and/or DNA sequencing. The forward universal priming site (e.g., Illumina's P5-S1 sequence) can be part of the original recording tag design and the reverse universal priming site (e.g., Illumina's P7-S2' sequence) can be added as a final step in the extension of the recording tag. This final step may be done independently of a binding agent. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In a third aspect, provided herein are a kit and kit components for use in a method, the method comprising the steps of: (a) providing a peptide and an associated recording tag joined to a solid support; (b) modifying the N-terminal amino acid (NTAA) of the peptide with a chemical moiety to produce a modified NTAA; (c) contacting the peptide with a first binding agent capable of binding to the modified NTAA, wherein the first binding agent comprises a first coding tag with identifying information regarding the first binding agent; (d) transferring the information of the first coding tag to the recording tag to generate an extended recording tag; and (e) analyzing the extended recording tag (see, e.g. FIG. 3).

In certain embodiments, step (c) further comprises contacting the peptide with a second (or higher order) binding agent comprising a second (or higher order) coding tag with identifying information regarding the second (or higher order) binding agent, wherein the second (or higher order) binding agent is capable of binding to a modified NTAA other than the modified NTAA of step (b). In further embodiments, contacting the peptide with the second (or higher order) binding agent occurs in sequential order following the peptide being contacted with the first binding agent, e.g., the first binding agent and the second (or higher order) binding agent are contacted with the peptide in separate binding cycle reactions. In other embodiments, contacting the peptide with the second (or higher order) binding agent occurs simultaneously with the peptide being contacted with the first binding agent, e.g., as in a single binding cycle reaction comprising the first binding agent and the second (or higher order) binding agent). Kit components are provided to perform these steps.

In certain embodiments, the chemical moiety is added to the NTAA via chemical reaction or enzymatic reaction.

In certain embodiments, the chemical moiety used for modifying the NTAA is a phenylthiocarbamoyl (PTC), dinitrophenol (DNP) moiety; a sulfonyloxynitrophenyl (SNP) moiety, a dansyl moiety; a 7-methoxy coumarin moiety; a thioacyl moiety; a thioacetyl moiety; an acetyl moiety; a guanidinyl moiety; or a thiobenzyl moiety.

A chemical moiety may be added to the NTAA using a chemical agent. In certain embodiments, the chemical agent for modifying an NTAA with a PTC moiety is a phenyl isothiocyanate or derivative thereof, the chemical agent for modifying an NTAA with a DNP moiety is 2,4-dinitrobenzenesulfonic acid (DNBS) or an aryl halide such as 1-Fluoro-2,4-dinitrobenzene (DNFB); the chemical agent for modifying an NTAA with a sulfonyloxynitrophenyl (SNP) moiety is 4-sulfonyl-2-nitrofluorobenzene (SNFB); the chemical agent for modifying an NTAA with a dansyl group is a sulfonyl chloride such as dansyl chloride; the chemical agent for modifying an NTAA with a 7-methoxy coumarin moiety is 7-methoxycoumarin acetic acid (MCA); the chemical agent for modifying an NTAA with a thioacyl moiety is a thioacylation reagent; the chemical agent for modifying an NTAA with a thioacetyl moiety is a thioacetylation reagent; the chemical agent for modifying an NTAA with an acetyl moiety is an acetylating reagent (e.g., acetic anhydride); the chemical agent for modifying an NTAA with a guanidinyl (amidinyl) moiety is a guanidinylating reagent, or the chemical agent for modifying an NTAA with a thiobenzyl moiety is a thiobenzylation reagent. Any of these chemical moieties and chemical agents may be provided as a component of the kit disclosed herein.

In a fourth aspect the present disclosure provides a kit and kit components for use in a method comprising the steps of: (a) providing a peptide and an associated recording tag joined to a solid support; (b) modifying the N-terminal amino acid (NTAA) of the peptide with a chemical moiety to produce a modified NTAA; (c) contacting the peptide with a first binding agent capable of binding to the modified NTAA, wherein the first binding agent comprises a first coding tag with identifying information regarding the first binding agent; (d) transferring the information of the first coding tag to the recording tag to generate a first extended recording tag; (e) removing the modified NTAA to expose a new NTAA; (f) modifying the new NTAA of the peptide with a chemical moiety to produce a newly modified NTAA; (g) contacting the peptide with a second binding agent capable of binding to the newly modified NTAA, wherein the second binding agent comprises a second coding tag with identifying information regarding the second binding agent; (h) transferring the information of the second coding tag to the first extended recording tag to generate a second extended recording tag; and (i) analyzing the second extended recording tag.

In certain embodiments, the contacting steps (c) and (g) are performed in sequential order, e.g., the first binding agent and the second binding agent are contacted with the peptide in separate binding cycle reactions. Kit components are provided to perform these steps.

In certain embodiments, the method further comprises between steps (h) and (i) the following steps: (x) repeating steps (e), (f), and (g) one or more times by replacing the second binding agent with a third (or higher order) binding agent capable of binding to the modified NTAA, wherein the third (or higher order) binding agent comprises a third (or higher order) coding tag with identifying information regarding the third (or higher order) bind agent; and (y) transferring the information of the third (or higher order) coding tag to the second (or higher order) extended recording tag to generate a third (or higher order) extended recording tag; and (z) analysing the third (or higher order) extended recording tag. Kit components are provided to perform these steps.

In certain embodiments, the chemical moiety is added to the NTAA via chemical reaction or enzymatic reaction.

In certain embodiments, the chemical moiety is a phenylthiocarbamoyl (PTC), dinitrophenol (DNP) moiety; a sulfonyloxynitrophenyl (SNP) moiety, a dansyl moiety; a 7-methoxy coumarin moiety; a thioacyl moiety; a thioacetyl moiety; an acetyl moiety; a guanyl moiety; or a thiobenzyl moiety.

A chemical moiety may be added to the NTAA using a chemical agent. In certain embodiments, the chemical agent for modifying an NTAA with a PTC moiety is a phenyl isothiocyanate or derivative thereof, the chemical agent for modifying an NTAA with a DNP moiety is 2,4-dinitrobenzenesulfonic acid (DNBS) or an aryl halide such as 1-Fluoro-2,4-dinitrobenzene (DNFB); the chemical agent for modifying an NTAA with a sulfonyloxynitrophenyl (SNP) moiety is 4-sulfonyl-2-nitrofluorobenzene (SNFB); the chemical agent for modifying an NTAA with a dansyl group is a sulfonyl chloride such as dansyl chloride; the chemical reagent for modifying an NTAA with a 7-methoxy coumarin moiety is 7-methoxycoumarin acetic acid (MCA); the chemical agent for modifying an NTAA with a thioacyl moiety is a thioacylation reagent; the chemical agent for modifying an NTAA with a thioacetyl moiety is a thioacetylation reagent; the chemical agent for modifying an NTAA with an acetyl moiety is an acetylating agent (e.g., acetic anhydride); the chemical agent for modifying an NTAA with a guanyl moiety is a guanidinylating reagent, or the chemical agent for modifying an NTAA with a thiobenzyl moiety is a thiobenzylation reagent. Any of these chemical moieties and chemical agents may be provided as a component of the kit disclosed herein.

In a fifth aspect, a kit and kit components for use in a method for analyzing a polypeptide are provided, the method comprising the steps of: (a) providing a peptide and an associated recording tag joined to a solid support; (b) contacting the peptide with a first binding agent capable of binding to the N-terminal amino acid (NTAA) of the peptide, wherein the first binding agent comprises a first coding tag with identifying information regarding the first binding agent; (c) transferring the information of the first coding tag to the recording tag to generate an extended recording tag; and (d) analyzing the extended recording tag.

In certain embodiments, step (b) further comprises contacting the peptide with a second (or higher order) binding agent comprising a second (or higher order) coding tag with identifying information regarding the second (or higher order) binding agent, wherein the second (or higher order) binding agent is capable of binding to a NTAA other than the NTAA of the peptide. In further embodiments, the contacting the peptide with the second (or higher order) binding agent occurs in sequential order following the peptide being contacted with the first binding agent, e.g., the first binding agent and the second (or higher order) binding agent are contacted with the peptide in separate binding cycle reactions. In other embodiments, the contacting the peptide with the second (or higher order) binding agent occurs at the same time as the peptide the being contacted with first binding agent, e.g., as in a single binding cycle reaction comprising the first binding agent and the second (or higher order) binding agent.

In a sixth aspect, a kit and kit components for use in a method are provided, the method comprising the steps of: (a) providing a peptide and an associated recording tag joined to a solid support; (b) contacting the peptide with a first binding agent capable of binding to the N-terminal amino acid (NTAA) of the peptide, wherein the first binding agent comprises a first coding tag with identifying information regarding the first binding agent; (c) transferring the information of the first coding tag to the recording tag to generate a first extended recording tag; (d) removing the NTAA to expose a new NTAA of the peptide; (e) contacting the peptide with a second binding agent capable of binding to the new NTAA, wherein the second binding agent comprises a second coding tag with identifying information regarding the second binding agent; (f) transferring the information of the second coding tag to the first extended recording tag to generate a second extended recording tag; and (g) analyzing the second extended recording tag.

In certain embodiments, the method further comprises between steps (f) and (g) the following steps: (x) repeating steps (d), (e), and (f) one or more times by replacing the second binding agent with a third (or higher order) binding agent capable of binding to the macromolecule, wherein the third (or higher order) binding agent comprises a third (or higher order) coding tag with identifying information regarding the third (or higher order) bind agent; and (y) transferring the information of the third (or higher order) coding tag to the second (or higher order) extended recording tag to generate a third (or higher order) extended recording tag; and wherein the third (or higher order) extended recording tag is analyzed in step (g). Kit components are provided to perform these steps.

In certain embodiments, the contacting steps (b) and (e) are performed in sequential order, e.g., the first binding agent and the second binding agent are contacted with the peptide in separate binding cycle reactions.

In any of the embodiments provided herein, the methods comprise analyzing a plurality of macromolecules in parallel. In a preferred embodiment, the methods comprise analyzing a plurality of peptides in parallel.

In any of the embodiments provided herein, the step of contacting a macromolecule (or peptide) with a binding agent comprises contacting the macromolecule (or peptide) with a plurality of binding agents.

In any of the embodiments provided herein, the macromolecule may be a protein, polypeptide, or peptide. In further embodiments, the peptide may be obtained by fragmenting a protein or polypeptide from a biological sample.

In any of the embodiments provided herein, the macromolecule may be or comprise a carbohydrate, lipid, nucleic acid, or macrocycle.

In any of the embodiments provided herein, the recording tag may be a DNA molecule, a DNA molecule with modified bases, an RNA molecule, a BNA, molecule, a XNA molecule, an LNA molecule, a PNA molecule, a γPNA molecule (Dragulescu-Andrasi et al., 2006, *J. Am. Chem. Soc.* 128: 10258-10267), a GNA molecule, or any combination thereof.

In any of the embodiments provided herein, the recording tag may comprise a universal priming site. In further embodiments, the universal priming site comprises a priming site for amplification, ligation, sequencing, or a combination thereof.

In any of the embodiments provided herein, the recording tag may comprise a unique molecular identifier, a compartment tag, a partition barcode, sample barcode, a fraction barcode, a spacer sequence, or any combination thereof.

In any of the embodiments provided herein, the coding tag may comprise a unique molecular identifier (UMI), an encoder sequence, a binding cycle specific sequence, a spacer sequence, or any combination thereof.

In any of the embodiments provided herein, the binding cycle specific sequence in the coding tag may be a binding cycle-specific spacer sequence.

In certain embodiments, a binding cycle specific sequence is encoded as a separate barcode from the encoder sequence. In other embodiments, the encoder sequence and binding cycle specific sequence is set forth in a single barcode that is unique for the binding agent and for each cycle of binding.

In certain embodiments, the spacer sequence comprises a common binding cycle sequence that is shared among binding agents from the multiple binding cycles. In other embodiments, the spacer sequence comprises a unique binding cycle sequence that is shared among binding agents from the same binding cycle.

In any of the embodiments provided herein, the recording tag may comprise a barcode.

In any of the embodiments provided herein, the macromolecule and the associated recording tag(s) may be covalently joined to the solid support.

In any of the embodiments provided herein, the solid support may be a bead, a porous bead, a porous matrix, an expandable gel bead or matrix, an array, a glass surface, a silicon surface, a plastic surface, a filter, a membrane, nylon, a silicon wafer chip, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere.

In any of the embodiments provided herein, the solid support may be a polystyrene bead, a polymer bead, an agarose bead, an acrylamide bead, a solid core bead, a porous bead, a paramagnetic bead, glass bead, or a controlled pore bead.

In any of the embodiments provided herein, a plurality of macromolecules and associated recording tags may be joined to a solid support. In further embodiments, the plurality of analytes (such as macromolecules) are spaced apart on the solid support at an average distance >50 nm, >100 nm, or >200 nm.

In any of the embodiments provided herein, the binding agent may be a polypeptide or protein. In further embodiments, the binding agent is a modified or variant aminopeptidase, a modified or variant amino acyl tRNA synthetase, a modified or variant anticalin, or a modified or variant ClpS.

In any of the embodiments provided herein, the binding agent may be capable of selectively binding to the macromolecule.

In any of the embodiments provided herein, the coding tag may be a DNA molecule, DNA molecule with modified bases, an RNA molecule, a BNA molecule, an XNA molecule, a LNA molecule, a GNA molecule, a PNA molecule, a γPNA molecule, or a combination thereof.

In any of the embodiments provided herein, the binding agent and the coding tag may be joined by a linker.

In any of the embodiments provided herein, the binding agent and the coding tag may be joined by a SpyTag/SpyCatcher, a SpyTag-KTag/SpyLigase (where two moieties to be joined have the SpyTag/KTag pair, and the SpyLigase joins SpyTag to KTag, thus joining the two moieties), a sortase, and/or SnoopTag/SnoopCatcher peptide-protein pair (Zakeri, et al., 2012, Proc Natl Acad Sci USA 109(12): E690-697; Veggiani et al., 2016, Proc. Natl. Acad. Sci. USA 113:1202-1207, each of which is incorporated by reference in its entirety).

The SpyLigase is a protein domain that ligates two peptide tags to each other, in order to form irreversible peptide-peptide interaction. Fierer et al., (2014), "SpyLigase peptide-peptide ligation polymerizes affibodies to enhance magnetic cancer cell capture," PNAS 111(13): E1176-E1181, which is incorporated by reference in its entirety.

A sortase may also be used to join the binding agent and the coding tag. For example, a sortase may selectively join a LPXTG Tag (where X represents any amino acid) to a poly G moiety, such as GGG. A sortase A5, for example, from ActiveMotif, San Diego, or as disclosed in U.S. Pat. No. 9,267,127 B2 may be used. In another example, a sortase comprising an amino acid sequence that is at least about 50%, at least about 60%, at least about 70%, at least about 75%, at least about 80%, at least about 85%, at least about 90%, at least about 95%, at least about 99%, or 100% identical to the amino acid sequence of *Staphylococcus aureus* (*S. aureus*) Sortase A may be used.

In any of the embodiments provided herein, the transferring of information of the coding tag to the recording tag is mediated by a ligase, such as a DNA ligase, e.g., a single-stranded DNA (ssDNA) ligase. In one aspect, the 5' end of one of the two single strand polynucleotides to be ligated is blocked to prevent ligation at that 5' end. In any of the preceding embodiments, the ssDNA ligase can be a *Thermus* bacteriophage RNA ligase such as a bacteriophage TS2126 RNA ligase (e.g., CircLigase™ and CircLigase II™) or a variant, homologue, mutant, or modified version thereof, or an archaebacterium RNA ligase such as *Methanobacterium thermoautotrophicum* RNA ligase 1 or a variant, homologue, mutant, or modified version thereof. In other aspects, the ssDNA ligase is an RNA ligase, such as a T4 RNA ligase, e.g., T4 RNA ligase 2, T4 RNA ligase 2 truncated, T4 RNA ligase 2 truncated KQ, or T4 RNA ligase 2 truncated K227Q. In one aspect, the ligation reaction may be optimized by using a crowding agent, such as PEG 4000. T4 DNA Ligase and Ampligase® DNA Ligase may also be used, when DNA ends to be ligated are annealed adjacent to each other on a complementary DNA sequence.

Alternatively, the transferring of information of the coding tag to the recording tag is mediated by a DNA polymerase or chemical ligation. In some embodiments, the chemical ligation comprises Michael additions, such as thiol-maleimide couplings. In some embodiments, the chemical ligation comprises copper catalysed azide-alkyne cycloaddition. In some embodiments, the chemical ligation comprises amide bond formation. In some embodiments, the amide bond formation proceeds between an NHS ester and amine or a carboxylic acid and amine in the presence of peptide coupling agents. In some embodiments, the chemical ligation comprises imine formation via an amine and aldehyde followed by reduction using sodium cyanoborohydride. In some embodiments, the chemical ligation comprises a thiolene coupling. In some embodiments, the chemical ligation comprises native chemical ligation (e.g., (thio)(l)ester plus cysteine). In some embodiments, the reagent for chemical ligation comprises strained alkynes (e.g., cyclooctyne) and azides. In some embodiments, the chemical ligation comprises traceless and non-traceless Staudinger ligation.

In any of the embodiments provided herein, analyzing the extended recording tag may comprise nucleic acid sequencing. In further embodiments, nucleic acid sequencing is sequencing by synthesis, sequencing by ligation, sequencing by hybridization, polony sequencing, ion semiconductor sequencing, or pyrosequencing. In other embodiments, nucleic acid sequencing is single molecule real-time sequencing, nanopore-based sequencing, nanogap tunneling sequencing, or direct imaging of DNA using advanced microscopy.

In any of the embodiments provided herein, the extended recording tag may be amplified prior to analysis.

In any of the embodiments provided herein, the order of the coding tag information contained on the extended recording tag may provide information regarding the order of binding by the binding agents to the macromolecule and thus, the sequence of analytes detected by the binding agents.

In any of the embodiments provided herein, the frequency of a particular coding tag information (e.g., encoder sequence) contained on the extended recording tag may provide information regarding the frequency of binding by a particular binding agent to the macromolecule and thus, the frequency of the analyte in the macromolecule detected by the binding agent.

In any of the embodiments disclosed herein, multiple macromolecule (e.g., protein) samples, wherein a population of macromolecules within each sample are labeled with recording tags comprising a sample specific barcode, can be pooled. Such a pool of macromolecule samples may be subjected to binding cycles within a single-reaction tube.

In any of the embodiments provided herein, the plurality of extended recording tags representing a plurality of macromolecules may be analyzed in parallel.

In any of the embodiments provided herein, the plurality of extended recording tags representing a plurality of macromolecules may be analyzed in a multiplexed assay.

In any of the embodiments provided herein, the plurality of extended recording tags may undergo a target enrichment assay prior to analysis.

In any of the embodiments provided herein, the plurality of extended recording tags may undergo a subtraction assay prior to analysis.

In any of the embodiments provided herein, the plurality of extended recording tags may undergo a normalization assay to reduce highly abundant species prior to analysis.

In any of the embodiments provided herein, the NTAA may be removed by a modified aminopeptidase, a modified amino acid tRNA synthetase, a mild Edman degradation, an Edmanase enzyme, or anhydrous TFA.

In any of the embodiments provided herein, at least one binding agent may bind to a terminal amino acid residue. In certain embodiments the terminal amino acid residue is an N-terminal amino acid or a C-terminal amino acid.

In any of the embodiments described herein, at least one binding agent may bind to a post-translationally modified amino acid.

In some embodiments, provided herein is a small molecule-protein binding matrix. In some embodiments, this can be a rather large matrix, even when a small molecule library of $10^9$ diversity incubated with the entire immobilized human proteome ($2\times10^4$). The matrix size will be $10^9 \times 2 \times 10^4$ with $2\times10^{13}$ different measurements. In some embodiments, high affinity binding interactions (<low nM) can easily be recorded with the above approach, even after a wash step, but moderate to low affinity interactions will likely be lost. In some embodiments, in order to record low affinity interactions (~μM), a homogenous reaction in which binding and simultaneous information transfer occurs is desirable. In some embodiments, this requires that the polymerization or ligation step needs to have fast kinetics relative to the binding occupancy time. Polymerization time scales are on the order of seconds, and is compatible with the binding occupancy time at pM concentrations (~10-100 sec). The ligation time scale can be on the order of seconds as well (e.g., for rapid chemical ligation, see, e.g., Abe et al., (2008), "Rapid DNA chemical ligation for amplification of RNA and DNA signal," *Bioconjug Chem* 19(1): 327-333). In some embodiments, a ligase or a polymerase can be included in the reaction mix along with one or more binders, particularly for analyzing or detecting low affinity interactions. Alternatively, the ligase or polymerase can be co-localized to the agent site using hybridization via DNA tag interacting with a site within the recording tag. By making the combining the bind and "write" (i.e., information transfer) steps, it is easier to "record" low affinity interactions.

In one embodiment, the attachment of the DNA tags to either the protein targets or to the peptide or small molecule ligands (or a peptidomimetic ligand, e.g., a peptoid ligand, a β-peptide ligand, or a D-peptide peptidomimetic ligand, or a polysaccharide ligand) can be accomplished via individual attachment of barcoded DNA tags to individually produced protein targets or individually produced small molecule/peptide targets. In another embodiment, the attachment of DNA tags to protein occurs via ribosome or mRNA/cDNA display in which the DNA barcode is contained within the mRNA sequence. In the process of mRNA/cDNA display, the mRNA is translated into a protein using an in vitro translation reaction. The mRNA is configured to have a puromycin molecule attached to the 3' end of the mRNA via a linker (see, e.g., Liu et al., (2000), "Optimized synthesis of RNA-protein fusions for in vitro protein selection," In Methods in Enzymology, Academic Press, 318:268-293). Puromycin, an analogue of tyrosyl-tRNA, is tethered to the 3' end of the mRNA transcript and incorporates into the growing polypeptide strand when the ribosome nears the 3' end, terminates translation, and effectively creates an mRNA-protein fusion linking the RNA/DNA transcript and associated barcode to its corresponding translated protein (e.g., as disclosed in US 2012/0258871 A1, US 2017/0107566 A1, or Kozlov et al., (2012), *PLoS One* 7(6): e37441, all of which are incorporated herein by reference).

Figure 50A:
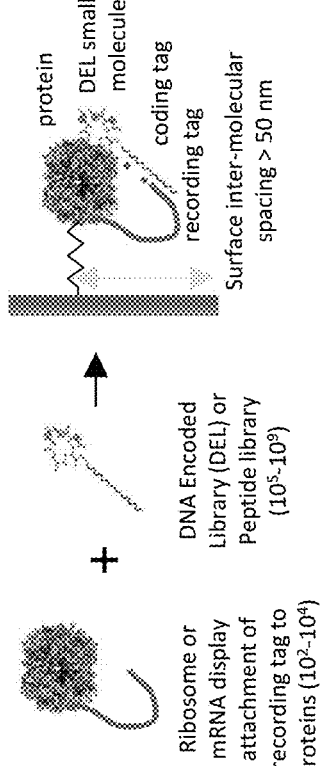
FIG. 50A-50C illustrate labeling a protein or peptide with a DNA recording Tag using mRNA Display. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.
Figure 50B:
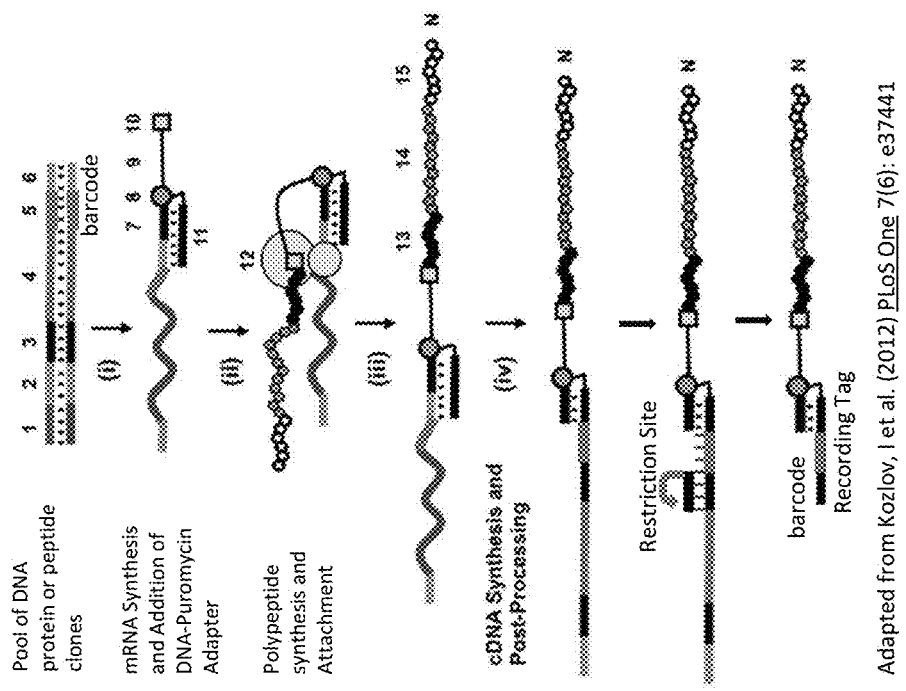
Figure 50C:
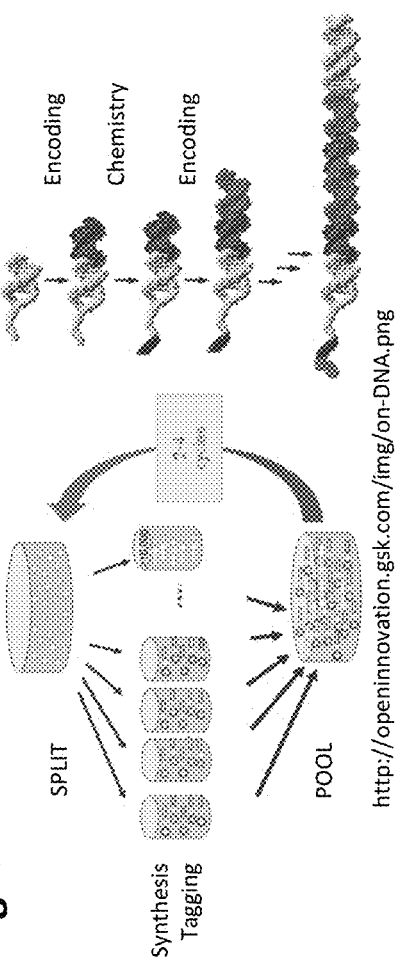

In one embodiment, the barcode sequence and associate DNA recording tag functional elements such as a universal primer site and spacer sequence for downstream information transfer is engineered into the 3' end of the mRNA transcript. In one embodiment, a unique restriction site is also included just 5' of the DNA barcode and DNA recording tag functional elements. After in vitro translation and creation of the mRNA-protein fusion, the mRNA is reverse translated into cDNA. The cDNA is cleaved 5' to the barcode by annealing an exogenous oligo and incubation with a restriction enzyme. This leaves a DNA tag which serves as a recording tag for subsequent assays (see, e.g., FIG. 50A-C).

In another aspect, disclosed herein are Next Generation Protein Assays with a single cycle. In some embodiments, the assay uses amino acid binders, such as NTAA binders (e.g., mono-, di-, or tri-amino acids at N-terminus).

Typical protein identification by bottom-up mass spectrometry (MS) uses a protease digestion step, such as trypsin digestion, to generate a set of peptides (~20-40 peptides) from each protein. A single peptide species can be analyzed on LC-MS/MS and provide identification of the entire protein species. WO/2015/042506, incorporated herein by reference, also discloses a protein identification method on the single molecule level. Reagents and method steps of WO/2015/042506 may be combined with the present disclosure.

An alternative approach for protein identification, on the single molecule level, is to partition the protein molecules into millions to billions of partitions (e.g., partitions comprising compartment barcodes), and barcode all the molecules in a sample with a partition barcode. In one aspect, for a given compartment (e.g., individual bead surface), all the molecules within that compartment are labeled with the same barcode. In another aspect, a partition comprises all the compartments sharing the same barcode. For example, if there are $10^6$ barcodes on 108 beads, some of the beads will have the same barcode. In this example, each individual bead surface can be a compartment, and the compartments sharing the same barcode form a partition that is distinguishable from the other partitions based on the differences in barcodes. In the preferred embodiment, proteins are first denatured and alkylated, and then labeled with "click" chemistry handles throughout the polypeptide. After attachment of "click" handles, a universal DNA primer is attached to the "click" handles using click chemistry. This DNA primer will form the initial portion of the DNA recording tag. The polypeptides are purified from excess DNA primers. After labeling of polypeptides with DNA primers, the polypeptide is exposed to a population of DNA barcoded beads with compartment barcodes and a universal primer complementary to that on the polypeptide (see, e.g., FIG. 51A-E). Individual polypeptide molecules interact with a particular bead and essentially "zip-up" on the bead via hybridization through the universal primer sequence. More than one molecule can become associated with any given bead, but ideally the number of molecules is kept to a minimum. Once a polypeptide is "zipped" onto the bead, a primer extension or ligation reaction is used to transfer the bead's barcode information onto the many universal primers attached to the polypeptide. In this way, the polypeptide is now "compartment" barcoded, forming the basis for the partitioning of a proteome. Extended DNA tags on a polypeptide molecule constitute recording tags for subsequent steps in the assay. Next the polypeptides on the bead (can be removed first) are fragmented using a protease digestion step (e.g. trypsin digestion). After digestion, the recording tag labeled peptides are eluted from the beads. The labeled peptides are immobilized to a substrate at single molecule density (e.g. inter-peptide distance is such that the average distance between immobilized peptides largely restricts information transfer to only intra-molecular binding events). Exemplary distances for the spacing may be equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 μm.

In one embodiment, the peptides originate from a tryptic digest. For the human proteome, there are roughly 500,000 different tryptic peptides with about 20-30 tryptic peptides per protein. To quantitate and characterize the protein molecules in a sample, the proteins are converted to a set of peptides labeled with partition barcoded recording tags. All the information from binding to tryptic peptides originating from a given molecule can be mapped back to the molecule (or small subset of molecules) by the partition barcode. In a preferred embodiment, N-terminal dipeptide and/or tripeptide (also referred to as N-terminal diamino/triamino acid) binding agents, labeled with DNA coding tags comprised of barcode information identifying the binder, are incubated with the immobilized peptides (such that the N-terminus is free). Upon or after binding, information is transferred from the coding tag to the recording tag (or vice versa) by polymerase extension or ligation. This process can be repeated multiple cycles to reduce errors from cross-reactive binding events. A complete set of N-terminal dipeptide binders would constitute a set of 400 different binders, each labeled with a different identifying barcode. A single binding cycle should be more than sufficient to identify the entire human proteome using the partition concept. For instance, even if only 5 tryptic peptides out of a set of 20 peptides from a given protein molecule are detected, the N-terminal di-amino acid information in combination with the tryptic digest information, is more than sufficient to uniquely identify the protein.

Alternative to first immobilizing polypeptides to a partition barcoded bead and re-immobilizing to an analysis substrate, the denatured peptide can be directly immobilized on a DNA barcoded bead through covalent or non-covalent interactions, wherein the entire bead is covered with a population of identical barcoded recording tags (see, e.g., FIG. 52A-E). The polypeptide is digested on bead into fragments, such as a tryptic digest. After protease digestion, binding of N-terminal dipeptide binders to the exposed N-termini of the polypeptide on the barcoded bead ensues. Information transfer occurs between the coding tag on the dipeptide binder and any of the recording tags attached to the bead. Unlike the previous "distantly spaced" peptide model (see, e.g., FIG. 51A-E), the peptide complexes do not have to be spaced apart as in the previous embodiment so long as only a single cycle of binding is performed. After binding and information transfer, the resultant extended recording tags can be amplified directly from the bead surface into solution using linear amplification or PCR.

In some embodiments, the assays disclosed above do not require the cyclic transfer of information between a coding tag and a recording tag. Therefore, these assays can be conducted in a single binding cycle.

Features of the aforementioned embodiments are provided in further detail in the following sections.

B. Macromolecules

In one aspect, the present disclosure relates to the analysis of macromolecules. A macromolecule is a large molecule composed of smaller subunits. In certain embodiments, a macromolecule is a protein, a protein complex, polypeptide, peptide, nucleic acid molecule, carbohydrate, lipid, macrocycle, or a chimeric macromolecule.

A macromolecule (e.g., protein, polypeptide, peptide) analyzed according the kits and methods disclosed herein may be obtained from a suitable source or sample, including but not limited to: biological samples, such as cells (both primary cells and cultured cell lines), cell lysates or extracts, cell organelles or vesicles, including exosomes, tissues and tissue extracts; biopsy; fecal matter; bodily fluids (such as blood, whole blood, serum, plasma, urine, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (normal joint or a joint affected by disease such as rheumatoid arthritis, osteoarthritis, gout or septic arthritis) of virtually any organism, with mammalian-derived samples, including microbiome-containing samples, being preferred and human-derived samples, including microbiome-containing samples, being particularly preferred; environmental samples (such as air, agricultural, water and soil samples); microbial samples including samples derived from microbial biofilms and/or communities, as well as microbial spores; research samples including extracellular fluids, extracellular supernatants from cell cultures, inclusion bodies in bacteria, cellular compartments including mitochondrial compartments, and cellular periplasm.

In certain embodiments, a macromolecule is a protein, a protein complex, a polypeptide, or peptide. Amino acid sequence information and post-translational modifications of a peptide, polypeptide, or protein are transduced into a nucleic acid encoded library that can be analyzed via next generation sequencing methods. A peptide may comprise L-amino acids, D-amino acids, or both. A peptide, polypeptide, protein, or protein complex may comprise a standard, naturally occurring amino acid, a modified amino acid (e.g., post-translational modification), an amino acid analog, an amino acid mimetic, or any combination thereof. In some embodiments, a peptide, polypeptide, or protein is naturally occurring, synthetically produced, or recombinantly expressed. In any of the aforementioned peptide embodiments, a peptide, polypeptide, protein, or protein complex may further comprise a post-translational modification.

Standard, naturally occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). Non-standard amino acids include selenocysteine, pyrrolysine, and N-formylmethionine, 3-amino acids, Homo-amino acids, Proline and Pyruvic acid derivatives, 3-substituted Alanine derivatives, Glycine derivatives, Ring-substituted Phenylalanine and Tyrosine Derivatives, Linear core amino acids, and N-methyl amino acids.

A post-translational modification (PTM) of a peptide, polypeptide, or protein may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation (e.g., N-linked, O-linked, C-linked, phosphoglycosylation), glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide, polypeptide, or protein. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is C1-C4 alkyl). A post-translational modification also includes modifications, such as but not limited to those described above, of amino acids falling between the amino and carboxy termini of a peptide, polypeptide, or protein. Post-translational modification can regulate a protein's "biology" within a cell, e.g., its activity, structure, stability, or localization. Phosphorylation is the most common post-translational modification and plays an important role in regulation of protein, particularly in cell signaling (Prabakaran et al., 2012, Wiley Interdiscip Rev Syst Biol Med 4: 565-583). The addition of sugars to proteins, such as glycosylation, has been shown to promote protein folding, improve stability, and modify regulatory function. The attachment of lipids to proteins enables targeting to the cell membrane. A post-translational modification can also include peptide, polypeptide, or protein modifications to include one or more detectable labels.

In certain embodiments, a peptide, polypeptide, or protein can be fragmented. For example, the fragmented peptide can be obtained by fragmenting a protein from a sample, such as a biological sample. The peptide, polypeptide, or protein can be fragmented by any means known in the art, including fragmentation by a protease or endopeptidase. In some embodiments, fragmentation of a peptide, polypeptide, or protein is targeted by use of a specific protease or endopeptidase. A specific protease or endopeptidase binds and cleaves at a specific consensus sequence (e.g., TEV protease which is specific for ENLYFQ\S consensus sequence). In other embodiments, fragmentation of a peptide, polypeptide, or protein is non-targeted or random by use of a non-specific protease or endopeptidase. A non-specific protease may bind and cleave at a specific amino acid residue rather than a consensus sequence (e.g., proteinase K is a non-specific serine protease). Proteinases and endopeptidases are well known in the art, and examples of such that can be used to cleave a protein or polypeptide into smaller peptide fragments include proteinase K, trypsin, chymotrypsin, pepsin, thermolysin, thrombin, Factor Xa, furin, endopeptidase, papain, pepsin, subtilisin, elastase, enterokinase, Genenase™ I, Endoproteinase LysC, Endoproteinase AspN, Endoproteinase GluC, etc. (Granvogl et al., 2007, Anal Bioanal Chem 389: 991-1002). In certain embodiments, a peptide, polypeptide, or protein is fragmented by proteinase K, or optionally, a thermolabile version of proteinase K to enable rapid inactivation. Proteinase K is quite stable in denaturing reagents, such as urea and SDS, enabling digestion of completely denatured proteins. Protein and polypeptide fragmentation into peptides can be performed before or after attachment of a DNA tag or DNA recording tag.

Chemical reagents can also be used to digest proteins into peptide fragments. A chemical reagent may cleave at a specific amino acid residue (e.g., cyanogen bromide hydrolyzes peptide bonds at the C-terminus of methionine residues). Chemical reagents for fragmenting polypeptides or proteins into smaller peptides include cyanogen bromide (CNBr), hydroxylamine, hydrazine, formic acid, BNPS-skatole [2-(2-nitrophenylsulfenyl)-3-methylindole], iodosobenzoic acid, •NTCB+Ni (2-nitro-5-thiocyanobenzoic acid), etc.

In certain embodiments, following enzymatic or chemical cleavage, the resulting peptide fragments are approximately the same desired length, e.g., from about 10 amino acids to about 70 amino acids, from about 10 amino acids to about 60 amino acids, from about 10 amino acids to about 50 amino acids, about 10 to about 40 amino acids, from about 10 to about 30 amino acids, from about 20 amino acids to about 70 amino acids, from about 20 amino acids to about 60 amino acids, from about 20 amino acids to about 50 amino acids, about 20 to about 40 amino acids, from about 20 to about 30 amino acids, from about 30 amino acids to about 70 amino acids, from about 30 amino acids to about 60 amino acids, from about 30 amino acids to about 50 amino acids, or from about 30 amino acids to about 40 amino acids. A cleavage reaction may be monitored, for example in real time, by spiking the protein or polypeptide sample with a short test FRET (fluorescence resonance energy transfer) peptide comprising a peptide sequence containing a proteinase or endopeptidase cleavage site. In the intact FRET peptide, a fluorescent group and a quencher group are attached to either end of the peptide sequence containing the cleavage site, and fluorescence resonance energy transfer between the quencher and the fluorophore leads to low fluorescence. Upon cleavage of the test peptide by a protease or endopeptidase, the quencher and fluorophore are separated giving a large increase in fluorescence. A cleavage reaction can be stopped when a certain fluorescence intensity is achieved, allowing a reproducible cleavage end point to be achieved.

A sample of macromolecules (e.g., peptides, polypeptides, or proteins) can undergo protein fractionation methods prior to attachment to a solid support, where proteins or peptides are separated by one or more properties such as cellular location, molecular weight, hydrophobicity, or isoelectric point, or protein enrichment methods. Alternatively, or additionally, protein enrichment methods may be used to select for a specific protein or peptide (see, e.g., Whiteaker et al., 2007, Anal. Biochem. 362:44-54, incorporated by reference in its entirety) or to select for a particular post translational modification (see, e.g., Huang et al., 2014. J. Chromatogr. A 1372:1-17, incorporated by reference in its entirety). Alternatively, a particular class or classes of proteins such as immunoglobulins, or immunoglobulin (Ig) isotypes such as IgG, can be affinity enriched or selected for analysis. In the case of immunoglobulin molecules, analysis of the sequence and abundance or frequency of hypervariable sequences involved in affinity binding are of particular interest, particularly as they vary in response to disease progression or correlate with healthy, immune, and/or or disease phenotypes. Overly abundant proteins can also be subtracted from the sample using standard immunoaffinity methods. Depletion of abundant proteins can be useful for plasma samples where over 80% of the protein constituent is albumin and immunoglobulins. Several commercial products are available for depletion of plasma samples of overly abundant proteins, such as PROTIA and PROT20 (Sigma-Aldrich).

In certain embodiments, the macromolecule is comprised of a protein or polypeptide. In one embodiment, the protein or polypeptide is labeled with DNA recording tags through standard amine coupling chemistries (see, e.g., FIG. 2B, FIG. 2C, FIG. 28A-D, FIG. 29A-E, FIG. 31A-E, FIG. 40A-I). The s-amino group (e.g., of lysine residues) and the N-terminal amino group are particularly susceptible to labeling with amine-reactive coupling agents, depending on the pH of the reaction (Mendoza and Vachet 2009). In a particular embodiment (see, e.g., FIG. 2B and FIG. 29A-E), the recording tag is comprised of a reactive moiety (e.g., for conjugation to a solid surface, a multifunctional linker, or a macromolecule), a linker, a universal priming sequence, a barcode (e.g., compartment tag, partition barcode, sample barcode, fraction barcode, or any combination thereof), an optional UMI, and a spacer (Sp) sequence for facilitating information transfer to/from a coding tag. In another embodiment, the protein can be first labeled with a universal DNA tag, and the barcode-Sp sequence (representing a sample, a compartment, a physical location on a slide, etc.) are attached to the protein later through and enzymatic or chemical coupling step (see, e.g., FIG. 20, FIG. 30A-E, FIG. 31A-E, FIG. 40A-I). A universal DNA tag comprises a short sequence of nucleotides that are used to label a protein or polypeptide macromolecule and can be used as point of attachment for a barcode (e.g., compartment tag, recording tag, etc.). For example, a recording tag may comprise at its terminus a sequence complementary to the universal DNA tag. In certain embodiments, a universal DNA tag is a universal priming sequence. Upon hybridization of the universal DNA tags on the labeled protein to complementary sequence in recording tags (e.g., bound to beads), the annealed universal DNA tag may be extended via primer extension, transferring the recording tag information to the DNA tagged protein. In a particular embodiment, the protein is labeled with a universal DNA tag prior to proteinase digestion into peptides. The universal DNA tags on the labeled peptides from the digest can then be converted into an informative and effective recording tag.

Figure 2B:
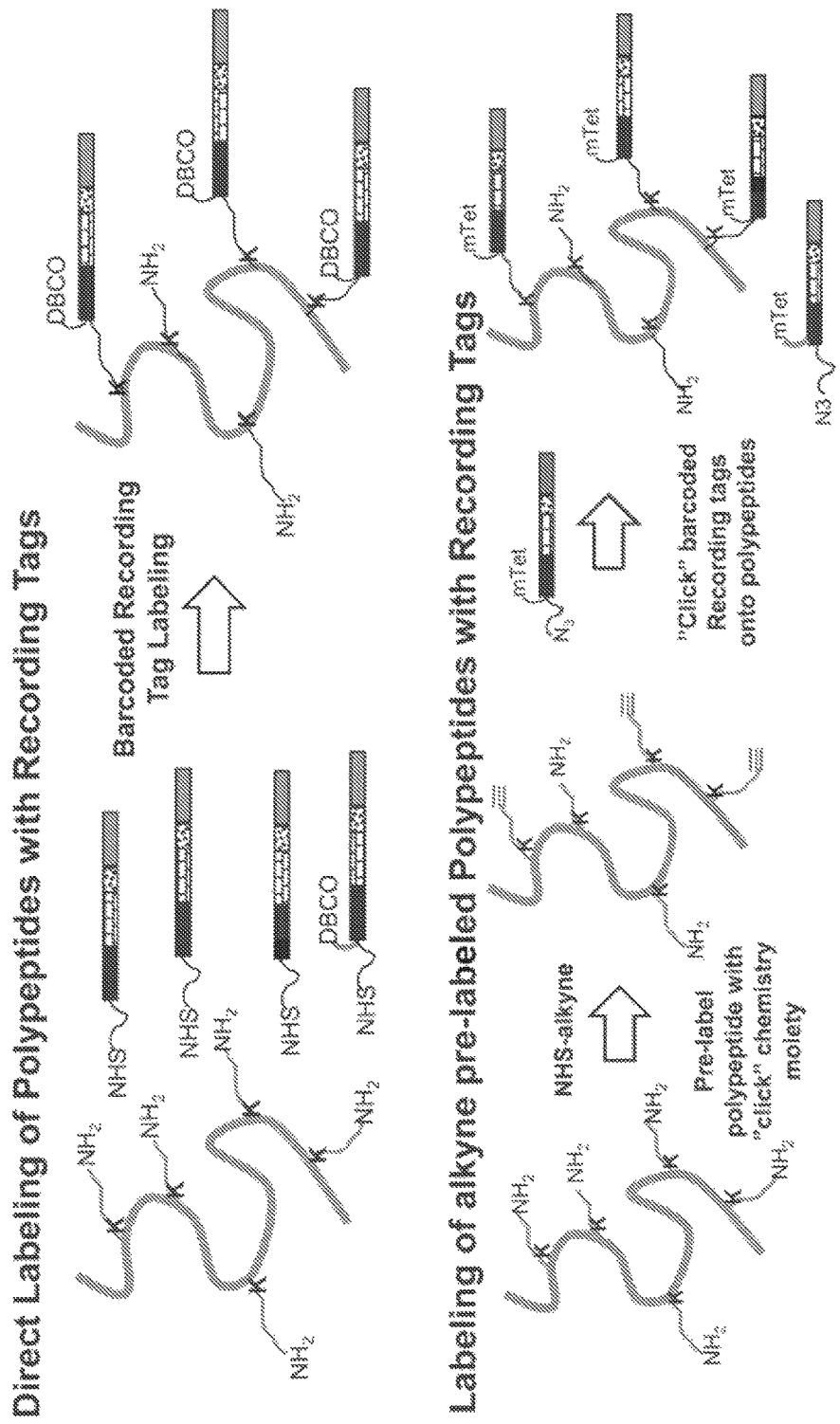
Figure 2C:
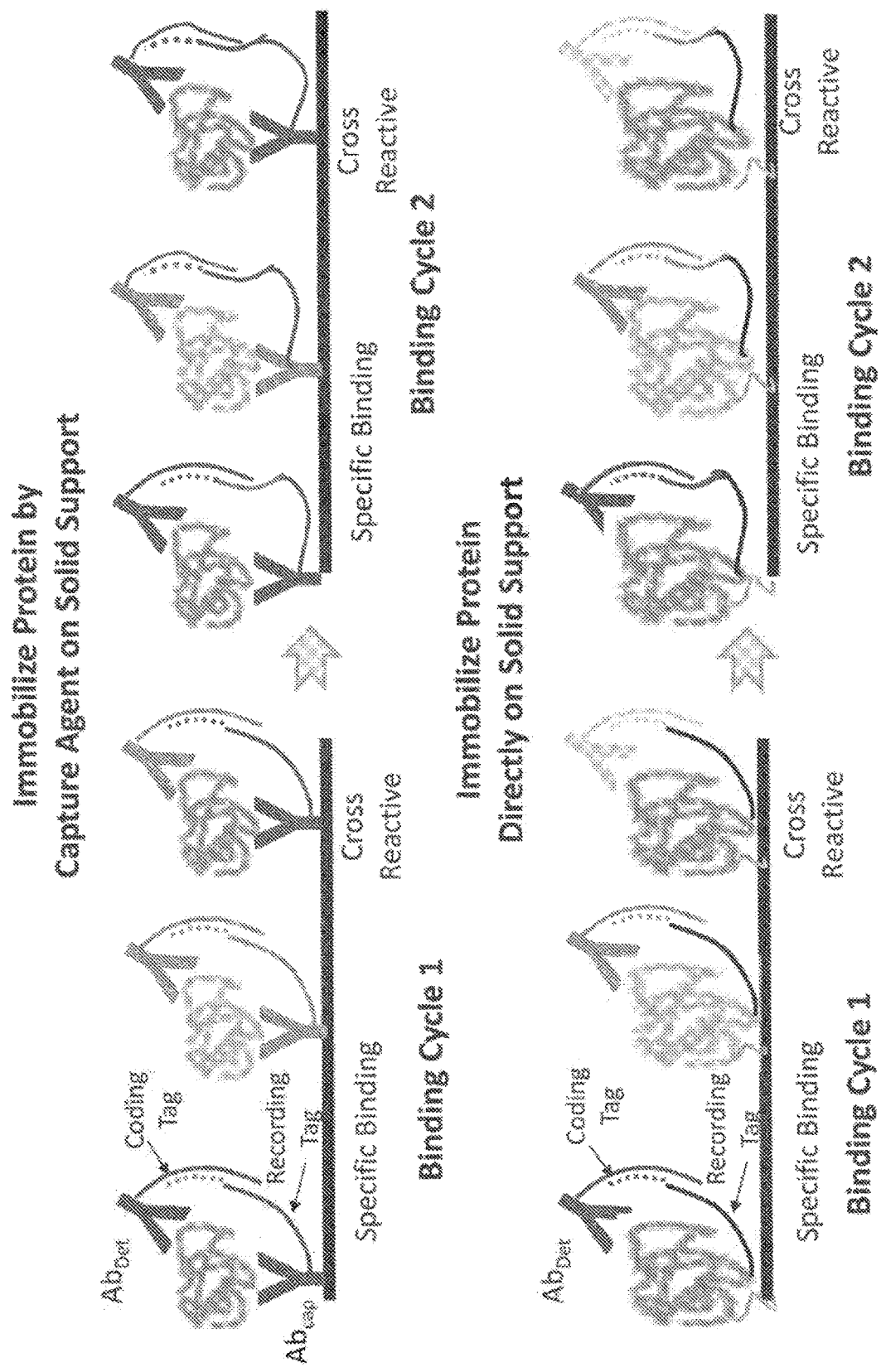
Figure 2D:
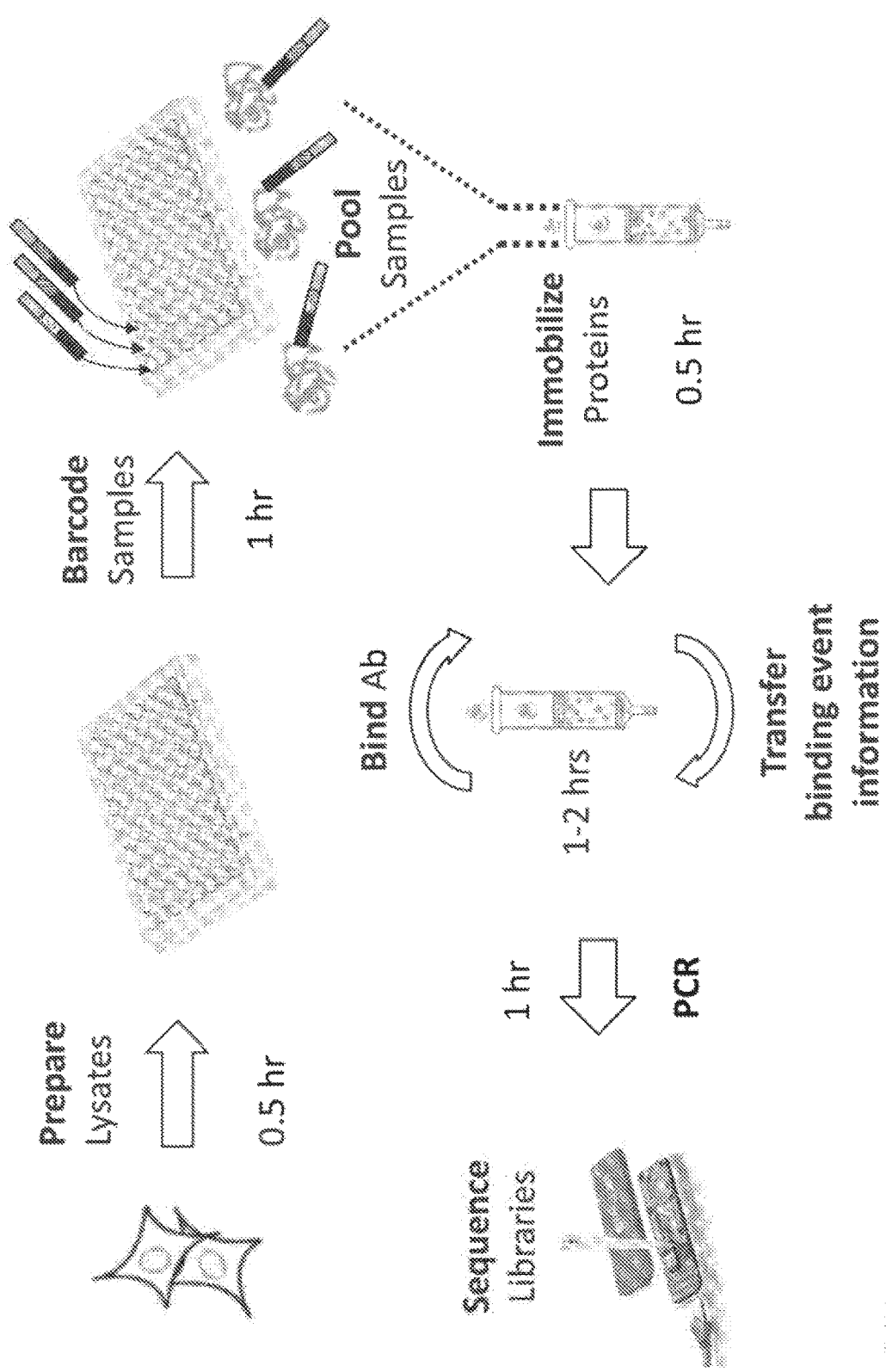

In certain embodiments, a protein macromolecule can be immobilized to a solid support by an affinity capture reagent (and optionally covalently crosslinked), wherein the recording tag is associated with the affinity capture reagent directly, or alternatively, the protein can be directly immobilized to the solid support with a recording tag (see, e.g., FIG. 2C).

C. Support Such as Solid Support

Macromolecules of the present disclosure are joined to a surface of a solid support (also referred to as "substrate surface"). The solid support can be any porous or non-porous support surface including, but not limited to, a bead, a microbead, an array, a glass surface, a silicon surface, a plastic surface, a filter, a membrane, nylon, a silicon wafer chip, a flow cell, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere. Materials for a solid support include but are not limited to acrylamide, agarose, cellulose, nitrocellulose, glass, gold, quartz, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polyactic acid, polyorthoesters, functionalized silane, polypropylfumerate, collagen, glycosaminoglycans, polyamino acids, or any combination thereof. Solid supports further include thin film, membrane, bottles, dishes, fibers, woven fibers, shaped polymers such as tubes, particles, beads, microparticles, or any combination thereof. For example, when solid surface is a bead, the bead can include, but is not limited to, a polystyrene bead, a polymer bead, an agarose bead, an acrylamide bead, a solid core bead, a porous bead, a paramagnetic bead, glass bead, or a controlled pore bead.

In certain embodiments, a solid support is a flow cell. Flow cell configurations may vary among different next generation sequencing platforms. For example, the Illumina flow cell is a planar optically transparent surface similar to a microscope slide, which contains a lawn of oligonucleotide anchors bound to its surface. Template DNA, comprise adapters ligated to the ends that are complimentary to oligonucleotides on the flow cell surface. Adapted single-stranded DNAs are bound to the flow cell and amplified by solid-phase "bridge" PCR prior to sequencing. The 454 flow cell (454 Life Sciences) supports a "picotiter" plate, a fiber optic slide with about 1.6 million 75-picoliter wells. Each individual molecule of sheared template DNA is captured on a separate bead, and each bead is compartmentalized in a private droplet of aqueous PCR reaction mixture within an oil emulsion. Template is clonally amplified on the bead surface by PCR, and the template-loaded beads are then distributed into the wells of the picotiter plate for the sequencing reaction, ideally with one or fewer beads per well. SOLiD (Supported Oligonucleotide Ligation and Detection) instrument from Applied Biosystems, like the 454 system, amplifies template molecules by emulsion PCR. After a step to cull beads that do not contain amplified template, bead-bound template is deposited on the flow cell.

A flow cell may also be a simple filter frit, such as a TWIST™ DNA synthesis column (Glen Research).

In certain embodiments, a solid support is a bead, which may refer to an individual bead or a plurality of beads. In some embodiments, the bead is compatible with a selected next generation sequencing platform that will be used for downstream analysis (e.g., SOLiD or 454). In some embodiments, a solid support is an agarose bead, a paramagnetic bead, a polystyrene bead, a polymer bead, an acrylamide bead, a solid core bead, a porous bead, a glass bead, or a controlled pore bead. In further embodiments, a bead may be coated with a binding functionality (e.g., amine group, affinity ligand such as streptavidin for binding to biotin labeled macromolecule, antibody) to facilitate binding to a macromolecule.

Proteins, polypeptides, or peptides can be joined to the solid support, directly or indirectly, by any means known in the art, including covalent and non-covalent interactions, or any combination thereof (see, e.g., Chan et al., 2007, PLoS One 2:e1164; Cazalis et al., Bioconj. Chem. 15:1005-1009; Soellner et al., 2003, J. Am. Chem. Soc. 125:11790-11791; Sun et al., 2006, Bioconjug. Chem. 17-52-57; Decreau et al., 2007, J. Org. Chem. 72:2794-2802; Camarero et al., 2004, J. Am. Chem. Soc. 126:14730-14731; Girish et al., 2005, Bioorg. Med. Chem. Lett. 15:2447-2451; Kalia et al., 2007, Bioconjug. Chem. 18:1064-1069; Watzke et al., 2006, Angew Chem. Int. Ed. Engl. 45:1408-1412; Parthasarathy et al., 2007, Bioconjugate Chem. 18:469-476; and Bioconjugate Techniques, G. T. Hermanson, Academic Press (2013), and are each hereby incorporated by reference in their entirety). For example, the peptide may be joined to the solid support by a ligation reaction. Alternatively, the solid support can include an agent or coating to facilitate joining, either direct or indirectly, the peptide to the solid support. Any suitable molecule or materials may be employed for this purpose, including proteins, nucleic acids, carbohydrates and small molecules. For example, in one embodiment the agent is an affinity molecule. In another example, the agent is an azide group, which group can react with an alkynyl group in another molecule to facilitate association or binding between the solid support and the other molecule.

Proteins, polypeptides, or peptides can be joined to the solid support using methods referred to as "click chemistry." For this purpose, any reaction which is rapid and substantially irreversible can be used to attach proteins, polypeptides, or peptides to the solid support. Exemplary reactions include the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2]cycloaddition, alkene and tetrazine inverse electron demand Diels-Alder (IEDDA) reaction (e.g., m-tetrazine (mTet) and trans-cyclooctene (TCO)), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate or the like.

In some embodiments the macromolecule and solid support are joined by a functional group capable of formation by reaction of two complementary reactive groups, for example a functional group which is the product of one of the foregoing "click" reactions. In various embodiments, functional group can be formed by reaction of an aldehyde, oxime, hydrazone, hydrazide, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester, pentynoic acid STP ester), ketone, α,β-unsaturated carbonyl, alkene, maleimide, α-haloimide, epoxide, aziridine, tetrazine, tetrazole, phosphine, biotin or thiirane functional group with a complementary reactive group. An exemplary reaction is a reaction of an amine (e.g., primary amine) with an N-hydroxysuccinimide ester or isothiocyanate.

In yet other embodiments, the functional group comprises an alkene, ester, amide, thioester, disulfide, carbocyclic, heterocyclic or heteroaryl group. In further embodiments, the functional group comprises an alkene, ester, amide, thioester, thiourea, disulfide, carbocyclic, heterocyclic or heteroaryl group. In other embodiments, the functional group comprises an amide or thiourea. In some more specific embodiments, functional group is a triazolyl functional group, an amide, or thiourea functional group.

In a preferred embodiment, iEDDA click chemistry is used for immobilizing macromolecules (e.g., proteins, polypeptides, peptides) to a solid support since it is rapid and delivers high yields at low input concentrations. In another preferred embodiment, m-tetrazine rather than tetrazine is used in an iEDDA click chemistry reaction, as m-tetrazine has improved bond stability.

In a preferred embodiment, the substrate surface is functionalized with TCO, and the recording tag-labeled protein, polypeptide, peptide is immobilized to the TCO coated substrate surface via an attached m-tetrazine moiety (see, e.g., FIG. 34C).

Proteins, polypeptides, or peptides can be immobilized to a surface of a solid support by its C-terminus, N-terminus, or an internal amino acid, for example, via an amine, carboxyl, or sulfydryl group. Standard activated supports used in coupling to amine groups include CNBr-activated, NHS-activated, aldehyde-activated, azlactone-activated, and CDI-activated supports. Standard activated supports used in carboxyl coupling include carbodiimide-activated carboxyl moieties coupling to amine supports. Cysteine coupling can employ maleimide, idoacetyl, and pyridyl disulfide activated supports. An alternative mode of peptide carboxy terminal immobilization uses anhydrotrypsin, a catalytically inert derivative of trypsin that binds peptides containing lysine or arginine residues at their C-termini without cleaving them.

In certain embodiments, a protein, polypeptide, or peptide is immobilized to a solid support via covalent attachment of a solid surface bound linker to a lysine group of the protein, polypeptide, or peptide.

Recording tags can be attached to the protein, polypeptide, or peptides pre- or post-immobilization to the solid support. For example, proteins, polypeptides, or peptides can be first labeled with recording tags and then immobilized to a solid surface via a recording tag comprising at two functional moieties for coupling (see, e.g., FIG. 28A-D). One functional moiety of the recording tag couples to the protein, and the other functional moiety immobilizes the recording tag-labeled protein to a solid support.

Alternatively, proteins, polypeptides, or peptides are immobilized to a solid support prior to labeling of the proteins, polypeptides or peptides with recording tags. For example, proteins can first be derivitized with reactive groups such as click chemistry moieties. The activated protein molecules can then be attached to a suitable solid support and then labeled with recording tags using the complementary click chemistry moiety. As an example, proteins derivatized with alkyne and mTet moieties may be immobilized to beads derivatized with azide and TCO and attached to recording tags labeled with azide and TCO.

It is understood that the methods provided herein for attaching macromolecules (e.g., proteins, polypeptides, or peptides) to the solid support may also be used to attach recording tags to the solid support or attach recording tags to macromolecules (e.g., proteins polypeptides, or peptides).

Figure 36A:
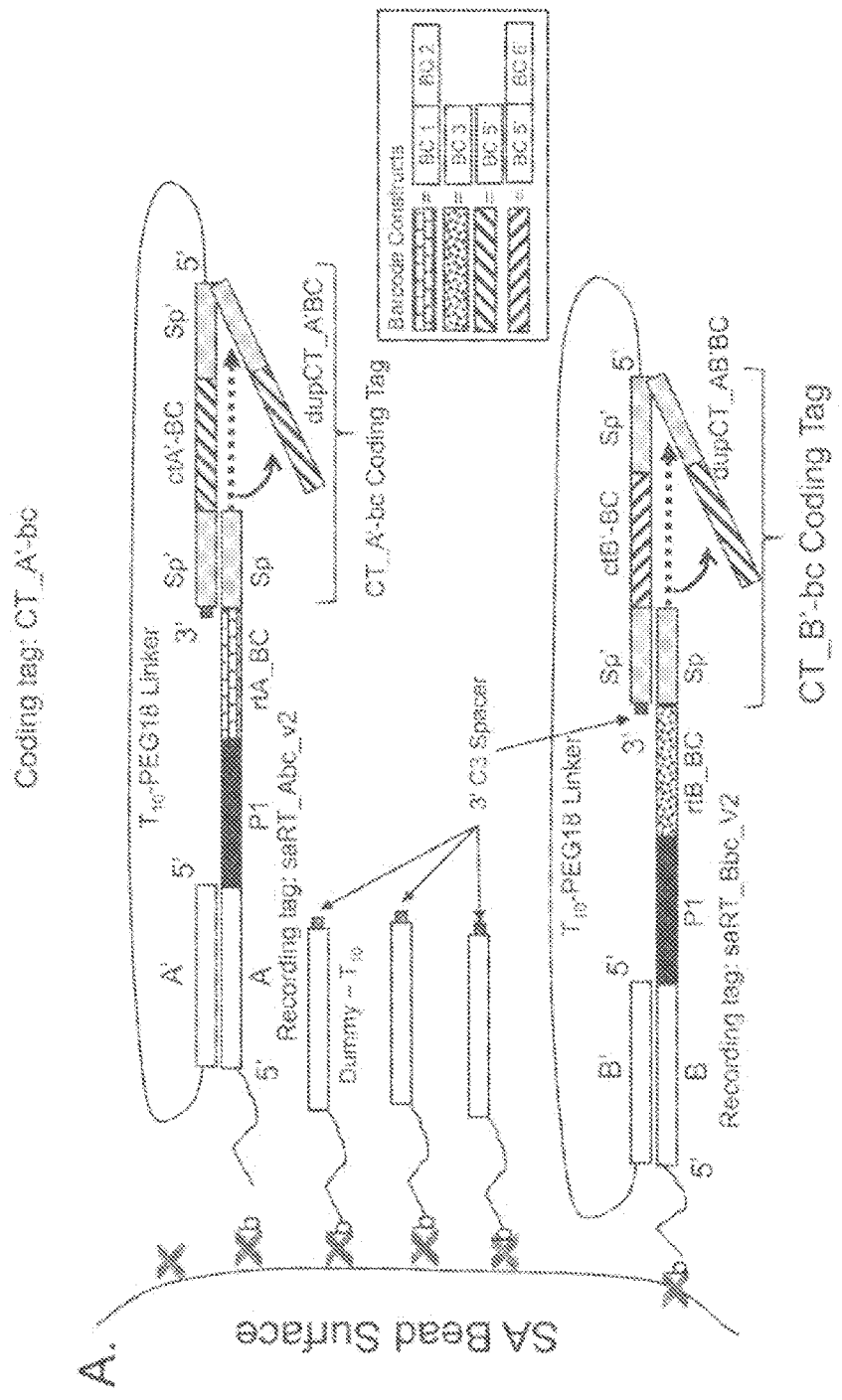
Figure 36E:
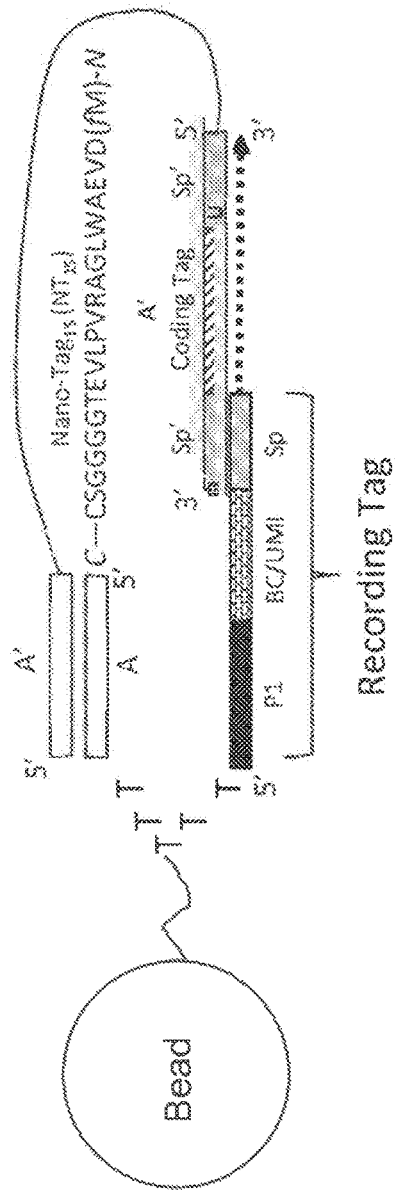
Figure 36F:
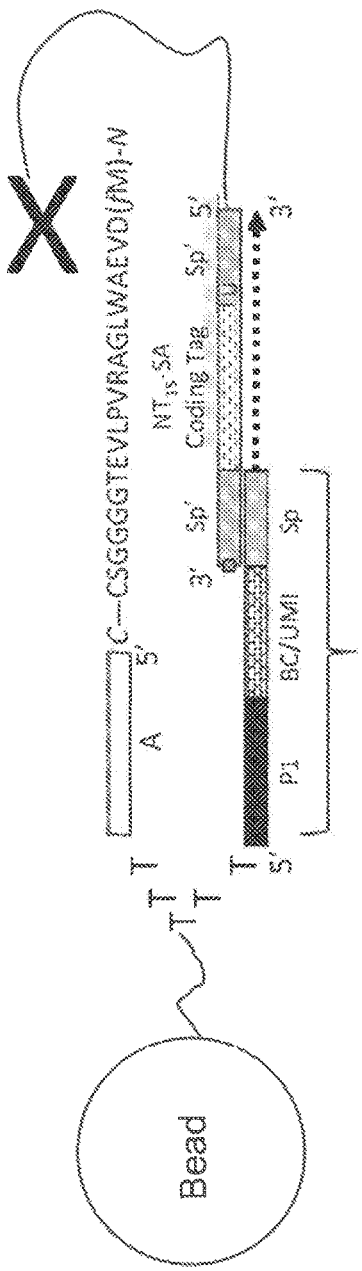

In certain embodiments, the surface of a solid support is passivated (blocked) to minimize non-specific absorption to binding agents. A "passivated" surface refers to a surface that has been treated with outer layer of material to minimize non-specific binding of a binding agent. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), and diamond-like carbon (DLC), DLC+PEG (Stavis et al., 2011, Proc. Natl. Acad. Sci. USA 108:983-988). In addition to covalent surface modifications, a number of passivating agents can be employed as well including surfactants like Tween-20, polysiloxane in solution (Pluronic series), poly vinyl alcohol, (PVA), and proteins like BSA and casein. Alternatively, density of proteins, polypeptide, or peptides can be titrated on the surface or within the volume of a solid substrate by spiking a competitor or "dummy" reactive molecule when immobilizing the proteins, polypeptides or peptides to the solid substrate (see, e.g., FIG. 36A).

In certain embodiments where multiple macromolecules are immobilized on the same solid support, the macromolecules can be spaced appropriately to reduce the occurrence of or prevent a cross-binding or inter-molecular event, e.g., where a binding agent binds to a first macromolecule and its coding tag information is transferred to a recording tag associated with a neighboring macromolecule rather than the recording tag associated with the first macromolecule. To control macromolecule (e.g., protein, polypeptide, or peptide spacing) spacing on the solid support, the density of functional coupling groups (e.g., TCO) may be titrated on the substrate surface (see, e.g., FIG. 34A-C). In some embodiments, multiple macromolecules are spaced apart on the surface or within the volume (e.g., porous supports) of a solid support at a distance of about 50 nm to about 500 nm, or about 50 nm to about 400 nm, or about 50 nm to about 300 nm, or about 50 nm to about 200 nm, or about 50 nm to about 100 nm. In some embodiments, multiple macromolecules are spaced apart on the surface of a solid support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, multiple macromolecules are spaced apart on the surface of a solid support with an average distance of at least 50 nm. In some embodiments, macromolecules are spaced apart on the surface or within the volume of a solid support such that, empirically, the relative frequency of inter- to intra-molecular events is <1:10; <1:100; <1:1,000; or <1:10,000. A suitable spacing frequency can be determined empirically using a functional assay (see, e.g., Example 23), and can be accomplished by dilution and/or by spiking a "dummy" spacer molecule that competes for attachments sites on the substrate surface.

For example, as shown in FIG. 34A, PEG-5000 (MW~5000) is used to block the interstitial space between peptides on the substrate surface (e.g., bead surface). In addition, the peptide is coupled to a functional moiety that is also attached to a PEG-5000 molecule. In a preferred embodiment, this is accomplished by coupling a mixture of NHS-PEG-5000-TCO+NHS-PEG-5000-Methyl to amine-derivitized beads (see, e.g., FIG. 34A-C). The stoichiometric ratio between the two PEGs (TCO vs. methyl) is titrated to generate an appropriate density of functional coupling moieties (TCO groups) on the substrate surface; the methyl-PEG is inert to coupling. The effective spacing between TCO groups can be calculated by measuring the density of TCO groups on the surface. In certain embodiments, the mean spacing between coupling moieties (e.g., TCO) on the solid surface is at least 50 nm, at least 100 nm, at least 250 nm, or at least 500 nm. After PEG5000-TCO/methyl derivitization of the beads, the excess $NH_2$ groups on the surface are quenched with a reactive anhydride (e.g., acetic or succinic anhydride) inhibitor.

In particular embodiments, the analyte molecules and/or the recording tags are immobilized on a substrate or support at a density such that the interaction between (i) a coding agent bound to a first analyte (particularly, the coding tag in that bound coding agent), and (ii) a second analyte and/or its recording tag, is reduced, minimized, or completely eliminated. Therefore, false positive assay signals resulting from "intermolecular" engagement can be reduced, minimized, or eliminated.

In certain embodiments, the density of the analyte molecules and/or the recording tags on a substrate is determined for each type of analyte. For example, the longer a denatured polypeptide chain is, the lower the density should be in order to prevent "intermolecular" interactions. In certain aspects, increasing the spacing between the analyte molecules and/or the recording tags (i.e., lowering the density) increases the signal to background ratio of the presently disclosed assays.

In some embodiments, the analyte molecules and/or the recording tags are deposited or immobilized on a substrate at an average density of about 0.0001 molecule/$\mu m^2$, 0.001 molecule/$\mu m^2$, 0.01 molecule/$\mu m^2$, 0.1 molecule/$\mu m^2$, 1 molecule/$\mu m^2$, about 2 molecules/$\mu m^2$, about 3 molecules/$\mu m^2$, about 4 molecules/$\mu m^2$, about 5 molecules/$\mu m^2$, about 6 molecules/$\mu m^2$, about 7 molecules/$\mu m^2$, about 8 molecules/$\mu m^2$, about 9 molecules/$\mu m^2$, or about 10 molecules/$\mu m^2$. In other embodiments, the analyte molecules and/or the recording tags are deposited or immobilized at an average density of about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, or about 200 molecules/$\mu m^2$ on a substrate. In other embodiments, the analyte molecules and/or the recording tags are deposited or immobilized at an average density of about 1 molecule/$mm^2$, about 10 molecules/$mm^2$, about 50 molecules/$mm^2$, about 100 molecules/$mm^2$, about 150 molecules/$mm^2$, about 200 molecules/$mm^2$, about 250 molecules/$mm^2$, about 300 molecules/$mm^2$, about 350 molecules/$mm^2$, 400 molecules/$mm^2$, about 450 molecules/$mm^2$, about 500 molecules/$mm^2$, about 550 molecules/$mm^2$, about 600 molecules/$mm^2$, about 650 molecules/$mm^2$, about 700 molecules/$mm^2$, about 750 molecules/$mm^2$, about 800 molecules/$mm^2$, about 850 molecules/$mm^2$, about 900 molecules/$mm^2$, about 950 molecules/$mm^2$, or about 1000 molecules/$mm^2$. In still other embodiments, the analyte molecules and/or the recording tags are deposited or immobilized on a substrate at an average density between about $1 \times 10^3$ and about $0.5 \times 10^4$ molecules/$mm^2$, between about $0.5 \times 10^4$ and about $1 \times 10^4$ molecules/$mm^2$, between about $1 \times 10^4$ and about $0.5 \times 10^5$ molecules/$mm^2$, between about $0.5 \times 10^5$ and about $1 \times 10^5$ molecules/$mm^2$, between about $1 \times 10^5$ and about $0.5 \times 10^6$ molecules/$mm^2$, or between about $0.5 \times 10^6$ and about $1 \times 10^6$ molecules/$mm^2$. In other embodiments, the average density of the analyte molecules and/or the recording tags deposited or immobilized on a substrate can be, for example, between about 1 molecule/$cm^2$ and about 5 molecules/$cm^2$, between about 5 and about 10 molecules/$cm^2$, between about 10 and about 50 molecules/$cm^2$, between about 50 and about 100 molecules/$cm^2$, between about 100 and about $0.5 \times 10^3$ molecules/$cm^2$, between about $0.5 \times 10^3$ and about $1 \times 10^3$ molecules/$cm^2$, $1 \times 10^3$ and about $0.5 \times 10^4$ molecules/$cm^2$, between about $0.5 \times 10^4$ and about $1 \times 10^4$ molecules/$cm^2$, between about $1 \times 10^4$ and about $0.5 \times 10^5$ molecules/$cm^2$, between about $0.5 \times 10^5$ and about $1 \times 10^5$ molecules/$cm^2$, between about $1 \times 10^5$ and about $0.5 \times 10^6$ molecules/$cm^2$, or between about $0.5 \times 10^6$ and about $1 \times 10^6$ molecules/$cm^2$.

In certain embodiments, the concentration of the binding agents in a solution is controlled to reduce background and/or false positive results of the assay.

In some embodiments, the concentration of a binding agent is about 0.0001 nM, about 0.001 nM, about 0.01 nM, about 0.1 nM, about 1 nM, about 2 nM, about 5 nM, about 10 nM, about 20 nM, about 50 nM, about 100 nM, about 200 nM, about 500 nM, or about 1000 nM. In other embodiments, the concentration of a soluble conjugate used in the assay is between about 0.0001 nM and about 0.001 nM, between about 0.001 nM and about 0.01 nM, between about 0.01 nM and about 0.1 nM, between about 0.1 nM and about 1 nM, between about 1 nM and about 2 nM, between about 2 nM and about 5 nM, between about 5 nM and about 10 nM, between about 10 nM and about 20 nM, between about 20 nM and about 50 nM, between about 50 nM and about 100 nM, between about 100 nM and about 200 nM, between about 200 nM and about 500 nM, between about 500 nM and about 1000 nM, or more than about 1000 nM.

In some embodiments, the ratio between the soluble binding agent molecules and the immobilized analyte molecules and/or the recording tags is about 0.00001:1, about 0.0001:1, about 0.001:1, about 0.01:1, about 0.1:1, about 1:1, about 2:1, about 5:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about 104:1, about 105:1, about $10^6$:1, or higher, or any ratio in between the above listed ratios. Higher ratios between the soluble binding agent molecules and the immobilized analyte molecules and/or the recording tags can be used to drive the binding and/or the coding tag/recoding tag information transfer to completion. This may be particularly useful for detecting and/or analyzing low abundance protein analytes in a sample.

D. Recording Tags

Figure 5:
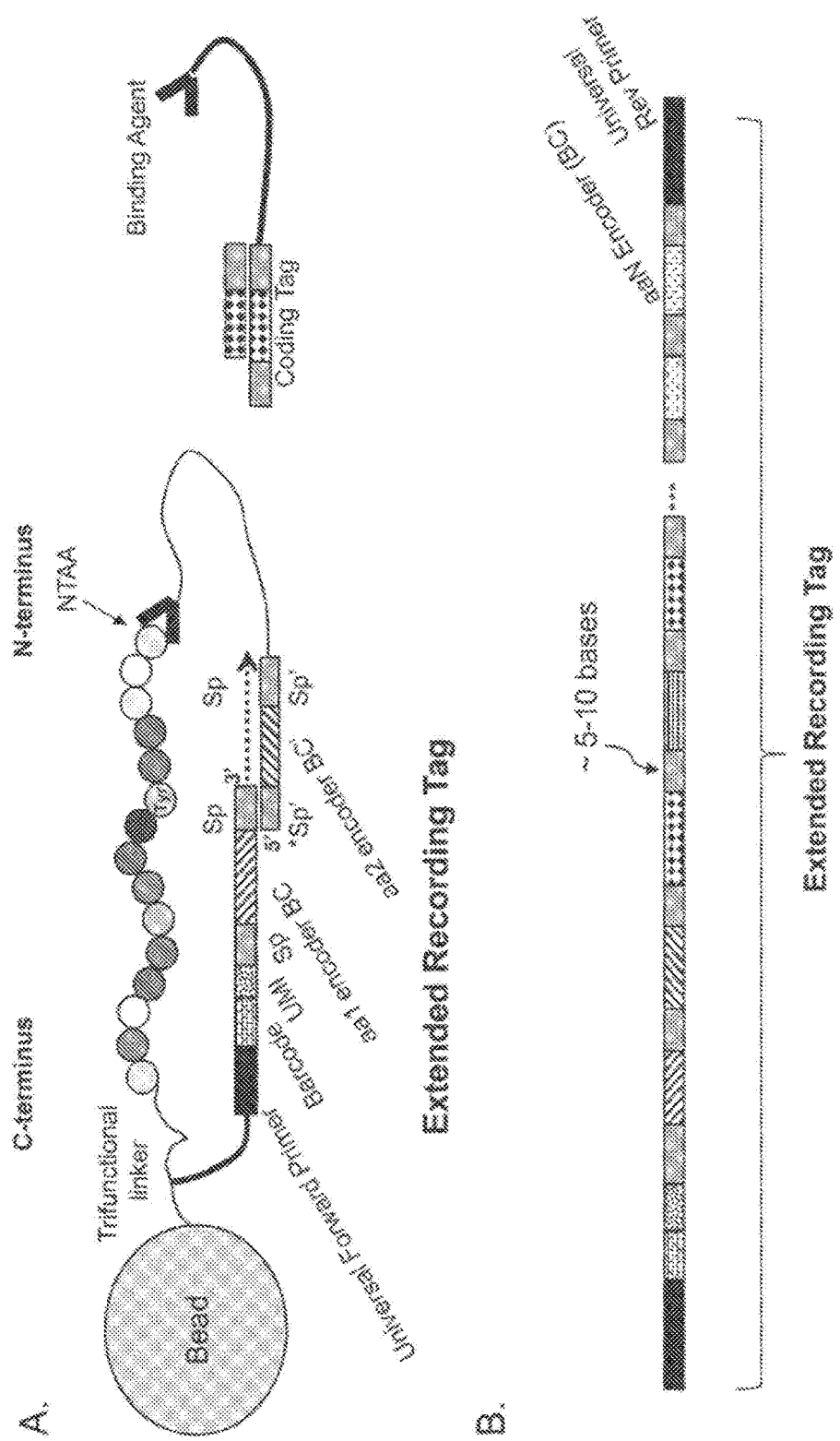
FIG. 5 illustrates an overview of an exemplary construction of an extended recording tag using primer extension to transfer identifying information of a coding tag of a binding agent to a recording tag associated with an analyte such as a macromolecule (e.g., a polypeptide) to generate an extended recording tag. A coding tag comprising a unique encoder sequence with identifying information regarding the binding agent is optionally flanked on each end by a common spacer sequence (Sp'). Step (A) illustrates an NTAA binding agent comprising a coding tag binding to an NTAA of a polypeptide which is labeled with a recording tag and linked to a bead. The recording tag anneals to the coding tag via complementary spacer sequences (Sp anneals to Sp'), and a primer extension reaction mediates transfer of coding tag information to the recording tag using the spacer (Sp) as a priming site. The coding tag is illustrated as a duplex with a single stranded spacer (Sp') sequence at the terminus distal to the binding agent. This configuration minimizes hybridization of the coding tag to internal sites in the recording tag and favors hybridization of the recording tag's terminal spacer (Sp) sequence with the single stranded spacer overhang (Sp') of the coding tag. Moreover, the extended recording tag may be pre-annealed with one or more oligonucleotides (e.g., complementary to an encoder and/or a spacer sequence) to block hybridization of the coding tag to internal recording tag sequence elements. Step (B) shows a final extended recording tag produced after "n" cycles of binding ("***" represents intervening binding cycles not shown in the extended recording tag) and transfer of coding tag information and the addition of a universal priming site at the 3' end. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In some embodiments, at least one recording tag is associated or co-localized directly or indirectly with the macromolecule and joined to the solid support (see, e.g., FIG. 5). A recording tag may comprise DNA, RNA, PNA, γPNA, GNA, BNA, XNA, TNA, a protected DNA or RNA base, polynucleotide analogs, or a combination thereof. A recording tag may be single stranded, or partially or completely double stranded. A recording tag may have a blunt end or overhanging end. In certain embodiments, upon binding of a binding agent to a macromolecule, identifying information of the binding agent's coding tag is transferred to the recording tag to generate an extended recording tag. Further extensions to the extended recording tag can be made in subsequent binding cycles.

A recording tag can be joined to the solid support, directly or indirectly (e.g., via a linker), by any means known in the art, including covalent and non-covalent interactions, or any combination thereof. For example, the recording tag may be joined to the solid support by a ligation reaction. Alternatively, the solid support can include an agent or coating to facilitate joining, either direct or indirectly, of the recording tag, to the solid support. Strategies for immobilizing nucleic acid molecules to solid supports (e.g., beads) have been described in U.S. Pat. No. 5,900,481; Steinberg et al. (2004, Biopolymers 73:597-605); Lund et al., 1988 (Nucleic Acids Res. 16: 10861-10880); and Steinberg et al. (2004, Biopolymers 73:597-605), each of which is incorporated herein by reference in its entirety.

In certain embodiments, the co-localization of a macromolecule (e.g., peptide) and associated recording tag is achieved by conjugating macromolecule and recording tag to a bifunctional linker attached directly to the solid support surface Steinberg et al. (2004, Biopolymers 73:597-605). In further embodiments, a trifunctional moiety is used to derivitize the solid support (e.g., beads), and the resulting bifunctional moiety is coupled to both the macromolecule and recording tag.

Methods and reagents (e.g., click chemistry reagents and photoaffinity labelling reagents) such as those described for attachment of macromolecules and solid supports, may also be used for attachment of recording tags.

In a particular embodiment, a single recording tag is attached to a macromolecule (e.g., peptide), for example via the attachment to a de-blocked N- or C-terminal amino acid. In another embodiment, multiple recording tags are attached to the macromolecule (e.g., protein, polypeptide, or peptide), for example to the lysine residues or peptide backbone. In some embodiments, a macromolecule (e.g., protein or polypeptide) labeled with multiple recording tags is fragmented or digested into smaller peptides, with each peptide labeled on average with one recording tag.

In certain embodiments, a recording tag comprises an optional, unique molecular identifier (UMI), which provides a unique identifier tag for each macromolecule (e.g., protein, polypeptide, peptide) to which the UMI is associated with. A UMI can be about 3 to about 40 bases, about 3 to about 30 bases, about 3 to about 20 bases, or about 3 to about 10 bases, or about 3 to about 8 bases. In some embodiments, a UMI is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, or 40 bases in length. A UMI can be used to de-convolute sequencing data from a plurality of extended recording tags to identify sequence reads from individual macromolecules. In some embodiments, within a library of macromolecules, each macromolecule is associated with a single recording tag, with each recording tag comprising a unique UMI. In other embodiments, multiple copies of a recording tag are associated with a single macromolecule, with each copy of the recording tag comprising the same UMI. In some embodiments, a UMI has a different base sequence than the spacer or encoder sequences within the binding agents' coding tags to facilitate distinguishing these components during sequence analysis.

In certain embodiments, a recording tag comprises a barcode, e.g., other than the UMI if present. A barcode is a nucleic acid molecule of about 3 to about 30 bases, about 3 to about 25 bases, about 3 to about 20 bases, about 3 to about 10 bases, about 3 to about 10 bases, about 3 to about 8 bases in length. In some embodiments, a barcode is about 3 bases, 4 bases, 5 bases, 6 bases, 7 bases, 8 bases, 9 bases, 10 bases, 11 bases, 12 bases, 13 bases, 14 bases, 15 bases, 20 bases, 25 bases, or 30 bases in length. In one embodiment, a barcode allows for multiplex sequencing of a plurality of samples or libraries. A barcode may be used to identify a partition, a fraction, a compartment, a sample, a spatial location, or library from which the macromolecule (e.g., peptide) derived. Barcodes can be used to de-convolute multiplexed sequence data and identify sequence reads from an individual sample or library. For example, a barcoded bead is useful for methods involving emulsions and partitioning of samples, e.g., for purposes of partitioning the proteome.

A barcode can represent a compartment tag in which a compartment, such as a droplet, microwell, physical region on a solid support, etc. is assigned a unique barcode. The association of a compartment with a specific barcode can be achieved in any number of ways such as by encapsulating a single barcoded bead in a compartment, e.g., by direct merging or adding a barcoded droplet to a compartment, by directly printing or injecting a barcode reagent to a compartment, etc. The barcode reagents within a compartment are used to add compartment-specific barcodes to the macromolecule or fragments thereof within the compartment. Applied to protein partitioning into compartments, the barcodes can be used to map analysed peptides back to their originating protein molecules in the compartment. This can greatly facilitate protein identification. Compartment barcodes can also be used to identify protein complexes.

In other embodiments, multiple compartments that represent a subset of a population of compartments may be assigned a unique barcode representing the subset.

Alternatively, a barcode may be a sample identifying barcode. A sample barcode is useful in the multiplexed analysis of a set of samples in a single reaction vessel or immobilized to a single solid substrate or collection of solid substrates (e.g., a planar slide, population of beads contained in a single tube or vessel, etc.). Macromolecules from many different samples can be labeled with recording tags with sample-specific barcodes, and then all the samples pooled together prior to immobilization to a solid support, cyclic binding, and recording tag analysis. Alternatively, the samples can be kept separate until after creation of a DNA-encoded library, and sample barcodes attached during PCR amplification of the DNA-encoded library, and then mixed together prior to sequencing. This approach could be useful when assaying analytes (e.g., proteins) of different abundance classes. For example, the sample can be split and barcoded, and one portion processed using binding agents to low abundance analytes, and the other portion processed using binding agents to higher abundance analytes. In a particular embodiment, this approach helps to adjust the dynamic range of a particular protein analyte assay to lie within the "sweet spot" of standard expression levels of the protein analyte.

In certain embodiments, peptides, polypeptides, or proteins from multiple different samples are labeled with recording tags containing sample-specific barcodes. The multi-sample barcoded peptides, polypeptides, or proteins can be mixed together prior to a cyclic binding reaction. In this way, a highly-multiplexed alternative to a digital reverse phase protein array (RPPA) is effectively created (Guo, Liu et al. 2012, Assadi, Lamerz et al. 2013, Akbani, Becker et al. 2014, Creighton and Huang 2015). The creation of a digital RPPA-like assay has numerous applications in translational research, biomarker validation, drug discovery, clinical, and precision medicine.

In certain embodiments, a recording tag comprises a universal priming site, e.g., a forward or 5' universal priming site. A universal priming site is a nucleic acid sequence that may be used for priming a library amplification reaction and/or for sequencing. A universal priming site may include, but is not limited to, a priming site for PCR amplification, flow cell adaptor sequences that anneal to complementary oligonucleotides on flow cell surfaces (e.g., Illumina next generation sequencing), a sequencing priming site, or a combination thereof. A universal priming site can be about 10 bases to about 60 bases. In some embodiments, a universal priming site comprises an Illumina P5 primer (5'-AATGATACGGCGACCACCGA-3'—SEQ ID NO: 133) or an Illumina P7 primer (5'-CAAGCAGAAGACGGCAT-ACGAGAT-3'—SEQ ID NO: 134).

In certain embodiments, a recording tag comprises a spacer at its terminus, e.g., 3' end. As used herein reference to a spacer sequence in the context of a recording tag includes a spacer sequence that is identical to the spacer sequence associated with its cognate binding agent, or a spacer sequence that is complementary to the spacer sequence associated with its cognate binding agent. The terminal, e.g., 3', spacer on the recording tag permits transfer of identifying information of a cognate binding agent from its coding tag to the recording tag during the first binding cycle (e.g., via annealing of complementary spacer sequences for primer extension or sticky end ligation).

In one embodiment, the spacer sequence is about 1-20 bases in length, about 2-12 bases in length, or 5-10 bases in length. The length of the spacer may depend on factors such as the temperature and reaction conditions of the primer extension reaction for transferring coding tag information to the recording tag.

In a preferred embodiment, the spacer sequence in the recording is designed to have minimal complementarity to other regions in the recording tag; likewise the spacer sequence in the coding tag should have minimal complementarity to other regions in the coding tag. In other words, the spacer sequence of the recording tags and coding tags should have minimal sequence complementarity to components such unique molecular identifiers, barcodes (e.g., compartment, partition, sample, spatial location), universal primer sequences, encoder sequences, cycle specific sequences, etc. present in the recording tags or coding tags.

As described for the binding agent spacers, in some embodiments, the recording tags associated with a library of macromolecules share a common spacer sequence. In other embodiments, the recording tags associated with a library of macromolecules have binding cycle specific spacer sequences that are complementary to the binding cycle specific spacer sequences of their cognate binding agents, which can be useful when using non-concatenated extended recording tags (see, e.g., FIG. 10A-C).

The collection of extended recording tags can be concatenated after the fact (see, e.g., FIG. 10A-C). After the binding cycles are complete, the bead solid supports, each bead comprising on average one or fewer than one macromolecule per bead, each macromolecule having a collection of extended recording tags that are co-localized at the site of the macromolecule, are placed in an emulsion. The emulsion is formed such that each droplet, on average, is occupied by at most 1 bead. An optional assembly PCR reaction is performed in-emulsion to amplify the extended recording tags co-localized with the macromolecule on the bead and assemble them in co-linear order by priming between the different cycle specific sequences on the separate extended recording tags (Xiong, Peng et al. 2008). Afterwards the emulsion is broken and the assembled extended recording tags are sequenced.

In another embodiment, the DNA recording tag is comprised of a universal priming sequence (U1), one or more barcode sequences (BCs), and a spacer sequence (Sp1) specific to the first binding cycle. In the first binding cycle, binding agents employ DNA coding tags comprised of an Sp1 complementary spacer, an encoder barcode, and optional cycle barcode, and a second spacer element (Sp2). The utility of using at least two different spacer elements is that the first binding cycle selects one of potentially several DNA recording tags and a single DNA recording tag is extended resulting in a new Sp2 spacer element at the end of the extended DNA recording tag. In the second and subsequent binding cycles, binding agents contain just the Sp2' spacer rather than Sp1'. In this way, only the single extended recording tag from the first cycle is extended in subsequent cycles. In another embodiment, the second and subsequent cycles can employ binding agent specific spacers.

In some embodiments, a recording tag comprises from 5' to 3' direction: a universal forward (or 5') priming sequence, a UMI, and a spacer sequence. In some embodiments, a recording tag comprises from 5' to 3' direction: a universal forward (or 5') priming sequence, an optional UMI, a barcode (e.g., sample barcode, partition barcode, compartment barcode, spatial barcode, or any combination thereof), and a spacer sequence. In some other embodiments, a recording tag comprises from 5' to 3' direction: a universal forward (or 5') priming sequence, a barcode (e.g., sample barcode, partition barcode, compartment barcode, spatial barcode, or any combination thereof), an optional UMI, and a spacer sequence.

Figure 12A:
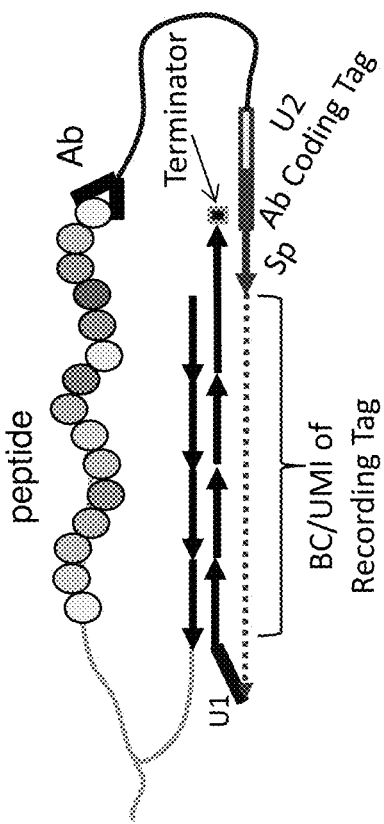
FIG. 12A-12D illustrate design of PNA combinatorial barcode/UMI recording tag and di-tag detection of binding events.
Figure 12B:
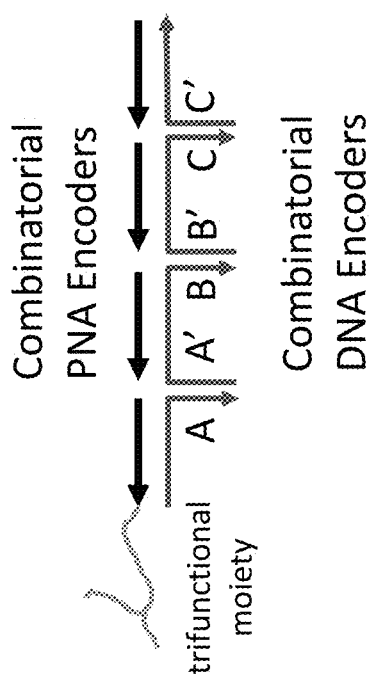
Figure 12C:
Figure 12D:
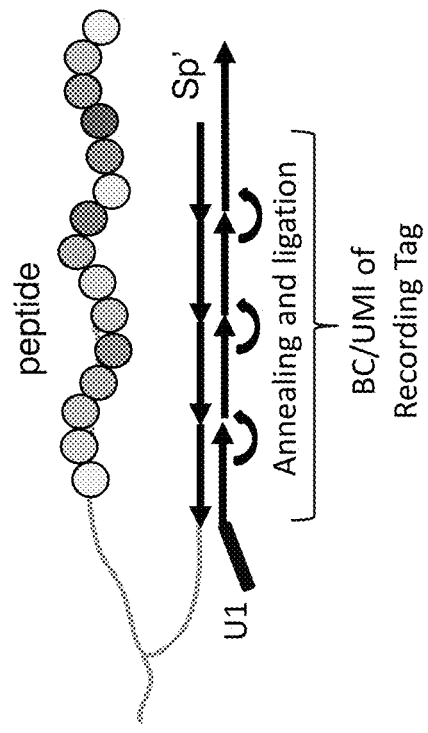

Combinatorial approaches may be used to generate UMIs from modified DNA and PNAs. In one example, a UMI may be constructed by "chemical ligating" together sets of short word sequences (4-15mers), which have been designed to be orthogonal to each other (Spiropulos and Heemstra 2012). A DNA template is used to direct the chemical ligation of the "word" polymers. The DNA template is constructed with hybridizing arms that enable assembly of a combinatorial template structure simply by mixing the sub-components together in solution (see, e.g., FIG. 12C). In certain embodiments, there are no "spacer" sequences in this design. The size of the word space can vary from 10's of words to 10,000's or more words. In certain embodiments, the words are chosen such that they differ from one another to not cross hybridize, yet possess relatively uniform hybridization conditions. In one embodiment, the length of the word will be on the order of 10 bases, with about 1000's words in the subset (this is only 0.1% of the total 10-mer word space $\sim 4^{10}=1$ million words). Sets of these words (1000 in subset) can be concatenated together to generate a final combinatorial UMI with complexity=$1000^n$ power. For 4 words concatenated together, this creates a UMI diversity of $10^{12}$ different elements. These UMI sequences will be appended to the macromolecule (peptides, proteins, etc.) at the single molecule level. In one embodiment, the diversity of UMIs exceeds the number of molecules of macromolecules to which the UMIs are attached. In this way, the UMI uniquely identifies the macromolecule of interest. The use of combinatorial word UMI's facilitates readout on high error rate sequencers, (e.g. nanopore sequencers, nanogap tunneling sequencing, etc.) since single base resolution is not required to read words of multiple bases in length. Combinatorial word approaches can also be used to generate other identity-informative components of recording tags or coding tags, such as compartment tags, partition barcodes, spatial barcodes, sample barcodes, encoder sequences, cycle specific sequences, and barcodes. Methods relating to nanopore sequencing and DNA encoding information with error-tolerant words (codes) are known in the art (see, e.g., Kiah et al., 2015, *Codes for DNA sequence profiles*. IEEE International Symposium on Information Theory (ISIT); Gabrys et al., 2015, *Asymmetric Lee distance codes for DNA-based storage*. IEEE Symposium on Information Theory (ISIT); Laure et al., 2016, *Coding in 2D: Using Intentional Dispersity to Enhance the Information Capacity of Sequence-Coded Polymer Barcodes*. Angew. Chem. Int. Ed. doi: 10.1002/anie.201605279; Yazdi et al., 2015, IEEE Transactions on Molecular, Biological and Multi-Scale Communications 1:230-248; and Yazdi et al., 2015, Sci Rep 5:14138, each of which is incorporated by reference in its entirety). Thus, in certain embodiments, an extended recording tag, an extended coding tag, or a di-tag construct in any of the embodiments described herein is comprised of identifying components (e.g., UMI, encoder sequence, barcode, compartment tag, cycle specific sequence, etc.) that are error correcting codes. In some embodiments, the error correcting code is selected from: Hamming code, Lee distance code, asymmetric Lee distance code, Reed-Solomon code, and Levenshtein-Tenengolts code. For nanopore sequencing, the current or ionic flux profiles and asymmetric base calling errors are intrinsic to the type of nanopore and biochemistry employed, and this information can be used to design more robust DNA codes using the aforementioned error correcting approaches. An alternative to employing robust DNA nanopore sequencing barcodes, one can directly use the current or ionic flux signatures of barcode sequences (U.S. Pat. No. 7,060,507, incorporated by reference in its entirety), avoiding DNA base calling entirely, and immediately identify the barcode sequence by mapping back to the predicted current/flux signature as described by Laszlo et al. (2014, Nat. Biotechnol. 32:829-833, incorporated by reference in its entirety). In this paper, Laszlo et al. describe the current signatures generated by the biological nanopore, MspA, when passing different word strings through the nanopore, and the ability to map and identify DNA strands by mapping resultant current signatures back to an in silico prediction of possible current signatures from a universe of sequences (2014, Nat. Biotechnol. 32:829-833). Similar concepts can be applied to DNA codes and the electrical signal generated by nanogap tunneling current-based DNA sequencing (Ohshiro et al., 2012, Sci Rep 2: 501).

Thus, in certain embodiments, the identifying components of a coding tag, recording tag, or both are capable of generating a unique current or ionic flux or optical signature, wherein the analysis step of any of the methods provided herein comprises detection of the unique current or ionic flux or optical signature in order to identify the identifying components. In some embodiments, the identifying components are selected from an encoder sequence, barcode, UMI, compartment tag, cycle specific sequence, or any combination thereof.

In certain embodiments, all or substantially amount of the macromolecules (e.g., proteins, polypeptides, or peptides) (e.g., at least 50%, 55%, 60%, 65%, 70%, 75%, 80%, 85%, 90%, 95%, 96%, 97%, 98%, 99%, or 100%) within a sample are labeled with a recording tag. Labeling of the macromolecules may occur before or after immobilization of the macromolecules to a solid support.

In other embodiments, a subset of macromolecules (e.g., proteins, polypeptides, or peptides) within a sample are labeled with recording tags. In a particular embodiment, a subset of macromolecules from a sample undergo targeted (analyte specific) labeling with recording tags. Targeted recording tag labeling of proteins may be achieved using target protein-specific binding agents (e.g., antibodies, aptamers, etc.) that are linked a short target-specific DNA capture probe, e.g., analyte-specific barcode, which anneal to complementary target-specific bait sequence, e.g., analyte-specific barcode, in recording tags (see, e.g., FIG. 28A). The recording tags comprise a reactive moiety for a cognate reactive moiety present on the target protein (e.g., click chemistry labeling, photoaffinity labeling). For example, recording tags may comprise an azide moiety for interacting with alkyne-derivatized proteins, or recording tags may comprise a benzophenone for interacting with native proteins, etc. (see, e.g., FIG. 28A-B). Upon binding of the target protein by the target protein specific binding agent, the recording tag and target protein are coupled via their corresponding reactive moieties (see, e.g., FIG. 28B-C). After the target protein is labeled with the recording tag, the target-protein specific binding agent may be removed by digestion of the DNA capture probe linked to the target-protein specific binding agent. For example, the DNA capture probe may be designed to contain uracil bases, which are then targeted for digestion with a uracil-specific excision reagent (e.g., USER™), and the target-protein specific binding agent may be dissociated from the target protein.

Figure 28A:
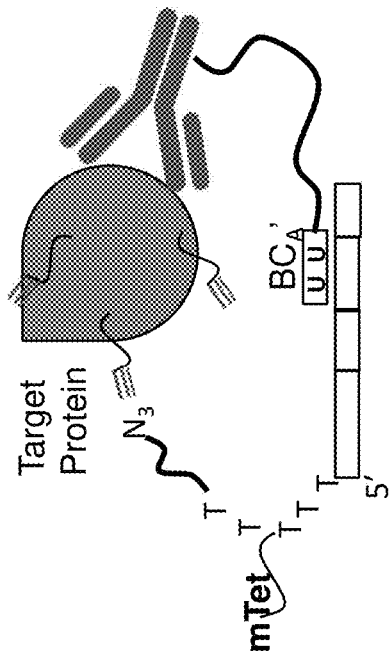
FIG. 28A-28D illustrate examples for the analyte-specific labeling of proteins with recording tags.

In one example, antibodies specific for a set of target proteins can be labeled with a DNA capture probe (e.g., analyte barcode $BC_A$ in FIG. 28A) that hybridizes with recording tags designed with complementary bait sequence (e.g., analyte barcode $BC_A'$ in FIG. 28A). Sample-specific labeling of proteins can be achieved by employing DNA-capture probe labeled antibodies hybridizing with complementary bait sequence on recording tags comprising of sample-specific barcodes.

In another example, target protein-specific aptamers are used for targeted recording tag labeling of a subset of proteins within a sample. A target specific-aptamer is linked to a DNA capture probe that anneals with complementary bait sequence in a recording tag. The recording tag comprises a reactive chemical or photo-reactive chemical probes (e.g. benzophenone (BP)) for coupling to the target protein having a corresponding reactive moiety. The aptamer binds to its target protein molecule, bringing the recording tag into close proximity to the target protein, resulting in the coupling of the recording tag to the target protein.

Photoaffinity (PA) protein labeling using photo-reactive chemical probes attached to small molecule protein affinity ligands has been previously described (Park, Koh et al. 2016). Typical photo-reactive chemical probes include probes based on benzophenone (reactive diradical, 365 nm), phenyldiazirine (reactive carbon, 365 nm), and phenylazide (reactive nitrene free radical, 260 nm), activated under irradiation wavelengths as previously described (Smith and Collins 2015). In a preferred embodiment, target proteins within a protein sample are labeled with recording tags comprising sample barcodes using the method disclosed by Li et al., in which a bait sequence in a benzophenone labeled recording tag is hybridized to a DNA capture probe attached to a cognate binding agent, e.g., nucleic acid aptamer (see, e.g., FIG. 28A-D) (Li, Liu et al. 2013). For photoaffinity labeled protein targets, the use of DNA/RNA aptamers as target protein-specific binding agents are preferred over antibodies since the photoaffinity moiety can self-label the antibody rather than the target protein. In contrast, photoaffinity labeling is less efficient for nucleic acids than proteins, making aptamers a better vehicle for DNA-directed chemical or photo-labeling. Similar to photo-affinity labeling, one can also employ DNA-directed chemical labeling of reactive lysine's (or other moieties) in the proximity of the aptamer binding site in a manner similar to that described by Rosen et al. (Rosen, Kodal et al. 2014, Kodal, Rosen et al. 2016).

Figure 28B:
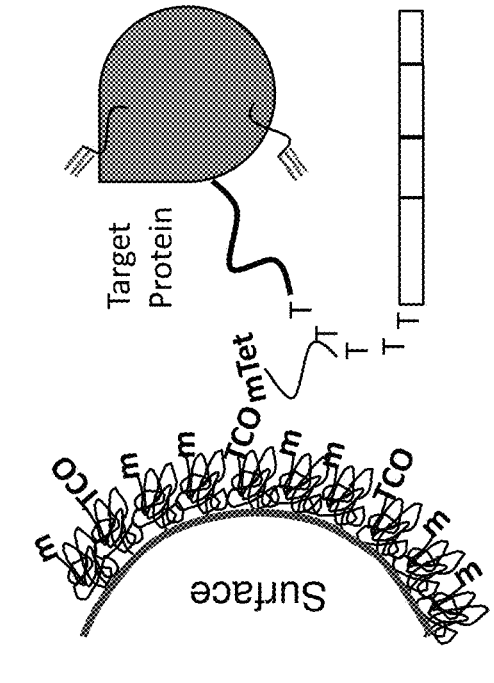
Figure 28C:
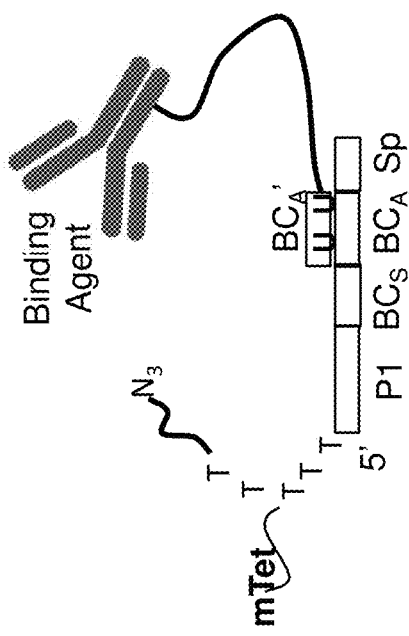
Figure 28D:
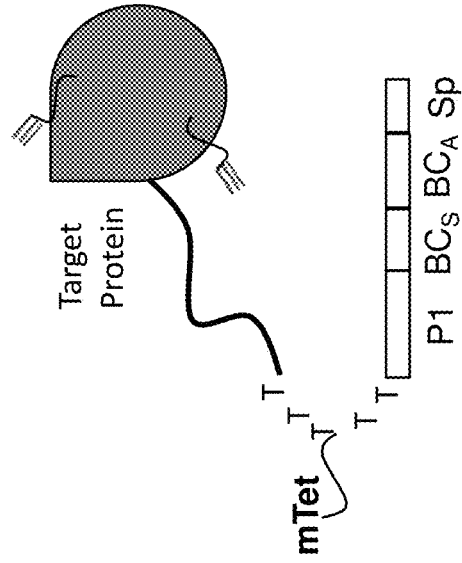

In the aforementioned embodiments, other types of linkages besides hybridization can be used to link the target specific binding agent and the recording tag (see, e.g., FIG. 28A). For example, the two moieties can be covalently linked, using a linker that is designed to be cleaved and release the binding agent once the captured target protein (or other macromolecule) is covalently linked to the recording tag as shown in FIG. 28B. A suitable linker can be attached to various positions of the recording tag, such as the 3' end, or within the linker attached to the 5' end of the recording tag.

E. Binding Agents and Coding Tags

In one aspect, the kits described herein comprise a binding agent capable of binding to an analyte, e.g., a macromolecule. A binding agent can be any molecule (e.g., peptide, polypeptide, protein, nucleic acid, carbohydrate, small molecule, and the like) capable of binding to a component or feature of a macromolecule. A binding agent can be a naturally occurring, synthetically produced, or recombinantly expressed molecule. A binding agent may bind to a single monomer or subunit of a macromolecule (e.g., a single amino acid of a peptide) or bind to multiple linked subunits of a macromolecule (e.g., dipeptide, tripeptide, or higher order peptide of a longer peptide molecule).

In certain embodiments, a binding agent may be designed to bind covalently. Covalent binding can be designed to be conditional or favored upon binding to the correct moiety. For example, an NTAA and its cognate NTAA-specific binding agent may each be modified with a reactive group such that once the NTAA-specific binding agent is bound to the cognate NTAA, a coupling reaction is carried out to create a covalent linkage between the two. Non-specific binding of the binding agent to other locations that lack the cognate reactive group would not result in covalent attachment. Covalent binding between a binding agent and its target allows for more stringent washing to be used to remove binding agents that are non-specifically bound, thus increasing the specificity of the assay.

In certain embodiments, a binding agent may be a selective binding agent. As used herein, selective binding refers to the ability of the binding agent to preferentially bind to a specific ligand (e.g., amino acid or class of amino acids) relative to binding to a different ligand (e.g., amino acid or class of amino acids). Selectivity is commonly referred to as the equilibrium constant for the reaction of displacement of one ligand by another ligand in a complex with a binding agent. Typically, such selectivity is associated with the spatial geometry of the ligand and/or the manner and degree by which the ligand binds to a binding agent, such as by hydrogen bonding or Van der Waals forces (non-covalent interactions) or by reversible or non-reversible covalent attachment to the binding agent. It should also be understood that selectivity may be relative, and as opposed to absolute, and that different factors can affect the same, including ligand concentration. Thus, in one example, a binding agent selectively binds one of the twenty standard amino acids. In an example of non-selective binding, a binding agent may bind to two or more of the twenty standard amino acids.

In the practice of the kits and methods disclosed herein, the ability of a binding agent to selectively bind a feature or component of a macromolecule need only be sufficient to allow transfer of its coding tag information to the recording tag associated with the macromolecule, transfer of the recording tag information to the coding tag, or transferring of the coding tag information and recording tag information to a di-tag molecule. Thus, selectively need only be relative to the other binding agents to which the macromolecule is exposed. It should also be understood that selectivity of a binding agent need not be absolute to a specific amino acid, but could be selective to a class of amino acids, such as amino acids with nonpolar or non-polar side chains, or with electrically (positively or negatively) charged side chains, or with aromatic side chains, or some specific class or size of side chains, and the like.

In a particular embodiment, the binding agent has a high affinity and high selectivity for the macromolecule of interest. In particular, a high binding affinity with a low off-rate is efficacious for information transfer between the coding tag and recording tag. In certain embodiments, a binding agent has a $K_d$ of or less than about 50 nM, of or less than about 10 nM, of or less than about 5 nM, of or less than about 1 nM, of or less than about 0.5 nM, or of or less than about 0.1 nM. In a particular embodiment, the binding agent is added to the macromolecule at a concentration >10×, >100×, or >1000× its $K_d$ to drive binding to completion. A detailed discussion of binding kinetics of an antibody to a single protein molecule is described in Chang et al. (Chang, Rissin et al. 2012).

To increase the affinity of a binding agent to small N-terminal amino acids (NTAAs) of peptides, the NTAA may be modified with an "immunogenic" hapten, such as dinitrophenol (DNP). This can be implemented in a cyclic sequencing approach using Sanger's reagent, dinitrofluorobenzene (DNFB), which attaches a DNP group to the amine group of the NTAA. Commercial anti-DNP antibodies have affinities in the low nM range (~8 nM, LO-DNP-2) (Bilgicer, Thomas et al. 2009); as such it stands to reason that it should be possible to engineer high-affinity NTAA binding agents to a number of NTAAs modified with DNP (via DNFB) and simultaneously achieve good binding selectivity for a particular NTAA. In another example, an NTAA may be modified with sulfonyl nitrophenol (SNP) using 4-sulfonyl-2-nitrofluorobenzene (SNFB). Similar affinity enhancements may also be achieved with alternative NTAA modifiers, such as an acetyl group or an amidinyl (guanidinyl) group.

In certain embodiments, a binding agent may bind to an NTAA, a CTAA, an intervening amino acid, dipeptide (sequence of two amino acids), tripeptide (sequence of three amino acids), or higher order peptide of a peptide molecule. In some embodiments, each binding agent in a library of binding agents selectively binds to a particular amino acid, for example one of the twenty standard naturally occurring amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr).

In certain embodiments, a binding agent may bind to a post-translational modification of an amino acid. In some embodiments, a peptide comprises one or more post-translational modifications, which may be the same of different. The NTAA, CTAA, an intervening amino acid, or a combination thereof of a peptide may be post-translationally modified. Post-translational modifications to amino acids include acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopanteteinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation (see, also, Seo and Lee, 2004, J. Biochem. Mol. Biol. 37:35-44).

In certain embodiments, a lectin is used as a binding agent for detecting the glycosylation state of a protein, polypeptide, or peptide. Lectins are carbohydrate-binding proteins that can selectively recognize glycan epitopes of free carbohydrates or glycoproteins. A list of lectins recognizing various glycosylation states (e.g., core-fucose, sialic acids, N-acetyl-D-lactosamine, mannose, N-acetyl-glucosamine) include: A, AAA, AAL, ABA, ACA, ACG, ACL, AOL, ASA, BanLec, BC2L-A, BC2LCN, BPA, BPL, Calsepa, CGL2, CNL, Con, ConA, DBA, Discoidin, DSA, ECA, EEL, F17AG, Gal1, Gal1-S, Gal2, Gal3, Gal3C-S, Gal7-S, Gal9, GNA, GRFT, GS-I, GS-II, GSL-I, GSL-II, HHL, HIHA, HPA, I, II, Jacalin, LBA, LCA, LEA, LEL, Lentil, Lotus, LSL-N, LTL, MAA, MAH, MAL_I, Malectin, MOA, MPA, MPL, NPA, Orysata, PA-IIL, PA-IL, PALa, PHA-E, PHA-L, PHA-P, PHAE, PHAL, PNA, PPL, PSA, PSL1a, PTL, PTL-I, PWM, RCA120, RS-Fuc, SAMB, SBA, SJA, SNA, SNA-I, SNA-II, SSA, STL, TJA-I, TJA-II, TxLCI, UDA, UEA-I, UEA-II, VFA, VVA, WFA, WGA (see, Zhang et al., 2016, MABS 8:524-535).

In certain embodiments, a binding agent may bind to a modified or labeled NTAA. A modified or labeled NTAA can be one that is labeled with PITC, 1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), an acetylating reagent, a guanidinylation reagent, a thioacylation reagent, a thioacetylation reagent, or a thiobenzylation reagent.

In certain embodiments, a binding agent can be an aptamer (e.g., peptide aptamer, DNA aptamer, or RNA aptamer), an antibody, an anticalin, an ATP-dependent Clp protease adaptor protein (ClpS), an antibody binding fragment, an antibody mimetic, a peptide, a peptidomimetic, a protein, or a polynucleotide (e.g., DNA, RNA, peptide nucleic acid (PNA), a γPNA, bridged nucleic acid (BNA), xeno nucleic acid (XNA), glycerol nucleic acid (GNA), or threose nucleic acid (TNA), or a variant thereof).

As used herein, the terms antibody and antibodies are used in a broad sense, to include not only intact antibody molecules, for example but not limited to immunoglobulin A, immunoglobulin G, immunoglobulin D, immunoglobulin E, and immunoglobulin M, but also any immunoreactivity component(s) of an antibody molecule that immuno-specifically bind to at least one epitope. An antibody may be naturally occurring, synthetically produced, or recombinantly expressed. An antibody may be a fusion protein. An antibody may be an antibody mimetic. Examples of antibodies include but are not limited to, Fab fragments, Fab' fragments, F(ab')2 fragments, single chain antibody fragments (scFv), miniantibodies, diabodies, crosslinked antibody fragments, Affibody™, nanobodies, single domain antibodies, DVD-Ig molecules, alphabodies, affimers, affitins, cyclotides, molecules, and the like. Immunoreactive products derived using antibody engineering or protein engineering techniques are also expressly within the meaning of the term antibodies. Detailed descriptions of antibody and/or protein engineering, including relevant protocols, can be found in, among other places, J. Maynard and G. Georgiou, 2000, Ann. Rev. Biomed. Eng. 2:339-76; Antibody Engineering, R. Kontermann and S. Dubel, eds., Springer Lab Manual, Springer Verlag (2001); U.S. Pat. No. 5,831, 012; and S. Paul, Antibody Engineering Protocols, Humana Press (1995).

As with antibodies, nucleic acid and peptide aptamers that specifically recognize a peptide can be produced using known methods. Aptamers bind target molecules in a highly specific, conformation-dependent manner, typically with very high affinity, although aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, and viral proteins. Aptamers have been shown to retain functional activity after biotinylation, fluorescein labeling, and when attached to glass surfaces and microspheres. (see, Jayasena, 1999, Clin Chem 45:1628-50; Kusser2000, J. Biotechnol. 74: 27-39; Colas, 2000, Curr Opin Chem Biol 4:54-9). Aptamers which specifically bind arginine and AMP have been described as well (see, Patel and Suri, 2000, J. Biotech. 74:39-60). Oligonucleotide aptamers that bind to a specific amino acid have been disclosed in Gold et al. (1995, Ann. Rev. Biochem. 64:763-97). RNA aptamers that bind amino acids have also been described (Ames and Breaker, 2011, RNA Biol. 8; 82-89; Mannironi et al., 2000, RNA 6:520-27; Famulok, 1994, J. Am. Chem. Soc. 116:1698-1706).

A binding agent can be made by modifying naturally-occurring or synthetically-produced proteins by genetic engineering to introduce one or more mutations in the amino acid sequence to produce engineered proteins that bind to a specific component or feature of a macromolecule (e.g., NTAA, CTAA, or post-translationally modified amino acid or a peptide). For example, exopeptidases (e.g., aminopeptidases, carboxypeptidases), exoproteases, mutated exoproteases, mutated anticalins, mutated ClpSs, antibodies, or tRNA synthetases can be modified to create a binding agent that selectively binds to a particular NTAA. In another example, carboxypeptidases can be modified to create a binding agent that selectively binds to a particular CTAA. A binding agent can also be designed or modified, and utilized, to specifically bind a modified NTAA or modified CTAA, for example one that has a post-translational modification (e.g., phosphorylated NTAA or phosphorylated CTAA) or one that has been modified with a label (e.g., PTC, 1-fluoro-2,4-dinitrobenzene (using Sanger's reagent, DNFB), dansyl chloride (using DNS-Cl, or 1-dimethylaminonaphthalene-5-sulfonyl chloride), or using a thioacylation reagent, a thioacetylation reagent, an acetylation reagent, an amidination (guanidinylation) reagent, or a thiobenzylation reagent).

Strategies for directed evolution of proteins are known in the art (e.g., reviewed by Yuan et al., 2005, Microbiol. Mol. Biol. Rev. 69:373-392), and include phage display, ribosomal display, mRNA display, CIS display, CAD display, emulsions, cell surface display method, yeast surface display, bacterial surface display, etc.

In some embodiments, a binding agent that selectively binds to a modified NTAA can be utilized. For example, the NTAA may be reacted with phenylisothiocyanate (PITC) to form a phenylthiocarbamoyl-NTAA derivative. In this manner, the binding agent may be fashioned to selectively bind both the phenyl group of the phenylthiocarbamoyl moiety as well as the alpha-carbon R group of the NTAA. Use of PITC in this manner allows for subsequent cleavage of the NTAA by Edman degradation as discussed below. In another embodiment, the NTAA may be reacted with Sanger's reagent (DNFB), to generate a DNP-labeled NTAA (see, e.g., FIG. 3). Optionally, DNFB is used with an ionic liquid such as 1-ethyl-3-methylimidazolium bis[(trifluoromethyl) sulfonyl]imide ([emim][Tf2N]), in which DNFB is highly soluble. In this manner, the binding agent may be engineered to selectively bind the combination of the DNP and the R group on the NTAA. The addition of the DNP moiety provides a larger "handle" for the interaction of the binding agent with the NTAA, and should lead to a higher affinity interaction. In yet another embodiment, a binding agent may be an aminopeptidase that has been engineered to recognize the DNP-labeled NTAA providing cyclic control of aminopeptidase degradation of the peptide. Once the DNP-labeled NTAA is cleaved, another cycle of DNFB derivitization is performed in order to bind and cleave the newly exposed NTAA. In preferred particular embodiment, the aminopeptidase is a monomeric metallo-protease, such an aminopeptidase activated by zinc (Calcagno and Klein 2016). In another example, a binding agent may selectively bind to an NTAA that is modified with sulfonyl nitrophenol (SNP), e.g., by using 4-sulfonyl-2-nitrofluorobenzene (SNFB). In yet another embodiment, a binding agent may selectively bind to an NTAA that is acetylated or amidinated.

Other reagents that may be used to modify the NTAA include trifluoroethyl isothiocyanate, allyl isothiocyanate, and dimethylaminoazobenzene isothiocyanate.

A binding agent may be engineered for high affinity for a modified NTAA, high specificity for a modified NTAA, or both. In some embodiments, binding agents can be developed through directed evolution of promising affinity scaffolds using phage display. For moderate to lower affinity binding agents, efficient information transfer can be effected by using a concomitant binding/encoding step, or alternatively, the temperature of the encoding or information writing step can be decreased to slow the off rate of the binding agent. In some embodiments, the concomitant binding/encoding step can be combined with a decreased temperature of the encoding or information writing step. In some embodiments, after the initial binding of a binding moiety to the analyte, the binding moiety of the binding agent may be covalently bound (directly or indirectly), e.g., by cross-linking, to the analyte, in order to slow the off rate of the binding agent. This may be useful for moderate to lower affinity binding agents.

Engineered aminopeptidase mutants that bind to and cleave individual or small groups of labelled (biotinylated) NTAAs have been described (see e.g., PCT Publication No. WO2010/065322, incorporated by reference in its entirety). Aminopeptidases are enzymes that cleave amino acids from the N-terminus of proteins or peptides. Natural aminopeptidases have very limited specificity, and generically cleave N-terminal amino acids in a processive manner, cleaving one amino acid off after another (Kishor et al., 2015, Anal. Biochem. 488:6-8). However, residue specific aminopeptidases have been identified (Eriquez et al., J. Clin. Microbiol. 1980, 12:667-71; Wilce et al., 1998, Proc. Natl. Acad. Sci. USA 95:3472-3477; Liao et al., 2004, Prot. Sci. 13:1802-10). Aminopeptidases may be engineered to specifically bind to 20 different NTAAs representing the standard amino acids that are labeled with a specific moiety (e.g., PTC, DNP, SNP, etc.). Control of the stepwise degradation of the N-terminus of the peptide is achieved by using engineered aminopeptidases that are only active (e.g., binding activity or catalytic activity) in the presence of the label. In another example, Havranak et al. (U.S. Patent Publication 2014/0273004) describes engineering aminoacyl tRNA synthetases (aaRSs) as specific NTAA binders. The amino acid binding pocket of the aaRSs has an intrinsic ability to bind cognate amino acids, but generally exhibits poor binding affinity and specificity. Moreover, these natural amino acid binders don't recognize N-terminal labels. Directed evolution of aaRS scaffolds can be used to generate higher affinity, higher specificity binding agents that recognized the N-terminal amino acids in the context of an N-terminal label.

In another example, highly-selective engineered ClpSs have also been described in the literature. Emili et al. describe the directed evolution of an *E. coli* ClpS protein via phage display, resulting in four different variants with the ability to selectively bind NTAAs for aspartic acid, arginine, tryptophan, and leucine residues (U.S. Pat. No. 9,566,335, incorporated by reference in its entirety). In one embodiment, the binding moiety of the binding agent comprises a member of the evolutionarily conserved ClpS family of adaptor proteins involved in natural N-terminal protein recognition and binding or a variant thereof. The ClpS family of adaptor proteins in bacteria are described in Schuenemann et al., (2009), "Structural basis of N-end rule substrate recognition in *Escherichia coli* by the ClpAP adaptor protein ClpS," *EMBO Reports* 10(5), and Roman-Hernandez et al., (2009), "Molecular basis of substrate selection by the N-end rule adaptor protein ClpS," *PNAS* 106(22):8888-93. See also Guo et al., (2002), *JBC* 277(48): 46753-62, and Wang et al., (2008), "The molecular basis of N-end rule recognition," *Molecular Cell* 32: 406-414. In some embodiments, the amino acid residues corresponding to the ClpS hydrophobic binding pocket identified in Schuenemann et al. are modified in order to generate a binding moiety with the desired selectivity. ClpS family members include and are not limited to ClpS1 RPA1203, ClpS2 bll5154, ClpS2 RPA3148, ClpS BAV2091, ClpS BP2756, ClpS ECP_0896, ClpS ECSE_0939, ClpS SG1101, ClpS SCO2916, SCE19A.16c, ClpS Sputw3181_1781, ClpS VC_1143, ClpS WS0336, ClpS XCC1966, ClpS Tcr_1111, ClpS TDE_2123, ClpS ZM01725, ClpS1 bll2636, ClpS BCAN_A1188, ClpS BamMC406_2437, ClpS Bamb_2567, ClpS BMA10247_2157, ClpS BMASAVP1_A0575, ClpS BURPS1106A_0963, ClpS Bcepl808_2597, ClpS CCNA_02552, and a fragment, variant, mutant, homologue, or modified version thereof.

In one embodiment, the binding moiety of the binding agent comprises a ClpS2 protein or polypeptide or fragment thereof, such as disclosed in Stein et al., (2016), "Structural Basis of an N-Degron Adaptor with More Stringent Specificity," *Structure* 24(2): 232-242. In some embodiments, a CipS protein or polypeptide disclosed herein include a variant, mutant, homologue, or modified version that shares sequence identity with a reference ClpS protein or polypeptide, such as *A. tumefaciens* ClpS2 (e.g., SEQ ID NO: 198), E. coli ClpS (e.g., SEQ ID NO: 199), and/or C. crescentus ClpS (e.g., SEQ ID NO: 200). In one aspect, the binding moiety of the binding agent comprises a polypeptide sequence with about 10% sequence identity, about 15% sequence identity, about 20% sequence identity, about 25% sequence identity, about 30% sequence identity, about 35% sequence identity, about 40% sequence identity, about 45% sequence identity, about 50% sequence identity, about 55% sequence identity, about 60% sequence identity, about 65% sequence identity, about 70% sequence identity, about 75% sequence identity, about 80% sequence identity, about 85% sequence identity, about 90%, 91%, 92%, 93%, 94%, 95%, 96%, 97%, 98%, or 99% sequence identity, or about 100% sequence identity, with SEQ ID NO: 198, with SEQ ID NO: 199, and/or with SEQ ID NO: 200.

In one embodiment, the binding moiety comprises a member of the UBR box recognition sequence family, or a variant of the UBR box recognition sequence family. UBR recognition boxes are described in Tasaki et al., (2009), JBC 284(3): 1884-95. For example, the binding moiety may comprise UBR1, UBR2, or a mutant, variant, or homologue thereof.

In certain embodiments, the binding agent further comprises one or more detectable labels such as fluorescent labels, in addition to the binding moiety. In some embodiments, the binding agent does not comprise a polynucleotide such as a coding tag. Optionally, the binding agent comprises a synthetic or natural antibody. In some embodiments, the binding agent comprises an aptamer. In one embodiment, the binding agent comprises a polypeptide, such as a modified member of the ClpS family of adaptor proteins, such as a variant of a E. coli ClpS binding polypeptide, and a detectable label. In one embodiment, the detectable label is optically detectable. In some embodiments, the detectable label comprises a fluorescently moiety, a color-coded nanoparticle, a quantum dot or any combination thereof. In one embodiment the label comprises a polystyrene dye encompassing a core dye molecule such as a FluoSphere™, Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. In one embodiment, the detectable label is resistant to photobleaching while producing lots of signal (such as photons) at a unique and easily detectable wavelength, with high signal-to-noise ratio.

In a particular embodiment, anticalins are engineered for both high affinity and high specificity to labeled NTAAs (e.g., DNP, SNP, acetylated, etc.). Certain varieties of anticalin scaffolds have suitable shape for binding single amino acids, by virtue of their beta barrel structure. An N-terminal amino acid (either with or without modification) can potentially fit and be recognized in this "beta barrel" bucket. High affinity anticalins with engineered novel binding activities have been described (reviewed by Skerra, 2008, FEBS J. 275: 2677-2683). For example, anticalins with high affinity binding (low nM) to fluorescein and digoxygenin have been engineered (Gebauer and Skerra 2012). Engineering of alternative scaffolds for new binding functions has also been reviewed by Banta et al. (2013, Annu. Rev. Biomed. Eng. 15:93-113).

The functional affinity (avidity) of a given monovalent binding agent may be increased by at least an order of magnitude by using a bivalent or higher order multimer of the monovalent binding agent (Vauquelin and Charlton 2013). Avidity refers to the accumulated strength of multiple, simultaneous, non-covalent binding interactions. An individual binding interaction may be easily dissociated. However, when multiple binding interactions are present at the same time, transient dissociation of a single binding interaction does not allow the binding protein to diffuse away and the binding interaction is likely to be restored. An alternative method for increasing avidity of a binding agent is to include complementary sequences in the coding tag attached to the binding agent and the recording tag associated with the macromolecule.

In some embodiments, a binding agent can be utilized that selectively binds a modified C-terminal amino acid (CTAA). Carboxypeptidases are proteases that cleave terminal amino acids containing a free carboxyl group. A number of carboxypeptidases exhibit amino acid preferences, e.g., carboxypeptidase B preferentially cleaves at basic amino acids, such as arginine and lysine. A carboxypeptidase can be modified to create a binding agent that selectively binds to particular amino acid. In some embodiments, the carboxypeptidase may be engineered to selectively bind both the modification moiety as well as the alpha-carbon R group of the CTAA. Thus, engineered carboxypeptidases may specifically recognize 20 different CTAAs representing the standard amino acids in the context of a C-terminal label. Control of the stepwise degradation from the C-terminus of the peptide is achieved by using engineered carboxypeptidases that are only active (e.g., binding activity or catalytic activity) in the presence of the label. In one example, the CTAA may be modified by a para-Nitroanilide or 7-amino-4-methylcoumarinyl group.

Other potential scaffolds that can be engineered to generate binders for use in the methods described herein include: an anticalin, an amino acid tRNA synthetase (aaRS), ClpS, an Affilin®, an Adnectin™, a T cell receptor, a zinc finger protein, a thioredoxin, GST A1-1, DARPin, an affimer, an affitin, an alphabody, an avimer, a Kunitz domain peptide, a monobody, a single domain antibody, EETI-II, HPSTI, intrabody, lipocalin, PHD-finger, V(NAR) LDTI, evibody, Ig(NAR), knottin, maxibody, neocarzinostatin, pVIII, tendamistat, VLR, protein A scaffold, MTI-II, ecotin, GCN4, Im9, kunitz domain, microbody, PBP, trans-body, tetranectin, WW domain, CBM4-2, DX-88, GFP, iMab, Ldl receptor domain A, Min-23, PDZ-domain, avian pancreatic polypeptide, charybdotoxin/10Fn3, domain antibody (Dab), a2p8 ankyrin repeat, insect defensing A peptide, Designed AR protein, C-type lectin domain, staphylococcal nuclease, Src homology domain 3 (SH3), or Src homology domain 2 (SH2).

A binding agent may be engineered to withstand higher temperatures and mild-denaturing conditions (e.g., presence of urea, guanidinium thiocyanate, ionic solutions, etc.). The use of denaturants helps reduce secondary structures in the surface bound peptides, such as α-helical structures, β-hairpins, β-strands, and other such structures, which may interfere with binding of binding agents to linear peptide epitopes. In one embodiment, an ionic liquid such as 1-ethyl-3-methylimidazolium acetate ([EMIM]+[ACE] is used to reduce peptide secondary structure during binding cycles (Lesch, Heuer et al. 2015).

Any binding agent described also comprises a coding tag containing identifying information regarding the binding agent. A coding tag is a nucleic acid molecule of about 3 bases to about 100 bases that provides unique identifying information for its associated binding agent. A coding tag may comprise about 3 to about 90 bases, about 3 to about 80 bases, about 3 to about 70 bases, about 3 to about 60 bases, about 3 bases to about 50 bases, about 3 bases to about 40 bases, about 3 bases to about 30 bases, about 3 bases to about 20 bases, about 3 bases to about 10 bases, or about 3 bases to about 8 bases. In some embodiments, a coding tag is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, 40 bases, 55 bases, 60 bases, 65 bases, 70 bases, 75 bases, 80 bases, 85 bases, 90 bases, 95 bases, or 100 bases in length. A coding tag may be composed of DNA, RNA, polynucleotide analogs, or a combination thereof. Polynucleotide analogs include PNA, gamma-PNA, BNA, GNA, TNA, LNA, morpholino polynucleotides, 2'-O-Methyl polynucleotides, alkyl ribosyl substituted polynucleotides, phosphorothioate polynucleotides, and 7-deaza purine analogs.

A coding tag comprises an encoder sequence that provides identifying information regarding the associated binding agent. An encoder sequence is about 3 bases to about 30 bases, about 3 bases to about 20 bases, about 3 bases to about 10 bases, or about 3 bases to about 8 bases. In some embodiments, an encoder sequence is about 3 bases, 4 bases, 5 bases, 6 bases, 7 bases, 8 bases, 9 bases, 10 bases, 11 bases, 12 bases, 13 bases, 14 bases, 15 bases, 20 bases, 25 bases, or 30 bases in length. The length of the encoder sequence determines the number of unique encoder sequences that can be generated. Shorter encoding sequences generate a smaller number of unique encoding sequences, which may be useful when using a small number of binding agents. Longer encoder sequences may be desirable when analyzing a population of macromolecules. For example, an encoder sequence of 5 bases would have a formula of 5'-NNNNN-3' (SEQ ID NO: 135), wherein N may be any naturally occurring nucleotide, or analog. Using the four naturally occurring nucleotides A, T, C, and G, the total number of unique encoder sequences having a length of 5 bases is 1,024. In some embodiments, the total number of unique encoder sequences may be reduced by excluding, for example, encoder sequences in which all the bases are identical, at least three contiguous bases are identical, or both. In a specific embodiment, a set of >50 unique encoder sequences are used for a binding agent library.

In some embodiments, identifying components of a coding tag or recording tag, e.g., the encoder sequence, barcode, UMI, compartment tag, partition barcode, sample barcode, spatial region barcode, cycle specific sequence or any combination thereof, is subject to Hamming distance, Lee distance, asymmetric Lee distance, Reed-Solomon, Levenshtein-Tenengolts, or similar methods for error-correction. Hamming distance refers to the number of positions that are different between two strings of equal length. It measures the minimum number of substitutions required to change one string into the other. Hamming distance may be used to correct errors by selecting encoder sequences that are reasonable distance apart. Thus, in the example where the encoder sequence is 5 base, the number of useable encoder sequences is reduced to 256 unique encoder sequences (Hamming distance of 1→44 encoder sequences=256 encoder sequences). In another embodiment, the encoder sequence, barcode, UMI, compartment tag, cycle specific sequence, or any combination thereof is designed to be easily read out by a cyclic decoding process (Gunderson, 2004, Genome Res. 14:870-7). In another embodiment, the encoder sequence, barcode, UMI, compartment tag, partition barcode, spatial barcode, sample barcode, cycle specific sequence, or any combination thereof is designed to be read out by low accuracy nanopore sequencing, since rather than requiring single base resolution, words of multiple bases (~5-20 bases in length) need to be read. A subset of 15-mer, error-correcting Hamming barcodes that may be used in the methods of the present disclosure are set forth in SEQ ID NOs: 1-65 and their corresponding reverse complementary sequences as set forth in SEQ ID NO: 66-130.

In some embodiments, each unique binding agent within a library of binding agents has a unique encoder sequence. For example, 20 unique encoder sequences may be used for a library of 20 binding agents that bind to the 20 standard amino acids. Additional coding tag sequences may be used to identify modified amino acids (e.g., post-translationally modified amino acids). In another example, 30 unique encoder sequences may be used for a library of 30 binding agents that bind to the 20 standard amino acids and 10 post-translational modified amino acids (e.g., phosphorylated amino acids, acetylated amino acids, methylated amino acids). In other embodiments, two or more different binding agents may share the same encoder sequence. For example, two binding agents that each bind to a different standard amino acid may share the same encoder sequence.

In certain embodiments, a coding tag further comprises a spacer sequence at one end or both ends. A spacer sequence is about 1 base to about 20 bases, about 1 base to about 10 bases, about 5 bases to about 9 bases, or about 4 bases to about 8 bases. In some embodiments, a spacer is about 1 base, 2 bases, 3 bases, 4 bases, 5 bases, 6 bases, 7 bases, 8 bases, 9 bases, 10 bases, 11 bases, 12 bases, 13 bases, 14 bases, 15 bases or 20 bases in length. In some embodiments, a spacer within a coding tag is shorter than the encoder sequence, e.g., at least 1 base, 2, bases, 3 bases, 4 bases, 5 bases, 6, bases, 7 bases, 8 bases, 9 bases, 10 bases, 11 bases, 12 bases, 13 bases, 14 bases, 15 bases, 20 bases, or 25 bases shorter than the encoder sequence. In other embodiments, a spacer within a coding tag is the same length as the encoder sequence. In certain embodiments, the spacer is binding agent specific so that a spacer from a previous binding cycle only interacts with a spacer from the appropriate binding agent in a current binding cycle. An example would be pairs of cognate antibodies containing spacer sequences that only allow information transfer if both antibodies sequentially bind to the macromolecule. A spacer sequence may be used as the primer annealing site for a primer extension reaction, or a splint or sticky end in a ligation reaction. A 5' spacer on a coding tag (see, e.g., FIG. 5, "*Sp'") may optionally contain pseudo complementary bases to a 3' spacer on the recording tag to increase Tm (Lehoud et al., 2008, Nucleic Acids Res. 36:3409-3419).

In some embodiments, the coding tags within a collection of binding agents share a common spacer sequence used in an assay (e.g., the entire library of binding agents used in a multiple binding cycle method possess a common spacer in their coding tags). In another embodiment, the coding tags are comprised of a binding cycle tags, identifying a particular binding cycle. In other embodiments, the coding tags within a library of binding agents have a binding cycle specific spacer sequence. In some embodiments, a coding tag comprises one binding cycle specific spacer sequence. For example, a coding tag for binding agents used in the first binding cycle comprise a "cycle 1" specific spacer sequence, a coding tag for binding agents used in the second binding cycle comprise a "cycle 2" specific spacer sequence, and so on up to "n" binding cycles. In further embodiments, coding tags for binding agents used in the first binding cycle comprise a "cycle 1" specific spacer sequence and a "cycle 2" specific spacer sequence, coding tags for binding agents used in the second binding cycle comprise a "cycle 2"

specific spacer sequence and a "cycle 3" specific spacer sequence, and so on up to "n" binding cycles. This embodiment is useful for subsequent PCR assembly of non-concatenated extended recording tags after the binding cycles are completed (see, e.g., FIG. 10A-C). In some embodiments, a spacer sequence comprises a sufficient number of bases to anneal to a complementary spacer sequence in a recording tag or extended recording tag to initiate a primer extension reaction or sticky end ligation reaction.

A cycle specific spacer sequence can also be used to concatenate information of coding tags onto a single recording tag when a population of recording tags is associated with a macromolecule. The first binding cycle transfers information from the coding tag to a randomly-chosen recording tag, and subsequent binding cycles can prime only the extended recording tag using cycle dependent spacer sequences. More specifically, coding tags for binding agents used in the first binding cycle comprise a "cycle 1" specific spacer sequence and a "cycle 2" specific spacer sequence, coding tags for binding agents used in the second binding cycle comprise a "cycle 2" specific spacer sequence and a "cycle 3" specific spacer sequence, and so on up to "n" binding cycles. Coding tags of binding agents from the first binding cycle are capable of annealing to recording tags via complementary cycle 1 specific spacer sequences. Upon transfer of the coding tag information to the recording tag, the cycle 2 specific spacer sequence is positioned at the 3' terminus of the extended recording tag at the end of binding cycle 1. Coding tags of binding agents from the second binding cycle are capable of annealing to the extended recording tags via complementary cycle 2 specific spacer sequences. Upon transfer of the coding tag information to the extended recording tag, the cycle 3 specific spacer sequence is positioned at the 3' terminus of the extended recording tag at the end of binding cycle 2, and so on through "n" binding cycles. This embodiment provides that transfer of binding information in a particular binding cycle among multiple binding cycles will only occur on (extended) recording tags that have experienced the previous binding cycles. However, sometimes a binding agent will fail to bind to a cognate macromolecule. Oligonucleotides comprising binding cycle specific spacers after each binding cycle as a "chase" step can be used to keep the binding cycles synchronized even if the event of a binding cycle failure. For example, if a cognate binding agent fails to bind to a macromolecule during binding cycle 1, adding a chase step following binding cycle 1 using oligonucleotides comprising both a cycle 1 specific spacer, a cycle 2 specific spacer, and a "null" encoder sequence. The "null" encoder sequence can be the absence of an encoder sequence or, for example, a specific barcode that positively identifies a "null" binding cycle. The "null" oligonucleotide is capable of annealing to the recording tag via the cycle 1 specific spacer, and the cycle 2 specific spacer is transferred to the recording tag. Thus, binding agents from binding cycle 2 are capable of annealing to the extended recording tag via the cycle 2 specific spacer despite the failed binding cycle 1 event. The "null" oligonucleotide marks binding cycle 1 as a failed binding event within the extended recording tag.

Figures 35A, 35B, 35C:
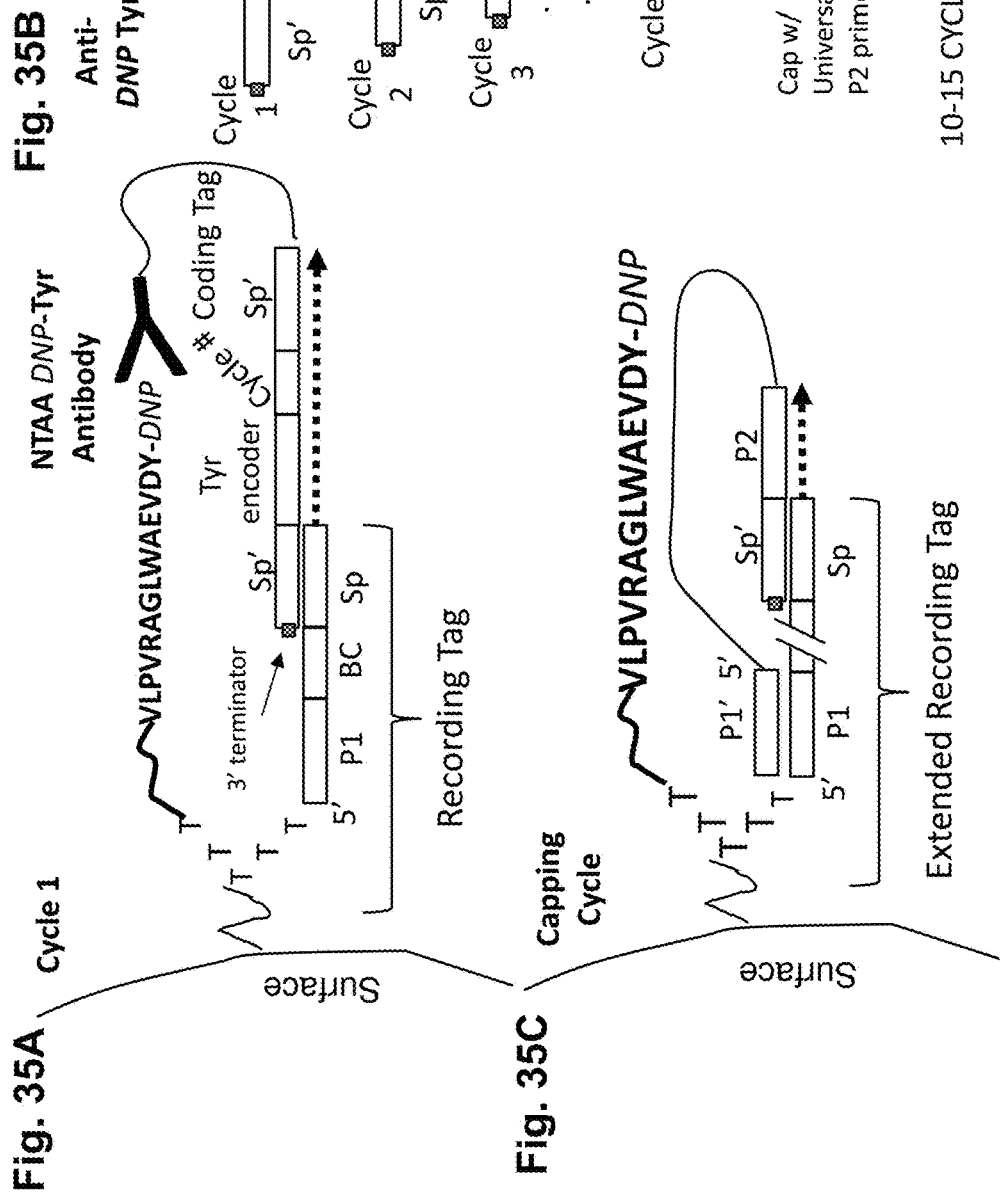
FIG. 35A-35C illustrate examples for Next Generation Protein Sequencing (NGPS) binding cycle-specific coding tags.

In preferred embodiment, binding cycle-specific encoder sequences are used in coding tags. Binding cycle-specific encoder sequences may be accomplished either via the use of completely unique analyte (e.g., NTAA)-binding cycle encoder barcodes or through a combinatoric use of an analyte (e.g., NTAA) encoder sequence joined to a cycle-specific barcode (see, e.g., FIG. 35A-C). The advantage of using a combinatoric approach is that fewer total barcodes need to be designed. For a set of 20 analyte binding agents used across 10 cycles, only 20 analyte encoder sequence barcodes and 10 binding cycle specific barcodes need to be designed. In contrast, if the binding cycle is embedded directly in the binding agent encoder sequence, then a total of 200 independent encoder barcodes may need to be designed. An advantage of embedding binding cycle information directly in the encoder sequence is that the total length of the coding tag can be minimized when employing error-correcting barcodes on a nanopore readout. The use of error-tolerant barcodes allows highly accurate barcode identification using sequencing platforms and approaches that are more error-prone, but have other advantages such as rapid speed of analysis, lower cost, and/or more portable instrumentation. One such example is a nanopore-based sequencing readout.

Figure 32E:
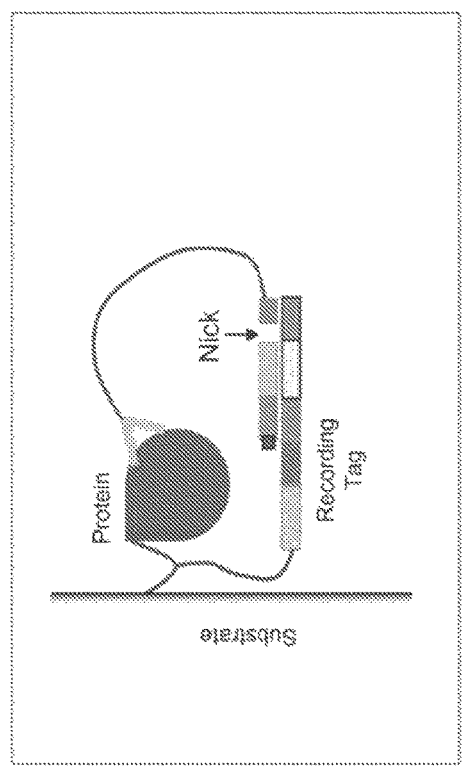

In some embodiments, a coding tag comprises a cleavable or nickable DNA strand within the second (3') spacer sequence proximal to the binding agent (see, e.g., FIG. 32E). For example, the 3' spacer may have one or more uracil bases that can be nicked by uracil-specific excision reagent (USER). USER generates a single nucleotide gap at the location of the uracil. In another example, the 3' spacer may comprise a recognition sequence for a nicking endonuclease that hydrolyzes only one strand of a duplex. For example, the enzyme used for cleaving or nicking the 3' spacer sequence acts only on one DNA strand (the 3' spacer of the coding tag), such that the other strand within the duplex belonging to the (extended) recording tag is left intact. These embodiments is particularly useful in assays analysing proteins in their native conformation, as it allows the non-denaturing removal of the binding agent from the (extended) recording tag after primer extension has occurred and leaves a single stranded DNA spacer sequence on the extended recording tag available for subsequent binding cycles.

The coding tags may also be designed to contain palindromic sequences. Inclusion of a palindromic sequence into a coding tag allows a nascent, growing, extended recording tag to fold upon itself as coding tag information is transferred. The extended recording tag is folded into a more compact structure, effectively decreasing undesired intermolecular binding and primer extension events.

In some embodiments, a coding tag comprises analyte-specific spacer that is capable of priming extension only on recording tags previously extended with binding agents recognizing the same analyte. An extended recording tag can be built up from a series of binding events using coding tags comprising analyte-specific spacers and encoder sequences. In one embodiment, a first binding event employs a binding agent with a coding tag comprised of a generic 3' spacer primer sequence and an analyte-specific spacer sequence at the 5' terminus for use in the next binding cycle; subsequent binding cycles then use binding agents with encoded analyte-specific 3' spacer sequences. This design results in amplifiable library elements being created only from a correct series of cognate binding events. Off-target and cross-reactive binding interactions will lead to a non-amplifiable extended recording tag. In one example, a pair of cognate binding agents to a particular macromolecule analyte is used in two binding cycles to identify the analyte. The first cognate binding agent contains a coding tag comprised of a generic spacer 3' sequence for priming extension on the generic spacer sequence of the recording tag, and an encoded analyte-specific spacer at the 5' end, which will be used in the next binding cycle. For matched cognate binding agent pairs, the 3' analyte-specific spacer of the second binding agent is matched to the 5' analyte-specific spacer of the first binding agent. In this way, only correct binding of the cognate pair of binding agents will result in an amplifiable extended recording tag. Cross-reactive binding agents will not be able to prime extension on the recording tag, and no amplifiable extended recording tag product generated. This approach greatly enhances the specificity of the methods disclosed herein. The same principle can be applied to triplet binding agent sets, in which 3 cycles of binding are employed. In a first binding cycle, a generic 3' Sp sequence on the recording tag interacts with a generic spacer on a binding agent coding tag. Primer extension transfers coding tag information, including an analyte specific 5' spacer, to the recording tag. Subsequent binding cycles employ analyte specific spacers on the binding agents' coding tags.

In certain embodiments, a coding tag may further comprise a unique molecular identifier for the binding agent to which the coding tag is linked. A UMI for the binding agent may be useful in embodiments utilizing extended coding tags or di-tag molecules for sequencing readouts, which in combination with the encoder sequence provides information regarding the identity of the binding agent and number of unique binding events for a macromolecule.

In another embodiment, a coding tag includes a randomized sequence (a set of N's, where N=a random selection from A, C, G, T, or a random selection from a set of words). After a series of "n" binding cycles and transfer of coding tag information to the (extended) recording tag, the final extended recording tag product will be composed of a series of these randomized sequences, which collectively form a "composite" unique molecule identifier (UMI) for the final extended recording tag. If for instance each coding tag contains an (NN) sequence (4*4=16 possible sequences), after 10 sequencing cycles, a combinatoric set of 10 distributed 2-mers is formed creating a total diversity of $16^{10} \sim 10^{12}$ possible composite UMI sequences for the extended recording tag products. Given that a peptide sequencing experiment uses $\sim 10^9$ molecules, this diversity is more than sufficient to create an effective set of UMIs for a sequencing experiment. Increased diversity can be achieved by simply using a longer randomized region (NNN, NNNN, etc.) within the coding tag.

A coding tag may include a terminator nucleotide incorporated at the 3' end of the 3' spacer sequence. After a binding agent binds to a macromolecule and their corresponding coding tag and recording tags anneal via complementary spacer sequences, it is possible for primer extension to transfer information from the coding tag to the recording tag, or to transfer information from the recording tag to the coding tag. Addition of a terminator nucleotide on the 3' end of the coding tag prevents transfer of recording tag information to the coding tag. It is understood that for embodiments described herein involving generation of extended coding tags, it may be for example to include a terminator nucleotide at the 3' end of the recording tag to prevent transfer of coding tag information to the recording tag.

A coding tag may be a single stranded molecule, a double stranded molecule, or a partially double stranded. A coding tag may comprise blunt ends, overhanging ends, or one of each. In some embodiments, a coding tag is partially double stranded, which prevents annealing of the coding tag to internal encoder and spacer sequences in a growing extended recording tag.

A coding tag is joined to a binding agent directly or indirectly, by any means known in the art, including covalent and non-covalent interactions. In some embodiments, a coding tag may be joined to binding agent enzymatically or chemically. In some embodiments, a coding tag may be joined to a binding agent via ligation. In other embodiments, a coding tag is joined to a binding agent via affinity binding pairs (e.g., biotin and streptavidin).

Figure 43:
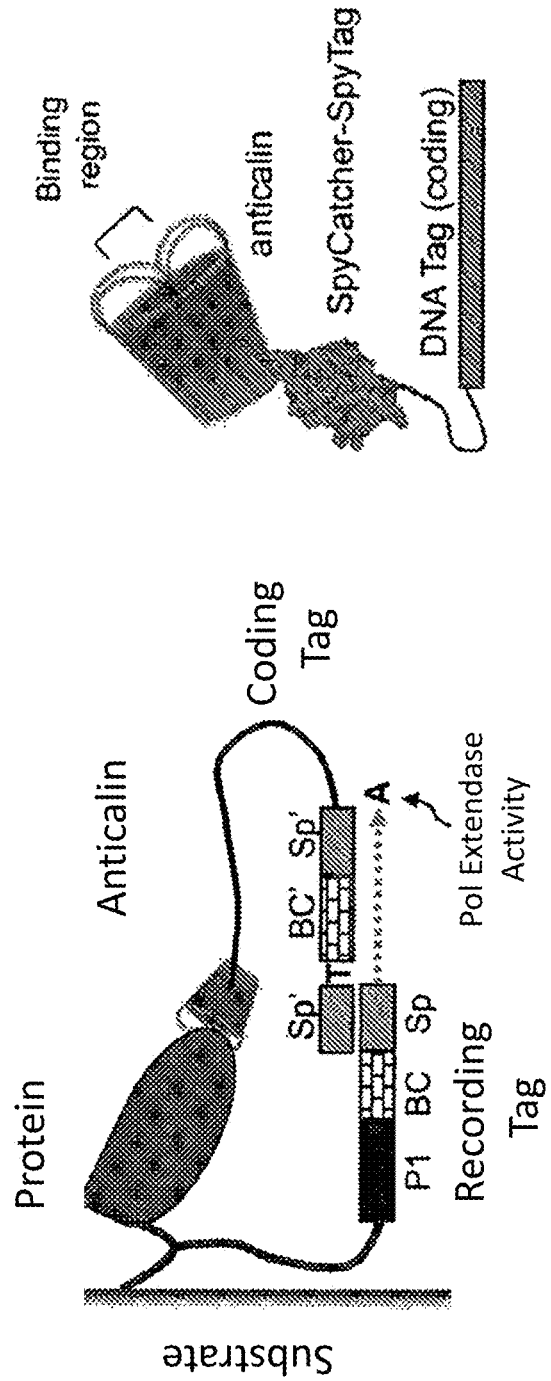
FIG. 43A-43B illustrate exemplary recording tag-coding tag design features.
Figure 44:
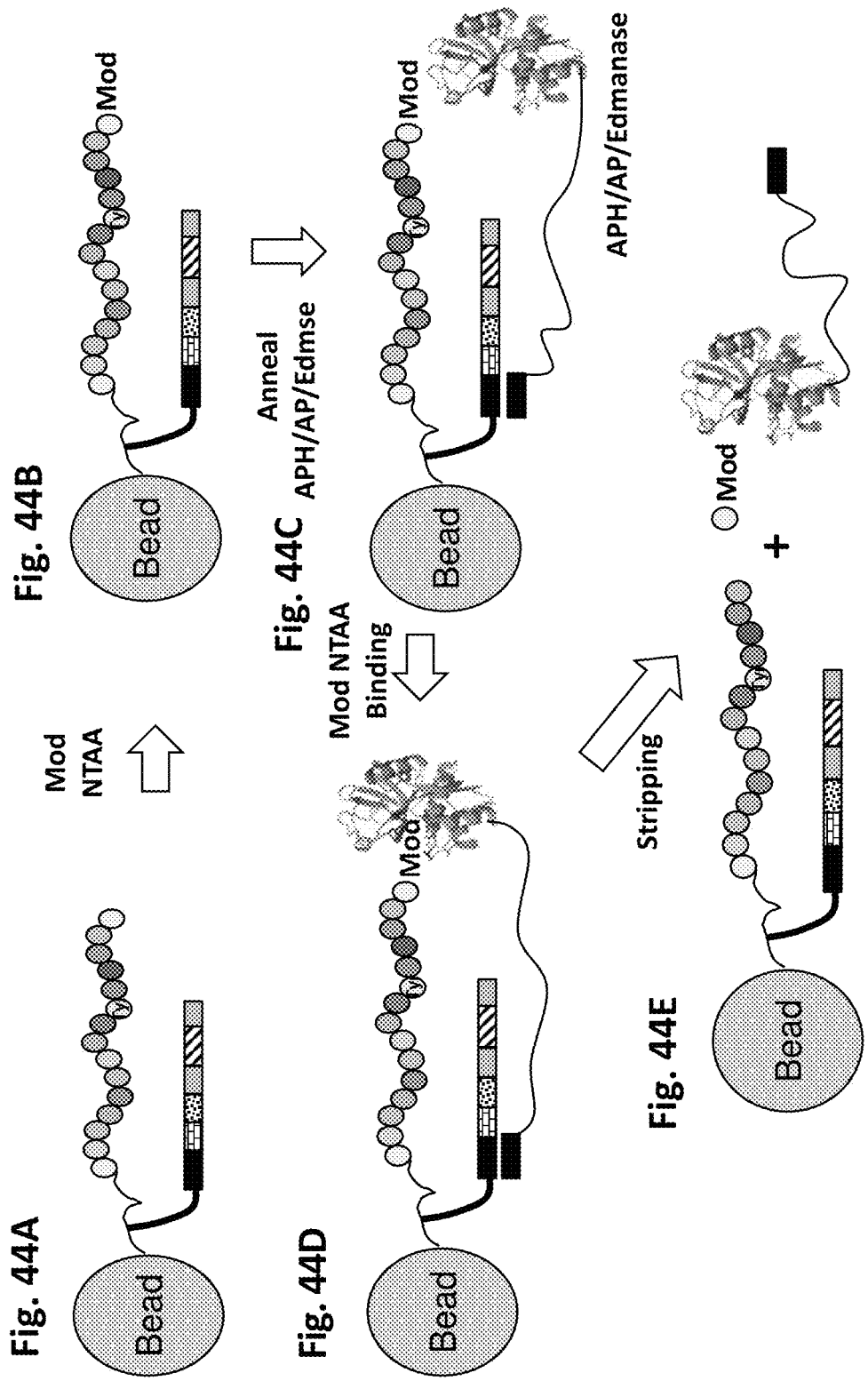
FIG. 44A-44E illustrate examples for enhancement of NTAA cleavage reaction using hybridization of cleavage agent to recording tag.

In some embodiments, a binding agent is joined to a coding tag via SpyCatcher-SpyTag interaction (see, e.g., FIG. 43B). The SpyTag peptide forms an irreversible covalent bond to the SpyCatcher protein via a spontaneous isopeptide linkage, thereby offering a genetically encoded way to create peptide interactions that resist force and harsh conditions (Zakeri et al., 2012, Proc. Natl. Acad. Sci. 109: E690-697; Li et al., 2014, J. Mol. Biol. 426:309-317). A binding agent may be expressed as a fusion protein comprising the SpyCatcher protein. In some embodiments, the SpyCatcher protein or a variant thereof (e.g., the SpyTag002 or SpyCatcher002 variant, for example, disclosed in Keeble et al, "Evolving accelerated amidation by SpyTag/SpyCatcher to analyze membrane dynamics," *Angew. Chem. Int. Ed.* 10.1002/anie.201707623) is appended on the N-terminus or C-terminus of the binding agent. The SpyTag peptide can be coupled to the coding tag using standard conjugation chemistries (Bioconjugate Techniques, G. T. Hermanson, Academic Press (2013)).

In other embodiments, a binding agent is joined to a coding tag via SnoopTag-SnoopCatcher peptide-protein interaction. The SnoopTag peptide forms an isopeptide bond with the SnoopCatcher protein (Veggiani et al., *Proc. Natl. Acad. Sci. USA*, 2016, 113:1202-1207). A binding agent may be expressed as a fusion protein comprising the SnoopCatcher protein. In some embodiments, the SnoopCatcher protein is appended on the N-terminus or C-terminus of the binding agent. The SnoopTag peptide can be coupled to the coding tag using standard conjugation chemistries.

In yet other embodiments, a binding agent is joined to a coding tag via the HaloTag® protein fusion tag and its chemical ligand. HaloTag is a modified haloalkane dehalogenase designed to covalently bind to synthetic ligands (HaloTag ligands) (Los et al., 2008, ACS Chem. Biol. 3:373-382). The synthetic ligands comprise a chloroalkane linker attached to a variety of useful molecules. A covalent bond forms between the HaloTag and the chloroalkane linker that is highly specific, occurs rapidly under physiological conditions, and is essentially irreversible.

In certain embodiments, a macromolecule is also contacted with a non-cognate binding agent. As used herein, a non-cognate binding agent is referring to a binding agent that is selective for a different macromolecule feature or component than the particular macromolecule being considered. For example, if the n NTAA is phenylalanine, and the peptide is contacted with three binding agents selective for phenylalanine, tyrosine, and asparagine, respectively, the binding agent selective for phenylalanine would be first binding agent capable of selectively binding to the $n^{th}$ NTAA (i.e., phenylalanine), while the other two binding agents would be non-cognate binding agents for that peptide (since they are selective for NTAAs other than phenylalanine). The tyrosine and asparagine binding agents may, however, be cognate binding agents for other peptides in the sample. If the $n^{th}$ NTAA (phenylalanine) was then cleaved from the peptide, thereby converting the $(n-1)^{th}$ amino acid of the peptide to the $(n-1)^{th}$ NTAA (e.g., tyrosine), and the peptide was then contacted with the same three binding agents, the binding agent selective for tyrosine would be second binding agent capable of selectively binding to the $(n-1)^{th}$ NTAA (i.e., tyrosine), while the other two binding agents would be non-cognate binding agents (since they are selective for NTAAs other than tyrosine).

Thus, it should be understood that whether an agent is a binding agent or a non-cognate binding agent will depend on the nature of the particular macromolecule feature or component currently available for binding. Also, if multiple macromolecules are analyzed in a multiplexed reaction, a binding agent for one macromolecule may be a non-cognate binding agent for another, and vice versa. According, it should be understood that the following description concerning binding agents is applicable to any type of binding agent described herein (i.e., both cognate and non-cognate binding agents).

F. Kit and Kit Components for Cyclic Transfer of Coding Tag Information to Recording Tags In the kits and methods described herein, upon binding of a binding agent to a macromolecule, identifying information of its linked coding tag is transferred to a recording tag associated with the macromolecule, thereby generating an "extended recording tag." An extended recording tag may comprise information from a binding agent's coding tag representing each binding cycle performed. However, an extended recording tag may also experience a "missed" binding cycle, e.g., because a binding agent fails to bind to the macromolecule, because the coding tag was missing, damaged, or defective, because the primer extension reaction failed. Even if a binding event occurs, transfer of information from the coding tag to the recording tag may be incomplete or less than 100% accurate, e.g., because a coding tag was damaged or defective, because errors were introduced in the primer extension reaction). Thus, an extended recording tag may represent 100%, or up to 95%, 90%, 85%, 80%, 75%, 70%, 65%, 60%, 65%, 55%, 50%, 45%, 40%, 35%, 30% of binding events that have occurred on its associated macromolecule. Moreover, the coding tag information present in the extended recording tag may have at least 30%, 35%, 40%, 45%, 50%, 55%, 60%, 65%, 70%, 75%, 80%, 85%, 90%, 95%, or 100% identity the corresponding coding tags.

In certain embodiments, an extended recording tag may comprise information from multiple coding tags representing multiple, successive binding events. In these embodiments, a single, concatenated extended recording tag can be representative of a single macromolecule (see, e.g., FIG. 2A). As referred to herein, transfer of coding tag information to a recording tag also includes transfer to an extended recording tag as would occur in methods involving multiple, successive binding events.

In certain embodiments, the binding event information is transferred from a coding tag to a recording tag in a cyclic fashion (see, e.g., FIGS. 2A and 2C). Cross-reactive binding events can be informatically filtered out after sequencing by requiring that at least two different coding tags, identifying two or more independent binding events, map to the same class of binding agents (cognate to a particular protein). An optional sample or compartment barcode can be included in the recording tag, as well an optional UMI sequence. The coding tag can also contain an optional UMI sequence along with the encoder and spacer sequences. Universal priming sequences (U1 and U2) may also be included in extended recording tags for amplification and NGS sequencing (see, e.g., FIG. 2A).

Coding tag information associated with a specific binding agent may be transferred to a recording tag using a variety of methods. In certain embodiments, information of a coding tag is transferred to a recording tag via primer extension (Chan, McGregor et al. 2015). A spacer sequence on the 3'-terminus of a recording tag or an extended recording tag anneals with complementary spacer sequence on the 3' terminus of a coding tag and a polymerase (e.g., strand-displacing polymerase) extends the recording tag sequence, using the annealed coding tag as a template (see, e.g., FIG. 5-7). In some embodiments, oligonucleotides complementary to coding tag encoder sequence and 5' spacer can be pre-annealed to the coding tags to prevent hybridization of the coding tag to internal encoder and spacer sequences present in an extended recording tag. The 3' terminal spacer, on the coding tag, remaining single stranded, for example binds to the terminal 3' spacer on the recording tag. In other embodiments, a nascent recording tag can be coated with a single stranded binding protein to prevent annealing of the coding tag to internal sites. Alternatively, the nascent recording tag can also be coated with RecA (or related homologues such as uvsX) to facilitate invasion of the 3' terminus into a completely double stranded coding tag (Bell et al., 2012, Nature 491:274-278). This configuration prevents the double stranded coding tag from interacting with internal recording tag elements, yet is susceptible to strand invasion by the RecA coated 3' tail of the extended recording tag (Bell, et al., 2015, Elife 4: e08646). The presence of a single-stranded binding protein can facilitate the strand displacement reaction.

In a preferred embodiment, a DNA polymerase that is used for primer extension possesses strand-displacement activity and has limited or is devoid of 3'-5 exonuclease activity. Several of many examples of such polymerases include Klenow exo- (Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9° N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs).

Additives useful in strand-displacement replication include any of a number of single-stranded DNA binding proteins (SSB proteins) of bacterial, viral, or eukaryotic origin, such as SSB protein of *E. coli*, phage T4 gene 32 product, phage T7 gene 2.5 protein, phage Pf3 SSB, replication protein A RPA32 and RPA14 subunits (Wold, 1997); other DNA binding proteins, such as adenovirus DNA-binding protein, herpes simplex protein ICP8, BMRF1 polymerase accessory subunit, herpes virus UL29 SSB-like protein; any of a number of replication complex proteins known to participate in DNA replication, such as phage T7 helicase/primase, phage T4 gene 41 helicase, *E. coli* Rep helicase, *E. coli* recBCD helicase, recA, *E. coli* and eukaryotic topoisomerases (Champoux, 2001).

Mis-priming or self-priming events, such as when the terminal spacer sequence of the recoding tag primes extension self-extension may be minimized by inclusion of single stranded binding proteins (T4 gene 32, *E. coli* SSB, etc.), DMSO (1-10%), formamide (1-10%), BSA (10-100 µg/ml), TMACl (1-5 mM), ammonium sulfate (10-50 mM), betaine (1-3 M), glycerol (5-40%), or ethylene glycol (5-40%), in the primer extension reaction.

Most type A polymerases are devoid of 3' exonuclease activity (endogenous or engineered removal), such as Klenow exo-, T7 DNA polymerase exo- (Sequenase 2.0), and Taq polymerase catalyzes non-templated addition of a nucleotide, for example an adenosine base (to lesser degree a G base, dependent on sequence context) to the 3' blunt end of a duplex amplification product. For Taq polymerase, a 3' pyrimidine (C>T) minimizes non-templated adenosine addition, whereas a 3' purine nucleotide (G>A) favours non-templated adenosine addition. In embodiments using Taq polymerase for primer extension, placement of a thymidine base in the coding tag between the spacer sequence distal from the binding agent and the adjacent barcode sequence (e.g., encoder sequence or cycle specific sequence) accommodates the sporadic inclusion of a non-templated adenosine nucleotide on the 3' terminus of the spacer sequence of the recording tag (see, e.g., FIG. 43A). In this manner, the extended recording tag (with or without a non-templated adenosine base) can anneal to the coding tag and undergo primer extension.

Alternatively, addition of non-templated base can be reduced by employing a mutant polymerase (mesophilic or thermophilic) in which non-templated terminal transferase activity has been greatly reduced by one or more point mutations, especially in the 0-helix region (see, e.g., U.S. Pat. No. 7,501,237) (Yang, Astatke et al. 2002). Pfu exo-, which is 3' exonuclease deficient and has strand-displacing ability, also does not have non-templated terminal transferase activity.

In another embodiment, optimal polymerase extension buffers are comprised of 40-120 mM buffering agent such as Tris-Acetate, Tris-HCl, HEPES, etc. at a pH of 6-9.

Self-priming/mis-priming events initiated by self-annealing of the terminal spacer sequence of the extended recording tag with internal regions of the extended recording tag may be minimized by including pseudo-complementary bases in the recording/extended recording tag (Lahoud, Timoshchuk et al. 2008), (Hoshika, Chen et al. 2010). Pseudo-complementary bases show significantly reduced hybridization affinities for the formation of duplexes with each other due the presence of chemical modification. However, many pseudo-complementary modified bases can form strong base pairs with natural DNA or RNA sequences. In certain embodiments, the coding tag spacer sequence is comprised of multiple A and T bases, and commercially available pseudo-complementary bases 2-aminoadenine and 2-thiothymine are incorporated in the recording tag using phosphoramidite oligonucleotide synthesis. Additional pseudocomplementary bases can be incorporated into the extended recording tag during primer extension by adding pseudo-complementary nucleotides to the reaction (Gamper, Arar et al. 2006).

To minimize non-specific interaction of the coding tag labeled binding agents in solution with the recording tags of immobilized proteins, competitor (also referred to as blocking) oligonucleotides complementary to recording tag spacer sequences are added to binding reactions to minimize non-specific interaction s (see, e.g., FIG. 32A-D). Blocking oligonucleotides are relatively short. Excess competitor oligonucleotides are washed from the binding reaction prior to primer extension, which effectively dissociates the annealed competitor oligonucleotides from the recording tags, especially when exposed to slightly elevated temperatures (e.g., 30-50° C.). Blocking oligonucleotides may comprise a terminator nucleotide at its 3' end to prevent primer extension.

In certain embodiments, the annealing of the spacer sequence on the recording tag to the complementary spacer sequence on the coding tag is metastable under the primer extension reaction conditions (i.e., the annealing Tm is similar to the reaction temperature). This allows the spacer sequence of the coding tag to displace any blocking oligonucleotide annealed to the spacer sequence of the recording tag.

Figure 6:
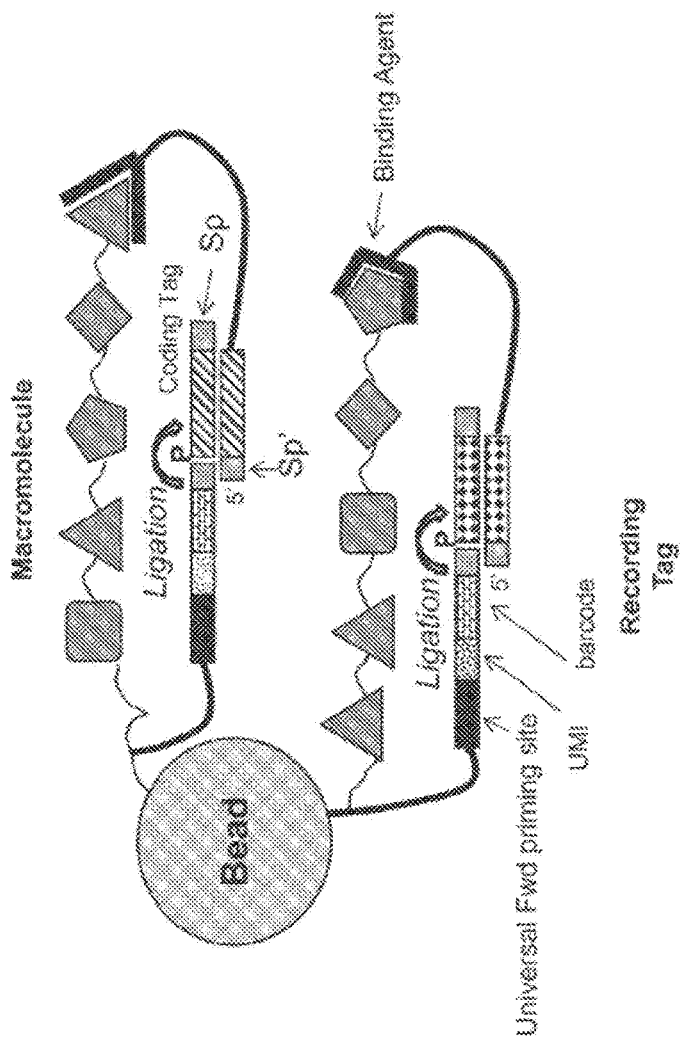
FIG. 6 illustrates coding tag information being transferred to an extended recording tag via enzymatic ligation. Two different analytes are shown with their respective recording tags, with recording tag extension proceeding in parallel. Ligation can be facilitated by designing the double stranded coding tags so that the spacer sequences (Sp') have a "sticky end" overhang on one strand that anneals with a complementary spacer (Sp) on the recording tag. This "sticky end" (also known as "cohesive end") can be 0-8 bases in length, for example, around 2-4 bases. The complementary strand of the double stranded coding tag, after being ligated to the recording tag, transfers information to the recording tag. The complementary strand may comprise another spacer sequence, which may be the same as or different from the Sp of the recording tag before the ligation. When ligation is used to extend the recording tag, the direction of extension can be 5' to 3' as illustrated, or optionally 3' to 5'. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.
Figure 7:
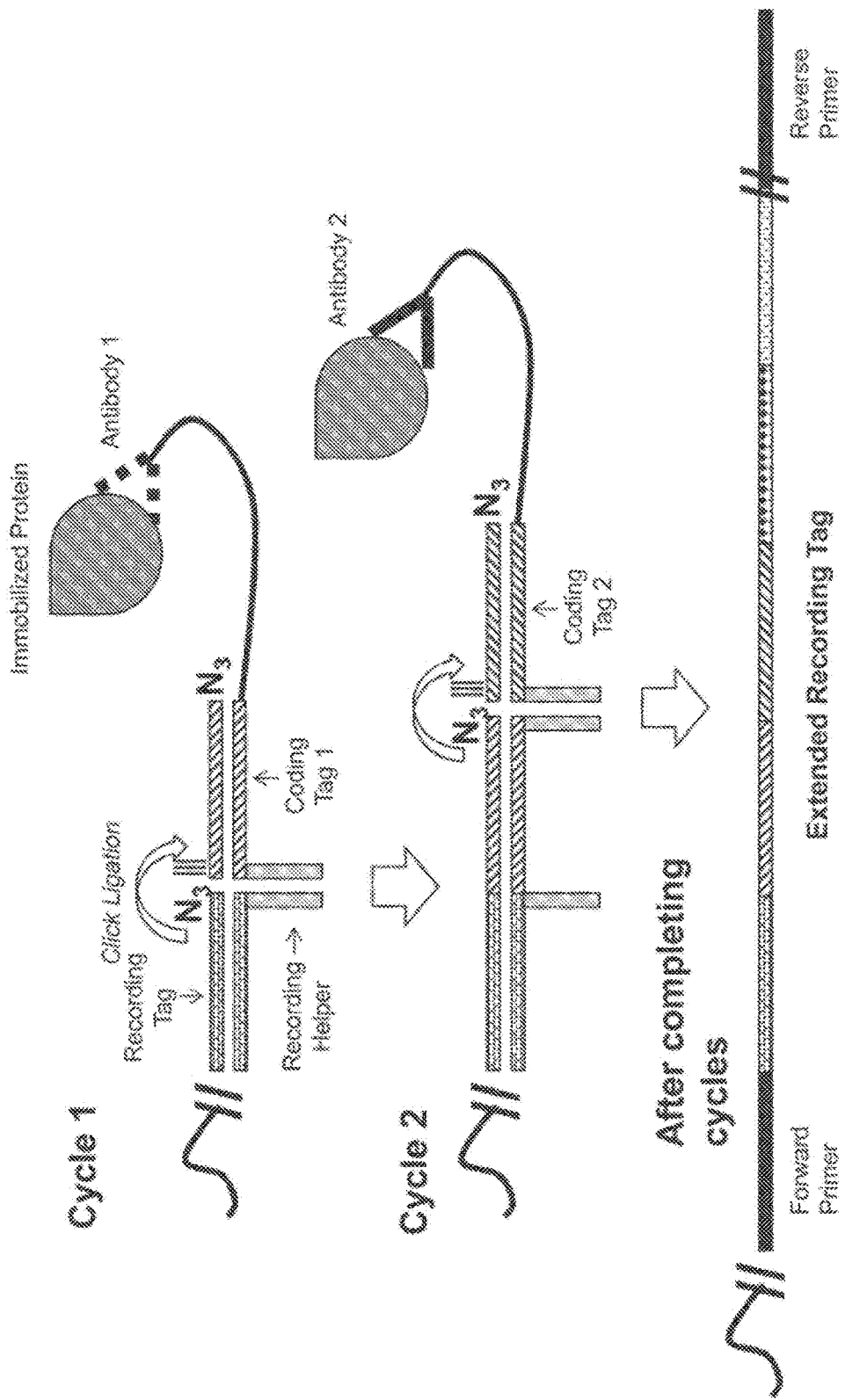
FIG. 7 illustrates a "spacer-less" approach of transferring coding tag information to a recording tag via chemical ligation to link the 3' nucleotide of a recording tag or extended recording tag to the 5' nucleotide of the coding tag (or its complement) without inserting a spacer sequence into the extended recording tag. The orientation of the extended recording tag and coding tag could also be inverted such that the 5' end of the recording tag is ligated to the 3' end of the coding tag (or complement). In the example shown, hybridization between complementary "helper" oligonucleotide sequences on the recording tag ("recording helper") and the coding tag are used to stabilize the complex to enable specific chemical ligation of the recording tag to coding tag complementary strand. The resulting extended recording tag is devoid of spacer sequences. Also illustrated is a "click chemistry" version of chemical ligation (e.g., using azide and alkyne moieties (shown as a triple line symbol)) which can employ DNA, PNA, or similar nucleic acid polymers. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.
Figure 46C:
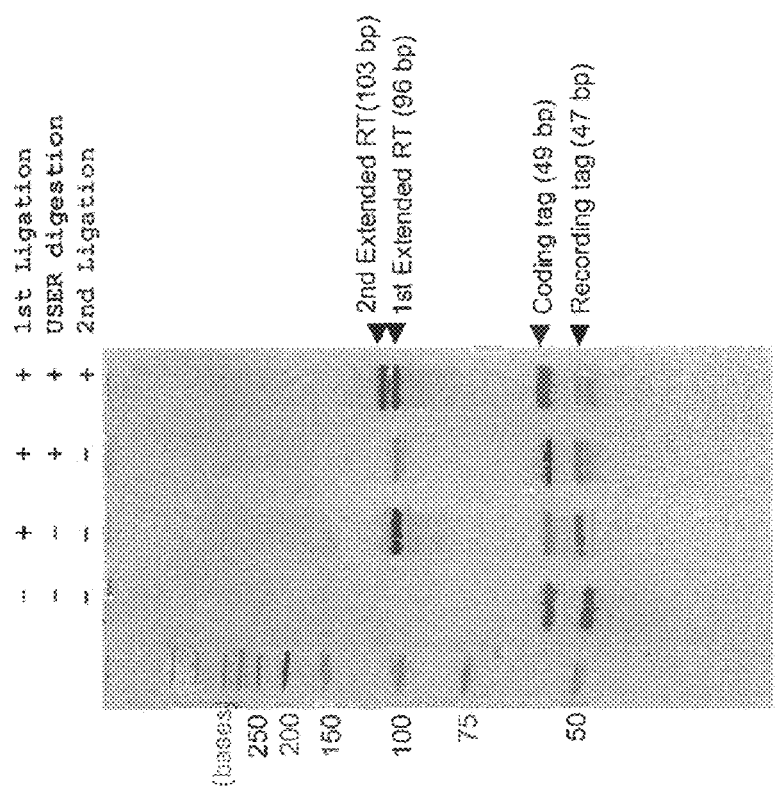

Coding tag information associated with a specific binding agent may also be transferred to a recording tag via ligation (see, e.g., FIG. 6 and FIG. 7). Ligation may be a blunt end ligation or sticky end ligation. Ligation may be an enzymatic ligation reaction. Examples of ligases include, but are not limited to T4 DNA ligase, T7 DNA ligase, T3 DNA ligase, Taq DNA ligase, E. coli DNA ligase, 9° N DNA ligase, Electroligase®. Alternatively, a ligation may be a chemical ligation reaction (see, e.g., FIG. 7). In the illustration, a spacer-less ligation is accomplished by using hybridization of a "recording helper" sequence with an arm on the coding tag. The annealed complement sequences are chemically ligated using standard chemical ligation or "click chemistry" (Gunderson, Huang et al. 1998, Peng, Li et al. 2010, El-Sagheer, Cheong et al. 2011, El-Sagheer, Sanzone et al. 2011, Sharma, Kent et al. 2012, Roloff and Seitz 2013, Litovchick, Clark et al. 2014, Roloff, Ficht et al. 2014). In one aspect, a "spacer-less" ligation can also be accomplished using a ssDNA ligase, such as CircLigase I or II (e.g., from Lucigen), for example, as shown in FIG. 46A-C. The use of "spacer-less" ligation is advantageous in greatly reducing the overall length of the library element and/or reducing or minimizing template switching during library amplification.

In one embodiment, the kit comprises a single-stranded DNA (ssDNA) ligase. A ssDNA ligase is capable of ligating ends of ssDNA in the absence of a complementary sequence. For example, CircLigase™ ssDNA Ligase and CircLigase™ II ssDNA Ligase are both thermostable ligases that are typically used to catalyze intramolecular ligation (i.e., circularization) of ssDNA templates having a 5'-phosphate and a 3'-hydroxyl group. In contrast to T4 DNA Ligase and Ampligase® DNA Ligase, which ligate DNA ends that are annealed adjacent to each other on a complementary DNA sequence, a ssDNA ligase ligates ends of ssDNA in the absence of a complementary sequence. The enzyme is therefore useful for making circular ssDNA molecules from linear ssDNA. Circular ssDNA molecules can be used as substrates for rolling-circle replication or rolling-circle transcription. In addition to its activity on ssDNA, a CircLigase enzyme also has activity in ligating a single-stranded nucleic acid having a 3'-hydroxyl ribonucleotide and a 5'-phosphorylated ribonucleotide or deoxyribonucleotide.

Either CircLigase™ ssDNA Ligase or CircLigase™ II ssDNA Ligase can be used in the present disclosure. The two enzymes are different in that CircLigase I is far less adenylated than CircLigase II and requires ATP for best activity. CircLigase I recircularizes ssDNA in the presence of ATP. CircLigase II is nearly 100% adenylated, therefore it is not necessary to add ATP to the reaction buffer. CircLigase II works as a stoichiometric reaction, where the enzyme bonds the 5'-end of an oligo that is adenylated in the enzyme active site, and then ligates the oligo and stops. Since the reaction doesn't contain ATP, CircLigase II works in a 1:1 enzyme:oligo configuration. In particular embodiments, the kit herein comprises a *Thermus* bacteriophage RNA ligase such as a bacteriophage TS2126 RNA ligase (e.g., CircLigase™ and CircLigase II™), or an archaebacterium RNA ligase such as *Methanobacterium thermoautotrophicum* RNA ligase 1. In any of the preceding embodiments, the kit can comprise an RNA ligase, such as a T4 RNA ligase, e.g., T4 RNA ligase 2, T4 RNA ligase 2 truncated, T4 RNA ligase 2 truncated KQ, or T4 RNA ligase 2 truncated K227Q.

In another embodiment, transfer of PNAs can be accomplished with chemical ligation using published techniques. The structure of PNA is such that it has a 5' N-terminal amine group and an unreactive 3' C-terminal amide. Chemical ligation of PNA requires that the termini be modified to be chemically active. This is typically done by derivitizing the 5' N-terminus with a cysteinyl moiety and the 3' C-terminus with a thioester moiety. Such modified PNAs easily couple using standard native chemical ligation conditions (Roloff et al., 2013, Bioorgan. Med. Chem. 21:3458-3464).

In some embodiments, coding tag information can be transferred using topoisomerase. Topoisomerase can be used be used to ligate a topo-charged 3' phosphate on the recording tag to the 5' end of the coding tag, or complement thereof (Shuman et al., 1994, J. Biol. Chem. 269:32678-32684).

Figure 8:
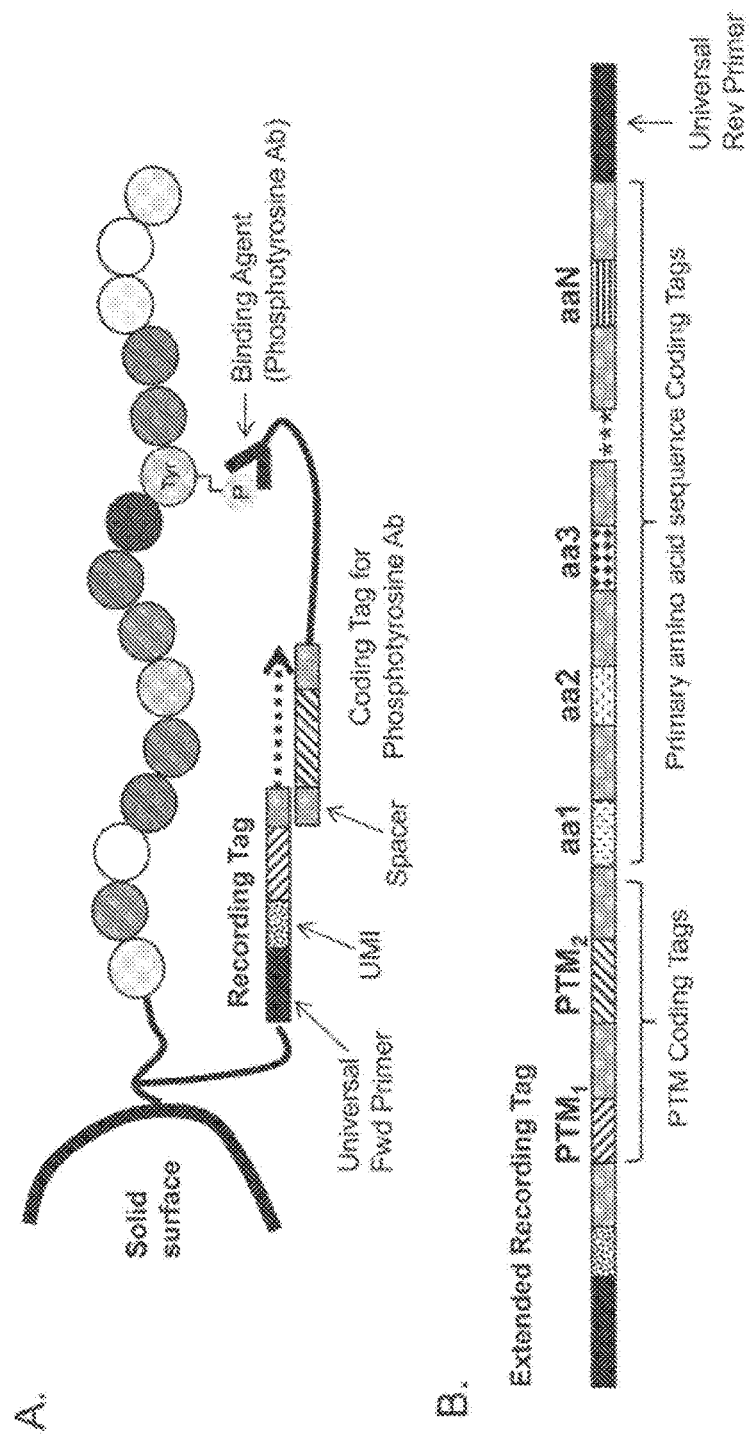
FIG. 8 illustrates an exemplary method of writing of post-translational modification (PTM) information of a polypeptide into an extended recording tag prior to N-terminal amino acid degradation. Step (A). A binding agent comprising a coding tag with identifying information regarding the binding agent (e.g., a phosphotyrosine antibody comprising a coding tag with identifying information for phosphotyrosine antibody) is capable of binding to the polypeptide. If phosphotyrosine is present in the recording tag-labeled polypeptide, as illustrated, upon binding of the phosphotyrosine antibody to phosphotyrosine, the coding tag and recording tag anneal via complementary spacer sequences and the coding tag information is transferred to the recording tag to generate an extended recording tag. Step (B). An extended recording tag may comprise coding tag information for both primary amino acid sequence (e.g., "$aa_1$", "$aa_2$", "$aa_3$", . . . , "$aa_N$") and post-translational modifications (e.g., "$PTM_1$", "$PTM_2$") of the peptide. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

As described herein, a binding agent may bind to a post-translationally modified amino acid. Thus, in certain embodiments involving peptide macromolecules, an extended recording tag comprises coding tag information relating to amino acid sequence and post-translational modifications. In some embodiments, detection of internal post-translationally modified amino acids (e.g., phosphorylation, glycosylation, succinylation, ubiquitination, S-Nitrosylation, methylation, N-acetylation, lipidation, etc.) is be accomplished prior to detection and cleavage of terminal amino acids (e.g., NTAA or CTAA). In one example, a peptide is contacted with binding agents for PTM modifications, and associated coding tag information are transferred to the recording tag as described above (see, e.g., FIG. 8, Step (A)). Once the detection and transfer of coding tag information relating to amino acid modifications is complete, the PTM modifying groups can be removed before detection and transfer of coding tag information for the primary amino acid sequence using N-terminal or C-terminal degradation methods. Thus, resulting extended recording tags indicate the presence of post-translational modifications in a peptide sequence, though not the sequential order, along with primary amino acid sequence information (see, e.g., FIG. 8, Step (B)).

In some embodiments, detection of internal post-translationally modified amino acids may occur concurrently with detection of primary amino acid sequence. In one example, an NTAA (or CTAA) is contacted with a binding agent specific for a post-translationally modified amino acid, either alone or as part of a library of binding agents (e.g., library composed of binding agents for the 20 standard amino acids and selected post-translational modified amino acids). Successive cycles of terminal amino acid cleavage and contact with a binding agent (or library of binding agents) follow. Thus, resulting extended recording tags indicate the presence and order of post-translational modifications in the context of a primary amino acid sequence.

Figure 9A:
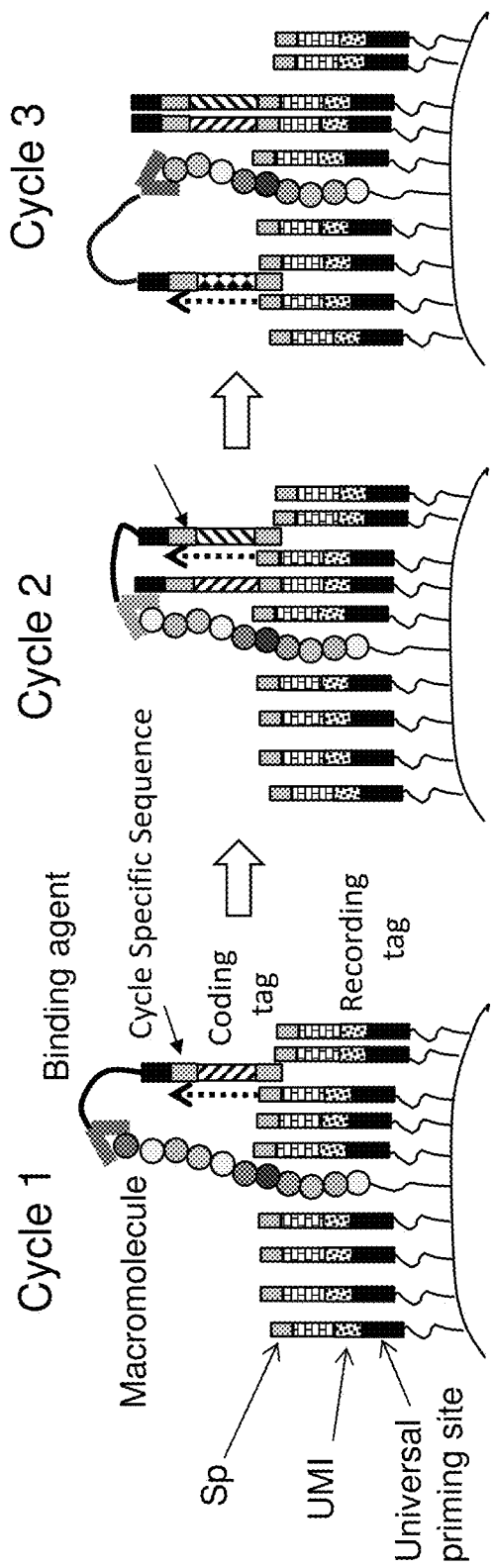
FIG. 9A-9B illustrate a process of multiple cycles of binding of a binding agent to an analyte (e.g., a macromolecule such as a polypeptide) and transferring information of a coding tag that is attached to a binding agent to an individual recording tag among a plurality of recording tags, for example, which are co-localized at a site of a single analyte attached to a solid support (e.g., a bead), thereby generating multiple extended recording tags that collectively represent the analyte information (e.g., presence or absence, level, or amount in a sample, binding profile to a library of binders, activity or reactivity, amino acid sequence, post-translational modification, sample origin, or any combination thereof). In this figure, for purposes of example only, the analyte is a polypeptide and each cycle involves binding a binding agent to an N-terminal amino acid (NTAA), recording the binding event by transferring coding tag information to a recording tag, followed by removal of the NTAA to expose a new NTAA.
Figure 9B:
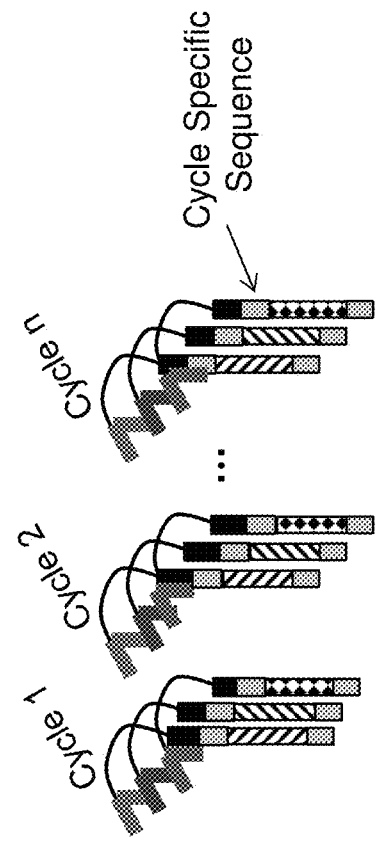

In certain embodiments, an ensemble of recording tags may be employed per macromolecule to improve the overall robustness and efficiency of coding tag information transfer (see, e.g., FIG. 9A-B). The use of an ensemble of recording tags associated with a given macromolecule rather than a single recording tag improves the efficiency of library construction due to potentially higher coupling yields of coding tags to recording tags, and higher overall yield of libraries. The yield of a single concatenated extended recording tag is directly dependent on the stepwise yield of concatenation, whereas the use of multiple recording tags capable of accepting coding tag information does not suffer the exponential loss of concatenation.

An example of such an embodiment is shown in FIG. 9A-B and FIG. 10A-C. In FIGS. 9A and 10A, multiple recording tags are associated with a single macromolecule (by spatial co-localization or confinement of a single macromolecule to a single bead) on a solid support. Binding agents are exposed to the solid support in cyclical fashion and their corresponding coding tag transfers information to one of the co-localized multiple recording tags in each cycle. In the example shown in FIG. 9A, the binding cycle information is encoded into the spacer present on the coding tag. For each binding cycle, the set of binding agents is marked with a designated cycle-specific spacer sequence (see, e.g., FIG. 9A and FIG. 9B). For example, in the case of NTAA binding agents, the binding agents to the same amino acid residue are be labelled with different coding tags or comprise cycle-specific information in the spacer sequence to denote both the binding agent identity and cycle number.

Figure 4A:
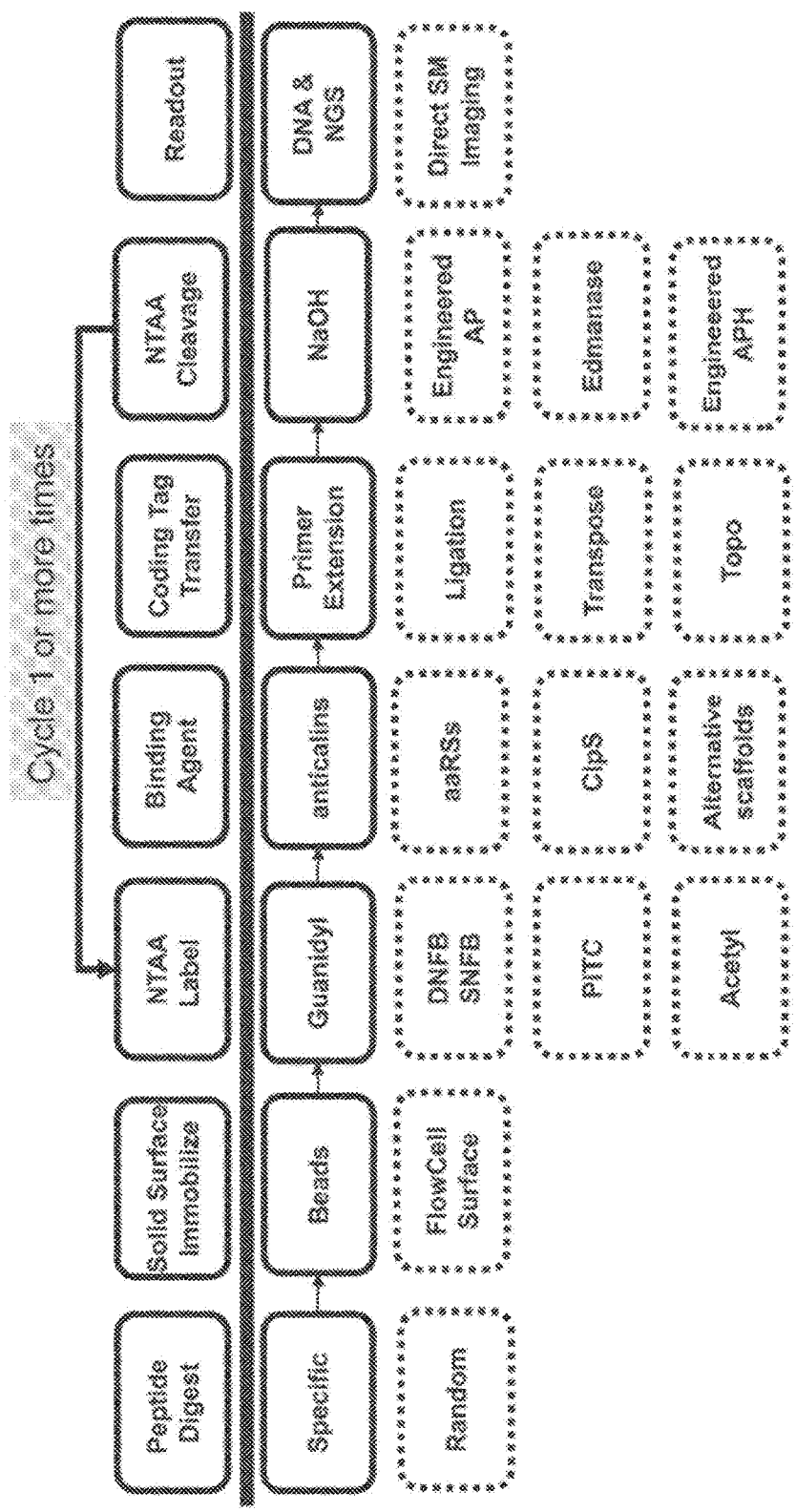
FIG. 4A-4B illustrate exemplary protein sequencing workflows according to the methods disclosed herein.
Figure 4B:
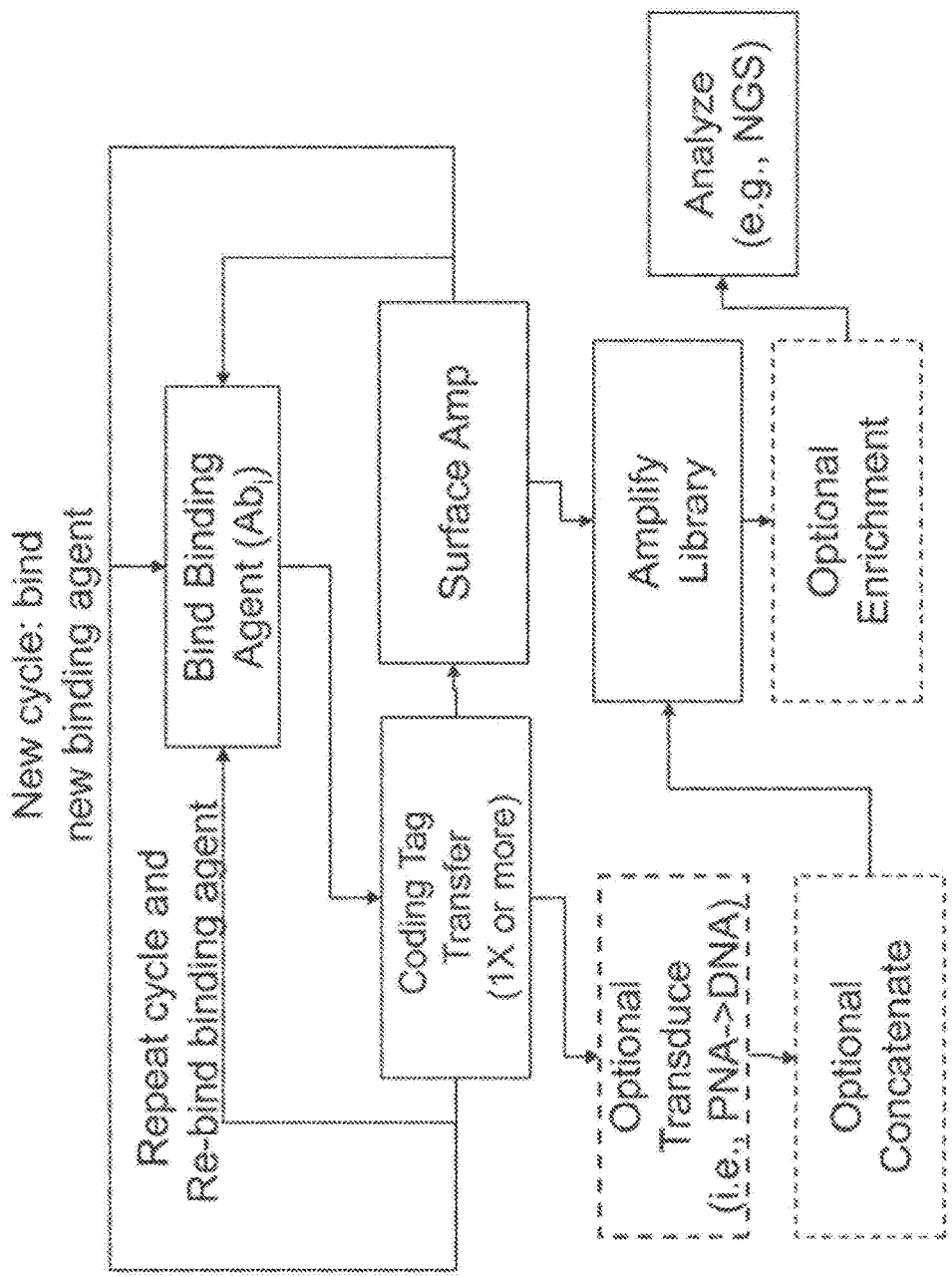

As illustrated in FIG. 9A, in a first cycle of binding (Cycle 1), a plurality of NTAA binding agents is contacted with the macromolecule. The binding agents used in Cycle 1 possess a common spacer sequence that is complementary to the spacer sequence of the recording tag. The binding agents used in Cycle 1 also possess a 3'-spacer sequence comprising Cycle 1 specific sequence. During binding Cycle 1, a first NTAA binding agent binds to the free terminus of the macromolecule, the complementary sequences of the common spacer sequence in the first coding tag and recording tag anneal, and the information of a first coding tag is transferred to a cognate recording tag via primer extension from the common spacer sequence. Following removal of the NTAA to expose a new NTAA, binding Cycle 2 contacts a plurality of NTAA binding agents that possess a common spacer sequence that is complementary to the spacer sequence of a recording tag. The binding agents used in Cycle 2 also possess a 3'-spacer sequence comprising Cycle 2 specific sequence. A second NTAA binding agent binds to the NTAA of the macromolecule, and the information of a second coding tag is transferred to a recording tag via primer extension. These cycles are repeated up to "n" binding cycles, generating a plurality of extended recording tags co-localized with the single macromolecule, wherein each extended recording tag possesses coding tag information from one binding cycle. Because each set of binding agents used in each successive binding cycle possess cycle specific spacer sequences in the coding tags, binding cycle information can be associated with binding agent information in the resulting extended recording tags In an alternative embodiment, multiple recording tags are associated with a single macromolecule on a solid support (e.g., bead) as in FIG. 9A, but in this case binding agents used in a particular binding cycle have coding tags flanked by a cycle-specific spacer for the current binding cycle and a cycle specific spacer for the next binding cycle (see, e.g., FIG. 10A and FIG. 10B). The reason for this design is to support a final assembly PCR step (see, e.g., FIG. 10C) to convert the population of extended recording tags into a single co-linear, extended recording tag. A library of single, co-linear extended recording tag can be subjected to enrichment, subtraction and/or normalization methods prior to sequencing. In the first binding cycle (Cycle 1), upon binding of a first binding agent, the information of a coding tag comprising a Cycle 1 specific spacer (C'1) is transferred to a recording tag comprising a complementary Cycle 1 specific spacer ($C_1$) at its terminus. In the second binding cycle (Cycle 2), upon binding of a second binding agent, the information of a coding tag comprising a Cycle 2 specific spacer (C'2) is transferred to a different recording tag comprising a complementary Cycle 2 specific spacer ($C_2$) at its terminus. This process continues until the $n^{th}$ binding cycle. In some embodiments, the $n^{th}$ coding tag in the extended recording tag is capped with a universal reverse priming sequence, e.g., the universal reverse priming sequence can be incorporated as part of the $n^{th}$ coding tag design or the universal reverse priming sequence can be added in a subsequent reaction after the $n^{th}$ binding cycle, such as an amplification reaction using a tailed primer. In some embodiments, at each binding cycle a macromolecule is exposed to a collection of binding agents joined to coding tags comprising identifying information regarding their corresponding binding agents and binding cycle information (see, e.g., FIG. 9A-B and FIG. 10A-C). In a particular embodiment, following completion of the $n^{th}$ binding cycle, the bead substrates coated with extended recording tags are placed in an oil emulsion such that on average there is fewer than or approximately equal to 1 bead/droplet. Assembly PCR is then used to amplify the extended recording tags from the beads, and the multitude of separate recording tags are assembled collinear order by priming via the cycle specific spacer sequences within the separate extended recording tags (see, e.g., FIG. 10C) (Xiong et al., 2008, FEMS Microbiol. Rev. 32:522-540). Alternatively, instead of using cycle-specific spacer with the binding agents' coding tags, a cycle specific spacer can be added separately to the extended recording tag during or after each binding cycle. One advantage of using a population of extended recording tags, which collectively represent a single macromolecule vs. a single concatenated extended recording tag representing a single macromolecule is that a higher concentration of recording tags can increase efficiency of transfer of the coding tag information. Moreover, a binding cycle can be repeated several times to ensure completion of cognate binding events. Furthermore, surface amplification of extended recording tags may be able to provide redundancy of information transfer (see, e.g., FIG. 4B). If coding tag information is not always transferred, it should in most cases still be possible to use the incomplete collection of coding tag information to identify macromolecules that have very high information content, such as proteins. Even a short peptide can embody a very large number of possible protein sequences. For example, a 10-mer peptide has 2010 possible sequences. Therefore, partial or incomplete sequence that may contain deletions and/or ambiguities can often still be mapped uniquely.

Figure 32F:
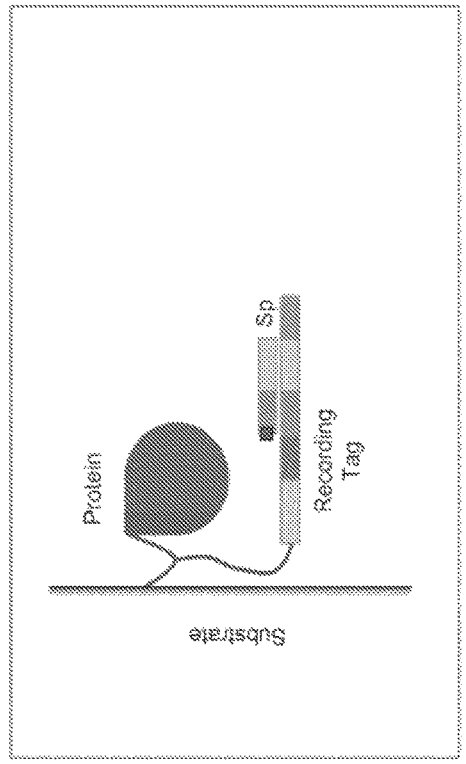
Figure 32G:
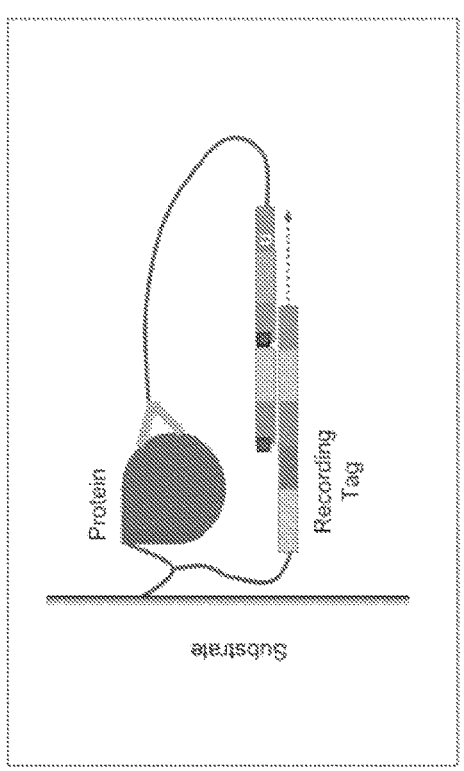
Figure 32H:
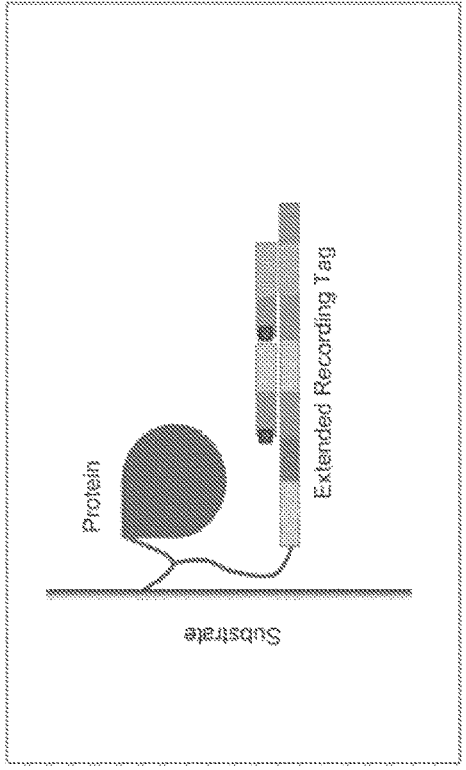
Figure 33A:
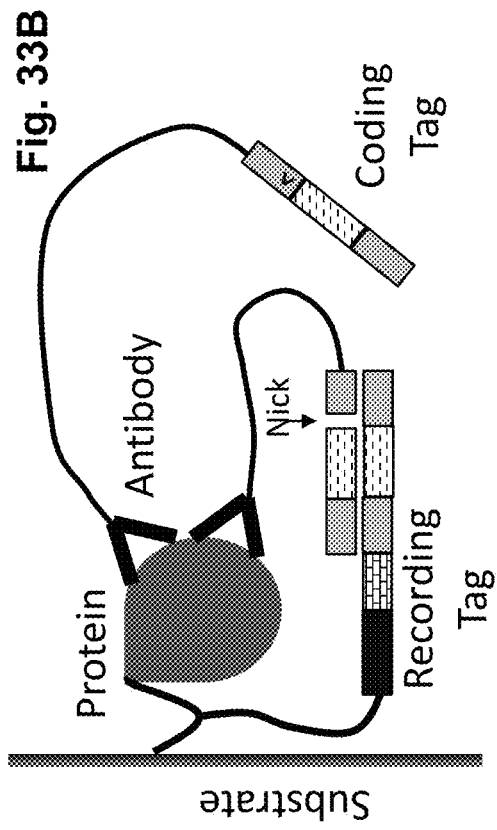
FIG. 33A-33D illustrate examples for a single-step Next Generation Protein Assay (NGPA) using multiple binding agents and enzymatically-mediated sequential information transfer. NGPA assay with immobilized protein molecule simultaneously bound by two cognate binding agents (e.g., antibodies). After multiple cognate antibody binding events, a combined primer extension and DNA nicking step is used to transfer information from the coding tags of bound antibodies to the recording tag. The caret symbol (^) in the coding tags represents a double stranded DNA nicking endonuclease site.
Figure 33B:
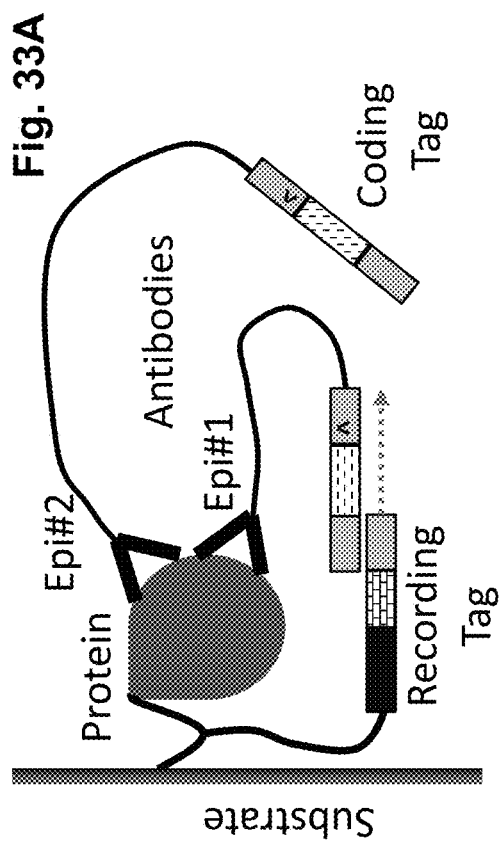
Figure 33C:
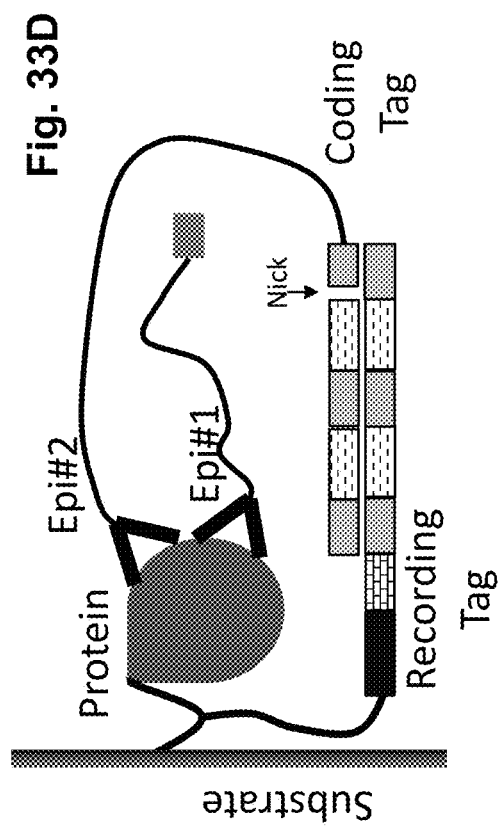
Figure 33D:
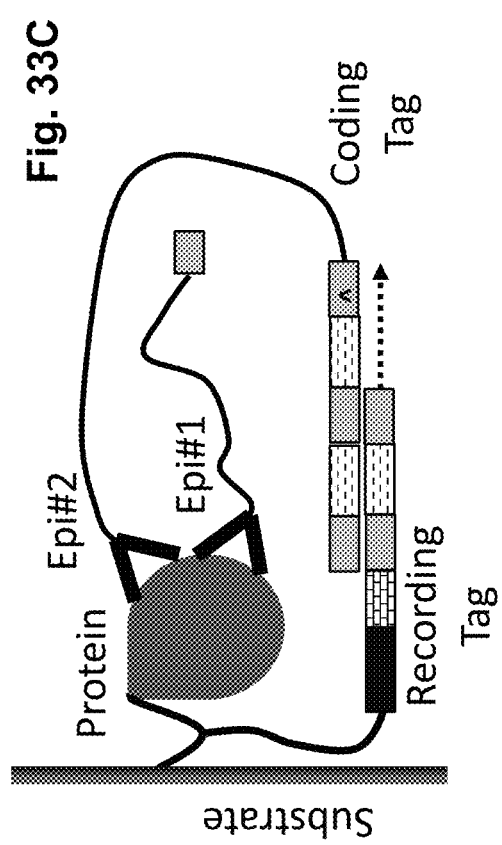

In some embodiments, in which proteins in their native conformation are being queried, the cyclic binding assays are performed with binding agents harbouring coding tags comprised of a cleavable or nickable DNA strand within the spacer element proximal to the binding agent (see, e.g., FIG. 32E). For example, the spacer proximal to the binding agent may have one or more uracil bases that can be nicked by uracil-specific excision reagent (USER). In another example, the spacer proximal to the binding agent may comprise a recognition sequence for a nicking endonuclease that hydrolyzes only one strand of a duplex. This design allows the non-denaturing removal of the binding agent from the extended recording tag and creates a free single stranded DNA spacer element for subsequent immunoassay cycles. In a preferred embodiment, a uracil base is incorporated into the coding tag to permit enzymatic USER removal of the binding agent after the primer extension step (see, e.g., FIG. 32E-F). After USER excision of uracils, the binding agent and truncated coding tag can be removed under a variety of mild conditions including high salt (4M NaCl, 25% formamide) and mild heat to disrupt the protein-binding agent interaction. The other truncated coding tag DNA stub remaining annealed on the recording tag (see, e.g., FIG. 32F) readily dissociates at slightly elevated temperatures.

Coding tags comprised of a cleavable or nickable DNA strand within the spacer element proximal to the binding agent also allows for a single homogeneous assay for transferring of coding tag information from multiple bound binding agents (see, e.g., FIG. 33A-D). In a preferred embodiment, the coding tag proximal to the binding agent comprises a nicking endonuclease sequence motif, which is recognized and nicked by a nicking endonuclease at a defined sequence motif in the context of dsDNA. After binding of multiple binding agents, a combined polymerase extension (devoid of strand-displacement activity)+nicking endonuclease reagent mix is used to generate repeated transfers of coding tags to the proximal recording tag or extended recording tag. After each transfer step, the resulting extended recording tag-coding tag duplex is nicked by the nicking endonuclease releasing the truncated spacer attached to the binding agent and exposing the extended recording tag 3' spacer sequence, which is capable of annealing to the coding tags of additional proximal bound binding agents (see, e.g., FIG. 33B-D). The placement of the nicking motif in the coding tag spacer sequence is designed to create a metastable hybrid, which can easily be exchanged with a non-cleaved coding tag spacer sequence. In this way, if two or more binding agents simultaneously bind the same protein molecule, binding information via concatenation of coding tag information from multiply bound binding agents onto the recording tag occurs in a single reaction mix without any cyclic reagent exchanges (see, e.g., FIG. 33C-D). This embodiment is particularly useful for the next generation protein assay (NGPA), especially with polyclonal antibodies (or mixed population of monoclonal antibody) to multivalent epitopes on a protein.

For embodiments involving analysis of denatured proteins, polypeptides, and peptides, the bound binding agent and annealed coding tag can be removed following primer extension by using highly denaturing conditions (e.g., 0.1-0.2 N NaOH, 6M Urea, 2.4 M guanidinium isothiocyanate, 95% formamide, etc.).

G. Kit and Kit Components for Cyclic Transfer of Recording Tag Information to Coding Tags or Di-Tag Constructs In another aspect, rather than writing information from the coding tag to the recording tag following binding of a binding agent to a macromolecule, information may be transferred from the recording tag comprising an optional UMI sequence (e.g. identifying a particular peptide or protein molecule) and at least one barcode (e.g., a compartment tag, partition barcode, sample barcode, spatial location barcode, etc.), to the coding tag, thereby generating an extended coding tag (see, e.g., FIG. 11A). In certain embodiments, the binding agents and associated extended coding tags are collected following each binding cycle and, optionally, prior to Edman degradation chemistry steps. In certain embodiments, the coding tags comprise a binding cycle specific tag. After completion of all the binding cycles, such as detection of NTAAs in cyclic Edman degradation, the complete collection of extended coding tags can be amplified and sequenced, and information on the peptide determined from the association between UMI (peptide identity), encoder sequence (NTAA binding agent), compartment tag (single cell or subset of proteome), binding cycle specific sequence (cycle number), or any combination thereof. Library elements with the same compartment tag/UMI sequence map back to the same cell, subset of proteome, molecule, etc. and the peptide sequence can be reconstructed. This embodiment may be useful in cases where the recording tag sustains too much damage during the Edman degradation process.

Provided herein are methods for analyzing a plurality of macromolecules, comprising: (a) providing a plurality of macromolecules and associated recording tags joined to a solid support; (b) contacting the plurality of macromolecules with a plurality of binding agents capable of binding to the plurality of macromolecules, wherein each binding agent comprises a coding tag with identifying information regarding the binding agent; (c) (i) transferring the information of the macromolecule associated recording tags to the coding tags of the binding agents that are bound to the macromolecules to generate extended coding tags (see, e.g., FIG. 11A); or (ii) transferring the information of macromolecule associated recording tags and coding tags of the binding agents that are bound to the macromolecules to a di-tag construct (see, e.g., FIG. 11B); (d) collecting the extended coding tags or di-tag constructs; (e) optionally repeating steps (b)-(d) for one or more binding cycles; (f) analyzing the collection of extended coding tags or di-tag constructs.

Figure 11A:
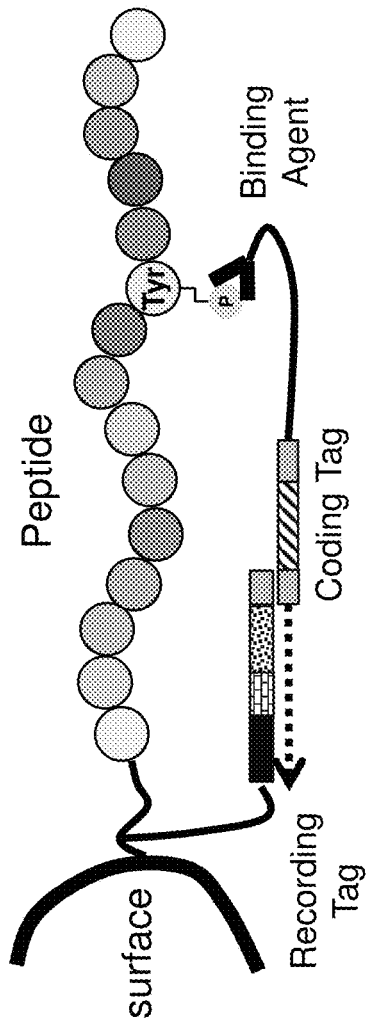
FIG. 11A-11B illustrate information transfer from recording tag to a coding tag or di-tag construct. Two methods of recording binding information are illustrated in (A) and (B). A binding agent may be any type of binding agent as described herein; an anti-phosphotyrosine binding agent is shown for illustration purposes only. For extended coding tag or di-tag construction, rather than transferring binding information from the coding tag to the recording tag, information is either transferred from the recording tag to the coding tag to generate an extended coding tag (FIG. 11A), or information is transferred from both the recording tag and coding tag to a third di-tag-forming construct (FIG. 11B). The di-tag and extended coding tag comprise the information of the recording tag (containing a barcode, an optional UMI sequence, and an optional compartment tag (CT) sequence (not illustrated)) and the coding tag. The di-tag and extended coding tag can be eluted from the recording tag, collected, and optionally amplified and read out on a next generation sequencer. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In certain embodiments, the information transfer from the recording tag to the coding tag can be accomplished using a primer extension step where the 3' terminus of recording tag is optionally blocked to prevent primer extension of the recording tag (see, e.g., FIG. 11A). The resulting extended coding tag and associated binding agent can be collected after each binding event and completion of information transfer. In an example illustrated in FIG. 11B, the recording tag is comprised of a universal priming site (U2'), a barcode (e.g., compartment tag "CT"), an optional UMI sequence, and a common spacer sequence (Sp1). In certain embodiments, the barcode is a compartment tag representing an individual compartment, and the UMI can be used to map sequence reads back to a particular protein or peptide molecule being queried. As illustrated in the example in FIG. 11B, the coding tag is comprised of a common spacer sequence (Sp2'), a binding agent encoder sequence, and universal priming site (U3). Prior to the introduction of the coding tag-labeled binding agent, an oligonucleotide (U2) that is complementary to the U2' universal priming site of the recording tag and comprises a universal priming sequence U1 and a cycle specific tag, is annealed to the recording tag U2'. Additionally, an adapter sequence, Sp1'-Sp2, is annealed to the recording tag Sp1. This adapter sequence also capable of interacting with the Sp2' sequence on the coding tag, bringing the recording tag and coding tag in proximity to each other. A gap-fill extension ligation assay is performed either prior to or after the binding event. If the gap fill is performed before the binding cycle, a post-binding cycle primer extension step is used to complete di-tag formation. After collection of di-tags across a number of binding cycles, the collection of di-tags is sequenced, and mapped back to the originating peptide molecule via the UMI sequence. It is understood that to maximize efficacy, the diversity of the UMI sequences must exceed the diversity of the number of single molecules tagged by the UMI.

In certain embodiments, the macromolecule is a protein or a peptide. The peptide may be obtained by fragmenting a protein from a biological sample.

The recording tag may be a DNA molecule, RNA molecule, PNA molecule, BNA molecule, XNA molecule, LNA molecule a γPNA molecule, or a combination thereof. The recording tag comprises a UMI identifying the macromolecule (e.g., peptide) to which it is associated. In certain embodiments, the recording tag further comprises a compartment tag. The recording tag may also comprise a universal priming site, which may be used for downstream amplification. In certain embodiments, the recording tag comprises a spacer at its 3' terminus. A spacer may be complementary to a spacer in the coding tag. The 3'-terminus of the recording tag may be blocked (e.g., photo-labile 3' blocking group) to prevent extension of the recording tag by a polymerase, facilitating transfer of information of the macromolecule associated recording tag to the coding tag or transfer of information of the macromolecule associated recording tag and coding tag to a di-tag construct.

The coding tag comprises an encoder sequence identifying the binding agent to which the coding agent is linked. In certain embodiments, the coding tag further comprises a unique molecular identifier (UMI) for each binding agent to which the coding tag is linked. The coding tag may comprise a universal priming site, which may be used for downstream amplification. The coding tag may comprise a spacer at its 3'-terminus. The spacer may be complementary to the spacer in the recording tag and can be used to initiate a primer extension reaction to transfer recording tag information to the coding tag. The coding tag may also comprise a binding cycle specific sequence, for identifying the binding cycle from which an extended coding tag or di-tag originated.

Transfer of information of the recording tag to the coding tag may be effected by primer extension or ligation. Transfer of information of the recording tag and coding tag to a di-tag construct may be generated a gap fill reaction, primer extension reaction, or both.

A di-tag molecule comprises functional components similar to that of an extended recording tag. A di-tag molecule may comprise a universal priming site derived from the recording tag, a barcode (e.g., compartment tag) derived from the recording tag, an optional unique molecular identifier (UMI) derived from the recording tag, an optional spacer derived from the recording tag, an encoder sequence derived from the coding tag, an optional unique molecular identifier derived from the coding tag, a binding cycle specific sequence, an optional spacer derived from the coding tag, and a universal priming site derived from the coding tag.

Figure 11B:
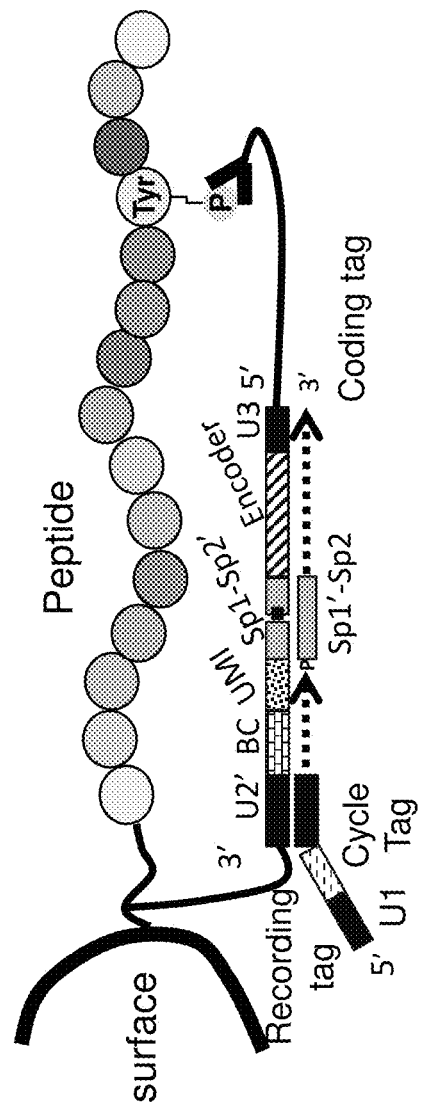

In certain embodiments, the recording tag can be generated using combinatorial concatenation of barcode encoding words. The use of combinatorial encoding words provides a method by which annealing and chemical ligation can be used to transfer information from a PNA recording tag to a coding tag or di-tag construct (see, e.g., FIG. 12A-D). In certain embodiments where the methods of analyzing a peptide disclosed herein involve cleavage of a terminal amino acid via an Edman degradation, it may be desirable employ recording tags resistant to the harsh conditions of Edman degradation, such as PNA. One harsh step in the Edman degradation protocol is anhydrous TFA treatment to cleave the N-terminal amino acid. This step will typically destroy DNA. PNA, in contrast to DNA, is highly-resistant to acid hydrolysis. The challenge with PNA is that enzymatic methods of information transfer become more difficult, i.e., information transfer via chemical ligation is a preferred mode. In FIG. 11B, recording tag and coding tag information are written using an enzymatic gap-fill extension ligation step, but this is not currently feasibly with PNA template, unless a polymerase is developed that uses PNA. The writing of the barcode and UMI from the PNA recording tag to a coding tag is problematic due to the requirement of chemical ligation, products which are not easily amplified. Methods of chemical ligation have been extensively described in the literature (Gunderson et al. 1998, Genome Res. 8:1142-1153; Peng et al., 2010, Eur. J. Org. Chem. 4194-4197; El-Sagheer et al., 2011, Org. Biomol. Chem. 9:232-235; El-Sagheer et al., 2011, Proc. Natl. Acad. Sci. USA 108:11338-11343; Litovchick et al., 2014, Artif. DNA PNA XNA 5: e27896; Roloff et al., 2014, Methods Mol. Biol. 1050:131-141).

To create combinatorial PNA barcodes and UMI sequences, a set of PNA words from an n-mer library can be combinatorially ligated. If each PNA word derives from a space of 1,000 words, then four combined sequences generate a coding space of $1,000^4=10^{12}$ codes. In this way, from a starting set of 4,000 different DNA template sequences, over $10^{12}$ PNA codes can be generated (see, e.g., FIG. 12A). A smaller or larger coding space can be generated by adjusting the number of concatenated words, or adjusting the number of elementary words. As such, the information transfer using DNA sequences hybridized to the PNA recording tag can be completed using DNA word assembly hybridization and chemical ligation (see, e.g., FIG. 12B). After assembly of the DNA words on the PNA template and chemical ligation of the DNA words, the resulting intermediate can be used to transfer information to/from the coding tag (see, e.g., FIG. 12C and FIG. 12D).

In certain embodiments, the macromolecule and associated recording tag are covalently joined to the solid support. The solid support may be a bead, an array, a glass surface, a silicon surface, a plastic surface, a filter, a membrane, nylon, a silicon wafer chip, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere. The solid support may be a polystyrene bead, a polymer bead, an agarose bead, an acrylamide bead, a solid core bead, a porous bead, a paramagnetic bead, a glass bead, or a controlled pore bead.

In certain embodiments, the binding agent is a protein or a polypeptide. In some embodiments, the binding agent is a modified or variant aminopeptidase, a modified or variant amino acyl tRNA synthetase, a modified or variant anticalin, a modified or variant ClpS, or a modified or variant antibody or binding fragment thereof. In certain embodiments, the binding agent binds to a single amino acid residue, a di-peptide, a tri-peptide, or a post-translational modification of the peptide. In some embodiments, the binding agent binds to an N-terminal amino acid residue, a C-terminal amino acid residue, or an internal amino acid residue. In some embodiments, the binding agent binds to an N-terminal peptide, a C-terminal peptide, or an internal peptide. In some embodiments, the binding agent is a site-specific covalent label of an amino acid of post-translational modification of a peptide.

In certain embodiments, following contacting the plurality of macromolecules with a plurality of binding agents in step (b), complexes comprising the macromolecule and associated binding agents are dissociated from the solid support and partitioned into an emulsion of droplets or microfluidic droplets. In some embodiments, each microfluidic droplet comprises at most one complex comprising the macromolecule and the binding agents.

Figure 13:
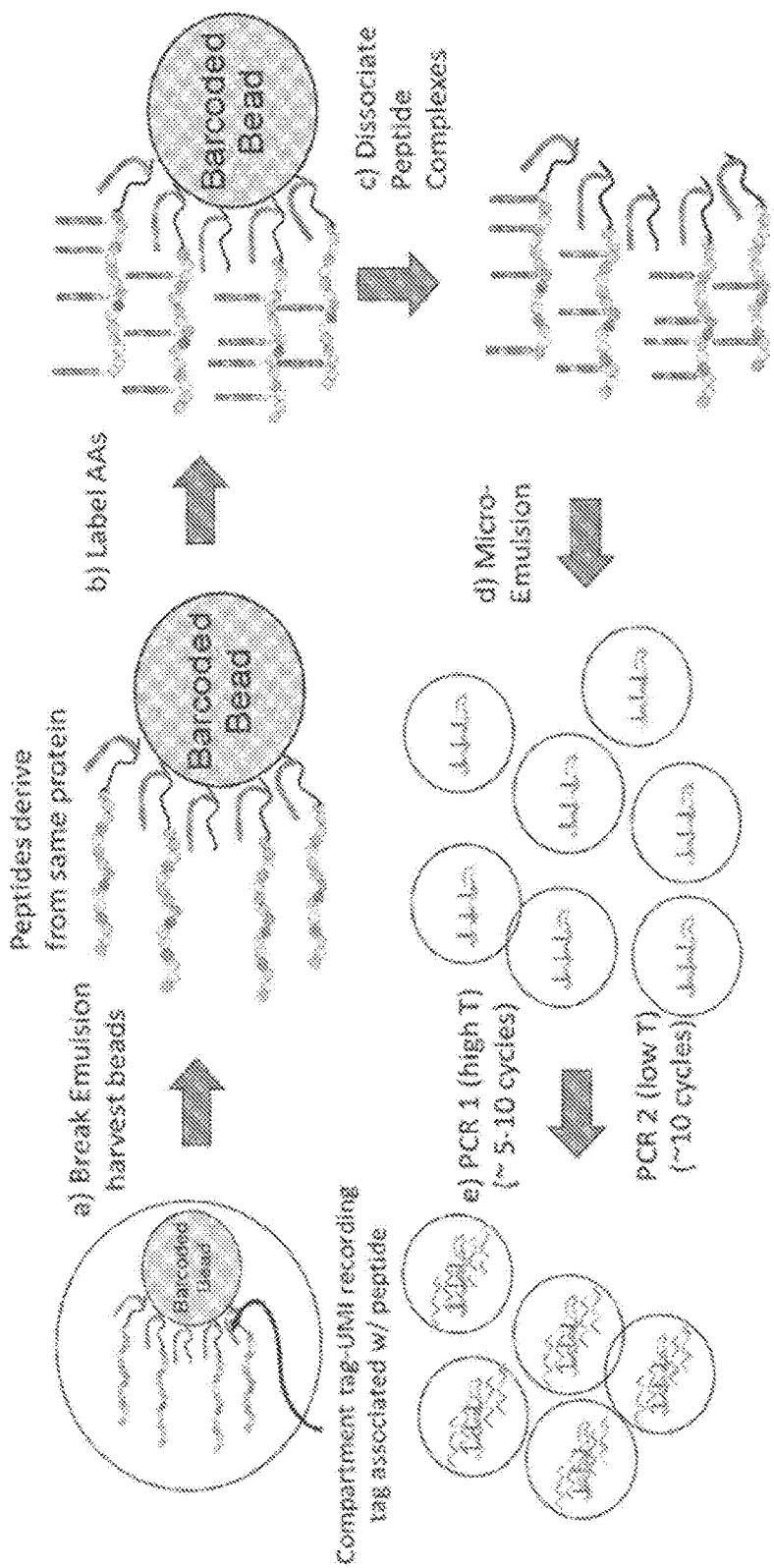
FIG. 13 illustrates proteome partitioning on a compartment barcoded bead, and subsequent di-tag assembly via emulsion fusion PCR to generate a library of elements representing polypeptide sequence composition. The amino acid content of the polypeptide can be subsequently characterized through N-terminal sequencing or alternatively through attachment (covalent or non-covalent) of amino acid specific chemical labels or binding agents associated with a coding tag. The coding tag comprises universal priming sequence, as well as an encoder sequence for the amino acid identity, a compartment tag, and an amino acid UMI. After information transfer, the di-tags are mapped back to the originating molecule via the recording tag UMI. In Step (a), the proteome is compartmentalized into droplets with barcoded beads. Peptides with associated recording tags (comprising compartment barcode information) are attached to the bead surface. The droplet emulsion is broken, releasing barcoded beads with partitioned peptides. In Step (b), specific amino acid residues on the peptides are chemically labeled with DNA coding tags that are conjugated to site-specific labeling moieties. The DNA coding tags comprise amino acid barcode information and optionally an amino acid UMI. Step (c): Labeled peptide-recording tag complexes are released from the beads. Step (d): The labeled peptide-recording tag complexes are emulsified into nano or microemulsions such that there is, on average, less than one peptide-recording tag complex per compartment. Step (e): An emulsion fusion PCR transfers recording tag information (e.g., compartment barcode) to all of the DNA coding tags attached to the amino acid residues. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.
Figure 14:
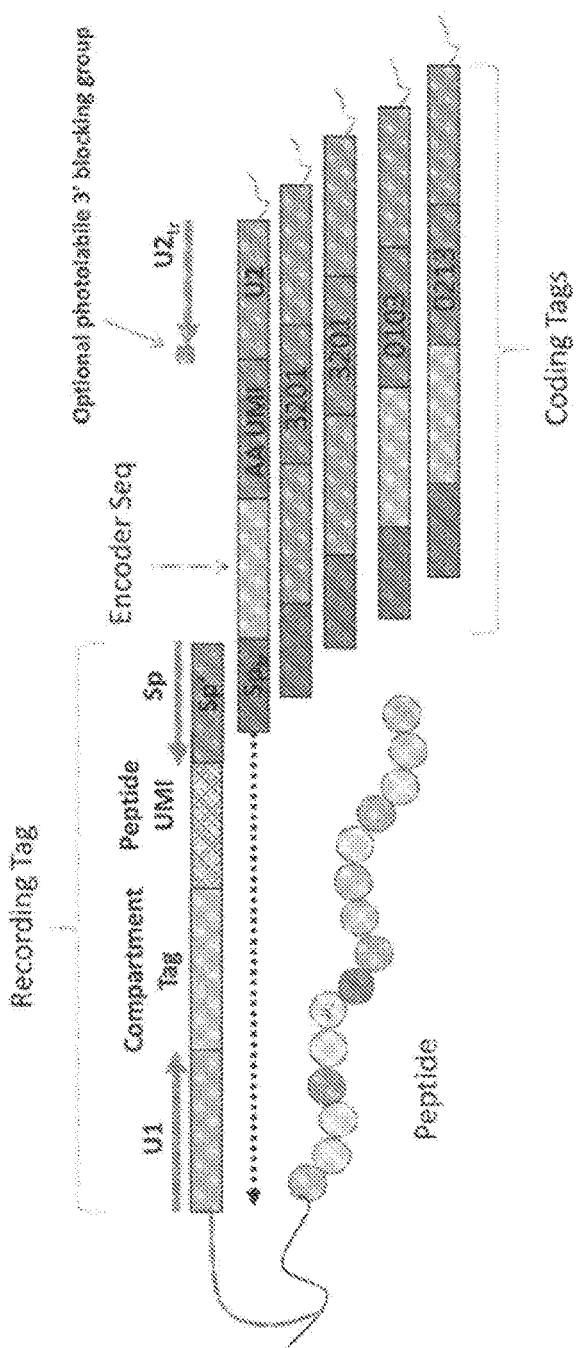
FIG. 14 illustrates generation of extended coding tags from emulsified peptide recording tag-coding tags complex. The peptide complexes from FIG. 13, Step (C) are co-emulsified with PCR reagents into droplets with on average a single peptide complex per droplet. A three-primer fusion PCR approach is used to amplify the recording tag associated with the peptide, fuse the amplified recording tags to multiple binding agent coding tags or coding tags of covalently labeled amino acids, extend the coding tags via primer extension to transfer peptide UMI and compartment tag information from the recording tag to the coding tag, and amplify the resultant extended coding tags. There are multiple extended coding tag species per droplet, with a different species for each amino acid encoder sequence-UMI coding tag present. In this way, both the identity and count of amino acids within the peptide can be determined. The U1 universal primer and Sp primer are designed to have a higher melting T. than the $U2_{tr}$ universal primer. This enables a two-step PCR in which the first few cycles are performed at a higher annealing temperature to amplify the recording tag, and then stepped to a lower Tm so that the recording tags and coding tags prime on each other during PCR to produce an extended coding tag, and the U1 and $U2_{tr}$ universal primers are used to prime amplification of the resultant extended coding tag product. In certain embodiments, premature polymerase extension from the $U2_{tr}$ primer can be prevented by using a photo-labile 3' blocking group (Young et al., 2008, *Chem. Commun.* (Camb) 4:462-464). After the first round of PCR amplifying the recording tags, and a second-round fusion PCR step in which the coding tag $Sp_{tr}$ primes extension of the coding tag on the amplified Sp' sequences of the recording tag, the 3' blocking group of $U2_{tr}$ is removed, and a higher temperature PCR is initiated for amplifying the extended coding tags with U1 and $U2_{tr}$ primers. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In certain embodiments, the recording tag is amplified prior to generating an extended coding tag or di-tag construct. In embodiments where complexes comprising the macromolecule and associated binding agents are partitioned into droplets or microfluidic droplets such that there is at most one complex per droplet, amplification of recording tags provides additional recording tags as templates for transferring information to coding tags or di-tag constructs (see, e.g., FIG. 13 and FIG. 14). Emulsion fusion PCR may be used to transfer the recording tag information to the coding tag or to create a population of di-tag constructs.

The collection of extended coding tags or di-tag constructs that are generated may be amplified prior to analysis. Analysis of the collection of extended coding tags or di-tag constructs may comprise a nucleic acid sequencing method. The sequencing by synthesis, sequencing by ligation, sequencing by hybridization, polony sequencing, ion semiconductor sequencing, or pyrosequencing. The nucleic acid sequencing method may be single molecule real-time sequencing, nanopore-based sequencing, or direct imaging of DNA using advanced microscopy.

Edman degradation and methods that chemically label N-terminal amines such as PITC, Sanger's agent (DNFB), SNFB, acetylation reagents, amidination (guanidinylation) reagents, etc. can also modify internal amino acids and the exocyclic amines on standard nucleic acid or PNA bases such as adenine, guanine, and cytosine. In certain embodiments, the peptide's F-amines of lysine residues are blocked with an acid anhydride, a guandination agent, or similar blocking reagent, prior to sequencing. Although exocyclic amines of DNA bases are much less reactive the primary N-terminal amine of peptides, controlling the reactivity of amine reactive agents toward N-terminal amines reducing non-target activity toward internal amino acids and exocyclic amines on DNA bases is important to the sequencing assay. The selectivity of the modification reaction can be modulated by adjusting reaction conditions such as pH, solvent (aqueous vs. organic, aprotic, non-polar, polar aprotic, ionic liquids, etc.), bases and catalysts, co-solvents, temperature, and time. In addition, reactivity of exocyclic amines on DNA bases is modulated by whether the DNA is in ssDNA or dsDNA form. To minimize modification, prior to NTAA chemical modification, the recording tag can be hybridized with complementary DNA probes: P1', {Sample BCs}', {Sp-BC}', etc. In another embodiment, the use of nucleic acids having protected exocyclic amines can also be used (Ohkubo, Kasuya et al. 2008). In yet another embodiment, "less reactive" amine labeling compounds, such as SNFB, mitigates off-target labeling of internal amino acids and exocyclic amines on DNA (Carty and Hirs 1968). SNFB is less reactive than DNFB due to the fact that the para sulfonyl group is more electron withdrawing than the para nitro group, leading to less active fluorine substitution with SNFB than DNFB.

Titration of coupling conditions and coupling reagents to optimize NTAA α-amine modification and minimize off-target amino acid modification or DNA modification is possible through careful selection of chemistry and reaction conditions (concentrations, temperature, time, pH, solvent type, etc.). For instance, DNFB is known to react with secondary amines more readily in aprotic solvents such as acetonitrile versus in water. Mild modification of the exocyclic amines may still allow a complementary probe to hybridize the sequence but would likely disrupt polymerase-based primer extension. It is also possible to protect the exocyclic amine while still allowing hydrogen bonding. This was described in a recent publication in which protected bases are still capable of hybridizing to targets of interest (Ohkubo, Kasuya et al. 2008). In one embodiment, an engineered polymerase is used to incorporate nucleotides with protected bases during extension of the recording tag on a DNA coding tag template. In another embodiment, an engineered polymerase is used to incorporate nucleotides on a recording tag PNA template (w/ or w/o protected bases) during extension of the coding tag on the PNA recording tag template. In another embodiment, the information can be transferred from the recording tag to the coding tag by annealing an exogenous oligonucleotide to the PNA recording tag. Specificity of hybridization can be facilitated by choosing UMIs which are distinct in sequence space, such as designs based on assembly of n-mer words (Gerry, Witowski et al. 1999).

While Edman-like N-terminal peptide degradation sequencing can be used to determine the linear amino acid sequence of the peptide, an alternative embodiment can be used to perform partial compositional analysis of the peptide with methods utilizing extended recording tags, extended coding tags, and di-tags. Binding agents or chemical labels can be used to identify both N-terminal and internal amino acids or amino acid modifications on a peptide. Chemical agents can covalently modify amino acids (e.g., label) in a site-specific manner (Sletten and Bertozzi 2009, Basle, Joubert et al. 2010) (Spicer and Davis 2014). A coding tag can be attached to a chemical labeling agent that targets a single amino acid, to facilitate encoding and subsequent identification of site-specific labeled amino acids (see, e.g., FIG. 13).

Peptide compositional analysis does not require cyclic degradation of the peptide, and thus circumvents issues of exposing DNA containing tags to harsh Edman chemistry. In a cyclic binding mode, one can also employ extended coding tags or di-tags to provide compositional information (amino acids or dipeptide/tripeptide information), PTM information, and primary amino acid sequence. In one embodiment, this composition information can be read out using an extended coding tag or di-tag approach described herein. If combined with UMI and compartment tag information, the collection of extended coding tags or di-tags provides compositional information on the peptides and their originating compartmental protein or proteins. The collection of extended coding tags or di-tags mapping back to the same compartment tag (and ostensibly originating protein molecule) is a powerful tool to map peptides with partial composition information. Rather than mapping back to the entire proteome, the collection of compartment tagged peptides is mapped back to a limited subset of protein molecules, greatly increasing the uniqueness of mapping.

Binding agents used herein may recognize a single amino acid, dipeptide, tripeptide, or even longer peptide sequence motifs. Tessler (2011, Digital Protein Analysis: Technologies for Protein Diagnostics and Proteomics through Single Molecule Detection. Ph.D., Washington University in St. Louis) demonstrated that relatively selective dipeptide antibodies can be generated for a subset of charged dipeptide epitopes (Tessler 2011). The application of directed evolution to alternate protein scaffolds (e.g., aaRSs, anticalins, ClpSs, etc.) and aptamers may be used to expand the set of dipeptide/tripeptide binding agents. The information from dipeptide/tripeptide compositional analysis coupled with mapping back to a single protein molecule may be sufficient to uniquely identify and quantitate each protein molecule. At a maximum, there are a total of 400 possible dipeptide combinations. However, a subset of the most frequent and most antigenic (charged, hydrophilic, hydrophobic) dipeptide should suffice to which to generate binding agents. This number may constitute a set of 40-100 different binding agents. For a set of 40 different binding agents, the average 10-mer peptide has about an 80% chance of being bound by at least one binding agent. Combining this information with all the peptides deriving from the same protein molecule may allow identification of the protein molecule. All this information about a peptide and its originating protein can be combined to give more accurate and precise protein sequence characterization.

Figure 15:
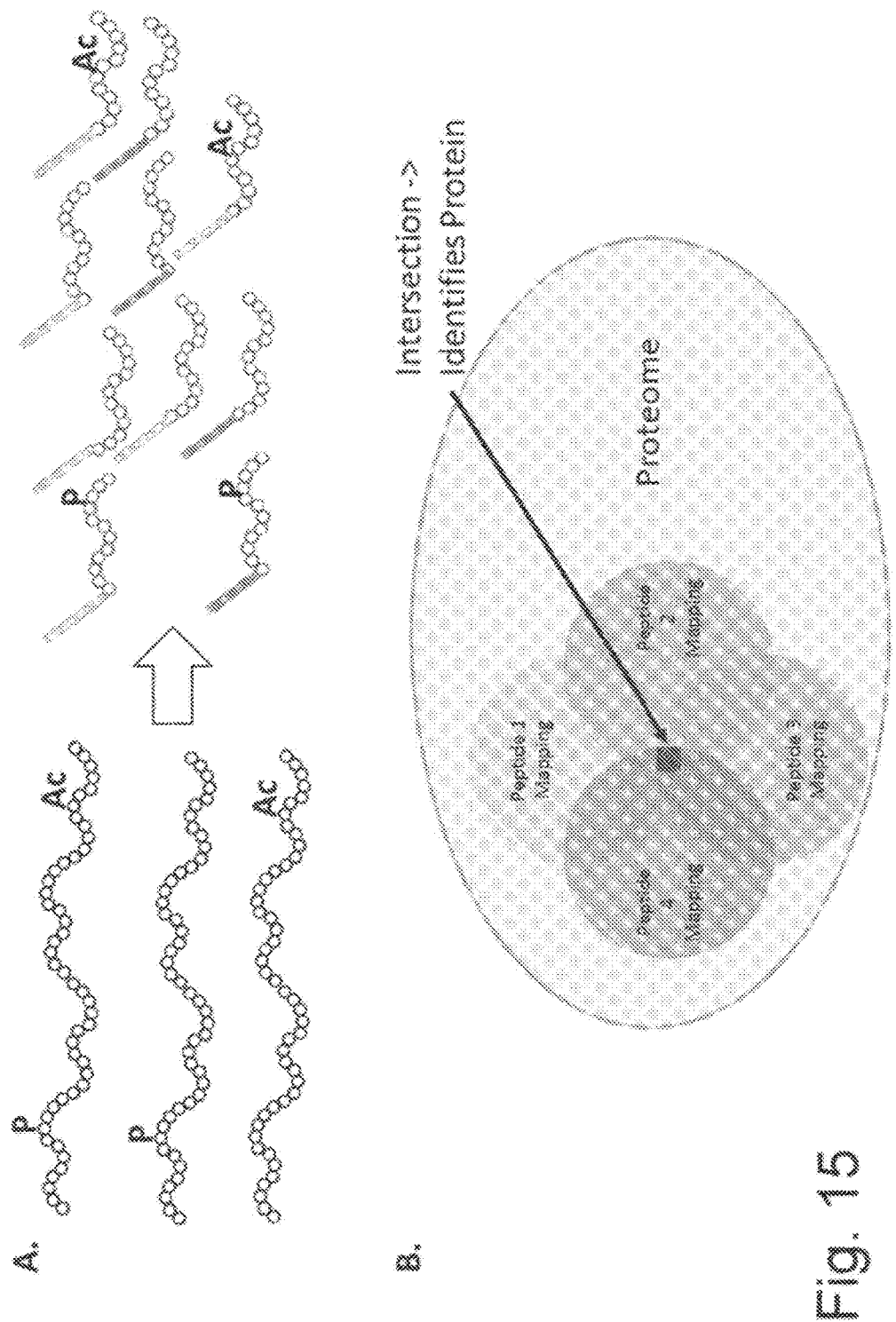
FIG. 15 illustrates use of proteome partitioning and barcoding facilitating enhanced mappability and phasing of proteins. In polypeptide sequencing, proteins are typically digested into peptides. In this process, information about the relationship between individual polypeptides that originated from a parent protein molecule, and their relationship to the parent protein molecule is lost. In order to reconstruct this information, individual peptide sequences are mapped back to a collection of protein sequences from which they may have derived. The task of finding a unique match in such a set is rendered more difficult with short and/or partial peptide sequences, and as the size and complexity of the collection (e.g., proteome sequence complexity) increases. The partitioning of the proteome into barcoded (e.g., compartment tagged) compartments or partitions, subsequent digestion of the protein into peptides, and the joining of the compartment tags to the peptides reduces the "protein" space to which a peptide sequence needs to be mapped to, greatly simplifying the task in the case of complex protein samples. Labeling of a protein with unique molecular identifier (UMI) prior to digestion into peptides facilitates mapping of peptides back to the originating protein molecule and allows annotation of phasing information between post-translational modified (PTM) variants derived from the same protein molecule and identification of individual proteoforms. Part (A) shows an example of proteome partitioning comprising labeling proteins with recording tags comprising a compartment or partition barcode and subsequent fragmentation into recording-tag labeled peptides. Part (B): For partial peptide sequence information or even just composition information, this mapping is highly-degenerate. However, partial peptide sequence or composition information coupled with information from multiple peptides from the same protein, allow unique identification of the originating protein molecule. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

A recent digital protein characterization assay has been proposed that uses partial peptide sequence information (Swaminathan et al., 2015, PLoS Comput. Biol. 11:e1004080) (Yao, Docter et al. 2015). Namely, the approach employs fluorescent labeling of amino acids which are easily labeled using standard chemistry such as cysteine, lysine, arginine, tyrosine, aspartate/glutamate (Basle, Joubert et al. 2010). The challenge with partial peptide sequence information is that the mapping back to the proteome is a one-to-many association, with no unique protein identified. This one-to-many mapping problem can be solved by reducing the entire proteome space to limited subset of protein molecules to which the peptide is mapped back. In essence, a single partial peptide sequence may map back to 100's or 1000's of different protein sequences, however if it is known that a set of several peptides (for example, 10 peptides originating from a digest of a single protein molecule) all map back to a single protein molecule contained in the subset of protein molecules within a compartment, then it is easier to deduce the identity of the protein molecule. For instance, an intersection of the peptide proteome maps for all peptides originating from the same molecule greatly restricts the set of possible protein identities (see, e.g., FIG. 15).

Figure 16:
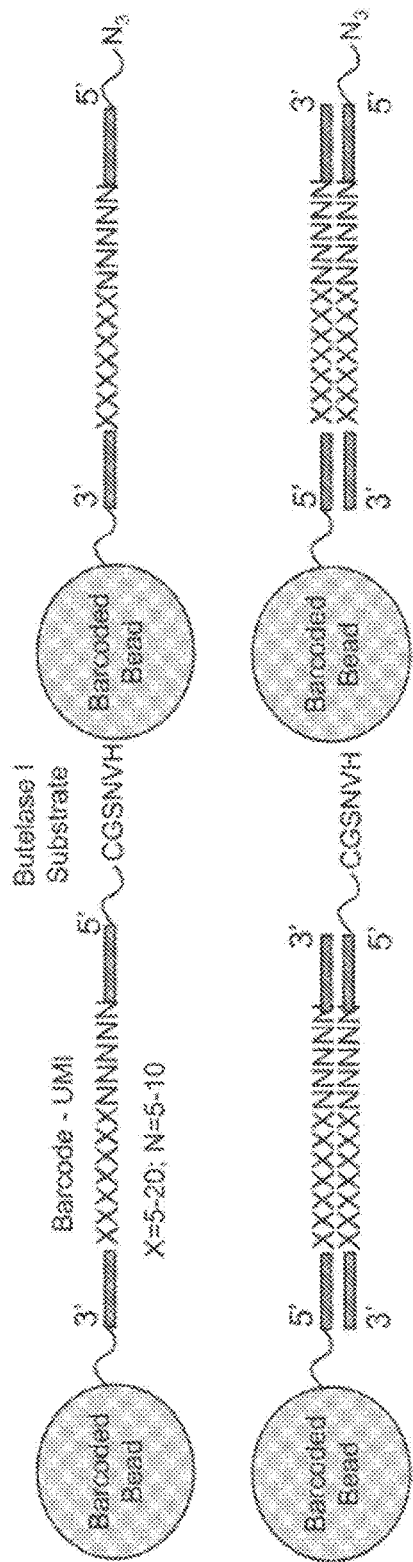
FIG. 16 illustrates exemplary modes of compartment tagged bead sequence design. The compartment tags comprise a barcode of $X_{5-20}$ to identify an individual compartment and a unique molecular identifier (UMI) of $N_{5-10}$ to identify the peptide to which the compartment tag is joined, where X and N represent degenerate nucleobases or nucleobase words. Compartment tags can be single stranded (upper depictions) or double stranded (lower depictions). Optionally, compartment tags can be a chimeric molecule comprising a peptide sequence with a recognition sequence for a protein ligase (e.g., butelase I) for joining to a peptide of interest (left depictions). Alternatively, a chemical moiety can be included on the compartment tag for coupling to a peptide of interest (e.g., azide as shown in right depictions). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

In particular, mappability of a partial peptide sequence or composition is significantly enhanced by making innovative use of compartmental tags and UMIs. Namely, the proteome is initially partitioned into barcoded compartments, wherein the compartmental barcode is also attached to a UMI sequence. The compartment barcode is a sequence unique to the compartment, and the UMI is a sequence unique to each barcoded molecule within the compartment (see, e.g., FIG. 16). In one embodiment, this partitioning is accomplished using methods similar to those disclosed in PCT Publication WO2016/061517, which is incorporated by reference in its entirety, by direct interaction of a DNA tag labeled polypeptide with the surface of a bead via hybridization to DNA compartment barcodes attached to the bead (see, e.g., FIG. 31A-E). A primer extension step transfers information from the bead-linked compartment barcode to the DNA tag on the polypeptide (see, e.g., FIG. 20D). In another embodiment, this partitioning is accomplished by co-encapsulating UMI containing, barcoded beads and protein molecules into droplets of an emulsion. In addition, the droplet optionally contains a protease that digests the protein into peptides. A number of proteases can be used to digest the reporter tagged polypeptides (Switzar, Giera et al. 2013). Co-encapsulation of enzymatic ligases, such as butelase I, with proteases may call for modification to the enzyme, such as pegylation, to make it resistant to protease digestion (Frokjaer and Otzen 2005, Kang, Wang et al. 2010). After digestion, the peptides are ligated to the barcode-UMI tags. In the preferred embodiment, the barcode-UMI tags are retained on the bead to facilitate downstream biochemical manipulations (see, e.g., FIG. 13).

After barcode-UMI ligation to the peptides, the emulsion is broken and the beads harvested. The barcoded peptides can be characterized by their primary amino acid sequence, or their amino acid composition. Both types of information about the peptide can be used to map it back to a subset of the proteome. In general, sequence information maps back to a much smaller subset of the proteome than compositional information. Nonetheless, by combining information from multiple peptides (sequence or composition) with the same compartment barcode, it is possible to uniquely identify the protein or proteins from which the peptides originate. In this way, the entire proteome can be characterized and quantitated. Primary sequence information on the peptides can be derived by performing a peptide sequencing reaction with extended recording tag creation of a DNA Encoded Library (DEL) representing the peptide sequence. In the preferred embodiment, the recording tag is comprised of a compartmental barcode and UMI sequence. This information is used along with the primary or PTM amino acid information transferred from the coding tags to generate the final mapped peptide information.

An alternative to peptide sequence information is to generate peptide amino acid or dipeptide/tripeptide compositional information linked to compartmental barcodes and UMIs. This is accomplished by subjecting the beads with UMI-barcoded peptides to an amino acid labeling step, in which select amino acids (internal) on each peptide are site-specifically labeled with a DNA tag comprising amino acid code information and another amino acid UMI (AA UMI) (see, e.g., FIG. 13). The amino acids (AAs) most tractable to chemical labeling are lysines, arginines, cysteines, tyrosines, tryptophans, and aspartates/glutamates, but it may also be feasible to develop labeling schemes for the other AAs as well (Mendoza and Vachet, 2009). A given peptide may contain several AAs of the same type. The presence of multiple amino acids of the same type can be distinguished by virtue of the attached AA UMI label. Each labeling molecule has a different UMI within the DNA tag enabling counting of amino acids. An alternative to chemical labeling is to "label" the AAs with binding agents. For instance, a tyrosine-specific antibody labeled with a coding tag comprising AA code information and an AA UMI could be used mark all the tyrosines of the peptides. The caveat with this approach is the steric hindrance encountered with large bulky antibodies, ideally smaller scFvs, anticalins, or ClpS variants would be used for this purpose.

In one embodiment, after tagging the AAs, information is transferred between the recording tag and multiple coding tags associated with bound or covalently coupled binding agents on the peptide by compartmentalizing the peptide complexes such that a single peptide is contained per droplet and performing an emulsion fusion PCR to construct a set of extended coding tags or di-tags characterizing the amino acid composition of the compartmentalized peptide. After sequencing the di-tags, information on peptides with the same barcodes can be mapped back to a single protein molecule.

In a particular embodiment, the tagged peptide complexes are disassociated from the bead (see, e.g., FIG. 13), partitioned into small mini-compartments (e.g., micro-emulsion) such that on average only a single labeled/bound binding agent peptide complex resides in a given compartment. In a particular embodiment, this compartmentalization is accomplished through generation of micro-emulsion droplets (Shim, Ranasinghe et al. 2013, Shembekar, Chaipan et al. 2016). In addition to the peptide complex, PCR reagents are also co-encapsulated in the droplets along with three primers (U1, Sp, and U2$_{tr}$). After droplet formation, a few cycles of emulsion PCR are performed (~5-10 cycles) at higher annealing temperature such than only U1 and Sp anneal and amplify the recording tag product (see, e.g., FIG. 13). After this initial 5-10 cycles of PCR, the annealing temperature is reduced such that U2tr and the Sptr on the amino acid code tags participate in the amplification, and another ~10 rounds are performed. The three-primer emulsion PCR effectively combines the peptide UMI-barcode with all the AA code tags generating a di-tag library representation of the peptide and its amino acid composition. Other modalities of performing the three primer PCR and concatenation of the tags can also be employed. Another embodiment is the use of a 3' blocked U2 primer activated by photo-deblocking, or addition of an oil soluble reductant to initiate 3' deblocking of a labile blocked 3' nucleotide. Post-emulsion PCR, another round of PCR can be performed with common primers to format the library elements for NGS sequencing.

In this way, the different sequence components of the library elements are used for counting and classification purposes. For a given peptide (identified by the compartment barcode-UMI combination), there are many library elements, each with an identifying AA code tag and AA UMI (see, e.g., FIG. 13). The AA code and associated UMI is used to count the occurrences of a given amino acid type in a given peptide. Thus the peptide (perhaps a GluC, LysC, or Endo AsnN digest) is characterized by its amino acid composition (e.g., 2 Cys, 1 Lys, 1 Arg, 2 Tyr, etc.) without regard to spatial ordering. This nonetheless provides a sufficient signature to map the peptide to a subset of the proteome, and when used in combination with the other peptides derived from the same protein molecule, to uniquely identify and quantitate the protein.

H. Kit and Kit Components for Terminal Amino Acid (TAA) Labelling

In certain embodiments, a terminal amino acid (e.g., NTAA or CTAA) of a peptide is modified or labeled prior to contacting the peptide with a binding agent in the methods described herein. Kits and kit components are described herein for such modification and/or labeling.

In some embodiments, the NTAA is reacted with phenylisothiocyanate (PITC) to generate a phenylthiocarbamoyl (PTC)-NTAA derivative. Edman degradation typically uses phenyl isothiocyanate (PITC) to label the N-terminus. PITC has two properties well suited for the methods disclosed herein: (1) PITC labels the N-terminus amine group with high efficiency; and (2) the resultant PTC derivitized NTAA undergoes self-isomerization, upon acid treatment, resulting in cleaving of the amino acid from the remaining peptide.

Other reagents that may be used to label the NTAA include: 4-sulfophenyl isothiocyanate, 3-pyridyl isothiocyante (PYITC), 2-piperidinoethyl isothiocyanate (PEITC), 3-(4-morpholino) propyl isothiocyanate (MPITC), 3-(diethylamino)propyl isothiocyanate (DEPTIC) (Wang et al., 2009, Anal Chem 81: 1893-1900), (1-fluoro-2,4-dinitrobenzene (Sanger's reagent, DNFB), dansyl chloride (DNS-Cl, or 1-dimethylaminonaphthalene-5-sulfonyl chloride), 4-sulfonyl-2-nitrofluorobenzene (SNFB), acetylation reagents, amidination (guanidinylation) reagents, 2-carboxy-4,6-dinitrochlorobenzene, 7-methoxycoumarin acetic acid, a thioacylation reagent, a thioacetylation reagent, and a thiobenzylation reagent. If the NTAA is blocked to labelling, there are a number of approaches to unblock the terminus, such as removing N-acetyl blocks with acyl peptide hydrolase (APH) (Farries, Harris et al., 1991, Eur. J. Biochem. 196:679-685). Methods of unblocking the N-terminus of a peptide are known in the art (see, e.g., Krishna et al., 1991, Anal. Biochem. 199:45-50; Leone et al., 2011, Curr. Protoc. Protein Sci., Chapter 11:Unit 11.7; Fowler et al., 2001, Curr. Protoc. Protein Sci., Chapter 11: Unit 11.7, each of which is hereby incorporated by reference in its entirety).

Dansyl chloride reacts with the free amine group of a peptide to yield a dansyl derivative of the NTAA. DNFB and SNFB react with the ε-amine groups of a peptide to produce DNP-NTAA, and SNP-NTAA, respectively. Additionally, both DNFB and SNFB also react with the ε-amine of lysine residues. DNFB also reacts with tyrosine and histidine amino acid residues. SNFB has better selectivity for amine groups than DNFB, and is preferred for NTAA modification (Carty and Hirs 1968). In certain embodiments, lysine ε-amines are pre-blocked with an organic anhydride prior to polypeptide protease digestion into peptides.

Another useful NTAA modifier is an acetyl group since a known enzyme exists to remove acetylated NTAAs, namely acyl peptide hydrolases (APH) which cleaves the N-terminal acetylated amino acid, effectively shortening the peptide by a single amino acid {Chang, 2015 #373; Friedmann, 2013 #374}. The NTAA can be chemically acetylated with acetic anhydride or enzymatically acetylated with N-terminal acetyltransferases (NAT) {Chang, 2015 #373; Friedmann, 2013 #374}. Yet another useful NTAA modifier is an amidinyl (guanidinyl) moiety since a proven cleavage chemistry of the amidinated NTAA is known in the literature, namely mild incubation of the N-terminal amidinated peptide with 0.5-2% NaOH results in cleavage of the N-terminal amino acid {Hamada, 2016 #383}. This effectively provides a mild Edman-like chemical N-terminal degradation peptide sequencing process. Moreover, certain amidination (guanidinylation) reagents and the downstream NaOH cleavage are quite compatible with DNA encoding.

The presence of the DNP/SNP, acetyl, or amidinyl (guanidinyl) group on the NTAA may provide a better handle for interaction with an engineered binding agent. A number of commercial DNP antibodies exist with low nM affinities. Other methods of labeling the NTAA include labeling with trypligase (Liebscher et al., 2014, Angew Chem Int Ed Engl 53:3024-3028) and amino acyl transferase (Wagner, et al., 2011, J Am Chem Soc 133:15139-15147).

Isothiocyates, in the presence of ionic liquids, have been shown to have enhanced reactivity to primary amines. Ionic liquids are excellent solvents (and serve as a catalyst) in organic chemical reactions and can enhance the reaction of isothiocyanates with amines to form thioureas. An example is the use of the ionic liquid 1-butyl-3-methyl-imidazolium tetraflouoraborate [Bmim][BF4] for rapid and efficient labeling of aromatic and aliphatic amines by phenyl isothiocyanate (PITC) (Le, Chen et al. 2005). Edman degradation involves the reaction of isothiocyanates, such as PITC, with the amino N-terminus of peptides. As such, in one embodiment ionic liquids are used to improve the efficiency of the Edman degradation process by providing milder labeling and degradation conditions. For instance, the use of 5% (vol./vol.) PITC in ionic liquid [Bmim][BF4] at 25° C. for 10 min. is more efficient than labeling under standard Edman PITC derivatization conditions which employ 5% (vol./vol.) PITC in a solution containing pyridine, ethanol, and ddH2O (1:1:1 vol./vol./vol.) at 55° C. for 60 min (Wang, Fang et al. 2009). In a preferred embodiment, internal lysine, tyrosine, histidine, and cysteine amino acids are blocked within the polypeptide prior to fragmentation into peptides. In this way, only the peptide α-amine group of the NTAA is accessible for modification during the peptide sequencing reaction. This is particularly relevant when using DNFB (Sanger' reagent) and dansyl chloride.

In certain embodiments, the NTAA have been blocked prior to the NTAA labelling step (particularly the original N-terminus of the protein). If so, there are a number of approaches to unblock the N-terminus, such as removing N-acetyl blocks with acyl peptide hydrolase (APH) (Farries, Harris et al. 1991). A number of other methods of unblocking the N-terminus of a peptide are known in the art (see, e.g., Krishna et al., 1991, *Anal. Biochem.* 199:45-50; Leone et al., 2011, *Curr. Protoc. Protein Sci.*, Chapter 11:Unit11.7; Fowler et al., 2001, *Curr. Protoc. Protein Sci.*, Chapter 11: Unit 11.7, each of which is hereby incorporated by reference in its entirety).

The CTAA can be modified with a number of different carboxyl-reactive reagents as described by Hermanson (Hermanson 2013). In another example, the CTAA is modified with a mixed anhydride and an isothiocyanate to generate a thiohydantoin ((Liu and Liang 2001) and U.S. Pat. No. 5,049,507). The thiohydantoin modified peptide can be cleaved at elevated temperature in base to expose the penultimate CTAA, effectively generating a C-terminal based peptide degradation sequencing approach (Liu and Liang 2001). Other modifications that can be made to the CTAA include addition of a para-nitroanilide group and addition of 7-amino-4-methylcoumarinyl group.

I. Kit and Kit Components for Terminal Amino Acid Cleavage

In certain embodiments relating to analyzing peptides, following binding of a terminal amino acid (N-terminal or C-terminal) by a binding agent and transfer of coding tag information to a recording tag, transfer of recording tag information to a coding tag, transfer of recording tag information and coding tag information to a di-tag construct, the terminal amino acid is removed or cleaved from the peptide to expose a new terminal amino acid. In some embodiments, the terminal amino acid is an NTAA. In other embodiments, the terminal amino acid is a CTAA.

Cleavage of a terminal amino acid can be accomplished by any number of known techniques, including chemical cleavage and enzymatic cleavage. An example of chemical cleavage is Edman degradation. During Edman degradation of the peptide the n NTAA is reacted with phenyl isothiocyanate (PITC) under mildly alkaline conditions to form the phenylthiocarbamoyl-NTAA derivative. Next, under acidic conditions, the phenylthiocarbamoyl-NTAA derivative is cleaved generating a free thiazolinone derivative, and thereby converting the $(n-1)^{th}$ amino acid of the peptide to an N-terminal amino acid (the $(n-1)^{th}$ NTAA). The steps in this process are illustrated below.

Typical Edman Degradation, as described above requires deployment of harsh high temperature chemical conditions (e.g., anhydrous TFA) for long incubation times. These conditions are generally not compatible with nucleic acid encoding of macromolecules.

To convert chemical Edman Degradation to a nucleic acid encoding-friendly approach, the harsh chemical steps are replaced with mild chemical degradation or efficient enzymatic steps. In one embodiment, chemical Edman degradation can be employed using milder conditions than original described. Several milder cleavage conditions for Edman degradation have been described in the literature, including replacing anhydrous TFA with triethylamine acetate in acetonitrile (see, e.g., Barrett, 1985, *Tetrahedron Lett.* 26:4375-4378, incorporated by reference in its entirety). Cleavage of the NTAA may also be accomplished using thioacylation degradation, which uses milder cleavage conditions as compared to Edman degradation (see, U.S. Pat. No. 4,863,870).

In another embodiment, cleavage by anhydrous TFA may be replaced with an "Edmanase", an engineered enzyme that catalyzes the removal of the PITC-derivatized N-terminal amino acid via nucleophilic attack of the thiourea sulfur atom on the carbonyl group of the scissile peptide bond under mild conditions (see, U.S. Patent Publication US2014/0273004, incorporated by reference in its entirety). Edmanase was made by modifying cruzain, a cysteine protease from *Trypanosoma cruzi* (Borgo, 2014). A $C_{25}G$ mutation removes the catalytic cysteine residue while three mutations (G65S, A138C, L160Y) were selected to create steric fit with the phenyl moiety of the Edman reagent (PITC).

Enzymatic cleavage of a NTAA may also be accomplished by an aminopeptidase. Aminopeptidases naturally occur as monomeric and multimeric enzymes, and may be metal or ATP-dependent. Natural aminopeptidases have very limited specificity, and generically cleave N-terminal amino acids in a processive manner, cleaving one amino acid off after another. For the methods described here, aminopeptidases may be engineered to possess specific binding or catalytic activity to the NTAA only when modified with an N-terminal label. For example, an aminopeptidase may be engineered such than it only cleaves an N-terminal amino acid if it is modified by a group such as DNP/SNP, PTC, dansyl chloride, acetyl, amidinyl, etc. In this way, the aminopeptidase cleaves only a single amino acid at a time from the N-terminus, and allows control of the degradation cycle. In some embodiments, the modified aminopeptidase is non-selective as to amino acid residue identity while being selective for the N-terminal label. In other embodiments, the modified aminopeptidase is selective for both amino acid residue identity and the N-terminal label. An example of a model of modifying the specificity of enzymatic NTAA degradation is illustrated by Borgo and Havranek, where through structure-function aided design, a methionine aminopeptidase was converted into a leucine aminopeptidase (Borgo and Havranek 2014). A similar approach can be taken with a modified NTAA, such as DNP/SNP-modified NTAAs, wherein an aminopeptidase is engineered (using both structural-function based-design and directed evolution) to cleave only an N-terminal amino acid having a DNP/SNP group present. Engineered aminopeptidase mutants that bind to and cleave individual or small groups of labelled (biotinylated) NTAAs have been described (see, PCT Publication No. WO2010/065322).

In certain embodiments, a compact monomeric metalloenzymatic aminopeptidase is engineered to recognize and cleave DNP-labeled NTAAs. The use of a monomeric metallo-aminopeptidase has two key advantages: 1) compact monomeric proteins are much easier to display and screen using phage display; 2) a metallo-aminopeptidase has the unique advantage in that its activity can be turned on/off at will by adding or removing the appropriate metal cation. Exemplary aminopeptidases include the M28 family of aminopeptidases, such as *Streptomyces* sp. KK506 (SKAP) (Yoo, Ahn et al. 2010), *Streptomyces griseus* (SGAP), *Vibrio proteolyticus* (VPAP), (Spungin and Blumberg 1989, Ben-Meir, Spungin et al. 1993). These enzymes are stable, robust, and active at room temperature and pH 8.0, and thus compatible with mild conditions preferred for peptide analysis.

In another embodiment, cyclic cleavage is attained by engineering the aminopeptidase to be active only in the presence of the N-terminal amino acid label. Moreover, the aminopeptidase may be engineered to be non-specific, such that it does not selectively recognize one particular amino acid over another, but rather just recognizes the labeled N-terminus. In a preferred embodiment, a metallopeptidase monomeric aminopeptidase (e.g. Vibro leucine aminopeptidase) (Hernandez-Moreno, Villasenor et al. 2014), is engineered to cleave only modified NTAAs (e.g., PTC, DNP, SNP, acetylated, acylated, etc.)

In yet another embodiment, cyclic cleavage is attained by using an engineered acylpeptide hydrolase (APH) to cleave an acetylated NTAA. APH is a serine peptidase that is capable of catalyzing the removal of Nα-acetylated amino acids from blocked peptides, and is a key regulator of N-terminally acetylated proteins in eukaryal, bacterial and archaeal cells. In certain embodiments, the APH is a dimeric and has only exopeptidase activity (Gogliettino, Balestrieri et al. 2012, Gogliettino, Riccio et al. 2014). The engineered APH may have higher affinity and less selectivity than endogenous or wild type APHs.

In yet another embodiment, amidination (guanidinylation) of the NTAA is employed to enable mild cleavage of the labeled NTAA using NaOH (Hamada, 2016, incorporated by reference in its entirety). A number of amidination (guanidinylation) reagents are known in the art including: S-methylisothiurea, 3,5-dimethylpyrazole-1-carboxamidine, S-ethylthiouronium bromide, S-ethylthiouronium chloride, O-methylisourea, O-methylisouronium sulfate, O-methylisourea hydrogen sulfate, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole, N,N'-bis(ortho-chloro-Cbz)-S-methylisothiourea and N,N'-bis(ortho-bromo-Cbz)-S-methylisothiourea (Katritzky, 2005, incorporated by reference in its entirety).

Figure 41:
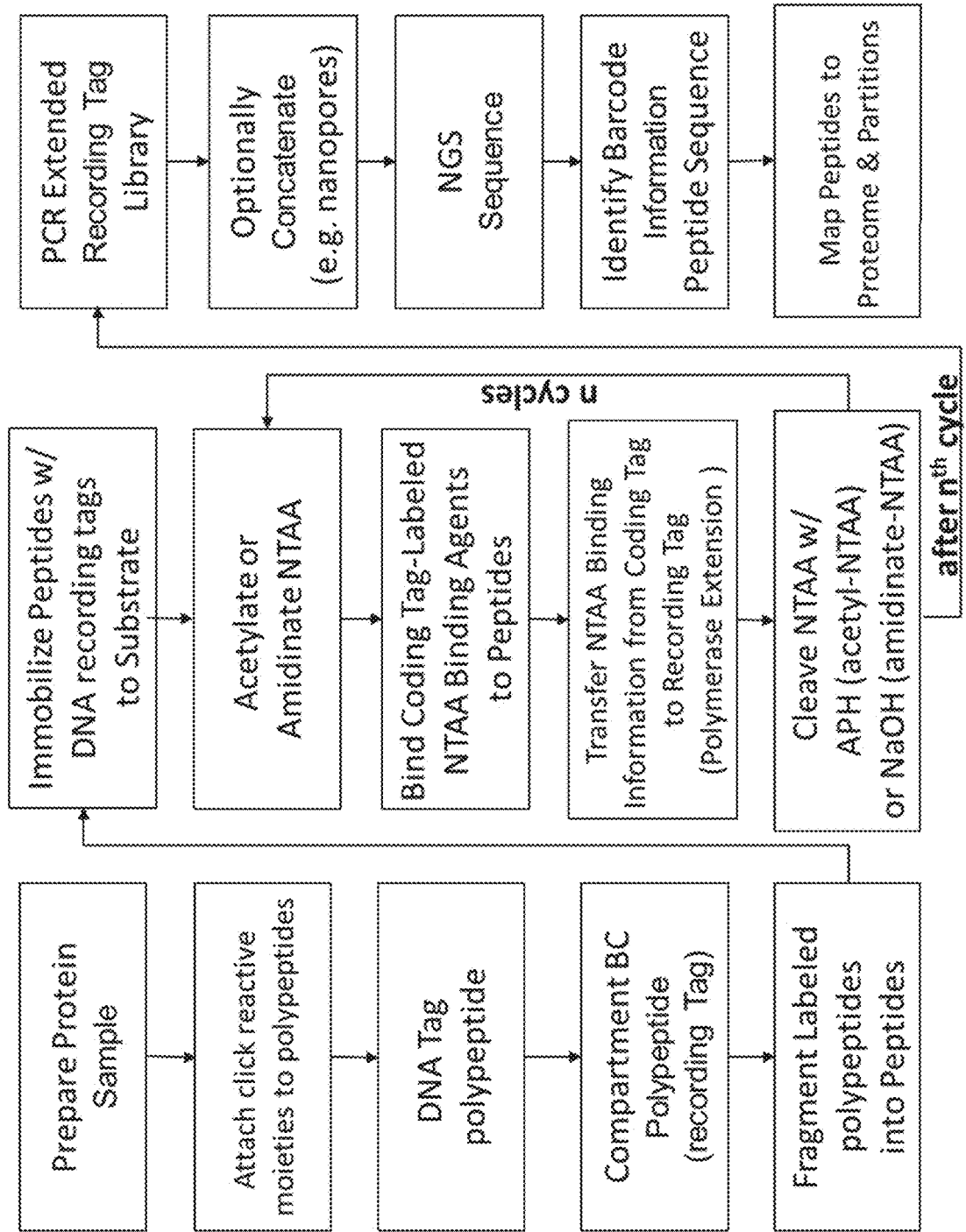
FIG. 41 illustrates an exemplary workflow for an embodiment of the NGPS assay.
Figure 42:
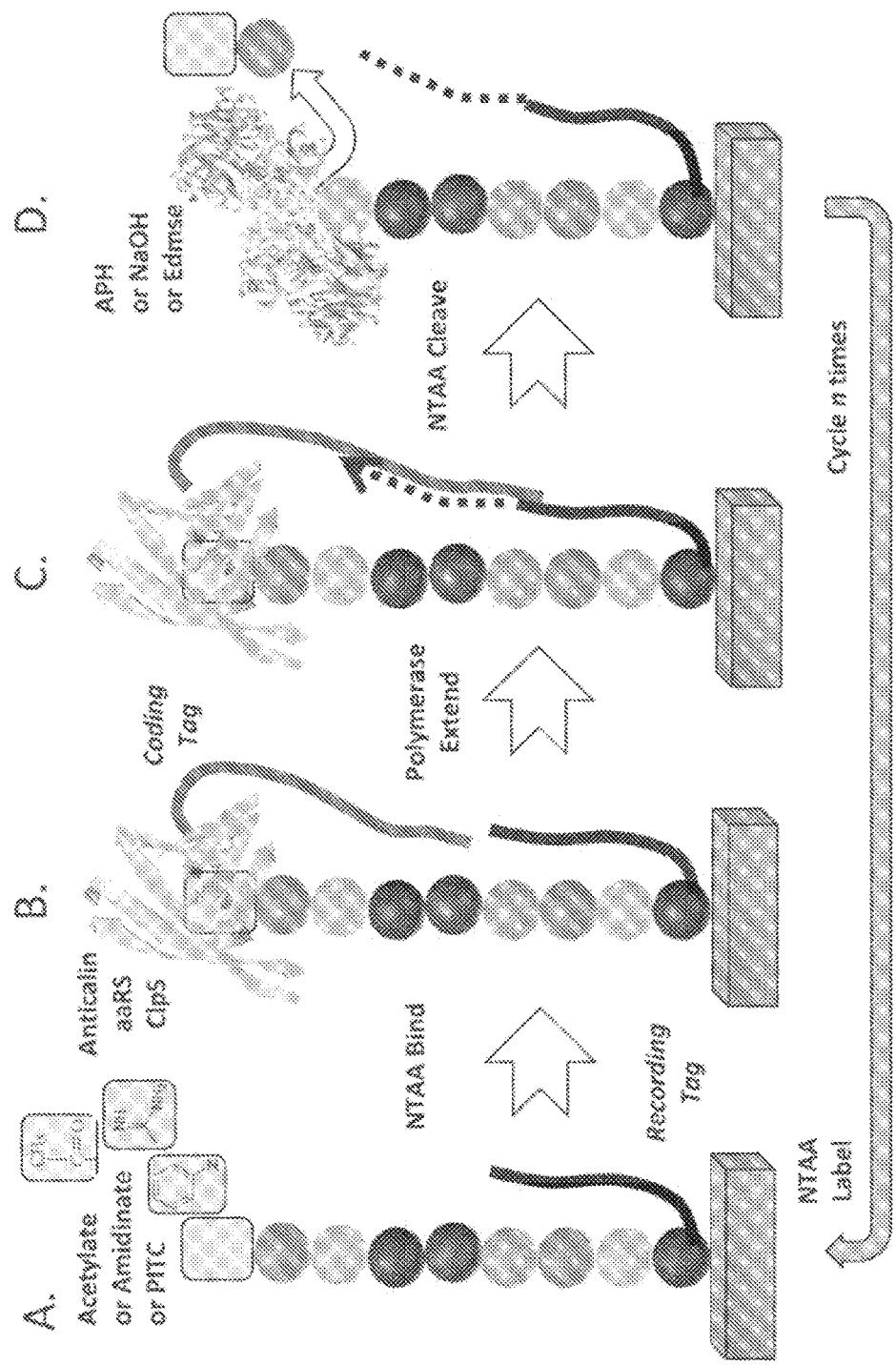
FIG. 42 illustrates exemplary steps of NGPS sequencing assay. An N-terminal amino acid (NTAA) acetylation or amidination step on a recording tag-labeled, surface bound peptide can occur before or after binding by an NTAA binding agent, depending on whether NTAA binding agents have been engineered to bind to acetylated NTAAs or native NTAAs. In the first case, step (A) the peptide is initially acetylated at the NTAA by chemical means using acetic anhydride or enzymatically with an N-terminal acetyltransferase (NAT). Step (B). The NTAA is recognized by an NTAA binding agent, such as an engineered anticalin, aminoacyl tRNA synthetase (aaRS), CipS, etc. A DNA coding tag is attached to the binding agent and comprises a barcode encoder sequence that identifies the particular NTAA binding agent. Step (C). After binding of the acetylated NTAA by the NTAA binding agent, the DNA coding tag transiently anneals to the recording tag via complementary sequences and the coding tag information is transferred to the recording tag via polymerase extension. In an alternative embodiment, the recording tag information is transferred to the coding tag via polymerase extension. Step (D). The acetylated NTAA is cleaved from the peptide by an engineered acylpeptide hydrolase (APH), which catalyzes the hydrolysis of terminal acetylated amino acid from acetylated peptides. After cleavage of the acetylated NTAA, the cycle repeats itself starting with acetylation of the newly exposed NTAA. N-terminal acetylation is used as an exemplary mode of NTAA modification/cleavage, but other N-terminal moieties, such as a guanyl moiety can be substituted with a concomitant change in cleavage chemistry. If guanidinylation is employed, the guanylated NTAA can be cleaved under mild conditions using 0.5-2% NaOH solution (see Hamada, 2016, incorporated by reference in its entirety). APH is a serine peptidase able to catalyse the removal of Nα-acetylated amino acids from blocked peptides and it belongs to the prolyl oligopeptidase (POP) family (clan SC, family S9). It is a crucial regulator of N-terminally acetylated proteins in eukaryal, bacterial and archaeal cells. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

An example of a NTAA labeling, binding, and degradation workflow is as follows (see, e.g., FIG. 41 and FIG. 42): a large collection of recording tag labeled peptides (e.g., 50 million-1 billion) from a proteolytic digest are immobilized randomly on a single molecule sequencing substrate (e.g., porous beads) at an appropriate intramolecular spacing. In a cyclic manner, the N-terminal amino acid (NTAA) of each peptide are modified with a small chemical moiety (e.g., DNP, SNP, acetyl) to provide cyclic control of the NTAA degradation process, and enhance binding affinity by a cognate binding agent. The modified N-terminal amino acid (e.g., DNP-NTAA, SNP-NTAA, acetyl-NTAA) of each immobilized peptide is bound by the cognate NTAA binding agent, and information from the coding tag associated with the bound NTAA binding agent is transferred to the recording tag associated with the immobilized peptide. After NTAA recognition, binding, and transfer of coding tag information to the recording tag, the labelled NTAA is removed by exposure to an engineered aminopeptidase (e.g., for DNP-NTAA or SNP-NTAA) or engineered APH (e.g., for acetyl-NTAA), that is capable of NTAA cleavage only in the presence of the label. Other NTAA labels (e.g., PITC) could also be employed with a suitably engineered aminopeptidase. In a particular embodiment, a single engineered aminopeptidase or APH universally cleaves all possible NTAAs (including post-translational modification variants) that possess the N-terminal amino acid label. In another particular embodiment, two, three, four, or more engineered aminopeptidases or APHs are used to cleave the repertoire of labeled NTAAs.

Aminopeptidases with activity to DNP or SNP labeled NTAAs may be selected using a screen combining tight-binding selection on the apo-enzyme (inactive in absence of metal cofactor) followed by a functional catalytic selection step, like the approach described by Ponsard et al. in engineering the metallo-beta-lactamase enzyme for benzylpenicillin (Ponsard, Galleni et al. 2001, Fernandez-Gacio, Uguen et al. 2003). This two-step selection is involves using a metallo-AP activated by addition of $Zn^{2+}$ ions. After tight binding selection to an immobilized peptide substrate, $Zn^{2+}$ is introduced, and catalytically active phage capable of hydrolyzing the NTAA labeled with DNP or SNP leads to release of the bound phage into the supernatant. Repeated selection rounds are performed to enrich for active APs for DNP or SNP labeled NTAA cleavage.

Figure 39:
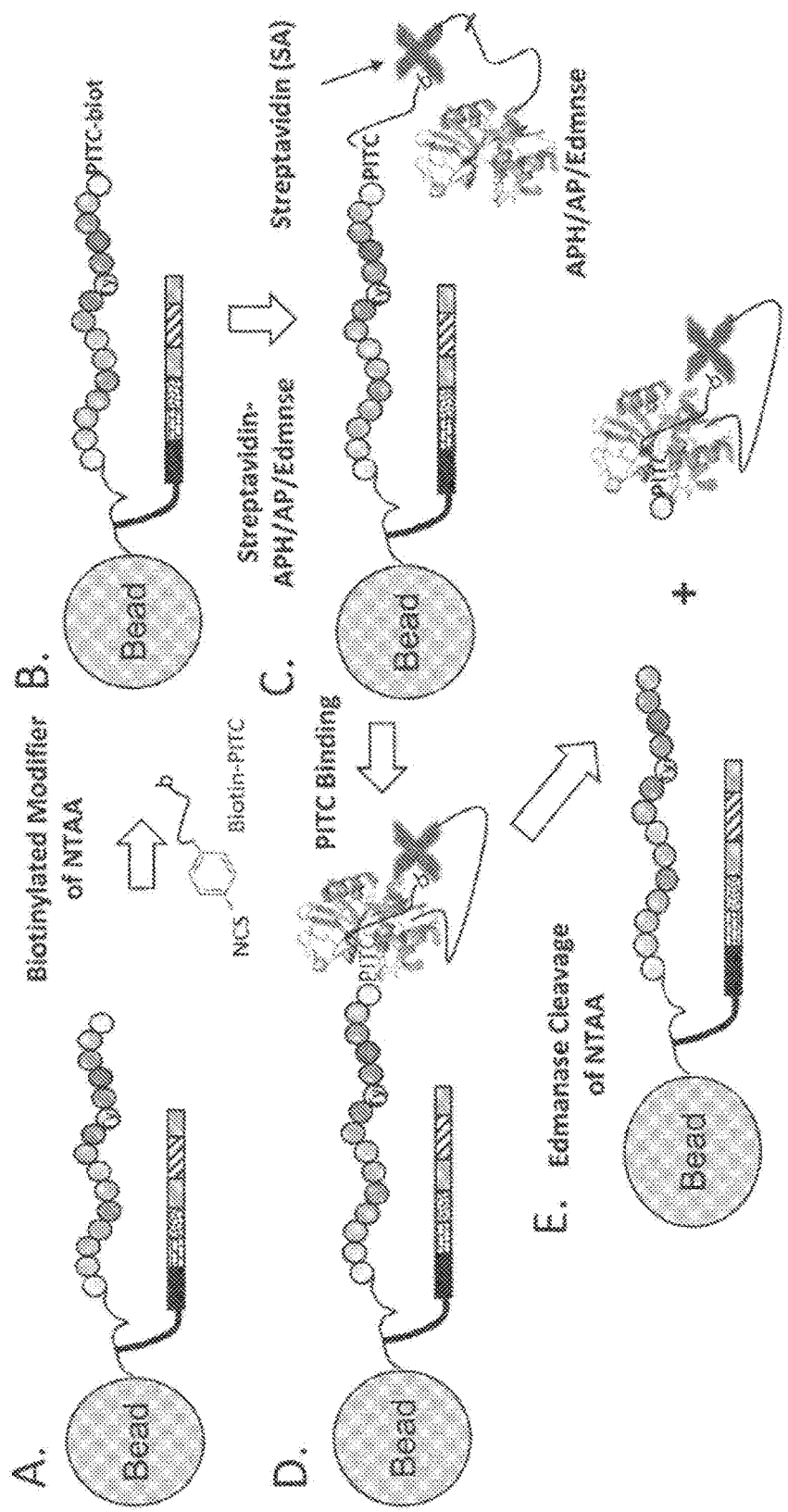
FIG. 39 illustrates examples for enhancement of amino acid cleavage reaction using a bifunctional N-terminal amino acid (NTAA) modifier and a chimeric cleavage reagent. Steps (A) and (B). A peptide attached to a solid-phase substrate is modified with a bifunctional NTAA modifier, such as biotin-phenyl isothiocyanate (PITC). Step (C). A low affinity Edmanase (>µM Kd) is recruited to biotin-PITC labeled NTAAs using a streptavidin-Edmanase chimeric protein. Step (D). The efficiency of Edmanase cleavage is greatly improved due to the increase in effective local concentration as a result of the biotin-strepavidin interaction. Step (E). The cleaved biotin-PITC labeled NTAA and associated streptavidin-Edmanase chimeric protein diffuse away after cleavage. A number of other bioconjugation recruitment strategies can also be employed. An azide modified PITC is commercially available (4-Azidophenyl isothiocyanate, Sigma), allowing a number of simple transformations of azide-PITC into other bioconjugates of PITC, such as biotin-PITC via a click chemistry reaction with alkyne-biotin. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.
Figure 40F:
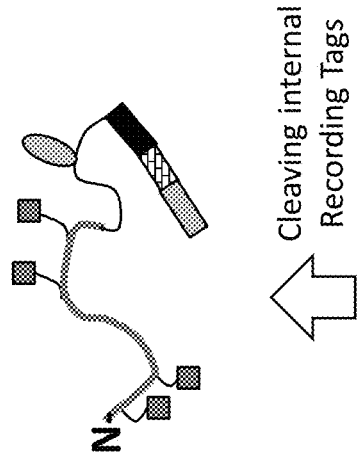
Figure 40G:
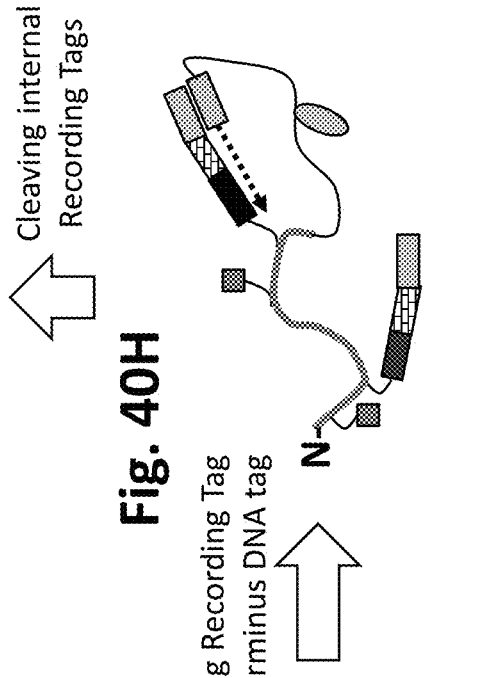
Figure 40H:
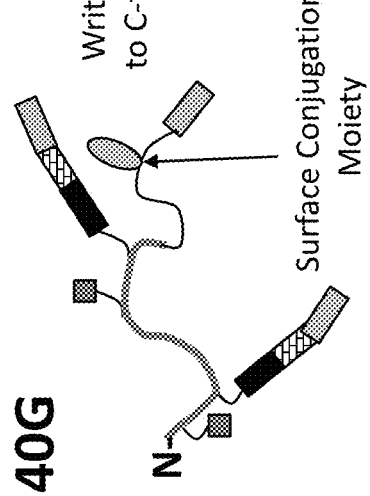
Figure 40I:
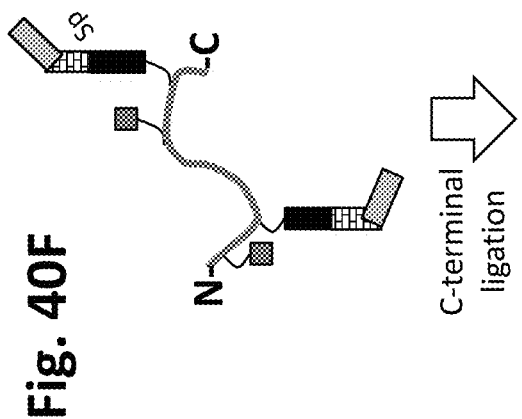

In any of the embodiments provided herein, recruitment of an NTAA cleavage reagent to the NTAA may be enhanced via a chimeric cleavage enzyme and chimeric NTAA modifier, wherein the chimeric cleavage enzyme and chimeric NTAA modifier each comprise a moiety capable of a tight binding reaction with each other (e.g., biotin-streptavidin) (see, e.g., FIG. 39). For example, an NTAA may be modified with biotin-PITC, and a chimeric cleavage enzyme (streptavidin-Edmanase) is recruited to the modified NTAA via the streptavidin-biotin interaction, improving the affinity and efficiency of the cleavage enzyme. The modified NTAA is cleaved and diffuses away from the peptide along with the associated cleavage enzyme. In the example of a chimeric Edmanase, this approach effectively increases the affinity KD from pM to sub-picomolar. A similar cleavage enhancement can also be realized via tethering using a DNA tag on the cleavage agent interacting with the recording tag (see, e.g., FIG. 44A-E).

Figure 45:
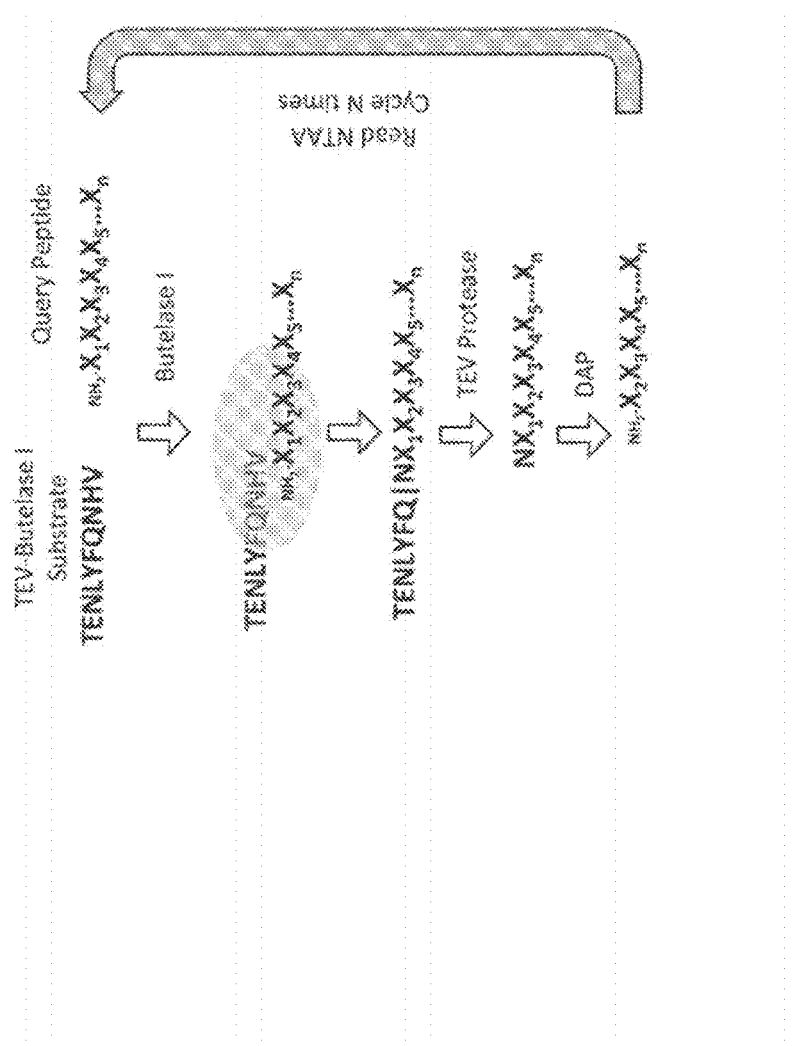
FIG. 45 illustrates an exemplary cyclic degradation peptide sequencing using peptide ligase+protease+diaminopeptidase. Butelase I ligates the TEV-Butelase I peptide substrate (TENLYFQNHV, SEQ ID NO: 132) to the NTAA of the query peptide. Butelase requires an NHV motif at the C-terminus of the peptide substrate. After ligation, Tobacco Etch Virus (TEV) protease is used to cleave the chimeric peptide substrate after the glutamine (Q) residue, leaving a chimeric peptide having an asparagine (N) residue attached to the N-terminus of the query peptide. Diaminopeptidase (DAP) or Dipeptidyl-peptidase, which cleaves two amino acid residues from the N-terminus, shortens the N-added query peptide by two amino acids effectively removing the asparagine residue (N) and the original NTAA on the query peptide. The newly exposed NTAA is read using binding agents as provided herein, and then the entire cycle is repeated "n" times for "n" amino acids sequenced. The use of a streptavidin-DAP metalloenzyme chimeric protein and tethering a biotin moiety to the N-terminal asparagine residue may allow control of DAP processivity. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

As an alternative to NTAA cleavage, a dipeptidyl aminopeptidase (DAP) can be used to cleave the last two N-terminal amino acids from the peptide. In certain embodiments, a single NTAA can be cleaved (see, e.g., FIG. 45). FIG. 45 depicts an approach to N-terminal degradation in which N-terminal ligation of a butelase I peptide substrate attaches a TEV endopeptidase substrate to the N-terminal of the peptide. After attachment, TEV endopeptidase cleaves the newly ligated peptide from the query peptide (peptide undergoing sequencing) leaving a single asparagine (N) attached to the NTAA. Incubation with DAP, which cleaves two amino acids from the N-terminus, results in a net removal of the original NTAA. This whole process can be cycled in the N-terminal degradation process.

For embodiments relating to CTAA binding agents, methods of cleaving CTAA from peptides are also known in the art. For example, U.S. Pat. No. 6,046,053 discloses a method of reacting the peptide or protein with an alkyl acid anhydride to convert the carboxy-terminal into oxazolone, liberating the C-terminal amino acid by reaction with acid and alcohol or with ester. Enzymatic cleavage of a CTAA may also be accomplished by a carboxypeptidase. Several carboxypeptidases exhibit amino acid preferences, e.g., carboxypeptidase B preferentially cleaves at basic amino acids, such as arginine and lysine. As described above, carboxypeptidases may also be modified in the same fashion as aminopeptidases to engineer carboxypeptidases that specifically bind to CTAAs having a C-terminal label. In this way, the carboxypeptidase cleaves only a single amino acid at a time from the C-terminus, and allows control of the degradation cycle. In some embodiments, the modified carboxypeptidase is non-selective as to amino acid residue identity while being selective for the C-terminal label. In other embodiments, the modified carboxypeptidase is selective for both amino acid residue identity and the C-terminal label.

J. Kit and Kit Components for Processing and Analysis of Extended Recording Tags, Extended Coding Tags, or Di-Tags Extended recording tag, extended coding tag, and di-tag libraries representing the macromolecule(s) of interest can be processed and analysed using a variety of nucleic acid sequencing methods. Examples of sequencing methods include, but are not limited to, chain termination sequencing (Sanger sequencing); next generation sequencing methods, such as sequencing by synthesis, sequencing by ligation, sequencing by hybridization, polony sequencing, ion semiconductor sequencing, and pyrosequencing; and third generation sequencing methods, such as single molecule real time sequencing, nanopore-based sequencing, duplex interrupted sequencing, and direct imaging of DNA using advanced microscopy.

A library of extended recording tags, extended coding tags, or di-tags may be amplified in a variety of ways. A library of extended recording tags, extended coding tags, or di-tags may undergo exponential amplification, e.g., via PCR or emulsion PCR. Emulsion PCR is known to produce more uniform amplification (Hori, Fukano et al. 2007). In some embodiments, for sequences that have repetitive barcodes or spacer sequences, the risk of PCR template switching is high and emulsion PCR or linear amplification can be used to reduce that risk. For example, emulsion PCR as disclosed in U.S. Pat. No. 9,593,375 B2, which is incorporated herein by reference for all purposes, may be used.

Alternatively, a library of extended recording tags, extended coding tags, or di-tags may undergo linear amplification, e.g., via in vitro transcription of template DNA using T7 RNA polymerase and a reverse transcription (RT) polymerase to copy back to cDNA. In one aspect, the linear amplification also reduces or eliminates template switching. The library of extended recording tags, extended coding tags, or di-tags can be amplified using primers compatible with the universal forward priming site and universal reverse priming site contained therein. A library of extended recording tags, extended coding tags, or di-tags can also be amplified using tailed primers to add sequence to either the 5'-end, 3'-end or both ends of the extended recording tags, extended coding tags, or di-tags. Sequences that can be added to the termini of the extended recording tags, extended coding tags, or di-tags include library specific index sequences to allow multiplexing of multiple libraries in a single sequencing run, adaptor sequences, read primer sequences, or any other sequences for making the library of extended recording tags, extended coding tags, or di-tags compatible for a sequencing platform. An example of a library amplification in preparation for next generation sequencing is as follows: a 20 µl PCR reaction volume is set up using an extended recording tag library eluted from ~1 mg of beads (~10 ng), 200 µM dNTP, 1 pM of each forward and reverse amplification primers, 0.5 µl (1 U) of Phusion Hot Start enzyme (New England Biolabs) and subjected to the following cycling conditions: 98° C. for 30 sec followed by 20 cycles of 98° C. for 10 sec, 60° C. for 30 sec, 72° C. for 30 sec, followed by 72° C. for 7 min, then hold at 4° C.

In certain embodiments, either before, during or following amplification, the library of extended recording tags, extended coding tags, or di-tags can undergo target enrichment. Target enrichment can be used to selectively capture or amplify extended recording tags representing macromolecules of interest from a library of extended recording tags, extended coding tags, or di-tags before sequencing. Target enrichment for protein sequence is challenging because of the high cost and difficulty in producing highly-specific binding agents for target proteins. Antibodies are notoriously non-specific and difficult to scale production across thousands of proteins. The methods of the present disclosure circumvent this problem by converting the protein code into a nucleic acid code which can then make use of a wide range of targeted DNA enrichment strategies available for DNA libraries. Peptides of interest can be enriched in a sample by enriching their corresponding extended recording tags. Methods of targeted enrichment are known in the art, and include hybrid capture assays, PCR-based assays such as TruSeq custom Amplicon (Illumina), padlock probes (also referred to as molecular inversion probes), and the like (see, Mamanova et al., 2010, Nature Methods 7: 111-118; Bodi et al., J. Biomol. Tech. 2013, 24:73-86; Ballester et al., 2016, Expert Review of Molecular Diagnostics 357-372; Mertes et al., 2011, Brief Funct. Genomics 10:374-386; Nilsson et al., 1994, Science 265:2085-8; each of which are incorporated herein by reference in their entirety).

Figure 17A:
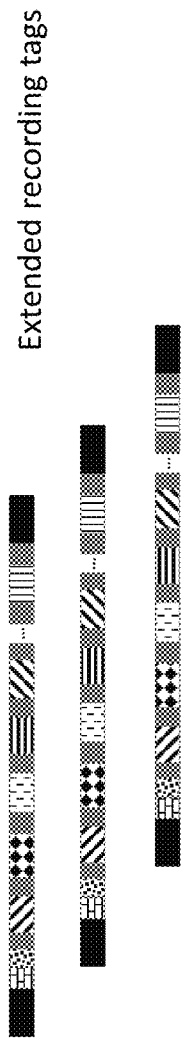
FIG. 17A-17B illustrate.
Figure 17B:
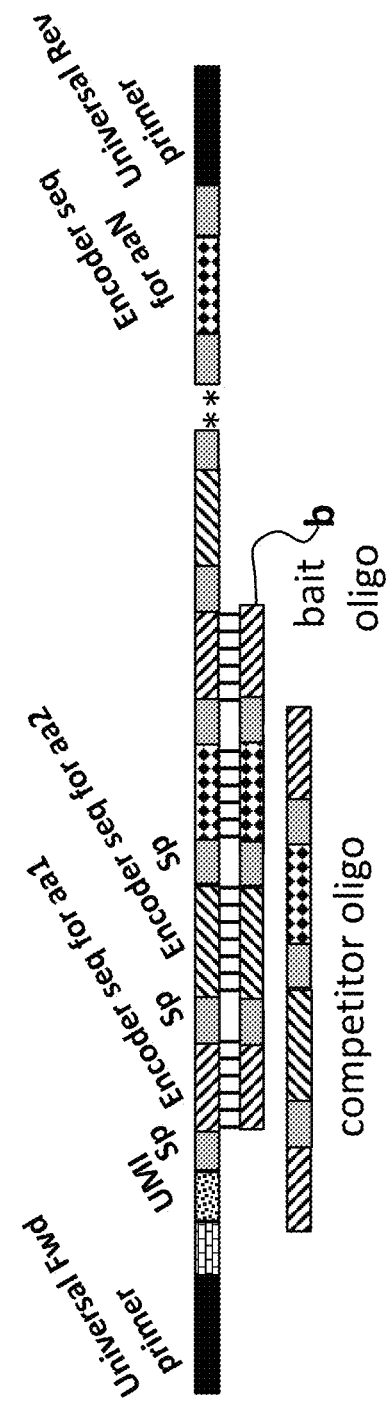

In one embodiment, a library of extended recording tags, extended coding tags, or di-tags is enriched via a hybrid capture-based assay (see, e.g., FIG. 17A and FIG. 17B). In a hybrid-capture based assay, the library of extended recording tags, extended coding tags, or di-tags is hybridized to target-specific oligonucleotides or "bait oligonucleotide" that are labelled with an affinity tag (e.g., biotin). Extended recording tags, extended coding tags, or di-tags hybridized to the target-specific oligonucleotides are "pulled down" via their affinity tags using an affinity ligand (e.g., streptavidin coated beads), and background (non-specific) extended recording tags are washed away (see, e.g., FIG. 17A-B). The enriched extended recording tags, extended coding tags, or di-tags are then obtained for positive enrichment (e.g., eluted from the beads).

For bait oligonucleotides synthesized by array-based "in situ" oligonucleotide synthesis and subsequent amplification of oligonucleotide pools, competing baits can be engineered into the pool by employing several sets of universal primers within a given oligonucleotide array. For each type of universal primer, the ratio of biotinylated primer to non-biotinylated primer controls the enrichment ratio. The use of several primer types enables several enrichment ratios to be designed into the final oligonucleotide bait pool.

A bait oligonucleotide can be designed to be complementary to an extended recording tag, extended coding tag, or di-tag representing a macromolecule of interest. The degree of complementarity of a bait oligonucleotide to the spacer sequence in the extended recording tag, extended coding tag, or di-tag can be from 0% to 100%, and any integer in between. This parameter can be easily optimized by a few enrichment experiments. In some embodiments, the length of the spacer relative to the encoder sequence is minimized in the coding tag design or the spacers are designed such that they unavailable for hybridization to the bait sequences. One approach is to use spacers that form a secondary structure in the presence of a cofactor. An example of such a secondary structure is a G-quadruplex, which is a structure formed by two or more guanine quartets stacked on top of each other (Bochman, Paeschke et al. 2012). A guanine quartet is a square planar structure formed by four guanine bases that associate through Hoogsteen hydrogen bonding. The G-quadruplex structure is stabilized in the presence of a cation, e.g., $K^+$ ions vs. $Li^+$ ions.

To minimize the number of bait oligonucleotides employed, a set of relatively unique peptides from each protein can be bioinformatically identified, and only those bait oligonucleotides complementary to the corresponding extended recording tag library representations of the peptides of interest are used in the hybrid capture assay. Sequential rounds or enrichment can also be carried out, with the same or different bait sets.

To enrich the entire length of a macromolecule (e.g., protein or polypeptide) in a library of extended recording tags, extended coding tags, or di-tags representing fragments thereof (e.g., peptides), "tiled" bait oligonucleotides can be designed across the entire nucleic acid representation of the protein.

In another embodiment, primer extension and ligation-based mediated amplification enrichment (AmpliSeq, PCR, TruSeq TSCA, etc.) can be used to select and module fraction enriched of library elements representing a subset of macromolecules. Competing oligos can also be employed to tune the degree of primer extension, ligation, or amplification. In the simplest implementation, this can be accomplished by having a mix of target specific primers comprising a universal primer tail and competing primers lacking a 5' universal primer tail. After an initial primer extension, only primers with the 5' universal primer sequence can be amplified. The ratio of primer with and without the universal primer sequence controls the fraction of target amplified. In other embodiments, the inclusion of hybridizing but non-extending primers can be used to modulate the fraction of library elements undergoing primer extension, ligation, or amplification.

Targeted enrichment methods can also be used in a negative selection mode to selectively remove extended recording tags, extended coding tags, or di-tags from a library before sequencing. Thus, in the example described above using biotinylated bait oligonucleotides and streptavidin coated beads, the supernatant is retained for sequencing while the bait-oligonucleotide:extended recording tag, extended coding tag, or di-tag hybrids bound to the beads are not analysed. Examples of undesirable extended recording tags, extended coding tags, or di-tags that can be removed are those representing over abundant macromolecule species, e.g., for proteins, albumin, immunoglobulins, etc.

A competitor oligonucleotide bait, hybridizing to the target but lacking a biotin moiety, can also be used in the hybrid capture step to modulate the fraction of any particular locus enriched. The competitor oligonucleotide bait competes for hybridization to the target with the standard biotinylated bait effectively modulating the fraction of target pulled down during enrichment (see, e.g., FIG. 17A-B). The ten orders dynamic range of protein expression can be compressed by several orders using this competitive suppression approach, especially for the overly abundant species such as albumin. Thus, the fraction of library elements captured for a given locus relative to standard hybrid capture can be modulated from 100% down to 0% enrichment.

Additionally, library normalization techniques can be used to remove overly abundant species from the extended recording tag, extended coding tag, or di-tag library. This approach works best for defined length libraries originating from peptides generated by site-specific protease digestion such as trypsin, LysC, GluC, etc. In one example, normalization can be accomplished by denaturing a double-stranded library and allowing the library elements to re-anneal. The abundant library elements re-anneal more quickly than less abundant elements due to the second-order rate constant of bimolecular hybridization kinetics (Bochman, Paeschke et al. 2012). The ssDNA library elements can be separated from the abundant dsDNA library elements using methods known in the art, such as chromatography on hydroxyapatite columns (VanderNoot, et al., 2012, Biotechniques 53:373-380) or treatment of the library with a duplex-specific nuclease (DSN) from Kamchatka crab (Shagin et al., 2002, Genome Res. 12:1935-42) which destroys the dsDNA library elements.

Any combination of fractionation, enrichment, and subtraction methods, of the macromolecules before attachment to the solid support and/or of the resulting extended recording tag library can economize sequencing reads and improve measurement of low abundance species.

In some embodiments, a library of extended recording tags, extended coding tags, or di-tags is concatenated by ligation or end-complementary PCR to create a long DNA molecule comprising multiple different extended recorder tags, extended coding tags, or di-tags, respectively (Du et al., 2003, BioTechniques 35:66-72; Muecke et al., 2008, Structure 16:837-841; U.S. Pat. No. 5,834,252, each of which is incorporated by reference in its entirety). This embodiment is for example for nanopore sequencing in which long strands of DNA are analyzed by the nanopore sequencing device.

In some embodiments, direct single molecule analysis is performed on an extended recording tag, extended coding tag, or di-tag (see, e.g., Harris et al., 2008, Science 320: 106-109). The extended recording tags, extended coding tags, or di-tags can be analysed directly on the solid support, such as a flow cell or beads that are compatible for loading onto a flow cell surface (optionally microcell patterned), wherein the flow cell or beads can integrate with a single molecule sequencer or a single molecule decoding instrument. For single molecule decoding, hybridization of several rounds of pooled fluorescently-labelled of decoding oligonucleotides (Gunderson et al., 2004, Genome Res. 14:970-7) can be used to ascertain both the identity and order of the coding tags within the extended recording tag. To deconvolute the binding order of the coding tags, the binding agents may be labelled with cycle-specific coding tags as described above (see also, Gunderson et al., 2004, Genome Res. 14:970-7). Cycle-specific coding tags will work for both a single, concatenated extended recording tag representing a single macromolecule, or for a collection of extended recording tags representing a single macromolecule.

Following sequencing of the extended reporter tag, extended coding tag, or di-tag libraries, the resulting sequences can be collapsed by their UMIs and then associated to their corresponding macromolecules (e.g., peptides, proteins, protein complex) and aligned to the totality of the macromolecule type in the cell (e.g., proteome for peptide, polypeptide, protein macromolecules). Resulting sequences can also be collapsed by their compartment tags and associated to their corresponding compartmental proteome, which in a particular embodiment contains only a single or a very limited number of protein molecules. Both protein identification and quantification can easily be derived from this digital peptide information.

In some embodiments, the coding tag sequence can be optimized for the particular sequencing analysis platform. In a particular embodiment, the sequencing platform is nanopore sequencing. In some embodiments, the sequencing platform has a per base error rate of >5%, >10%, >15%, >20%, >25%, or >30%. For example, if the extended recording tag is to be analyzed using a nanopore sequencing instrument, the barcode sequences (e.g., encoder sequences) can be designed to be optimally electrically distinguishable in transit through a nanopore. Peptide sequencing according to the methods described herein may be well-suited for nanopore sequencing, given that the single base accuracy for nanopore sequencing is still rather low (75%-85%), but determination of the "encoder sequence" should be much more accurate (>99%). Moreover, a technique called duplex interrupted nanopore sequencing (DI) can be employed with nanopore strand sequencing without the need for a molecular motor, greatly simplifying the system design (Derrington, Butler et al. 2010). Readout of the extended recording tag via DI nanopore sequencing requires that the spacer elements in the concatenated extended recording tag library be annealed with complementary oligonucleotides. The oligonucleotides used herein may comprise LNAs, or other modified nucleic acids or analogs to increase the effective Tm of the resultant duplexes. As the single-stranded extended recording tag decorated with these duplex spacer regions is passed through the pore, the double strand region will become transiently stalled at the constriction zone enabling a current readout of about three bases adjacent to the duplex region. In a particular embodiment for DI nanopore sequencing, the encoder sequence is designed in such a way that the three bases adjacent to the spacer element create maximally electrically distinguishable nanopore signals (Derrington et al., 2010, Proc. Natl. Acad. Sci. USA 107:16060-5). As an alternative to motor-free DI sequencing, the spacer element can be designed to adopt a secondary structure such as a G-quartet, which will transiently stall the extended recording tag, extended coding tag, or di-tag as it passes through the nanopore enabling readout of the adjacent encoder sequence (Shim, Tan et al. 2009, Zhang, Zhang et al. 2016). After proceeding past the stall, the next spacer will again create a transient stall, enabling readout of the next encoder sequence, and so forth.

The methods disclosed herein can be used for analysis, including detection, quantitation and/or sequencing, of a plurality of macromolecules (e.g., peptides) simultaneously (multiplexing). Multiplexing as used herein refers to analysis of a plurality of macromolecules in the same assay. The plurality of macromolecules can be derived from the same sample or different samples. The plurality of macromolecules can be derived from the same subject or different subjects. The plurality of macromolecules that are analyzed can be different macromolecules (e.g., peptides), or the same macromolecule (e.g., peptide) derived from different samples. A plurality of macromolecules includes 2 or more macromolecules, 5 or more macromolecules, 10 or more macromolecules, 50 or more macromolecules, 100 or more macromolecules, 500 or more macromolecules, 1000 or more macromolecules, 5,000 or more macromolecules, 10,000 or more macromolecules, 50,000 or more macromolecules, 100,000 or more macromolecules, 500,000 or more macromolecules, or 1,000,000 or more macromolecules.

Sample multiplexing can be achieved by upfront barcoding of recording tag labeled macromolecule samples. Each barcode represents a different sample, and samples can be pooled prior to cyclic binding assays or sequence analysis. In this way, many barcode-labeled samples can be simultaneously processed in a single tube. This approach is a significant improvement on immunoassays conducted on reverse phase protein arrays (RPPA) (Akbani, Becker et al. 2014, Creighton and Huang 2015, Nishizuka and Mills 2016). In this way, the present disclosure essentially provides a highly digital sample and analyte multiplexed alternative to the RPPA assay with a simple workflow.

K. Kit and Kit Components for Macromolecule Characterization Via Cyclic Rounds of NTAA Recognition, Recording Tag Extension, and NTAA Cleavage In certain embodiments, the methods using the present kits for analyzing a macromolecule provided in the present disclosure comprise multiple binding cycles, where the macromolecule is contacted with a plurality of binding agents, and successive binding of binding agents transfers historical binding information in the form of a nucleic acid based coding tag to at least one recording tag associated with the macromolecule. In this way, a historical record containing information about multiple binding events is generated in a nucleic acid format.

In embodiments relating to methods of analyzing peptide macromolecules using an N-terminal degradation based approach (see, e.g., FIG. 3, FIG. 4, FIG. 41, and FIG. 42), following contacting and binding of a first binding agent to an $n^{th}$ NTAA of a peptide of n amino acids and transfer of the first binding agent's coding tag information to a recording tag associated with the peptide, thereby generating a first order extended recording tag, the $n^{th}$ NTAA is cleaved as described herein. Cleavage of the $n^{th}$ NTAA converts the (n−1)$^{th}$ amino acid of the peptide to an N-terminal amino acid, which is referred to herein as an (n−1)$^{th}$ NTAA. As described herein, the n$^{th}$ NTAA may optionally be labeled with a moiety (e.g., PTC, DNP, SNP, acetyl, amidinyl, etc.), which is particularly useful in conjunction with cleavage enzymes that are engineered to bind to a labeled form of NTAA. If the n$^{th}$ NTAA was labeled, the (n−1)$^{th}$ NTAA is then labeled with the same moiety. A second binding agent is contacted with the peptide and binds to the (n−1)$^{th}$ NTAA, and the second binding agent's coding tag information is transferred to the first order extended recording tag thereby generating a second order extended recording tag (e.g., for generating a concatenated n$^{th}$ order extended recording tag representing the peptide), or to a different recording tag (e.g., for generating multiple extended recording tags, which collectively represent the peptide). Cleavage of the (n−1)$^{th}$ NTAA converts the (n−2)$^{th}$ amino acid of the peptide to an N-terminal amino acid, which is referred to herein as (n−2)$^{th}$ NTAA. Additional binding, transfer, cleavage, and optionally NTAA labeling, can occur as described above up to n amino acids to generate an n$^{th}$ order extended recording tag or n separate extended recording tags, which collectively represent the peptide. As used herein, an n$^{th}$ "order" when used in reference to a binding agent, coding tag, or extended recording tag, refers to the n$^{th}$ binding cycle, wherein the n$^{th}$ binding agent and its associated coding tag is used or the n binding cycle where the extended recording tag is created.

In some embodiments, contacting of the first binding agent and second binding agent to the macromolecule, and optionally any further binding agents (e.g., third binding agent, fourth binding agent, fifth binding agent, and so on), are performed at the same time. For example, the first binding agent and second binding agent, and optionally any further order binding agents, can be pooled together, for example to form a library of binding agents. In another example, the first binding agent and second binding agent, and optionally any further order binding agents, rather than being pooled together, are added simultaneously to the macromolecule. In one embodiment, a library of binding agents comprises at least 20 binding agents that selectively bind to the 20 standard, naturally occurring amino acids.

In other embodiments, the first binding agent and second binding agent, and optionally any further order binding agents, are each contacted with the macromolecule in separate binding cycles, added in sequential order. In certain embodiments, the use of multiple binding agents at the same time is preferred, because the parallel approach saves time and because the binding agents are in competition, which reduces non-specific binding by non-cognate binding agents to a site that is bound by a cognate binding agent.

The length of the final extended recording tags generated by the methods described herein is dependent upon multiple factors, including the length of the coding tag (e.g., encoder sequence and spacer), the length of the recording tag (e.g., unique molecular identifier, spacer, universal priming site, bar code), the number of binding cycles performed, and whether coding tags from each binding cycle are transferred to the same extended recording tag or to multiple extended recording tags. In an example for a concatenated extended recording tag representing a peptide and produced by an Edman degradation like cleavage method, if the coding tag has an encoder sequence of 5 bases that is flanked on each side by a spacer of 5 bases, the coding tag information on the final extended recording tag, which represents the peptide's binding agent history, is 10 bases×number of Edman Degradation cycles. For a 20-cycle run, the extended recording is at least 200 bases (not including the initial recording tag sequence). This length is compatible with standard next generation sequencing instruments.

After the final binding cycle and transfer of the final binding agent's coding tag information to the extended recording tag, the recorder tag can be capped by addition of a universal reverse priming site via ligation, primer extension or other methods known in the art. In some embodiments, the universal forward priming site in the recording tag is compatible with the universal reverse priming site that is appended to the final extended recording tag. In some embodiments, a universal reverse priming site is an Illumina P7 primer (5'-CAAGCAGAAGACGGCATACGAGAT-3'—SEQ ID NO: 134) or an Illumina P5 primer (5'-AATGATACGGCGACCACCGA-3'—SEQ ID NO: 133). The sense or antisense P7 may be appended, depending on strand sense of the recording tag. An extended recording tag library can be cleaved or amplified directly from the solid support (e.g., beads) and used in traditional next generation sequencing assays and protocols.

In some embodiments, a primer extension reaction is performed on a library of single stranded extended recording tags to copy complementary strands thereof.

The NGPS peptide sequencing assay comprises several chemical and enzymatic steps in a cyclical progression. The fact that NGPS sequencing is single molecule confers several key advantages to the process. The first key advantage of single molecule assay is the robustness to inefficiencies in the various cyclical chemical/enzymatic steps. This is enabled through the use of cycle-specific barcodes present in the coding tag sequence.

Using cycle-specific coding tags, we track information from each cycle. Since this is a single molecule sequencing approach, even 70% efficiency at each binding/transfer cycle in the sequencing process is more than sufficient to generate mappable sequence information. As an example, a ten-base peptide sequence "CPVQLWVDST" (SEQ ID NO: 169) might be read as "CPXQXWXDXT" (SEQ ID NO: 170) on our sequence platform (where X=any amino acid; the presence an amino acid is inferred by cycle number tracking). This partial amino acid sequence read is more than sufficient to uniquely map it back to the human p53 protein using BLASTP. As such, none of our processes have to be perfect to be robust. Moreover, when cycle-specific barcodes are combined with our partitioning concepts, absolute identification of the protein can be accomplished with only a few amino acids identified out of 10 positions since we know what set of peptides map to the original protein molecule (via compartment barcodes).

Protein normalization via fractionation, compartmentalization, and limited binding capacity resins.

One of the key challenges with proteomics analysis is addressing the large dynamic range in protein abundance within a sample. Proteins span greater than 10 orders of dynamic range within plasma (even "Top 20" depleted plasma). In certain embodiments, subtraction of certain protein species (e.g., highly abundant proteins) from the sample is performed prior to analysis. This can be accomplished, for example, using commercially available protein depletion reagents such as Sigma's PROT20 immuno-depletion kit, which deplete the top 20 plasma proteins. Additionally, it would be useful to have an approach that greatly reduced the dynamic range even further to a manageable 3-4 orders. In certain embodiments, a protein sample dynamic range can be modulated by fractionating the protein sample using standard fractionation methods, including electrophoresis and liquid chromatography (Zhou, Ning et al. 2012), or partitioning the fractions into compartments (e.g., droplets)

loaded with limited capacity protein binding beads/resin (e.g., hydroxylated silica particles) (McCormick 1989) and eluting bound protein. Excess protein in each compartmentalized fraction is washed away.

Examples of electrophoretic methods include capillary electrophoresis (CE), capillary isoelectric focusing (CIEF), capillary isotachophoresis (CITP), free flow electrophoresis, gel-eluted liquid fraction entrapment electrophoresis (GEL-FrEE). Examples of liquid chromatography protein separation methods include reverse phase (RP), ion exchange (IE), size exclusion (SE), hydrophilic interaction, etc. Examples of compartment partitions include emulsions, droplets, microwells, physically separated regions on a flat substrate, etc. Exemplary protein binding beads/resins include silica nanoparticles derivitized with phenol groups or hydroxyl groups (e.g., StrataClean Resin from Agilent Technologies, RapidClean from LabTech, etc.). By limiting the binding capacity of the beads/resin, highly-abundant proteins eluting in a given fraction will only be partially bound to the beads, and excess proteins removed.

L. Kit and Kit Components for Partitioning of Proteome of a Single Cell or Molecular Subsampling In another aspect, the present disclosure provides kits and methods for massively-parallel analysis of proteins in a sample using barcoding and partitioning techniques. Current approaches to protein analysis involve fragmentation of protein macromolecules into shorter peptide molecules suitable for peptide sequencing. Information obtained using such approaches is therefore limited by the fragmentation step and excludes, e.g., long range continuity information of a protein, including post-translational modifications, protein-protein interactions occurring in each sample, the composition of a protein population present in a sample, or the origin of the protein macromolecule, such as from a particular cell or population of cells. Long range information of post-translation modifications within a protein molecule (e.g., proteoform characterization) provides a more complete picture of biology, and long range information on what peptides belong to what protein molecule provides a more robust mapping of peptide sequence to underlying protein sequence (see, e.g., part (A) of FIG. 15). This is especially relevant when the peptide sequencing technology only provides incomplete amino acid sequence information, such as information from only 5 amino acid types. By using the partitioning methods disclosed herein, combined with information from a number of peptides originating from the same protein molecule, the identity of the protein molecule (e.g., proteoform) can be more accurately assessed. Association of compartment tags with proteins and peptides derived from same compartment(s) facilitates reconstruction of molecular and cellular information. In typical proteome analysis, cells are lysed and proteins digested into short peptides, disrupting global information on which proteins derive from which cell or cell type, and which peptides derive from which protein or protein complex. This global information is important to understanding the biology and biochemistry within cells and tissues.

Partitioning refers to the random assignment of a unique barcode to a subpopulation of macromolecules from a population of macromolecules within a sample. Partitioning may be achieved by distributing macromolecules into compartments. A partition may be comprised of the macromolecules within a single compartment or the macromolecules within multiple compartments from a population of compartments.

A subset of macromolecules or a subset of a protein sample that has been separated into or on the same physical compartment or group of compartments from a plurality (e.g., millions to billions) of compartments are identified by a unique compartment tag. Thus, a compartment tag can be used to distinguish constituents derived from one or more compartments having the same compartment tag from those in another compartment (or group of compartments) having a different compartment tag, even after the constituents are pooled together.

Figure 18:
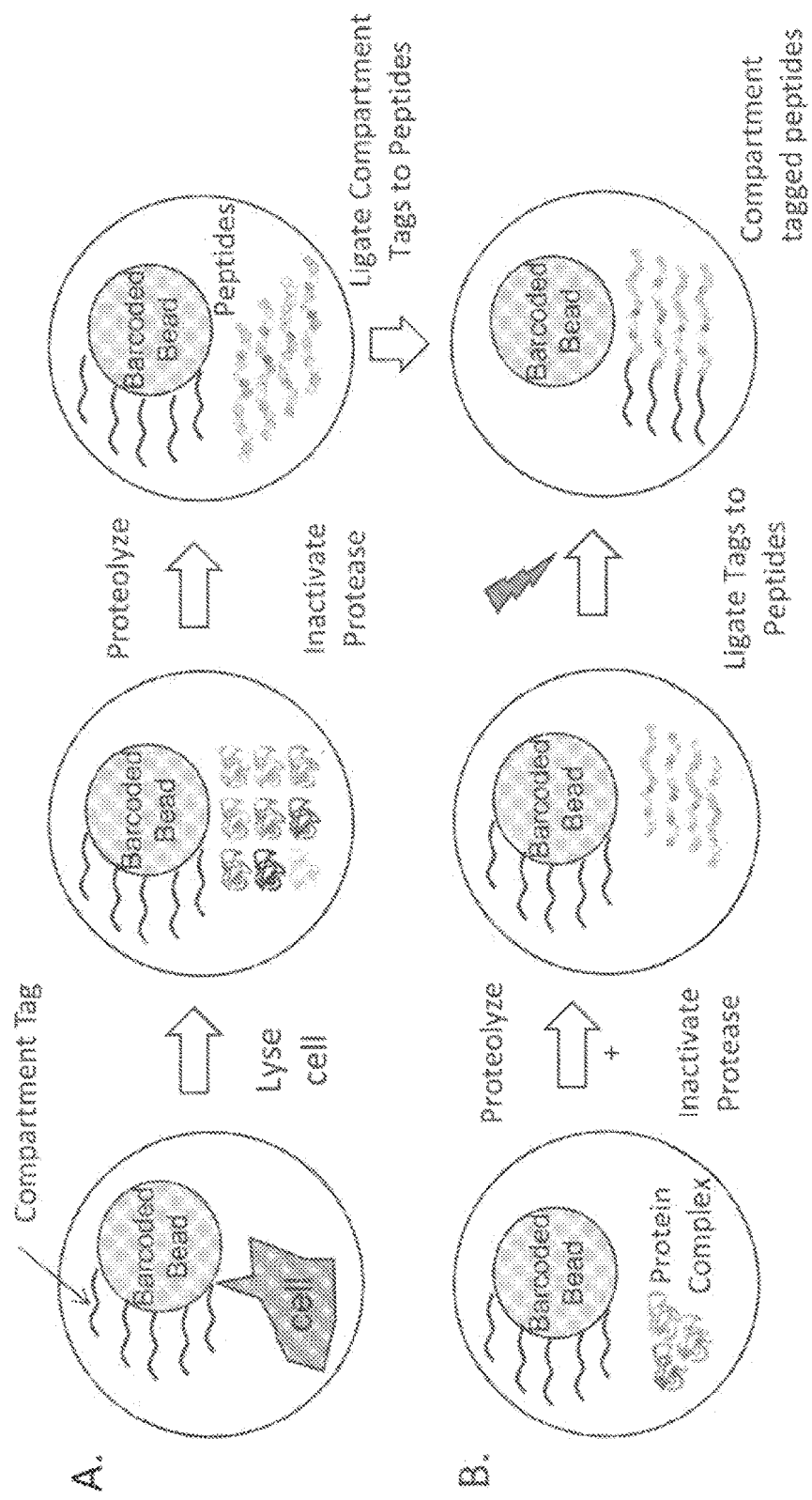
FIG. 18 illustrates exemplary methods of single cell and bulk proteome partitioning into individual droplets, each droplet comprising a bead having a plurality of compartment tags attached thereto to correlate peptides to their originating protein complex, or to proteins originating from a single cell. The compartment tags comprise barcodes. Manipulation of droplet constituents after droplet formation: (Step (A)) Single cell partitioning into an individual droplet followed by cell lysis to release the cell proteome, and proteolysis to digest the cell proteome into peptides, and inactivation of the protease following sufficient proteolysis; (Step (B)) Bulk proteome partitioning into a plurality of droplets wherein an individual droplet comprises a protein complex followed by proteolysis to digest the protein complex into peptides, and inactivation of the protease following sufficient proteolysis. A heat labile metallo-protease can be used to digest the encapsulated proteins into peptides after photo-release of photo-caged divalent cations to activate the protease. The protease can be heat inactivated following sufficient proteolysis, or the divalent cations may be chelated. Droplets contain hybridized or releasable compartment tags comprising nucleic acid barcodes (separate from recording tag) capable of being ligated to either an N- or C-terminal amino acid of a peptide. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.
Figure 19:
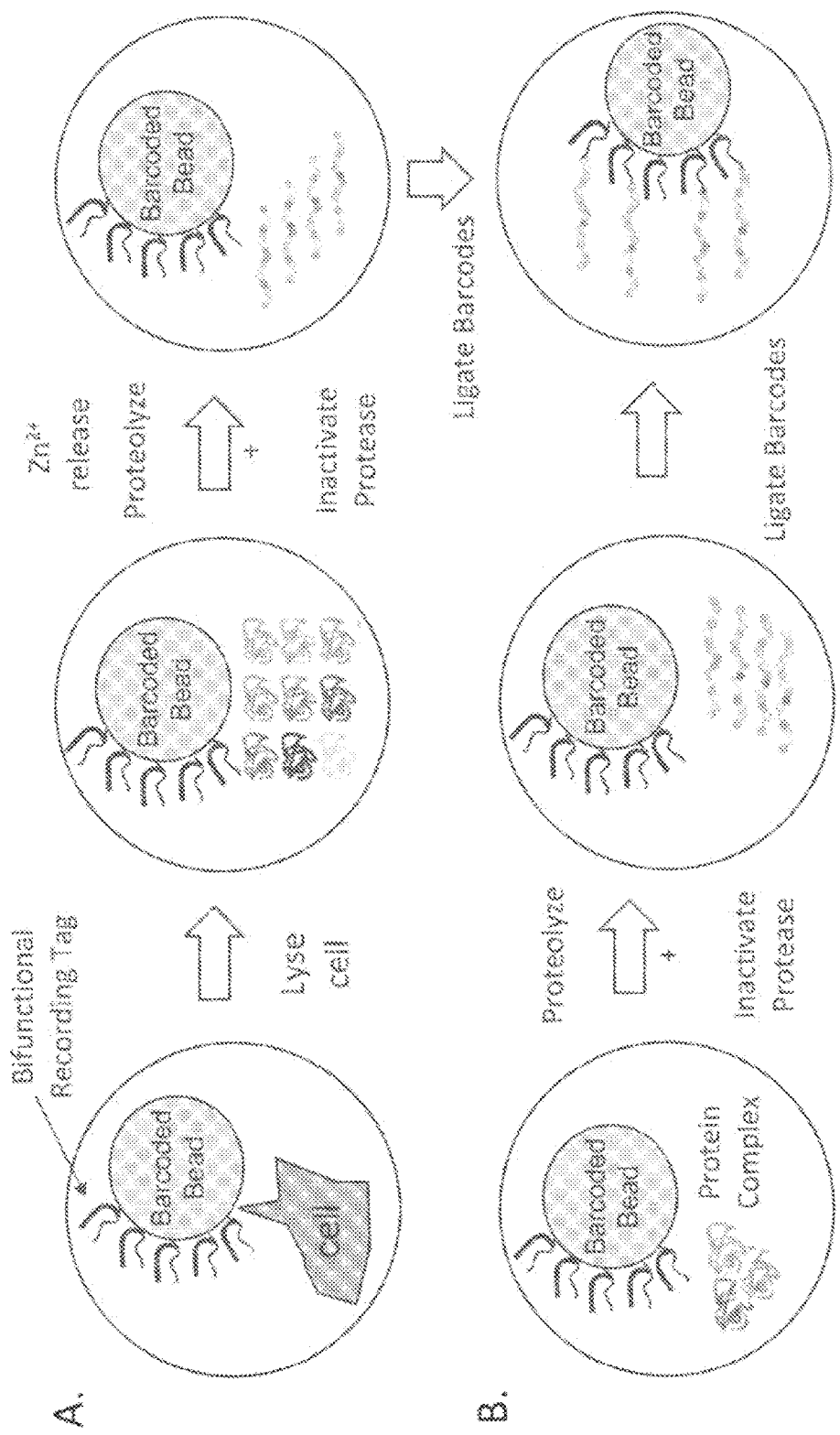
FIG. 19 illustrates exemplary methods of single cell and bulk proteome partitioning into individual droplets, each droplet comprising a bead having a plurality of bifunctional recording tags with compartment tags attached thereto to correlate peptides to their originating protein or protein complex, or proteins to originating single cell. Manipulation of droplet constituents after post droplet formation: (Step (A)) Single cell partitioning into an individual droplet followed by cell lysis to release the cell proteome, and proteolysis to digest the cell proteome into peptides, and inactivation of the protease following sufficient proteolysis; (Step (B)) Bulk proteome partitioning into a plurality of droplets wherein an individual droplet comprises a protein complex followed by proteolysis to digest the protein complex into peptides, and inactivation of the protease following sufficient proteolysis. A heat labile metallo-protease can be used to digest the encapsulated proteins into peptides after photo-release of photo-caged divalent cations (e.g., $Zn^{2+}$). The protease can be heat inactivated following sufficient proteolysis or the divalent cations may be chelated. Droplets contain hybridized or releasable compartment tags comprising nucleic acid barcodes (separate from recording tag) capable of being ligated to either an N- or C-terminal amino acid of a peptide. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

The present disclosure provides methods of enhancing protein analysis by partitioning a complex proteome sample (e.g., a plurality of protein complexes, proteins, or polypeptides) or complex cellular sample into a plurality of compartments, wherein each compartment comprises a plurality of compartment tags that are the same within an individual compartment (save for an optional UMI sequence) and are different from the compartment tags of other compartments (see, e.g., FIG. 18-20). The compartments optionally comprise a solid support (e.g., bead) to which the plurality of compartment tags are joined thereto. The plurality of protein complexes, proteins, or polypeptides are fragmented into a plurality of peptides, which are then contacted to the plurality of compartment tags under conditions sufficient to permit annealing or joining of the plurality of peptides with the plurality of compartment tags within the plurality of compartments, thereby generating a plurality of compartment tagged peptides. Alternatively, the plurality of protein complexes, proteins, or polypeptides are joined to a plurality of compartment tags under conditions sufficient to permit annealing or joining of the plurality of protein complexes, proteins or polypeptides with the plurality of compartment tags within a plurality of compartments, thereby generating a plurality of compartment tagged protein complexes, proteins, polypeptides. The compartment tagged protein complexes, proteins, or polypeptides are then collected from the plurality of compartments and optionally fragmented into a plurality of compartment tagged peptides. One or more compartment tagged peptides are analyzed according to any of the methods described herein.

In certain embodiments, compartment tag information is transferred to a recording tag associated with an analyte, such as a macromolecule (e.g., polypeptide) via primer extension (see, e.g., FIG. 5 and FIG. 48A-E) or ligation (see, e.g., FIG. 6, FIG. 46A-C, and FIG. 47A-B).

In some embodiments, the compartment tags are free in solution within the compartments. In other embodiments, the compartment tags are joined directly to the surface of the compartment (e.g., well bottom of microtiter or picotiter plate) or a bead or bead within a compartment.

A compartment can be an aqueous compartment (e.g., microfluidic droplet) or a solid compartment. A solid compartment includes, for example, a nanoparticle, a microsphere, a microtiter or picotiter well or a separated region on an array, a glass surface, a silicon surface, a plastic surface, a filter, a membrane, nylon, a silicon wafer chip, a flow cell, a flow through chip, a biochip including signal transducing electronics, an ELISA plate, a spinning interferometry disc, a nitrocellulose membrane, or a nitrocellulose-based polymer surface. In certain embodiments, each compartment contains, on average, a single cell.

A solid support can be any support surface including, but not limited to, a bead, a microbead, an array, a glass surface, a silicon surface, a plastic surface, a filter, a membrane, nylon, a silicon wafer chip, a flow cell, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere. Materials for a solid support include but are not limited to acrylamide, agarose, cellulose, nitrocellulose, glass, gold, quartz, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polyactic acid, polyorthoesters, functionalized silane, polypropylfumerate, collagen, glycosaminoglycans, polyamino acids, or any combination thereof. In certain embodiments, a solid support is a bead, for example, a polystyrene bead, a polymer bead, an agarose bead, an acrylamide bead, a solid core bead, a porous bead, a paramagnetic bead, glass bead, or a controlled pore bead.

Various methods of partitioning samples into compartments with compartment tagged beads is reviewed in Shembekar et al., (Shembekar, Chaipan et al. 2016). In one example, the proteome is partitioned into droplets via an emulsion to enable global information on protein molecules and protein complexes to be recorded using the methods disclosed herein (see, e.g., FIG. 18 and FIG. 19). In certain embodiments, the proteome is partitioned in compartments (e.g., droplets) along with compartment tagged beads, an activate-able protease (directly or indirectly via heat, light, etc.), and a peptide ligase engineered to be protease-resistant (e.g., modified lysines, pegylation, etc.). In certain embodiments, the proteome can be treated with a denaturant to assess the peptide constituents of a protein or polypeptide. If information regarding the native state of a protein is desired, an interacting protein complex can be partitioned into compartments for subsequent analysis of the peptides derived therefrom.

Figure 22A:
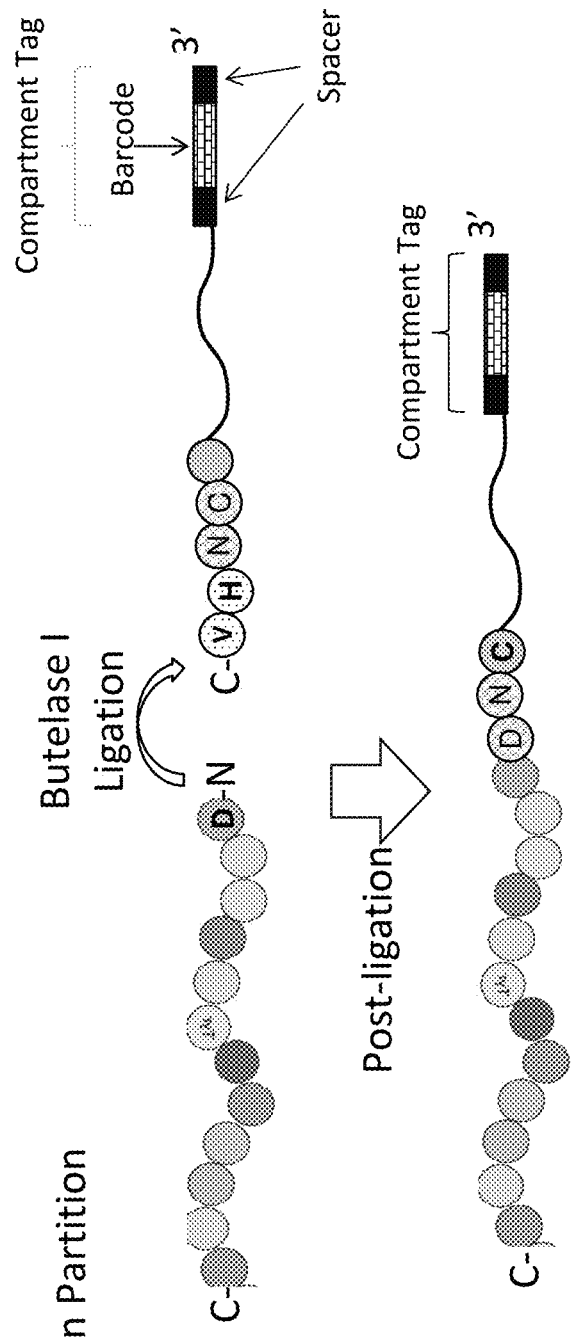
FIG. 22A-22B illustrate exemplary tagging details.
Figure 22B:
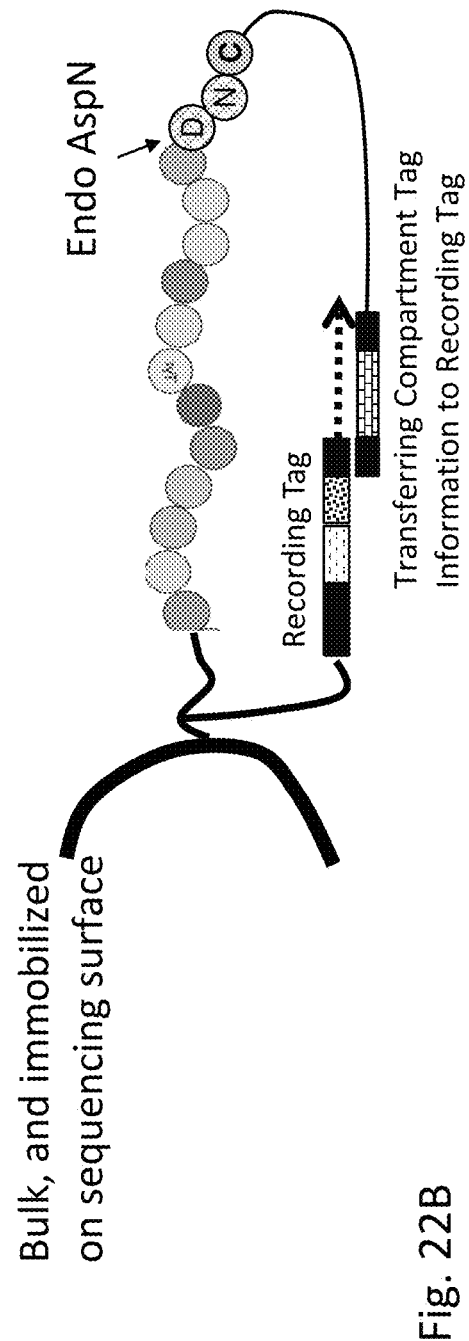

A compartment tag comprises a barcode, which is optionally flanked by a spacer or universal primer sequence on one or both sides. The primer sequence can be complementary to the 3' sequence of a recording tag, thereby enabling transfer of compartment tag information to the recording tag via a primer extension reaction (see, e.g., FIG. 22A-B). The barcode can be comprised of a single stranded nucleic acid molecule attached to a solid support or compartment or its complementary sequence hybridized to solid support or compartment, or both strands (see, e.g., FIG. 16). A compartment tag can comprise a functional moiety, for example attached to the spacer, for coupling to a peptide. In one example, a functional moiety (e.g., aldehyde) is one that is capable of reacting with the N-terminal amino acid residue on the plurality of peptides. In another example, the functional moiety is capable of reacting with an internal amino acid residue (e.g., lysine or lysine labeled with a "click" reactive moiety) on the plurality of peptides. In another embodiment, the functional moiety may simply be a complementary DNA sequence capable of hybridizing to a DNA tag-labeled protein. Alternatively, a compartment tag can be a chimeric molecule, further comprising a peptide comprising a recognition sequence for a protein ligase (e.g., butelase I or homolog thereof) to allow ligation of the compartment tag to a peptide of interest (see, e.g., FIG. 22A). A compartment tag can be a component within a larger nucleic acid molecule, which optionally further comprises a unique molecular identifier for providing identifying information on the peptide that is joined thereto, a spacer sequence, a universal priming site, or any combination thereof. This UMI sequence generally differs among a population of compartment tags within a compartment. In certain embodiments, a compartment tag is a component within a recording tag, such that the same tag that is used for providing individual compartment information is also used to record individual peptide information for the peptide attached thereto.

In certain embodiments, compartment tags can be formed by printing, spotting, ink-jetting the compartment tags into the compartment. In certain embodiments, a plurality of compartment tagged beads is formed, wherein one barcode type is present per bead, via split-and-pool oligonucleotide ligation or synthesis as described by Klein et al., 2015, Cell 161:1187-1201; Macosko et al., 2015, Cell 161:1202-1214; and Fan et al., 2015, Science 347:1258367. Compartment tagged beads can also be formed by individual synthesis or immobilization. In certain embodiments, the compartment tagged beads further comprise bifunctional recording tags, in which one portion comprises the compartment tag comprising a recording tag, and the other portion comprises a functional moiety to which the digested peptides can be coupled (see, e.g., FIG. 19).

In certain embodiments, the plurality of proteins or polypeptides within the plurality of compartments is fragmented into a plurality of peptides with a protease. A protease can be a metalloprotease. In certain embodiments, the activity of the metalloprotease is modulated by photo-activated release of metallic cations. Examples of endopeptidases that can be used include: trypsin, chymotrypsin, elastase, thermolysin, pepsin, clostripan, glutamyl endopeptidase (GluC), endopeptidase ArgC, peptidyl-asp metallo-endopeptidase (AspN), endopeptidase LysC and endopeptidase LysN. Their mode of activation varies depending on buffer and divalent cation requirements. Optionally, following sufficient digestion of the proteins or polypeptides into peptide fragments, the protease is inactivated (e.g., heat, fluoro-oil or silicone oil soluble inhibitor, such as a divalent cation chelation agent).

Figure 20A:
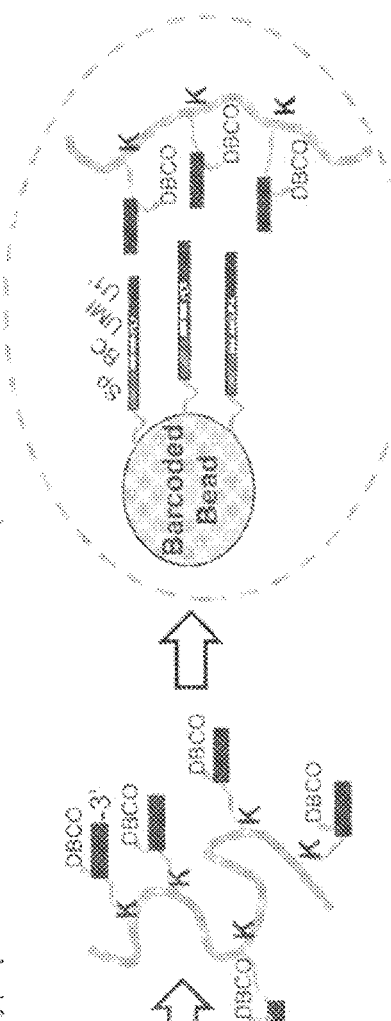
Figure 20B:
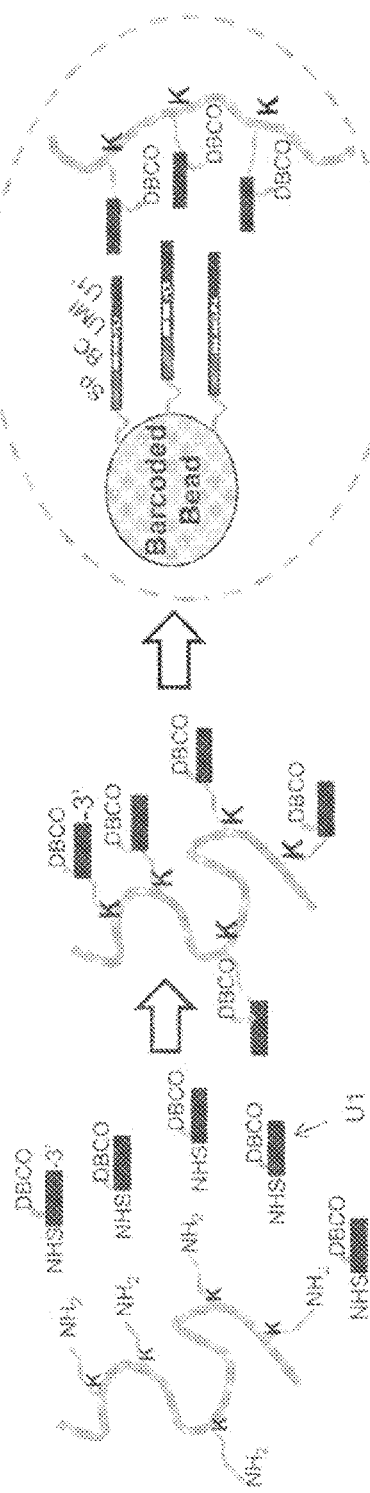
Figure 20C:
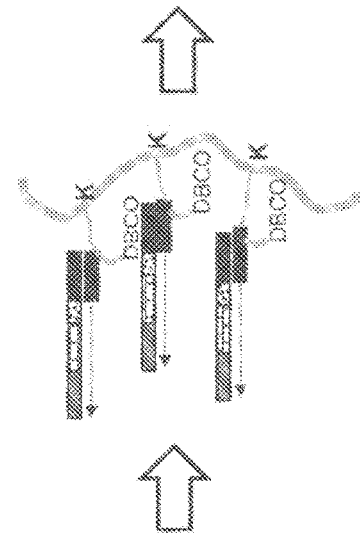
Figure 20D:
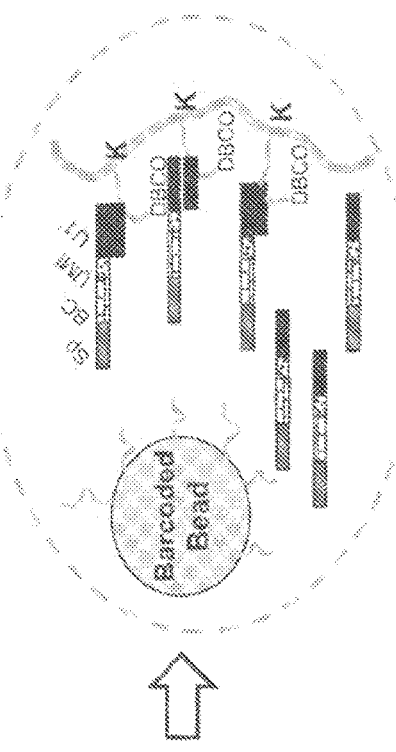
Figure 20G:
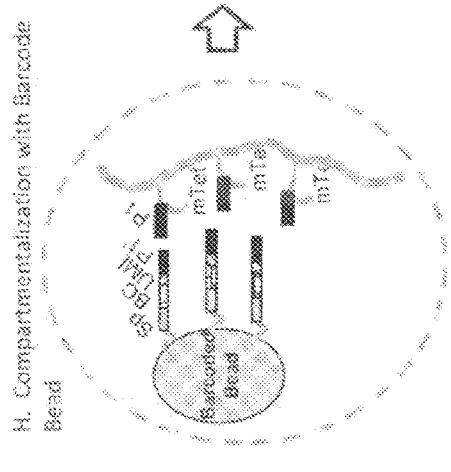
Figure 20H:
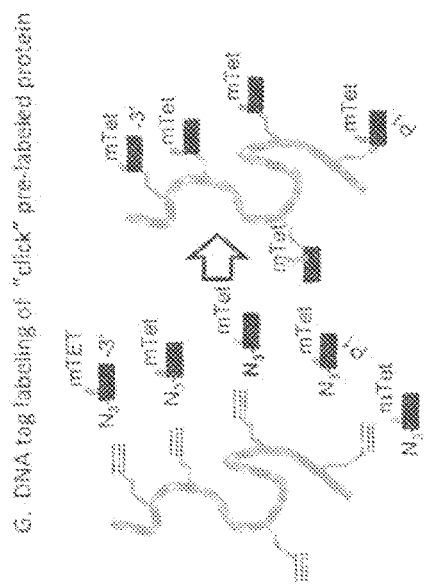
Figure 20I:
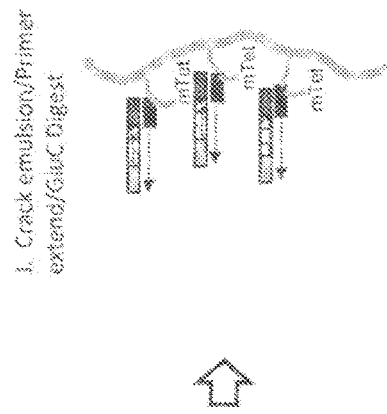
Figure 20J:
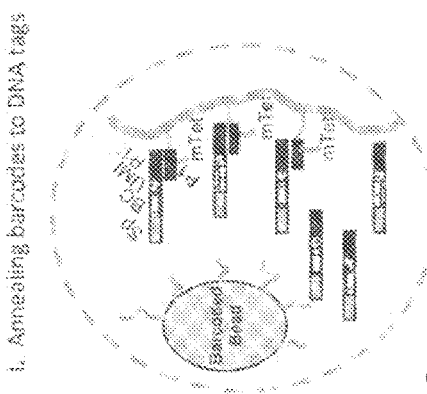
Figure 20K:
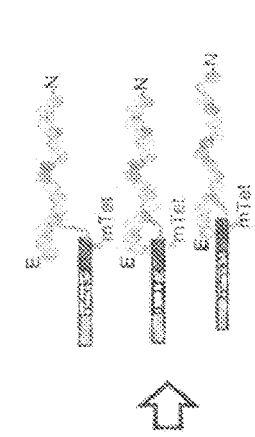
Figure 20L:
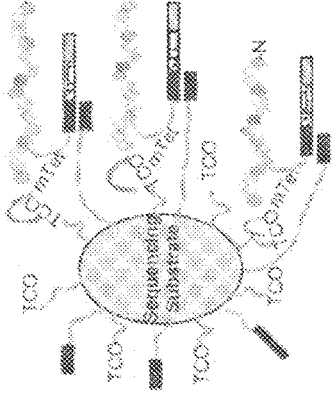

In certain embodiments of peptide barcoding with compartment tags, a protein molecule (optionally, denatured polypeptide) is labeled with DNA tags by conjugation of the DNA tags to F-amine moieties of the protein's lysine groups or indirectly via click chemistry attachment to a protein/polypeptide pre-labeled with a reactive click moiety such as alkyne (see, e.g., FIG. 2B and FIG. 20A). The DNA tag-labeled polypeptides are then partitioned into compartments comprising compartment tags (e.g., DNA barcodes bound to beads contained within droplets) (see, e.g., FIG. 20B), wherein a compartment tag contains a barcode that identifies each compartment. In one embodiment, a single protein/polypeptide molecule is co-encapsulated with a single species of DNA barcodes associated with a bead (see, e.g., FIG. 20B). In another embodiment, the compartment can constitute the surface of a bead with attached compartment (bead) tags similar to that described in PCT Publication WO2016/061517 (incorporated by reference in its entirety), except as applied to proteins rather than DNA. The compartment tag can comprise a barcode (BC) sequence, a universal priming site (U1'), a UMI sequence, and a spacer sequence (Sp). In one embodiment, concomitant with or after partitioning, the compartment tags are cleaved from the bead and hybridize to the DNA tags attached to the polypeptide, for example via the complementary U1 and U1' sequences on the DNA tag and compartment tag, respectively. For partitioning on beads, the DNA tag-labeled protein can be directly hybridized to the compartment tags on the bead surface (see, e.g., FIG. 20C). After this hybridization step, the polypeptides with hybridized DNA tags are extracted from the compartments (e.g., emulsion "cracked", or compartment tags cleaved from bead), and a polymerase-based primer extension step is used to write the barcode and UMI information to the DNA tags on the polypeptide to yield a compartment barcoded recording tag (see, e.g., FIG. 20D). A LysC protease digestion may be used to cleave the polypeptide into constituent peptides labeled at their C-terminal lysine with a recording tag containing universal priming sequences, a compartment tag, and a UMI (see, e.g., FIG. 20E). In one embodiment, the LysC protease is engineered to tolerate DNA-tagged lysine residues. The resultant recording tag labeled peptides are immobilized to a solid substrate (e.g., bead) at an appropriate density to minimize intermolecular interactions between recording tagged peptides (see, e.g., FIGS. 20E and 20F).

Attachment of the peptide to the compartment tag (or vice versa) can be directly to an immobilized compartment tag, or to its complementary sequence (if double stranded). Alternatively, the compartment tag can be detached from the solid support or surface of the compartment, and the peptide and solution phase compartment tag joined within the compartment. In one embodiment, the functional moiety on the compartment tag (e.g., on the terminus of oligonucleotide) is an aldehyde which is coupled directly to the amine N-terminus of the peptide through a Schiff base (see, e.g., FIG. 16). In another embodiment, the compartment tag is constructed as a nucleic acid-peptide chimeric molecule comprising peptide motif (n-X . . . XXCGSHV-c) for a protein ligase. The nucleic acid-peptide compartment tag construct is conjugated to digested peptides using a peptide ligase, such as butelase I or a homolog thereof. Butelase I, and other asparaginyl endopeptidase (AEP) homologues, can be used to ligate the C-terminus of the oligonucleotide-peptide compartment tag construct to the N-terminus of the digested peptides (Nguyen, Wang et al. 2014, Nguyen, Cao et al. 2015). This reaction is fast and highly efficient. The resultant compartment tagged peptides can be subsequently immobilized to a solid support for nucleic-acid peptide analysis as described herein.

In certain embodiments, compartment tags that are joined to a solid support or surface of a compartment are released prior to joining the compartment tags with the plurality of fragmented peptides (see, e.g., FIG. 18). In some embodiments, following collection of the compartment tagged peptides from the plurality of compartments, the compartment tagged peptides are joined to a solid support in association with recording tags. Compartment tag information can then be transferred from the compartment tag on the compartment tagged peptide to the associated recording tag (e.g., via a primer extension reaction primed from complementary spacer sequences within the recording tab and compartment tag). In some embodiments, the compartment tags are then removed from the compartment tagged peptides prior to peptide analysis according to the methods described herein. In further embodiments, the sequence specific protease (e.g., Endo AspN) that is initially used to digest the plurality of proteins is also used to remove the compartment tag from the N terminus of the peptide after transfer of the compartment tag information to the associated recording tag (see, e.g., FIG. 22B).

Figure 21:
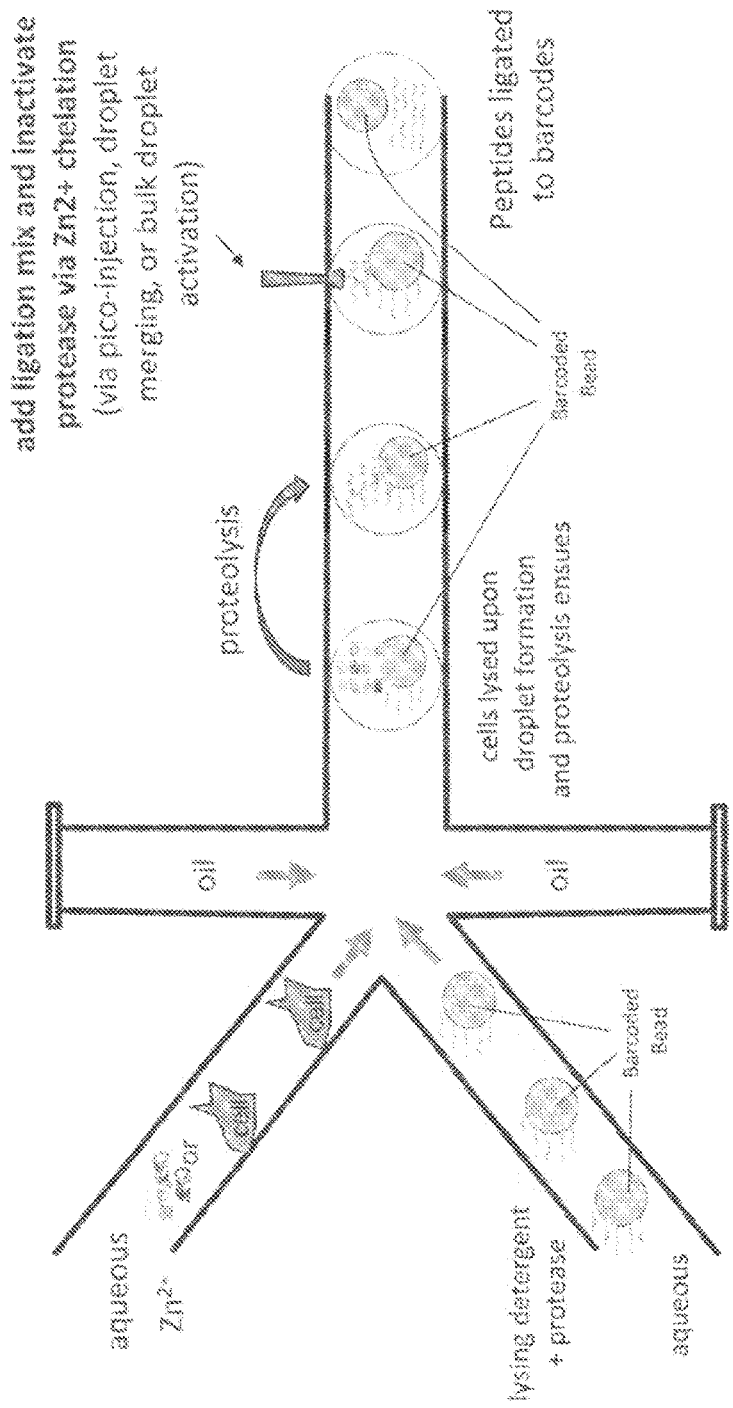
FIG. 21 illustrates an exemplary method using flow-focusing T-junction for single cell and compartment tagged (e.g., barcode) compartmentalization with beads. With two aqueous flows, cell lysis and protease activation ($Zn^{2+}$ mixing) can easily be initiated upon droplet formation.

Approaches for compartmental-based partitioning include droplet formation through microfluidic devices using T-junctions and flow focusing, emulsion generation using agitation or extrusion through a membrane with small holes (e.g., track etch membrane), etc. (see, e.g., FIG. 21). A challenge with compartmentalization is addressing the interior of the compartment. In certain embodiments, it may be difficult to conduct a series of different biochemical steps within a compartment since exchanging fluid components is challenging. As previously described, one can modify a limited feature of the droplet interior, such as pH, chelating agent, reducing agents, etc. by addition of the reagent to the fluoro-oil of the emulsion. However, the number of compounds that have solubility in both aqueous and organic phases is limited. One approach is to limit the reaction in the compartment to essentially the transfer of the barcode to the molecule of interest.

After labeling of the proteins/peptides with recording tags comprised of compartment tags (barcodes), the protein/peptides are immobilized on a solid-support at a suitable density to favor intramolecular transfer of information from the coding tag of a bound cognate binding agent to the corresponding recording tag/tags attached to the bound peptide or protein molecule. Intermolecular information transfer is minimized by controlling the intermolecular spacing of molecules on the surface of the solid-support.

In certain embodiments, the compartment tags need not be unique for each compartment in a population of compartments. A subset of compartments (two, three, four, or more) in a population of compartments may share the same compartment tag. For instance, each compartment may be comprised of a population of bead surfaces which act to capture a subpopulation of macromolecules from a sample (many molecules are captured per bead). Moreover, the beads comprise compartment barcodes which can be attached to the captured macromolecules. Each bead has only a single compartment barcode sequence, but this compartment barcode may be replicated on other beads with in the compartment (many beads mapping to the same barcode). There can be (although not required) a many-to-one mapping between physical compartments and compartment barcodes, moreover, there can be (although not required) a many-to-one mapping between macromolecules within a compartment. A partition barcode is defined as an assignment of a unique barcode to a subsampling of macromolecules from a population of macromolecules within a sample. This partition barcode may be comprised of identical compartment barcodes arising from the partitioning of macromolecules within compartments labeled with the same barcode. The use of physical compartments effectively subsamples the original sample to provide assignment of partition barcodes. For instance, a set of beads labeled with 10,000 different compartment barcodes is provided. Furthermore, suppose in a given assay, that a population of 1 million beads are used in the assay. On average, there are 100 beads per compartment barcode (Poisson distribution). Further suppose that the beads capture an aggregate of 10 million macromolecules. On average, there are 10 macromolecules per bead, with 100 compartments per compartment barcode, there are effectively 1000 macromolecules per partition barcode (comprised of 100 compartment barcodes for 100 distinct physical compartments).

Figures 37A, 37B:
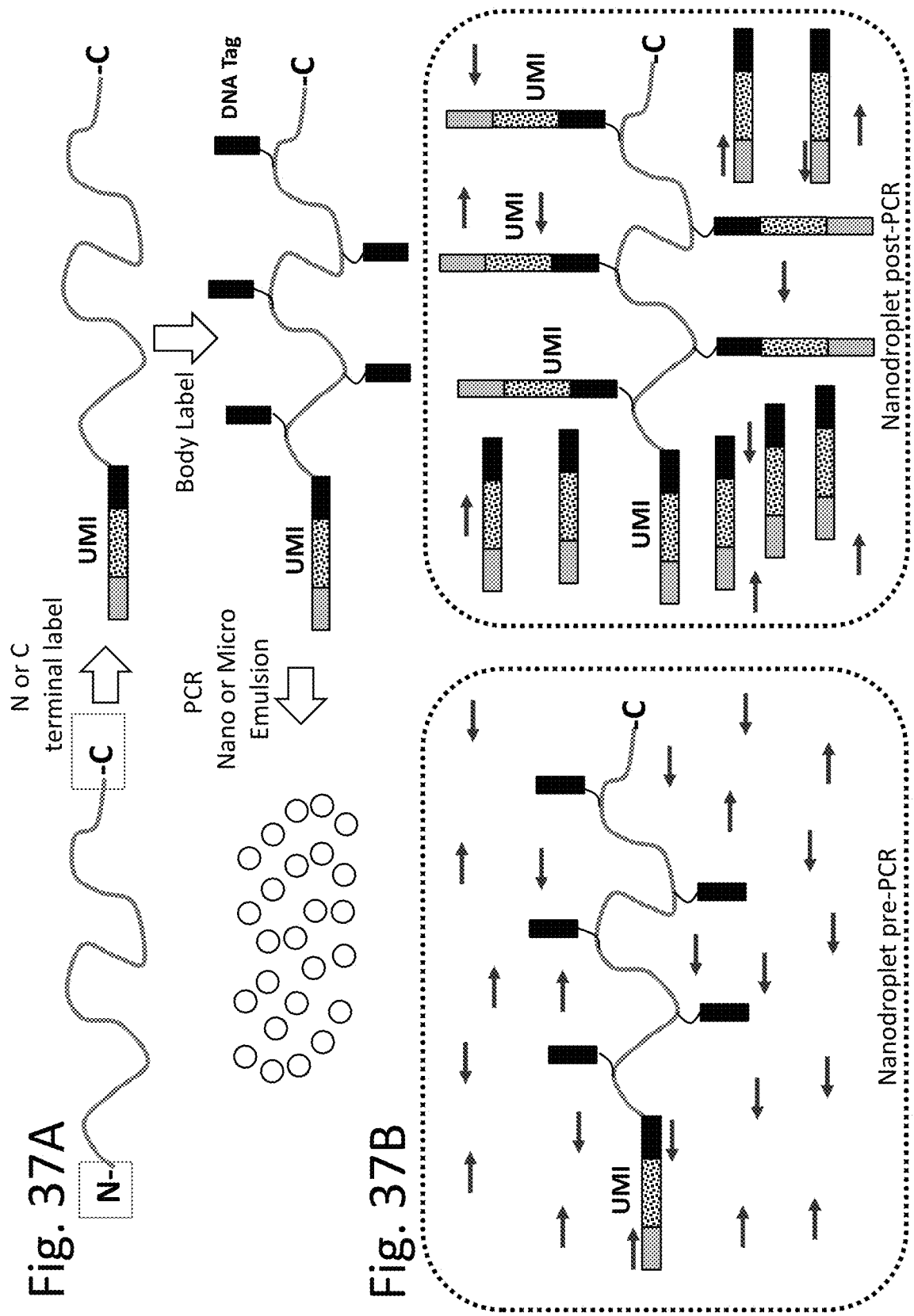
FIG. 37A-37B illustrate examples for use of nano- or micro-emulsion PCR to transfer information from UMI-labeled N or C terminus to DNA tags labeling body of polypeptide.

In another embodiment, single molecule partitioning and partition barcoding of polypeptides is accomplished by labeling polypeptides (chemically or enzymatically) with an amplifiable DNA UMI tag (e.g., recording tag) at the N or C terminus, or both (see, e.g., FIG. 37A-B). DNA tags are attached to the body of the polypeptide (internal amino acids) via non-specific photo-labeling or specific chemical attachment to reactive amino acids such as lysines as illustrated in FIG. 2B. Information from the recording tag attached to the terminus of the peptide is transferred to the DNA tags via an enzymatic emulsion PCR (Williams, Peisajovich et al. 2006, Schutze, Rubelt et al. 2011) or emulsion in vitro transcription/reverse transcription (IVT/RT) step. In the preferred embodiment, a nanoemulsion is employed such that, on average, there is fewer than a single polypeptide per emulsion droplet with size from 50 nm-1000 nm (Nishikawa, Sunami et al. 2012, Gupta, Eral et al. 2016). Additionally, all the components of PCR are included in the aqueous emulsion mix including primers, dNTPs, $Mg^{2+}$, polymerase, and PCR buffer. If IVT/RT is used, then the recording tag is designed with a T7/SP6 RNA polymerase promoter sequence to generate transcripts that hybridize to the DNA tags attached to the body of the polypeptide (Ryckelynck, Baudrey et al. 2015). A reverse transcriptase (RT) copies the information from the hybridized RNA molecule to the DNA tag. In this way, emulsion PCR or IVT/RT can be used to effectively transfer information from the terminus recording tag to multiple DNA tags attached to the body of the polypeptide.

Encapsulation of cellular contents via gelation in beads is a useful approach to single cell analysis (Tamminen and Virta 2015, Spencer, Tamminen et al. 2016). Barcoding single cell droplets enables all components from a single cell to be labeled with the same identifier (Klein, Mazutis et al. 2015, Gunderson, Steemers et al. 2016, Zilionis, Nainys et al. 2017). Compartment barcoding can be accomplished in a number of ways including direct incorporation of unique barcodes into each droplet by droplet joining (Raindance), by introduction of a barcoded beads into droplets (10× Genomics), or by combinatorial barcoding of components of the droplet post encapsulation and gelation using and split-pool combinatorial barcoding as described by Gunderson et al. (Gunderson, Steemers et al. 2016) and PCT Publication WO2016/130704, incorporated by reference in its entirety. A similar combinatorial labeling scheme can also be applied to nuclei as described by Adey et al. (Vitak, Torkenczy et al. 2017).

Figure 38:
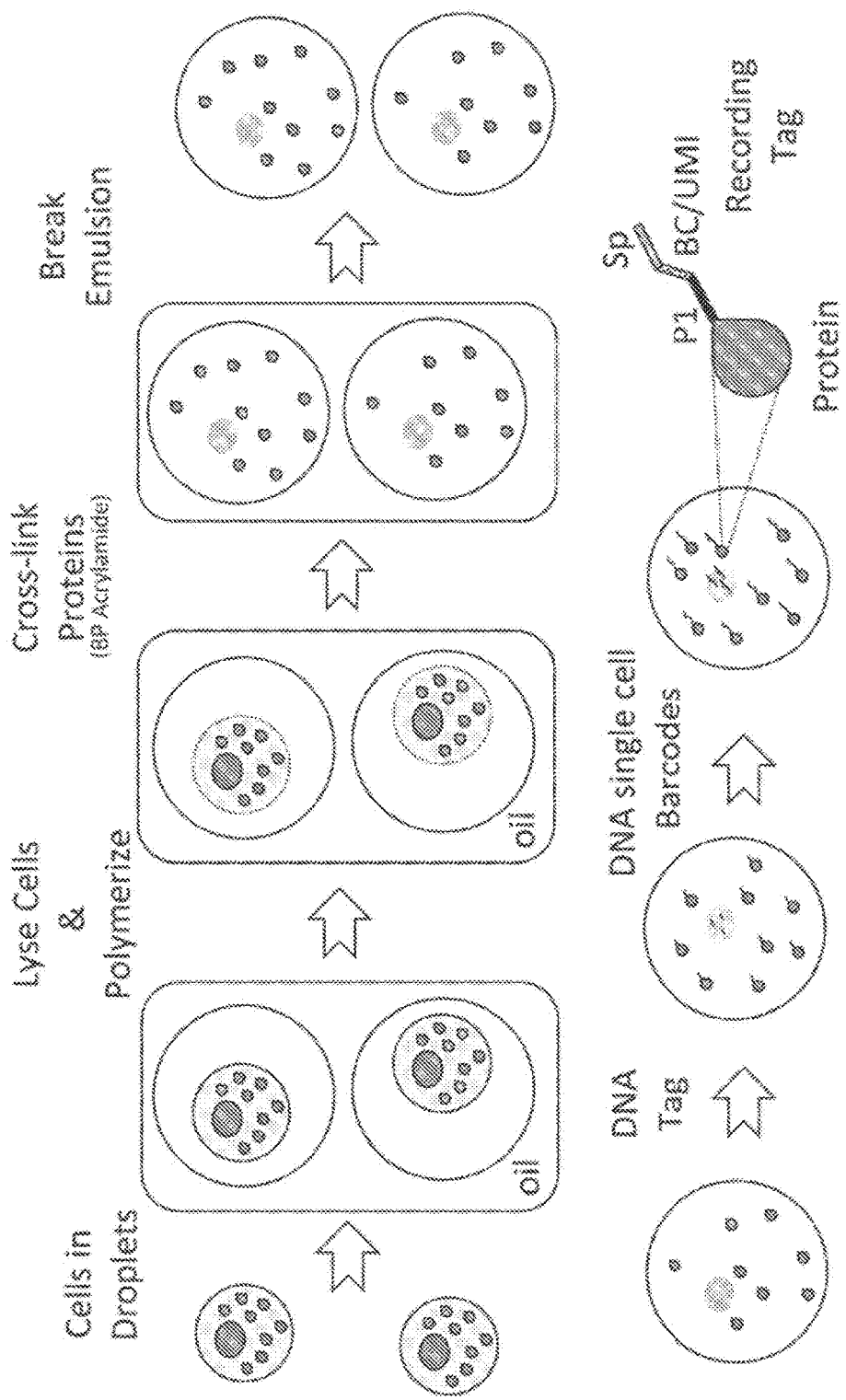
FIG. 38 illustrates examples for single cell proteomics. Cells are encapsulated and lysed in droplets containing polymer-forming subunits (e.g., acrylamide). The polymer-forming subunits are polymerized (e.g., polyacrylamide), and proteins are cross-linked to the polymer matrix. The emulsion droplets are broken and polymerized gel beads that contain a single cell protein lysate attached to the permeable polymer matrix are released. The proteins are cross-linked to the polymer matrix in either their native conformation or in a denatured state by including a denaturant such as urea in the lysis and encapsulation buffer. Recording tags comprising a compartment barcode and other recording tag components (e.g., universal priming sequence (P1), spacer sequence (Sp), optional unique molecular identifier (UMI)) are attached to the proteins using a number of methods known in the art and disclosed herein, including emulsification with barcoded beads, or combinatorial indexing. The polymerized gel bead containing the single cell protein can also be subjected to proteinase digest after addition of the recording tag to generate recording tag labeled peptides suitable for peptide sequencing. In certain embodiments, the polymer matrix can be designed such that is dissolves in the appropriate additive such as disulfide cross-linked polymer that break upon exposure to a reducing agent such as tris(2-carboxyethyl)phosphine (TCEP) or dithiothreitol (DTT). In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

The above droplet barcoding approaches have been used for DNA analysis but not for protein analysis. Adapting the above droplet barcoding platforms to work with proteins requires several innovative steps. The first is that barcodes are primarily comprised of DNA sequences, and this DNA sequence information needs to be conferred to the protein analyte. In the case of a DNA analyte, it is relatively straightforward to transfer DNA information onto a DNA analyte. In contrast, transferring DNA information onto proteins is more challenging, particularly when the proteins are denatured and digested into peptides for downstream analysis. This requires that each peptide be labeled with a compartment barcode. The challenge is that once the cell is encapsulated into a droplet, it is difficult to denature the proteins, protease digest the resultant polypeptides, and simultaneously label the peptides with DNA barcodes. Encapsulation of cells in polymer forming droplets and their polymerization (gelation) into porous beads, which can be brought up into an aqueous buffer, provides a vehicle to perform multiple different reaction steps, unlike cells in droplets (Tamminen and Virta 2015, Spencer, Tamminen et al. 2016) (Gunderson, Steemers et al. 2016). For example, the encapsulated proteins are crosslinked to the gel matrix to prevent their subsequent diffusion from the gel beads. This gel bead format allows the entrapped proteins within the gel to be denatured chemically or enzymatically, labeled with DNA tags, protease digested, and subjected to a number of other interventions. FIG. 38 depicts exemplary encapsulation and lysis of a single cell in a gel matrix.

M. Kit and Kit Components for Tissue and Single Cell Spatial Proteomics

Another use of barcodes is the spatial segmentation of a tissue on the surface an array of spatially distributed DNA barcode sequences. If tissue proteins are labelled with DNA recording tags comprising barcodes reflecting the spatial position of the protein within the cellular tissue mounted on the array surface, then the spatial distribution of protein analytes within the tissue slice can later be reconstructed after sequence analysis, much as is done for spatial transcriptomics as described by Stahl et al. (2016, Science 353(6294):78-82) and Crosetto et al. (Corsetto, Bienko et al., 2015). The attachment of spatial barcodes can be accomplished by releasing array-bound barcodes from the array and diffusing them into the tissue section, or alternatively, the proteins in the tissue section can be labeled with DNA recording tags, and then the proteins digested with a protease to release labeled peptides that can diffuse and hybridize to spatial barcodes on the array. The barcode information can then be transferred (enzymatically or chemically) to the recording tags attached to the peptides.

Spatial barcoding of the proteins within a tissue can be accomplished by placing a fixed/permeabilized tissue slice, chemically labelled with DNA recording tags, on a spatially encoded DNA array, wherein each feature on the array has a spatially identifiable barcode (see, e.g., FIG. 23A-C). To attach an array barcode to the DNA tag, the tissue slice can be digested with a protease, releasing DNA tag labelled peptides, which can diffuse and hybridize to proximal array features adjacent to the tissue slice. The array barcode information can be transferred to the DNA tag using chemical/enzymatic ligation or polymerase extension. Alternatively, rather than allowing the labelled peptides to diffuse to the array surface, the barcodes sequences on the array can be cleaved and allowed to diffuse into proximal areas on the tissue slice and hybridize to DNA tag-labelled proteins therein. Once again, the barcoding information can be transferred by chemical/enzymatic ligation or polymerase extension. In this second case, protease digestion can be performed following transfer of barcode information. The result of either approach is a collection of recording tag-labelled protein or peptides, wherein the recording tag comprises a barcode harbouring 2-D spatial information of the protein/peptides's location within the originating tissue. Moreover, the spatial distribution of post-translational modifications can be characterized. This approach provides a sensitive and highly-multiplexed in situ digital immunohistochemistry assay, and should form the basis of modern molecular pathology leading to much more accurate diagnosis and prognosis.

In another embodiment, spatial barcoding can be used within a cell to identify the protein constituents/PTMs within the cellular organelles and cellular compartments (Christoforou et al., 2016, Nat. Commun. 7:8992, incorporated by reference in its entirety). A number of approaches can be used to provide intracellular spatial barcodes, which can be attached to proximal proteins. In one embodiment, cells or tissue can be sub-cellular fractionated into constituent organelles, and the different protein organelle fractions barcoded. Other methods of spatial cellular labelling are described in the review by Marx, 2015, Nat Methods 12:815-819, incorporated by reference in its entirety; similar approaches can be used herein.

N. Nanopore Based Sequencing

In any of the preceding embodiments, the analysis of the sequence information of the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), can be done using a single-molecule sequencing method, such as a nanopore based sequencing technology. In one aspect, the single-molecule sequencing method is a direct single-molecule sequencing method. WO 2017125565 A1 discloses certain aspects of exemplary nanopore based sequencing, the content of which is incorporated by reference in its entirety.

Nanopore sequencing of DNA and RNA may be achieved by strand sequencing and/or exosequencing of DNA and RNA. Strand sequencing comprises methods whereby nucleotide bases of a sample polynucleotide strand are determined directly as the nucleotides of the polynucleotide template are threaded through a nanopore. Alternatively, strand sequencing of the polynucleotide strand determines the sequence of the template indirectly by determining nucleotides that are incorporated into a growing strand that is complementary to that of the sample template strand.

In some embodiments, DNA, e.g., single stranded DNA, may be sequenced by detecting tags of tagged nucleotides that are released from the nucleotide base as the nucleotide is incorporated by a polymerase into a strand complementary to that of a template associated with the polymerase in an enzyme-polymer complex. The single molecule nanopore-based sequencing by synthesis (Nano-SBS) technique that uses tagged nucleotides is described, for example, in WO2014/074727, which is incorporated by reference in its entirety. Accordingly, in some embodiments, the enzyme-polynucleotide complex that may be attached to the inserted nanopore may be a DNA polymerase-DNA complex. In some embodiments, the DNA polymerase-DNA complex may be attached to a wild-type or variant monomeric nanopore. In some embodiments, the DNA polymerase-DNA complex may be attached to a wild-type, variant, or modified variant homo-oligomeric nanopore. In some embodiments, the DNA polymerase-DNA complex may be attached to a wild-type, a variant, or a modified variant hetero-oligomeric nanopore. In some embodiments, the DNA polymerase-DNA complex may be attached to a wild-type, variant, or modified variant aHL nanopore. In other embodiments, the DNA polymerase-DNA complex may be attached to a wild-type OmpG nanopore or variants thereof.

In other embodiments, the enzyme-polynucleotide complex may be an RNA polymerase-RNA complex. The RNA polymerase-RNA complex may be attached to a wild-type or variant oligomeric or monomeric nanopore. In some embodiments, the RNA polymerase-RNA complex is attached to a wild-type or variant OmpG nanopore. In other embodiments, the RNA polymerase-RNA complex is attached to a wild-type or variant aHL nanopore. In yet other embodiments, the enzyme-polynucleotide complex may be a reverse transcriptase-RNA complex. The reverse transcriptase-RNA complex may be attached to a wild-type or variant oligomeric or monomeric nanopore. In some embodiments, the reverse transcriptase-RNA complex is attached to a wild-type or variant OmpG nanopore. In other embodiments, the reverse transcriptase-RNA complex is attached to a wild-type or variant aHL nanopore. In some embodiments, individual nucleic acids may be sequenced by the identification of nucleoside 5'-monophosphates as they are released by processive exonucleases (Astier et al., 2006, *J Am Chem Soc* 128:1705-1710). Accordingly, in some embodiments, the enzyme-polynucleotide complex that may be attached to the inserted nanopore may be an exonuclease-polynucleotide complex. In some embodiments, the exonuclease-polynucleotide complex may be attached to a wild-type or variant monomeric nanopore. In some embodiments, the exonuclease-polynucleotide complex may be attached to a wild-type or variant homo-oligomeric nanopore. In some embodiments, the exonuclease-polynucleotide complex may be attached to a wild-type or variant hetero-oligomeric nanopore. In some embodiments, the exonuclease-polynucleotide complex may be attached to a wild-type aHL nanopore or variants thereof. In other embodiments, the exonuclease-polynucleotide complex may be attached to a wild-type OmpG nanopore or variants thereof.

In some embodiments, a non-nucleic acid polymer may also be move through a nanopore and be sequenced. For example, proteins and polypeptides can move through nanopores, and sequencing of a protein or a polynucleotide using a nanopore can be performed by controlling the unfolding and translocation of the protein through the nanopore. The controlled unfolding and subsequent translocation can be achieved by the action of an unfoldase enzyme coupled to the protein to be sequenced (see e.g., Nivala et al., 2013, *Nature Biotechnol* 31:247-250). In some embodiments, the enzyme-polymer complex that is attached to the nanopore in the membrane may be an enzyme-polypeptide complex, e.g., an unfoldase-protein complex. In some embodiments, the unfoldase-protein complex may be attached to a wild-type or variant monomeric nanopore. In some embodiments, the unfoldase-protein complex may be attached to a wild-type or variant homo-oligomeirc nanopore. In some embodiments, the unfoldase-protein complex may be attached to a wild-type or variant hetero-oligomeric nanopore. In some embodiments, the unfoldase-protein complex may be attached to a wild-type aHL nanopore or variants thereof. In other embodiments, the unfoldase-protein complex may be attached to a wild-type OmpG nanopore or variants thereof.

In some embodiments, other non-nucleic acid polymers may also be sequenced, for example, by moving through a nanopore. For example, WO 1996013606 A1 discloses exo-sequencing of saccharide material, such as a polysaccharide including heparan sulphate (HS) and heparin, and U.S. Pat. No. 8,846,363 B2 discloses enzymes (such as a sulfatase from *Flavobacterium heparinum*) that can be applied (e.g., in tandem) toward the exo-sequencing of a polysaccharide, such as heparin-derived oligosaccharides. Both patent documents are incorporated herein by reference in their entireties for all purposes.

Enzymes of enzyme-polymer complexes and enzyme-nanopore complexes may include polynucleotide and polypeptide processing enzymes, e.g. DNA and RNA polymerases, reverse transcriptases, exonucleases, unfoldases, ligases, and sulfatases. The enzyme of the enzyme-polymer complex and enzyme-nanopore complex can be a wild-type enzyme, or it can be a variant form of the wild-type enzyme. Variant enzymes can be engineered to possess characteristics that are altered relative to those of the parent enzyme. In some embodiments, the enzyme of the enzyme-polymer complex that is altered is a polymerase. The altered characteristics of the polymerase enzyme include changes in enzyme activity, fidelity, processivity, elongation rate, stability, or solubility. The polymerase can be mutated to reduce the rate at which the polymerase incorporates a nucleotide into a nucleic acid strand (e.g., a growing nucleic acid strand). The reduced velocities (and improved sensitivities) can be achieved by a combination of site-specific mutagenesis of the nanopore protein and the incorporation of DNA processing enzymes, e.g., DNA polymerase, into the nanopore.

In some cases, the rate at which a nucleotide is incorporated into a nucleic acid strand can be reduced by functionalizing the nucleotide and/or template strand to provide steric hindrance, such as, for example, through methylation of the template nucleic acid strand. In some instances, the rate is reduced by incorporating methylated nucleotides.

The enzymes of the enzyme-polymer complex and enzyme-nanopore complex may be modified to comprise one or more attachment components and/or attachment sites that serve to link the enzyme-polymer complex to the nanopore inserted into the membrane. Similarly, the nanopore of the enzyme-nanopore complex and the nanopore to which the enzyme-polymer complex is attached may also be modified to comprise one or more attachment components and/or attachment sites to link the nanopore to the enzyme-polymer complex.

The nanopores of the nanopore sequencing complex include without limitation biological nanopores, solid state nanopores, and hybrid biological-solid state nanopores. In some embodiments, the nanopore sequencing complex includes solid state nanopores such as graphene, (indium tin oxide) ITO, pore lines with carbon nanotubes, or other inorganic solid state layers, or a combination of any of the foregoing. Biological nanopores of the nanopore sequencing complexes include OmpG from *E. coli* sp., *Salmonella* sp., *Shigella* sp., and *Pseudomonas* sp., and alpha hemolysin from *S. aureus* sp., MspA from *M. smegmatis* sp. The nanopores may be wild-type nanopores, variant nanopores, or modified variant nanopores. Variant nanopores can be engineered to possess characteristics that are altered relative to those of the parental enzyme. See, for example, U.S. patent application Ser. No. 14/924,861 filed Oct. 28, 2015, entitled "alpha-Hemolysin Variants with Altered Characteristics." In some embodiments, the characteristics are altered relative to the wild-type enzyme. In some embodiments, the variant nanopore of the nanopore sequencing complex is engineered to reduce the ionic current noise of the parental nanopore from which it is derived. An example of a variant nanopore having an altered characteristic is the OmpG nanopore having one or more mutations at the constriction site (WO2017050722 A1, entitled "OmpG Variants," filed on Sep. 22, 2015, which is incorporated by reference herein in its entirety), which decrease the ionic noise level relative to that of the parent OmpG. The reduced ionic current noise provides for the use of these OmpG nanopore variants in single molecule sensing of polynucleotides and proteins. In other embodiments, the variant OmpG polypeptide can be further mutated to bind molecular adapters, which while resident in the pore slow the movement of analytes, e.g., nucleotide bases, through the pore and consequently improve the accuracy of the identification of the analyte. Modified variant nanopores are often or typically multimeric nanopores whose subunits have been engineered to affect inter-subunit interaction (US 2017-0088890 A1, entitled "Alpha-Hemolysin Variants," which is incorporated by reference herein in its entirety). Altered subunit interactions can be exploited to specify the sequence and order with which monomers oligomerize to form the multimeric nanopore in a lipid bilayer. This technique provides control of the stoichiometry of the subunits that form the nanopore. An example of a multimeric nanopore whose subunits can be modified to determine the sequence of interaction of subunits during oligomerization is an aHL nanopore. Means of attaching The enzyme-polymer complex can be attached to the nanopore in any suitable way. Attaching enzyme-polymer complexes to nanopores may be achieved using the SpyTag/SpyCatcher peptide system (Zakeri et al., 2012, PNAS 109:E690-E697) native chemical ligation (Thapa et al., 2014, Molecules 19:14461-14483), sortase system (Wu and Guo, 2012, J Carbohydr Chem 31:48-66; Heck et al., 2013, Appl Microbiol Biotechnol 97:461-475), transglutaminase systems (Dennler et al., 2014, Bioconjug Chem 25:569-578), formylglycine linkage (Rashidian et al., 2013, Bioconjug Chem 24:1277-1294), or other chemical ligation techniques known in the art.

In some instances, the enzyme is linked to the nanopore using Solulink™ chemistry. See e.g., WO 2017/125565 A1. Solulink™ can be a reaction between HyNic (6-hydrazino-nicotinic acid, an aromatic hydrazine) and 4FB (4-formyl-benzoate, an aromatic aldehyde). In some instances, the polymerase is linked to the nanopore using Click chemistry (available from LifeTechnologies, for example; also see e.g., WO 2014/190322 A2). In some cases, zinc finger mutations are introduced into the hemolysin molecule and then a molecule is used (e.g., a DNA intermediate molecule) to link the enzyme to the zinc finger sites on the hemolysin.

O. Non-Nucleic Acid Polymers

In any of the preceding embodiments (e.g., those described in Sections A-N supra), the encoding tag and/or the recording tag, or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer. In some aspects, the encoding tag and/or the recording tag, or any portion thereof (e.g., a universal primer, a spacer, a UMI, a recording tag barcode, an encoder sequence, a binding cycle-specific barcode, etc.), give clearly resolvable signals, such as via a nanopore based sequencing. A wide range of polymers can be used, and optionally with click chemistry, tags that are compatible with an Edman-type degradation can be used to read out the sequence information of a target protein and/or polypeptide. In some embodiments, the method disclosed herein comprises an amplification step. In other embodiments, without an amplification step, a single molecule can be processed through a nanopore multiple times to give multiple reads, in order to give resolvable signals.

In any of the preceding embodiments, the recording tag comprises a polymer to be read, wherein the encoder within the coding tag comprises or is one or more small molecule portions, one or more subunits of a sequenceable non-nucleic acid polymer, one or more monomers of a sequenceable non-nucleic acid polymer. In this example, the encoder portion is akin to a bead on a string (e.g., an extended recording tag).

In some embodiments, the sequenceable polymer is linear. In other embodiments, the sequenceable polymer comprises one or more linear chains, one or more branches, one or more circles, or any combination thereof.

In some embodiments, the sequenceable polymer is not cross-linked. In other embodiments, the sequenceable polymer is cross-linked, for example, weakly cross-linked (e.g., the cross-linked polymer comprises between about 0.1% and about 1% cross-linkers).

In some embodiments, the sequenceable polymer is neutral, e.g., having an overall neutral charge. In particular embodiments, the sequenceable polymer comprises an acrylamide, an acrylate, a styrene, a nylon, a kapton, a NiPAM polymer, a PEG, a polylactam, a polylactone, an epoxide, a polysilicone, a polyester, a polycarbodiimide, a polyurethane, a polypyroldinone, a polyisothiocyanate, or any combination thereof.

In other embodiments, the sequenceable polymer is charged. In specific embodiments, the sequenceable polymer is negatively charged, for example, the sequenceable polymer may comprise a polysulfonate, and/or a negatively charged acrylamide (e.g., copolymerized with acrylic acid).

In other embodiments, the sequenceable polymer is positively charged, for example, the sequenceable polymer may comprise a polyamine, a polyaniline, a polyimine, and/or an acrylamide with an amine functional group which may be substituted or unsubstituted. In still other embodiments, the sequenceable polymer may comprise an ionomer.

In other embodiments, the sequenceable polymer comprises a polymorpholino and/or a zwitterionic polymer.

In some embodiments, the sequenceable polymer comprises a hydrophobic polymer and/or a hydrophilic polymer. In some aspects, the sequenceable polymer comprises a hydrophobic polymer, such as a styrene, a kapton, a fluoropolymer, or an isoprene, or any combination thereof. In other aspects, the sequenceable polymer comprises a hydrophilic polymer, such as a polyethylene glycol, a polylysine, a polyenimine, a polyimine, an acrylamide, or an acrylate, or any combination thereof.

In some embodiments, the sequenceable polymer comprises metathesis products, for example, a polymer product formed by ring-opening or linear metathesis.

In some embodiments, the sequenceable polymer comprises copolymers, block copolymers, diblock copolymers, or triblock copolymers, or any combination thereof. In some embodiments, the sequenceable polymer is formed by continuous polymerization or ligation of polymer products.

In other embodiments, the sequenceable polymer comprises biopolymers: In specific embodiments, the sequenceable polymer comprises polysaccharides, polypeptides, peptides, or polyamides, or any combination thereof.

In some embodiments, the sequenceable polymer comprises naturally occurring biopolymers, biopolymer mimics, or synthetic biopolymers, or hybrids thereof.

In some embodiments, the sequenceable polymer comprises biopolymer mimics, such as peptoids. In some embodiments, the sequenceable polymer comprises star polymers or dendrimers.

In some embodiments, the sequenceable polymer comprises stimulus triggered degradable polymers. Examples of stimuli include, but are not limited to, chemical stimulus, biochemical stimulus, enzymatic stimulus, light, time, and temperature.

In some embodiments, the sequenceable polymer comprises caged or protected polymers.

In some embodiments, the sequenceable polymer comprises reversible covalent bonded polymers. In some embodiments, the sequenceable polymer comprises a disulfide, thio(l)ester, tempo derived nitroxide polymers, or polyimines, or any combination thereof.

In some embodiments, the sequenceable polymer comprises polymers with low polydispersity index (PDI) or high PDI. Polydispersity index (PDI), or heterogeneity index, or simply dispersity (Đ), is a measure of the distribution of molecular mass in a given polymer sample. Typical dispersities vary based on the mechanism of polymerization and can be affected by a variety of reaction conditions. In synthetic polymers, it can vary greatly due to reactant ratio, how close the polymerization went to completion, etc. For typical addition polymerization, Đ can range around 5 to 20. For typical step polymerization, most probable values of Đ are around 2 or below. Living polymerization, a special case of addition polymerization, leads to values very close to 1. Such is the case also in biological polymers, where the dispersity can be very close or equal to 1, indicating only one length of polymer is present.

In some embodiments, the sequenceable polymer comprises polymers with low PDI, such as products of living polymerizations. In other embodiments, the sequenceable polymer comprises polymers with higher PDI, such as products of ATRP or other statistically driven distributions.

In some embodiments, the sequenceable polymer comprises conjugated polymers capable of acting as chromophores or conductive materials In other embodiments, the sequenceable polymer comprises structured or unstructured (e.g., folded or non-folded) polymers such as foldamers. In some embodiments, the coding polymers are relatively short, e.g., made up of 2 subunits. In other embodiments, the polymers are large, e.g., made up of subunits totaling ~100 kDa.

A number of polymer backbones are suitable for comprising a sequenceable polymer. The polyphosphate backbone described by Ouahabi et al. is useful for nanopore sequencing (Al Ouahabi, Charles et al. 2015). The phosphate group confers a negative charge to the backbone enabling electrically-controlled translocation through the pore. Different R groups can be used to provide different current blockade signatures. Peptoid polymers provide another useful polymer. A peptoid consists of a glycine backbone with side chain R groups connected to the nitrogen of the peptide-like backbone, instead of the α-carbon as in peptides. Solid phase synthesis of peptoids offers synthetic efficiency, high yield, and R group side chain diversity (hundreds of different R groups available) while reducing synthesis time and costs (Knight, Zhou et al. 2015). The peptoid backbone is neutral, but charged R groups can be employed along the length of the polymer to promote electrically-controlled translocation. Exemplar charged R groups include N-(2-aminoethyl) glycine (Nae) and N-(2-carboxyethyl) glycine (Nce). For a review of peptoid, see e.g., Seto et al., 2011, "Peptoids: Synthesis, Characterization, and Nanostructures," *Comprehensive Biomaterials*, vol. 2, pp. 53-76, which is incorporated herein by reference.

R groups for current blockade can be selected from a long list of functional moieties (incorporated by reference US20160075734). Functional moieties include substituted and/or functionalized groups such as alkoxy, halo, mercapto, azido, cyano, formyl, carboxyl, hydroxyl, nitro, acyl, aryloxy, alkylthio, amino, alkylamino, arylalkylamino, substituted amino, acylamino, acyloxy, ester, thioester, carboxylic thioester, ether, amide, amidino, sulfate, sulfoxyl, sulfonyl, sulfonyl, sulfonic acid, sulfonamide, urea, alkoxylacylamino, aminoacyloxy, guanidino, aldehyde, keto, imine, nitrile, phosphate, thiol, epoxide, peroxide, thiocyanate, amidine, oxime, nitrile, diazo, heterocyclo, etc., these terms including combinations of these groups. "Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)m, haloalkyl-S(O)m, alkenyl-S(O)m, alkynyl-S(O)m, cycloalkyl-S(O)m, cycloalkylalkyl-S(O)m, aryl-S(O)m, arylalkyl-S(O)m, heterocyclo-S(O)m, heterocycloalkyl-S(O)m, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

In any of the preceding embodiments, the recording tag and/or the coding tag can be a small molecule, or a subunit, monomer, residue, or building block of a sequenceable polymer, such as a polynucleotide or a non-nucleic acid sequenceable polymer.

In any of the preceding embodiments, the recording tag and/or the coding tag can be a sequenceable polymer, such as a polynucleotide or a non-nucleic acid sequenceable polymer.

In any of the preceding embodiments, the recording tag and/or the coding tag can comprise a small molecule, or a subunit, monomer, residue, or building block of a sequenceable polymer, such as a polynucleotide or a non-nucleic acid sequenceable polymer.

In any of the preceding embodiments, the coding tag can be a small molecule, or a subunit, monomer, residue, or building block of a sequenceable polymer, such as a polynucleotide or a non-nucleic acid sequenceable polymer, while the recording tag is a sequenceable polymer. In some embodiments, the coding tag (a small molecule, subunit, or monomer etc.) can be added to the recording tag in order to form a sequenceable polymer, akin to beads (e.g., various coding tags) on a string (e.g., the extended recording tag).

In any of the preceding embodiments, the extended recording tag and/or the extended coding tag can be a sequenceable polymer, such as a polynucleotide or a non-nucleic acid sequenceable polymer.

IV. Exemplary Embodiments

The following embodiments provide additional illustration of the present disclosure.

Embodiment 1. A kit, comprising: (a) a recording tag configured to associate directly or indirectly with an analyte; (b) (i) a coding tag which comprises identifying information regarding a binding moiety capable of binding to the analyte, and which is configured to associate directly or indirectly with the binding moiety to form a binding agent, and/or (ii) a label, wherein the recording tag and the coding tag are configured to allow transfer of information between them, upon binding between the binding agent and the analyte; and optionally (c) the binding moiety.

Embodiment 2. The kit of Embodiment 1, wherein the recording tag and/or the analyte are configured to be immobilized directly or indirectly to a support.

Embodiment 3. The kit of Embodiment 2, wherein the recording tag is configured to be immobilized to the support, thereby immobilizing the analyte associated with the recording tag.

Embodiment 4. The kit of Embodiment 2, wherein the analyte is configured to be immobilized to the support, thereby immobilizing the recording tag associated with the analyte.

Embodiment 5. The kit of Embodiment 2, wherein each of the recording tag and the analyte is configured to be immobilized to the support.

Embodiment 6. The kit of Embodiment 5, wherein the recording tag and the analyte are configured to co-localize when both are immobilized to the support.

Embodiment 7. The kit of any of Embodiments 1-6, further comprising an immobilizing linker configured to: (i) be immobilized directly or indirectly to a support, and (ii) associate directly or indirectly with the recording tag and/or the analyte.

Embodiment 8. The kit of Embodiment 7, wherein the immobilizing linker is configured to associate with the recording tag and the analyte.

Embodiment 9. The kit of Embodiment 7 or 8, wherein the immobilizing linker is configured to be immobilized directly to the support, thereby immobilizing the recording tag and/or the analyte which are associated with the immobilizing linker.

Embodiment 10. The kit of any one of Embodiments 2-9, further comprising the support.

Embodiment 11. The kit of any one of Embodiments 1-10, further comprising one or more reagents for transferring information between the coding tag and the recording tag, upon binding between the binding agent and the analyte.

Embodiment 12. The kit of Embodiment 11, wherein the one or more reagents are configured to transfer information from the coding tag to the recording tag, thereby generating an extended recording tag.

Embodiment 13. The kit of Embodiment 11, wherein the one or more reagents are configured to transfer information from the recording tag to the coding tag, thereby generating an extended coding tag.

Embodiment 14. The kit of Embodiment 11, wherein the one or more reagents are configured to generate a di-tag construct comprising information from the coding tag and information from the recording tag.

Embodiment 15. The kit of any one of Embodiments 1-14, which comprises at least two of the recording tags.

Embodiment 16. The kit of any one of Embodiments 1-15, which comprises at least two of the coding tags each comprising identifying information regarding its associated binding moiety.

Embodiment 17. The kit of any one of Embodiments 1-16, which comprises at least two of the binding agents.

Embodiment 18. The kit of Embodiment 17, which comprises: (i) one or more reagents for transferring information from a first coding tag of a first binding agent to the recording tag to generate a first order extended recording tag, upon binding between the first binding agent and the analyte, and/or (ii) one or more reagents for transferring information from a second coding tag of a second binding agent to the first order extended recording tag to generate a second order extended recording tag, upon binding between the second binding agent and the analyte, wherein the one or more reagents of (i) and the one or more reagents of (ii) can be the same or different.

Embodiment 19. The kit of Embodiment 18, which further comprises: (iii) one or more reagents for transferring information from a third (or higher order) coding tag of a third (or higher order) binding agent to the second order extended recording tag to generate a third (or higher order) order extended recording tag, upon binding between the third (or higher order) binding agent and the analyte.

Embodiment 20. The kit of Embodiment 17, which comprises: (i) one or more reagents for transferring information from a first coding tag of a first binding agent to a first recording tag to generate a first extended recording tag, upon binding between the first binding agent and the analyte, and/or (ii) one or more reagents for transferring information from a second coding tag of a second binding agent to a second recording tag to generate a second extended recording tag, upon binding between the second binding agent and the analyte, wherein the one or more reagents of (i) and the one or more reagents of (ii) can be the same or different.

Embodiment 21. The kit of Embodiment 20, which further comprises: (iii) one or more reagents for transferring information from a third (or higher order) coding tag of a third (or higher order) binding agent to a third (or higher order) recording tag to generate a third (or higher order) extended recording tag, upon binding between the third (or higher order) binding agent and the analyte.

Embodiment 22. The kit of Embodiment 20 or 21, wherein the first recording tag, the second recording tag, and/or the third (or higher order) recording tag are configured to associate directly or indirectly with the analyte.

Embodiment 23. The kit of any one of Embodiments 20-22, wherein the first recording tag, the second recording tag, and/or the third (or higher order) recording tag are configured to be immobilized on a support.

Embodiment 24. The kit of any one of Embodiments 20-23, wherein the first recording tag, the second recording tag, and/or the third (or higher order) recording tag are configured to co-localize with the analyte, for example, to allow transfer of information between the first, second, or third (or higher order) coding tag and the first, second, or third (or higher order) recording tag, respectively, upon binding between the first, second, or third (or higher order) binding agent and the analyte.

Embodiment 25. The kit of any one of Embodiments 20-24, wherein each of the first coding tag, the second coding tag, and/or the third (or higher order) coding tag comprises a binding cycle specific barcode, such as a binding cycle specific spacer sequence $C_n$, and/or a coding tag specific spacer sequence $C_n$, wherein n is an integer and $C_n$ indicates binding between the $n^{th}$ binding agent and the polypeptide; or wherein a binding cycle tag $C_n$ is added exogenously, for example, the binding cycle tag $C_n$ may be exogenous to the coding tag(s).

Embodiment 26. The kit of any one of Embodiments 1-25, wherein the analyte comprises a polypeptide.

Embodiment 27. The kit of Embodiment 26, wherein the binding moiety is capable of binding to one or more N-terminal or C-terminal amino acids of the polypeptide, or capable of binding to the one or more N-terminal or C-terminal amino acids modified by a functionalizing reagent.

Embodiment 28. The kit of Embodiment 26 or 27, further comprising the functionalizing reagent.

Embodiment 29. The kit of any one of Embodiments 26-28, further comprising an eliminating reagent for removing (e.g., by chemical cleavage or enzymatic cleavage) the one or more N-terminal, internal, or C-terminal amino acids of the polypeptide, or removing the functionalized N-terminal, internal, or C-terminal amino acid(s), optionally wherein the eliminating reagent comprises a carboxypeptidase or an aminopeptidase or variant, mutant, or modified protein thereof; a hydrolase or variant, mutant, or modified protein thereof; a mild Edman degradation reagent; an Edmanase enzyme; anhydrous TFA, a base; or any combination thereof.

Embodiment 30. The kit of any one of Embodiments 26-29, wherein the one or more N-terminal, internal, or C-terminal amino acids comprise: (i) an N-terminal amino acid (NTAA); (ii) an N-terminal dipeptide sequence; (iii) an N-terminal tripeptide sequence; (iv) an internal amino acid; (v) an internal dipeptide sequence; (vi) an internal tripeptide sequence; (vii) a C-terminal amino acid (CTAA); (viii) a C-terminal dipeptide sequence; or (ix) a C-terminal tripeptide sequence, or any combination thereof, optionally wherein any one or more of the amino acid residues in (i)-(ix) are modified or functionalized.

Embodiment 31. A kit, comprising: at least (a) a first binding agent comprising (i) a first binding moiety capable of binding to an N-terminal amino acid (NTAA) or a functionalized NTAA of a polypeptide to be analyzed, and (ii) a first coding tag comprising identifying information regarding the first binding moiety, optionally (b) a recording tag configured to associate directly or indirectly with the polypeptide, and further optionally (c) a functionalizing reagent capable of modifying a first NTAA of the polypeptide to generate a first functionalized NTAA, wherein the recording tag and the first binding agent are configured to allow transfer of information between the first coding tag and the recording tag, upon binding between the first binding agent and the polypeptide.

Embodiment 32. The kit of Embodiment 31, further comprising one or more reagents for transferring information from the first coding tag to the recording tag, thereby generating a first order extended recording tag.

Embodiment 33. The kit of Embodiment 31 or 32, wherein the functionalizing reagent comprises a chemical agent, an enzyme, and/or a biological agent, such as an isothiocyanate derivative, 2,4-dinitrobenzenesulfonic (DNBS), 4-sulfonyl-2-nitrofluorobenzene (SNFB) 1-fluoro-2,4-dinitrobenzene, dansyl chloride, 7-methoxycoumarin acetic acid, a thioacylation reagent, a thioacetylation reagent, or a thiobenzylation reagent.

Embodiment 34. The kit of any one of Embodiments 31-33, further comprising an eliminating reagent for removing (e.g., by chemical cleavage or enzymatic cleavage) the first functionalized NTAA to expose the immediately adjacent amino acid residue, as a second NTAA.

Embodiment 35. The kit of Embodiment 34, wherein the second NTAA is capable of being functionalized by the same or a different functionalizing reagent to generate a second functionalized NTAA, which may be the same as or different from the first functionalized NTAA.

Embodiment 36. The kit of Embodiment 35, further comprising: (d) a second (or higher order) binding agent comprising (i) a second (or higher order) binding moiety capable of binding to the second functionalized NTAA, and (ii) a second (or higher order) coding tag comprising identifying information regarding the second (or higher order) binding moiety, wherein the first coding tag and the second (or higher order) coding tag can be the same or different.

Embodiment 37. The kit of Embodiment 36, wherein the first functionalized NTAA and the second functionalized NTAA are selected, independent from each other, from the group consisting of a functionalized N-terminal Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

Embodiment 38. The kit of Embodiment 36 or 37, further comprising one or more reagents for transferring information from the second (or higher order) coding tag to the first order extended recording tag, thereby generating a second (or higher order) order extended recording tag.

Embodiment 39. A kit, comprising: at least (a) one or more binding agents each comprising (i) a binding moiety capable of binding to an N-terminal amino acid (NTAA) or a functionalized NTAA of a polypeptide to be analyzed, and (ii) a coding tag comprising identifying information regarding the binding moiety, and/or (b) one or more recording tags configured to associate directly or indirectly with the polypeptide, wherein the one or more recording tags and the one or more binding agents are configured to allow transfer of information between the coding tags and the recording tags, upon binding between each binding agent and the polypeptide, and optionally (c) a functionalizing reagent capable of modifying a first NTAA of the polypeptide to generate a first functionalized NTAA.

Embodiment 40. The kit of Embodiment 39, further comprising an eliminating reagent for removing (e.g., by chemical cleavage or enzymatic cleavage) the first functionalized NTAA to expose the immediately adjacent amino acid residue, as a second NTAA.

Embodiment 41. The kit of Embodiment 40, wherein the second NTAA is capable of being functionalized by the same or a different functionalizing reagent to generate a second functionalized NTAA, which may be the same as or different from the first functionalized NTAA.

Embodiment 42. The kit of Embodiment 41, wherein the first functionalized NTAA and the second functionalized NTAA are selected, independent from each other, from the group consisting of a functionalized N-terminal Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

Embodiment 43. The kit of any one of Embodiments 39-42, which comprises: (i) one or more reagents for transferring information from a first coding tag of a first binding agent to a first recording tag to generate a first extended recording tag, upon binding between the first binding agent and the polypeptide, and/or (ii) one or more reagents for transferring information from a second coding tag of a second binding agent to a second recording tag to generate a second extended recording tag, upon binding between the second binding agent and the polypeptide, wherein the one or more reagents of (i) and the one or more reagents of (ii) can be the same or different.

Embodiment 44. The kit of Embodiment 43, which further comprises: (iii) one or more reagents for transferring information from a third (or higher order) coding tag of a third (or higher order) binding agent to a third (or higher order) recording tag to generate a third (or higher order) extended recording tag, upon binding between the third (or higher order) binding agent and the polypeptide.

Embodiment 45. The kit of Embodiment 43 or 44, wherein the first recording tag, the second recording tag, and/or the third (or higher order) recording tag are configured to associate directly or indirectly with the polypeptide.

Embodiment 46. The kit of any one of Embodiments 43-45, wherein the first recording tag, the second recording tag, and/or the third (or higher order) recording tag are configured to be immobilized on a support.

Embodiment 47. The kit of any one of Embodiments 43-46, wherein the first recording tag, the second recording tag, and/or the third (or higher order) recording tag are configured to co-localize with the polypeptide, for example, to allow transfer of information between the first, second, or third (or higher order) coding tag and the first, second, or third (or higher order) recording tag, respectively, upon binding between the first, second, or third (or higher order) binding agent and the polypeptide.

Embodiment 48. The kit of any one of Embodiments 43-47, wherein each of the first coding tag, the second coding tag, and/or the third (or higher order) coding tag comprises a binding cycle specific barcode, such as a binding cycle specific spacer sequence $C_n$, and/or a coding tag specific spacer sequence $C_n$, wherein n is an integer and $C_n$ indicates binding between the $n^{th}$ binding agent and the polypeptide. Alternatively, a binding cycle tag $C_n$ may be added exogenously, for example, the binding cycle tag $C_n$ may be exogenous to the coding tag(s).

Embodiment 49. The kit of any one of Embodiments 1-48, wherein the analyte or the polypeptide comprises a protein or a polypeptide chain or a fragment thereof, a lipid, a carbohydrate, or a macrocycle.

Embodiment 50. The kit of any one of Embodiments 1-49, wherein the analyte or the polypeptide comprises a macromolecule or a complex thereof, such as a protein complex or subunit thereof.

Embodiment 51. The kit of any one of Embodiments 1-50, wherein the recording tag comprises a nucleic acid, an oligonucleotide, a modified oligonucleotide, a DNA molecule, a DNA with pseudo-complementary bases, a DNA with protected bases, an RNA molecule, a BNA molecule, an XNA molecule, a LNA molecule, a PNA molecule, a γPNA molecule, or a morpholino, or a combination thereof.

Embodiment 52. The kit of any one of Embodiments 1-51, wherein the recording tag comprises a universal priming site.

Embodiment 53. The kit of any one of Embodiments 1-52, wherein the recording tag comprises a priming site for amplification, sequencing, or both, for example, the universal priming site comprises a priming site for amplification, sequencing, or both.

Embodiment 54. The kit of any one of Embodiments 1-53, wherein the recording tag comprises a unique molecule identifier (UMI).

Embodiment 55. The kit of any one of Embodiments 1-54, wherein the recording tag comprises a barcode.

Embodiment 56. The kit of any one of Embodiments 1-55, wherein the recording tag comprises a spacer at its 3'-terminus.

Embodiment 57. The kit of any one of Embodiments 1-56, comprising a solid support, such as a rigid solid support, a flexible solid support, or a soft solid support, and including a porous support or a non-porous support.

Embodiment 58. The kit of any one of Embodiments 1-57, comprising a support comprising a bead, a porous bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

Embodiment 59. The kit of Embodiment 58, wherein the support comprises a polystyrene bead, a polymer bead, an agarose bead, an acrylamide bead, a solid core bead, a porous bead, a paramagnetic bead, glass bead, or a controlled pore bead, or any combination thereof.

Embodiment 60. The kit of any one of Embodiments 1-59, which comprises a support and is for analyzing a plurality of the analytes or the polypeptides, in sequential reactions, in parallel reactions, or in a combination of sequential and parallel reactions.

Embodiment 61. The kit of Embodiment 60, wherein the analytes or the polypeptides are spaced apart on the support at an average distance equal to or greater than about 10 nm, equal to or greater than about 15 nm, equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, or equal to or greater than about 500 nm.

Embodiment 62. The kit of any one of Embodiments 1-61, wherein the binding moiety comprises a polypeptide or fragment thereof, a protein or polypeptide chain or fragment thereof, or a protein complex or subunit thereof, such as an antibody or antigen binding fragment thereof.

Embodiment 63. The kit of any one of Embodiments 1-62, wherein the binding moiety comprises a carboxypeptidase or an aminopeptidase or variant, mutant, or modified protein thereof; an aminoacyl tRNA synthetase or variant, mutant, or modified protein thereof; an anticalin or variant, mutant, or modified protein thereof, a ClpS or variant, mutant, or modified protein thereof, a UBR box protein or variant, mutant, or modified protein thereof, a modified small molecule that binds amino acid(s), i.e. vancomycin or a variant, mutant, or modified molecule thereof; or any combination thereof, or wherein in each binding agent, the binding moiety comprises a small molecule, the coding tag comprises a polynucleotide that identifies the small molecule, whereby a plurality of the binding agents form an encoded small molecule library, such as a DNA-encoded small molecule library.

Embodiment 64. The kit of any one of Embodiments 1-63, wherein the binding moiety is capable of selectively and/or specifically binding to the analyte or the polypeptide.

Embodiment 65. The kit of any one of Embodiments 1-64, wherein the coding tag comprises a nucleic acid, an oligonucleotide, a modified oligonucleotide, a DNA molecule, a DNA with pseudo-complementary bases, a DNA or RNA with one or more protected bases, an RNA molecule, a BNA molecule, an XNA molecule, a LNA molecule, a PNA molecule, a γPNA molecule, or a morpholino, or a combination thereof.

Embodiment 66. The kit of any one of Embodiments 1-65, wherein the coding tag comprises a barcode sequence, such as an encoder sequence, e.g., one that identifies the binding moiety.

Embodiment 67. The kit of any one of Embodiments 1-66, wherein the coding tag comprises a spacer, a binding cycle specific sequence, a unique molecular identifier (UMI), a universal priming site, or any combination thereof, optionally wherein a binding cycle specific sequence is added to the recording tag after each binding cycle.

Embodiment 68. The kit of any one of Embodiments 1-67, wherein the binding moiety and the coding tag are joined by a linker or a binding pair.

Embodiment 69. The kit of any one of Embodiments 1-68, wherein the binding moiety and the coding tag are joined by a SpyTag/SpyCatcher, a SpyTag-KTag/SpyLigase (where two moieties to be joined have the SpyTag/KTag pair, and the SpyLigase joins SpyTag to KTag, thus joining the two moieties), a sortase, a SnoopTag/SnoopCatcher peptide-protein pair, or a HaloTag/HaloTag ligand pair, or any combination thereof.

Embodiment 70. The kit of any one of Embodiments 1-69, further comprising a reagent for transferring information between the coding tag and the recording tag in a templated or non-templated reaction, optionally wherein the reagent is (i) a chemical ligation reagent or a biological ligation reagent, for example, a ligase, such as a DNA ligase or RNA ligase for ligating single-stranded nucleic acid or double-stranded nucleic acid, or (ii) a reagent for primer extension of single-stranded nucleic acid or double-stranded nucleic acid, optionally wherein the kit further comprises a ligation reagent comprising at least two ligases or variants thereof (e.g., at least two DNA ligases, or at least two RNA ligases, or at least one DNA ligase and at least one RNA ligase), wherein the at least two ligases or variants thereof comprises an adenylated ligase and a constitutively non-adenylated ligase, or optionally wherein the kit further comprises a ligation reagent comprising a DNA or RNA ligase and a DNA/RNA deadenylase.

Embodiment 71. The kit of any one of Embodiments 1-70, further comprising a polymerase, such as a DNA polymerase or RNA polymerase or a reverse transcriptase, for transferring information between the coding tag and the recording tag.

Embodiment 72. The kit of any one of Embodiments 1-71, further comprising one or more reagents for nucleic acid sequence analysis.

Embodiment 73. The kit of Embodiment 72, wherein the nucleic acid sequence analysis comprises sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy, or any combination thereof.

Embodiment 74. The kit of any one of Embodiments 1-73, further comprising one or more reagents for nucleic acid amplification, for example, for amplifying one or more extended recording tags, optionally wherein the nucleic acid amplification comprises an exponential amplification reaction (e.g., polymerase chain reaction (PCR), such as an emulsion PCR to reduce or eliminate template switching) and/or a linear amplification reaction (e.g., isothermal amplification by in vitro transcription, or Isothermal Chimeric primer-initiated Amplification of Nucleic acids (ICAN)).

Embodiment 75. The kit of any one of Embodiments 1-74, comprising one or more reagents for transferring coding tag information to the recording tag to form an extended recording tag, wherein the order and/or frequency of coding tag information on the extended recording tag indicates the order and/or frequency in which the binding agent binds to the analyte or the polypeptide.

Embodiment 76. The kit of any one of Embodiments 1-75, further comprising one or more reagents for target enrichment, for example, enrichment of one or more extended recording tags.

Embodiment 77. The kit of any one of Embodiments 1-76, further comprising one or more reagents for subtraction, for example, subtraction of one or more extended recording tags.

Embodiment 78. The kit of any one of Embodiments 1-77, further comprising one or more reagents for normalization, for example, to reduce highly abundant species such as one or more analytes or polypeptides.

Embodiment 79. The kit of any one of Embodiments 1-78, wherein at least one binding agent binds to a terminal amino acid residue, terminal di-amino-acid residues, or terminal triple-amino-acid residues.

Embodiment 80. The kit of any one of Embodiments 1-79, wherein at least one binding agent binds to a post-translationally modified amino acid.

Embodiment 81. The kit of any one of Embodiments 1-80, further comprising one or more reagents or means for partitioning a plurality of the analytes or polypeptides in a sample into a plurality of compartments, wherein each compartment comprises a plurality of compartment tags optionally joined to a support (e.g., a solid support), wherein the plurality of compartment tags are the same within an individual compartment and are different from the compartment tags of other compartments.

Embodiment 82. The kit of Embodiment 81, further comprising one or more reagents or means for fragmenting the plurality of the analytes or polypeptides (such as a plurality of protein complexes, proteins, and/or polypeptides) into a plurality of polypeptide fragments.

Embodiment 83. The kit of Embodiment 81 or 82, further comprising one or more reagents or means for annealing or joining of the plurality of polypeptide fragments with the compartment tag within each of the plurality of compartments, thereby generating a plurality of compartment tagged polypeptide fragments.

Embodiment 84. The kit of any one of Embodiments 81-83, wherein the plurality of compartments comprise a microfluidic droplet, a microwell, or a separated region on a surface, or any combination thereof.

Embodiment 85. The kit of any one of Embodiments 81-84, wherein each of the plurality of compartments comprises on average a single cell.

Embodiment 86. The kit of any one of Embodiments 81-85, further comprising one or more universal DNA tags for labeling the plurality of the analytes or polypeptides in the sample.

Embodiment 87. The kit of any one of Embodiments 81-86, further comprising one or more reagents for labeling the plurality of the analytes or polypeptides in the sample with one or more universal DNA tags.

Embodiment 88. The kit of any one of Embodiments 81-87, further comprising one or more reagents for primer extension or ligation.

Embodiment 89. The kit of any one of Embodiments 81-88, wherein the support comprises a bead, such as a polystyrene bead, a polymer bead, an agarose bead, an acrylamide bead, a solid core bead, a porous bead, a paramagnetic bead, glass bead, or a controlled pore bead, or any combination thereof.

Embodiment 90. The kit of any one of Embodiments 81-89, wherein the compartment tag comprises a single stranded or double stranded nucleic acid molecule.

Embodiment 91. The kit of any one of Embodiments 81-90, wherein the compartment tag comprises a barcode and optionally a UMI.

Embodiment 92. The kit of any one of Embodiments 81-91, wherein the support is a bead and the compartment tag comprises a barcode.

Embodiment 93. The kit of any one of Embodiments 81-92, wherein the support comprises a bead, and wherein beads comprising the plurality of compartment tags joined thereto are formed by split-and-pool synthesis, individual synthesis, or immobilization.

Embodiment 94. The kit of any one of Embodiments 81-93, further comprising one or more reagents for split-and-pool synthesis, individual synthesis, or immobilization.

Embodiment 95. The kit of any one of Embodiments 81-94, wherein the compartment tag is a component within a recording tag, wherein the recording tag optionally further comprises a spacer, a barcode sequence, a unique molecular identifier, a universal priming site, or any combination thereof.

Embodiment 96. The kit of any one of Embodiments 81-95, wherein the compartment tags further comprise a functional moiety capable of reacting with an internal amino acid, the peptide backbone, or N-terminal amino acid on the plurality of analytes or polypeptides (such as protein complexes, proteins, or polypeptides).

Embodiment 97. The kit of Embodiment 96, wherein the functional moiety comprises an aldehyde, an azide/alkyne, a malemide/thiol, an epoxy/nucleophile, an inverse Electron Demand Diels-Alder (iEDDA) group, a click reagent, or any combination thereof.

Embodiment 98. The kit of any one of Embodiments 81-97, wherein the compartment tag further comprises a peptide, such as a protein ligase recognition sequence, optionally wherein the protein ligase is butelase I or a homolog thereof.

Embodiment 99. The kit of any one of Embodiments 81-98, further comprising a chemical or biological reagent, such as an enzyme, for example, a protease (e.g., a metalloprotease), for fragmenting the plurality of analytes or polypeptides.

Embodiment 100. The kit of any one of Embodiments 81-99, further comprising one or more reagents for releasing the compartment tags from the support.

Embodiment 101. The kit of any one of Embodiments 1-100, further comprising one or more reagents for forming an extended coding tag or a di-tag construct.

Embodiment 102. The kit of Embodiment 101, wherein the 3'-terminus of the recording tag is blocked to prevent extension of the recording tag by a polymerase.

Embodiment 103. The kit of Embodiment 101 or 102, wherein the coding tag comprises an encoder sequence, a UMI, a universal priming site, a spacer at its 3'-terminus, a binding cycle specific sequence, or any combination thereof.

Embodiment 104. The kit of any one of Embodiments 101-103, wherein the di-tag construct is generated by gap fill, primer extension, or a combination thereof.

Embodiment 105. The kit of any one of Embodiments 101-104, wherein the di-tag molecule comprises a universal priming site derived from the recording tag, a compartment tag derived from the recording tag, a unique molecular identifier derived from the recording tag, an optional spacer derived from the recording tag, an encoder sequence derived from the coding tag, a unique molecular identifier derived from the coding tag, an optional spacer derived from the coding tag, and a universal priming site derived from the coding tag.

Embodiment 106. The kit of any one of Embodiments 101-105, wherein the binding agent is a polypeptide or protein.

Embodiment 107. The kit of any one of Embodiments 101-106, wherein the binding agent comprises an aminopeptidase or variant, mutant, or modified protein thereof, an aminoacyl tRNA synthetase or variant, mutant, or modified protein thereof, an anticalin or variant, mutant, or modified protein thereof, a ClpS or variant, mutant, or modified protein thereof, or a modified small molecule that binds amino acid(s), i.e. vancomycin or a variant, mutant, or modified molecule thereof, or an antibody or binding fragment thereof, or any combination thereof.

Embodiment 108. The kit of any one of Embodiments 101-107, wherein the binding agent binds to a single amino acid residue (e.g., an N-terminal amino acid residue, a C-terminal amino acid residue, or an internal amino acid residue), a dipeptide (e.g., an N-terminal dipeptide, a C-terminal dipeptide, or an internal dipeptide), a tripeptide (e.g., an N-terminal tripeptide, a C-terminal tripeptide, or an internal tripeptide), or a post-translational modification of the analyte or polypeptide.

Embodiment 109. The kit of any one of Embodiments 101-107, wherein the binding agent binds to an N-terminal polypeptide, a C-terminal polypeptide, or an internal polypeptide.

Embodiment 110. The kit of any one of Embodiments 1-109, wherein the coding tag and/or the recording tag comprise one or more error correcting codes, one or more encoder sequences, one or more barcodes, one or more UMIs, one or more compartment tags, one or more cycle specific sequences, or any combination thereof.

Embodiment 111. The kit of Embodiment 110, wherein the error correcting code is selected from Hamming code, Lee distance code, asymmetric Lee distance code, Reed-Solomon code, and Levenshtein-Tenengolts code.

Embodiment 112. The kit of any one of Embodiments 1-111, wherein the coding tag and/or the recording tag comprise a cycle label.

Embodiment 113. The kit of any one of Embodiments 1-112, further comprising a cycle label independent of the coding tag and/or the recording tag.

Embodiment 114. The kit of any one of Embodiments 1-113, which comprises: (a) a reagent for generating a cell lysate or a protein sample; (b) a reagent for blocking an amino acid side chain, such as via alkylation of cysteine or blocking lysine; (c) a protease, such as trypsin, LysN, or LysC; (d) a reagent for immobilizing a nucleic acid-labeled polypeptide (such as a DNA-labeled protein) to a support; (e) a reagent for degradation-based polypeptide sequencing; and/or (f) a reagent for nucleic acid sequencing.

Embodiment 115. The kit of any one of Embodiments 1-113, which comprises: (a) a reagent for generating a cell lysate or a protein sample; (b) a reagent for blocking an amino acid side chain, such as via alkylation of cysteine or blocking lysine; (c) a protease, such as trypsin, LysN, or LysC; (d) a reagent for immobilizing a polypeptide (such as a protein) to a support comprising immobilized recording tags; (e) a reagent for degradation-based polypeptide sequencing; and/or (f) a reagent for nucleic acid sequencing.

Embodiment 116. The kit of any one of Embodiments 1-113, which comprises: (a) a reagent for generating a cell lysate or a protein sample; (b) a denaturing reagent; (c) a reagent for blocking an amino acid side chain, such as via alkylation of cysteine or blocking lysine; (d) a universal DNA primer sequence; (e) a reagent for labeling a polypeptide with a universal DNA primer sequence; (f) a barcoded bead for annealing the labeled polypeptide via a primer; (g) a reagent for polymerase extension for writing the barcode from the bead to the labeled polypeptide; (h) a protease, such as trypsin, LysN, or LysC; (i) a reagent for immobilizing a nucleic acid-labeled polypeptide (such as a DNA-labeled protein) to a support; (j) a reagent for degradation-based polypeptide sequencing; and/or (k) a reagent for nucleic acid sequencing.

Embodiment 117. The kit of any one of Embodiments 1-113, which comprises: (a) a cross-linking reagent; (b) a reagent for generating a cell lysate or a protein sample; (c) a reagent for blocking an amino acid side chain, such as via alkylation of cysteine or blocking lysine; (d) a universal DNA primer sequence; (e) a reagent for labeling a polypeptide with a universal DNA primer sequence; (f) a barcoded bead for annealing the labeled polypeptide via a primer; (g) a reagent for polymerase extension for writing the barcode from the bead to the labeled polypeptide; (h) a protease, such as trypsin, LysN, or LysC; (i) a reagent for immobilizing a nucleic acid-labeled polypeptide (such as a DNA-labeled protein) to a support; (j) a reagent for degradation-based polypeptide sequencing; and/or (k) a reagent for nucleic acid sequencing.

Embodiment 118. The kit of any one of Embodiments 1-117, wherein one or more components are provided in a solution or on a support, for example, a solid support.

V. EXAMPLES

The following examples are included for illustrative purposes only and are not intended to limit the scope of the invention.

Example 1: Digestion of Protein Sample with Proteinase K

A library of peptides is prepared from a protein sample by digestion with a protease such as trypsin, Proteinase K, etc. Trypsin cleaves for example at the C-terminal side of positively charged amino acids like lysine and arginine, whereas Proteinase K cleaves non-selectively across the protein. As such, Proteinase K digestions require careful titration using a preferred enzyme-to-polypeptide ratio to provide sufficient proteolysis to generate short peptides (~30 amino acids), but not over-digest the sample. In general, a titration of the functional activity needs to be performed for a given Proteinase K lot. In this example, a protein sample is digested with proteinase K, for 1 h at 37° C. at a 1:10-1:100 (w/w) enzyme:protein ratio in 1×PBS/1 mM EDTA/0.5 mM CaCl2/0.5% SDS (pH 8.0). After incubation, PMSF is added to a 5 mM final concentration to inhibit further digestion.

The specific activity of Proteinase K can be measured by incubating the "chemical substrate" benzoyl arginine-p-nitroanilide with Proteinase K and measuring the development of the yellow colored p-nitroaniline product that absorbs at ~410 nm. Enzyme activity is measured in units, where one unit equals 1 µmole of p-nitroanilide produced/min, and specific activity is measured in units of enzyme activity/mg total protein. The specific activity is then calculated by dividing the enzyme activity by the total amount of protein in the solution.

Example 2: Sample Prep Using Sp3 on Bead Protease Digestion and Labeling

Proteins are extracted and denatured using an SP3 sample prep protocol as described by Hughes et al. (2014, Mol Syst Biol 10:757). After extraction, the protein mix (and beads) is solubilized in 50 mM borate buffer (pH 8.0) w/ 1 mM EDTA supplemented with 0.02% SDS at 37° C. for 1 hr. After protein solubilization, disulfide bonds are reduced by adding DTT to a final concentration of 5 mM, and incubating the sample at 50° C. for 10 min. The cysteines are alkylated by addition of iodoacetamide to a final concentration of 10 mM and incubated in the dark at room temperature for 20 min. The reaction is diluted two-fold in 50 mM borate buffer, and Glu-C or Lys-C is added in a final proteinase:protein ratio of 1:50 (w/w). The sample is incubated at 37° C. o/n (~16 hrs.) to complete digestion. After sample digestion as described by Hughes et al. (supra), the peptides are bound to the beads by adding 100% acetonitrile to a final concentration of 95% acetonitrile and washed with acetonitrile in an 8 min. incubation. After washing, peptides are eluted off the beads in 10 µl of 2% DMSO by a 5 min. pipette mixing step.

Example 3: Coupling of the Recording Tag to the Peptide

A DNA recording tag is coupled to a peptide in several ways (see, Aslam et al., 1998, Bioconjugation: Protein Coupling Techniques for the Biomedical Sciences, Macmillan Reference LTD; Hermanson G T, 1996, Bioconjugate Techniques, Academic Press Inc., 1996). In one approach, an oligonucleotide recording tag is constructed with a 5' amine that couples to the C-terminus of the peptide using carbodiimide chemistry, and an internal strained alkyne, DBCO-dT (Glen Research, VA), that couples to azide beads using click chemistry. The recording tag is coupled to the peptide in solution using large molar excess of recording tag to drive the carbodiimide coupling to completion, and limit peptide-peptide coupling. Alternatively, the oligonucleotide is constructed with a 5' strained alkyne (DBCO-dT), and is coupled to an azide-derivitized peptide (via azide-PEG-amine and carbodiimide coupling to C-terminus of peptide), and the coupled to aldehyde-reactive HyNic hydrazine beads. The recording tag oligonucleotide can easily be labeled with an internal aldehyde formylindole (Trilink) group for this purpose. Alternatively, rather than coupling to the C-terminal amine, the recording tags can instead be coupled to internal lysine residues (for example after a Lys-C digest, or alternatively a Glu-C digest). In one approach, this can be accomplished by activating the lysine amine with an NHS-azide (or NHS-PEG-azide) group and then coupling to a 5' amine-labeled recording tag. In another approach, a 5' amine-labeled recording tag can be reacted with excess NHS homo-bifunctional cross-linking reagents, such as DSS, to create a 5' NHS activated recording tag. This 5' NHS activated recording tag can be directly coupled to the δ-amino group of the lysine residues of the peptide.

Example 4: Site-Specific Labeling of Amino Acids on a Peptide

Amino acids can be site-selectively modified with DNA tags either directly or indirectly. For direct labeling, DNA tags can be activated with site-selective chemistries, or alternatively for indirect labeling a heterobifunctional chemistry can be used to convert a specific amino acid reactive moiety to a universal click chemistry to which a DNA tag can later be attached (Lundblad 2014). In one instance, examples of labeling five different amino acids site-selectively are described—five different examples of amino acids on proteins or peptides can be modified directly with activated DNA tags (using activation with heterobifunctional amino acid site-specific reagents) or indirectly via click chemistry heterobifunctional reagent that site-specifically labels amino acids with a click moiety that is later used to attach a cognate click moiety on the DNA tag.

A typical protein input comprises 1 pg protein in 50 µl appropriate aqueous buffer containing 0.1% RapiGest™ SF surfactant, and 5 mM TCEP. RapiGest™ SD is useful as an acid degradable surfactant for denaturing proteins into polypeptides for improving labeling or digestion. The following amino acid labeling strategies can be used: cysteines using maleimide chemistry—200 pM Sulfo-SMCC-activated DNA tags are used to site-specifically label cysteines in 100 mM MES buffer (pH 6.5)+1% TX-100 for 1 hr.; lysines using NHS chemistry—200 µM DSS or $BS^3$-activated DNA tags are used to site-specifically label lysine on solution phase proteins or the bead-bound peptides in borate buffer (50 mM, pH 8.5)+1% TX-100 for 1 hr. at room temp; tyrosine is modified with 4-Phenyl-3H-1,2,4-triazoline-3,5 (4H)-diones (PTAD) or diazonium chemistry—for diazonium chemistry, DNA Tags are activated with EDC and 4-carboxylbenzene diazonium tetrafluoroborate (Aikon International, China). The diazo linkage with tyrosine is created by incubating the protein or bead-bound peptides with 200 µM diazonium-derivitized DNA tags in borate buffer (50 mM, pH 8.5)+1% TX-100 for 1 h on ice (Nguyen, Cao et al. 2015). Aspartate/glutamate is modified using EDC chemistry—an amine-labeled DNA tag is incubated with the bead-bound peptides and 100 mM EDC/50 mM imidazole in pH 6.5 MES for 1 hr. at room temperature (Basle et al., 2010, Chem. Biol. 17:213-227). After labeling, excess activated DNA tags are removed using protein binding elution from $C_4$ resin ZipTips (Millipore). The eluted proteins are brought up 50 µl 1×PBS buffer.

Example 5: Immobilizing Strained Alkyne Recording Tag-Labeled Peptides to Azide-Activated Beads Azide-derivitized Dynabeads® M-270 beads are generated by reacting commercially-available amine Dynabeads® M-270 with an azide PEG NHS ester heterobifunctional linker (JenKem Technology, TX). Moreover, the surface density of azide can be titrated by mixing in methoxy or hydroxyl PEG NHS ester in the appropriate ratio. For a given peptide sample, 1-2 mg azide-derivitized Dynabeads® M-270 beads (~$1.3 \times 10^8$ beads) is diluted in 100 µl borate buffer (50 mM sodium borate, pH 8.5), 1 ng recording tag-peptide is added, and incubated for 1 hr. at 23-37° C. Wash 3× with 200 µl borate buffer.

Example 6: Creating Formylindole Reactive Hynic Beads

HyNic derivitization of amine beads creates formylindole reactive beads. An aliquot of 20 mg Dynabeads® M-270 Amine beads (2.8 µm) beads are suspended in 200 µl borate buffer. After a brief sonication, 1-2 mg Sulfo-S-HyNic (succinimidyl 6-hydrazinonicotinate acetone hydrazone, SANH) (Catalog #5-1002, Solulink, San Diego) is added and the reaction mixture is shaken for 1 hr. at room temperature. The beads are then washed 2× with borate buffer, and 1× with citrate buffer (200 mM sodium citrate). The beads are suspended in a final concentration of 10 mg/ml in citrate buffer.

Example 7: Immobilizing Recording Tag Formlindole-Labeled Peptides to Activated Beads An aliquot of 1-2 mg HyNic activated Dynabeads® M-270 beads (~1.3×10$^8$ beads) are diluted in 100 µl citrate buffer supplemented with 50 mM aniline, ~1 ng recording tag peptide conjugate is added and incubated for 1 hr. at 37° C. The beads are washed 3× with 200 µl citrate buffer, and re-suspended in 100 µl borate buffer.

Figure 24A:
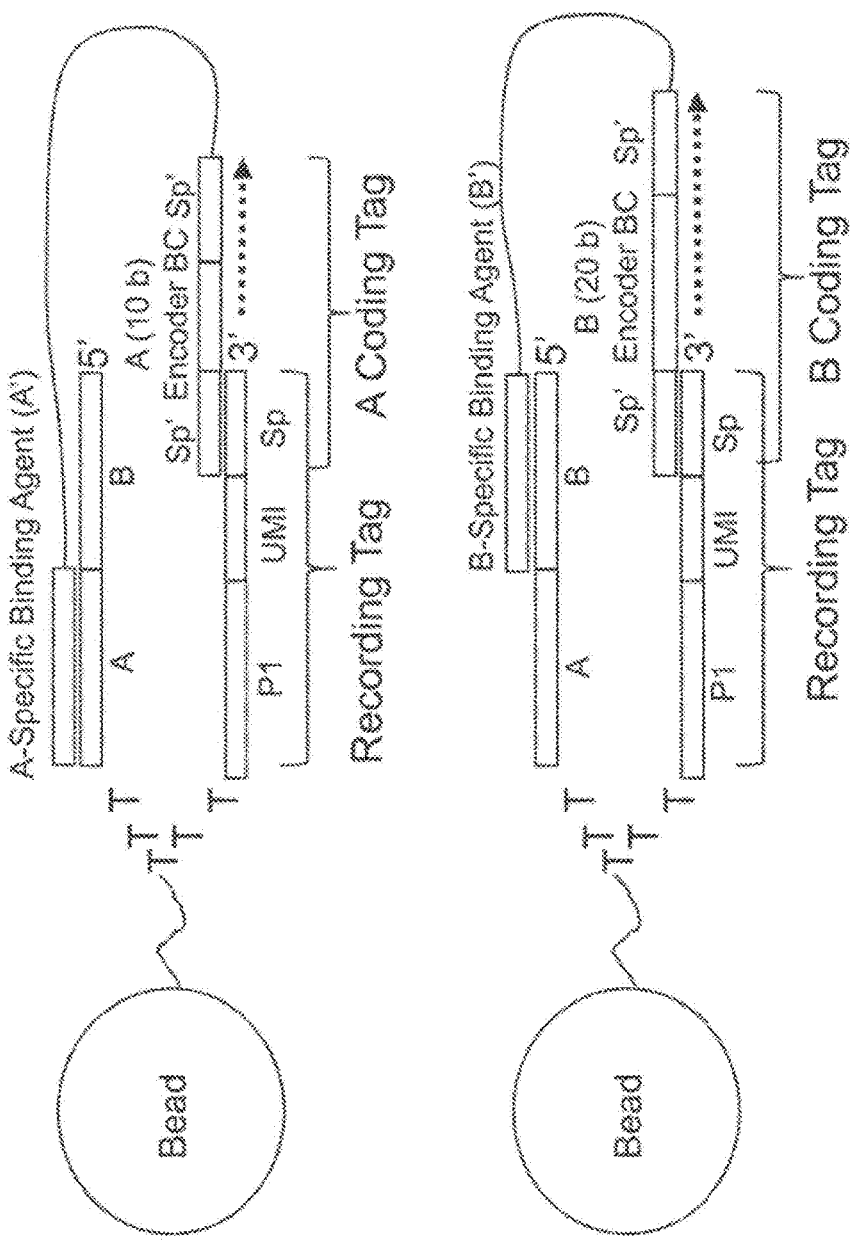
FIG. 24A-24B illustrate two different exemplary DNA target analytes (AB and CD) that are immobilized on beads and assayed by binding agents attached to coding tags. This model system serves to illustrate the single molecule behavior of coding tag transfer from a bound agent to a proximal reporting tag. In the preferred embodiment, the coding tags are incorporated into an extended recoding tag via primer extension.

Example 8: Oligonucleotide Model System—Recording of Binding Agent History by Transfer of Identifying Information of Coding Tag to Recording Tag in Cyclic Fashion For nucleic acid coding tags and recording tags, information can be transferred from the coding tag on the bound binding agent to the proximal recording tag by ligation or primer extension using standard nucleic acid enzymology. This can be demonstrated with a simple model system consisting of an oligonucleotide with the 5' portion representing the binding agent target, and the 3' portion representing the recording tag. The oligonucleotide can be immobilized at an internal site using click chemistry through a dT-alkyne modification (DBCO-dT, Glen Research). In the example shown in FIG. 24A, the immobilized oligonucleotide (AB target) contains two target binding regions, labeled A and B, to which cognate oligonucleotide "binding agents" can bind, the A oligo and the B oligo. The A oligo and B oligonucleotides are linked to coding tags (differing in sequence and length) which interact with the recording tag through a common spacer (Sp) to initiate primer extension (or ligation). The length of Sp should be kept short (e.g., 6-9 bases) to minimize non-specific interaction during binding agent binding. In this particular example, the length of the coding tag is designed to easily distinguish by gel analysis an "A" oligo binding event (10 base encoder sequence) from a "B" oligo binding event (20 base encoder sequence).

Figure 24B:
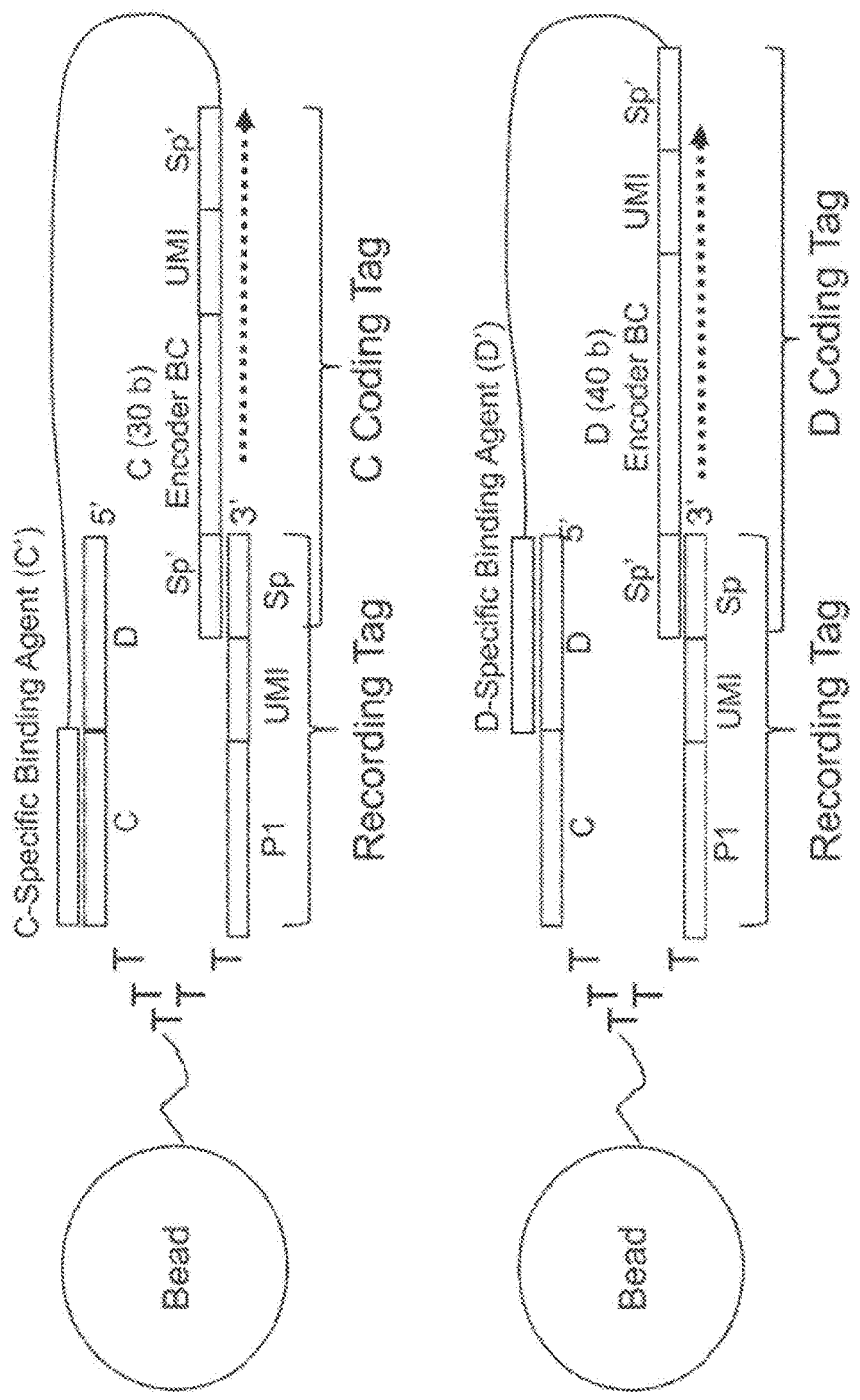

Simple analysis on a PAGE gel enables measurement of the efficiency of A or B coding tag transfer, and allows easy optimization of experimental parameters. In addition to the AB target sequence, a similar oligonucleotide CD target sequence is employed (see, e.g., FIG. 24B), except C and D are different hybridization sequences non-interacting with A and B. Furthermore, C and D contain coding tags of differing sequences and lengths, comprising a 30 base DNA code and 40 base DNA code, respectively. The purpose of the second target sequence, CD, is to assess cross interaction between the AB and CD target molecules. Given specific hybridization, the extended recording tag for the CD target should not contain A or B coding tag information unless intermolecular crossing occurs between the A or B coding tags connected to oligos bound to the AB target. Likewise, the extended recording tag for the AB target should contain no C or D coding tag information. In the situation where the AB and CD targets are in close physical proximity (i.e., <50 nm), there is likely to be cross talk. Therefore, it is important to appropriately space out the target macromolecules on the surface.

Figure 25:
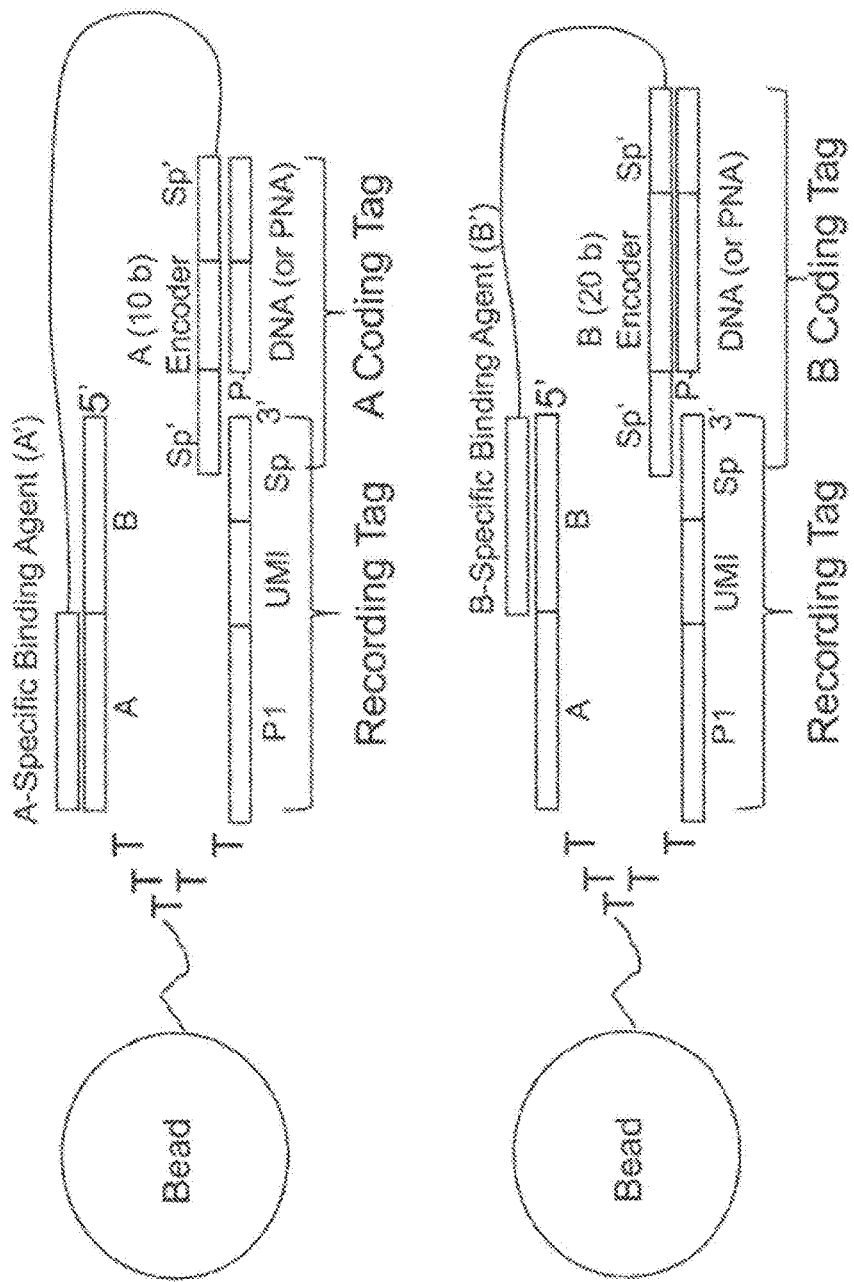
FIG. 25 illustrates exemplary DNA target macromolecules (AB) and immobilized on beads and assayed by binding agents attached to coding tags. An A-specific binding agent ("A"', oligonucleotide complementary to A component of AB macromolecule) interacts with an AB macromolecule and information of an associated coding tag is transferred to a recording tag by ligation. A B-specific binding agent ("B"', an oligonucleotide complementary to B component of AB macromolecule) interacts with an AB macromolecule and information of an associated coding tag is transferred to a recording tag by ligation. Coding tags A and B are of different sequence and for ease of identification in this illustration are also of different length. The different lengths facilitate analysis of coding tag transfer by gel electrophoresis, but are not required for analysis by next generation sequencing. In any of the examples shown in this figure, the encoding tag and/or the recording tag (and/or the di-tag, the compartment tag, or the partition tag, if applicable), or any portion thereof (e.g., a universal primer, a spacer, a UMI, a recording tag barcode, an encoder sequence, a binding cycle-specific barcode, etc.), may comprise or be replaced with a sequenceable polymer, such as a non-nucleic acid sequenceable polymer.

This oligonucleotide model system enables a full characterization of the recording capability of binding agent history. FIG. 25 illustrates information transfer via ligation rather than primer extension. After initial optimization on gels, various binding and assay protocols are performed and assessed by sequencing. A unique molecular identifier (UMI) sequence is used for counting purposes, and enables identification of reads originating from a single macromolecule and provides a measure of overall total macromolecule complexity in the original sample. Exemplary historical binding protocols include: A-B-C-B-A, A-B-A-A-B-A, A-B-C-D-A-C, etc. The resultant final products should read: UMI-Sp-A-Sp-B-Sp-B-Sp-A-Sp+UMI-Sp-C-Sp; UMI-Sp-A-Sp-B-Sp-A-Sp-A-Sp-B-Sp-A; UMI-A-Sp-B-Sp-A+UMI-Sp-C-Sp-D-Sp-C-Sp, respectively. The results of this analysis allow further optimization.

Figure 26A:
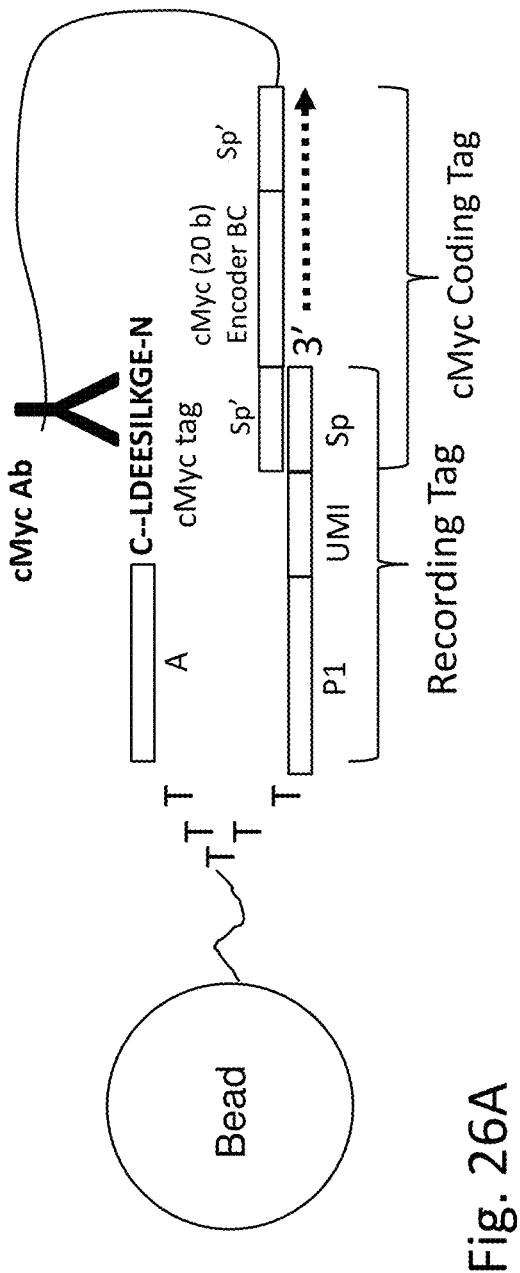
FIG. 26A-26B illustrate exemplary DNA-peptide analytes (such as macromolecules) for binding/coding tag transfer via primer extension.
Figure 26B:
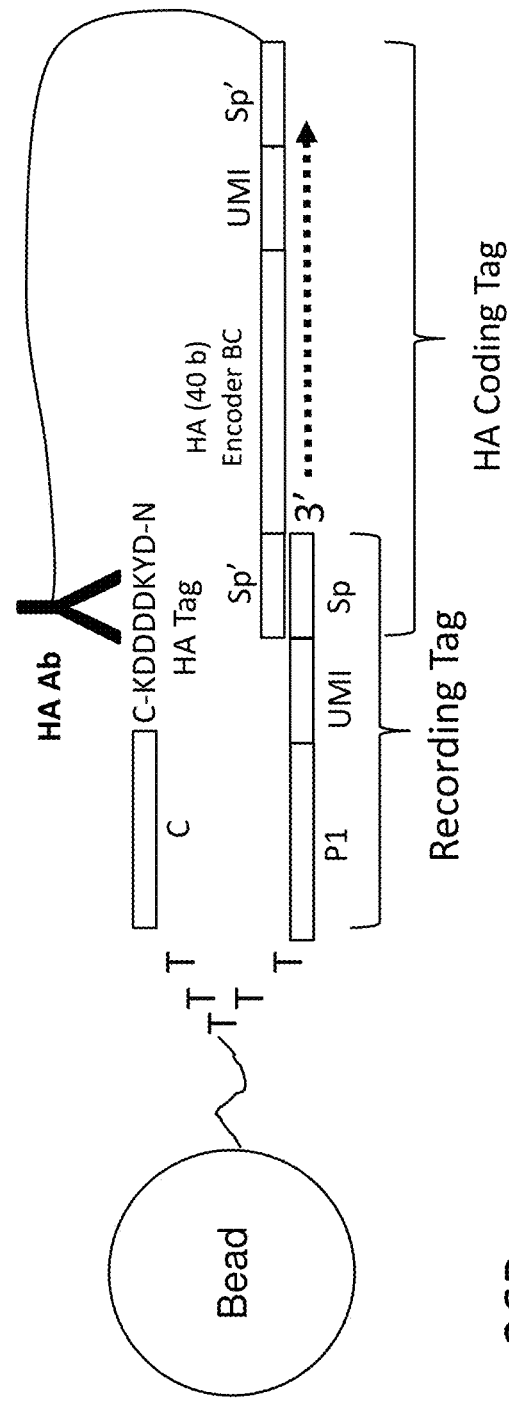

Example 9: Oligonucleotide-Peptide Model System—Recording of Binding Agent History by Transfer of Identifying Information of Coding Tag to Recording Tag in Cyclic Fashion After validating the oligonucleotide model system, a peptide model system is constructed from the oligonucleotide system by conjugating a peptide epitope tag to the 5' end of the exemplary target oligonucleotide sequence (see, e.g., FIG. 26A and FIG. 26B). Exemplary peptide epitope tags include: FLAG (DYKDDDDK) (SEQ ID NO: 171), V5 (GKPIPNPLLGLDST) (SEQ ID NO: 172), c-Myc (EQKLISEEDL) (SEQ ID NO: 173), HA (YPYDVPDYA) (SEQ ID NO: 174), V5 (GKPIPNPLLGLDST) (SEQ ID NO: 175), StrepTag II (NWSHPQFEK) (SEQ ID NO: 176), etc. An optional Cys-Ser-Gly linker can be included for coupling of the peptide epitope tag to the oligonucleotide. The AB oligonucleotide template of Example 7 is replaced with an A_oligonucleotide-cMyc peptide construct, and the CD oligonucleotide template of Example 7 is replaced with an C_oligonucleotide-HA peptide construct (see, e.g., FIG. 26A-B). The A_oligonucleotide-cMyc peptide construct also contains a CSG linker and N-terminal phosphotyrosine. Likewise, the cognate peptide binding agents, cMyc antibody and HA antibody, are tagged with the B oligonucleotide coding tag, and D oligonucleotide coding tag, respectively. The phosphotyrosine specific antibody is tagged with a separate "E" coding tag. In this way, the peptide model system parallels the oligonucleotide system, and both oligo binding and antibody binding are tested in this model system.

Antibody staining of the immobilized DNA-peptide construct using anti-c-myc antibody (2G8D5, mouse monoclonal, GenScript), anti-HA antibody (5E11D8, mouse monoclonal, GenScript), strep-tag II antibody (5A9F9, mouse monoclonal, GenScript), or anti-FLAG antibody (5AE85, mouse monoclonal, GenScript) is performed using 0.1-1 µg/ml in 1×PBST (PBS+0.1% Tween 20). Incubations are typically done at room temperature for 30 min. Standard pre-blocking using 1% PVP in 1×PBST, and post-stain washing are also performed. Antibody de-staining is effectively accomplished by washing with a high salt (1 M NaCl), and either low pH (glycine, pH 2.5) or high pH (triethylamine, pH 11.5).

The target oligonucleotide contains an internal alkyne label for attachment to azide beads, and the 5' terminus contains an amino group for an SMCC-mediated attachment to a C-terminal cysteine of the peptide as described by Williams et al. (2010, Curr Protoc Nucleic Acid Chem. Chapter 4: Unit 4.41). Alternatively, standard carbodiimide coupling is used for a conjugation reaction of the oligonucleotide and peptide (Lu et al., 2010, Bioconjug. Chem. 21:187-202). In this case, an excess of oligo is used to drive the carbodiimide reaction and minimized peptide-peptide coupling. After conjugation, the final product is purified by excision and elution from a PAGE gel.

Example 10: Coding Tag Transfer Via Ligation of DNA/PNA Coding Tag Complement to Recording Tag A coding tag is transferred either directly or indirectly by ligation to the recording tag to generate an extended recording tag. In one implementation, an annealed complement of the coding tag is ligated to the recording tag (see, e.g., FIG. 25). This coding tag complement can either be a nucleic acid (DNA or RNA), peptide nucleic acid (PNA), or some other coding molecule capable of being ligated to a growing recording tag. The ligation can be enzymatic in the case of DNA and RNA using standard ATP-dependent and NADH-dependent ligases, or ligation can be chemical-mediated for both DNA/RNA and especially the peptide nucleic acid, PNA.

For enzymatic ligation of DNA, the annealed coding tag requires a 5' phosphate to ligate to the 3' hydroxyl of the recording tag. Exemplary enzymatic ligation conditions are as follows (Gunderson, Huang et al. 1998): The standard T4 DNA ligation reaction includes: 50 mM Tris-HCl (pH 7.8), 10 mM $MgCl_2$, 10 mM DTT, 1 mM ATP, 50 µg/ml BSA, 100 mM NaCl, 0.1% TX-100 and 2.0 U/µl T4 DNA ligase (New England Biolabs). E. coli DNA ligase reaction includes 40 mM Tris-HCl (pH 8.0), 10 mM $MgCl_2$, 5 mM DTT, 0.5 mM NADH, 50 µg/ml BSA, 0.1% TX-100, and 0.025 U/µl E. coli DNA ligase (Amersham). Taq DNA ligation reaction includes 20 mM Tris-HCl (pH 7.6), 25 mM potassium acetate, 10 mM magnesium acetate, 10 mM DTT, 1 mM NADH, 50 µg/ml BSA, 0.1% Triton X-100, 10% PEG, 100 mM NaCl, and 1.0 U/µl Taq DNA ligase (New England Biolabs). T4 and E. coli DNA ligase reactions are performed at room temperature for 1 hr., and Taq DNA ligase reactions are performed at 40° C. for 1 hr.

Several methods of chemical ligation of templated of DNA/PNA can be employed for DNA/PNA coding tag transfer. These include standard chemical ligation and click chemistry approaches. Exemplary chemical ligation conditions for template DNA ligation is as follows (Gunderson, Huang et al. 1998): ligation of a template 3' phosphate reporter tag to a 5' phosphate coding tag takes place within 1 hr. at room temperature in a reaction consisting of 50 mM 2-[N-morpholino]ethanesulfonic acid (MES) (pH 6.0 with KOH), 10 mM $MgCl_2$, 0.001% SDS, freshly prepared 200 mM EDC, 50 mM imidazole (pH 6.0 with HCl) or 50 mM HOBt (pH 6.0 with HCl) and 3.0-4.0 M TMACl (Sigma).

Exemplary conditions for template-dependent ligation of PNA include ligation of $NH_2$-PNA-CHO polymers (e.g., coding tag complement and extended recorder tag) and are described by Brudno et al. (Brudno, Birnbaum et al. 2010). PNA has a 5' amine equivalent and a 3' aldehyde equivalent wherein chemical ligation couples the two moieties to create a Schiff base which is subsequently reduced with sodium cyanoborohydride. The typical reaction conditions for this coupling are: 100 mM TAPS (pH 8.5), 80 mM NaCl, and 80 mM sodium cyanoborohydride at room temperature for 60 min. Exemplary conditions for native chemical ligation using functionalized PNAs containing 5' amino terminal 1,2-aminothiol modifications and 3' C-terminal thioester modifications is described by Roloff et al. (2014, Methods Mol. Biol. 1050:131-141). Other N- and C-terminal PNA moieties can also be used for ligation. Another example involves the chemical ligation of PNAs using click chemistry. Using the approach of Peng et al. (2010, European J. Org. Chem. 2010: 4194-4197), PNAs can be derivitized with 5' azide and 3' alkyne and ligated using click chemistry. An exemplary reaction condition for the "click" chemical ligation is: 1-2 mg beads with templated PNA-PNA in 100 µl of reaction mix containing 10 mM potassium phosphate buffer, 100 mM KCl, 5 mM THPTA (tris-hydroxypropyl trizolyl amine), 0.5 mM $CuSO_4$, and 2.5 mM Na-ascorbate. The chemical ligation reaction is incubated at room temperature for 1 hr. Other exemplary methods of PNA ligation are described by Sakurai et al. (Sakurai, Snyder et al. 2005).

Example 11: PNA Translation to DNA

PNA is translated into DNA using click chemistry-mediated polymerization of DNA oligonucleotides annealed onto the PNA template. The DNA oligos contain a reactive 5' azide and 3' alkyne to create an inter-nucleotide triazole linkage capable of being replicated by DNA polymerases (El-Sagheer et al., 2011, Proc. Natl. Acad. Sci. USA 108: 11338-11343). A complete set of DNA oligos (10 nM, in 1× hybridization buffer: 10 mM Na-borate (pH 8.5), 0.2 M NaCl) complementary to all possible coding tags in the PNA is incubated (23-50° C.) for 30 minutes with the solid-phase bound PNA molecules. After annealing, the solid-phase bound PNA-DNA constructs are washed 1× with sodium ascorbate buffer (10 mM sodium ascorbate, 200 mM NaCl). The 'click chemistry' reaction conditions are as follows: PNA-DNA on beads are incubated in fresh sodium ascorbate buffer and combined 1:1 with a mix of 10 mM THPTA+2 mM $CuSO_4$ and incubated for 1 hr. at room temperature. The beads are then washed 1× with hybridization buffer and 2× with PCR buffer. After chemical ligation, the resultant ligated DNA product is amplified by PCR under conditions as described by El-Sagheer et al. (2011, Proc. Natl. Acad. Sci. USA 108:11338-11343).

Example 12: Mild N-Terminal Edman Degradation Compatible with Nucleic Acid Recording and Coding Tags Compatibility between N-terminal Edman degradation and DNA encoding allows this approach to work for peptide sequencing. The standard conditions for N-terminal Edman degradation, employing anhydrous TFA, destroys DNA. However, this effect is mitigated by developing milder cleavage conditions and developing modified DNA with greater acid resistance. Milder conditions for N-terminal Edman degradation are developed using a combination of cleavage optimization of phenylthiocarbamoyl (PTC)-peptides and measured stability of DNA/PNA encoded libraries under the cleavage conditions. Moreover, native DNA can be stabilized against acid hydrolysis, by using base modifications, such as 7-deaza purines which reduce depurination at low pH, and 5' methyl modified cytosine which reduces depyrimidation (Schneider and Chait, 1995, Nucleic Acids Res. 23:1570-1575). T-rich coding tags may also be useful given that thymine is the most stable base to acid fragmentation. The conditions for mild N-terminal Edman degradation replace anhydrous TFA cleavage with a mild 10 min. base cleavage using triethylamine acetate in acetonitrile at 60° C. as described by Barrett et al. (1985, Tetrahedron Lett. 26:4375-4378, incorporated by reference in its entirety). These mild conditions are compatible with most types of DNA reporting and coding tags. As an alternative, PNAs are used in coding tags since they are completely acid-stable (Ray and Norden, 2000, FASEB J. 14:1041-1060). In addition to the above approaches, DNA barcodes can be empirically selected by screening that survive both Edman labeling and cleavage.

The compatibility of using DNA coding tags/recording tags to encode the identity of NTAA binders and perform mild N-terminal Edman degradation reaction is demonstrated using the following assay. Both anti-phosphotyrosine and anti-cMyc antibodies are used to read out the model peptide. C-Myc and N-terminal phosphotyrosine detection, coding tag writing, and removal of the N-terminal phosphotyrosine using a single Edman degradation step. After this step, the peptide is stained again with anti-phosphotyrosine and anti-cMyc antibodies. Stability of the recording tag to N-terminal degradation is assessed by qPCR. Effective removal of the phosphotyrosine is indicated by absence of the E-oligonucleotide coding tag information in the final recording tag sequence as analyzed by sequencing, qPCR, or gel electrophoresis.

Example 13: Preparation of Compartment Tagged Beads

For preparation of compartment tagged beads, barcodes are incorporated into oligonucleotides immobilized on beads using a split-and-pool synthesis approach, using either phosphoramidite synthesis or through split-and-pool ligation. A compartment tag can further comprise a unique molecular identifier (UMI) to uniquely label each peptide or protein molecule to which the compartment tag is joined. An exemplary compartment tag sequence is as follows: 5'-NH$_2$-GCGCAATCAG-XXXXXXXXXXXX-NNNNN-TGCAAGGAT-3' (SEQ ID NO: 177). The XXXXXXXXXXXX (SEQ ID NO: 178) barcode sequence is a fixed population of nucleobase sequences per bead generated by split-pool on bead synthesis, wherein the fixed sequence differs from bead to bead. The NNNNN (SEQ ID NO: 179) sequence is randomized within a bead to serve as a unique molecule identifier (UMI) for the peptide molecule that is subsequently joined thereto. The barcode sequence can be synthesized on beads using a split-and-pool approach as described by Macosko et al. (2015, Cell 161:1202-1214, incorporated by reference in its entirety). The UMI sequences can be created by synthesizing an oligonucleotide using a degenerate base mixture (mixture of all four phosphoramidite bases present at each coupling step). The 5'-NH$_2$ is activated with succinimidyl 4-(N-maleimidomethyl)cyclohexane-1-carboxylate (SMCC) and a cysteine containing butelase I peptide substrate with the sequence from N-terminus to C-terminus "CGGSSGSNHV" (SEQ ID NO: 180) is coupled to the SMCC activated compartment tagged beads using a modified protocol described by Williams et al. (2010, Curr Protoc Nucleic Acid Chem. Chapter 4:Unit 4.41). Namely, 200 µl of magnetic beads (10 mg/ml) are placed in a 1.5 ml Eppendorf tube. 1 ml of coupling buffer (100 mM KH$_2$PO$_4$ buffer, pH 7.2 with 5 mM EDTA, 0.01% Tween 20, pH 7.4) is added to the tube and vortexed briefly. Freshly prepared 40 µl Sulfo-SMCC (50 mg/ml in DMSO, ThermoFisher) is added to the magnetic beads and mixed. The reaction is incubated for 1 hr. at room temperature on a rotary mixer. After incubation, the beads are separated from the supernatant on a magnet, and washed 3× with 500 µl coupling buffer. The beads are re-suspended in 400 µl coupling buffer. 1 mL of CGGSSGSNHV (SEQ ID NO: 180) peptide is added (1 mg/mL in coupling buffer after TCEP-reduction (5 mM) and ice cold acetone precipitation) to the magnetic beads. The reaction is incubated at room temperature for 2 hours on a rotary mixer. The reaction is washed 1× with coupling buffer. 400 µl quenching buffer (100 mM KH$_2$PO$_4$ buffer, pH 7.2 with 10 mg/mL Mercaptosuccinic Acid, pH 7.4) is added to the reaction mixture and incubated for 2 hrs. on a rotary mixer. The reaction mixture is washed 3× with coupling buffer. The resultant beads are re-suspended in storage buffer (10 mM KH$_2$PO$_4$ buffer, pH 7.2 with 0.02% NaN$_3$, 0.01% Tween 20, pH 7.4) and stored at 4° C.

Example 14: Generation of Encapsulated Beads and Proteins

Compartment tagged beads and proteins are combined with a zinc metallo-endopeptidase, such as endoproteinase AspN (Endo AspN), an optional photo-caged Zn chelator (e.g., ZincCleav I), and an engineered thermos-tolerant butelase I homolog (Bandara, Kennedy et al. 2009, Bandara, Walsh et al. 2011, Cao, Nguyen et al. 2015). Compartment tagged beads from Example 12 are mixed with proteins and emulsified through a T-junction microfluidic or flow focusing device (see, e.g., FIG. 21). In a two-aqueous flow configuration, the protein and Zn$^{2+}$ in one flow can be combined with the metallo-endopeptidase from the other flow to initiate digestion immediately upon droplet formation. In the one flow configuration, all reagents are premixed and emulsified together. This requires use of the optional photo-caged Zn chelator (e.g., ZincCleav I) to initiate protein digestion post droplet formation via exposure to UV light. The concentrations and flow conditions are adjusted such that, on average, there is less than one bead per droplet. In an optimized experiment, 108 femto-droplets can be made with an occupancy of about 10% of the droplets containing beads (Shim et al., 2013, ACS Nano 7:5955-5964). In the one flow approach, after forming droplets, the protease is activated by exposing the emulsion to UV-365 nm light to release the photo-caged Zn$^{2+}$, activating the Endo AspN protease. The emulsion is incubated for 1 hr. at 37° C. to digest the proteins into peptides. After digestion, the Endo AspN is inactivated by heating the emulsion to 80° C. for 15 min. In the two-flow formulation, the Zn$^{2+}$ is introduced during the combining of the two flows into a droplet. In this case, the Endo AspN can be inactivated by using a photo-activated Zn$^{2+}$ caging molecule in which the chelator is activated upon exposure to UV light, or by adding an amphipathic Zn$^{2+}$ chelating agent to the oil phase, such as 2-alkylmalonic acid, or EDTA-MO. Examples of amphipathic EDTA molecules include: EDTA-MO, EDTA-BO, EDTA-BP, DPTA-MO, DPTA-BO, DPTA-BP, etc. (Ojha, Singh et al. 2010, Moghaddam, de Campo et al. 2012). Other modalities can also be used to control the reaction within the droplet interior including changing the pH of the droplet through addition of amphipathic acids or bases to the emulsion oil. For example, droplet pH can be lowered using water/oil soluble acetic acid. Addition of acetic acid to a fluoro-emulsion leads to reduction of pH within the droplet compartment due to the amphipathic nature of the acetic acid molecule (Mashaghi and van Oijen, 2015, Sci Rep 5:11837). Likewise, addition of the base, propyl amine, alkalinizes the droplet interior. Similar approaches can be used for other types of amphipathic molecules such as oil/water soluble redox reagents, reducing agents, chelating agents and catalysts.

After digestion of the compartmentalized proteins into peptides, the peptides are ligated to the compartment tags (oligonucleotide peptide barcode chimeras) on the bead using butelase I or a chemical ligation (e.g., aldehyde-amino, etc.) (see, e.g., FIG. 16 and FIG. 22A). In an optional approach, an oligo-thiodepsipeptide "chemical substrate" is employed to make the butelase I ligation irreversible (Nguyen, Cao et al. 2015). After ligation, the emulsion is "cracked", and the beads with immobilized compartment tagged peptide constructs collected in bulk, or the compartment tagged peptides are cleaved from the beads, and collected in bulk. If the bead immobilized compartment tagged peptides comprise a recording tag, these beads can be used directly in nucleic acid encoding based peptide analysis methods described herein. In contrast, if the compartment tagged peptides are cleaved from the bead substrate, the compartment tagged peptides are then associated with a recording tag by conjugation to the C-terminus of the compartment tagged peptide, and immobilized on a solid support for subsequent binding cycles with coding tagged binding agents and sequencing analysis as described herein. Association of a recording tag with a compartment tagged peptide can be accomplished using a trifunctional linker molecule. After immobilization of the compartment tagged peptide with an associated recording tag to a solid support for cyclic sequencing analysis, the compartment information is transferred to the associated recording tag using primer extension or ligation (see, e.g., FIG. 22B). After transferring the compartment tag information to the recording tag, the compartment tag can be cleaved from the peptide using the same enzyme used in the original peptide digestion (see, e.g., FIG. 22B). This restores the original N-terminal end of the peptide, thus enabling N-terminal degradation peptide sequencing methods as described herein.

Example 15: Di-Tag Generation by Associating Recording Tags of Peptides Covalently Modified with Amino Acid-Specific Coding Tags Via Three Primer Fusion Emulsion PCR Peptides with recording tags comprised of a compartment tag and a molecular UMI are chemically modified with coding tag site-specific chemical labels. The coding tag also contains a UMI to enable counting of the number of amino acids of a given type within a modified peptide. Using a modified protocol from Tyson and Armor (Tyson and Armour 2012), emulsionPCRs are prepared in a total aqueous volume of 100 µl, containing 1× PHUSION™ GC reaction buffer (Thermo Fisher Scientific), 200 µM each dNTPs (New England Biolabs), 1 µM primer U1, 1 µM primer U2tr, 25 nM primer Sp, 14 units PHUSION™ high fidelity DNA polymerase (Thermo Fisher Scientific). 10 µl aqueous phase is added every 5 to 10 seconds to 200 µl oil phase (4.5% vol./vol.) Span 80, 0.4% vol./vol. Tween 80 and 0.05% Triton X-100 dissolved in light mineral oil (Sigma)) in a 2 ml cryo-vial while stirring at 1000 rpm for a total of 5 minutes as previously described by Turner and Hurles (2009, Nat. Protoc. 4:1771-1783). Average droplet size of the resultant emulsion was about 5 microns. Other methods of emulsion generation, such as the use of T-junctions and flow focusing, can also be employed (Brouzes, Medkova et al. 2009). After emulsion generation, 100 µl of aqueous/oil mixture is transferred to 0.5 ml PCR tubes and first-round amplification carried out at the following conditions: 98° C. for 30 seconds; 40 cycles of 98° C. for 10 seconds, 70° C. for 30 seconds and 72° C. for 30 seconds; followed by extension at 72° C. for 5 minutes. A second-round amplification reaction is carried out at the following conditions: 98° C. for 30 seconds; 40 cycles of 98° C. for 10 seconds, 55° C. for 30 seconds and 72° C. for 30 seconds; followed by hold at 4° C. Emulsions are disrupted as soon as possible after the final cycle of the PCR by adding 200 µl hexane (Sigma) directly to the PCR tube, vortexing for 20 seconds, and centrifuging at 13,000 g for 3 minutes.

Example 16: Sequencing Extended Recording Tag, Extended Coding Tag, or Di-Tag Constructs The spacer (Sp) or universal priming sites of a recording tag or coding tag can be designed using only three bases (e.g., A, C, and T) in the body of the sequence, and a fourth base (e.g., G) at the 5' end of the sequence. For sequencing by synthesis (SBS), this enables rapid dark base incorporation across the spacer sequence using a mix of standard dark (unlabeled and non-terminated) nucleotides (dATP, dGTP, and dTTP) and a single ffC dye-labeled reversible terminator (e.g., fully functional cytosine triphosphate). In this way, only the relevant encoder sequence, unique molecular identifier(s), compartment tags, binding cycle sequence of the extended reporter tag, extended coding tag, or di-tag are SBS sequenced, and the non-relevant spacer or universal priming sequences are "skipped over". The identities of the bases for the spacer and the fourth base at the 5' end of the sequence may be changed and the above identities are provided for purposes of illustration only.

Example 17: Preparation of Protein Lysates

There are a wide variety of protocols known in the art for making protein lysates from various sample types. Most variations on the protocol depend on cell type and whether the extracted proteins in the lysate in are to be analyzed in a non-denatured or denatured state. For the NGPA assay, either native conformation or denatured proteins can be immobilized to a solid substrate (see, e.g., FIG. 32A-H). Moreover, after immobilization of native proteins, the proteins immobilized on the substrate's surface can be denatured. The advantage of employing denatured proteins are two-fold. First of all, many antibody reagents bind linear epitopes (e.g., Western Blot Abs), and denatured proteins provide better access to linear epitopes. Secondly, the NGPA assay workflow is simplified when using denatured proteins since the annealed coding tag can be stripped from the extended recording tag using alkaline (e.g., 0.1 N NaOH) stripping conditions since the immobilized protein is already denatured. This contrasts with the removal of annealed coding tags using assays comprising proteins in their native conformation, that require an enzymatic removal of the annealed coding tag following binding event and information transfer.

Examples of non-denaturing protein lysis buffers include: RPPA buffer consisting of 50 mm HEPES (pH 7.4), 150 mM NaCl, 1% Triton X-100, 1.5 mM MgCl2, 10% glycerol; and commercial buffers such as M-PER mammalian protein extraction reagent (Thermo-Fisher). A denaturing lysis buffer comprises 50 mm HEPES (pH 8.), 1% SDS. The addition of Urea (1M-3M) or Guanidine HCl (1-8M) can also be used in denaturing the protein sample. In addition to the above components of lysis buffers, protease and phosphatase inhibitors are also generally included. Examples of protease inhibitors and typical concentrations include aptrotinin (2 µg/ml), leupeptin (5-10 µg/ml), benzamidine (15 µg/ml), pepstatin A (1 µg/ml), PMSF (1 mM), EDTA (5 mM), and EGTA (1 mM). Examples of phosphatase inhibitors include Na pyrophosphate (10 mM), sodium fluoride (5-100 mM) and sodium orthovanadate (1 mM). Additional additives can include DNAaseI to remove DNA from the protein sample, and reducing agents such as DTT to reduce disulfide bonds.

An example of a non-denaturing protein lysate protocol prepared from tissue culture cells is as follows: Adherent cells are trypsinized (0.05% trypsin-EDTA in PBS), collected by centrifugation (200 g for 5 min.), and washed 2× in ice cold PBS. Ice-cold M-PER mammalian extraction reagent (~1 mL per $10^7$ cells/100 mm dish or 150 $cm^2$ flask) supplemented with protease/phosphatase inhibitors and additives (e.g., EDTA free complete inhibitors (Roche) and PhosStop (Roche) is added. The resulting cell suspension is incubated on a rotating shaker at 4° C. for 20 min. and then centrifuged at 4° C. at ~12,000 rpm (depending on cell type) for 20 min to isolate the protein supernatant. The protein is quantitated using the BCA assay, and resuspended at 1 mg/ml in PBS. The protein lysates can be used immediately or snap frozen in liquid nitrogen and stored at −80° C.

An example of a denaturing protein lysate protocol, based on the SP3 protocol of Hughs et al., prepared from tissue culture cells is as follows: adherent cells are trypsinized (0.05% trypsin-EDTA in PBS), collected by centrifugation (200 g for 5 min.), and washed 2× in ice cold PBS. Ice-cold denaturing lysis buffer (~1 mL per $10^7$ cells/100 mm dish or 150 $cm^2$ flask) supplemented with protease/phosphatase inhibitors and additives (e.g., 1× complete Protease Inhibitor Cocktail (Roche)) is added. The resulting cell suspension is incubated at 95° C. for 5 min. and placed on ice for 5 min. Benzonase Nuclease (500 U/ml) is added to the lysate and incubated at 37° C. for 30 min. to remove DNA and RNA.

The proteins are reduced by addition of 5 µL of 200 mM DTT per 100 µl of lysate and incubated for 45° C. for 30 min. Alklylation of protein cysteine groups is accomplished by addition of 10 µl of 400 mM iodoacetamide per 100 µl of lysate and incubated in the dark at 240 for 30 min. Reactions are quenched by addition of 10 µl of 200 mM DTT per 100 µl of lysate. Proteins are optionally acylated by adding 2 µl an acid anhydride and 100 µl of 1 M Na2CO3 (pH 8.5) per 100 µl of lysate. Incubate for 30 min. at room temp. Valeric, benzoic, and proprionic anhydride are recommended rather than acetic anhydride to enable "in vivo" acetylated lysines to be distinguished from "in situ" blocking of lysine groups by acylation (Sidoli, Yuan et al. 2015). The reaction is quenched by addition of 5 mg of Tris(2-aminoethyl)amine, polymer (Sigma) and incubation at room temperature for 30 min. Polymer resin is removed by centrifuging lysate at 2000 g for 1 min. through a 0.45 um cellulose acetate Spin-X tube (Corning). The protein is quantitated using the BCA assay, and resuspended at 1 mg/ml in PBS.

In additional examples, labeled peptides are generated using a filter-aided sample preparation (FASP) protocol, as described by Erde et al. in which a MWCO filtration device is used for protein entrapment, alkylation, and peptidase digestion (Erde, Loo et al. 2014, Feist and Hummon 2015).

Example 18: Generation of Partition-Tagged Peptides

A DNA tag (with an optional sample barcode, and an orthogonal attachment moiety) is used to label the 8-amino groups on lysines of denatured polypeptides using standard bioconjugation methods (Hermanson 2013), or alternatively, are attached to the polypeptide using photoaffinity labeling (PAL) methods such as benzophenone (Li, Liu et al. 2013). After labeling of the polypeptide with DNA tags at lysine groups or randomly on CH groups (via PAL) and blocking unlabeled groups via acylation with an acyl anhydride, the DNA-tag labeled, acylated polypeptides are annealed to compartment beads with attached DNA oligonucleotides comprising a universal priming sequence, a compartment barcode, an optional UMI, and a primer sequence complementary to a portion of the DNA tag attached to the polypeptides (see, e.g., FIG. 31A-E). Because of the cooperativity of multiple DNA hybridization tags, single polypeptide molecule interacts primarily with a single bead enabling writing of the same compartment barcode to all DNA tags of the polypeptide molecule. After annealing, the polypeptide-bound DNA tag primes a polymerase extension reaction on the annealed bead-bound DNA sequence. In this manner, the compartment barcodes and other functional elements are written onto the DNA tags attached to the bound polypeptide. Upon completion of this step, the polypeptide has a plurality of recording tags attached, wherein the recording tag has a common spacer sequence, barcode sequences (e.g. sample, fraction, compartment, spatial, etc.), optional UMIs and other functional elements. This labeled polypeptide can be digested into peptide fragments using standard endoproteases such as trypsin, GluC, proteinase K, etc. Note: if trypsin is used for digestion of lysine-labeled polypeptides, the polypeptide is only cleaved at Arg residues not Lys residues (since Lys residues are labeled). The protease digestion can be done on directly on the beads or after removal of the labeled polypeptide from the barcoded beads.

Example 19: Preparing DNA Recording Tag-Peptide Conjugates for Model System

The recording tag oligonucleotides are synthesized with a 5' $NH_2$ group, and an internal mTetrazine group for later coupling to beads (alkyne-dT is converted to mTetrazine-dT via an mTet-PEG-$N_3$ heterobifunctional crosslinking agent). The 5' $NH_2$ of the oligonucleotide is coupled to a reactive cysteine on a peptide using an NHS/maleimide heterobifunctional cross-linker, such as LC-SMCC (ThermoFisher Scientific), as described by Williams et al. (Williams and Chaput 2010). In particular, 20 nmols of 5' $NH_2$-labeled oligonucleotides are ethanol precipitated and resuspended in 180 µl of phosphate coupling buffer (0.1 M potassium phosphate buffer, pH 7.2) in a siliconized tube. 5 mg of LC-SMCC is resuspended in 1 mL of DMF (5 mg/ml) (store in aliquots at ~20). An aliquot of 20 µl LC-SMCC (5 mg/ml) is added to 180 µl of the resuspended oligonucleotides, mixed and incubated at room temperature for 1 hr. The mixture is 2× ethanol precipitated. The resultant malemide-derivitized oligonucleotide is resuspended in 200 µl phosphate coupling buffer. A peptide containing a cysteine residue (>95% purity, desalted) is resuspended at 1 mg/ml (~0.5 mM) in DMSO. Approximately 50 nmol of peptide (100 µl) are added to the reaction mix, and incubated at room temperature overnight. The resultant DNA recording tag-peptide conjugate is purified using native-PAGE as described by William et al. (Williams and Chaput 2010). Conjugates are resuspended in phosphate coupling buffer at 100 µM concentration in siliconized tubes.

Example 20: Development of Substrate for DNA-Peptide Immobilization

Figure 29A:
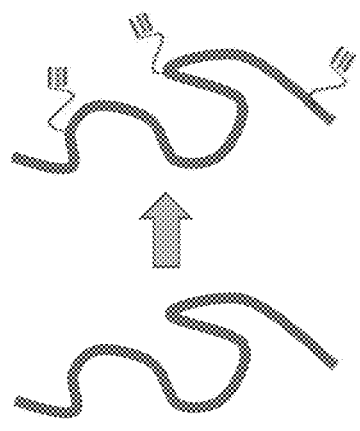
FIG. 29A-29E illustrate examples for the conjugation of DNA recording tags to polypeptides.
Figure 29B:
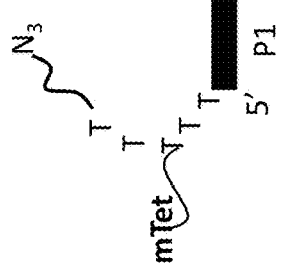
Figure 29C:
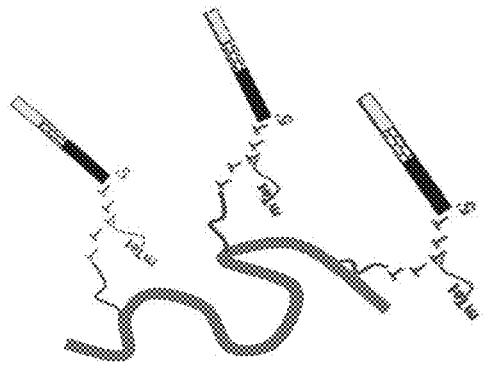
Figure 29D:
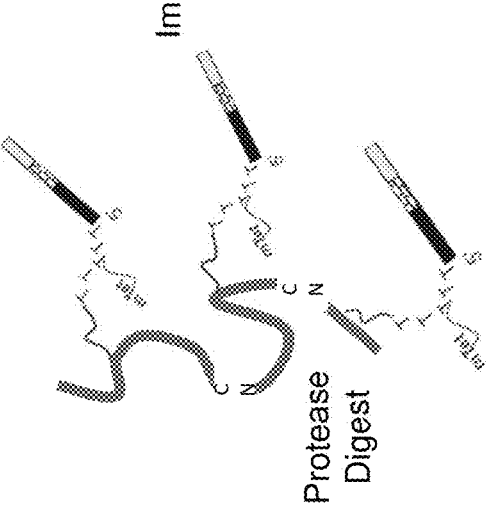
Figure 29E:
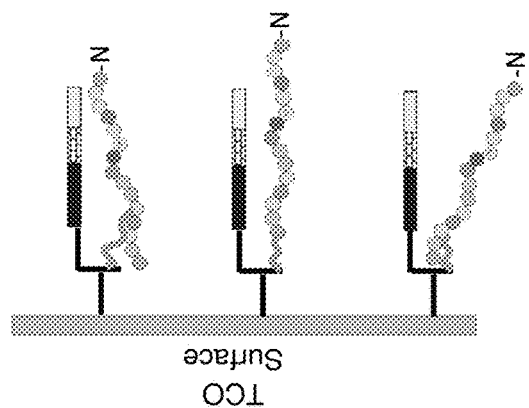

In some experiments, magnetic beads suitable for click-chemistry immobilization are created by converting M-270 amine magnetic Dynabeads to either azide or TCO-derivatized beads capable of coupling to alkyne or methyl Tetrazine-labeled oligo-peptide conjugates, respectively (see, e.g., FIG. 29D-E; FIG. 30D-E). Namely, 10 mg of M-270 beads are washed and resuspended in 500 µl borate buffer (100 mM sodium borate, pH 8.5). A mixture of TCO-PEG (12-120)-NHS (Nanocs) and methyl-PEG (12-120)-NHS is resuspended at 1 mM in DMSO and incubated with M-270 amine beads at room temperature overnight. The ratio of the Methyl to TCO PEG is titrated to adjust the final TCO surface density on the beads such that there is <100 TCO moieties/um$^2$ (see, e.g., FIG. 31E; FIG. 34A). Unreacted amine groups are capped with a mixture of 0.1M acetic anhydride and 0.1M DIEA in DMF (500 µl for 10 mg of beads) at room temperature for 2 hrs. After capping and washing 3× in DMF, the beads are resuspended in phosphate coupling buffer at 10 mg/ml.

In one experiment, the total of 10 nmol recording tags that included 5' amino-group and internal alkyne-group modifications were incubated in 0.1 M Hepes, pH 7.5, 5 mM Methyltetrazine-PEG4-Azide (BroadPharm), 2.5 mM $CuSO_4$, 5 mM Tris(3-hydroxypropyltriazolylmethyl)amine (Glen Research), 8 mM sodium ascorbate, at room temperature. After 16 hours incubation, the recording tags were precipitated with $LiClO_4$ and 83% acetone, and then dissolved in 50 µl of 150 mM NaCl/NaPhos pH 7.4, 1 mM EDTA. The recording tags concentration was estimated by measurement of A260 by nanodrop spectrophotometer (Thermo Fisher), and adjusted to 100 µM.

TCO (trans-cyclooctene) beads were prepared from Dynabeads M-270 Amine (Thermo Fisher). The total of 0.45 mg Dynabeads M-270 Amine were washed twice with 150 µl of 150 mM NaCl/NaPhos pH 7.4, and resuspended in 150 µl of 150 mM NaCl/NaPhos pH 7.4. On the other hand, the DMF solution of TCO-PEG12-NHS/mPEG-SCM mixture was prepared by titrating TCO-PEG12-NHS ester (BroadPharm)/DMF against the mPEG-SCM, MW550 (Creative PEGWorks)/DMF in ratios of 1:10$^2$, 1:10$^3$, and 1:10$^4$. Total 10 µl of individual TCO-PEG12-NHS/mPEG-SCM mixture was added to 150 ul of pre-washed beads suspension, and incubated at room temperature for 30 minutes to coat beads with TCO in different distributions. The TCO-coated beads were washed twice with 150 µL of 150 mM NaCl/NaPhos pH 7.4, and resuspended in 150 ul 150 mM NaCl/NaPhos pH 7.4. The residual amine groups on beads were blocked by 15 minutes incubation with 6.7 µM NHS-acetate (TCI) at room temperature. The resulting beads were washed twice with 150 µL of 150 mM NaCl/NaPhos pH 7.4.

Total 0.45 mg of individual TCO-modified beads were resuspended in 10 µl of 100 µM Methyltetrazine-modified recording tags solution, incubated at room temperature for 30 minutes, and washed twice with 150 µl of 150 mM NaCl/NaPhos pH 7.4. The recording tag immobilized beads were resuspended in 75 µl of 150 mM NaCl/NaPhos pH 7.4, 1 mM EDTA.

The cysteine-containing peptides were attached to 5' amine group of recording tag on beads via SM(PEG)8 (Thermo Fisher). Total 5 µl of 100 mM SM(PEG)/DMF solution was added to 150 µl of beads suspension, incubated at room temperature for 30 minutes. The resulting beads were washed twice with 150 µl of 150 mM NaCl/NaPhos pH 7.4, and resuspended in 20 µl of 150 mM NaCl/NaPhos pH 7.4, 1 mM EDTA. Total 6 µl of 8 mM peptide/DMF solution was added to 20 µL of beads suspension, and incubated at room temperature for 2 hours and then 4° C. for 16 hours. The beads were washed twice with 150 µl of 150 mM NaCl/NaPhos pH 7.4, resuspended in 150 µl of 10 µg/ml L-Cysteine (Sigma-Aldrich) solution, and incubated at room temperature for 2 hours to remove residual maleimide groups. The beads were washed twice with 150 µl of 150 mM NaCl/NaPhos pH 7.4, and resuspended in 75 µl of 150 mM NaCl/NaPhos pH 7.4, 1 mM EDTA.

Example 21: Immobilization of Recording Tag Labeled Peptides to Substrate

For analysis, recording tag labeled peptides are immobilized on a substrate via an IEDDA click chemistry reaction using an mTet group on the recording tag and a TCO group on the surface of activated beads or substrate. This reaction is fast and efficient, even at low input concentrations of reactants. Moreover, the use of methyl tetrazine confers greater stability to the bond (Selvaraj and Fox 2013, Knall, Hollauf et al. 2014, Wu and Devaraj 2016). Between about 200 µg and about 500 µg of M-270 TCO beads are resuspended in 100 µl phosphate coupling buffer. 5 pmol of DNA recording tag labeled peptides comprising an mTet moiety on the recording tag is added to the beads for a final concentration of ~ 50 nM. The reaction is incubated for 1 hour at room temperature. After immobilization, unreacted TCO groups on the substrate are quenched with 1 mM methyl tetrazine acid in phosphate coupling buffer for 1 hr. at room temperature.

Bulk preparation of peptide beads. The total of 10 nmol recording tags that included 5' amino-group and internal alkyne-group modifications were incubated in 0.1 M Hepes, pH 7.5, 5 mM Methyltetrazine-PEG4-Azide (BroadPharm), 2.5 mM $CuSO_4$, 5 mM Tris(3-hydroxypropyltriazolylmethyl)amine (Glen Research), 8 mM sodium ascorbate, at room temperature. After 16 hours incubation, the recording tags were precipitated with $LiClO_4$ and 83% acetone, and then dissolved in 50 µl of 150 mM NaCl/NaPhos pH 7.4, 1 mM EDTA. The recording tags concentration was estimated by measurement of A260 by nanodrop spectrophotometer (Thermo Fisher), and adjusted to 100 µM. TCO (trans-cyclooctene) beads were prepared from Dynabeads M-270 Amine (Thermo Fisher). The total of 0.45 mg Dynabeads M-270 Amine were washed twice with 150 µl of 150 mM NaCl/NaPhos pH 7.4, and resuspended in 150 µl of 150 mM NaCl/NaPhos pH 7.4. On the other hand, the DMF solution of TCO-PEG12-NHS/mPEG-SCM mixture was prepared by titrating TCO-PEG12-NHS ester (BroadPharm)/DMF against the mPEG-SCM, MW550 (Creative PEGWorks)/DMF in ratios of 1:10$^2$, 1:10$^3$, and 1:10$^4$. Total 10 µl of individual TCO-PEG12-NHS/mPEG-SCM mixture was added to 150 µl of pre-washed beads suspension, and incubated at room temperature for 30 minutes to coat beads with TCO in different distributions. The TCO-coated beads were washed twice with 150 µL of 150 mM NaCl/NaPhos pH 7.4, and resuspended in 150 µl 150 mM NaCl/NaPhos pH 7.4. The residual amine groups on beads were blocked by 15 minutes incubation with 6.7 µM NHS-acetate (TCI) at room temperature. The resulting beads were washed twice with 150 µL of 150 mM NaCl/NaPhos pH 7.4. Total 0.45 mg of individual TCO-modified beads were resuspended in 10 µl of 100 µM Methyltetrazine-modified recording tags solution, incubated at room temperature for 30 minutes, and washed twice with 150 µl of 150 mM NaCl/NaPhos pH 7.4. The recording tag immobilized beads were resuspended in 75 µl of 150 mM NaCl/NaPhos pH 7.4, 1 mM EDTA. The cysteine-containing peptides were attached to 5' amine group of recording tag on beads via SM(PEG)8 (Thermo Fisher). Total 5 µl of 100 mM SM(PEG)/DMF solution was added to 150 µl of beads suspension, incubated at room temperature for 30 minutes. The resulting beads were washed twice with 150 µl of 150 mM NaCl/NaPhos pH 7.4, and resuspended in 20 µl of 150 mM NaCl/NaPhos pH 7.4, 1 mM EDTA. Total 6 µl of 8 mM peptide/DMF solution was added to 20 µL of beads suspension, and incubated at room temperature for 2 hours and then 4° C. for 16 hours. The beads were washed twice with 150 µl of 150 mM NaCl/NaPhos pH 7.4, resuspended in 150 µl of 10 µg/ml L-Cysteine (Sigma-Aldrich) solution, and incubated at room temperature for 2 hours to remove residual maleimide groups. The beads were washed twice with 150 µl of 150 mM NaCl/NaPhos pH 7.4, and resuspended in 75 µl of 150 mM NaCl/NaPhos pH 7.4, 1 mM EDTA.

Example 22: N-Terminal Amino Acid (NTAA) Modification

Chemical NTAA Acetylation:

The NTAA of a peptide is acetylated using either acetic anhydride or NHS-acetate in organic or aqueous solutions (sulfo-NHS-acetate). For acetic anhydride derivatization, 10 mM of acetic anhydride in DMF is incubated with the peptide for 30 min. at RT (Halpin, Lee et al. 2004). Alternatively, the peptide is acetylated in aqueous solution using 50 mM acetic anhydride in 100 mM 2-(N-morpholino) ethanesulfonate (MES) buffer (pH 6.0) and 1M NaCl at RT for 30 min (Tse, Snyder et al. 2008). For NHS-acetate derivatization, a stock solution of sulfo-NHS-acetate (100 mM in DMSO) is prepared and added at a final concentration of 5-10 mM in 100 mM sodium phosphate buffer (pH 8.0) or 100 mM borate buffer (pH 9.4) and incubated for 10-30 min. at RT (Goodnow 2014).

Enzymatic NTAA Acetylation:

NTAA of a peptide is enzymatically acetylated by exposure to N-Acetyl Transferase (SsArd1 from *Sulfolobus solfataricus*) using the following conditions: peptides are incubated with 2 µM SsArd1 in NAT buffer (20 mM Tris-HCl, pH 8.0, 100 mM NaCl, 1 mM EDTA, 1 mM acetyl-CoA) at 65° C. for 10 min (Chang and Hsu 2015).

Chemical NTAA Amidination (Guanidinylation):

Peptides are incubated with 10 mM N,N-bis(tert-butoxycarbonyl) thiourea, 20 mM trimethylamine, and 12 mM Mukayama's reagent (2-chloro-1-methylpyridinium iodide) in DMF at RT for 30 min. Alternatively, the peptides are incubated with 10 mM 1H-Pyrazole-1-carboxamidine Hydrochloride, 10 mM DIEA in DMF at RT for 30 min. Standard deblocking methods are used to remove protecting groups. Alternatively, the peptides are incubated with 10 mM S-methylisothiourea in PBS buffer (pH 8.0) or 100 mM borate buffer (pH 8.0) for 30 min. at 10° C. (Tse, Snyder et al. 2008).

PITC Labeling:

Peptide is incubated with 5% (vol./vol.) PITC in ionic liquid [Bmim][BF4] at room temperature for 5 min. The reaction time is optimized for quantitative PITC labelling of NTAA while minimizing ectopic labeling of the exocyclic amines on nucleotide bases present in the extended DNA recording tag.

DNFB Labeling:

2,4-Dinitrofluorobenzene (DNFB) is prepared as a 5 mg/ml stock in methanol. The solution is protected from light and prepared fresh daily. Peptides are labeled by incubation in 0.5-5.0 µg/ml DNFB in 10 mM borate buffer (pH 8.0) at 37° C. for 5-30 min.

SNFB Labeling:

4-sulfonyl-2-nitro-fluorobenzene (SNFB) is prepared as a 5 mg/ml stock in methanol. The solution should be protected from light and prepared fresh daily. Peptides are labeled by incubation in 0.5-5.0 µg/ml DNFB in 10 mM borate buffer (pH 8.0) at 37° C. for 5-30 min.

Cleavage of Acetylated NTAA Peptides:

The acetylated NTAA is cleaved from the peptide by incubation with 10 µM acylpeptide hydrolase (APH) enzyme (from *Sulfolobus solfataricus*, SS02693) in 25 mM Tris-HCl (pH 7.5) at 90° C. for 10 min (Gogliettino, Balestrieri et al. 2012).

Cleavage of Amidinated (Guanidinylated) NTAA Peptides:

The amidinated (guanidinylated) NTAA is cleaved from the peptide by incubation in between about 0.1N and about 0.5N NaOH for 10 minutes at 37° C. (Hamada 2016).

Example 23: Demonstration of Intramolecular Transfer of Coding Tag Information to Recording Tags with Model System DNA model system was used to test the "intra-molecular" transfer of coding tag information to recording tags that are immobilized to beads (see, e.g., FIG. 36A). Two different types of recording tag oligonucleotides were used. saRT_Abc_v2 (SEQ ID NO: 141) contained an "A" DNA capture sequence (SEQ ID NO: 153) (mimic epitope for "A'" binding agent) and a corresponding "A" barcode (rtA_BC); saRT_Bbc_V2 (SEQ ID NO: 142) contained a "B" DNA capture sequence (SEQ ID NO: 154) (mimic epitope for "B'" binding agent) and a corresponding "B" barcode (rtB_BC). These barcodes were combinations of the elementary 65 set of 15-mer barcodes (SEQ ID Nos: 1-65) and their reverse complementary sequences (SEQ ID Nos: 66-130). rtA_BC is a collinear combination of two barcodes, BC_1 and BC 2, and rtB_BC is just the one barcode, BC_3. Likewise the barcodes (encoder sequences) on the coding tags were also comprised of barcodes from the elementary set of 65 15-mer barcodes (SEQ ID Nos: 1-65). CT_A'-bc_1PEG (SEQ ID NO: 144) and CT_B'-bc (SEQ ID NO: 147) coding tags were comprised of complementary capture sequences, A' and B', respectively, and were assigned the 15-mer barcodes, BC_5, and BC_5 & BC_6, respectively. This design set-up for the recording tags and coding tags enables easy gel analysis. The desired "intra-molecular" primer extension generates oligonucleotide products of similar size, whereas the undesired "inter-molecular" extension generates one oligo product 15 bases larger and another oligo product 15 bases shorter than the "intra-molecular" product (see, e.g., FIG. 36B).

The effect of recording tag density on "intra-molecular" vs. "inter-molecular" information transfer was evaluated. For correct information transfer, "intra-molecular" information transfer ("A'" coding tag to A recording tag; B' coding tag to B recording tag), should be observed rather than "inter-molecular" information transfer (A' coding tag binding to A recording tag but transferring information to B recording tag, and vice versa). To test the effect of recording tags spacing on the bead surface, biotinylated recording tag oligonucleotides, saRT_Abc_v2 (SEQ ID NO: 141) and saRT_Bbc_v2 (SEQ ID NO: 142), were mixed in a 1:1 ratio, and then titrated against the saDummy-T10 oligonucleotide (SEQ ID NO: 143) in ratios of 1:0, 1:10, 1:10$^2$, 1:103, and 1:104. A total of 20 pmols of recording tag oligonucleotides was incubated with 5 µl of M270 streptavidin beads (Thermo) in 50 µl Immobilization buffer (5 mM Tris-Cl (pH 7.5), 0.5 mM EDTA, 1 M NaCl) for 15 min. at 37° C. The beads were washed 3× with 100 µl Immobilization buffer at room temperature. Most subsequent wash steps used a volume of 100 µl. Coding tags (duplex annealing with DupCT sequences required for later cycles) were annealed to the recording tags immobilized on the beads by resuspending the beads in 25 µl of 5× Annealing buffer (50 mM Tris-Cl (pH 7.5), 10 mM MgCl2) and adding the coding tag mix. The coding tags annealed to the recording tags by heating to 65° C. for 1 min, and then allowed to slow cool to room temperature (0.2° C./sec). Alternatively, coding tags can be annealed in PBST buffer at 37° C. Beads were washed PBST (PBS+0.1% Tween-20) at room temp, and washed 2× with PBST at 37° C. for 5 min. and washed 1× with PBST at room temp. and a final wash in 1× Annealing buffer. The beads were resuspended in 19.5 µl Extension buffer (50 mM Tris-Cl (pH 7.5), 2 mM MgSO$_4$, 125 µM dNTPs, 50 mM NaCl, 1 mM dithiothreitol (DTT), 0.1% Tween-20, and 0.1 mg/ml BSA) and incubated at 37° C. for 15 min. Klenow exo-DNA polymerase (NEB, 5 U/µl) was added to the beads for a final concentration of 0.125 U/ul, and incubated at 37° C. for 5 min. After primer extension, beads were washed 2× with PBST, and 1× with 50 µl 0.1 NaOH at room temp for 5 min., and 3× with PBST and 1× with PBS. To add the downstream PCR adapter sequence, R1', the EndCap2T oligo (comprised of R1 (SEQ ID NO: 152) was hybridized and extended on the beads as done for the coding tag oligonucleotides. After adding the adapter sequence, the final extended recording tag oligonucleotides were eluted from the streptavidin beads by incubation in 95% formamide/10 mM EDTA at 65° C. for 5 min. Approximately $\frac{1}{100}^{th}$ of the eluted product was PCR amplified in 20 µl for 18 cycles, and 1 µl of PCR product analyzed on a 10% denaturing PAGE gel. The resulting gels demonstrates proof of principle of writing coding tag information to the recording tag by polymerase extension (see, e.g., FIG. 36C), and the ability to generate a primarily "intra-molecular" extension events relative to "inter-molecular" extension events upon dilution of recording tag density on the surface of the bead.

In this model system, the size of PCR products from recording tags RT_ABC and RT_BBC that contain the corresponding encoder sequence and universal reverse primer site is 100 base pairs (see, e.g., FIG. 36C), while the products by incorrect pairings of saRT_ABC (SEQ ID NO: 141)/CT_B'BC (SEQ ID NO: 147) and saRT_BBC (SEQ ID NO: 142)/CT_A'BC (SEQ ID NO: 144) are 115 and 85 base pairs, respectively. As shown in FIG. 36D, three bands were observed in the presence of saRT_ABC (SEQ ID NO: 141) and saRT_BBC (SEQ ID NO: 142) on beads at high density. It was expected that the recoding tag extended on proximal coding tag binding to itself (intra-molecular event) or neighbor recoding tag (inter-molecular event) at the high density. However, the bands of products by incorrect pairings decreased by diluting the recoding tags in dummy oligonucleotide, and disappeared at a ratio of 1:10000. This result demonstrated that the recording tags were spaced out on beads surface at the low density, resulting in decreased intermolecular events.

TABLE 1

Model System Sequences

| Name | Sequence (5'-3') | SEQ ID NO: |
|---|---|---|
| saRT_Abc_v2 | /5Biosg/TTTTTGCAAATGGCATTCTGACATCCCGTAGTCCGCGACAC TAGATGTCTAGCATGCCGCCGTGTCATGTGGAAACTGAGTG | 141 |
| saRT_Bbc_v2 | /5Biosg/TTTTTTTTTTGACTGGTTCCAATTGACAAGCCGTAGTCCGC GACACTAGTAAGCCGGTATATCAACTGAGTG | 142 |
| saDummy-pT10 | /5Biosg/TTTTTTTTTT/3SpC3/ | 143 |
| CT_A'-bc | GGATGTCAGAATGCCATTTGCTTTTTTTTTT/iSP18/CACTCAGTCCT AACGCGTATACGCACTCAGT/3SpC3/ | 144 |
| CT_A'-bc_1PEG | GGATGTCAGAATGCCATTTGCTTTTTTTTTT/iSP18/CACTCAGTCCT AACGCGTATACGTCACTCAGT/3SpC3/ | 145 |
| CT_A'bc-5PEG | GGATGTCAGAATGCCATTTGCTTTTTTTTTT/iSP18//iSP18//iSP18// iSP18//iSP18/CACTCAGTCCTAACGCGTATACGTCACTCAGT/3SpC3/ | 146 |
| CT_B'bc | GCTTGTCAATTGGAACCAGTCTTTT/iSp18/CACTCAGTCCTAACGCG TATACGGGAATCTCGGCAGTTCACTCAGT/3SpC3/ | 147 |
| EndCap2T | CGATTTGCAAGGATCACTCGTCACTCAGTCCTAACGCGTATACG/ 3SpC3/ | 148 |
| Sp | ACTGAGTG | 149 |
| Sp' | CACTCAGT | 150 |
| P1_f2 | CGTAGTCCGCGACACTAG | 151 |
| R1 | CGATTTGCAAGGATCACTCG | 152 |
| dupCT_A'BC | CGTATACGCGTTAGGACTGAGTG/3SpC3/ | 155 |
| dupCT_B'BC | AACTGCCGAGATTCCCGTATACGCGTTAGGACTGAGTG/3SpC3/ | 156 |

Figures 27A, 27B:
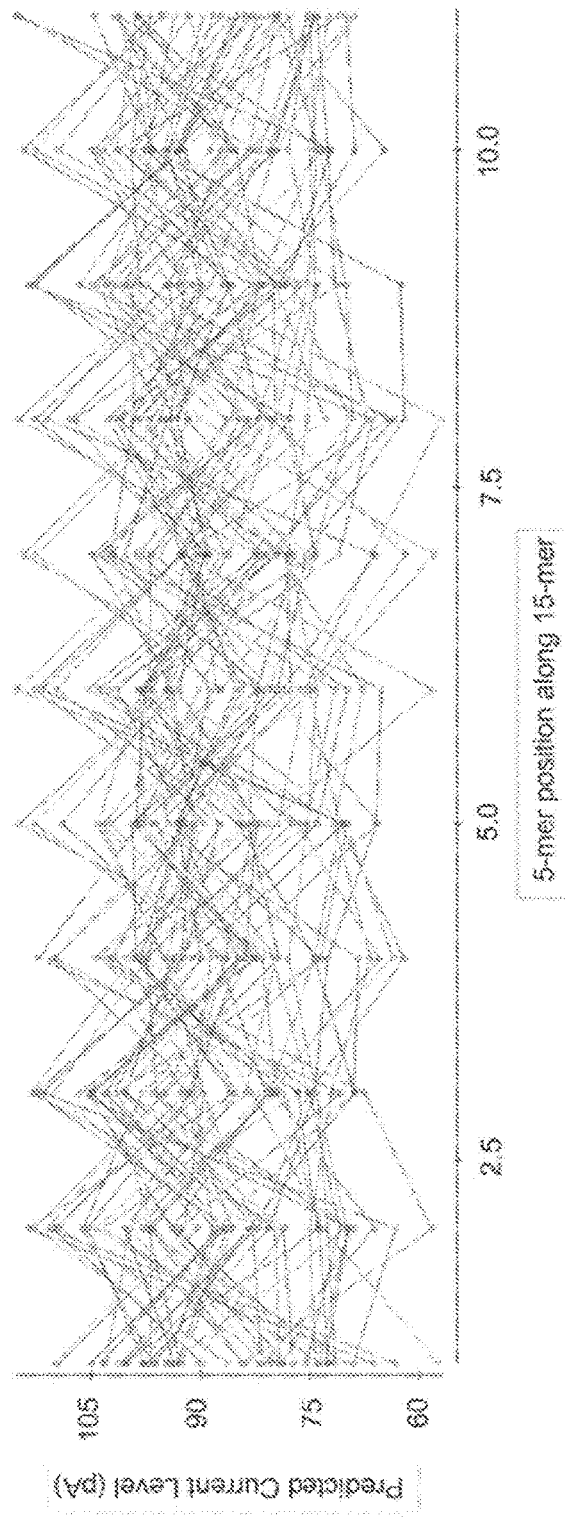

/3SpC3/ = 3' C3 (three carbon) spacer
/5Biosg/ = 5' Biotin
/iSP18/ = 18-atom hexa-ethyleneglycol spacer Example 24: Sequencing Extended Recording Tag, Extended Coding Tag, or Di-Tag Constructs on Nanopore Sequencers DNA barcodes can be designed to be tolerant to highly-error prone NGS sequencers, such as nanopore-based sequencers where the current base call error rate is on the order of 10% or more. A number of error correcting code systems have been described in the literature. These include Hamming codes, Reed-Solomon codes, Levenshtein codes, Lee codes, etc. Error-tolerant barcodes were based on Hamming and Levenshtein codes using R Bioconductor package, "DNAbarcodes" capable of correcting insertion, deletion, and substitution errors, depending on the design parameters chosen (Buschmann and Bystrykh 2013). A set of 65 different 15-mer Hamming barcodes are shown in FIG. 27A (as set forth in SEQ ID Nos: 1-65 and their reverse complementary sequences in SEQ ID Nos: 66-130, respectively). These barcodes have a minimum Hamming distance of 10 and are self-correcting out to four substitution errors and two indel errors, more than sufficient to be accurately readout on a nanopore sequencer with a 10% error rate. Moreover, these barcodes have been filtered from a set of 77 original barcodes using the predicted nanopore current signatures (see, e.g., FIG. 27B). They were filtered to have large current level differences across the barcode, and to be maximally uncorrelated with other barcodes in the set. In this way, actual raw nanopore current level plots from assays using these barcodes can be mapped directly to the predicted barcode signature without using base calling algorithms (Laszlo, Derrington et al. 2014).

Figure 27C:
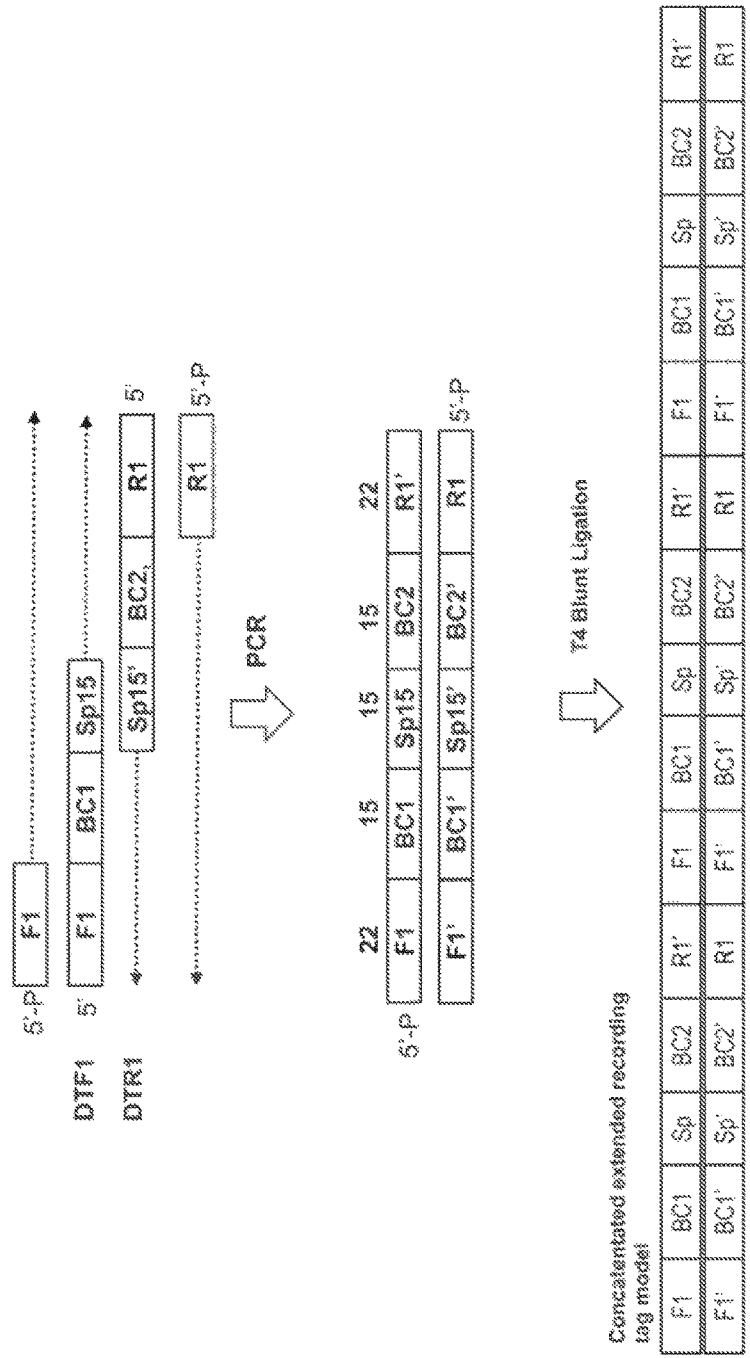

To mimic the analysis of extended recording tags, extended coding tags, or di-tag constructs using nanopore sequencing, PCR products comprised of a small subset of 15-mer barcodes using four forward primers (DTF1 (SEQ ID NO:157), DTF2 (SEQ ID NO:158), DTF3 (SEQ ID NO:159), DTF4 (SEQ ID NO:160)) and four reverse primers (DTR9 (SEQ ID NO:161), DTR10 (SEQ ID NO: 162), DTR11 (SEQ ID NO: 163), DTR12 (SEQ ID NO: 164)) were generated (see, e.g., FIG. 27C). This set of 8 primers was included in a PCR reaction along with a flanking forward primer F1 (SEQ ID NO: 165), and reverse primer R1 (SEQ ID NO: 166). The DTF and DTR primers annealed via a complementary 15-mer spacer sequence (Sp15) (SEQ ID NO: 167). The combination of 4 DTF forward and 4 DTR reverse primers leads to a set of 16 possible PCR products. PCR Conditions:

| Reagent | Final Conc. |
| --- | --- |
| F1 (5' phosphorylated) (SEQ ID NO: 165) | 1 uM |
| R1 (5' phosphorylated) (SEQ ID NO: 166) | 1 uM |
| DTF1-4 (SEQ ID NOS: 157-160); DTR9-12 (SEQ ID NOS: 161-164) | 0.3 nM ea |
| VeraSeq Buffer 2 | 1× |
| dNTPs | 200 uM |
| water | |
| VeraSeq 2.0 Ultra Pol | 2 U/100 ul |

PCR Cycling:

| 98° C. | 30 sec |
| --- | --- |
| 50° C. | 2 min |
| 98° C. | 10 sec |
| 55° C. | 15 sec |
| 72° C. | 15 sec |
| Repeat last 3 steps for 19 cycles | |
| 72° C. | 5 min |

After PCR, the amplicons were concatenated by blunt end ligation (see, e.g., FIG. 27C) as follows: 20 µl PCR product was mixed directly with 20 µl Quick Ligase Mix (NEB) and incubated overnight at room temp. The resultant ligated product, ~0.5-2 kb in length, was purified using a Zymo purification column and eluted into 20 µl water. About 7 µl of this purified ligation product was used directly in the MinIon Library Rapid Sequencing Prep kit (SQK-RAD002) and analyzed on a MinION Mk 1B (R9.4) device. An example of a 734 bp nanopore read of quality score 7.2 (~80% accuracy) is shown in FIG. 27D. Despite the poor sequencing accuracy, a large number of barcodes are easily readable in the sequence as indicated by lalign-based alignment of the barcodes to the MinIon sequence read (FIG. 27D showing SEQ ID NO: 168, the sequence of an extended recording tag construct).

Example 25: Encapsulated Single Cells in Gel Beads

Single cells are encapsulated into droplets (~50 µm) using standard techniques (Tamminen and Virta 2015, Spencer, Tamminen et al. 2016) (see, e.g., FIG. 38). A Polyacrylamide (Acrylamide:bisacrylamide (29:1) (30% w/vol.)), benzophenone methacrylamide (BM), and APS is included in the discontinuous phase along with the cells to create droplets capable of polymerizing upon addition of TEMED in the continuous oil phase (diffuses into droplets). Benzophenone is cross-linked into the matrix of the polyacrylamide gel droplet. This allows subsequent photoaffinity crosslinking of the proteins to the polyacrylamide matrix (Hughes, Spelke et al. 2014, Kang, Yamauchi et al. 2016). The proteins immobilized within the resulting single cell gel bead, can be single cell barcoded using a variety of methods. In one embodiment, DNA tags are chemically or photo-chemically attached to the immobilized proteins in the single cell gel beads using amine-reactive agents or a photo-active benzophenone DNA tag as previously described. The single cell gel beads can be encapsulated in droplets containing barcodes via co-encapsulation of barcoded beads as previously described and the DNA barcode tag transferred to the proteins, or alternatively proteins within single cell gel beads can be combinatorically indexed through a series of pool-and-split steps as described by Amini, Cusanovich, and Gunderson et al. (Amini, Pushkarev et al. 2014, Cusanovich, Daza et al. 2015)(Gunderson, Steemers et al. 2016). In the simplest implementation, the proteins within single cell gel beads are first labeled with "click-chemistry" moieties (see, e.g., FIG. 40A-I), and then combinatorial DNA barcodes are clicked onto the protein samples using the pool-and-split approach.

Example 26: Demonstration of Information Transfer by Single Strand DNA Ligation Using DNA Based Model System A DNA model system was used to test transfer of coding tag information to recording tags that are immobilized on beads (see, e.g., FIG. 46A). Two different types of recording tag oligonucleotides were used: a saRT_Bbca_ssLig (SEQ ID NO: 181) ssDNA construct that is 5' phosphorylated and 3' biotinylated and contains a unique 6 base DNA barcodes, Bca, a universal forward primer sequence, and target binding "B" sequence; a saRT_Abca_ssLig (SEQ ID NO: 182) ssDNA construct that is 5' phosphorylated and 3' biotinylated and contains a unique 6 base DNA barcode, Bca, a universal forward primer sequence, and target binding "A" sequence. The coding tag oligonucleotide, CT_B'bcb_ssLig (SEQ ID NO: 183) contains a B' sequence. This design of recording tags and coding tags and associated binding elements enables easy gel analysis. The desired single strand DNA ligation product is generated by CircLigase II (Lucigen) wherein the 5' phosphate group of recording tag and 3' hydroxyl group of coding tag are brought into close proximity via annealing of the B' sequence on the coding tag to the B sequence on the recording tag immobilized on solid surface.

Information transfer via specific interaction between the B coding tag and B recording tag was assessed by gel analysis. The density of the recording tags on the surface was adjusted by titrating mPEG-Biotin, MW550 (Creative PEGWorks) in ratio of 1:10 with biotinylated recording tag oligonucleotides, saRT_Bbc_ssLig or saRT_Abc_ssLig. A total of 2 pmols recording tag oligonucleotide was incubated with 5 µl of M270 streptavidin beads (Thermo) in 50 µl Immobilization buffer (5 mM Tris-Cl, pH 7.5, 0.5 mM EDTA, 1 M NaCl) for 15 minutes at 37° C., washed once with 150 µl Immobilization buffer, and washed once with 150 µl PBST+ 40% formamide. For the model assay, total of 40 pmols CT_B'bcb_ssLig was incubated with 5 µl of recording tag-immobilized beads in 50 µl PBST for 15 minutes at 37° C. The beads were washed twice with 150 µl PBST+40% formamide at room temperature. The beads were resuspended in 10 µl CircLigase II reaction mix (0.033 M Tris-Acetate, pH 7.5, 0.066 M potassium acetate, 0.5 mM DTT, 2 mM MnCl$_2$, 0.5 M Betaine, and 4 U/µL CircLigase II ssDNA Ligase) and incubated at 45° C. for 2 hours. After ligation reaction, beads were washed once with Immobilization buffer+40% formamide, and once with PBST+40% formamide. The final extended recording tag oligonucleotides were eluted from the streptavidin beads by incubation in 10 µl 95% formamide/10 mM EDTA at 65° C. for 5 minutes, and 2.5 µl of elution was loaded to a 15% PAGE-Urea gel.

In this model system, the size of ligated products from 47 bases recording tags is 96 bases (see, e.g., FIG. 46B). The ligated product band was observed in the presence of saRT_Bbca_ssLig, while no product bands were observed in the presence of saRT_Abcb_ssLig. This result demonstrated that specific B/B' seq binding event was encoded by information transfer of coding tag to recording tag. Moreover, the first cycle ligated product was treated with USER Enzyme, and used for $2^{nd}$ information transfer. These events were observed by gel analysis (see, e.g., FIG. 46C).

TABLE 2

Peptide Based and DNA Based Model System Sequences

| Name | Sequence (5'-3') | SEQ ID NO: |
|---|---|---|
| saRT_Bbca_ssLig | /5Phos/TGACATCTAGTGTCGCGGACTACGTGCTTGTCA ATTGGAACCAGTCT/3Bio/ | 181 |
| saRT_Abca_ssLig | /5Phos/TGACATGTGAAATTGTTATCCGCTCATGGATGTC AGAATGCCATTTGCT/3Bio/ | 182 |
| CT_B'bcb_ssLig | GACTGGTTCCAATTGACAAGC/iSP18//iSP18//iSP18/CGA TTTGCAAGGATCACTCGUTTTAGGT | 183 |

/5Phos/ = 5'-phosphorylated
/3Bio/ = 3'-biotinylated
/iSP18/ = 18-atom hexa-ethyleneglycol spacer Example 27: Demonstration of Information Transfer by Double Strand DNA Ligation Using DNA Based Model System DNA model system was used to test transferring of coding tag information to recording tags that are immobilized to beads (see FIG. 47A). The recording tag oligonucleotides are composed of two strands. saRT_Abc_dsLig (SEQ ID NO: 184) is 5' biotinylated DNA that contains a target binding agent A sequence, a universal forward primer sequence, two unique 15 bases DNA barcodes BC1 and BC2, and 4 bases overhang; Blk_RT_Abc_dsLig (SEQ ID NO: 185) is 5' phosphorylated and 3' C$_3$ spacer modified DNA that contains two unique 15 bases DNA barcodes BC2' and BC1', a universal forward primer sequence. A double strand coding tag oligonucleotides are composed of two strands. The one strand, CT_A'bc5_dsLig (SEQ ID NO: 186) that contains dU, a unique BC5 and overhang links to targeting agent A' sequence via polyethylene glycol linker. The other strand of coding tag is Dup_CT_A'bc5 (SEQ ID NO: 187) that contains 5' phosphate, dU and a unique barcode BC5'. This design set-up for the recording tags and coding tags enables easy gel analysis. The desired double strand DNA ligation product is ligated by T4 DNA ligase (NEB) when the 5' phosphate group and 3' hydroxyl group of both tags are close each other via hybridization of targeting agent A' in coding tag to target binding agent A in recording tag immobilized on solid surface.

The information transfer via specific interaction between target binding agent A and targeting agent A' was evaluated. To space the recording tags out on the bead surface, biotinylated recording tag oligonucleotides, a total of 2 pmols saRT_Abc_dsLig hybridized to Blk_RT_Abc_dsLig was titrated against the mPEG-SCM, MW550 (Creative PEG-Works) in ratio of 1:10, and was incubated with 5 µl of M270 streptavidin beads (Thermo) in 50 µl Immobilization buffer (5 mM Tris-Cl, pH 7.5, 0.5 mM EDTA, 1 M NaCl) for 15 minutes at 37° C. The recording tag immobilized beads were washed 1× with 150 µl Immobilization buffer, and washed 1× with 150 µl Immobilization buffer+40% Formamide. For the first cycle assay, total of 40 pmols double strand coding tag, CT_A'bc5_dsLig:Dup_CT_A'bc5 was incubated with 5 µl of recording tag-immobilized beads in 50 µl PBST for 15 minutes at 37° C. The beads were washed 2× with 150 µl PBST+40% formamide at room temperature. The beads were resuspended in 10 µl T4 DNA ligase reaction mix (50 mM Tris-HCl, pH 7.5, 10 mM MgCl2, 1 mM DTT, 1 mM ATP, 7.5% PAG8000, 0.1 µg/µl BSA, and 20 U/µl T4 DNA ligase) and incubated at r.t. for 60 minutes. After ligation reaction, beads were washed 1× with Immobilization buffer+40% Formamide, and 1× with PBST+40% Formamide. The beads were treated with USER Enzyme (NEB) to remove the double strand coding tag, and used for the second cycle ligation assay with CT_A'bc13-R_dsLig: Dup_CT_A'bcl3-R_dsLig (SEQ ID NO: 188 and SEQ ID NO: 189, respectively). After each treatments, the double strand recording tag were eluted from the streptavidin beads by incubation in 10 µl 95% formamide/10 mM EDTA at 65° C. for 5 minutes, and 2.5 µl of elution was loaded to a 15% PAGE-Urea gel.

Figure 47A:
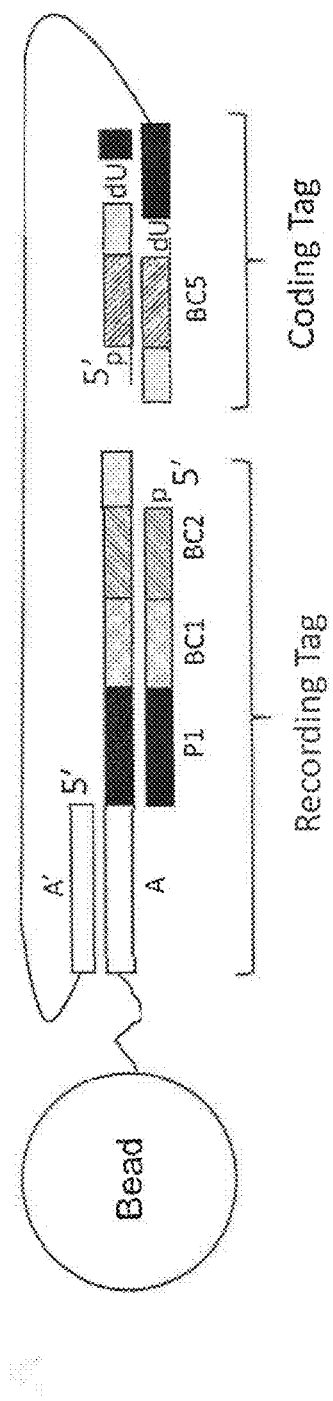
FIG. 47A-47B illustrate an exemplary coding tag transfer via ligation of double strand DNA coding tag to double strand DNA recording tag. Multiple information transfer of coding tag via double strand DNA ligation was demonstrated by DNA based model system.
Figure 47B:
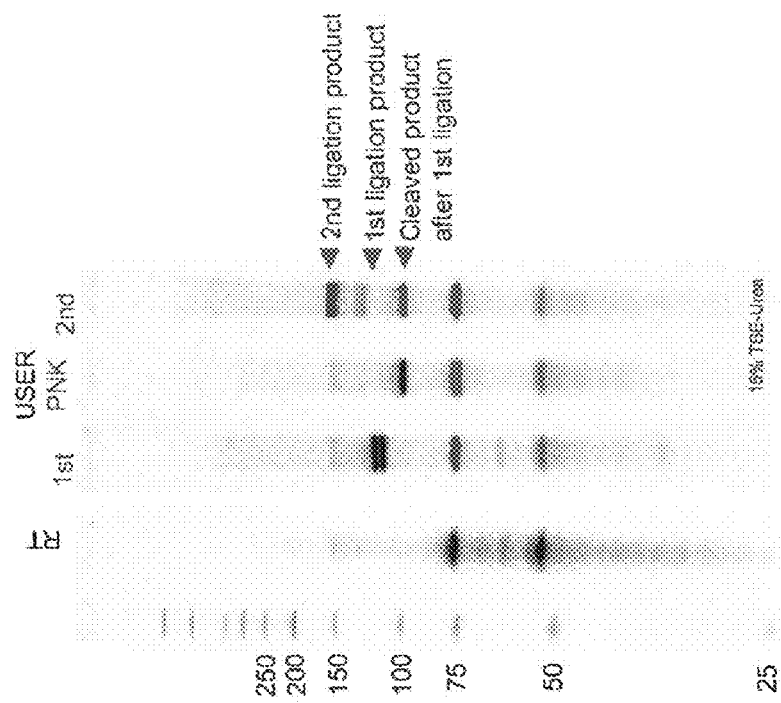
Figure 48A:
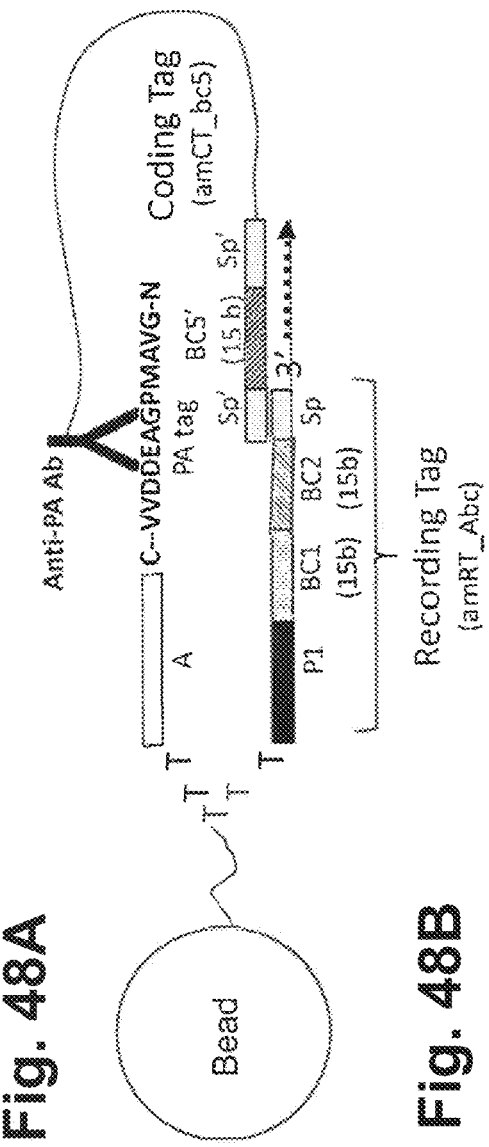
Figure 48B:
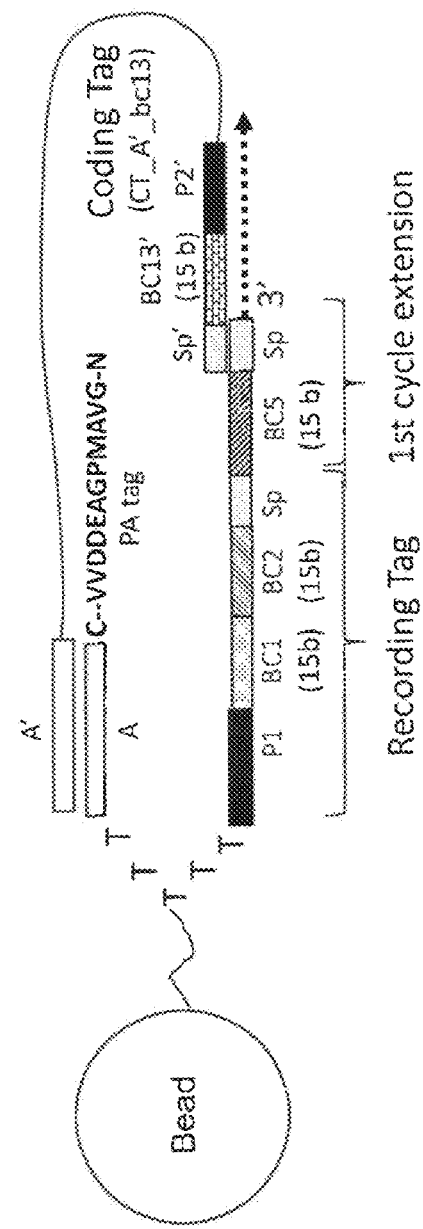
Figure 49A:
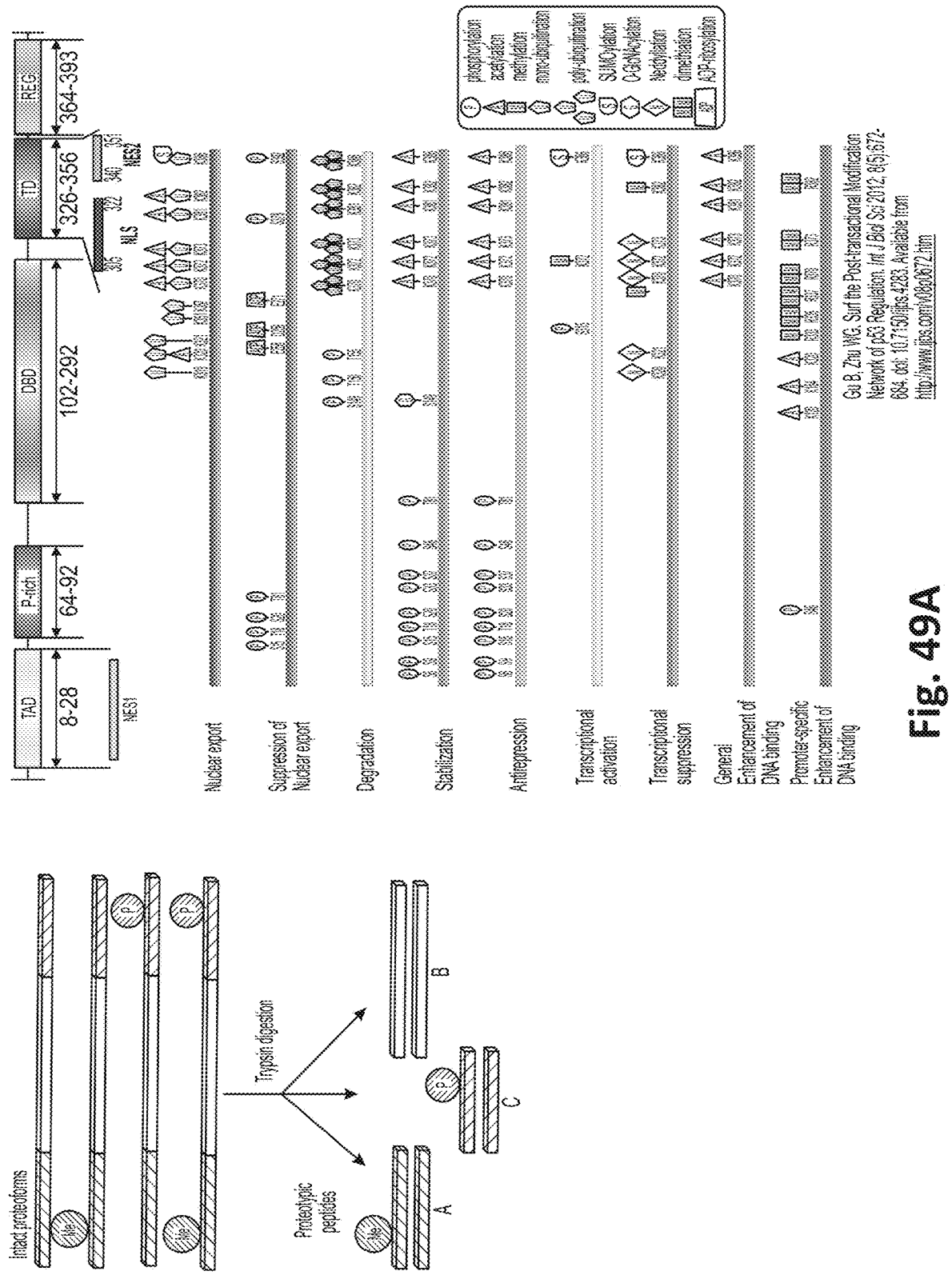

In this model system, the size of ligated products of 76 bases and 54 bases recording tags with double strand coding tag is 116 and 111 bases, respectively (see, e.g., FIG. 47B). The first cycle ligated products were completely disappeared by USER Enzyme (NEB) digestion, and used in the second cycle assay. The second cycle ligated product bands were observed at around 150 bases. These results demonstrated that specific A seq/A' seq binding event was encoded at the first cycle and the second cycle double strand ligation assay.

recording tag (see, e.g., FIG. 48B). The CT_A'_bcl3 was comprised of complementary capture sequence A', and was assigned the 15-mer barcode, BC5 (SEQ ID Nos: 66-130). This design enables easy gel analysis after PCR amplification with specific primer sets.

The internal alkyne-modified recording tag oligonucleotide, amRT_Abc (SEQ ID NO: 190) was modified with Methyltetrazine-PEG4-Azide (BroadPharm). To control the density of recording tags on the bead surface, beads with various densities of functional coupling sites (trans-cyclooctene, TCO) were prepared from M-270 Amine Dynabeads (Thermo Fisher) derivitized389 by titration of TCO-PEG12-NHS ester (BroadPharm) against the mPEG-SCM, MW550 (Creative PEGWorks) in ratios of $1:10^2$, $1:10^3$, and $1:10^4$. The methyltetrazine-modified amRT_Abc recording tags were attached to the trans-cyclooctene (TCO)-derivitized beads. The Cys-containing peptide was attached to 5' amine group of amRT_Abc on beads via SM(PEG)8 (Thermo Fisher). The conjugation of anti-PA antibody (Wako Chemicals) with amCT_bc5 coding tag was accomplished using Protein-Oligonucleotide Conjugation Kit (Solulink). Briefly, the 5' amine group of amCT_bc5 was modified with S-4FB, and then desalted by 0.5 mL Zeba

TABLE 3

Peptide Based and DNA Based Model System Sequences

| Name | Sequence (5'-3') | SEQ ID NO: |
|---|---|---|
| saRT_Abc_dsLig | /5Biosg/TTTTTGCAAATGGCATTCTGACATCCCGTAGTCCGC GACACTAGATGTCTAGCATGCCGCCGTGTCATGTGGAAGA | 184 |
| Blk_RT_Abc_dsLig | /5Phos/CTCTTCTTCCACATGACACGGCGGCATGCTAGACATC TAGTGTCGCGGACTACG/3SpC3/ | 185 |
| CT_A'bc5_dsLig | GGATGUCAGAAUGCCATTTGCTTTTTTTTTT/iSP18/CGGTCT CUCTCTTCCCTAACGCGTATACGGA | 186 |
| Dup_CT_A'bc5_dsLig | /5Phos/AGAGTCCGTATACGCGTTAGGGAUGAGAGAGACCG/ 3SpC3/ | 187 |
| CT_A'bc13-R_dsLig | GGATGUCAGAAUGCCATTTGCTTTTTTTTTT/iSP18/CGGTCT CUCGATTTGCAAGGATCACTCGCCGTTATTGACGCTCGA | 188 |
| Dup_CT_A'bc13-R_dsLig | /5Phos/AGAGTCGAGCGTCAATAACGGCGAGTGATCCTTGCA AATCGAGAGACCG/3SpC3/ | 189 |

/5Biosg/ = 5' Biotin
/3SpC3/ = 3' C3 (three carbon) spacer
/5Phos/ = 5'-phosphorylated
/iSP18/ = 18-atom hexa-ethyleneglycol spacer Example 28: Demonstration of Sequential Information Transfer Cycles Using Peptide and DNA Based Model System The peptide model system was used to test the first cycle transfer of coding tag information to recording tag complexes immobilized on beads (see, e.g., FIG. 48A). The PA peptide sequence (SEQ ID NO: 195) was attached to recording tag oligonucleotide, amRT_Abc (SEQ ID NO: 190) immobilized on beads. The amRT_Abc sequence contains an "A" DNA capture sequence (mimic epitope for "A'" binding agent) and corresponding "A" barcode (rtA-BC). The rtA_BC sequence is a collinear combination of two barcodes, BC_1 and BC_2 (SEQ ID Nos: 1-65). For the binding agent, an anti-PA antibody was attached to the coding tag oligonucleotide, amCT_bc5 (SEQ ID NO: 191) comprised of the 15-mer barcode BC5 (SEQ ID Nos: 66-130). Moreover, DNA model system was used to test the second cycle transfer of coding tag information to the column. The anti-PA antibody was modified with S-HyNic, and then desalted by 0.5 mL Zeba column. Finally, the 4FB-modified amCT_bc5 and HyNic-modified anti-PA antibody was mixed to prepare antibody-coding tag conjugate, followed by size exclusion using Bio-Gel P100 (Bio-Rad).

For the first cycle binding assay, 5 µl of peptide-recording tag (RT)-immobilized beads was incubated with SuperBlock T20 (TBS) Blocking Buffer (Thermo Fisher) at r.t. for 15 minutes to block the beads. A total of 2 pmols of antibody-coding tag conjugate was incubated with 5 µl of peptide-recording tag-immobilized beads in 50 µl PBST for 30 minutes at 37° C. The beads were washed 2× with 1000 µl PBST+30% formamide at room temperature. The beads were resuspended in 50 µl extension reaction master mix (50 mM Tris-Cl (pH 7.5), 2 mM MgSO4, 125 µM dNTPs, 50 mM NaCl, 1 mM dithiothreitol (DTT), 0.1% Tween-20, 0.1 mg/ml BSA, and 0.05 U/µL Klenow exo-DNA polymerase) and incubated at 37° C. for 5 min. After primer extension, beads were washed once with Immobilization buffer (5 mM Tris-Cl (pH 7.5), 0.5 mM EDTA, 1 M NaCl, 30% formamide), once with 50 μl 0.1 N NaOH at room temp for 5 minutes, and once with PBST+30% formamide and once with PBS. For the second binding cycle assay, the CT_A' bcl3 was used to bind to its cognate A sequence within the recording tag, and enable extension of the first cycle extended recording tags to extend upon the second cycle coding tag sequence. After extension, the final extended recording tag oligonucleotides were PCR amplified in 20 μl PCR mixture with specific primers and 1 μl of PCR product was analyzed on a 10% PAGE gel. The resulting gels demonstrate proof of principle of writing coding tag information to the recording tag by polymerase extension (FIG. 48C-E).

In the model system shown in FIG. 48A, the size of PCR products from recording tags amRT_Abc using primer sets P1_F2 and Sp/BC2 is 56 base pairs. As shown in FIG. 48C, amRT_Abc density-dependent band intensities were observed. For the first cycle binding assay with anti-PA antibody-amCT_bc5 conjugate, strong bands at 80 base pairs PCR products were observed when the cognate PA-tag immobilized beads were used in the assay, while minimal PCR product yield was observed when the non-cognate amyloid-beta (AP 16-27) or nano-tag immobilized beads were used (see, e.g., FIG. 48D). For the second binding assay employing an A' DNA tag attached to the CT_A'_bcl3 coding tag (see, e.g., FIG. 48B), all three flavors of peptide recording tag conjugates extend on the annealed CT_A'_bcl3 sequence. As shown in FIG. 48E, relatively strong bands of PCR products were observed at 117 base pairs for all peptide immobilized beads, which correspond to only the second cycle extension on original recording tags (BC1+BC2+BC13). The bands corresponding to the second extension on the first extended recording tags (BC1+BC2+BC5+BC13) were observed at 93 base pairs only when PA-tag immobilized beads were used in the assay. These results demonstrated that specific peptide/antibody and A seq/A' seq binding event was encoded at the first cycle and the second cycle assay, respectively.

TABLE 4

Peptide Based and DNA Based Model System Sequences

| Name | Sequence (5'-3') | SEQ ID NO: |
|---|---|---|
| amRT_Abc | /5AmMC6/GCAAATGGCATTCTGACATCCTT/i5OctdU/TTCGUAGUCCGCGACACTAGATGTCTAGCATGCCGCCGTGTCATGTGGAAACTGAGTG | 190 |
| amCT_bc5 | /5AmMC6//iSP18/CACTCAGTCCTAACGCGTATACGTCACTCAGT/3SpC3/ | 191 |
| CT_A'_bc13 | GGATGTCAGAATGCCATTTGCTTTTTTTTTT/iSP18/CGATTTGCAAGGATCACTCGCCGTTATTGACGCTCTCACTCAGT/3SpC3/ | 192 |
| Sp | ACTGAGTG | 149 |
| Sp' | CACTCAGT | 150 |
| P1_f2 | CGTAGTCCGCGACACTAG | 151 |
| R1 | CGATTTGCAAGGATCACTCG | 152 |
| Sp/BC2 | CACTCAGTTTCCACATGACACGGC | 193 |
| Sp/BC5 | CACTCAGTCCTAACGCGTATA | 194 |
| PA peptide | GVAMPGAEDDVVGGGGSC | 195 |
| Nanotag Peptide | Formyl-MDVEAWLGARVPLVETGSGSGSC | 196 |
| Aβ Peptide | HQKLVFFAEDVGSGSGSC | 197 |

/3SpC3/ = 3' C3 (three carbon) spacer
/i5OctdU/ = 5'-Octadiynyl dU
/iSP18/ = 18-atom hexa-ethyleneglycol spacer Example 29: Labeling a Protein or Peptide with a DNA Recording Tag Using mRNA Display Individual barcode is installed to the 3' end of each DNA encoding protein by PCR and barcoded DNAs are pooled. Amplified DNA pools are transcribed using AmpliScribe T7 Flash (Lucigen). Transcription reactions are cleaned up using Rneasy Mini Kit (Qiagen) and quantified by NanoDrop 3000 (Fisher Scientific). The DNA adaptor is attached to the 3' end of mRNAs using T4 DNA ligase (NEB). Ligated mRNA molecules are purified using 10% TBE-Urea denaturing gel. The mRNA-puromycin molecules are translated in vitro using PURExpress kit (NEB). During in vitro translation, a stalled ribosome allows the puromycin residue to enter the ribosome A-site and attach to the C-terminus of the protein, creating a protein-mRNA fusion. The protein-mRNA fusions are captured via complementary oligonucleotides attached to silica beads. The mRNA portions are converted into cDNA using ProtoScript II Reverse Transcriptase (NEB). The protein-cDNA/RNA pools are treated with Rnase H (NEB) and Rnase cocktail (Thermo Fisher) to generate protein-cDNA, and then purified by cut-out filter. The complementary sequence to the type II restriction site in cDNA is added to form double strand, and incubated with restriction enzyme to generate spacer sequence (Sp) at the 3' end of cDNA. A portion of the pool is used for sequencing to characterize protein representation in the starting protein-cDNA pool.

Example 30: Ribosome Display-Based Protein Barcoding

For protein libraries of relatively small size (e.g., <200 in this work), a barcoding sequence can be introduced to DNA templates by performing individual PCR reactions with a barcoded primer. Barcoded linear DNA templates are pooled and in vitro transcribed using a HiScribe T7 kit (NEB). Transcribed mRNAs are treated with a DNA-free kit (Ambion), purified with an Rneasy Mini kit (Qiagen) and quantified by Nanodrop 1000 (Thermo Scientific). To generate mRNA-cDNA hybrids, cDNAs are synthesized by incubating 0.10 µM mRNA, 1 µM 5'-acrydite and desthiobiotin-modified primer, 0.5 mM each dNTP, 10 U/µL Superscript III, 2 U/µLRNaseOUT (Invitrogen) and 5 mM dithiothreitol (DTT) in a buffer (50 mM Tris-HCl, pH 8.3, 75 mM KCl, and 5 mM MgCl2) at 50° C. for 30 min. Resultant mRNA-cDNA hybrids are enriched by isopropanol precipitation and purified with streptavidin-coated magnetic beads (Dynabeads M-270 Streptavidin, Life Technologies). A PURExpress A Ribosome kit (NEB) is applied to display proteins on E. coli ribosomes. Typically, a 250 µL. IVT reaction with 0.40 µM mRNA-cDNA hybrids and 0.30 µM ribosome is incubated at 37° C. for 30 min, quenched by addition of 250 µL, ice-cold buffer HKM (50 mM HEPES, pH 7.0, 250 mM KOAc, 25 mM Mg(Oac)2, 0.25 U/mL Rnasin (Promega), 0.5 mg/mL chloramphenicol, 5 mM 2-mercaptoethanol and 0.1% (v/v) Tween 20) and centrifuged (14,000 g, 4° C.) for 10 min to remove insoluble components. PRMC complexes, always kept on ice or in cold room, are subjected to two-step Flag tag and desthiobiotin tag affinity purification to enrich full-length and barcoded target proteins. Thus, proteins are sequentially purified using anti-Flag M2 (Sigma-Aldrich) and the streptavidin magnetic beads, which are blocked with the buffer HKM supplemented with 100 µg/mL yeast tRNA and 10 mg/mL BSA. The bound proteins are eluted with the buffer HKM containing 100 g/ml Flag peptide or 5 mM biotin, and their barcoding DNAs are quantitated by real-time PCR.

Example 31: Information Transfer by Single Strand DNA Spacer Ligation Using NTAA Detection System For DNA/Polymer chimera coding tags and recording tags, information can be transferred from the coding tag on the bound binding agent to the proximal recording tag by ligation using standard nucleic acid enzymology (FIG. 54). An NTAA detection system can be used to test transfer of polymer coding tag information to recording tags that are immobilized on beads (see, FIG. 1A). The DNA/Polymer chimera recording tag is used: single-strand DNA/Polymer chimera construct that is 5' phosphorylated, internal alkyne-modified and 3' amino-modified and contains a DNA spacer (e.g. 1-6 bases), a polymer barcode (e.g. protected DNA, PNA, peptoid, non-DNA polymer, etc.), universal polymer adaptor (e.g. cholesterol, biotin, tether DNA sequence, etc.), dU for USER Enzyme (NEB) digestion. The DNA/Polymer chimera coding tag is 5' amino-modified and contains a universal polymer adapter, a polymer barcode (e.g. protected DNA, PNA, peptoid, etc.), and a DNA spacer (e.g. 1-6 bases). This design of recording tag and coding tag and associated binding elements enables easy gel analysis. The desired single strand DNA ligation product is generated by CircLigase II (Lucigen) where the 5' phosphate group of recording tag and 3' hydroxyl group of coding tag are brought into close proximity via binding of NTAA on the coding tag to the NTAA of peptide on the recording tag immobilized on solid surface.

Information transfer via specific interaction between the NTAA binder coding tag and the NTAA of peptide recording tag can be assessed by gel analysis. The density of the recording tags on the surface can be adjusted as following. The internal alkyne-modified DNA/Polymer chimera recording tag is modified with Methyltetrazine-PEG4-Azide (BroadPharm). To control the density of recording tags on the bead surface, beads with various densities of functional coupling sites (trans-cyclooctene, TCO) are prepared from M-270 Amine Dynabeads (Thermo Fisher) derivitized394 by titration of TCO-PEG12-NHS ester (BroadPharm) against the mPEG-SCM, MW550 (Creative PEGWorks) in ratios of 1:102, 1:103, and 1:104. The methyltetrazine-modified recording tags are attached to the trans-cyclooctene (TCO)-derivitized beads. The Cys-containing peptide is attached to 3' amine group of recording tag on beads via SM(PEG)8 (Thermo Fisher).

A total of 2 pmols recording tag is incubated with 5 ul of M270 streptavidin beads (Thermo) in 50 ul Immobilization buffer (5 mM Tris-Cl, pH 7.5, 0.5 mM EDTA, 1 M NaCl) for 15 minutes at 37° C., washed once with 150 ul Immobilization buffer, and washed once with 150 ul PBST+30% formamide. For the model system, total of 30 pmols coding tag attached NTAA binder is incubated with 5 ul of recording tag-immobilized beads in 50 ul PBST for 15 minutes at 37° C. The beads are washed twice with 150 ul PBST+30% formamide at room temperature. The beads are resuspended in 10 ul CircLigase II reaction mix (0.033 M Tris-Acetate, pH 7.5, 0.066 M potassium acetate, 0.5 mM DTT, 2 mM MnCl2, 0.5 M Betaine, and 4 U/uL CircLigase II ssDNA Ligase) and incubated at 45° C. for 2 hr. After ligation reaction, beads are washed once with Immobilization buffer+30% formamide, and once with PBST+30% formamide. The final extended recording tags are eluted from beads by 5 ul of USER Enzyme treatment at 37° C. for 5 minutes, and 2.5 ul of elution is loaded to a 15% PAGE-Urea gel. The ligated recording tag can be used on nanopore sequencing.

Example 32: Information Transfer by Double Strand DNA Spacer Ligation Using NTAA Detection System For DNA/Polymer chimera coding tags and recording tags, information can be transferred from the coding tag on the bound binding agent to the proximal recording tag by ligation using standard nucleic acid enzymology. An NTAA detection system can be used to test transfer of polymer coding tag information to recording tags that are immobilized on beads (see, FIG. 54). The DNA/Polymer chimera recording tag is used: single-strand DNA/Polymer chimera construct that is 5' phosphorylated, internal alkyne-modified and 3' amino-modified and contains a DNA spacer (e.g. 5-20 bases), a polymer barcode (e.g. protected DNA, PNA, peptoid, etc.), universal polymer adaptor (e.g. cholesterol, biotin, tether DNA sequence, etc.), dU for USER Enzyme (NEB) digestion. The DNA/Polymer chimera coding tag is 5' amino-modified and contains a universal polymer adapter, a polymer barcode (e.g. protected DNA, PNA, peptoid, etc.), and a DNA spacer (e.g. 5-20 bases).

This design of recording tag and coding tag and associated binding elements enables easy gel analysis. The desired single strand DNA ligation product is generated by splint DNA hybridization followed by T4 DNA ligase (NEB) where the 5' phosphate group of recording tag and 3' hydroxyl group of coding tag are brought into close proximity via binding of NTAA on the coding tag to the NTAA of peptide on the recording tag immobilized on solid surface.

Information transfer via specific interaction between the NTAA binder coding tag and the NTAA of peptide recording tag can be assessed by gel analysis. The density of the recording tags on the surface can be adjusted as following. The internal alkyne-modified DNA/Polymer chimera recording tag is modified with Methyltetrazine-PEG4-Azide (BroadPharm). To control the density of recording tags on the bead surface, beads with various densities of functional coupling sites (trans-cyclooctene, TCO) are prepared from M-270 Amine Dynabeads (Thermo Fisher) derivitized395 by titration of TCO-PEG12-NHS ester (BroadPharm) against the mPEG-SCM, MW550 (Creative PEGWorks) in ratios of 1:102, 1:103, and 1:104. The methyltetrazine-modified recording tags are attached to the trans-cyclooctene (TCO)-derivitized beads. The Cys-containing peptide is attached to 3' amine group of recording tag on beads via SM(PEG)8 (Thermo Fisher).

A total of 2 pmols recording tag is incubated with 5 ul of M270 streptavidin beads (Thermo) in 50 ul Immobilization buffer (5 mM Tris-Cl, pH 7.5, 0.5 mM EDTA, 1 M NaCl) for 15 minutes at 37° C., washed once with 150 ul Immobilization buffer, and washed once with 150 ul PBST+30% formamide. For the model system, total of 30 pmols coding tag attached NTAA binder is incubated with 5 ul of recording tag-immobilized beads in 50 ul PBST for 15 minutes at 37° C. The beads are washed twice with 150 ul PBST+30% formamide at room temperature. The beads are resuspended in 10 ul T4 DNA ligase reaction mix (50 mM Tris-HCl, pH 7.5, 10 mM MgCl2, 1 mM DTT, 1 mM ATP, 7.5% PAG8000, 0.1 ug/ul BSA, 30 pmols splint DNA and 20 U/ul T4 DNA ligase) and incubated at r.t. for 60 minutes. After ligation reaction, beads are washed once with Immobilization buffer+30% formamide, once with 0.1N NaOH at room temperature for 5 minutes and once with PBST+30% formamide. The final extended recording tags are eluted from beads by 5 ul of USER Enzyme treatment at 37° C. for 5 minutes, and 2.5 ul of elution is loaded to a 15% PAGE-Urea gel. The ligated recording tag can be used on nanopore sequencing.

Example 33: Coding Polymer Transfer to Recording Polymer Via Chemical Ligation

A coding polymer is transferred either directly or indirectly from a binder-coding polymer conjugate by ligation to the recording polymer to generate an extended recording polymer. In one implementation, this process is performed using chemical ligation methods. The coding polymers used can be linear or branched, charged or uncharged, hydrophobic or hydrophilic. The ligation chemistry used can be performed via Michael addition (thiol-maleimide), copper catalyzed azide-alkyne cycloaddition, ring strained azide-alkyne cycloaddition, amide bond formation via an activated ester and an amine, or other ligation chemistries detailed herein. The polymer ligation step can be performed using the same ligation reaction every cycle, alternating ligation reactions (to prevent cyclic byproducts) every other cycle, or a different ligation reaction every cycle.

In one example a solution of beads is present each with a polypeptide to be analyzed and an alkyne terminated PEG chain (~4000 Da, PDI 2.1) recording polymer anchored to it. The bead is treated with a cocktail of NTAA specific binders each ligated to the backbone of specific coding polymer chains via diisopropyl silyl ether linkages (80 uL of the binder cocktail, phosphate buffer, pH=8.0). The binders could be anticalins, ClpS or other binder derivatives noted herein. In one such example, one of the binder ligated coding polymers can be a linear acrylamide functionalized with bulky groups such as adamantane and charged groups such as carboxylic acids with a total molecular weight of ~1000 Da (50% acrylamide, 20% adamantyl397 acrylamide, 30% acrylic acid feed ratio, PDI=2.2). The linear acrylamide coding polymer is terminated on each end with an azide. Upon recognition of the NTAA by the binder, the azide terminated coding polymer is brought into close proximity with the alkyne terminated recording polymer present on the bead. Copper (II) sulfate (10 uL of a stock solution of 10 mM) and ascorbic acid (10 uL of a 500 mM stock solution) are added to the mixture and the coding polymer is ligated to the recording polymer via azide-alkyne cycloaddtion. The binder is then cleaved from the polymer backbone using a fluorine reagent such as tetra-n-butyl ammonium fluoride (TBAF, final concentration 1 mM) yielding the now diblock397 recording polymer (PEG-acrylamide) conjugate now terminated with an azide.

The NTAA of the polypeptide analyzed is cleaved using Edman degradation conditions. The NTAA is first treated with PITC (10 µL of a 5 M stock solution in DMF, added to 90 µL of the bead solution at 40° C., phosphate buffer pH=8.5, 2 h). Alternatively, the NTAA is first treated with PITC (10 µL of a 5 M stock solution in DMF, added to 90 µL of the bead solution at 40° C., ACN/Water (approximately 2:1 v/v). ACN refers to acetonitrile. The beads are washed. The PITC terminated NTAA is then treated with neat TFA to eliminate the NTAA and yield a new NTAA.

Following washing the beads, the new NTAA is again treated with a series of binder-coding polymer conjugates (80 uL of the binder cocktail, phosphate buffer, pH=8.0). In this cycle the polymer side chains are terminated on both ends with alkynes. In one such case the coding polymer is polyacrylate (~5 kDa, PDI=1.8). Upon recognition of the NTAA by the binder, the alkyne terminated coding polyacrylate polymer is brought into close proximity with the azide terminated recording polymer present on the bead. Copper (II) sulfate (10 uL of a stock solution of 10 mM) and ascorbic acid (10 uL of a 500 mM stock solution) are added to the mixture and the coding polymer is ligated to the recording polymer via azide-alkyne cycloaddtion. The beads are thoroughly washed with buffer. The binder is then cleaved from the polymer backbone using a fluorine reagent such as tetra-n-butyl ammonium fluoride (TBAF, final concentration 1 mM in THF) yielding the now triblock recording polymer (PEG-acrylamide-acrylate) terminated with an alkyne.

Example 34: Construction of a Sequenceable Polymer for Nanopore Sequencing

The recording tag and coding tag can be comprised of a sequenceable polymer and/or encoding subunits, and the final extended recording tag is comprised of a sequenceable polymer. For nanoelectronics sequencing such as nanopores, this sequenceable polymer needs to have encoding properties in which the encoding units, when passed through a nanopore or passed by a nanogap or nanoribbon device, modulate the electrical signature (Heerema and Dekker 2016) (See FIG. 56). An encoding unit can be made from a string of different elementary current blockade (or modulation) moieties to create a combinatorial current blockade signature (see FIG. 56). The combinatorial current blockade moieties can be interspersed with "stall" regions which stall the transit of the polymer through the nanopore (See FIG. 56). Alternatively, if the electronics are fast enough, the polymer can be readout directly on the nanopore, perhaps with multiple repeats of a blockade moiety to provide better signal (FIG. 56).

Example 35: Nanopore Sequencing of an Encoded Polymer

Nanopores comprised of M2-NNN MspA embedded in lipid bilayers are used to measure blockade currents of translocating polymers (Laszlo, Derrington et al. 2014) (see FIG. 57). In short, a lipid bilayer is created by painting 1,2-diphytanoyl-sn-glycerol-3-phosphocholine lipid (Avanti Polar Lipids) across a horizontal ~20 µm diameter aperture separating two ~60 µL chambers containing our operating buffers. An Axopatch 200B integrating patch clamp amplifier (Axon Instruments) applies a 180 mV voltage across the bilayer (trans side positive) and the ionic current through the pore is measured. The analog signal is low-pass filtered at 10 kHz with a 4-pole Bessel filter and digitized at five times the low-pass filter frequency. A salt solution of 1M KCl in 10 mM HEPES/KOH (pH 8.0) is used on both the cis and tran sides, and experiments are done at room temperature (23±1° C.). AgCl electrodes, made from fresh Ag wires with bleach, were inserted into both cis and trans sample reservoirs for ionic current measurement. The biological protein nanopore, M2-NNN MspA, is added to the grounded cis compartment to a final concentration of ~2.5 ng/ml. Once a single pore inserts, as seen by a characteristic increase in the conductance, the buffer is replaced with MspA-free buffer to prevent additional pore formation. Polymer (w/ biotin moiety) appended with a cholesterol adapter is added to the cis compartment to a final concentration of 1 nM. Monomeric streptavidin (mSA2), Kd~2-3 nM, is added to the cis side at 100 nM (Demonte, Drake et al. 2013). The cholesterol adapter captures the polymer on the membrane surface by cholesterol partitioning into the membrane. The negatively charged polymer is captured in the pore and translocation ensues. The polymer translocates through the nanopore until the first biotin-mSA2 complex reaches the pore entrance (see FIG. 58). At a voltage of 180 mV, the polymer stalls in the pore until the scSA dissociates due to the energetics of the applied force such that the mean stall time is on the order of msecs.

Example 36: Multiple Cycle Binding/Encoding Assay

A peptide model system was used to test three cycles of encoding wherein information from the coding tag was transferred to the recording tag immobilized on beads (FIG. 59). The PA peptide sequence (SEQ ID NO: 195) was attached to recording tag oligonucleotide, amRT_Bbc (SEQ ID NO: 214) immobilized on beads. The amRT_Bbc sequence contains BC_3 (SEQ Id NOs: 66-130). For the binding agent, an anti-PA antibody (Wako Chemical) was attached to the coding tag oligonucleotides amCT_bc4, amCT_bc5 and amCT bcl3r1 (SEQ Id NOs: 209-211) comprised of the 15-mer barcodes BC4, BC5 and BC13R1 (SEQ Id NOs: 66-130), respectively. This design facilitates gel analysis after PCR amplification with specific primer sets.
Generation of Magnetic Assay Beads-Two Step Process.

DNA recording tag-peptide chimeras were immobilized on magnetic beads at controlled density using a two-step immobilization process similar to the one step assay bead process described in FIG. 34A-C except for coupling the peptide post recording tag immobilization rather than coupling the chimera as a single unit. Namely, M-270 Amine Dynabeads beads (Thermo Fisher) were sparsely surface functionalized with Trans-Cyclooctene (TCO) groups by titrating TCO-PEG12-NHS ester (BroadPharm) with mPEG-SCM, MW550 (Creative PEGWorks) in ratios of 1:103. Excess amine group were capped with NHS-acetate. In the two-step chimera immobilization process, bifunctional DNA recording tags comprised of an internal alkyne modification and 5' amine modification were immobilized to TCO beads by first converting the internal alkyne oligonucleotide modifier to mTet, and then coupling directly to the TCO beads, after which the peptide was coupled to the 5' amine of the recording tag oligo. Specifically, the internal alkyne-modified recording tag oligonucleotide was modified with mTet-PEG4-Azide (BroadPharm) and then attached to the TCO-derivatized beads. To couple a peptide to the 5' amine recording tag on the bead, a cysteine-containing peptide was attached to 5' amine group of the immobilized recording tag via NHS-PEG8-Mal (Thermo Fisher).
Generation of Coding Tag Labeled PA Antibodies The conjugation of anti-PA antibodies with coding tags (amCT_bc4, or amCT_bc5, or amCT_bc13r1 oligonucleotides) were accomplished using Protein-Oligonucleotide Conjugation Kit (Solulink). Briefly, the 5' amine group of coding tag was modified with S-4FB, and then desalted by 0.5 mL Zeba column. The anti-PA antibody was modified with S-HyNic, and then desalted by 0.5 mL Zeba column. Finally, the 4FB-modified coding tag and HyNic-modified anti-PA antibody was mixed to prepare antibody-coding tag conjugate, followed by desalting using 0.5 mL Zeba column.
Antibody-Based Binding/Encoding Assay:

PA peptide-recording tags amRT_Bbc (SEQ ID NO: 214) beads were prepared as described above. For the 1 t cycle binding assay, one million beads were initially blocked by incubating with SuperBlock T20 (TBS) Blocking Buffer (Thermo Fisher) at room temperature (r.t.) for 15 minutes. The coding tag (BC4)-labeled PA antibody at 40 nM was incubated with the assay beads in 50 ul of PBST (1×PBS, 0.1% Tween-20) for 30 minutes at 37° C. The beads were washed once with 1 ml of PBST containing 10% formamide at r.t. The beads were resuspended in 50 ul of extension reaction master mix (50 mM Tris-Cl (pH 7.5), 2 mM MgSO$_4$, 125 µM dNTPs, 50 mM NaCl, 1 mM dithiothreitol, 0.1% Tween-20, 0.1 mg/ml BSA, and 0.05 U/uL Klenow exo-DNA polymerase) and incubated at 37° C. for 5 min. After primer extension, the beads were washed (at r.t.) once with 150 ul of PBST/10% formamide, once with 150 ul of 0.1 N NaOH for 5 minutes, once with 150 ul of PBST/10% formamide, and once with 50 ul of PBST. For the $2^{nd}$ and $3^{rd}$ binding cycle assays (see FIG. 59), coding tag (BC5)-labeled PA antibodies, and coding tag (BC13)-labeled PA antibodies, were used respectively in the binding/encoding assay. After the third encoding cycle extension, the final extended recording tags were PCR amplified in 20 ul PCR mixture with barcode specific primers and 1 ul of PCR product was analyzed on a 10% PAGE gel. The resulting gels demonstrates proof of principle of binding and writing three cycles of coding tag information to the recording tag by polymerase extension (see FIG. 59). In addition to gel analysis, the extended recording tags generated after $3^{rd}$ binding assay were amplified with primers to generate an NGS sequencing library. The resulting library was sequenced on an Illumina MiSeq instrument, and results shown in FIG. 59. Over 78% of extended recording tags contained 3 barcodes, indicating relatively efficient stepwise encoding.

Example 37: Enhanced Encoding with Assay Blocking Oligos (Also See FIG. 3 and FIG. 36A)

An oligo model system of binding and encoding was evaluated using different DNA blockers in a three-cycle encoding assay to evaluate the effect on encoding efficiency (FIG. 60). The recording tag oligonucleotide, amRT_Bbc (SEQ ID NO: 214) was immobilized on beads as previously described. This recording tag sequence contains a "B" DNA capture sequence (mimic epitope for "B"' binding agent) and a BC_3 barcode (SEQ ID NOs: 1-65). In this model system, the binder-coding tag employs an oligonucleotide with a B complementary sequence (B') appended to a DNA coding tag. Three types of DNA blockers were tested (part (A) of FIG. 60). The CT blocker hybridizes to the coding tag 5' Sp' region and the barcode sequence. The 3' Sp' sequence is free for annealing. On the recording tag, the Sp' blocker and RT blocker hybridize to the Sp spacer sequence, and Sp-barcodes on the recording tag, respectively. After encoding, the extended recording tag was PCR amplified and analyzed using PAGE. As shown in part (B) of FIG. 60, the 3rd cycle encoded band was observed in the PCR products from 3 cycles in the presence of CT blocker, but not in the presence of Sp' or RT blocker alone. The data indicated that the CT blocker facilitated efficient transfer of the coding tags information to recording tags.

Example 38: Minimize Template Switching During Extended Recording Tag Amplification Template switching during PCR was evaluated using two extended recording tag oligonucleotide model templates, TS_Ctrl1 (SEQ ID NO: 212) and TS_Ctrl4 (SEQ ID NO: 213) (FIG. 61). These model templates were designed to share common Sp and barcode sequences to mimic extended recording tag template structures. The model templates shown in FIG. 61 were mixed in a 1:1 ratio and amplified by PCR with different polymerases at various temperatures. The template switching rate was evaluated by analysis of PCR products using a 10% PAGE gel and also by NGS readout (not shown).

In detail, a 10 fmol 1:1 mixture of the above two templates were amplified in 10 ul PCR reaction using Fwd and Rev primers as shown in FIG. 61 and analyzed by 10% PAGE gel, and also analyzed by NGS using a MiSeq DNA sequencer (Illumina). Template switching rates of the following polymerases were assayed across a 50-68° C. annealing temperature window: Q5 Hot Start (New England Biolabs), Taq (New England Biolabs), Deep Vent (exo-) (New England Biolabs), KOD Xtreme Hot Start (EMID Millipore) and Herculase II Fusion DNA polymerases (Agilent). As shown in FIG. 61, two main bands (125 bp and 173 bp) corresponding to PCR products from TS_Ctrl1 and TS_Ctrl4 were observed. Template switching by-product bands were observed with many polymerases including Deep Vent exo- as seen by the lower molecular weight bands on the gel (see FIG. 61), but minimized with Taq DNA polymerase (see FIG. 61) and KOD Xtreme Hot Start DNA polymerase (data not shown), and these polymerases were subsequently analyzed in more detail by NGS which showed 5.6% and 2.4% of mapped read fractions exhibiting template switching with Taq and KOD Xtreme Hot Start DNA polymerase, respectively.

Example 39: Demonstration of the Full Cycle Proteocode Peptide Sequencing Assay

Demonstration of a one cycle ProteoCode NGPS assay is described in FIG. 62. The removal of an N-terminus amino acid of peptide by our N-terminal Functionalization and N-Terminal Elimination (NTF/NTE) reagents was detected by two cycles of an F-binder binding assay (see FIG. 62). N-terminal FA, AF and A peptides with an internal PA peptide sequence (SEQ ID NOs: 201, 202, and 203) were individually attached to the recording tag oligonucleotide, amRT_Cbc (SEQ ID NO: 215) immobilized on beads using the two-step process described in Example 1.

The conjugation of F-binder with coding tags, amCT bc4 and amCT_bc5 (SEQ ID NOs: 209, 210), was accomplished using SpyTag/SpyCatcher protein coupling method as previously described. Briefly, F-binder fused to SpyCatcher was expressed in *E. coli*, purified by Ni-NTA column, and dialyzed in PBS. The Cys-containing peptide SpyTag (SEQ ID NO: 198) was attached to the 5' amine of amCT_bc4 and amCT_bc5 via SM(PEG)24 (Thermo Fisher). Finally, the SpyTag-modified coding tag and SpyCatcher-fused F-binder were mixed to prepare F-binder-coding tag conjugate.

Two cycles of F binding and encoding were performed, pre-NTF/NTE chemistry and post-NTF/NTE chemistry. The binding and encoding assay was performed as described in Example 1. After 1st cycle F-binder binding/encoding assay, the assay beads were subjected to treatment with NTF/NTE reagents to remove the NTAA. For NTF treatment, the assay beads were incubated with 150 ul of 15 mM N-Boc-N'-TFA-pyrazole-1-carboxamidine (Sigma) in 0.5M triethylammonium acetate, pH 8.5/acetonitrile (1:1), 0.05% F-127 at 50° C. for 1 hour. The beads were washed 3× with 200 ul of 0.5M triethylammonium acetate, pH 8.5/acetonitrile (1:1), 0.05% F-127. The NTE treatment was performed by incubating the assay beads with 150 ul of 0.5M NaOH containing 0.05% Tween 20 at 40° C. for 1 hour. The beads were washed with 1 ml of PBST containing 10% formamide and used for 2nd cycle F-binder binding assay with F-binder-coding tag. The F-binder was conjugated with different cycle-specific barcode coding tags for the pre-chemistry vs. post-chemistry binding/encoding cycle. The extended recording tag of the assay was analyzed by NGS. The NGS results indicate the F-binder detects the FA peptide in the 1st cycle but minimally the AF peptide, in contrast the F-binder detects the AF peptide with higher efficiency in the 2nd cycle after NTF/NTE treatment whereas the FA peptide is poorly detected. In summary, the approximately 4-fold increase in F-binder encoding before and after chemistry detected on AF peptide-recording tag, while approximately 4-fold decrease in F-binder encoding on FA peptide before and after chemistry effectively demonstrates proof of principle single cycle peptide sequencing using DNA encoding.

Example 40: Crosstalk Measurement

FIG. 36A-F illustrates the effect of using a DNA model system chimera density on the bead and inter-molecular cross-talk. We developed a 4-plex peptide-recording tag (RT) crosstalk model system using surface titration of peptide-RT chimeras on mTet derivatized carboxyl M270-Dynal beads. To control the density of peptide-RT chimeras on the bead surface, beads with functional coupling sites (methyltetrazine, mTet) were prepared from activated M-270 Carboxyl Dynabeads (Thermo Fisher) derivatized by titration of NH2-PEG4-methyltetrazine (BroadPharm) against the m-PEG4-amine (BroadPharm) in ratios of 1:100, 1:1000, 1:10000 and 1:100000. By TCO/mTet coupling, 4-plex, no peptide, FA, AA and AF peptide-attached recording tags were immobilized on beads in the ratios of 1:100, 1:1000, 1:10000 and 1:100000.

A set of peptide-RT chimeras were created by first "activating" the 5' amine on the RT oligonucleotides by coupling to TCO-PEG12-NHS ester (Click Chemistry Tools). After TCO activation, the RT oligonucleotide, designed with an internal alkyne group, was coupled to azide-containing FA, AA and AF peptides. Peptides with N-terminal FA, AA and AF amino acid sequences and an internal PA epitope (SEQ ID NO:195) were individually attached to recording tag oligonucleotides, amRT_Cs2, amRT_Cs4, and amRT_Cs5 (SEQ ID NOs: 217-219), respectively. A fourth recording tag, amRT_Cs1 (SEQ ID NOs: 216), was included as a no peptide control. An F-binder binding agent was conjugated to the coding tag oligonucleotide, amCT_s7 (SEQ ID NO: 220) comprised of the 8-mer barcode BC_s7 (SEQ ID NO: 221). The four chimeras (FA peptide, AA peptide, AF peptide, and no peptide) were combined and immobilized to mTet beads using iEDDA TCO-mTet chemistry. F-binder coding tag constructs were created as described in Example 4.

The crosstalk assay signal between recording tags was detected by one cycle F-binding/encoding assay on 4-plex assay beads (see FIG. 63). Assay conditions were described in Example 1 except 200 nM of F-binder binding agent was employed. Absolute loading of the four different chimeras was measured by a 2nd cycle of binding/encoding with the universal PA antibody wherein all three peptide types contained a PA antigen sequence. FIG. 63 shows that all four chimeras were loaded in roughly equal amounts on the beads. Specific encoding was identified by F-binder encoding on the N-terminal F-peptide recording tag, as determined by NGS readout of barcodes in the extended recording tags. Crosstalk was identified by F-binder encoding on N-terminal non-F (AA peptide, AF peptide, and no peptide) peptide recording tags. As shown in FIG. 63, all chimera recording tags received F-binder barcodes on the 1:100 and 1:1000 active site beads while only FA recording tags received the F-binder barcodes on 1:10000 and 1:100000 beads. The data indicated that intermolecular as well as intra-molecular encoding occurred on high recording tag density beads (1:100 and 1:1000) and primarily only intra-molecular encoding occurred on the lower density beads (1:10,000 and 1:100,000). In conclusion, this model system demonstrated intra-molecular single molecule binding and encoding on sparsely populated beads. Note that the density titration of this example does not directly correlate with the DNA model system of Example 36 since different bead chemistries were employed.

Example 41: Encoding with Base-Protected DNA

The challenge of our NTF/NTE Edman-like chemistry is that highly-reactive NTF reagents in addition to modifying the N-terminal amine of peptide may also modify exocyclic and other amine groups on the nucleobases of DNA. DNA modification may compromise the encoding function of the DNA in the assay. Modification of DNA can be greatly reduced by employing nucleobase protected DNA. This approach allows the use of a much broader set of chemistry reactions and reaction conditions facilitating rapid modification of the NTAA group.

One challenge to implementing the above approach with nucleobase protected DNA is that most nucleobase protecting groups reduce the ability of DNA to form hybrids, a useful prerequisite for primer extension and many ligation encoding assay.

Surprisingly, the use of protected ssDNA in the DNA encoding process is enabled by using a ssDNA ligase, CircLigase, to ligate fully protected oligonucleotides together. We tested the ability of CircLigase to ligate fully protected oligonucleotides with a natural "T" oligonucleotide spacer sequence on either side (3' or 5') of the ligation junction. We found that efficient ligation could be accomplished in the absence of a T spacer on the 5' side using a protected G base immediately adjacent to the ligation junction. A natural T spacer was used on the 3' side.

The oligo model system was used to test the 1st cycle transfer of coding tag information to recording tag complexes immobilized on beads (FIG. 64). PRT_0T_B'_bio was immobilized on beads using a strong biotin-streptavidin interaction on streptavidin-functionalized beads. PRT_0T_B' bio sequences contain an "B'" DNA capture sequence (mimic epitope for "B" binding agent) and corresponding "B'" barcode comprised of the protected dA, dG and dC. For the binding agent, a complementary "B" binding sequence CT_B_thio (SEQ ID NO: 206) was coupled via a heterobifunctional linker to the coding tag oligonucleotide, PCT_1T (SEQ ID NO: 207) comprised of the protected dA, dG and dC was employed. The specific B seq/B' seq binding event was encoded by single strand ligation using CircLigase II, and confirmed by gel analysis.

The thiol-containing "B'" sequence RT_thio_B'_bio (SEQ ID NO: 204) was attached to 5' amine group of PRT_0T (dU) (SEQ ID NO: 205) via SM(PEG)8 (Thermo Fisher), and the resulting recording tag, PRT_0T_B'bio were purified by 15% denaturing PAGE. The recording tags were immobilized on M-270 Streptavidin Dynabeads (Thermo Fisher) derivatized by titration against the mPEG-biotin, MW1000 (Creative PEGWorks) in ratios of 1:10. The beads were treated with USER enzyme (New England Biolabs) to a generate phosphorylation site at 5' end of recording tags-5' phosphate G. The conjugation of "B" binding sequence, B_thio, with PCT_1T was linked via SM(PEG)8 (Thermo Fisher), and the cording tag conjugates were purified by 15% denaturing PAGE.

For the 1st cycle binding assay was similar to previously described except that 800 nM of coding tag conjugate was incubated with 5' phosphorylated recording tag-immobilized beads in 50 ul PBST for 30 minutes at 37° C. The beads were washed 2× with 50 ul of PBST containing 40% formamide and once with 50 ul of 33 mM Tris-HCl buffer, pH 7.5 at room temperature. The beads were resuspended in 50 ul CircLigase II ligation reaction master mix (33 mM Tris-acetate, pH 7.5, 66 mM potassium acetate, 0.5 mM DTT, 2.5 mM MnCl2, 1 M Betaine and 0.25 U CircLigase II ssDNA ligase (Illumina)), and incubated at 37° C. for 30 min. After ligation reaction, beads were washed once with Immobilization buffer (5 mM Tris-Cl (pH 7.5), 0.5 mM EDTA, 1 M NaCl, 40% formamide), once with PBST containing 40% formamide. The recording tags were eluted from beads by incubating at 65° C. in 95% formamide/10 mM EDTA for 5 min. The eluted conjugates were analyzed by PAGE gel. The resulting gel, with shift in the band in lane 4 of FIG. 64, demonstrates proof of principle of writing coding tag information to the recording tag comprised of the protected dA, dC and dG bases using single strand DNA ligation (see FIG. 64).

Example 42: Immobilization of DNA-Tagged Peptides Using Hybridization and Ligation to DNA Beads Efficient immobilization of peptide-recording tag DNA chimeras on beads is an important component of the ProteoCode assay and can be accomplished chemically, but can also be done via hybridization capture and enzymatic or chemical ligation. We find that hybridization-based capture is ~10,000-fold more efficient than chemical coupling. Here we demonstrate the utility of hybridization and enzymatic ligation immobilization of DNA tagged peptides on DNA capture beads.

DNA-peptide chimeras were hybridized and ligated to hairpin capture DNA that was chemically immobilized on magnetic beads (see FIG. 65). The capture DNA was conjugated to the beads using trans-cyclooctene (TCO) and methyltetrazine (mTet)-based click chemistry. TCO-modified short hairpin DNAs (16 basepair stem, 24 base 5' overhang) were reacted with mTet-coated magnetic beads. Phosphorylated DNA-peptide chimeras (1 nM) were annealed to the hairpin DNA beads in 5×SSC, 0.02% SDS, and incubated for 30 minutes at 37° C. The beads were washed once with PBST and resuspended in 1× Quick ligation solution (NEB), with and without T4 DNA ligase. After 30 minutes incubation at 25° C., the beads were washed once with PBST and resuspended in the 20 ul of PBST. The total capture DNA, DNA tagged peptides and ligated DNA tagged peptides were quantified by qPCR using specific primer sets (FIG. 65). As shown in FIG. 65, a low Ct value was obtained in the qPCR with bead/DNA peptide hybrids only in the presence of ligase, indicating that the DNA tagged peptides were effectively ligated and immobilized to the beads.

TABLE 5

Peptide Based and DNA Based Model System Sequences

| Name | Sequence(5'-3') | SEQ ID NO: |
|---|---|---|
| amRT_Abc | /5AmMC6/GCAAATGGCATTCTGACATCCTT/i5OctdU/TTCGUAGUCCGCGACACTAGATGTCTAGCATGCCGCCGTGTCATGTGGAAACTGAGTG | 190 |
| amCT_bc5 | /5AmMC6//iSP18/CACTCAGTCCTAACGCGTATACGTCACTCAGT/3SpC3/ | 191 |
| CT_A'_bc13 | GGATGTCAGAATGCCATTTGCTTTTTTTTTT/iSP18/CGATTTGCAAGGATCACTCGCCGTTATTGACGCTCTCACTCAGT/3SpC3/ | 192 |
| Sp | ACTGAGTG | 149 |
| Sp' | CACTCAGT | 150 |
| P1_f2 | CGTAGTCCGCGACACTAG | 151 |
| R1 | CGATTTGCAAGGATCACTCG | 152 |
| Sp/BC2 | CACTCAGTTTCCACATGACACGGC | 193 |
| Sp/BC5 | CACTCAGTCCTAACGCGTATA | 194 |
| PA peptide | GVAMPGAEDDVVGGGGSC | 195 |
| Nanotag Peptide | Formyl-MDVEAWLGARVPLVETGSGSGSC | 196 |
| Aβ Peptide | HQKLVFFAEDVGSGSGSC | 197 |
| Spytag | CGSGSGSAHIVMVDAYKPTK | 198 |
| FA-PA peptide | FAGVAMPGAEDDVVGSGSK(azide) | 201 |
| A-PA peptide | AGVAMPGAEDDVVGSGSK(azide) | 202 |
| AFA-PA peptide | AFAGVAMPGAEDDVVGSGSK(azide) | 203 |
| RT_thio_B'bio | /5ThioMC6-D/GCTTGTCAATTGGAACCAGTCT/3Bio/ | 204 |
| PRT_0T (dU) | (5'OH)TTTTTTT(dU)G*AC*A*TC*TA*G*TG*TC*G*C*G*G*AC*TA*C*G*(aminohexyl-dT)-3ProtP | 205 |
| CT_B_thio | GCTTGTCAATTGGAACCAGTC/3ThioMC3-D/ | 206 |
| PCT_1T | 5ProtP-(aminohexyl-dT)C*G*A*TTTG*C*A*A*G*G*A*TC*AC*TC*G*A*G*G*T(3'OH) | 207 |

TABLE 5-continued

Peptide Based and DNA Based Model System Sequences

| Name | Sequence(5'-3') | SEQ ID NO: |
|---|---|---|
| amRT_Bb | /5ThioMC6-D/GCTTGTCAATTGGAACCAGTCT/3Bio/ | 208 |
| amCT_bc4 | /5AmMC6//iSP18/CACTCAGTTTCCGTCATATCGAATC ACTCAGT/3SpC3/ | 209 |
| amCT_bc5 | /5AmMC6//iSP18/CACTCAGTCCTAACGCGTATACGTC ACTCAGT/3SpC3/ | 210 |
| amCT_bc13r1 | /5AmMC6//iSP18/CGATTTGCAAGGATCACTCGCCGTT ATTGACGCTCTCACTCAGT/3SpC3/ | 211 |
| TS_Ctrl1 | CGTAGTCCGCGACACTAGAATAAGCCGGTATATCAA CTGAGTGATTCGATATGACGGAAACTGAGTGACGTA TACGCGTTAGGACTGAGTGAGAGCGTCAATAACGGC GAGTGATCCTTGCAAATCGCCCTATAGTGAGTCGTA TTAATTCGC | 212 |
| TS_Ctrl4 | CGTAGTCCGCGACACTAGCGTATACGCGTTAGGACT GAGTGAGAGCGTCAATAACGGACTGAGTGAGAGTC GGTACCTTGAACTGAGTGAAACTGCCGAGATTCCAC TGAGTGATTCGATATGACGGAAACTGAGTGATAAGC CGGTATATCACGAGTGATCCTTGCAAATCGCCCTAT AGTGAGTCGTATTAATTCGC | 213 |
| amRT_Bbc | /5AmMC6/GACTGGTTCCAATTGACAAGCTT/i5OctdU/T TTTTTCGTAGTCCGCGACACTAGTAAGCCGGTATA TCAACTGAGTG | 214 |
| amRT_Cbc | /5AmMC6/TTT/i5OctdU/TTUCGTAGTCCGCGACACTAG TAAGCCGGTATATCAACTGAGTG | 215 |
| amRT_Cs1 | /5AmMC6/TTT/i5OctdU/TTUCGTAGTCCGCGACACTAG NNNNNNNNNNNTTAAGTCGACTGAGTG | 216 |
| amRT_Cs2 | /5AmMC6/TTT/i5OctdU/TTUCGTAGTCCGCGACACTAG NNNNNNNNNNNGTTAATGGACTGAGTG | 217 |
| amRT_Cs4 | /5AmMC6/TTT/i5OctdU/TTUCGTAGTCCGCGACACTAG NNNNNNNNNNNCAGTACCGACTGAGTG | 218 |
| amRT_Cs5 | /5AmMC6/TTT/i5OctdU/TTUCGTAGTCCGCGACACTAG NNNNNNNNNNNGTTGGTTAACTGAGTG | 219 |
| amCT_s7 | /5AmMC6//iSP18/CACTCAGTCAGACTATTCACTCAGT/ 3SpC3/ | 220 |
| BC_s7 | ATAGTCTG | 221 |

/3SpC3/ = 3' C3 (three carbon) spacer
/i5OctdU/ = 5'-Octadiynyl dU
/iSP18/ = 18-atom hexa-ethyleneglycol spacer
5ProtP = 5' cyanoethyl-protected phosphate
3ProtP = 3' cyanoethyl-protected phosphate
*= protected base (Bz-dA, ibu-dG, Ac-dC)

VI. Further Exemplary Embodiments

The following embodiments provide additional illustration of the present disclosure.

1A. A kit, comprising:
  (a) a recording polymer configured to associate directly or indirectly with an analyte;
  (b) (i) a coding polymer which comprises identifying information regarding a binding moiety capable of binding to the analyte, and which is configured to associate directly or indirectly with the binding moiety to form a binding agent, and/or (ii) a label,
  wherein the recording polymer and the coding polymer are configured to allow transfer of information between them, upon binding between the binding agent and the analyte; and optionally (c) the binding moiety.

2A. The kit of embodiment 1A, wherein the recording polymer and/or the analyte are configured to be immobilized directly or indirectly to a support.

3A. The kit of embodiment 2A, wherein the recording polymer is configured to be immobilized to the support, thereby immobilizing the analyte associated with the recording polymer.

4A. The kit of embodiment 2A, wherein the analyte is configured to be immobilized to the support, thereby immobilizing the recording polymer associated with the analyte.

5A. The kit of embodiment 2A, wherein each of the recording polymer and the analyte is configured to be immobilized to the support.

6A. The kit of embodiment 5A, wherein the recording polymer and the analyte are configured to co-localize when both are immobilized to the support.

7A. The kit of any of embodiments 1A-6A, further comprising an immobilizing linker configured to:
(i) be immobilized directly or indirectly to a support, and
(ii) associate directly or indirectly with the recording polymer and/or the analyte.

8A. The kit of embodiment 7A, wherein the immobilizing linker is configured to associate with the recording polymer and the analyte.

9A. The kit of embodiment 7A or 8A, wherein the immobilizing linker is configured to be immobilized directly to the support, thereby immobilizing the recording polymer and/or the analyte which are associated with the immobilizing linker.

10A. The kit of any one of embodiments 2A-9A, further comprising the support.

11A. The kit of any one of embodiments 1A-10A, further comprising one or more reagents for transferring information between the coding polymer and the recording polymer, upon binding between the binding agent and the analyte.

12A. The kit of embodiment 11A, wherein the one or more reagents are configured to transfer information from the coding polymer to the recording polymer, thereby generating an extended recording polymer.

13A. The kit of embodiment 11A, wherein the one or more reagents are configured to transfer information from the recording polymer to the coding polymer, thereby generating an extended coding polymer.

14A. The kit of embodiment 11A, wherein the one or more reagents are configured to generate a di-tag construct comprising information from the coding polymer and information from the recording polymer.

15A. The kit of any one of embodiments 1A-14A, which comprises at least two of the recording polymers.

16A. The kit of any one of embodiments 1A-15A, which comprises at least two of the coding polymers each comprising identifying information regarding its associated binding moiety.

17A. The kit of any one of embodiments 1A-16A, which comprises at least two of the binding agents.

18A. The kit of embodiment 17A, which comprises:
(i) one or more reagents for transferring information from a first coding polymer of a first binding agent to the recording polymer to generate a first order extended recording polymer, upon binding between the first binding agent and the analyte, and/or
(ii) one or more reagents for transferring information from a second coding polymer of a second binding agent to the first order extended recording polymer to generate a second order extended recording polymer, upon binding between the second binding agent and the analyte,
wherein the one or more reagents of (i) and the one or more reagents of (ii) can be the same or different.

19A. The kit of embodiment 18A, which further comprises:
(iii) one or more reagents for transferring information from a third (or higher order) coding polymer of a third (or higher order) binding agent to the second order extended recording polymer to generate a third (or higher order) order extended recording polymer, upon binding between the third (or higher order) binding agent and the analyte.

20A. The kit of embodiment 17A, which comprises:
(i) one or more reagents for transferring information from a first coding polymer of a first binding agent to a first recording polymer to generate a first extended recording polymer, upon binding between the first binding agent and the analyte, and/or
(ii) one or more reagents for transferring information from a second coding polymer of a second binding agent to a second recording polymer to generate a second extended recording polymer, upon binding between the second binding agent and the analyte,
wherein the one or more reagents of (i) and the one or more reagents of (ii) can be the same or different.

21A. The kit of embodiment 20A, which further comprises:
(iii) one or more reagents for transferring information from a third (or higher order) coding polymer of a third (or higher order) binding agent to a third (or higher order) recording polymer to generate a third (or higher order) extended recording polymer, upon binding between the third (or higher order) binding agent and the analyte.

22A. The kit of embodiment 20A or 21A, wherein the first recording polymer, the second recording polymer, and/or the third (or higher order) recording polymer are configured to associate directly or indirectly with the analyte.

23A. The kit of any one of embodiments 20A-22A, wherein the first recording polymer, the second recording polymer, and/or the third (or higher order) recording polymer are configured to be immobilized on a support.

24A. The kit of any one of embodiments 20A-23A, wherein the first recording polymer, the second recording polymer, and/or the third (or higher order) recording polymer are configured to co-localize with the analyte, for example, to allow transfer of information between the first, second, or third (or higher order) coding polymer and the first, second, or third (or higher order) recording polymer, respectively, upon binding between the first, second, or third (or higher order) binding agent and the analyte.

25A. The kit of any one of embodiments 20A-24A, wherein each of the first coding polymer, the second coding polymer, and/or the third (or higher order) coding polymer comprises a binding cycle specific barcode, such as a binding cycle specific spacer polymer sequence $C_n$, and/or a coding polymer specific spacer polymer sequence $C_n$, wherein n is an integer and $C_n$ indicates binding between the $n^{th}$ binding agent and the polypeptide; or wherein a binding cycle tag $C_n$ is added exogenously, for example, the binding cycle tag $C_n$ may be exogenous to the coding polymer(s).

26A. The kit of any one of embodiments 1A-25A, wherein the analyte comprises a polypeptide.

27A. The kit of embodiment 26A, wherein the binding moiety is capable of binding to one or more N-terminal or C-terminal amino acids of the polypeptide, or capable of binding to the one or more N-terminal or C-terminal amino acids modified by a functionalizing reagent.

28A. The kit of embodiment 26A or 27A, further comprising the functionalizing reagent.

29A. The kit of any one of embodiments 26-28, further comprising an eliminating reagent for removing (e.g., by chemical cleavage or enzymatic cleavage) the one or more N-terminal, internal, or C-terminal amino acids of the polypeptide, or removing the functionalized N-terminal, internal, or C-terminal amino acid(s), optionally wherein the eliminating reagent comprises a carboxypeptidase or an aminopeptidase or variant, mutant, or modified protein thereof; a hydrolase or variant, mutant, or modified protein thereof; a mild Edman degradation reagent; an Edmanase enzyme; anhydrous TFA, a base; or any combination thereof.

30A. The kit of any one of embodiments 26A-29A, wherein the one or more N-terminal, internal, or C-terminal amino acids comprise:
(i) an N-terminal amino acid (NTAA);
(ii) an N-terminal dipeptide sequence;
(iii) an N-terminal tripeptide sequence;
(iv) an internal amino acid;
(v) an internal dipeptide sequence;
(vi) an internal tripeptide sequence;
(vii) a C-terminal amino acid (CTAA);
(viii) a C-terminal dipeptide sequence; or
(ix) a C-terminal tripeptide sequence,
or any combination thereof,
optionally wherein any one or more of the amino acid residues in (i)-(ix) are modified or functionalized.

31A. A kit, comprising:
at least (a) a first binding agent comprising (i) a first binding moiety capable of binding to an N-terminal amino acid (NTAA) or a functionalized NTAA of a polypeptide to be analyzed, and (ii) a first coding polymer comprising identifying information regarding the first binding moiety,
optionally (b) a recording polymer configured to associate directly or indirectly with the polypeptide, and
further optionally (c) a functionalizing reagent capable of modifying a first NTAA of the polypeptide to generate a first functionalized NTAA,
wherein the recording polymer and the first binding agent are configured to allow transfer of information between the first coding polymer and the recording polymer, upon binding between the first binding agent and the polypeptide.

32A. The kit of embodiment 31A, further comprising one or more reagents for transferring information from the first coding polymer to the recording polymer, thereby generating a first order extended recording polymer.

33A. The kit of embodiment 31A or 32A, wherein the functionalizing reagent comprises a chemical agent, an enzyme, and/or a biological agent, such as an isothiocyanate derivative, 2,4-dinitrobenzenesulfonic (DNBS), 4-sulfonyl-2-nitrofluorobenzene (SNFB) 1-fluoro-2,4-dinitrobenzene, dansyl chloride, 7-methoxycoumarin acetic acid, a thioacylation reagent, a thioacetylation reagent, or a thiobenzylation reagent.

34A. The kit of any one of embodiments 31A-33A, further comprising an eliminating reagent for removing (e.g., by chemical cleavage or enzymatic cleavage) the first functionalized NTAA to expose the immediately adjacent amino acid residue, as a second NTAA.

35A. The kit of embodiment 34A, wherein the second NTAA is capable of being functionalized by the same or a different functionalizing reagent to generate a second functionalized NTAA, which may be the same as or different from the first functionalized NTAA.

36A. The kit of embodiment 35A, further comprising:
(d) a second (or higher order) binding agent comprising (i) a second (or higher order) binding moiety capable of binding to the second functionalized NTAA, and (ii) a second (or higher order) coding polymer comprising identifying information regarding the second (or higher order) binding moiety,
wherein the first coding polymer and the second (or higher order) coding polymer can be the same or different.

37A. The kit of embodiment 36A, wherein the first functionalized NTAA and the second functionalized NTAA are selected, independent from each other, from the group consisting of a functionalized N-terminal Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

38A. The kit of embodiment 36A or 37A, further comprising one or more reagents for transferring information from the second (or higher order) coding polymer to the first order extended recording polymer, thereby generating a second (or higher order) order extended recording polymer.

39A. A kit, comprising:
at least (a) one or more binding agents each comprising (i) a binding moiety capable of binding to an N-terminal amino acid (NTAA) or a functionalized NTAA of a polypeptide to be analyzed, and (ii) a coding polymer comprising identifying information regarding the binding moiety, and/or
(b) one or more recording polymers configured to associate directly or indirectly with the polypeptide,
wherein the one or more recording polymers and the one or more binding agents are configured to allow transfer of information between the coding polymers and the recording polymers, upon binding between each binding agent and the polypeptide, and
optionally (c) a functionalizing reagent capable of modifying a first NTAA of the polypeptide to generate a first functionalized NTAA.

40A. The kit of embodiment 39A, further comprising an eliminating reagent for removing (e.g., by chemical cleavage or enzymatic cleavage) the first functionalized NTAA to expose the immediately adjacent amino acid residue, as a second NTAA.

41A. The kit of embodiment 40A, wherein the second NTAA is capable of being functionalized by the same or a different functionalizing reagent to generate a second functionalized NTAA, which may be the same as or different from the first functionalized NTAA.

42A. The kit of embodiment 41A, wherein the first functionalized NTAA and the second functionalized NTAA are selected, independent from each other, from the group consisting of a functionalized N-terminal Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

43A. The kit of any one of embodiments 39A-42A, which comprises:
(i) one or more reagents for transferring information from a first coding polymer of a first binding agent to a first recording polymer to generate a first extended recording polymer, upon binding between the first binding agent and the polypeptide, and/or (ii) one or more reagents for transferring information from a second coding polymer of a second binding agent to a second recording polymer to generate a second extended recording polymer, upon binding between the second binding agent and the polypeptide, wherein the one or more reagents of (i) and the one or more reagents of (ii) can be the same or different.

44A. The kit of embodiment 43A, which further comprises:

(iii) one or more reagents for transferring information from a third (or higher order) coding polymer of a third (or higher order) binding agent to a third (or higher order) recording polymer to generate a third (or higher order) extended recording polymer, upon binding between the third (or higher order) binding agent and the polypeptide.

45A. The kit of embodiment 43A or 44A, wherein the first recording polymer, the second recording polymer, and/or the third (or higher order) recording polymer are configured to associate directly or indirectly with the polypeptide.

46A. The kit of any one of embodiments 43A-45A, wherein the first recording polymer, the second recording polymer, and/or the third (or higher order) recording polymer are configured to be immobilized on a support.

47A. The kit of any one of embodiments 43A-46A, wherein the first recording polymer, the second recording polymer, and/or the third (or higher order) recording polymer are configured to co-localize with the polypeptide, for example, to allow transfer of information between the first, second, or third (or higher order) coding polymer and the first, second, or third (or higher order) recording polymer, respectively, upon binding between the first, second, or third (or higher order) binding agent and the polypeptide.

48A. The kit of any one of embodiments 43A-47A, wherein each of the first coding polymer, the second coding polymer, and/or the third (or higher order) coding polymer comprises a binding cycle specific barcode, such as a binding cycle specific spacer polymer sequence $C_n$, or a coding polymer specific spacer polymer sequence $C_n$, or an exogenous binding cycle tag $C_n$, wherein n is an integer and $C_n$ indicates binding between the $n^{th}$ binding agent and the polypeptide.

49A. The kit of any one of embodiments 1A-48A, wherein the analyte or the polypeptide comprises a protein or a polypeptide chain or a fragment thereof, a lipid, a carbohydrate, or a macrocycle.

50A. The kit of any one of embodiments 1A-49A, wherein the analyte or the polypeptide comprises a macromolecule or a complex thereof, such as a protein complex or subunit thereof.

51A. The kit of any one of embodiments 1A-50A, wherein the recording polymer comprises a nucleic acid, an oligonucleotide, a modified oligonucleotide, a DNA molecule, a DNA with pseudo-complementary bases, a DNA or RNA with one or more protected bases, an RNA molecule, a BNA molecule, an XNA molecule, a LNA molecule, a PNA molecule, a γPNA molecule, or a morpholino, a non-nucleic acid sequenceable polymer, e.g., a polysaccharide, a polypeptide, a peptide, or a polyamide, or a combination thereof.

52A. The kit of any one of embodiments 1A-51A, wherein the recording polymer comprises a universal priming site.

53A. The kit of any one of embodiments 1A-52A, wherein the recording polymer comprises a priming site for amplification, sequencing, or both, for example, the universal priming site comprises a priming site for amplification, sequencing, or both.

54A. The kit of any one of embodiments 1A-53A, wherein the recording polymer and/or the coding polymer comprises a unique molecule identifier (UMI).

55A. The kit of any one of embodiments 1A-54A, wherein the recording polymer and/or the coding polymer comprises a barcode and/or a nuclease site, such as a nicking endonuclease site (e.g., a dsDNA nicking endonuclease site).

56A. The kit of any one of embodiments 1A-55A, wherein the recording polymer and/or the coding polymer comprises a spacer polymer at its 3'-terminus and/or at its 5'-terminus, for example, the recording polymer comprises a spacer polymer at its 3'-terminus.

57A. The kit of any one of embodiments 1A-56A, comprising a solid support, such as a rigid solid support, a flexible solid support, or a soft solid support, and including a porous support or a non-porous support.

58A. The kit of any one of embodiments 1A-57A, comprising a support comprising a bead, a porous bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

59A. The kit of embodiment 58A, wherein the support comprises a polystyrene bead, a polymer bead, an agarose bead, an acrylamide bead, a solid core bead, a porous bead, a paramagnetic bead, glass bead, or a controlled pore bead, or any combination thereof.

60A. The kit of any one of embodiments 1A-59A, which comprises a support and is for analyzing a plurality of the analytes or the polypeptides, in sequential reactions, in parallel reactions, or in a combination of sequential and parallel reactions.

61A. The kit of embodiment 60A, wherein the analytes or the polypeptides are spaced apart on the support at an average distance equal to or greater than about 10 nm, equal to or greater than about 15 nm, equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, or equal to or greater than about 500 nm.

62A. The kit of any one of embodiments 1A-61A, wherein the binding moiety comprises a polypeptide or fragment thereof, a protein or polypeptide chain or fragment thereof, or a protein complex or subunit thereof, such as an antibody or antigen binding fragment thereof.

63A. The kit of any one of embodiments 1A-62A, wherein the binding moiety comprises a carboxypeptidase or an aminopeptidase or variant, mutant, or modified protein thereof, an aminoacyl tRNA synthetase or variant, mutant, or modified protein thereof, an anticalin or variant, mutant, or modified protein thereof, a ClpS or variant, mutant, or modified protein thereof, a UBR box protein or variant, mutant, or modified protein thereof, a modified small molecule that binds amino acid(s), i.e. vancomycin or a variant, mutant, or modified molecule thereof, or any combination thereof, or wherein in each binding agent, the binding moiety comprises a small molecule, the coding polymer comprises a polynucleotide that identifies the small molecule, whereby a plurality of the binding agents form an encoded small molecule library, such as a DNA-encoded small molecule library.

64A. The kit of any one of embodiments 1A-63A, wherein the binding moiety is capable of selectively and/or specifically binding to the analyte or the polypeptide.

65A. The kit of any one of embodiments 1A-64A, wherein the coding polymer comprises a nucleic acid, an oligonucleotide, a modified oligonucleotide, a DNA molecule, a DNA with pseudo-complementary bases, a DNA or RNA with one or more protected bases, an RNA molecule, a BNA molecule, an XNA molecule, a LNA molecule, a PNA molecule, a γPNA molecule, or a morpholino, or a non-nucleic acid sequenceable polymer, e.g., a polysaccharide, a polypeptide, a peptide, or a polyamide, a combination thereof.

66A. The kit of any one of embodiments 1A-65A, wherein the coding polymer comprises a barcode sequence, such as an encoder sequence, e.g., one that identifies the binding moiety.

67A. The kit of any one of embodiments 1A-66A, wherein the coding polymer comprises a spacer polymer, a binding cycle specific sequence, a unique molecular identifier (UMI), a universal priming site, or any combination thereof, optionally wherein a binding cycle specific sequence is added to the recording polymer after each binding cycle.

68A. The kit of any one of embodiments 1A-67A, wherein the binding moiety and the coding polymer are joined by a linker or a binding pair.

69A. The kit of any one of embodiments 1A-68A, wherein the binding moiety and the coding polymer are joined by a SpyTag/SpyCatcher, a SpyTag-KTag/SpyLigase (where two moieties to be joined have the SpyTag/KTag pair, and the SpyLigase joins SpyTag to KTag, thus joining the two moieties), a sortase, a SnoopTag/SnoopCatcher peptide-protein pair, or a HaloTag/HaloTag ligand pair, or any combination thereof.

70A. The kit of any one of embodiments 1A-69A, further comprising a reagent for transferring information between the coding polymer and the recording polymer in a templated or non-templated reaction, optionally wherein the reagent is (i) a chemical ligation reagent or a biological ligation reagent, for example, a ligase, such as a DNA ligase or RNA ligase for ligating single-stranded nucleic acid or double-stranded nucleic acid, or (ii) a reagent for primer extension of single-stranded nucleic acid or double-stranded nucleic acid, optionally wherein the kit further comprises a ligation reagent comprising at least two ligases or variants thereof (e.g., at least two DNA ligases, or at least two RNA ligases, or at least one DNA ligase and at least one RNA ligase), wherein the at least two ligases or variants thereof comprises an adenylated ligase and a constitutively non-adenylated ligase, or optionally wherein the kit further comprises a ligation reagent comprising a DNA or RNA ligase and a DNA/RNA deadenylase.

71A. The kit of any one of embodiments 1A-70A, further comprising a polymerase, such as a DNA polymerase or RNA polymerase or a reverse transcriptase, [add ligase?] for transferring information between the coding polymer and the recording polymer.

72A. The kit of any one of embodiments 1A-71A, further comprising one or more reagents for nucleic acid sequence analysis.

73A. The kit of embodiment 72A, wherein the nucleic acid sequence analysis comprises sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy, or any combination thereof.

74A. The kit of any one of embodiments 1A-73A, further comprising one or more reagents for nucleic acid amplification, for example, for amplifying one or more extended recording polymers, optionally wherein the nucleic acid amplification comprises an exponential amplification reaction (e.g., polymerase chain reaction (PCR), such as an emulsion PCR to reduce or eliminate template switching) and/or a linear amplification reaction (e.g., isothermal amplification by in vitro transcription, or Isothermal Chimeric primer-initiated Amplification of Nucleic acids (ICAN)).

75A. The kit of any one of embodiments 1A-74A, comprising one or more reagents for transferring coding polymer information to the recording polymer to form an extended recording polymer, wherein the order and/or frequency of coding polymer information on the extended recording polymer indicates the order and/or frequency in which the binding agent binds to the analyte or the polypeptide.

76A. The kit of any one of embodiments 1A-75A, further comprising one or more reagents for target enrichment, for example, enrichment of one or more extended recording polymers.

77A. The kit of any one of embodiments 1A-76A, further comprising one or more reagents for subtraction, for example, subtraction of one or more extended recording polymers.

78A. The kit of any one of embodiments 1A-77A, further comprising one or more reagents for normalization, for example, to reduce highly abundant species such as one or more analytes or polypeptides.

79A. The kit of any one of embodiments 1A-78A, wherein at least one binding agent binds to a terminal amino acid residue, terminal di-amino-acid residues, or terminal triple-amino-acid residues.

80A. The kit of any one of embodiments 1A-79A, wherein at least one binding agent binds to a post-translationally modified amino acid.

81A. The kit of any one of embodiments 1A-80A, further comprising one or more reagents or means for partitioning a plurality of the analytes or polypeptides in a sample into a plurality of compartments, wherein each compartment comprises a plurality of compartment tags (e.g., in the form of non-nucleic acid sequenceable polymers) optionally joined to a support (e.g., a solid support), wherein the plurality of compartment tags are the same within an individual compartment and are different from the compartment tags of other compartments.

82A. The kit of embodiment 81A, further comprising one or more reagents or means for fragmenting the plurality of the analytes or polypeptides (such as a plurality of protein complexes, proteins, and/or polypeptides) into a plurality of polypeptide fragments.

83A. The kit of embodiment 81A or 82A, further comprising one or more reagents or means for annealing or joining of the plurality of polypeptide fragments with the compartment tag within each of the plurality of compartments, thereby generating a plurality of compartment tagged polypeptide fragments.

84A. The kit of any one of embodiments 81A-83A, wherein the plurality of compartments comprise a microfluidic droplet, a microwell, or a separated region on a surface, or any combination thereof.

85A. The kit of any one of embodiments 81A-84A, wherein each of the plurality of compartments comprises on average a single cell.

86A. The kit of any one of embodiments 81A-85A, further comprising one or more universal DNA tags for labeling the plurality of the analytes or polypeptides in the sample.

87A. The kit of any one of embodiments 81A-86A, further comprising one or more reagents for labeling the plurality of the analytes or polypeptides in the sample with one or more universal DNA tags.

88A. The kit of any one of embodiments 81A-87A, further comprising one or more reagents for primer extension or ligation.

89A. The kit of any one of embodiments 81A-88A, wherein the support comprises a bead, such as a polystyrene bead, a polymer bead, an agarose bead, an acrylamide bead, a solid core bead, a porous bead, a paramagnetic bead, glass bead, or a controlled pore bead, or any combination thereof.

90A. The kit of any one of embodiments 81A-89A, wherein the compartment tag comprises a single stranded or double stranded nucleic acid molecule.

91A. The kit of any one of embodiments 81A-90A, wherein the compartment tag comprises a barcode and optionally a UMI.

92A. The kit of any one of embodiments 81A-91A, wherein the support is a bead and the compartment tag comprises a barcode.

93A. The kit of any one of embodiments 81A-92A, wherein the support comprises a bead, and wherein beads comprising the plurality of compartment tags joined thereto are formed by split-and-pool synthesis, individual synthesis, or immobilization.

94A. The kit of any one of embodiments 81A-93A, further comprising one or more reagents for split-and-pool synthesis, individual synthesis, or immobilization.

95A. The kit of any one of embodiments 81A-94A, wherein the compartment tag is a component within a recording polymer, wherein the recording polymer optionally further comprises a spacer polymer, a barcode sequence, a unique molecular identifier, a universal priming site, or any combination thereof.

96A. The kit of any one of embodiments 81A-95A, wherein the compartment tags further comprise a functional moiety capable of reacting with an internal amino acid, the peptide backbone, or N-terminal amino acid on the plurality of analytes or polypeptides (such as protein complexes, proteins, or polypeptides).

97A. The kit of embodiment 96A, wherein the functional moiety comprises an aldehyde, an azide/alkyne, a malemide/thiol, an epoxy/nucleophile, an inverse Electron Demand Diels-Alder (iEDDA) group, a click reagent, or any combination thereof.

98A. The kit of any one of embodiments 81A-97A, wherein the compartment tag further comprises a peptide, such as a protein ligase recognition sequence, optionally wherein the protein ligase is butelase I or a homolog thereof.

99A. The kit of any one of embodiments 81A-98A, further comprising a chemical or biological reagent, such as an enzyme, for example, a protease (e.g., a metalloprotease), for fragmenting the plurality of analytes or polypeptides.

100A. The kit of any one of embodiments 81A-99A, further comprising one or more reagents for releasing the compartment tags from the support.

101A. The kit of any one of embodiments 1A-100A, further comprising one or more reagents for forming an extended coding polymer or a di-tag construct.

102A. The kit of embodiment 101A, wherein the 3'-terminus of the recording polymer is blocked to prevent extension of the recording polymer by a polymerase.

103A. The kit of embodiment 101A or 102A, wherein the coding polymer comprises an encoder sequence, a UMI, a universal priming site, a spacer polymer at its 3'-terminus, a binding cycle specific sequence, or any combination thereof.

104A. The kit of any one of embodiments 101A-103A, wherein the di-tag construct is generated by gap fill, primer extension, or a combination thereof.

105A. The kit of any one of embodiments 101A-104A, wherein the di-tag molecule comprises a universal priming site derived from the recording polymer, a compartment tag derived from the recording polymer, a unique molecular identifier derived from the recording polymer, an optional spacer polymer derived from the recording polymer, an encoder sequence derived from the coding polymer, a unique molecular identifier derived from the coding polymer, an optional spacer polymer derived from the coding polymer, and a universal priming site derived from the coding polymer.

106A. The kit of any one of embodiments 101A-105A, wherein the binding agent is a polypeptide or protein.

107A. The kit of any one of embodiments 101A-106A, wherein the binding agent comprises an aminopeptidase or variant, mutant, or modified protein thereof, an aminoacyl tRNA synthetase or variant, mutant, or modified protein thereof, an anticalin or variant, mutant, or modified protein thereof, a ClpS (such as ClpS2) or variant, mutant, or modified protein thereof, a UBR box protein or variant, mutant, or modified protein thereof, or a modified small molecule that binds amino acid(s), i.e. vancomycin or a variant, mutant, or modified molecule thereof; or an antibody or binding fragment thereof, or any combination thereof.

108A. The kit of any one of embodiments 101A-107A, wherein the binding agent binds to a single amino acid residue (e.g., an N-terminal amino acid residue, a C-terminal amino acid residue, or an internal amino acid residue), a dipeptide (e.g., an N-terminal dipeptide, a C-terminal dipeptide, or an internal dipeptide), a tripeptide (e.g., an N-terminal tripeptide, a C-terminal tripeptide, or an internal tripeptide), or a post-translational modification of the analyte or polypeptide.

109A. The kit of any one of embodiments 101A-107A, wherein the binding agent binds to an N-terminal polypeptide, a C-terminal polypeptide, or an internal polypeptide.

110A. The kit of any one of embodiments 1A-109A, wherein the coding polymer and/or the recording polymer comprise one or more error correcting codes (e.g., in the form of non-nucleic acid sequenceable polymers), one or more encoder sequences (e.g., in the form of non-nucleic acid sequenceable polymers), one or more barcodes (e.g., in the form of non-nucleic acid sequenceable polymers), one or more UMIs (e.g., in the form of non-nucleic acid sequenceable polymers), one or more compartment tags (e.g., in the form of non-nucleic acid sequenceable polymers), one or more cycle specific sequences (e.g., in the form of non-nucleic acid sequenceable polymers), or any combination thereof.

111A. The kit of embodiment 110A, wherein the error correcting code is selected from Hamming code, Lee distance code, asymmetric Lee distance code, Reed-Solomon code, and Levenshtein-Tenengolts code.

112A. The kit of any one of embodiments 1A-111A, wherein the coding polymer and/or the recording polymer comprise a cycle label.

113A. The kit of any one of embodiments 1A-112A, further comprising a cycle label independent of the coding polymer and/or the recording polymer.

114A. The kit of any one of embodiments 1A-113A, which comprises:
(a) a reagent for generating a cell lysate or a protein sample;
(b) a reagent for blocking an amino acid side chain, such as via alkylation of cysteine or blocking lysine;
(c) a protease, such as trypsin, LysN, or LysC;
(d) a reagent for immobilizing a nucleic acid-labeled polypeptide (such as a DNA-labeled protein) to a support;
(e) a reagent for degradation-based polypeptide sequencing; and/or
(f) a reagent for nucleic acid sequencing.

115A. The kit of any one of embodiments 1A-113A, which comprises:
(a) a reagent for generating a cell lysate or a protein sample;
(b) a reagent for blocking an amino acid side chain, such as via alkylation of cysteine or blocking lysine;
(c) a protease, such as trypsin, LysN, or LysC;
(d) a reagent for immobilizing a polypeptide (such as a protein) to a support comprising immobilized recording polymers;
(e) a reagent for degradation-based polypeptide sequencing; and/or
(f) a reagent for nucleic acid sequencing.

116A. The kit of any one of embodiments 1A-113A, which comprises:
(a) a reagent for generating a cell lysate or a protein sample;
(b) a denaturing reagent;
(c) a reagent for blocking an amino acid side chain, such as via alkylation of cysteine or blocking lysine;
(d) a universal DNA primer sequence;
(e) a reagent for labeling a polypeptide with a universal DNA primer sequence;
(f) a barcoded bead for annealing the labeled polypeptide via a primer;
(g) a reagent for polymerase extension for writing the barcode from the bead to the labeled polypeptide;
(h) a protease, such as trypsin, LysN, or LysC;
(i) a reagent for immobilizing a nucleic acid-labeled polypeptide (such as a DNA-labeled protein) to a support;
(j) a reagent for degradation-based polypeptide sequencing; and/or
(k) a reagent for nucleic acid sequencing.

117A. The kit of any one of embodiments 1A-113A, which comprises:
(a) a cross-linking reagent;
(b) a reagent for generating a cell lysate or a protein sample;
(c) a reagent for blocking an amino acid side chain, such as via alkylation of cysteine or blocking lysine;
(d) a universal DNA primer sequence;
(e) a reagent for labeling a polypeptide with a universal DNA primer sequence;
(f) a barcoded bead for annealing the labeled polypeptide via a primer;
(g) a reagent for polymerase extension for writing the barcode from the bead to the labeled polypeptide;
(h) a protease, such as trypsin, LysN, or LysC;
(i) a reagent for immobilizing a nucleic acid-labeled polypeptide (such as a DNA-labeled protein) to a support;
(j) a reagent for degradation-based polypeptide sequencing; and/or
(k) a reagent for nucleic acid sequencing.

118A. The kit of any one of embodiments 1A-117A, wherein one or more components are provided in a solution or on a support, for example, a solid support.

1B. A method, comprising:
(a) contacting a set of proteins, wherein each protein is associated directly or indirectly with a recording polymer, with a library of agents, wherein each agent comprises (i) a small molecule, a peptide or peptide mimetic, a peptidomimetic (e.g., a peptoid, a β-peptide, or a D-peptide peptidomimetic), a polysaccharide, or an aptamer (e.g., a nucleic acid aptamer, such as a DNA aptamer, or a peptide aptamer), and (ii) a coding polymer comprising identifying information regarding the small molecule, peptide or peptide mimetic, peptidomimetic (e.g., peptoid, β-peptide, or D-peptide peptidomimetic), polysaccharide, or aptamer,
wherein each protein and/or its associated recording polymer, or each agent, is immobilized directly or indirectly to a support;
(b) allowing transfer of information between (i) the recording polymer associated with each protein that binds and/or reacts with the small molecule(s), peptide(s) or peptide mimetic(s), peptidomimetic(s) (e.g., peptoid(s), β-peptide(s), or D-peptide peptidomimetic(s)), polysaccharide(s), or aptamer(s) of one or more agents, and (ii) the coding polymer of the one or more agents, to generate an extended recording polymer and/or an extended coding polymer; and
(c) analyzing the extended recording polymer and/or the extended coding polymer.

2B. The method of embodiment 1B, wherein each protein is spaced apart from other proteins on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 µm.

3B. The method of embodiment 1B or 2B, wherein each protein and its associated recording polymer is spaced apart from other proteins and their associated recording polymers on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 µm.

4B. The method of any one of embodiments 1B-3B, wherein one or more of the proteins and/or their associated recording polymers are covalently immobilized to the support (e.g., via a linker), or non-covalently immobilized to the support (e.g., via a binding pair).

5B. The method of any one of embodiments 1B-4B, wherein a subset of the proteins and/or their associated recording polymers are covalently immobilized to the support while another subset of the proteins and/or their associated recording polymers are non-covalently immobilized to the support.

6B. The method of any one of embodiments 1B-5B, wherein one or more of the recording polymers are immobilized to the support, thereby immobilizing the associated protein(s).

7B. The method of any one of embodiments 1B-6B, wherein one or more of the proteins are immobilized to the support, thereby immobilizing the associated recording polymer(s).

8B. The method of any one of embodiments 1B-7B, wherein at least one protein co-localizes with its associated recording polymer, while each is independently immobilized to the support.

9B. The method of any one of embodiments 1B-8B, wherein at least one protein and/or its associated recording polymer associates directly or indirectly with an immobilizing linker, and the immobilizing linker is immobilized directly or indirectly to the support, thereby immobilizing the at least one protein and/or its associated recording polymer to the support.

10B. The method of any one of embodiments 1B-9B, wherein the density of immobilized recording polymers is equal to or greater than the density of immobilized proteins.

11B. The method of embodiment 10B, wherein the density of immobilized recording polymers is at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, at least about 50-fold, at least about 100-fold, or more, of the density of immobilized proteins.

12B. The method of embodiment 1B, wherein each agent is spaced apart from other agents immobilized on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 µm.

13B. The method of embodiment 12B, wherein one or more of the agents are covalently immobilized to the support (e.g., via a linker), or non-covalently immobilized to the support (e.g., via a binding pair).

14B. The method of embodiment 12B or 13B, wherein a subset of the agents are covalently immobilized to the support while another subset of the agents are non-covalently immobilized to the support.

15B. The method of any one of embodiments 12B-14B, wherein for one or more of the agents, the small molecule, peptide or peptide mimetic, peptidomimetic (e.g., peptoid, β-peptide, or D-peptide peptidomimetic), polysaccharide, or aptamer is immobilized to the support, thereby immobilizing the coding polymer.

16B. The method of any one of embodiments 12B-15B, wherein for one or more of the agents, the coding polymer is immobilized to the support, thereby immobilizing the small molecule, peptide or peptide mimetic, peptidomimetic (e.g., peptoid, β-peptide, or D-peptide peptidomimetic), polysaccharide, or aptamer.

17B. The method of any one of embodiments 1B-16B, wherein information is transferred from at least one coding polymer to at least one recording polymer, thereby generating at least one extended recording polymer.

18B. The method of any one of embodiments 1B-17B, wherein information is transferred from at least one recording polymer to at least one coding polymer, thereby generating at least one extended coding polymer.

19B. The method of any one of embodiments 1B-18B, wherein at least one di-tag construct is generated comprising information from the coding polymer and information from the recording polymer.

20B. The method of any one of embodiments 1B-19B, wherein at least one of the proteins binds and/or reacts with the small molecules, peptides or peptide mimetics, peptidomimetics (e.g., peptoids, β-peptides, or D-peptide peptidomimetics), polysaccharides, or aptamers of two or more agents.

21B. The method of embodiment 20B, wherein the extended recording polymer or the extended coding polymer comprises identifying information regarding the small molecules, peptides or peptide mimetics, peptidomimetics (e.g., peptoids, β-peptides, or D-peptide peptidomimetics), polysaccharides, or aptamers of the two or more agents.

22B. The method of any one of embodiments 1B-21B, wherein at least one of the proteins is associated with two or more recording polymers, wherein the two or more recording polymers can be the same or different.

23B. The method of any one of embodiments 1B-22B, wherein at least one of the agents comprises two or more coding polymers, wherein the two or more coding polymers can be the same or different.

24B. The method of any one of embodiments 1B-23B, wherein the transfer of information is accomplished by ligation (e.g., an enzymatic or chemical ligation, a splint ligation, a sticky end ligation, a single-strand (ss) ligation such as a ssDNA ligation, or any combination thereof), a polymerase-mediated reaction (e.g., primer extension of single-stranded nucleic acid or double-stranded nucleic acid), or any combination thereof.

25B. The method of embodiment 24B, wherein the ligation and/or polymerase-mediated reaction have faster kinetics relative to the binding occupancy time or reaction time between the protein and the small molecule, peptide or peptide mimetic, peptidomimetic (e.g., peptoid, 3-peptide, or D-peptide peptidomimetic), polysaccharide, or aptamer, optionally wherein a reagent for the ligation and/or polymerase-mediated reaction is present in the same reaction volume as the binding or reaction between the protein and the small molecule, peptide or peptide mimetic, peptidomimetic (e.g., peptoid, P-peptide, or D-peptide peptidomimetic), polysaccharide, or aptamer.

26B. The method of any one of embodiments 1B-25B, wherein each protein associates with its recording polymer via individual attachment, and/or wherein each small molecule, peptide or peptide mimetic, peptidomimetic (e.g., peptoid, β-peptide, or D-peptide peptidomimetic), polysaccharide, or aptamer associates with its coding polymer via individual attachment.

27B. The method of embodiment 26B, wherein the attachment occurs via ribosome or mRNA/cDNA display in which the recording polymer and/or coding polymer sequence information is contained in the mRNA sequence.

28B. The method of embodiment 27B, wherein the recording polymer and/or coding polymer comprise a universal primer sequence, a barcode, and/or a spacer polymer sequence at the 3' end of the mRNA sequence.

29B. The method of embodiment 28B, wherein the recording polymer and/or coding polymer, at the 3' end, further comprise a restriction enzyme digestion site.

30B. The method of any one of embodiments 1B-29B, wherein the set of proteins is a proteome or subset thereof, optionally wherein the set of proteins are produced using in vitro transcription of a genome or subset thereof followed by in vitro translation, or produced using in vitro translation of a transcriptome or subset thereof.

31B. The method of embodiment 30B, wherein the subset of the proteome comprises a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glyco-proteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof.

32B. The method of any one of embodiments 1B-31B, wherein the set of proteins are from a mammal such as human, a non-human animal, a fish, an invertebrate, an arthropod, an insect, or a plant, e.g., a yeast, a bacterium, e.g., E. coli, a virus, e.g., HIV or HCV, or a combination thereof.

33B. The method of any one of embodiments 1B-32B, wherein the set of proteins comprise a protein complex or subunit thereof.

34B. The method of any one of embodiments 1B-33B, wherein the recording polymer comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, a non-nucleic acid sequenceable polymer, e.g., a polysaccharide, a polypeptide, a peptide, or a polyamide, or a combination thereof.

35B. The method of any one of embodiments 1B-34B, wherein the recording polymer comprises a universal priming site.

36B. The method of any one of embodiments 1B-35B, wherein the recording polymer comprises a priming site for amplification, sequencing, or both, for example, the universal priming site comprises a priming site for amplification, sequencing, or both.

37B. The method of any one of embodiments 1B-36B, wherein the recording polymer comprises a unique molecule identifier (UMI).

38B. The method of any one of embodiments 1B-37B, wherein the recording polymer comprises a barcode.

39B. The method of any one of embodiments 1B-38B, wherein the recording polymer comprises a spacer polymer at its 3'-terminus.

40B. The method of any one of embodiments 1B-39B, wherein the support is a solid support, such as a rigid solid support, a flexible solid support, or a soft solid support, and including a porous support or a non-porous support.

41B. The method of any one of embodiments 1B-40B, wherein the support comprises a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles (Fe$_3$O$_4$), gold nanoparticles, and/or silver nanoparticles), quantum dots, a nanoshell, a nanocage, a microsphere, or any combination thereof.

42B. The method of embodiment 41B, wherein the support comprises a polystyrene bead, a polymer bead, an agarose bead, an acrylamide bead, a solid core bead, a porous bead, a magnetic bead, a paramagnetic bead, a glass bead, or a controlled pore bead, or any combination thereof.

43B. The method of any one of embodiments 1B-42B, which is for parallel analysis of the interaction between the set of proteins and the library of small molecules, and/or peptides or peptide mimetics, and/or peptidomimetic (e.g., peptoids, β-peptides, or D-peptide peptidomimetics), and/or polysaccharides, and/or aptamers, in order to create a small molecule-protein binding matrix, and/or a peptide/peptide mimetic-protein binding matrix, and/or a peptidomimetic-protein binding matrix (e.g., a peptoid-protein binding matrix, a β-peptide-protein binding matrix, or a D-peptide peptidomimetic-protein binding matrix), and/or a polysaccharide-protein binding matrix, and/or an aptamer-protein binding matrix.

44B. The method of embodiment 43B, wherein the matrix size is of about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$, about $10^{14}$, or more, for example, of about $2 \times 10^{13}$.

45B. The method of any one of embodiments 1B-44B, wherein the coding polymer comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, a non-nucleic acid sequenceable polymer, e.g., a polysaccharide, a polypeptide, a peptide, or a polyamide, or a combination thereof.

46B. The method of any one of embodiments 1B-45B, wherein the coding polymer comprises an encoder sequence that identifies the small molecule, peptide or peptide mimetic, peptidomimetic (e.g., peptoid, β-peptide, or D-peptide peptidomimetic), polysaccharide, or aptamer.

47B. The method of any one of embodiments 1B-46B, wherein the coding polymer comprises a spacer polymer, a unique molecular identifier (UMI), a universal priming site, or any combination thereof.

48B. The method of any one of embodiments 1B-47B, wherein the small molecule, peptide or peptide mimetic, peptidomimetic (e.g., peptoid, β-peptide, or D-peptide peptidomimetic), polysaccharide, or aptamer and the coding polymer are joined by a linker or a binding pair.

49B. The method of any one of embodiments 1B-48B, wherein the small molecule, peptide or peptide mimetic, peptidomimetic (e.g., peptoid, β-peptide, or D-peptide peptidomimetic), polysaccharide, or aptamer and the coding polymer are joined by a SpyTag-KTag/SpyLigase (where two moieties to be joined have the SpyTag/KTag pair, and the SpyLigase joins SpyTag to KTag, thus joining the two moieties), a SpyTag/SpyCatcher, a SnoopTag/SnoopCatcher peptide-protein pair, a sortase, or a HaloTag/HaloTag ligand pair, or any combination thereof.

50B. A method for analyzing a polypeptide, comprising:
(a) contacting (i) a set of fragments of a polypeptide, wherein each fragment is associated directly or indirectly with a recording polymer, with (ii) a library of binding agents, wherein each binding agent comprises a binding moiety and a coding polymer comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent, and
wherein each fragment and/or its associated recording polymer, or each binding agent, is immobilized directly or indirectly to a support;
(b) allowing transfer of information between (i) the recording polymer associated with each fragment and (ii) the coding polymer, upon binding between the binding moiety and the one or more N-terminal, internal, or C-terminal amino acids of the fragment, to generate an extended recording polymer and/or an extended coding polymer; and
(c) analyzing the extended recording polymer and/or the extended coding polymer.

51B. The method of embodiment 50B, wherein the one or more N-terminal, internal, or C-terminal amino acids comprise:
(i) an N-terminal amino acid (NTAA);
(ii) an N-terminal dipeptide sequence;
(iii) an N-terminal tripeptide sequence;
(iv) an internal amino acid;
(v) an internal dipeptide sequence;
(vi) an internal tripeptide sequence;
(vii) a C-terminal amino acid (CTAA);
(viii) a C-terminal dipeptide sequence; or
(ix) a C-terminal tripeptide sequence,
or any combination thereof,
optionally wherein any one or more of the amino acid residues in (i)-(ix) are modified or functionalized.

52B. The method of embodiment 51B, wherein the one or more N-terminal, internal, or C-terminal amino acids are selected, independently at each residue, from the group consisting of Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr), in any combination thereof.

53B. The method of any one of embodiments 50B-52B, wherein the binding moiety comprises a polypeptide or fragment thereof, a protein or polypeptide chain or fragment thereof, or a protein complex or subunit thereof, such as an antibody or antigen binding fragment thereof.

54B. The method of any one of embodiments 50B-53B, wherein the binding moiety comprises an anticalin or variant, mutant, or modified protein thereof, an aminoacyl tRNA synthetase or variant, mutant, or modified protein thereof, an anticalin or variant, mutant, or modified protein thereof, a ClpS (such as ClpS2) or variant, mutant, or modified protein thereof, a UBR box protein or variant, mutant, or modified protein thereof, or a modified small molecule that binds amino acid(s), i.e. vancomycin or a variant, mutant, or modified molecule thereof, or any combination thereof.

55B. The method of any one of embodiments 50B-54B, wherein the binding moiety is capable of selectively and/or specifically binding to a functionalized N-terminal amino acid (NTAA), an N-terminal dipeptide sequence, or an N-terminal tripeptide sequence, or any combination thereof.

56B. A method for analyzing a plurality of polypeptides, comprising:
(a) labeling each molecule of a plurality of polypeptides with a plurality of universal tags;
(b) contacting the plurality of polypeptides with a plurality of compartment tags (e.g., in the form of non-nucleic acid sequenceable polymers), under a condition suitable for annealing or joining of the plurality of universal tags with the plurality of compartment tags, thereby partitioning the plurality of polypeptides into a plurality of compartments (e.g., a bead surface, a microfluidic droplet, a microwell, or a separated region on a surface, or any combination thereof), wherein the plurality of compartment tags are the same within each compartment and are different from the compartment tags of other compartments;
(c) fragmenting the polypeptide(s) in each compartment, thereby generating a set of polypeptide fragments each associated with a recording polymer comprising at least one universal polynucleotide tag and at least one compartment tag;
(d) immobilizing the set of polypeptide fragments, directly or indirectly, to a support;
(e) contacting the immobilized set of polypeptide fragments with a library of binding agents, wherein each binding agent comprises a binding moiety and a coding polymer comprising identifying information regarding the binding moiety,
wherein the binding moiety is capable of binding to one or more N-terminal, internal, or C-terminal amino acids of the fragment, or capable of binding to the one or more N-terminal, internal, or C-terminal amino acids modified by a functionalizing reagent;
(f) allowing transfer of information between (i) the recording polymer associated with each fragment and (ii) the coding polymer, upon binding between the binding moiety and the one or more N-terminal, internal, or C-terminal amino acids of the fragment, to generate an extended recording polymer and/or an extended coding polymer; and
(g) analyzing the extended recording polymer and/or the extended coding polymer.

57B. The method of embodiment 56B, wherein the plurality of polypeptides with the same compartment tag belong to the same protein.

58B. The method of embodiment 56B, wherein the plurality of polypeptides with the same compartment tag belong to different proteins, for example, two, three, four, five, six, seven, eight, nine, ten, or more proteins.

59B. The method of any one of embodiments 56B-58B, wherein the plurality of compartment tags are immobilized to a plurality of substrates, with each substrate defining a compartment.

60B. The method of embodiment 59B, wherein the plurality of substrates are selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

61B. The method of embodiment 59B or 60B, wherein each of the plurality of substrates comprises a bar-coded particle, such as a bar-coded bead, e.g., a polystyrene bead, a polymer bead, an agarose bead, an acrylamide bead, a solid core bead, a porous bead, a magnetic bead, a paramagnetic bead, a glass bead, or a controlled pore bead, or any combination thereof.

62B. The method of any one of embodiments 59B-61B, wherein the support is selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

63B. The method of embodiment 62B, wherein the support comprises a sequencing bead, e.g., a polystyrene bead, a polymer bead, an agarose bead, an acrylamide bead, a solid core bead, a porous bead, a magnetic bead, a paramagnetic bead, a glass bead, or a controlled pore bead, or any combination thereof.

64B. The method of any one of embodiments 56B-63B, wherein each fragment and its associated recording polymer is spaced apart from other fragments and their associated recording polymers on the support at an average distance equal to or greater than about 20 nm, equal to or greater than about 50 nm, equal to or greater than about 100 nm, equal to or greater than about 150 nm, equal to or greater than about 200 nm, equal to or greater than about 250 nm, equal to or greater than about 300 nm, equal to or greater than about 350 nm, equal to or greater than about 400 nm, equal to or greater than about 450 nm, equal to or greater than about 500 nm, equal to or greater than about 550 nm, equal to or greater than about 600 nm, equal to or greater than about 650 nm, equal to or greater than about 700 nm, equal to or greater than about 750 nm, equal to or greater than about 800 nm, equal to or greater than about 850 nm, equal to or greater than about 900 nm, equal to or greater than about 950 nm, or equal to or greater than about 1 µm.

65B. A method for analyzing a plurality of polypeptides, comprising:
(a) immobilizing a plurality of polypeptides to a plurality of substrates, wherein each substrate comprises a plurality of recording polymers each comprising a compartment tag, optionally wherein each compartment is a bead, a microfluidic droplet, a microwell, or a separated region on a surface, or any combination thereof;
(b) fragmenting (e.g., by a protease digestion) the polypeptide(s) immobilized on each substrate, thereby generating a set of polypeptide fragments immobilized to the substrate;

(c) contacting the immobilized set of polypeptide fragments with a library of binding agents, wherein each binding agent comprises a binding moiety and a coding polymer comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent;

(d) allowing transfer of information between (i) the recording polymer and (ii) the coding polymer, upon binding between the binding moiety and the one or more N-terminal, internal, or C-terminal amino acids of each fragment, to generate an extended recording polymer and/or an extended coding polymer; and (e) analyzing the extended recording polymer and/or the extended coding polymer.

66B. The method of embodiment 65B, wherein the plurality of polypeptides with the same compartment tag belong to the same protein.

67B. The method of embodiment 65B, wherein the plurality of polypeptides with the same compartment tag belong to different proteins, for example, two, three, four, five, six, seven, eight, nine, ten, or more proteins.

68B. The method of any one of embodiments 65B-67B, wherein each substrate defines a compartment.

69B. The method of any one of embodiments 65B-68B, wherein the plurality of substrates are selected from the group consisting of a bead, a porous bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof.

70B. The method of any one of embodiments 65B-69B, wherein each of the plurality of substrates comprises a bar-coded particle, such as a bar-coded bead, e.g., a polystyrene bead, a polymer bead, an agarose bead, an acrylamide bead, a solid core bead, a porous bead, a magnetic bead, a paramagnetic bead, a glass bead, or a controlled pore bead, or any combination thereof.

71B. The method of any one of embodiments 50B-70B, wherein the functionalizing reagent comprises a chemical agent, an enzyme, and/or a biological agent, such as an isothiocyanate derivative, 2,4-dinitrobenzenesulfonic (DNBS), 4-sulfonyl-2-nitrofluorobenzene (SNFB) 1-fluoro-2,4-dinitrobenzene, dansyl chloride, 7-methoxycoumarin acetic acid, a thioacylation reagent, a thioacetylation reagent, or a thiobenzylation reagent.

72B. The method of any one of embodiments 50B-71B, wherein the recording polymer comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, a non-nucleic acid sequenceable polymer, e.g., a polysaccharide, a polypeptide, a peptide, or a polyamide, or a combination thereof.

73B. The method of any one of embodiments 50B-72B, wherein the recording polymer comprises a universal priming site; a priming site for amplification, sequencing, or both; optionally, a unique molecule identifier (UMI); a barcode; optionally, a spacer polymer at its 3'-terminus; or a combination thereof.

74B. The method of any one of embodiments 50B-73B, which is for determining the sequence(s) of the polypeptide or plurality of polypeptides.

75B. The method of any one of embodiments 50B-74B, wherein the coding polymer comprises a nucleic acid, an oligonucleotide, a modified oligonucleotide, a DNA molecule, a DNA with pseudo-complementary bases, an RNA molecule, a BNA molecule, an XNA molecule, a LNA molecule, a PNA molecule, a γPNA molecule, or a morpholino, a non-nucleic acid sequenceable polymer, e.g., a polysaccharide, a polypeptide, a peptide, or a polyamide, or a combination thereof.

76B. The method of any one of embodiments 50B-75B, wherein the coding polymer comprises an encoder sequence, an optional spacer polymer, an optional unique molecular identifier (UMI), a universal priming site, or any combination thereof.

77B. The method of any one of embodiments 50B-76B, wherein the binding moiety and the coding polymer are joined by a linker or a binding pair.

78B. The method of any one of embodiments 50B-77B, wherein the binding moiety and the coding polymer are joined by a SpyTag-KTag/SpyLigase (where two moieties to be joined have the SpyTag/KTag pair, and the SpyLigase joins SpyTag to KTag, thus joining the two moieties), a SpyTag/SpyCatcher, a SnoopTag/SnoopCatcher peptide-protein pair, a sortase, or a HaloTag/HaloTag ligand pair, or any combination thereof.

79B. The method of any one of embodiments 1B-78B, wherein the coding polymer and/or the recording polymer comprise one or more error correcting codes (e.g., in the form of non-nucleic acid sequenceable polymers), one or more encoder sequences (e.g., in the form of non-nucleic acid sequenceable polymers), one or more barcodes (e.g., in the form of non-nucleic acid sequenceable polymers), one or more UMIs (e.g., in the form of non-nucleic acid sequenceable polymers), one or more compartment tags (e.g., in the form of non-nucleic acid sequenceable polymers), or any combination thereof.

80B. The method of embodiment 79B, wherein the error correcting code is selected from Hamming code, Lee distance code, asymmetric Lee distance code, Reed-Solomon code, and Levenshtein-Tenengolts code.

81B. The method of any one of embodiments 1B-80B, wherein analyzing the extended recording polymer and/or extended coding polymer comprises a nucleic acid sequence analysis.

82B. The method of embodiment 81B, wherein the nucleic acid sequence analysis comprises a nucleic acid sequencing method, such as sequencing by synthesis, sequencing by ligation, sequencing by hybridization, polony sequencing, ion semiconductor sequencing, or pyrosequencing, or any combination thereof.

83B. The method of embodiment 82B, wherein the nucleic acid sequencing method is single molecule real-time sequencing, nanopore-based sequencing, or direct imaging of DNA using advanced microscopy.

84B. The method of any one of embodiments 1B-83B, further comprising one or more washing steps.

85B. The method of any one of embodiments 1B-84B, wherein the extended recording polymer and/or extended coding polymer are amplified prior to analysis.

86B. The method of any one of embodiments 1B-85B, wherein the extended recording polymer and/or extended coding polymer undergo a target enrichment assay prior to analysis.

87B. The method of any one of embodiments 1B-86B, wherein the extended recording polymer and/or extended coding polymer undergo a subtraction assay prior to analysis.

88B. A kit, comprising:
(a) a library of agents, wherein each agent comprises (i) a small molecule, peptide or peptide mimetic, peptidomimetic (e.g., peptoid, β-peptide, or D-peptide peptidomimetic), polysaccharide, and/or aptamer, and (ii) a coding polymer comprising identifying information regarding the small molecule, peptide or peptide mimetic, peptidomimetic (e.g., peptoid, β-peptide, or D-peptide peptidomimetic), polysaccharide, or aptamer; and
optionally (b) a set of proteins, wherein each protein is associated directly or indirectly with a recording polymer,
wherein each protein and/or its associated recording polymer, or each agent, is immobilized directly or indirectly to a support, and
wherein the set of proteins, the recording polymers, and the library of agents are configured to allow information transfer between (i) the recording polymer associated with each protein that binds and/or reacts with the small molecule(s), peptide(s) or peptide mimetic(s), peptidomimetic(s) (e.g., peptoid(s), β-peptide(s), or D-peptide peptidomimetic(s)), polysaccharide(s), or aptamer(s) of one or more agents, and (ii) the coding polymer of the one or more agents, to generate an extended recording polymer and/or an extended coding polymer.

89B. A kit for analyzing a polypeptide, comprising:
(a) a library of binding agents, wherein each binding agent comprises a binding moiety and a coding polymer comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent; and
optionally (b) a set of fragments of a polypeptide, wherein each fragment is associated directly or indirectly with a recording polymer, or (b') a means for fragmenting a polypeptide, such as a protease,
wherein each fragment and/or its associated recording polymer, or each binding agent, is immobilized directly or indirectly to a support, and
wherein the set of fragments of a polypeptide, the recording polymers, and the library of binding agents are configured to allow transfer of information between (i) the recording polymer associated with each fragment and (ii) the coding polymer, upon binding between the binding moiety and the one or more N-terminal, internal, or C-terminal amino acids of the fragment, to generate an extended recording polymer and/or an extended coding polymer.

90B. A kit for analyzing a plurality of polypeptides, comprising: (a) a library of binding agents, wherein each binding agent comprises a binding moiety and a coding polymer comprising identifying information regarding the binding moiety, wherein the binding moiety is capable of binding to one or more N-terminal, internal, or C-terminal amino acids of the fragment, or capable of binding to the one or more N-terminal, internal, or C-terminal amino acids modified by a functionalizing reagent; and (b) a plurality of substrates, optionally with a plurality of polypeptides immobilized thereto, wherein each substrate comprises a plurality of recording polymers each comprising a compartment tag (e.g., in the form of a non-nucleic acid sequenceable polymer), optionally wherein each compartment is a bead, a microfluidic droplet, a microwell, or a separated region on a surface, or any combination thereof, wherein the polypeptide(s) immobilized on each substrate are configured to be fragmented (e.g., by a protease cleavage) to generate a set of polypeptide fragments immobilized to the substrate; wherein the plurality of polypeptides, the recording polymers, and the library of binding agents are configured to allow transfer of information between (i) the recording polymer and (ii) the coding polymer, upon binding between the binding moiety and the one or more N-terminal, internal, or C-terminal amino acids of each fragment, to generate an extended recording polymer and/or an extended coding polymer.

1C. The method or kit of any of the preceding embodiments, wherein the recording tag is a small molecule, or a subunit, monomer, residue, or building block of a sequenceable polymer, such as a polynucleotide or a non-nucleic acid sequenceable polymer.

2C. The method or kit of any of the preceding embodiments, wherein the recording tag is a sequenceable polymer, such as a polynucleotide or a non-nucleic acid sequenceable polymer.

3C. The method or kit of any of the preceding embodiments, wherein the coding tag comprises a small molecule, or a subunit, monomer, residue, or building block of a sequenceable polymer, such as a polynucleotide or a non-nucleic acid sequenceable polymer.

4C. The method or kit of any of the preceding embodiments, wherein the coding tag is a small molecule, or a subunit, monomer, residue, or building block of a sequenceable polymer, such as a polynucleotide or a non-nucleic acid sequenceable polymer.

5C. The method or kit of embodiment 4C, wherein the recording tag is a sequenceable polymer.

6C. The method or kit of any of the preceding embodiments, wherein the extended recording tag and/or extended coding tag is a sequenceable polymer, such as a polynucleotide or a non-nucleic acid sequenceable polymer.

1D. A method, comprising:
(a) contacting an analyte with a first binding agent capable of binding to the analyte, wherein the first binding agent comprises a first coding portion with identifying information regarding the first binding agent, the analyte is associated with a recording portion joined to a support, and the analyte and/or the recording portion is immobilized to a support;
(b) transferring the information of the first coding portion to the recording portion to generate a first order extended recording portion;
(c) contacting the analyte with a second binding agent capable of binding to the analyte, wherein the second binding agent comprises a second coding portion with identifying information regarding the second binding agent;
(d) transferring the information of the second coding portion to the first order extended recording portion to generate a second order extended recording portion; and
(e) analyzing the second order extended recording portion.

2D. The method of embodiment 1D, further comprising, between steps (d) and (e), the following steps:
(x) repeating steps (c) and (d) one or more times by replacing the second binding agent with a third (or higher order) binding agent capable of binding to the analyte, wherein the third (or higher order) binding agent comprises a third (or higher order) coding portion with identifying information regarding the third (or higher order) bind agent; and
(y) transferring the information of the third (or higher order) coding portion to the second (or higher order) extended recording portion to generate a third (or higher order) extended recording portion,
wherein the third (or higher order) extended recording portion is analyzed in step (e).

3D. The method of embodiment 1D or 2D, wherein the recording portion of step (a) is a small molecule, or a subunit, monomer, residue, or building block of a sequenceable polymer, such as a polynucleotide or a non-nucleic acid sequenceable polymer.

4D. The method of embodiment 1D or 2D, wherein the recording portion of step (a) is a sequenceable polymer, such as a polynucleotide or a non-nucleic acid sequenceable polymer.

5D. The method of embodiment 4D, wherein the first, second, third, and/or higher order coding portion comprises a small molecule, and/or a subunit, monomer, residue, or building block of a sequenceable polymer, such as a polynucleotide or a non-nucleic acid sequenceable polymer.

6D. The method of embodiment 4D or 5D, wherein the first, second, third, and/or higher order coding portion is a small molecule, or a subunit, monomer, residue, or building block of a sequenceable polymer, such as a polynucleotide or a non-nucleic acid sequenceable polymer.

7D. The method of any one of embodiments 1D-6D, wherein the first order extended recording portion, second order extended recording portion, third order extended recording portion, and/or higher order extended recording portion is a sequenceable polymer, such as a polynucleotide or a non-nucleic acid sequenceable polymer.

8D. A method, comprising:
(a) contacting a polypeptide with a first binding agent capable of binding to one or more N-terminal, internal, or C-terminal amino acid of the polypeptide, wherein the first binding agent comprises a first coding portion with identifying information regarding the first binding agent, the polypeptide is associated with a recording portion joined to a support, and the polypeptide and/or the recording portion is immobilized to a support;
(b) transferring the information of the first coding portion to the recording portion to generate a first order extended recording portion;
(c) contacting the analyte with a second binding agent capable of binding to a different one or more N-terminal, internal, or C-terminal amino acid of the polypeptide, wherein the second binding agent comprises a second coding portion with identifying information regarding the second binding agent;
(d) transferring the information of the second coding portion to the first order extended recording portion to generate a second order extended recording portion; and
(e) analyzing the second order extended recording portion.

9D. The method of embodiment 8D, wherein the one or more N-terminal, internal, or C-terminal amino acid and/or the different one or more N-terminal, internal, or C-terminal amino acid of the polypeptide is a modified amino acid, such as a modified N-terminal amino acid (NTAA).

10D. A method, comprising:
(a) contacting a polypeptide with a first binding agent capable of binding to one or more N-terminal or C-terminal amino acid of the polypeptide, wherein the first binding agent comprises a first coding portion with identifying information regarding the first binding agent, the polypeptide is associated with a recording portion joined to a support, and the polypeptide and/or the recording portion is immobilized to a support;
(b) transferring the information of the first coding portion to the recording portion to generate a first order extended recording portion;
(c) eliminating the one or more N-terminal or C-terminal amino acid of the polypeptide, to expose a different one or more N-terminal or C-terminal amino acid of the polypeptide;
(d) contacting the analyte with a second binding agent capable of binding to the different one or more N-terminal or C-terminal amino acid of the polypeptide, wherein the second binding agent comprises a second coding portion with identifying information regarding the second binding agent;
(e) transferring the information of the second coding portion to the first order extended recording portion to generate a second order extended recording portion; and
(f) analyzing the second order extended recording portion.

11D. The method of embodiment 10D, wherein the one or more N-terminal or C-terminal amino acid and/or the different one or more N-terminal or C-terminal amino acid of the polypeptide is a modified amino acid, such as a modified N-terminal amino acid (NTAA).

12D. The method of any one of embodiments 8D-111D, wherein the recording portion of step (a) is a small molecule, or a subunit, monomer, residue, or building block of a sequenceable polymer, such as a polynucleotide or a non-nucleic acid sequenceable polymer.

13D. The method of any one of embodiments 8D-11D, wherein the recording portion of step (a) is a sequenceable polymer, such as a polynucleotide or a non-nucleic acid sequenceable polymer.

14D. The method of embodiment 13D, wherein the first or second order coding portion comprises a small molecule, and/or a subunit, monomer, residue, or building block of a sequenceable polymer, such as a polynucleotide or a non-nucleic acid sequenceable polymer.

15D. The method of embodiment 13D or 14D, wherein the first or second order coding portion is a small molecule, or a subunit, monomer, residue, or building block of a sequenceable polymer, such as a polynucleotide or a non-nucleic acid sequenceable polymer.

16D. The method of any one of embodiments 8D-15D, wherein the first order extended recording portion or second order extended recording portion is a sequenceable polymer, such as a polynucleotide or a non-nucleic acid sequenceable polymer.

17D. The method of any one of embodiments 3D-16D, wherein the sequenceable polymer comprises one or more blockade group.

18D. The method of embodiment 17D, wherein the one or more blockade group is capable of generating a signature current blockade signal when the sequenceable polymer passes through a nanopore.

19D. The method of any one of embodiments 3D-18D, wherein the sequenceable polymer comprises one or more binding moiety capable of binding to a binding agent that stalls the sequenceable polymer when passing through a nanopore.

20D. The method of any one of embodiments 3D-19D, wherein the sequenceable polymer comprises one or more structure capable of stalling the sequenceable polymer when passing through a nanopore.

21D. The method of embodiment 20D, wherein the one or more structure comprises a secondary structure, such as an intrinsic meta-stable secondary structure.

22D. The method of any one of embodiments 3D-21D, wherein the sequenceable polymer comprises a polymer built using phosphoramidite chemistry, or a peptoid polymer, or a combination thereof.

23D. A kit, comprising any molecule, molecular complex or conjugate, reagent (e.g., chemical or biological), agent, structure (e.g., support, surface, particle, or bead), reaction intermediate, reaction product, binding complex, or any other article of manufacture disclosed and/or used in the method of any of embodiments 1D-23D, or any combination thereof.

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

REFERENCES

Harlow, Ed, and David Lane. Using Antibodies. Cold Spring Harbor, New York: Cold Spring Harbor Laboratory Press, 1999.

Hennessy B T, Lu Y, Gonzalez-Angulo A M, et al. A Technical Assessment of the Utility of Reverse Phase Protein Arrays for the Study of the Functional Proteome in Non-microdissected Human Breast Cancers. *Clinical proteomics.* 2010; 6(4):129-151.

Davidson, G. R., S. D. Armstrong and R. J. Beynon (2011). "Positional proteomics at the N-terminus as a means of proteome simplification." *Methods Mol Biol* 753: 229-242.

Zhang, L., Luo, S., and Zhang, B. (2016). The use of lectin microarray for assessing glycosylation of therapeutic proteins. mAbs 8, 524-535.

Akbani, R., K. F. Becker, N. Carragher, T. Goldstein, L. de Koning, U. Korf, L. Liotta, G. B. Mills, S. S. Nishizuka, M. Pawlak, E. F. Petricoin, 3rd, H. B. Pollard, B. Serrels and J. Zhu (2014). "Realizing the promise of reverse phase protein arrays for clinical, translational, and basic research: a workshop report: the RPPA (Reverse Phase Protein Array) society." *Mol Cell Proteomics* 13(7): 1625-1643.

Amini, S., D. Pushkarev, L. Christiansen, E. Kostem, T. Royce, C. Turk, N. Pignatelli, A. Adey, J. O. Kitzman, K. Vijayan, M. Ronaghi, J. Shendure, K. L. Gunderson and F. J. Steemers (2014). "Haplotype-resolved whole-genome sequencing by contiguity-preserving transposition and combinatorial indexing." *Nat Genet* 46(12): 1343-1349.

Assadi, M., J. Lamerz, T. Jarutat, A. Farfsing, H. Paul, B. Gierke, E. Breitinger, M. F. Templin, L. Essioux, S. Arbogast, M. Venturi, M. Pawlak, H. Langen and T. Schindler (2013). "Multiple protein analysis of formalin-fixed and paraffin-embedded tissue samples with reverse phase protein arrays." *Mol Cell Proteomics* 12(9): 2615-2622.

Bailey, J. M. and J. E. Shively (1990). "Carboxy-terminal sequencing: formation and hydrolysis of C-terminal peptidylthiohydantoins." *Biochemistry* 29(12): 3145-3156.

Bandara, H. M., D. P. Kennedy, E. Akin, C. D. Incarvito and S. C. Burdette (2009). "Photoinduced release of $Zn^{2+}$ with ZinCleav-1: a nitrobenzyl-based caged complex." *Inorg Chem* 48(17): 8445-8455.

Bandara, H. M., T. P. Walsh and S. C. Burdette (2011). "A Second-generation photocage for $Zn^{2+}$ inspired by TPEN: characterization and insight into the uncaging quantum yields of ZinCleav chelators." *Chemistry* 17(14): 3932-3941.

Basle, E., N. Joubert and M. Pucheault (2010). "Protein chemical modification on endogenous amino acids." *Chem Biol* 17(3): 213-227.

Bilgicer, B., S. W. Thomas, 3rd, B. F. Shaw, G. K. Kaufman, V. M. Krishnamurthy, L. A. Estroff, J. Yang and G. M. Whitesides (2009). "A non-chromatographic method for the purification of a bivalently active monoclonal IgG antibody from biological fluids." *J Am Chem Soc* 131(26): 9361-9367.

Bochman, M. L., K. Paeschke and V. A. Zakian (2012). "DNA secondary structures: stability and function of G-quadruplex structures." *Nat Rev Genet* 13(11): 770-780.

Borgo, B. and J. J. Havranek (2014). "Motif-directed redesign of enzyme specificity." *Protein Sci* 23(3): 312-320.

Brouzes, E., M. Medkova, N. Savenelli, D. Marran, M. Twardowski, J. B. Hutchison, J. M. Rothberg, D. R. Link, N. Perrimon and M. L. Samuels (2009). "Droplet microfluidic technology for single-cell high-throughput screening." *Proc Natl Acad Sci USA* 106(34): 14195-14200.

Brudno, Y., M. E. Birnbaum, R. E. Kleiner and D. R. Liu (2010). "An in vitro translation, selection and amplification system for peptide nucleic acids." *Nat Chem Biol* 6(2): 148-155.

Calcagno, S. and C. D. Klein (2016). "N-Terminal methionine processing by the zinc-activated *Plasmodium falciparum* methionine aminopeptidase 1b." *Appl Microbiol Biotechnol.*

Cao, Y., G. K. Nguyen, J. P. Tam and C. F. Liu (2015). "Butelase-mediated synthesis of protein thioesters and its application for tandem chemoenzymatic ligation." *Chem Commun (Camb)* 51(97): 17289-17292.

Carty, R. P. and C. H. Hirs (1968). "Modification of bovine pancreatic ribonuclease A with 4-sulfonyloxy-2-nitrofluorobenzene. Isolation and identification of modified proteins." *J Biol Chem* 243(20): 5244-5253.

Chang, L., D. M. Rissin, D. R. Fournier, T. Piech, P. P. Patel, D. H. Wilson and D. C. Duffy (2012). "Single molecule enzyme-linked immunosorbent assays: theoretical considerations." *J Immunol Methods* 378(1-2): 102-115.

Chang, Y. Y. and C. H. Hsu (2015). "Structural basis for substrate-specific acetylation of Nalpha-acetyltransferase Ard1 from *Sulfolobus solfataricus*." *Sci Rep* 5: 8673.

Christoforou, A., C. M. Mulvey, L. M. Breckels, A. Geladaki, T. Hurrell, P. C. Hayward, T. Naake, L. Gatto, R. Viner, A. Martinez Arias and K. S. Lilley (2016). "A draft map of the mouse pluripotent stem cell spatial proteome." *Nat Commun* 7: 8992.

Creighton, C. J. and S. Huang (2015). "Reverse phase protein arrays in signaling pathways: a data integration perspective." *Drug Des Devel Ther* 9: 3519-3527.

Crosetto, N., M. Bienko and A. van Oudenaarden (2015). "Spatially resolved transcriptomics and beyond." *Nat Rev Genet* 16(1): 57-66.

Cusanovich, D. A., R. Daza, A. Adey, H. A. Pliner, L. Christiansen, K. L. Gunderson, F. J. Steemers, C. Trapnell and J. Shendure (2015). "Multiplex single-cell profiling of chromatin accessibility by combinatorial cellular indexing." *Science* 348(6237): 910-914.

Derrington, I. M., T. Z. Butler, M. D. Collins, E. Manrao, M. Pavlenok, M. Niederweis and J. H. Gundlach (2010). "Nanopore DNA sequencing with MspA." *Proc Natl Acad Sci USA* 107(37): 16060-16065.

El-Sagheer, A. H., V. V. Cheong and T. Brown (2011). "Rapid chemical ligation of oligonucleotides by the Diels-Alder reaction." *Org Biomol Chem* 9(1): 232-235.

El-Sagheer, A. H., A. P. Sanzone, R. Gao, A. Tavassoli and T. Brown (2011). "Biocompatible artificial DNA linker that is read through by DNA polymerases and is functional in *Escherichia coli*." *Proc Natl Acad Sci USA* 108(28): 11338-11343.

Emili, A., M. McLaughlin, K. Zagorovsky, J. B. Olsen, W. C. W. Chan and S. S. Sidhu (2017). Protein Sequencing Method and Reagents. USPTO. USA, The Governing Council of University of Toronto. 9,566,335 B1.

Erde, J., R. R. Loo and J. A. Loo (2014). "Enhanced FASP (eFASP) to increase proteome coverage and sample recovery for quantitative proteomic experiments." *J Proteome Res* 13(4): 1885-1895.

Farries, T. C., A. Harris, A. D. Auffret and A. Aitken (1991). "Removal of N-acetyl groups from blocked peptides with acylpeptide hydrolase. Stabilization of the enzyme and its application to protein sequencing." *Eur J Biochem* 196 (3): 679-685.

Feist, P. and A. B. Hummon (2015). "Proteomic challenges: sample preparation techniques for microgram-quantity protein analysis from biological samples." *Int J Mol Sci* 16(2): 3537-3563.

Friedmann, D. R. and R. Marmorstein (2013). "Structure and mechanism of non-histone protein acetyltransferase enzymes." *FEBS J* 280(22): 5570-5581.

Frokjaer, S. and D. E. Otzen (2005). "Protein drug stability: a formulation challenge." *Nat Rev Drug Discov* 4(4): 298-306.

Fujii, Y., M. Kaneko, M. Neyazaki, T. Nogi, Y. Kato and J. Takagi (2014). "PA tag: a versatile protein tagging system using a super high affinity antibody against a dodecapeptide derived from human podoplanin." *Protein Expr Purif* 95: 240-247.

Gebauer, M. and A. Skerra (2012). "Anticalins small engineered binding proteins based on the lipocalin scaffold." *Methods Enzymol* 503: 157-188.

Gerry, N. P., N. E. Witowski, J. Day, R. P. Hammer, G. Barany and F. Barany (1999). "Universal DNA microarray method for multiplex detection of low abundance point mutations." *J Mol Biol* 292(2): 251-262.

Gogliettino, M., M. Balestrieri, E. Cocca, S. Mucerino, M. Rossi, M. Petrillo, E. Mazzella and G. Palmieri (2012). "Identification and characterisation of a novel acylpeptide hydrolase from *Sulfolobus solfataricus*: structural and functional insights." *PLoS One* 7(5): e37921.

Gogliettino, M., A. Riccio, M. Balestrieri, E. Cocca, A. Facchiano, T. M. D'Arco, C. Tesoro, M. Rossi and G. Palmieri (2014). "A novel class of bifunctional acylpeptide hydrolases—potential role in the antioxidant defense systems of the Antarctic fish *Trematomus bernacchii*." *FEBS J* 281(1): 401-415.

Granvogl, B., M. Ploscher and L. A. Eichacker (2007). "Sample preparation by in-gel digestion for mass spectrometry-based proteomics." *Anal Bioanal Chem* 389(4): 991-1002.

Gunderson, K. L., X. C. Huang, M. S. Morris, R. J. Lipshutz, D. J. Lockhart and M. S. Chee (1998). "Mutation detection by ligation to complete n-mer DNA arrays." *Genome Res* 8(11): 1142-1153.

Gunderson, K. L., F. J. Steemers, J. S. Fisher and R. Rigatti (2016). Methods and Compositions for Analyzing Cellular Components. WIPO, Illumina, Inc.

Gunderson, K. L., F. J. Steemers, J. S. Fisher and R. Rigatti (2016). Methods and compositions for analyzing cellular components, Illumina, Inc.

Guo, H., W. Liu, Z. Ju, P. Tamboli, E. Jonasch, G. B. Mills, Y. Lu, B. T. Hennessy and D. Tsavachidou (2012). "An efficient procedure for protein extraction from formalin-fixed, paraffin-embedded tissues for reverse phase protein arrays." *Proteome Sci* 10(1): 56.

Hamada, Y. (2016). "A novel N-terminal degradation reaction of peptides via N-amidination." *Bioorg Med Chem Lett* 26(7): 1690-1695.

Hermanson, G. (2013). *Bioconjugation Techniques*, Academic Press.

Hernandez-Moreno, A. V., F. Villasenor, E. Medina-Rivero, N. O. Perez, L. F. Flores-Ortiz, G. Saab-Rincon and G. Luna-Barcenas (2014). "Kinetics and conformational stability studies of recombinant leucine aminopeptidase." *Int J Biol Macromol* 64: 306-312.

Hori, M., H. Fukano and Y. Suzuki (2007). "Uniform amplification of multiple DNAs by emulsion PCR." *Biochem Biophys Res Commun* 352(2): 323-328.

Horisawa, K. (2014). "Specific and quantitative labeling of biomolecules using click chemistry." *Front Physiol* 5: 457.

Hoshika, S., F. Chen, N. A. Leal and S. A. Benner (2010). "Artificial genetic systems: self-avoiding DNA in PCR and multiplexed PCR." *Angew Chem Int Ed Engl* 49(32): 5554-5557.

Hughes, A. J., D. P. Spelke, Z. Xu, C. C. Kang, D. V. Schaffer and A. E. Herr (2014). "Single-cell western blotting." *Nat Methods* 11(7): 749-755.

Hughes, C. S., S. Foehr, D. A. Garfield, E. E. Furlong, L. M. Steinmetz and J. Krijgsveld (2014). "Ultrasensitive proteome analysis using paramagnetic bead technology." *Mol Syst Biol* 10: 757.

Kang, C. C., K. A. Yamauchi, J. Vlassakis, E. Sinkala, T. A. Duncombe and A. E. Herr (2016). "Single cell-resolution western blotting." *Nat Protoc* 11(8): 1508-1530.

Kang, T. S., L. Wang, C. N. Sarkissian, A. Gamez, C. R. Scriver and R. C. Stevens (2010). "Converting an injectable protein therapeutic into an oral form: phenylalanine ammonia lyase for phenylketonuria." *Mol Genet Metab* 99(1): 4-9.

Katritzky, A. R. and B. V. Rogovoy (2005). "Recent developments in guanylating agents." *ARKIVOC* iv (Issue in Honor of Prof. Nikolai Zefirov): 49-87.

Klein, A. M., L. Mazutis, I. Akartuna, N. Tallapragada, A. Veres, V. Li, L. Peshkin, D. A. Weitz and M. W. Kirschner (2015). "Droplet barcoding for single-cell transcriptomics applied to embryonic stem cells." *Cell* 161(5): 1187-1201.

Knall, A. C., M. Hollauf and C. Slugovc (2014). "Kinetic studies of inverse electron demand Diels-Alder reactions (iEDDA) of norbornenes and 3,6-dipyridin-2-yl-1,2,4,5-tetrazine." *Tetrahedron Lett* 55(34): 4763-4766.

Le, Z. G., Z. C. Chen, Y. Hu and Q. G. Zheng (2005). "Organic Reactions in Ionic Liquids: Ionic Liquid-promoted Efficient Synthesis of Disubstituted and Trisubstituted Thioureas Derivatives." *Chinese Chemical Letters* 16(2): 201-204.

Lesch, V., A. Heuer, V. A. Tatsis, C. Holm and J. Smiatek (2015). "Peptides in the presence of aqueous ionic liquids: tunable co-solutes as denaturants or protectants?" *Phys Chem Chem Phys* 17(39): 26049-26053.

Li, G., Y. Liu, Y. Liu, L. Chen, S. Wu, Y. Liu and X. Li (2013). "Photoaffinity labeling of small-molecule-binding proteins by DNA-templated chemistry." *Angew Chem Int Ed Engl* 52(36): 9544-9549.

Litovchick, A., M. A. Clark and A. D. Keefe (2014). "Universal strategies for the DNA-encoding of libraries of small molecules using the chemical ligation of oligonucleotide tags." *Artif DNA PNA XNA* 5(1): e27896.

Liu, Y. and S. Liang (2001). "Chemical carboxyl-terminal sequence analysis of peptides and proteins using tribenzylsilyl isothiocyanate." *J Protein Chem* 20(7): 535-541.

Lundblad, R. L. (2014). *Chemical reagents for protein modification*. Boca Raton, CRC Press, Taylor & Francis Group.

Mashaghi, S. and A. M. van Oijen (2015). "External control of reactions in microdroplets." *Sci Rep* 5: 11837.

McCormick, R. M. (1989). "A solid-phase extraction procedure for DNA purification." *Anal Biochem* 181(1): 66-74.

Mendoza, V. L. and R. W. Vachet (2009). "Probing protein structure by amino acid-specific covalent labeling and mass spectrometry." *Mass Spectrom Rev* 28(5): 785-815.

Mikami, T., T. Takao, K. Yanagi and H. Nakazawa (2012). "N (alpha) Selective Acetylation of Peptides." *Mass Spectrom* (Tokyo) 1(2): A0010.

Moghaddam, M. J., L. de Campo, N. Kirby and C. J. Drummond (2012). "Chelating DTPA amphiphiles: ion-tunable self-assembly structures and gadolinium complexes." *Phys Chem Chem Phys* 14(37): 12854-12862.

Mukherjee, S., M. Ura, R. J. Hoey and A. A. Kossiakoff (2015). "A New Versatile Immobilization Tag Based on the Ultra High Affinity and Reversibility of the Calmodulin-Calmodulin Binding Peptide Interaction." *J Mol Biol* 427(16): 2707-2725.

Namimatsu, S., M. Ghazizadeh and Y. Sugisaki (2005). "Reversing the effects of formalin fixation with citraconic anhydride and heat: a universal antigen retrieval method." *J Histochem Cytochem* 53(1): 3-11.

Nguyen, G. K., Y. Cao, W. Wang, C. F. Liu and J. P. Tam (2015). "Site-Specific N-Terminal Labeling of Peptides and Proteins using Butelase 1 and Thiodepsipeptide." *Angew Chem Int Ed Engl* 54(52): 15694-15698.

Nguyen, G. K., S. Wang, Y. Qiu, X. Hemu, Y. Lian and J. P. Tam (2014). "Butelase 1 is an Asx-specific ligase enabling peptide macrocyclization and synthesis." *Nat Chem Biol* 10(9): 732-738.

Nishizuka, S. S. and G. B. Mills (2016). "New era of integrated cancer biomarker discovery using reverse-phase protein arrays." *Drug Metab Pharmacokinet* 31(1): 35-45.

Ohkubo, A., R. Kasuya, K. Sakamoto, K. Miyata, H. Taguchi, H. Nagasawa, T. Tsukahara, T. Watanobe, Y. Maki, K. Seio and M. Sekine (2008). "'Protected DNA Probes' capable of strong hybridization without removal of base protecting groups." *Nucleic Acids Res* 36(6): 1952-1964.

Ojha, B., A. K. Singh, M. D. Adhikari, A. Ramesh and G. Das (2010). "2-Alkylmalonic acid: amphiphilic chelator and a potent inhibitor of metalloenzyme." *J Phys Chem B* 114(33): 10835-10842.

Peng, X., H. Li and M. Seidman (2010). "A Template-Mediated Click-Click Reaction: PNA-DNA, PNA-PNA (or Peptide) Ligation, and Single Nucleotide Discrimination." *European J Org Chem* 2010(22): 4194-4197.

Perbandt, M., O. Bruns, M. Vallazza, T. Lamla, C. Betzel and V. A. Erdmann (2007). "High resolution structure of streptavidin in complex with a novel high affinity peptide tag mimicking the biotin binding motif." *Proteins* 67(4): 1147-1153.

Rauth, S., D. Hinz, M. Borger, M. Uhrig, M. Mayhaus, M. Riemenschneider and A. Skerra (2016). "High-affinity Anticalins with aggregation-blocking activity directed against the Alzheimer beta-amyloid peptide." *Biochem J* 473(11): 1563-1578.

Ray, A. and B. Norden (2000). "Peptide nucleic acid (PNA): its medical and biotechnical applications and promise for the future." *FASEB J* 14(9): 1041-1060.

Riley, N. M., A. S. Hebert and J. J. Coon (2016). "Proteomics Moves into the Fast Lane." *Cell Syst* 2(3): 142-143.

Roloff, A., S. Ficht, C. Dose and O. Seitz (2014). "DNA-templated native chemical ligation of functionalized peptide nucleic acids: a versatile tool for single base-specific detection of nucleic acids." *Methods Mol Biol* 1050: 131-141.

Roloff, A. and O. Seitz (2013). "The role of reactivity in DNA templated native chemical PNA ligation during PCR." *Bioorg Med Chem* 21(12): 3458-3464.

Sakurai, K., T. M. Snyder and D. R. Liu (2005). "DNA-templated functional group transformations enable sequence-programmed synthesis using small-molecule reagents." *J Am Chem Soc* 127(6): 1660-1661.

Schneider, K. and B. T. Chait (1995). "Increased stability of nucleic acids containing 7-deaza-guanosine and 7-deaza-adenosine may enable rapid DNA sequencing by matrix-assisted laser desorption mass spectrometry." *Nucleic Acids Res* 23(9): 1570-1575.

Selvaraj, R. and J. M. Fox (2013). "trans-Cyclooctene—a stable, voracious dienophile for bioorthogonal labeling." *Curr Opin Chem Biol* 17(5): 753-760.

Sharma, A. K., A. D. Kent and J. M. Heemstra (2012). "Enzyme-linked small-molecule detection using split aptamer ligation." *Anal Chem* 84(14): 6104-6109.

Shembekar, N., C. Chaipan, R. Utharala and C. A. Merten (2016). "Droplet-based microfluidics in drug discovery, transcriptomics and high-throughput molecular genetics." *Lab Chip* 16(8): 1314-1331.

Shenoy, N. R., J. E. Shively and J. M. Bailey (1993). "Studies in C-terminal sequencing: new reagents for the synthesis of peptidylthiohydantoins." *J Protein Chem* 12(2): 195-205.

Shim, J. U., R. T. Ranasinghe, C. A. Smith, S. M. Ibrahim, F. Hollfelder, W. T. Huck, D. Klenerman and C. Abell (2013). "Ultrarapid generation of femtoliter microfluidic droplets for single-molecule-counting immunoassays." *ACS Nano* 7(7): 5955-5964.

Shim, J. W., Q. Tan and L. Q. Gu (2009). "Single-molecule detection of folding and unfolding of the G-quadruplex aptamer in a nanopore nanocavity." *Nucleic Acids Res* 37(3): 972-982.

Sidoli, S., Z. F. Yuan, S. Lin, K. Karch, X. Wang, N. Bhanu, A. M. Arnaudo, L. M. Britton, X. J. Cao, M. Gonzales-Cope, Y. Han, S. Liu, R. C. Molden, S. Wein, L. Afjehi-Sadat and B. A. Garcia (2015). "Drawbacks in the use of unconventional hydrophobic anhydrides for histone derivatization in bottom-up proteomics PTM analysis." *Proteomics* 15(9): 1459-1469.

Sletten, E. M. and C. R. Bertozzi (2009). "Bioorthogonal chemistry: fishing for selectivity in a sea of functionality." *Angew Chem Int Ed Engl* 48(38): 6974-6998.

Spencer, S. J., M. V. Tamminen, S. P. Preheim, M. T. Guo, A. W. Briggs, I. L. Brito, A. W. D, L. K. Pitkanen, F. Vigneault, M. P. Juhani Virta and E. J. Alm (2016). "Massively parallel sequencing of single cells by epicPCR links functional genes with phylogenetic markers." *ISME J* 10(2): 427-436.

Spicer, C. D. and B. G. Davis (2014). "Selective chemical protein modification." *Nat Commun* 5: 4740.

Spiropulos, N. G. and J. M. Heemstra (2012). "Templating effect in DNA proximity ligation enables use of non-bioorthogonal chemistry in biological fluids." *Artif DNA PNA XNA* 3(3): 123-128.

Switzar, L., M. Giera and W. M. Niessen (2013). "Protein digestion: an overview of the available techniques and recent developments." *J Proteome Res* 12(3): 1067-1077.

Tamminen, M. V. and M. P. Virta (2015). "Single gene-based distinction of individual microbial genomes from a mixed population of microbial cells." *Front Microbiol* 6: 195.

Tessler, L. (2011). Digital Protein Analysis: Technologies for Protein Diagnostics and Proteomics through Single-Molecule Detection. Ph.D., WASHINGTON UNIVERSITY IN ST. LOUIS. Tyson, J. and J. A. Armour (2012). "Determination of haplotypes at structurally complex regions using emulsion haplotype fusion PCR." *BMC Genomics* 13: 693.

Vauquelin, G. and S. J. Charlton (2013). "Exploring avidity: understanding the potential gains in functional affinity and target residence time of bivalent and heterobivalent ligands." *Br J Pharmacol* 168(8): 1771-1785.

Veggiani, G., T. Nakamura, M. D. Brenner, R. V. Gayet, J. Yan, C. V. Robinson and M. Howarth (2016). "Programmable polyproteams built using twin peptide superglues." *Proc Natl Acad Sci USA* 113(5): 1202-1207.

Wang, D., S. Fang and R. M. Wohlhueter (2009). "N-terminal derivatization of peptides with isothiocyanate analogues promoting Edman-type cleavage and enhancing sensitivity in electrospray ionization tandem mass spectrometry analysis." *Anal Chem* 81(5): 1893-1900.

Williams, B. A. and J. C. Chaput (2010). "Synthesis of peptide-oligonucleotide conjugates using a heterobifunctional crosslinker." *Curr Protoc Nucleic Acid Chem* Chapter 4: Unit4 41.

Wu, H. and N. K. Devaraj (2016). "Inverse Electron-Demand Diels-Alder Bioorthogonal Reactions." *Top Curr Chem* (J) 374(1): 3.

Xiong, A. S., R. H. Peng, J. Zhuang, F. Gao, Y. Li, Z. M. Cheng and Q. H. Yao (2008). "Chemical gene synthesis: strategies, softwares, error corrections, and applications." *FEMS Microbiol Rev* 32(3): 522-540.

Yao, Y., M. Docter, J. van Ginkel, D. de Ridder and C. Joo (2015). "Single-molecule protein sequencing through fingerprinting: computational assessment." *Phys Biol* 12(5): 055003.

Zakeri, B., J. O. Fierer, E. Celik, E. C. Chittock, U. Schwarz-Linek, V. T. Moy and M. Howarth (2012). "Peptide tag forming a rapid covalent bond to a protein, through engineering a bacterial adhesin." *Proc Natl Acad Sci USA* 109(12): E690-697.

Zhang, L., K. Zhang, S. Rauf, D. Dong, Y. Liu and J. Li (2016). "Single-Molecule Analysis of Human Telomere Sequence Interactions with G-quadruplex Ligand." *Anal Chem* 88(8): 4533-4540.

Zhou, H., Z. Ning, A. E. Starr, M. Abu-Farha and D. Figeys (2012). "Advancements in top-down proteomics." *Anal Chem* 84(2): 720-734.

Zilionis, R., J. Nainys, A. Veres, V. Savova, D. Zemmour, A. M. Klein and L. Mazutis (2017). "Single-cell barcoding and sequencing using droplet microfluidics." *Nat Protoc* 12(1): 44-73.

Vigneron et al., Proc. Natl. Acad. Sci. 1996, 93, 9682-9686.
Yong et al., J. Org. Chem. 1997, 62, 1540-1542.
Xu et al., Organometallics. 2015, 34, 1787-1801.
Kwon et al., Org. Lett. 2014, 16, 6048-6051.
Martin et al., Organometallics. 2006, 34, 1787-1801.
Bhattacharjree et al., J. Chem. Sci. 2016, 128(6):875-881.
Chi et al., 2015, Chem. Eur. J. 2015, 21, 10369-10378.
Hamada, Y., Bioog. Med. Chem. Lett. 2016, 26, 1690-1695.
Katritzky et al., *Arkivoc*. 2005, iv, 49-87.
Bachor et al., *Mol. Divers*. 2013, 17, 605-611.
Borgo et al., *Protein Science*. 2015, 24(4), 571-579.
Krishna et al., *Protein Science*. 1992, 1(5), 582-589.
Tian et al., *J. Am. Chem. Soc.,* 2016, 138(43), pp. 14234-14237.
Zhang et al., *Org. Lett.,* 2001, 3 (15), 2341-2344.
Musiol et al., *Org. Lett.,* 2001, 3 (15), 2341-2344.
Bentley et al., *Biochem. J.* 1973(135), 507-511.
Bentley et al., *Biochem. J* 1976(153), 137-138.
Tam et al., 2007, J. Am. Chem. Soc. 2007, 129, 12670-12671
Wu et al., *J. Am. Chem. Soc.* 2016, 138(44), 14554-14557
Huo et al., *J. Am. Chem. Soc.* 2007, 139, 9819-9822
Tornqvist et al., *Anal. Biochem.* 1986, 154, 255-266
Rydberg et al., *Chem. Res. Toxicol.,* 2002, 15(4), 570-581.
Proulx et al., *Peptide Science,* 2016, 106(5), 726-736.
Fang et al., *Peptide Science,* 2010, 96 (1), 97-102.
Buckingham et al., *J Am. Chem. Soc.* 1970, 92(19), 5571-5579.
Bader et al., *Arch Occup Environ Health,* 1994, 65(6), 411-414.
Barrett et al., *Tetrahedron Lett.,* 1985, 26(36), 4375-4378.
Sutton et al, *Acc. Chem. Res.* 1987, 20(10), 357-364.
Al Ouahabi, A., L. Charles and J. F. Lutz (2015). "Synthesis of non-natural sequence-encoded polymers using phosphoramidite chemistry." *J Am Chem Soc* 137(16): 5629-5635.
Demonte, D., E. J. Drake, K. H. Lim, A. M. Gulick and S. Park (2013). "Structure-based engineering of streptavidin monomer with a reduced biotin dissociation rate." *Proteins* 81(9): 1621-1633.

Heerema, S. J. and C. Dekker (2016). "Graphene nanodevices for DNA sequencing." *Nat Nanotechnol* 11(2): 127-136.

Knight, A. S., E. Y. Zhou, M. B. Francis and R. N. Zuckermann (2015). "Sequence Programmable Peptoid Polymers for Diverse Materials Applications." *Adv Mater* 27(38): 5665-5691.

Laszlo, A. H., I. M. Derrington, B. C. Ross, H. Brinkerhoff, A. Adey, I C. Nova, J. M. Craig, K. W. Langford, J. M. Samson, R. Daza, K. Doering, J. Shendure and J. H. Gundlach (2014). "Decoding long nanopore sequencing reads of natural DNA." *Nat Biotechnol* 32(8): 829-833.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure. The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet, including U.S. Provisional Patent Application No. 62/330,841, U.S. Provisional Patent Application No. 62/339,071, and U.S. Provisional Patent Application No. 62/376,886, International Patent Application No. PCT/US2017/030702, U.S. Provisional Patent Application Nos. 62/579,844, 62/582,312, 62/583,448, 62/579,870, 62/579,840 and 62/582,916 are incorporated herein by reference, in their entireties. Aspects of the embodiments can be modified, if necessary to employ concepts of the various patents, applications and publications to provide yet further embodiments.

The invention claimed is:

1. A kit for analyzing a polypeptide, comprising:
   (a) a functionalizing reagent that reacts with an N-terminal amino acid (NTAA) of the polypeptide to generate a functionalized NTAA of the polypeptide;
   (b) one or more nucleic acid recording tags configured to associate directly or indirectly with the polypeptide or with a component of the polypeptide obtained by a cleavage of the functionalized NTAA of the polypeptide, wherein each of the one or more nucleic acid recording tags comprises a unique molecular identifier (UMI); and
   (c) one or more binding agents each comprising:
      (i) a binding moiety that binds to the functionalized NTAA of the polypeptide or the component of the polypeptide obtained by the cleavage of the functionalized NTAA of the polypeptide; and
      (ii) a nucleic acid coding tag attached to the binding moiety and comprising a barcode sequence that comprises identifying information regarding the binding moiety;

wherein the one or more nucleic acid recording tags and the one or more nucleic acid coding tags are configured to allow transfer of sequence information of the barcode sequence and/or the UMI by ligation or primer extension, upon binding between each binding agent and the functionalized NTAA of the polypeptide or the component of the polypeptide, thereby generating one or more extended nucleic acid constructs each comprising the barcode sequence or a complement thereof and the UMI or a complement thereof.

2. The kit of claim 1, wherein the component of the polypeptide comprises one or more amino acid residues of the polypeptide.

3. The kit of claim 1, wherein the component of the polypeptide comprises one or more terminal amino acid residues of the polypeptide.

4. The kit of claim 1, wherein the component of the polypeptide is an N-terminal amino acid (NTAA) residue.

5. The kit of claim 1, which is for analyzing 1,000,000 or more polypeptide molecules.

6. The kit of claim 1, further comprising an instruction for using the kit in high throughput polypeptide analysis.

7. The kit of claim 1, comprising three or more different binding agents.

8. The kit of claim 1, wherein at least one of the one or more binding agents is capable of binding to a terminal amino acid residue of the polypeptide.

9. The kit of claim 1, wherein the component of the polypeptide comprises a modified or functionalized amino acid residue of the polypeptide.

10. The kit of claim 1, further comprising an eliminating reagent for removing the functionalized NTAA residue to expose its immediately adjacent amino acid residue, as a second NTAA.

11. The kit of claim 1, wherein the polypeptide or the component of the polypeptide is immobilized on a solid support.

12. The kit of claim 1, further comprising a solid support, wherein the one or more nucleic acid recording tags are configured to be: covalently immobilized directly or indirectly to the solid support; or associated with the polypeptide immobilized on the solid support.

13. The kit of claim 12, wherein the solid support is a bead.

14. The kit of claim 12, wherein the solid support comprises a plurality of nucleic acid hairpins immobilized on the solid support and configured to capture via hybridization the one or more nucleic acid recording tags associated with the polypeptide.

15. The kit of claim 1, wherein each of the one or more nucleic acid recording tags further comprises a sample barcode.

16. The kit of claim 1, further comprising a reagent for transferring sequence information of the barcode sequence and/or the UMI by ligation between the one or more nucleic acid recording tags and the one or more nucleic acid coding tags.

17. The kit of claim 1, further comprising a reagent for transferring sequence information of the barcode sequence and/or the UMI by primer extension of the one or more nucleic acid recording tags and/or the one or more nucleic acid coding tags.

18. The kit of claim 1, wherein each of the one or more nucleic acid recording tags and each of the one or more nucleic acid coding tags comprise complementary spacer sequences.

19. The kit of claim 1, wherein each nucleic acid coding tag attached to the binding moiety further comprises a cycle-specific barcode.

20. The kit of claim 1, wherein the one or more nucleic acid recording tags are configured to be covalently attached directly or indirectly to the polypeptide or to the component of the polypeptide.

* * * * *